United States Patent [19]

Bukh et al.

[11] Patent Number: 5,882,852
[45] Date of Patent: Mar. 16, 1999

[54] HEPATITIC C VIRUS (HCV) CORE GENE NUCLEOTIDE SEQUENCES AND RELATED METHODS OF DETECTING MAJOR AND MINOR GENOTYPES OF HCV ISOLATES

[75] Inventors: Jens Bukh, Bethesda; Roger H. Miller, Rockville; Robert H. Purcell, Boyds, all of Md.

[73] Assignee: The United States of America as represented by the Secretary of the Department of Health and Human Services, Washington, D.C.

[21] Appl. No.: 290,665

[22] Filed: Aug. 15, 1994

Related U.S. Application Data

[63] Continuation-in-part of Ser. No. 86,428, Jun. 29, 1993, Pat. No. 5,514,539.

[51] Int. Cl.[6] .............................. C12Q 1/70; C12P 19/34; C07H 21/04; C12N 15/00
[52] U.S. Cl. ................................. 435/5; 435/6; 435/91.1; 435/91.2; 435/91.32; 435/91.33; 435/810; 536/23.1; 536/24.3; 536/24.33; 935/8; 935/77; 935/78
[58] Field of Search ..................... 435/5, 6, 91.1, 435/91.2, 91.31, 91.32, 91.33, 810, 183; 536/23.1, 23.72, 24.33, 25.3; 935/5, 8, 16, 18, 77, 78

[56] References Cited

U.S. PATENT DOCUMENTS

| | | |
|---|---|---|
| 5,350,671 | 9/1994 | Houghton . |
| 5,372,928 | 12/1994 | Miyamura et al. ......................... 435/5 |
| 5,427,909 | 6/1995 | Okamoto et al. ......................... 435/54 |

FOREIGN PATENT DOCUMENTS

| | | |
|---|---|---|
| 0 586 065 | 3/1994 | European Pat. Off. . |
| WO 92 19743 | 11/1992 | WIPO . |
| WO 92 21759 | 12/1992 | WIPO . |
| WO 94 01778 | 1/1994 | WIPO . |
| WO 94 25601 | 11/1994 | WIPO . |
| WO 94 27153 | 11/1994 | WIPO . |
| WO 95 01442 | 1/1995 | WIPO . |

OTHER PUBLICATIONS

Choo, O.L. et al. (1989) *Science*, 244:359–362.
Okamoto, H. et al. (1994) *J. Gen. Virol.*, 75: 629–635.
Bukh, J. et al. (1993) *PNAS*, 90: 8234–8238.
Li, J., et al. (1991) *Gene*, 105: 167–172.
Houghton, M. (1991) *Hepatology*, 14: 381–388.
Machida, A. et al. (1992) *Hepatology*, 16: 886–891.
Okamoto, H. et al. (1993) *J. Gen. Virol.*, 74: 2385–2390.
Simmonds, P., et al. (1993) *J. Gen. Virol.*, 74: 661–668.
Stuyver, L. et al. (1993) *J. Gen. Virol.*, 74: 1093–1102.
Widell, A. et al. (1994) *J. Med. Virol.*, 44: 272–279.
Qu D. et al. (1994) *J. Gen. Virol.*, 75: 1063–1070.
Simmonds, P., et al. (1994) *J. Gen Virol.*, 75: 1053–1061.
Stuyver, L. et al. (1993) *J. Gen Virol.*, 74: 1093–1102.
Viazow, S., et al. (1994) *J. Virol Meth.*, 48: 81–92.
Simmonds, P., et al. (1993) *J. Clin Microbiol.*, 31: 1493–1503.
Hayashi, N., et al. (1993) *J. Hepatol.*, 17 (suppl 3) S94–S107.
Wang, Y., et al. (1993) *J. Med Viro.*, 40: 254–260.
Tanaka, T., et al. (1994) *Hepatology*, 19: 1347–1353.
Sakamoto, M., et al. (1994) *J. Gen Virol.*, 75; 1761–1768.
Simmonds P. et al., "Identification of genotypes of hepatitis C virus by sequence comparisons in the core, E1 and NS–5 regions," *Journal of General Virology*, 5:1053–1061 (1994).

(List continued on next page.)

*Primary Examiner*—Bradley L. Sisson
*Attorney, Agent, or Firm*—Morgan & Finnegan, L.L.P.

[57] ABSTRACT

The nucleotide and deduced amino acid sequences of cDNAs encoding the envelope 1 genes and core genes of isolates of hepatitis C virus (HCV) are disclosed. The invention relates to the oligonucleotides, peptides and recombinant envelope 1 and core proteins derived from these sequences and their use in diagnostic methods and vaccines.

14 Claims, 135 Drawing Sheets

OTHER PUBLICATIONS

Kao, J.H. et al., "Detection of divergent hepatitis C virus envelope sequences," *Journal of Biomedical Science*, 3:158–162 (1994).

Rogggendorf, M. et al., "Variability of the envelope regions of HCV in European isolated and its significance of diagnostic tool," *Archives of Virology Supplementum*, 7:27–39 (1993).

Li, Ji–Su et al., "Identification of the third major genotype of hepatitis C virus in France", *Biochem. Biophys. Res. Commun.*, 1474–81 (1994).

Sigma Molecular Biology Catalog, p. 54, 1989.

FIGURE 1A-1

| SEQ ID NO: | Isolate | | |
|---|---|---|---|
| 5 | S14 | 1 | TACCAAGTGCGCAACTCCACGGGGCTTTACCATGTtACCAATGATTGCCCTAACTCGAGTA |
| 1 | DK7 | 1 | TACCAAGTGCGCAACTCCACGGGGCTTTACCATGTCACCAATGATTGCCCTAACTCGAGTA |
| 8 | US11 | 1 | TACCAAGTaCGCAACTCCACGGGGCTTTACCATGTCACCAATGATTGCCCTAATTCGAGTA |
| 4 | DR4 | 1 | CACCAAGTGCGCAACTCCTACAGGGCTTTACCATGTCACCAATGATTGCCCTAATTCGAGTA |
| 3 | DR1 | 1 | CACCAAGTGCGCAACTCTACAGGGCTTTACCATGTCACCAATGATTGCCCTAACTCGAGTA |
| 2 | DK9 | 1 | TACCAAGTACGCAACTCCtCGGGCCCTcTACCATGTCACCAATGATTGCCCTAACTCGAGTA |
| 6 | S18 | 1 | CACCAAGTACGCAACTCCCaCGGGCCCTTTACCATGTCACCAATGATTGCCCTAACTCGAGTA |
| 7 | SW1 | 1 | TACCAAGTACGCAACTCCtCGGGCCCTTTACCATGTCACCAATGACTGCCCTAACTCGAGcA |
| 1-8 | consensus | | tACCAAGT-CGCAACTCcaCgGGgCTttTACCATGTcACCAATGAtTGCCCTAAcTCGAGtA |

| SEQ ID NO: | Isolate | | |
|---|---|---|---|
| 5 | S14 | 62 | TtGTGTACGAGaCaGCtGATGCtATCCTaCACgCTCCGGGaTGTGTCCCTTGCGTTCGtGA |
| 1 | DK7 | 62 | TcGTGTACGAGAGGCGGCCGATGCCGATCCTGCACACTCCGGGGTGTGTCCTTGCGTTCGCGA |
| 8 | US11 | 62 | TTGTGTACGAGAGGCGGCCGATGCCGATCCTGCACACTCCGGGGTGTGTtCCTTGCGTTCGCGA |
| 4 | DR4 | 62 | TTGTGTACGAGAGGCGGCCGATGCCGATCCTGCACACTCCGGGGTGTGTCCCTTGCGTTCGCGA |
| 3 | DR1 | 62 | TTGTGTACGAGAGGCGGCCGATGCCGATCCTGCACACgCTCCGGGGTGTGTCCCTTGCGTTCGCGA |
| 2 | DK9 | 62 | TTGTGTACGAGAGGCGGCCGATGCCGATCCTGCACgCGCCCGGGGTGTGTCCCTTGCGTTCGCGA |
| 6 | S18 | 62 | TTGTGTACGAGACGGCCGATGCCGATGCCGATCCTGCATTCTCCaGGGGTGTGTCCCTTGCGTTCGCGA |
| 7 | SW1 | 62 | TTGTGTACGAGAGGCGGCCGATaCCATCCTACACACTCCTCCaGGGGTGTGTCCCTTGCGTTCGCGA |
| 1-8 | consensus | | TtGTGTACGAGgCgGCcGATgCcATcCTgCAc-CtCCgGGgTGTGTcCCTTGCGTTCGcGA |

FIGURE 1A-2

| SEQ ID NO: | Isolate | | |
|---|---|---|---|
| 5 | S14 | 123 | GGGTAACacCTCGAGGTGTTGGGTGGCGATGACCCCCACGTGGCCACCAGGACGGCAAA |
| 1 | DK7 | 123 | GGGTAACGtCTCGAGGTGTTGGGTGGCGATGACCCCCACGTGGCCACCAGGAtGGCAAA |
| 8 | US11 | 123 | GGGTAACGCtTCGAGGTGTTGGGTGGCGATGACCCCCACGTGGCCACCAGGACGGCAAA |
| 4 | DR4 | 123 | GGGTAACaCaCCTCGAGGTGTGTTGGGTGGCGATGACCCCCACGTGGCCACCAGGACGGCAAA |
| 3 | DR1 | 123 | GGGTAACGCCTCGAGGTGTGTTGGGTGGCGACCCCGGTGACCCCCACGTGGCCACCAGGACGGCAAA |
| 2 | DK9 | 123 | GGGTAACGCCTCGAaATGTTGGGTGGCGGTGACCCCCACGTGGCCACCAGGACGGCAAg |
| 6 | S18 | 123 | GGGTAACGCCTCGAGaATGTTGGGTGCcCGGTGGCCGGTGACCCCCACGTGGCCACCAGGACGGCAAA |
| 7 | SW1 | 23 | GGaTggCGCCcGAagTGTTGGGTGgCGGTGACCCCCACAGTcGCCACtAGGGACGGCAAA |
| 1-8 | consensus | | GGGTaaCgcctCGAggTGTGGGTGgCGgTGaCCCCCACGtGgCCACcAGGGACGGCAAa |

| SEQ ID NO: | Isolate | | |
|---|---|---|---|
| 5 | S14 | 184 | CTCCCCgCAaaCGCAGCTTCGACGTtACATCGATCTGCTtGTCGGGAGcGCCACCCTCTGTT |
| 1 | DK7 | 184 | CTCCCCACACAgCGCAGCTTCGACGTTCACATCGATCTGCTCGTCGGGAGtGCCACCCTCTGTT |
| 8 | US11 | 184 | CTCCCCACAACGCAaCTTCGACGTTCACATCGATCTGCTCGTCGGGAGCGCCACCCTCTGTT |
| 4 | DR4 | 184 | CTCCCCACAACGCAGCTcCGACGTTCACATCGATCTGCTCGTTGTCGGGAGCGCCACCCTCTGCT |
| 3 | DR1 | 184 | CTCCCCACAACGCAGCTTCGACGTTCACATCGATCTGCTCGTTGTCGGGAGCGCCACCCTCTGCT |
| 2 | DK9 | 184 | CTCCCCGCAACGCAGCTTCGACGTTCACATCGATCTGCTCGTTGTCGGGAGCGCCACCCTCTGCT |
| 6 | S18 | 184 | CTCCCCGCAACGCAGCTTCGACGTTCACATCGATCTGCTCGTTGTtGGGAGCGCCACCCTCTGCT |
| 7 | SW1 | 184 | CTCCCtgCAACGCAGCTTCGACGTTCACATCGATCTGCTCGTTGTCGGaAGCGCCACCCTCTGCT |
| 1-8 | consensus | | CTCCCc-CAaCGCAgCTtCGACGTcACATCGAtCTGCTtGTcGGgAGcGCCACCCTCTGcT |

FIGURE 1A-3

| SEQ ID NO: | Isolate | | |
|---|---|---|---|
| 5 | S14 | 245 | CGGCCCCTCTACGTGGGGGACtTGTGCGGGTCTGTCTTTCTTGTCGGTCAgCTGTTTACCTT |
| 1 | DK7 | 245 | CGGCCCCTCTACGTGGGGGACCTGTGCGGGTCTGTCTTTCTTGTCGGTCAACTGTTTACCTT |
| 8 | S11 | 245 | CGGCCCCTCTACGTGGGGGACCTGTGCGGGTCTGTCTTTCTTGTCGGTCAACTGTTTACCTT |
| 4 | DR4 | 245 | CGGCCCCTCTACGTGGGGGACtTGTGCGGGTCTGTCTTCCTTGTCGGTCAACTGTTCACCTT |
| 3 | DR1 | 245 | CGGCCCCTCTACGTGGGGGACCTGTGCGGGTCTGTCTTCCTTGTCGGTCAACTGTTCACCTT |
| 2 | DK9 | 245 | CGGCCCCTCTATGTGGGGGACtTGTGCGGGTCTGTCTTCCTTGTCGGCCAACTGTTCACCTT |
| 6 | S18 | 245 | CGGCCCCTCTATGTGGGGGACcTGTGCGGGTCTGTCTTCCTTGTCAGCCAgCTGTTCACtaT |
| 7 | SW1 | 245 | CGGCCCCTCTAcGTGGGGGACtTGTGCGGGTCTGTCTTTCTcGTCGTCAGtCAaCTGTTCACgtT |
| 1-8 | consensus | | CGGCCCCTCTACGTGGGGGAC-TGTGCGGGTCTGTCTTtCTtGTCggtCAaCTGTTcACctT |

| SEQ ID NO: | Isolate | | |
|---|---|---|---|
| 5 | S14 | 306 | CTCTCCCAGGCGCCtCTGGACGACGCAAGaCTGCAATTGTTCTATCTATCCCGGCCATATA |
| 1 | DK7 | 306 | CTCTCCCAGGCGCCACTGGACGACGCAAGACTGCAATTGTTCTATCTATCCtGGCCATATA |
| 8 | S11 | 306 | CTCTCCCAGGCGCCACTGGACGACGCAAGACTGCAATTGTTCTATCTATCCCGGCCATATA |
| 4 | DR4 | 306 | CTCTCCCAGaCGCCACTGGACGACGCAAGGCTGCAATTGTTCTATCTATCCCGGCCATATA |
| 3 | DR1 | 306 | CTCTCCCAGGCaCCACTGGACAACGCAAGACTGCAATTGTTCCATCTATCCCGGCCATATA |
| 2 | DK9 | 306 | tTCTCCCAGGCGCCACTGGACAACGCAAGACTGCAATTGTTCTATCTATCCCGGCCATATA |
| 6 | S18 | 306 | CTCCCCAGaCGCCACTGGACAACGCAAGACTGCAACTGTTCTATCTACCCCGGCCATATt |
| 7 | SW1 | 306 | CTCCCCAGGCGCCACTGGACAACGCAAGACTGCAACTGTTCTATCTACCCCGGCCATATA |
| 1-8 | consensus | | cTCtCCCAGgCgCCaCTGGACaACGCAagaCTGCAAtTGTTCtATCTAtCCCGGCCAtATa |

FIGURE 1A-4

| SEQ ID NO: | Isolate | | |
|---|---|---|---|
| 5 | S14 | 367 | ACGGGTCAtCGCATGGCaTGGGATATGATGATGAACTGGTCCCCTACgACGGCacTGGTAG ---—-—-—-—-—-—-—-—-—-—-—-—-—-—-—-—-—-—- |
| 1 | DK7 | 367 | ACGGGTCACCGCATGGCgTGGGATATGATGATGAACTGGTCCCCTACCACGGCGTTGGTAG ---—-—-—-—-—-—-—-—-—-—-—-—-—-—-—-—-—-—- |
| 8 | S11 | 367 | ACGGGTCACCGCATGGCaTGGGATATGATGATGAACTGGTCCCCTACgCGGCGTTGGTgG ---—-—-—-—-—-—-—-—-—-—-—-—-—-—-—-—-—-—- |
| 4 | DR4 | 367 | ACGGGcCACCGCATGGCgTGGGATATGATGATGAACTGGTCCCCTACGACAGCGCTGGTAG ---—-—-—-—-—-—-—-—-—-—-—-—-—-—-—-—-—-—- |
| 3 | DR1 | 367 | ACGGGaCACCGtATGGCATGGGATATGATGATGAACTGGTCCCCTACGACAGCGCTGGTAA ---—-—-—-—-—-—-—-—-—-—-—-—-—-—-—-—-—-—- |
| 2 | DK9 | 367 | ACGGGTCAtCGcATGGCgTGGGATATGATGATGAACTGGTCCCCTACACAgCAGCGCTGGTAA ---—-—-—-—-—-—-—-—-—-—-—-—-—-—-—-—-—-—- |
| 6 | S18 | 367 | ACGGGTCACCGtATGGCATGGGATATGATGATGAACTGGTCCCCTACACAACGCTGGTAA ---—-—-—-—-—-—-—-—-—-—-—-—-—-—-—-—-—-—- |
| 7 | SW1 | 367 | ACGGGTCACCGCATGGCATGGGATATGATGATGAACTGGTCCCCCACAACaGCGCTGGTAg ---—-—-—-—-—-—-—-—-—-—-—-—-—-—-—-—-—-—- |
| 1-8 | consensus | | ACGGGtCAcCGcATGGCaTGGGATATGATGATGAACTGGTCCCCTACgaC-GCgcTGGTag |

| SEQ ID NO: | Isolate | | |
|---|---|---|---|
| 5 | S14 | 428 | TAGCTCAGCTGCTCCGGATCCCaCAAGCCATCTTGGAtATGATCGCTGGTGCTCACTGGGG ---—-—-—-—-—-—-—-—-—-—-—-—-—-—-—-—-—-—- |
| 1 | DK7 | 428 | TAGCTCAGCTGCTCCGGATCCCgCAAGCCATCTTGGACATGATCGCTGGTGCTCACTGGGG ---—-—-—-—-—-—-—-—-—-—-—-—-—-—-—-—-—-—- |
| 8 | S11 | 428 | TAGCTCAGCTGCTCCGGATCCCACAAGCCATCTTGGACATGATCGCTGGTGCTCACTGGGG ---—-—-—-—-—-—-—-—-—-—-—-—-—-—-—-—-—-—- |
| 4 | DR4 | 428 | TAGCTCAGCTGCTCCGGATCCCACAAGCCATCTTGGACATGATCGCTGGTGCCCACTGGGG ---—-—-—-—-—-—-—-—-—-—-—-—-—-—-—-—-—-—- |
| 3 | DR1 | 428 | TGGCTCAGCTGCTCCGGATCCCACAAGCCATCTTGGACATGATCGCTGGaGCCCACTGGGG ---—-—-—-—-—-—-—-—-—-—-—-—-—-—-—-—-—-—- |
| 2 | DK9 | 428 | TGGCgCAGCTGCTCAGGATCCCGCAAGCCagCCGTCCCCGCATGATCGCTGGTGCCACTGGGG ---—-—-—-—-—-—-—-—-—-—-—-—-—-—-—-—-—-—- |
| 6 | S18 | 428 | TAGCTCAGCTGCTCAGGaTCCCGCAAGCCCGCGTCCCGCATGATCGCTGGTGCCACTGGGG ---—-—-—-—-—-—-—-—-—-—-—-—-—-—-—-—-—-—- |
| 7 | SW1 | 428 | TAGCTCAGCTGCTCAGGaTCCCGCAAGCCGTCTCTTGGACATGATCGCTGGTGCCACTGGGG ---—-—-—-—-—-—-—-—-—-—-—-—-—-—-—-—-—-—- |
| 1-8 | consensus | | TaGCtCAGCTGCTCcGGaTCCC-CAagCCaTCTTGGACATGATCGCTGGtGCcCACTGGGG |

FIGURE 1A-5

| SEQ ID NO: | Isolate | | |
|---|---|---|---|
| 5 | S14 | 489 | AGTCCTaGCGGGCATAGCGTATTTcTCCATGGTGGaAACTGGGCGAAGGTCCTaGTgGTG--- |
| 1 | DK7 | 489 | AGTCCTgGCGGGCATAGCGTATTTtTCCATGGTGGGAACTGGGCGAAGGTCCTGGTAGTG--- |
| 8 | S11 | 489 | AGTCCTAGCGGGCATAGCGTATTTCTCCATGGTGGGAACTGGGCGAAGGTCCTGGTAGTG--- |
| 4 | DR4 | 489 | AGTCCTAGCGGGCATAGCGTATTTCTCCATGGTGGGAACTGGGCGAAGGTCCTGGTAGTG--- |
| 3 | DR1 | 489 | AGTCCTAGCGGGCATAGCGTATTTCTCCATGGTGGGAACTGGGCGAAGGTCGTGGTAGTG--- |
| 2 | DK9 | 489 | AGTCCTAGCGGGCATAGCGTATTTCTCCATGGTGGGAACTGGGCGAAGGTCGTGGTAGTG--- |
| 6 | S18 | 489 | AGTCCTAGCGGGCATAGCGTATTTCTCCATGGCGGGGAACTGGGCGAAGGTCCTGGTgGTa--- |
| 7 | SW1 | 489 | AGTCCTAGCGGGCATAGCGTATTTCTCCATGGtGGGGAACTGGGCGAAGGTCCTGaTAGTG--- |
| 1-8 | consensus | | AGTCCTaGCGGGCATAGCGTATTTcTCCATGGtGGGgAACTGGGCGAAGGTCCTggTaGTg--- |

| SEQ ID NO: | Isolate | | |
|---|---|---|---|
| 5 | S14 | 550 | CTGCTGCTATTcGCCGGCGTgACGCG--- |
| 1 | DK7 | 550 | CTGCTGCTATTTGCCGGCGTCGACGCG--- |
| 8 | US11 | 550 | CTGCTGCTATTTGCCGGCGTCGACGCG--- |
| 4 | DR4 | 550 | CTGCTGCTATTTGCCGGCGTCGACGCG--- |
| 3 | DR1 | 550 | CTGTTGCTGTTTGCCGGCGTTGATGCG--- |
| 2 | DK9 | 550 | CTGTTGCTGTTTGCCGGCGTTGATGCG--- |
| 6 | S18 | 550 | CTGTTGCTGTTTaCCGGCGTTGATGCG--- |
| 7 | SW1 | 550 | CTGTTGCTGTTTgCCGGCGTTGATGCG--- |
| 1-8 | consensus | | CTGtTGCTgTTtgCCGGCGTcGAtGCG |

FIGURE 1B-1

| SEQ ID NO: | Isolate | | |
|---|---|---|---|
| 11 | DK1 | 1 | TATGAAGTGCGCAACGTGTCCGGGgTGTACCAcGTCACaAACGACTGCTCCAACTCAAGCA |
| 24 | T10 | 1 | TATGAAGTGCGCAACGTGTCCGGGaTGTACCATGTCACgAACGACTGCTCCAACTCAAGCA |
| 10 | D3 | 1 | TATGAAGTGCGCAACGTGTCCGGGGTGTACCAaGTCACcAAtGACTGTTCCAACTCGAGCA |
| 9 | D1 | 1 | TATGAAGTGCGCAACGTGTCCGGGGTGTACCATGTCACGAACGACTGTTCCAACTCGAGCA |
| 14 | HK5 | 1 | TATGAAGTGCGCAACGTGTCCGGGGTATACCATGTCACGAACGACTGCTCCAACTtAAGCA |
| 15 | HK8 | 1 | TATGAAGTGCGCAACGTGTCCGGGGTATATACCATGTCACGAACGACTGCTCCAACTCAAGCA |
| 12 | HK3 | 1 | TATGAAGTGCGCAACGTGTCCGGGaTATACCATGTCACGAACGACTGCTCCAACTCAAGCg |
| 23 | T3 | 1 | TACGAAGTGCGCAACGTGTCCGGGGTGTACtATGTCACGAACGACTGTTCCAACTCAAGCA |
| 22 | SW2 | 1 | TATGAAGTGCGCAACGTGTCCGGGGTGTAtCATGTCACGAACGACTGTTCCAACTCAAGCA |
| 17 | IND8 | 1 | TATGAgGTGCGCAACGTGTCCGGGGTGTACCATGTCACGAACGACTGCTCCAACTCAAGTA |
| 16 | IND5 | 1 | TATGAAGTGCGCAACGTGTCCGGGGTGTACCATGTCACGAACGACTGCTCCAACTCAAGTA |
| 21 | SA10 | 1 | TATGAAGTGCGCAACGTGTCCGGGaTGTGTACCATGTCACGAACGACTGCTCCAACTCAAGCA |
| 20 | S45 | 1 | TATGAAGTGCGCAACGTGTCCGGGGTGTACCATGTCACGAACGACTGCTCCAACTCAAGCA |
| 25 | US6 | 1 | TATGAAGTGCGCAACGTGTCCGGGgcGTACCgTGTCACGAACGACTGCTCCAACTCAAGCA |
| 13 | HK4 | 1 | cATGAAGTGCGCaCAACGTGTaTCCGGGaTCTACCATGTCACGAACGACTGCTCCAACTCAAGTA |
| 18 | P10 | 1 | TATGAAGTGCGCAACGTgTCCGGGTGTACCATGTCACGAACGACTGCTCCAACTCAAGTA |
| 19 | S9 | 1 | TATGAAGTGCGCAACGTaTCCGGGGcGTACCATGTCACGAACGACTGCTCCAACTCAAGTA |
| 9-25 | consensus | | tAtGAaGTGCgCAACGTgTCCGGGgtgTAccAtGTCACgAAcGACTGcTCCAACTcaAGca |

FIGURE 1B-2

| SEQ ID NO: | Isolate | | |
|---|---|---|---|
| 11 | DK1 | 62 | TcGTGTaTGAGGCAGtGGACgTGATCATGCAtACCCCaGGGTGCGTGCCCTGCGTTCGGGA --- --- --- --- |
| 24 | T10 | 62 | TtGTGTtTGAGGCAGGCGGACTtTGATCATGCACACACCCCGGGTGCGTGCCCTGCGTTCGGGA --- --- --- --- |
| 10 | D3 | 62 | TcGTGTATGAGACAGCGGACACAGCGGACATGATCATGCACACACCCCGGGTGCGTGCCCTGCGTTCGGGA --- --- --- --- |
| 9 | D1 | 62 | TtGTGTATGAGACAGCGGACATGATCATGCACACACCCCGGGTGCGTGCCCTGCGTTCGGGA --- --- --- --- |
| 14 | HK5 | 62 | TCGTGTATGAGACAAcCGGACATGATCATGCACACACCCCTGGGTGCGTGCCCTGCGTTCGGGA --- --- --- --- |
| 15 | HK8 | 62 | TCGTGTATGAaACAGCGGACATGATtATGCATACCCCTGGATGCaTGCCCTGCGTTCGGGA --- --- --- --- |
| 12 | HK3 | 62 | TCGTGTATGAGACAGCaGACATGATCATGCATACCCCTGGATGCGTGCCCTGCGTaCGGGA --- --- --- --- |
| 23 | T3 | 62 | TCGTGTATGAGACAGCGGACACATGATCATGCACACACCCCTGGGTGCGTGCCCTGCGTTCGGGA --- --- --- --- |
| 22 | SW2 | 62 | TTGTGTATGAGACAGCGGACATGATCATGCATGATACCCCCGGGTGCGTGCCCTGCGTTCGGGA --- --- --- --- |
| 17 | IND8 | 62 | TTGTGTATGAGGCAGCGGACATGATCATGCACACACCCCCGGGTGCGTGCCCTGCGTTCGGGA --- --- --- --- |
| 16 | IND5 | 62 | TTGTGTATGAGGCAGCGGACATGATCATGCACACACtCCCGGGTGCGTGCCCTGCGTTCGGGA --- --- --- --- |
| 21 | SA10 | 62 | TTGTGTATGAGGCAGCGGACATGATCATGCACACACCCCCGGGTGCGTGCCCTGCGTTCGGGA --- --- --- --- |
| 20 | S45 | 62 | TTGTGTATGAGGCAGtGGACgTGATCCTGCACACCCCtGGGTGCGTGCCCTGCGTTCGGGA --- --- --- --- |
| 25 | US6 | 62 | TTGTGTATGAGGCAGCGGACATGATCATGCACACtCCCGGGTGCGTGCCCTGCGTgTGTTCGGGA --- --- --- --- |
| 13 | HK4 | 62 | TTGTGTATGAGGCAGCGGACATGATCATGCAtACCCCGGGTGCGTGCCCTGCGTcCGGGA --- --- --- --- |
| 18 | P10 | 62 | TTGTGTATGAGGCAGCGGACATGATaATGCAcACCCCGGGTGCGTGCCCTGtGTTCGGGA --- --- --- --- |
| 19 | S9 | 62 | TTGTGTAcGAGGCAGCGGACgTGATcATGCAtACCCCGGGTGtGTaCCCTGcGTTCaGGA --- --- --- --- |
| 9-25 | consensus | | TtGTGTatGAggCAgcgGACaTGATcaTGCAcACCCCgGGgTGcgTgCCCTGcGTTCgGGA |

FIGURE 1B-3

| SEQ ID NO: | Isolate | | |
|---|---|---|---|
| 11 | DK1 | 123 | GaaCAACcaCTCCCGtTGCTGGGTAGCGCTCACcCCCACGCTCGCGGCCAGGAACgCCAGC |
| 24 | T10 | 123 | GGgCAACTCCTCCCGCTGCTGGGTAGCGCTCACtCCCACGCTCGCGGCCAGGAACACCAGC |
| 10 | D3 | 123 | GGACAACTCCTCGCTCGCTGCTGGGTAGCGCTCACCCCCACGCTCGCGGCTAGGAATAGCAGC |
| 9 | D1 | 123 | GGACAACTCCTCGCTCTCGCTGCTGGGTAGCGCTCACCCCCACGCTCGCGGCTAGGAATGGCAaC |
| 14 | HK5 | 123 | aAACAACTCCTCCCCGTTGttTGGGTAGCGCTCgCCCCCACGCTCGCGGCCAGGAACgCCAGC |
| 15 | HK8 | 123 | GAACAACTCCTCCCCGTTGcTGGGTgGGTAGCGCTCACTCCCACGCTCGGCtAGGAAtGTCAGC |
| 12 | HK3 | 123 | GAACAACTCCTCCCCGCTGtTGGGTAGCGCTCACTCCCACGCTCGCGGCCAGGAACGTCAGC |
| 23 | T3 | 123 | GAgCAAtTCCTCCCCGCTGCTGGGTAGCGCTtACTCCCACGCTCGCGGCCAGGAACGCCAGC |
| 22 | SW2 | 123 | GGcCAACTCCTCCCCGCTGCTGGGTAGCGCTCACTCCCACGCTaGCaGCCAGGAACaCCAGC |
| 17 | IND8 | 123 | GGGCAACTtCTCTaGtTGCTGGGTAGCGCTCACTCTCGCGGCtAGGAACGCCAGC |
| 16 | IND5 | 123 | GGGCAACTCCTCCCCGCTGCTGGGTAGCGCTCACTCCCACGCTCGCGGCCAGGAACGCCAGC |
| 21 | SA10 | 123 | GAACAACTCCTCCCCGCTGCTGGGTAGCGCTCACTCCCACGCTCGCGGCCAGGAACTCCAGC |
| 20 | S45 | 123 | GAACAACTCCTCCCCGCTGCTGGGTgGGTAGCGCTCACTCCCACGCTCGCGGCCAGGAACTCCAGC |
| 25 | US6 | 123 | GAACAAtTCCTCCCGCgCTGCTGGGTAGCGCTCACTCCCACGCTCGCGGCCAGGAACGCtAGC |
| 13 | HK4 | 123 | GAACAACTCCTCCCCGCTGCTGGGTAGCGCTCACTCCCACGCTCGCGGCCAGGAACGCCAGC |
| 18 | P10 | 123 | GAACAACTCCTCCCCGCTGCTGGGTAGCGCTCACaCaCTCCACaCTCGCGGCTAGGAAttCCAGC |
| 19 | S9 | 123 | GggtAACTCCTCCCaaTGCTGGGTgGGTGCGCTCACcCCCACGCTCGCGGCCAGGAACgCtAcC |
| 9-25 | consensus | | gaacAActcCTCccgcTGcTGGTaGCGCTcactCCCACgCTcGCggCcAGGAACgccAgC |

| SEQ ID NO: | Isolate | | |
|---|---|---|---|
| 11 | DK1 | 245 | CCGCTATGTAcGTGGGgGACCTCTGCGGATCCGTTTTCCTCGTCTCTCCAGCTGTTCACCTT |
| 24 | T10 | 245 | CCGCTATGTAtGTGGaGAGACCTCTGCGGaGATCTGTTTTCCTCGTCTCTCCAGCTGTTCACCTT |
| 10 | D3 | 245 | CCGCCATGTACGTGGGGGATCTTGCGGATCTGTTTTCCTCGTCTCTCCAGCTGTTCACCTT |
| 9 | D1 | 245 | CCGCCATGTACGTGGGGGATCTcTGCGGATCTGTTTTCCTCaTCTCCCAGCTGTTCACCcT |
| 14 | HK5 | 245 | CCGCTATGTACGTGGGGGATCTtTGCGGATCTGTTTTCCTCGTCTCTCCAGCTGTTCACCTT |
| 15 | HK8 | 245 | CCGCTATGTACGTGGGGGATCTCTGCGGATCTGTTTTCCTCGTCTCTCCAGCTGTTCACCTT |
| 12 | HK3 | 245 | CCGCTATGTACGTGGGGGATCTCTGCGGATCTGTTTTCCTtGTCTCTCCAGCTGTTCACCTT |
| 23 | T3 | 245 | CCGCTATGTACGTGGGGGATCTCTGCGGATCTGTTTTCCTCGTCTCTCCAGCTGTTCACTTT |
| 22 | SW2 | 245 | CCGtTATGTACGTGGGGGATCTCTGCGGATCTGTTTTCCTCGTCTCTCCAGCTGTTCACCTT |
| 17 | IND8 | 245 | CCGCTATGTACGTGGGGGATCTCTGCGGATCTGTTTTCCTtGTCTCTCCAGCTGTTCACCTT |
| 16 | IND5 | 245 | CCGCTATGTACGTGGGGGATCTCTGCGGATCTGTTTTCCTCgTCTCTCCAGCTGTTCACCTT |
| 21 | SA10 | 245 | CCGCCATGTACGTGGGGGATCTaTGCGGATCTGTTTTCCTCaTCTCCCAGCTGTTCACCTT |
| 20 | S45 | 245 | CCGCcATGTACGTGGGGGACCTCTGCGGATCTGTTTCCTCGTCTCCCAGCTGTTCACCTT |
| 25 | US6 | 245 | CCGCcATGTACGTGGGGGATCTCTGCGGgTCcGTTTTCCTCGTTCTCTCCAGCTGTTCACCTT |
| 13 | HK4 | 245 | CCGCTATGTACGTGGGaGGAGATCTCTGCGGATCTGTcTTCCTCGTCTCTCCAGtTGTTCACCTT |
| 18 | P10 | 245 | CCGCTATGTACGTGGGGGATCTCTGCGGATCTGTTcTCCTCGTCTCTCCAGCTGTTCACCTT |
| 19 | S9 | 245 | CCGCTATGTACGTGGGGGAcCTgTGCGGATCTGTTcTCCTCaTCTCTCCAGCTGTTCACCaT |
| 9-25 | consensus | | CCGctATGTAcGTGGGgGAtCTcTGCGGaTCTGTtTCCTcgTcTCcCAGCTGTTCACCtT |

FIGURE 1B-6

| SEQ ID NO: | Isolate | | |
|---|---|---|---|
| 11 | DK1 | 306 | tTCaCCTCGCCGCCATGAGACagcaCAGGACTGCAACTGCTCAATCTATCCCGGCCAcgTt |
| 24 | T10 | 306 | CTCGCCTCGCCGCCATGAGACACTtTgCAGGACTGCAACTGCTCAATCTATCCCGGCCAtcTG |
| 10 | D3 | 306 | CTCGCCTCGCCGCCATGAGACAGGACAGTACAGGAaTGTAACTGCTCAATCTATCCCGGCCACGTG |
| 9 | D1 | 306 | CTCGCCTCGCCGCCATGAGAGACAGGACGGTACAGGAGTGTAAtTGCTCAATCTATCCCGGCCACGTG |
| 14 | HK5 | 306 | CTCGCCTCGCCGACACGAGACAGGACGGTACAGGAGTACAGGACTGCAACTGCTCAATCTATCCCGGCCACGTA |
| 15 | HK8 | 306 | CTCGCCTCGCCGACACGAGACAGGACGGTACAGGACGGTACAGGACTGCAACTGCTCAATCTATCCCGGCCACGTA |
| 12 | HK3 | 306 | CTCGCCTCGCCGCCATGAGACAGGACAGTACAGGACTGCAACTGCTCAATCTATCCCGGCCACGTA |
| 23 | T3 | 306 | CTCGCCTCGCCGGCAtGAGACAcGAGACAGTACAGGACAGTACAGGACTGCAAcTGCTCTATCCCGGCCACGTA |
| 22 | SW2 | 306 | tTCACCTCGCCGCCACGAGACAGTACAGGACAGTACAGGACTGCAACTGtTCCATCTATCCCGGCCACGTA |
| 17 | IND8 | 306 | CTCACCGGCGGCCATGAGACATGAGACAGTACAGGACTGCAATTGCTCCATCTATCCCGGCCACGTA |
| 16 | IND5 | 306 | CTCACCGGCGGCCATGAGACATGAGACAGTACAGGACTGCAATTGCTCCATCTATCCCGGCCACGTA |
| 21 | SA10 | 306 | CTCGCCTCGCCGGGtATGAGACAGTACAGGACTGCAATTGCTCAATCTATCCCGGCCACGTA |
| 20 | S45 | 306 | CTCGCCTCGCCGGCCATGAGACAGTACAGGACTGCAAcTGTTCAATCTATCCCGGCCACGTA |
| 25 | US6 | 306 | CTCGCCTCGTCGTCaGACAGTACAGGACAGTACAGGACTGCAATTGTTCAATCTATCCCGGCCACGTA |
| 13 | HK4 | 306 | CTCGCCTCGCCGCCATGAGACAGACGGTACAGTACAGGACTGCAATTGCTCAATCTATCCCGGCCACGTA |
| 18 | P10 | 306 | CTCaCCTCGCCGCCATtgGACAGTACAGGACTGCAATGtTCAATCTATCCtGGCCACGTA |
| 19 | S9 | 306 | CTCgCCcCGtCGGCCATgaGACAGTACAGaACAGTACAGAACTGCAATTGCTCAATCTATCCgGaCACGTg |
| 9-25 | consensus | | cTCgCCtCGcCggcAtgaGACAgtaCAGgAcTGcAAcTGcTCaaTCTATCCCGCCaCgTa |

FIGURE 1B-7

| SEQ ID NO: | Isolate | | |
|---|---|---|---|
| 11 | DK1 | 367 | TCAGGTCACCGCATGGCTTGGAtATGATGATGAACTGGTCaCCTACAACAGCcCTAGTGc------------TGG--- |
| 24 | T10 | 367 | TCAGGTCACCGCATGGCTTGGAcACATGATGATGAACTGGTCGCCTACAACAGCtCTAGTGG--- |
| 10 | D3 | 367 | ACAGGTCACCGCATGGCTTGGATATGATGATGAACTGGTCGCCTACAgCAGCCCTAGTGG--- |
| 9 | D1 | 367 | ACAGGTCACCGtATGGCTTGGATATGATGATGAACTGGTCACCTACAACAGCCtTAGTGG--- |
| 14 | HK5 | 367 | ACAGGTCACCGCATGGCTTGGATATGATGATGAACTGGTCACCTACAACAGCCCTAGTGG--- |
| 15 | HK8 | 367 | ACAGGTCACCGCATGGCTTGGATATGATGATGAACTGGTCgCCCACAACAGCCCTAGTGG--- |
| 12 | HK3 | 367 | TCAGGTCACCGCATGGCTTGGATATGATGATGAACTGGTCgCCCtACAgCAGCCCTAGTGG--- |
| 23 | T3 | 367 | aCAGGTCACCGtATGGCTTGGATATGATGATGAACTGGTCgCCCACAaCgGCaCTAGTGG--- |
| 22 | SW2 | 367 | TCAGGTCACCGCATGGCTTGGAcATGATGATGAACTGGTCACCTACAgCAGCCCTgGTGG--- |
| 17 | IND8 | 367 | TCAGGTCACCGCATGGCTTGGATATGATGATGAACTGGTCACCTACAgCgGCCCTAGTGG--- |
| 16 | IND5 | 367 | TCAGGTCACCGCATGGCCtGGATATGATGATGAACTGGTCACCTACAgCAGCCCTAGTGG--- |
| 21 | SA10 | 367 | ACAGGTCACCGCATGGCTTGGATATGATGATGATGAACTGGTCACCTACAaCAGCtCTAGTaG--- |
| 20 | S45 | 367 | ACAGGTCACCGCATGGCTTGGATATGATGATGATGAACTGGTCgCCTACAgCAGCCtTAGTGG--- |
| 25 | US6 | 367 | TCAGGTCACCGCATGGCTTGGATATGATGATGAAtTGGTCACCTACAgCAG

FIGURE 1B-8

| SEQ ID NO: | Isolate | | |
|---|---|---|---|
| 11 | DK1 | 428 | TaTCGCAGTTACTCCGaATCCCACAAGCTGTCGtGGACATGGTGgCgGGGGCCCACTGGGG |
| 24 | T10 | 428 | TgTCGCAGTTACTCCGGATCCCACAAGCTGTCaTGGACATGGTGaCaGGGGCCCACTGGGG |
| 10 | D3 | 428 | TATCGCAGTTACTCCGGATCCCACAAGCTGTCgTGGACATGGTGGCGGGGGCCCACTGGGG |
| 9 | D1 | 428 | TATCGCAGTTACTCCGGATCCCACAAGCTGTCaTGGACATGGTGCGGGGGCCCACTGGGG |
| 14 | HK5 | 428 | TGTCGCAGTTACTCCGGATCCCGCAAGCTGTCGTGGACATGGTGCGGGGGCCCACTGGGG |
| 15 | HK8 | 428 | TGTCGCAGTTACTCCGGATCCCGCAAGCTaTCGTGGACATGGTGCGGGGGCCCACTGGGG |
| 12 | HK3 | 428 | TGTCGCAaTTACTCCGGATCCCGCAAGCTGTCGTGGACATGGTGCGGGGGCCCACTGGGG |
| 23 | T3 | 428 | TGTCGCAGTTgCTCCGGATCCCACAAGCTGTCGTGGACATGGTGCGGGGGCCCACTGGGG |
| 22 | SW2 | 428 | TATCGCAGTTaCTCCGGATCCCACAAGCTGTCGTGGACATGGTaGCGGGGGCCCACTGGGG |
| 17 | IND8 | 428 | TATCGCAGTTGCTCCGGATCCCACAAGCTGTCGTGGATATGGTGCGGGGGCCCACTGGGG |
| 16 | IND5 | 428 | TATCGCAGTTGCTCCGGATCCCACAAGCTGTCGTGGATATGGTGCGGGGGCCCACTGGGG |
| 21 | SA10 | 428 | TATCGCAGTTACTCCGGATCCCACAAGCTaTCGTGGACATGGTGCGGGGGCCCACTGGGG |
| 20 | S45 | 428 | TATCGCAGTTACTCCGGATCCCACAAGCTaTCGTGGACATGGTGCGGGGGCCCACTGGGG |
| 25 | US6 | 428 | TATCGCAGTTACTCCGGATCCCACAAGCTGTCATGGACATGGTGCGGGGGCCCACTGGGG |
| 13 | HK4 | 428 | TATCGCAGCTACTCCGGATCCCACAAGCTGTCATGGACATGGTGCGGGaGCCCACTGGGG |
| 18 | P10 | 428 | TgTCGCAGCTACTCCGGATCCCACAAGCTaTCtTGGATgTGGTGCGGGGGCCCACTGGGG |
| 19 | S9 | 428 | TaTCGCAGCTACTCCGGATCCCACAAGCTgTCaTGGATaTGGTGGCGGGGGCCCACTGGGG |
| 9-25 | consensus | | TaTCGCAgTTaCTCCGgaTCCCaCAAGCTgTCgTGGAcaTGGTggCgGGgGCCCACTGGGG |

FIGURE 1B-9

| SEQ ID NO: | Isolate | | |
|---|---|---|---|
| 11 | DK1 | 489 | AGTCCTGGGCGGGCCTcGCCTACTAcTCCATGGCGGGGAACTGGGCcAAGGTTTTAATTGTG |
| 24 | T10 | 489 | AGTCCTGGGCGGGCCTtGCCTATTCCATGGCGGGGAACTGGGCTAAGGTTTTAATTGTG |
| 10 | D3 | 489 | GGTCCTGGGCGGGCCTCGCCTACTATTCCATGGTGGGGAACTGGGCTAAGGTTTTGATTGTG |
| 9 | D1 | 489 | GGTCCTGGGCGGGCCTCGCCTACTATTCCATGGTGGGGAACTGGGCTAAGGTTTTGATTGTG |
| 14 | HK5 | 489 | GGTCCTGGGCGGGCCTTGCCTATTCCATGGTGGGaAACTGGGCTAAGGTTTTGATTGTG |
| 15 | HK8 | 489 | AGTCCTAGCGGGCCTTGCCTATTCCATGGTGGGCAACTGGGCTAAGGTTTTGATTGTG |
| 12 | HK3 | 489 | AGTCCTAGCGGGCCTTGCCTATTCCATGGTGGGaAAACTGGGCTAAGGTTTTGATTGTG |
| 23 | T3 | 489 | AGTCCTGGGCGGGCCTTGCCTATTCCATGGTGGGGAACTGGGCTAAGGTTTTGATTGTG |
| 22 | SW2 | 489 | AGTCCTGGGCGGGCCTTGCaTACTATTCCATGGTGGGGAACTGGGCTAAGGTTTTGATTGTG |
| 17 | IND8 | 489 | AATCCTGGGCGGGCCTTGCCTATTCCATGGTAGGGAACTGGGCTAAGGTTTTGATTGTG |
| 16 | IND5 | 489 | AATCCTGGGCGGGCCTTGCCTATTCCATGGTAGGGAACTGGGCTAAGGTTTTGATTGTG |
| 21 | SA10 | 489 | AGTCCTaGCGGGCCTTGCtTACTATTCCATGGTGGGGAACTGGGCTAAGGTTTTGATTGTt |
| 20 | S45 | 489 | AGTCCTGGGCGGGCCTTGCCTATTCCATGGTGGGGAACTGGGCTAAGGTTCTGATTGTG |
| 25 | US6 | 489 | AGTCCTGGGCGGGCCTTGCCTATTCCATGGTGGGGAACTGGGCTAAGGTTCTGATTGTG |
| 13 | HK4 | 489 | AGTCCTaGCGGGCCTTGCCTATTCCATGGTGGGGAACTGGGCcAAGGTTTTGATTGTG |
| 18 | P10 | 489 | AGTCCTGGGCGGGCCTTGCCTATTCCATGGTGGGGAACTGGGCTAAGGTcTTGATTGTG |
| 19 | S9 | 489 | AGTCCTGGGCGGGCCTcGCCTACTATTCCATGGTGGGGAACTGGGCtAAGGTtTTGATTGTG |
| 9-25 | consensus | | agTCCTgGGCGGGCCTtGCCTACTAtTCCATGgtGGGaACTGGGCtAAGGTttTgATTGTg |

FIGURE 1B-10

| SEQ ID NO: | Isolate | | |
|---|---|---|---|
| 11 | DK1 | 550 | tTGCTACTCTTTGCCGGCGTTGATGGG |
| 24 | T10 | 550 | ATGCTACTCTTTGCCGGCGTTGATGGG |
| 10 | D3 | 550 | ATGCTACTCTTTGCTGGCGTCGACGGC |
| 9 | D1 | 550 | ATGCTACTCTTTGCTGGCGTTGACGGC |
| 14 | HK5 | 550 | ATGCTACTtTTTGCCGGCGTTGATGGG |
| 15 | HK8 | 550 | ATGCTACTgTTTGCCGGCGTTGATGGG |
| 12 | HK3 | 550 | ATGCTACTtTTTGCCGGCGTTGATGGG |
| 23 | T3 | 550 | cTGCTACTCTTTGCCGGCGTTGATGGG |
| 22 | SW2 | 550 | ATGCTACTCTTTGCtGGCGTTGACGGG |
| 17 | IND8 | 550 | ATGCTACTCTTTGCCGGCGTTGACGGG |
| 16 | IND5 | 550 | ATGCTACTCTTTGCCGGCGTTGACGGG |
| 21 | SA10 | 550 | ATGCTACTCTTTGCCGGCGTTGACGGG |
| 20 | S45 | 550 | ATGCTACTCTTTGCCGGCGTTGACGGG |
| 25 | US6 | 550 | tTGCTACTCTTTGCCGGCGTTGACGGG |
| 13 | HK4 | 550 | ATGCTACTCTTTGCCGGCGTTGACGGG |
| 18 | P10 | 550 | ATGCTACTCTTTGCCGGCGTTGACGGa |
| 19 | S9 | 550 | ATGCTACTtTTTGCtGGtGTTGACGGg |
| 9-25 | consensus | | aTGCTACTcTTTGCcGGcGTtGAcGGg |

FIGURE 1C-1

```
SEQ ID NO:  Isolate
    26        T2    1  GCcCAAGTGAgGAACACCAgccgCgGtTACATGGTGACtAACGACTGTTCcAATGAGAGCA
    27        T4    1  GCaCAAGTGAAGAAGAACACCACTAaCAGCTACATGGTGACcAACGACTGTTCtAATGACAGCA
    28        T9    1  GCCgAAGTGAAGAAGAACACCAGCTACCAGCTACATGGTGACaAATGACTGTTCCAACGACAGCA
    29       US10   1  GtCcAAGTGAAaAAACACCAGTACCAGCTAtATGGTGACcAATGACTGcTCCAACGACAGCA
  26-29  consensus     GcccAAGTGAagAACACCAgtacCaGcTAcATGGTGACcAA-GACTGtTCcAA-GAcAGCA SEQ ID NO:  Isolate
    26        T2   62  TCACcCTGGCAGCTCCAaGCCGCGGTcCTCCACGTCCCCGGGTGTaTCCCGTGtGAGAggct
    27        T4   62  TCACtTGGCAGCTCCAGGCCGCGGTCCTCCACGTCCCCGGGTGTGTCCCGTGCGAGAaAac
    28        T9   62  TCACcCTGGCAACTCCAGGCCGCGGTCCTCCACGTCCCCGGGTGcGTCCCCGTGCGAGAGAGT
    29       US10  62  TCACtTGGCAACTtgAGGGCtGCGGTCCTCCACGTtCCCGGGTGtGTCCCGTGCGAGAaAGT
  26-29  consensus     TCAC-TGGCA-CTccAgGCcGCGGTcCTCCACGTcCCCGGGTGtgTCCCGTGCGAGA-agt SEQ ID NO:  Isolate
    26        T2  123  GGGAAATACATCCcGaTGCTGGATACCGGTcaCACCAAACGTGGCCGTGCGGCAGCCCGGC
    27        T4  123  GGGAAATACATCtCGGTGCTGGATACCGGTGCTGCACCAAACGTGGCCGTGCGGCAGCCCGGC
    28        T9  123  tGGAAAcgCgTCgCGGTGCTGGATACCGGTCTCgCCAAACGTCTCgCCAAACGTGGCCGTGCGGCCTGGC
    29       US10 123  gGGAAAtaCaTCtCGGTGCTGGATACCGGTCTCCaCCAAAtGTgGCCgTGCGGCAGCCCTGGC
  26-29  consensus     gGGAAAtaCaTCtCGgTGCTGGATACCGGTctCaCCAAAcGTgGCcGTGC-GC-GCC-GGC
```

FIGURE 1C-2

| SEQ ID NO: | Isolate | | |
|---|---|---|---|
| 26 | T2 | 184 | GCtCTtACGCAGGGCTTGCGGACGCACATcGACATGGTTGTGATGTCCGCCACGCTCTGCT |
| 27 | T4 | 184 | GCCCTCACGCAGGGCTTGCGGACGCACACATtGACATGGTTGTGATGTCCGCCACGCTCTGCT |
| 28 | T9 | 184 | GCCCTCACGCAGGGCTTGCGGACGCACATCGACATGGTTGTGATGTCCGCCACGCTCTGCT |
| 29 | US10 | 184 | GCCCTCACGCAGGGCTTGCGGActCACATCGACATGGTcGTGATGTCCGCCACGCTCTGCT |
| 26-29 | consensus | | GCcCTcACGCAGGGCTTGCGGACgCACATcGACATGGTtGTGATGTCCGCCACGCTCTGCT |

| SEQ ID NO: | Isolate | | |
|---|---|---|---|
| 26 | T2 | 245 | CTGCcCTcTACGTGGGGACCCTCGCGGCGGGTGATGCTCGCAGCCCAGATGTTCATtGT |
| 27 | T4 | 245 | CTGCTCTtTACGTGGGGACCCTCGCGGCGGGTGATGCTCGCAGCCCAGATGTTCATcGT |
| 28 | T9 | 245 | CCGCTCTcTACGTGGGGAtCTCTCGCGGCGGGTaATGCTCGCcGCtCAGATGTTCATTaT |
| 29 | US10 | 245 | CCGCTCTtTACGTGGGGActTCTGCGGtGGGaTgATGCTCGCaGCcCAaATGTTCATTgT |
| 26-29 | consensus | | C-GCtCT-TACGTGGGGAccTCTGCGGcGGGgTgATGCTCGCaGCcCAGATGTTCATtgT |

| SEQ ID NO: | Isolate | | |
|---|---|---|---|
| 26 | T2 | 306 | CTCGCCGCgaACgcCACTGGTTTGTGCAAGAaTGCAATTGCTCcATCTACCCcGGtACCATC |
| 27 | T4 | 306 | CTCGCCGCAACAtCACTGGTTTGTGCAAGAcTGCAATTGCTCtATCTACCCTGGcACCATC |
| 28 | T9 | 306 | CTCGCCGCAgCACCACTGGTTTGTGCAGGAATGCAACTGCTCCATtTACCCTGGTACCATC |
| 29 | US10 | 306 | CTCGCCGCgcCACCACTCGTTTGTGCAGGAATGCAACTGCTCCATcTACCCcGGTACCATC |
| 26-29 | consensus | | CTCGCCGC-aCacCACTgGTTTGTGCA-GAaTGCAA-TGCTCcATcTACCC-GGtACCATC |

FIGURE 1C-3

| SEQ ID NO: | Isolate | | |
|---|---|---|---|
| 26 | T2 | 367 | ACTGGaCACCGTATGGCATGGACATGATGATGAACTGGTCGCCCACaGCCACCATGATCC |
| 27 | T4 | 367 | ACTGGaCACCGTATGGCATGGAtATGATGATGAACTGGTCGCCCACgGCCACCATGATCC |
| 28 | T9 | 367 | ACTGGaCACCGTATGGCATGGACATGATGATGAACTGGTCGCCCACaaCCACCATGATCt |
| 29 | US10 | 367 | ACcGGgCACCGTATGGCATGGACATGATGATGAACTGGTCGCCCACggCCACttTGATCc |
| 26-29 | consensus | | ACtGGaCACCGTATGGCATGGACATGATGATGAACTGGTCGCCCAC-gCCACcaTGATCc |

| SEQ ID NO: | Isolate | | |
|---|---|---|---|
| 26 | T2 | 428 | TGGCGTACgCGATGCGCGTTCCCGAGGTCATCaTAGACATCaTcgGCGGGGCtCACTGGGG |
| 27 | T4 | 428 | TGGCGTACgCGATGCGCGTTCCCGAGGTCATCaTCtTAGACATCgTtAGCGGGGCaCACTGGGG |
| 28 | T9 | 428 | TGGCGTACgCGATGCGCGTTCCCGAGGTCATCATAGACATCATCAGCGGaGCtCACTGGGG |
| 29 | US10 | 428 | TGGCGTACgtGATGCGCGTTCCCGAGGTCATCATAGACATCATtAGCGGGgGCgCAtTGGGG |
| 26-29 | consensus | | TGGCGTACgCGATGCGCGTTCCCGAGGTCATCATAGACATCaT-aGCGGgGCtCACTGGGG |

| SEQ ID NO: | Isolate | | |
|---|---|---|---|
| 26 | T2 | 489 | CGTCATGTTtGGCTTGGCCTACTTCTCTATGCAGGGAGCGTGGGCGAAgTCATTGTCATC |
| 27 | T4 | 489 | CGTCATGTTcGGCTTGGCCTACTTCTCTATGCAGGGAGCGTGGGCGAAaGTCGTTGTCATC |
| 28 | T9 | 489 | CGTCATGTTcGGCcTAGCCTACTTCTCTATGCAGGGAGCGTGGGCGAAgGTCGTTGTCATC |
| 29 | US10 | 489 | CGTCtTGTTcGGCtTAGCCTACTTCTCTATGCAGGGAGCGTGGGCGAAaGTCGTTGTCATC |
| 26-29 | consensus | | CGTCaTGTTcGGCtT-GCCTACTTCTCTATGCAgGGAGCGTGGGCGAA-GTCgTTGTCATC |

FIGURE 1C-4

| SEQ ID NO: | Isolate | | |
|---|---|---|---|
| 26 | T2 | 550 | CTctTGCTGGCtGCTGGGGTGGACGCG------------ |
| 27 | T4 | 550 | CTtcTGCTGGCCCGCTGGGGTGGACGCG------------ |
| 28 | T9 | 550 | CTgtTGCTcaCCGCTGGcGTGGACGCG------------ |
| 29 | US10 | 550 | CTtcTGCTagCCGCTGGgGTGGACGCG------------ |
| 26-29 | consensus | | CTt-TGCTggCcGCTGGgGTGGACGCG |

FIGURE 1D-1

| SEQ ID NO: | Isolate | | |
|---|---|---|---|
| 33 | T8 | 1 | GTGGAAGTtAGaAaACAccCAGTTttAGCTACTACGCCACCAATGATTGCTCgAACAACAGCA |
| 30 | DK8 | 1 | GTGGAAGTCAGGAACATCAGTTCcAGCTACTACGCCACCAATGATTGCTCAAACAACAGCA |
| 32 | SW3 | 1 | GTGGAAGTCAGGAACATCAGTTCTAGCTACTACTAtGCCACCAATGATTGCTCAAACAgCAGCA |
| 31 | DK11 | 1 | GTGGAAGTCAGGAACAcCAGTTCTAGTTACTACGCCACCAATGATTGCTCAAACAaCAGCA |
| 30-33 | consensus | | GTGGAAGTCAGgAACA-CAGTTctAGcTACTACGCCACCAATGATTGCTCaAACAcAGCA |

| SEQ ID NO: | Isolate | | |
|---|---|---|---|
| 33 | T8 | 62 | TCACCTGGCAgCTCACCaACGCAGTTCTCCACCTTCCCGATGCGTCCCATGTGAGAATGA |
| 30 | DK8 | 62 | TCACCTGGCAACTCACCgACGCAGTTCTCCACCTTCCCGATGCGTCCCATGTGAGAATGA |
| 32 | SW3 | 62 | TCACCTGGCAACTCACCAACGCAGTcCTCCACCTTCCCGATGCGTCCCGTGTGAGAATGA |
| 31 | DK11 | 62 | TCACCTGGCAACTCACCAACGCAGTtCTCCACCTTCCCGATGCGTCCCaTGTGAGAATGA |
| 30-33 | consensus | | TCACCTGGCAaCTCACCACGCAGTtCTCCACCTTCCCGATGCGTCCCATGTGAGAATGA |

| SEQ ID NO: | Isolate | | |
|---|---|---|---|
| 33 | T8 | 123 | CAATGGCACCCtTGCGCTGCTGGATACAAGTaACACCTAATGTGGCTGTGAAACACCGtGGC |
| 30 | DK8 | 123 | CAATGGCACCCTGCGCTGCTGGATACAAGTGACACCTAATGTGGCTGTGAAACACCGCGGC |
| 32 | SW3 | 123 | tAATGGCACCCTGCACTGCTGGATACAAGTGACACCTAATGTGGCTGTGAAACACCGCGGC |
| 31 | DK11 | 123 | cAATGGCACCCTGCACTGCTGGATACAAGTGACACCTAATGTGGCTGTGAAACACCGCGGC |
| 30-33 | consensus | | cAATGGCACCcTGC-CTGCTGGATACAAGTgACACCTAATGTGGCTGTGAAACACCGcGGC |

FIGURE 1D-2

```
SEQ ID NO:   Isolate
    33         T8      184 GCACTcACTCAcAAACCTGCGAACgCAtGTCGACGTGATCGTAATGGCAGCTACGGTCTGCT
    30         DK8     184 GCACTtACTCAtAAACCTGCGAACACACACGTCGACGTGATCGTAATGGCAGCTACGGTCTGCT
    32         SW3     184 GCgCTCACTCACAAACCTGCGAGCACACACGTCGATATGATCGTAATGGCAGCTACGGTCTGCT
    31         DK11    184 GCaCTTCACTCACAAACCTGCGAGCACACATaTaGATATGATtGTAATGGCAGCTACGGTCTGCT
  30-33     consensus      GCaCTcACTCAcAAACCTGCGA-CaCA-gTcGA--TGATcGTAATGGCAGCTACGGTCTGCT SEQ ID NO:   Isolate
    33         T8      245 CGGCCTTGTATGTGGGgGACGTgTGCGGGGCCCGTGATGATAGcGTCGCAGGCTtTCATAAT
    30         DK8     245 CGGCCTTGTATGTGGGAGACGTaTGCGGGGCCCGTGATGATCGTGTCGCAGGCTcTCATAAT
    32         SW3     245 CGGCCTTGTATGTGGGAGACaTGTGCGGGGCCCGTGATGATCGTGTCGCAGGCTTTCATAAT
    31         DK11    245 CGGCCTTGTATGTGGGAGACgTGTGCGGGGCCCGTGATGATCGTGTCGCAGGCTTTCATAgT
  30-33     consensus      CGGCCTTGTATGTGGGaGACgTgTGCGGGGCCCGTGATGATcGtGTCGCAGGCTtTCATAAT SEQ ID NO:   Isolate
    33         T8      306 ATCGCCaGAAACGCCACAACTTcACCCAGGAGTGCAACTGTTCCATCTACCAAGGTCATATC
    30         DK8     306 ATCGCCtGAAACGCCACAACTTTACCCAGGAGTGCAACTGTTCCATCTACCAAGGTCATATC
    32         SW3     306 ATCGCCAGAAACGCCACAACTTTACCCAAGAGTGCAACTGTTCCATCTACCAAGGTCgTATC
    31         DK11    306 ATCGCCAGAAACaCCACCACTTTACCCAAGAGTGCAACTGTTCCATCTACCAAGGTCacATC
  30-33     consensus      ATCGCCaGAAACgCCACaACTTtACCCA-GAGTGCAACTGTTCCATCTACCAAGGTCatATC
```

FIGURE 1D-3

| SEQ ID NO: | Isolate | | |
|---|---|---|---|
| 33 | T8 | 367 | ACCGGCCACCGCATGGACATGATGCTgAAACTGGTCACCAACTCTcACCATGATCC |
| 30 | DK8 | 367 | ACCGGCCACCGCATGGACATGATGCTAAACTGGTCACCAACTCTTACCATGATCC |
| 32 | SW3 | 367 | ACCGGCCACCGCATGGCGtGGGACATGATGCTAAACTGGTCACCAACTCTTACCATGATCC |
| 31 | DK11 | 367 | ACCGGCCACCGCATGGCaTGGGACATGATGCTtAACTGGTCACCAACTCTcACCATGATCC |
| 30-33 | consensus | | ACCGGCCACCGCATGGCaTGGGACATGATGCTaAACTGGTCACCAACTCT-ACCATGATCC |

| SEQ ID NO: | Isolate | | |
|---|---|---|---|
| 33 | T8 | 428 | TCGCCTACgCtGCTCGTGTgCCTGAacTAGtCCTtgAaGTTGTCTTCGGCGGCCATTGGGG |
| 30 | DK8 | 428 | TCGCCTATGCCGCTCGTGTTCCTGAGCCCTcCAgTTGTCTTCGGCGGCCATTGGGG |
| 32 | SW3 | 428 | TCGCCTATGCCGCTCGTGTTCCTGAGCTAGCCCTcCAgTTGTCTTCGGCGGCCATTGGGG |
| 31 | DK11 | 428 | TtGCCTATGCCGCTCGTGTTCCTGAGCTAGTCCTTGAAGTTGTCTTCGGCGGCCATTGGGG |
| 30-33 | consensus | | TcGCCTAtGCcGCtCGTGTcCCTGAgCTAGtCCTgAaGTtGTCTTCGGcGGcCATTGGGG |

| SEQ ID NO: | Isolate | | |
|---|---|---|---|
| 33 | T8 | 489 | CGTGGTGTTTGGCTTGGCCTATTTCTCCATGCAaGGAGCGTGGGCCAAAGTCATcGCCATC |
| 30 | DK8 | 489 | CGTGGTGTTTGGCTTGGCCTATTTCTCCATGCAgGGAGCGTGGGCCAAAGTCATTGCCATC |
| 32 | SW3 | 489 | CGTGGTGTTTGGCTTGGCCTATTTCTCCATGCAaGGAGCGTGGGCCAAGGTCATTGCCATC |
| 31 | DK11 | 489 | CGTGGTGTTTGGCTTGGCCTATTTCTCCATGCAgGGAGCGTGGGCCAAGGTCATTGCCATC |
| 30-33 | consensus | | cGTGGtGTTtGGCTTGGCCTATTTCTCCATGCA-GGAGCGTGGGCCAA-GTCAttGCCATC |

FIGURE 1D-4

| SEQ ID NO: | Isolate | | |
|---|---|---|---|
| 33 | T8 | 550 | CTCCTcCTTGTCGCAGGAGTGGAcGCA |
| 30 | DK8 | 550 | CTCCTtCTTGTCGCAGGAGTGGATGCA |
| 32 | SW3 | 550 | CTCCTgCTTGTCGCAGGAGTGGATGCA |
| 31 | DK11 | 550 | CTCCTtCTTGTaGCAGGAGTGGATGCA |
| 30-33 | consensus | | CTCCTtCTTGTCGCAGGAGTGGAtGCA |

FIGURE 1E-1

| SEQ ID NO: | Isolate | | |
|---|---|---|---|
| 35 | DK12 | 1 | tTAGAGTGGCGGAATGTGTCcGGCCTCTAcGTCCTTACCAACGACTGTtCCAATAGCAGTA |
| 36 | HK10 | 1 | CTAGAGTGGCGGAATGTGTCTGGCCCTCTATGTCCTTACCAACGACTGTtCCAATAGCAGTA |
| 37 | S2 | 1 | CTAGAGTGGCGGAATACGTCTGGCCCTCTATGTCCTcACCAACGACTGTTCCAATAGCAGTA |
| 39 | S54 | 1 | CTAGAGTGGCGGAATACGTCTGGCCCTCTATaTCCTTACCAACGACTGTtCCAATAGCAGTA |
| 38 | S52 | 1 | CTAGAGTGGCGGAATACGTCTGGCCCTCTATGtCCTTACCAACGACTGTtCCAATAGCAGTA |
| 35-39 | consensus | | cTAGAGTGGCGGAATAcGTCtGGCCTCTATgTCCTtACCAACGACTGTtCCAATAGCAGTA |

| SEQ ID NO: | Isolate | | |
|---|---|---|---|
| 35 | DK12 | 62 | TcGTGTATGAGGCCGATGACGTCATTCTGCACACACCTGGCTGTGTACCTTGTGTTCAGGA |
| 36 | HK10 | 62 | TTGTGTATGAGGCCGATGACGTCATTCTGCACACACCTGGCTGTGTACCTTGTGTTCAGGA |
| 37 | S2 | 62 | TTGTGTATGAGGCCGATGACGTtATTCTGCACACACCTGGCTGTGTACCTTGTGTTCAGGA |
| 39 | S54 | 62 | TTGTGTATGAGGCCGATGACGTCATTCTGCACACACCCGGCTGTGTACCTTGTGTTCAGGA |
| 38 | S52 | 62 | TTGTGTATGAGGCCGATGACGTCATTCTGCACACACCCGGCTGTGTACCTTGTGTTCAGGA |
| 35-39 | consensus | | TtGTGTATGAGGCCGATGACGTcATTCTGCACACCtGGCTGTGTACCTTGTGTTCAGGA |

FIGURE 1E-2

| SEQ ID NO: | Isolate | | |
|---|---|---|---|
| 35 | DK12 | 123 | CGGCAATACATCtACGTGCTGGACCTCaGTGACgCCTACAGTGGCAGTCAGGTACGTCGGA |
| 36 | HK10 | 123 | CGGCAATACATCCACGTGCTGGACCTGACCTCgGTGACACCTACAGTGGCAGTCAGGTACGTCGGA |
| 37 | S2 | 123 | CGGtAATACATCCACGTGCTGGACCTGGACCCCAGTGACACCTACAGTGGCAGTCAGGTATGTCGGA |
| 39 | S54 | 123 | CGGCAATACATCCACGTGCTGGACCCCAGTGACACCTACGGTGGCAGTCAGGTACGTCGGA |
| 38 | S52 | 123 | CGGCAATACATCCAtGTGCTGGACCCCAGTGACACCTACGGTGGCAGTCAGGTACGTCGGA |
| 35-39 | consensus | | CGGcAATACATCcAcGTGCTGGACCCcAgTGACaCCTACaGTGGCAGTCAGGTACGTCGGA |

| SEQ ID NO: | Isolate | | |
|---|---|---|---|
| 35 | DK12 | 184 | GCAACCACCGCTtCGATACGCAGTCATGTGGACCTGcTAGTGGGCGGCCACGATGTGCT |
| 36 | HK10 | 184 | GCAACCACCGCcTCGATACGCAGTCAGTCATGTGGACCTGTTAGTGGGCGCGCCACGATGTGCT |
| 37 | S2 | 184 | GCAACCACCGCTTCGATACGCAGTCAGTCATGTGGACCTATTgGTGGGCGCGGCCACtATGTGCT |
| 39 | S54 | 184 | GCAACCACCGCTTCGATACGCAGTCAGTCATGTGGACCTATTAGTGGGCGGCCACGCTGTGCT |
| 38 | S52 | 184 | GCAACCACCGCTTCGATACGCAGTCAGTCATGTGGACCTATTAGTGGGCGGCCACGCTGTGCT |
| 35-39 | consensus | | GCAACCACCGCTTCGATACGCAGTCAGTCATGTGGACCTatTAgTGGGCGGCCACGaTGTGCT |

FIGURE 1E-3

| SEQ ID NO: | Isolate | | |
|---|---|---|---|
| 35 | DK12 | 245 | CTGCGCTCTACGTGGGtGATgTGTGTGGGGCCGTCTTCCTgTGTGGGACAAGCCTTCACGTT |
| 36 | HK10 | 245 | CTGCGCTCTACGTGGGCgATATGTGTGGGGCCGTCTCTTCCTGTGGGACAAGCCTTCACGTT |
| 37 | S2 | 245 | CTGCGCTCTACGTGGGTGGGTGATATGTGTGGGGCCGTCTTTCTCGTGGGACAAGCCTTCACGTT |
| 39 | S54 | 245 | CTGCGCTCTCTATGTGGGTGATATGTGTGGGGCCGTCTTTTCTCGTGGGACAAGCCTTCACGTT |
| 38 | S52 | 245 | CTGCGCTCTCTATGTGGGTGATATGTGTGGGGCCGTCTCTTTCTCGTGGGACAAGCCTTCACGTT |
| 35-39 | consensus | | CTGCGCTCTACgTGGGtGATaTGTGTGTGGGGCCGTCTCTTtCTcGTGGGACAAGCCTTCACGTT |

| SEQ ID NO: | Isolate | | |
|---|---|---|---|
| 35 | DK12 | 306 | CAGACCTCGTCGCCATCAAACaGTCCAGACCTGTAACTGCTCGCTGTACCCAGGCCAtCTT |
| 36 | HK10 | 306 | CAGACCgCGTCGCCATCAAACGGTCCAGACCTGTAACTGCTCGCTGTACCCAGGCCAcCTT |
| 37 | S2 | 306 | CAGACCTCGTCGCCATCAAACGGTCCAGACCTGTAACTGCTCGCTGTACCCAGGCCATCTT |
| 39 | S54 | 306 | CAGACCTCGTCGCCATCAAACGGTCCAGACCTGTAACTGCTCGCTGTACCCAGGCCATCTT |
| 38 | S52 | 306 | CAGACCTCGTCGCCATCAAACGGTCCAGACCTGTAACTGCTCGCTGTACCCAGGCCATgTT |
| 35-39 | consensus | | CAGACCtCGTCGCCATCAAACgGTCCAGACCTGTAACTGCTCGCTGTACCCAGGCCAtcTT |

FIGURE 1E-4

| SEQ ID NO: | Isolate | | |
|---|---|---|---|
| 35 | DK12 | 367 | TCAGGACATCGAATGGCTTGGGATATGATGATGATGAATTGGTCCCCGCtGTGGGTATGGTGG |
| 36 | HK10 | 367 | TCAGGACATCGAATGGCTTGGGATATGATGATGATGAATTGGTCCCCGCcGTGGGTATGGTGG |
| 37 | S2 | 367 | TCAGGACATCGcATGGCTTGGGATATGATGATGATGAATTGGTCCCCGCTGTGGGTATGGTGG |
| 39 | S54 | 367 | TCAGGACATCGAATGGCTTGGGATATGATGATGATGAATTGGTCCCCGCTGTGGGTATGGTGG |
| 38 | S52 | 367 | TCAGGACATCGAATGGCTTGGGATATGATGATGATGAATTGGTCCCCGCTGTGGGTATGGTGG |
| 35-39 | consensus | | TCAGGACATCGaATGGCTTGGGATATGATGATGATGAATTGGTCCCCGCtGTGGGTATGGTGG |

| SEQ ID NO: | Isolate | | |
|---|---|---|---|
| 35 | DK12 | 428 | TaGCGCACGTCCTGCGtcTGCCCCAGACCTTGTTCGACATAATAGCtGGGGCCCATTGGGG |
| 36 | HK10 | 428 | TGGCGCACGTCCTGCGgTTGCCCCAGACCTTGTTCGACATAATAGCCGGGGCCCATTGGGG |
| 37 | S2 | 428 | TGGCGCACGTtCTGCGtTTGCCCCAGACCTTGTTCGACATAATAGCCGGGGCCCATTGGGG |
| 39 | S54 | 428 | TGGCGCACATCCTGCGATTGCCCCAGACCgTGTTCGACATACTGGCCGGGGCCCATTGGGG |
| 38 | S52 | 428 | TGGCGCACATCCTGCGATTGCCCCAGACCTTGTTTGACATACTGGCCGGGGCCCATTGGGG |
| 35-39 | consensus | | TgGCGCACgTcCTGCG-tTGCCCCAGACCtTGTTcGACATAaTaGCcGGGGCCCATTGGGG |

FIGURE 1E-5

| SEQ ID NO: | Isolate | | |
|---|---|---|---|
| 35 | DK12 | 489 | CATCaTGGCgGGGCCTAGCCTATTACTCCATGCAGGGCAACTGGGCCAAGGTCGCTATCATC |
| 36 | HK10 | 489 | CATCTTGGCCaGGCCTAGCCTATTACTCCATGCAGGGCAACTGGGCCAAGGTCGCTATCATC |
| 37 | S2 | 489 | CATCTTGGCCGGGCCTAGCCTATTACTCCATGCAaGGGCAACTGGGCCAAGGTCGCTATCATC |
| 39 | S54 | 489 | CATCTTGGCGGGGCCTAGCCTATTATTCTATGCAGGGCAACTGGGCCAAGGTCGCTATCATC |
| 38 | S52 | 489 | CATCTTGGCGGGGCCTAGCCTATTATTCTATGCAGGGCAACTGGGCCAAGGTCGCTATtgTC |
| 35-39 | consensus | | CATCtTGGCggGGCCTAGCCTATTACTCcATGCAggGCAACTGGGCCAAGGTCGCTATcaTC |

| SEQ ID NO: | Isolate | | |
|---|---|---|---|
| 35 | DK12 | 550 | ATGGTTATGTTTTCAGGaGTCGATGCC |
| 36 | HK10 | 550 | ATGGTTATGTTTTCAGGGGTCGATGCC |
| 37 | S2 | 550 | ATGGTTATGTTTTCAGGGGTCGAcGCC |
| 39 | S54 | 550 | ATGATTATGTTTTCAGGGGTCGATGCC |
| 38 | S52 | 550 | ATGATTATGTTTTCAGGGGTCGATGCC |
| 35-39 | consensus | | ATGgTTATGTTTTCAGGggTCGAtGCC |

FIGURE 1F-1

```
SEQ ID NO:      Isolate
    43             Z7      1   GTcAACTATCaCAATGCCTCGGGCGTCTATCACATCACCAACGACTGCCCGAACTCGAGCA
    42             Z6      1   GTtAACTATCGCAATGCCTCGGGCGTCTATCACGTCACCAACGACTGCCCGAACTCGAGCA
  42-43 consensus (Z6)         GTtAACTATCGCAATGCCTCGGGCGTCTATCACgTCACCAACGACTGCCCGAACTCGAGCA SEQ ID NO:      Isolate
    43             Z7      62  TAaTGTATGAGGCCGAACACCACATCCTACACCTCCCAGGGTGCGTACCCTGTGTGAGGGa
    42             Z6      62  TAGTGTATGAGGCCGAACACCACCAGATCTTACACCTCCCAGGGTGCTTGCCCTGTGTGAGGGt
  42-43 consensus (Z6)         TAgTGTATGAGGCCGAACACCACCAGATCtTACACCTCCCAGGGTGCTTGCCCTGTGTGAGGGt SEQ ID NO:      Isolate
    43             Z7     123  gGGGAACCAGTCACGCTGCTGGGCTGGGCCCCTTACTCCCACCGTGGGCGGCGCTTATATCGGT
    42             Z6     123  tGGGAAtCAGTCACGCTGCTGGGCTGGGCCCCTTACTCCCACCGTGGCGGtGtCTTATATCGGT
  42-43 consensus (Z6)         tGGGAAtCAGTCACGCTGCTGGGCTGGGCCCCTTACTCCCACCGTGGCGGtGtCTTATATCGGT SEQ ID NO:      Isolate
    43             Z7     184  GCaCCGCTTGAaTCCaTCCGGAGACATGTGGACCTGATGGTAGGCGCTgCTACaGTGTGCT
    42             Z6     184  GCTCCGCTTGAcTCCcTCCGGAGACATGTGGACCTGATGGTGGGCGCCGCTACTGTaTGCT
  42-43 consensus (Z6)         GCtCCGCTTGAcTCCcTCCGGAGACATGTGGACCTGATGGTgGGCGCCGCTACTGTaTGCT SEQ ID NO:      Isolate
    43             Z7     245  CcGCtCTCTACaTTGGGGACCTGTGCGGTGGCGtATTtTTGGTTGGtCAGATGTTtTCTTT
    42             Z6     245  CtGCCCTCTACgTTGGaGAtCTGTGCGGTGCATTCTTGGTTGGCCAGATGTTCTCCTT
  42-43 consensus (Z6)         CtGCCCTCTACgTTGGtGCATTCTTGGTTGGCCAGATGTTCTCCTT
```

FIGURE 1F-2

| SEQ ID NO: | Isolate | | |
|---|---|---|---|
| 43 | Z7 | 306 | CCAGCCGCGACGCCACTGGACTACGCAGGACTGCAATTGTTCCATCTAtGCgGGGCAcgTt |
| 42 | Z6 | 306 | CCAGCCGCGACGCCACTGGACTACGCAGGACTGCAATTGTTCtATCTACGCAGGCATATC |
| 42-43 consensus (Z6) | | | CCAGCCGCGACGCCACTGGACTACGCAGGACTGCAATTGTTCtATCTACgCaGGGCAtaTc |

| SEQ ID NO: | Isolate | | |
|---|---|---|---|
| 43 | Z7 | 367 | ACaGGGCCACAGaATGGCATGGGACATGATGATGAACTGGAGTCCCACAACCACCtTGgTCC |
| 42 | Z6 | 367 | ACgGGGCCACAGgATGGCATGGGACATGATGATGAACTGGAGTCCCACAACCCCtGcTtC |
| 42-43 consensus (Z6) | | | ACgGGGCCACAGgATGGCATGGGACATGATGATGAACTGGAGTCCCACAACCACCcTGcTtc |

| SEQ ID NO: | Isolate | | |
|---|---|---|---|
| 43 | Z7 | 428 | TCGCCCAGGTtATGAGGATCCCTAGCACTCTGGTgGACCTACTCaCTGGAGGGCACTGGGG |
| 42 | Z6 | 428 | TCGCCCAGGTcATGAGGATCCCTAGCACTCTGGTaGAtCTACTCGCTGGAGGGCACTGGGG |
| 42-43 consensus (Z6) | | | ACgGGGCCACAGgATGGCATGGGACATGATGATGAACTGGAGTCCCACAACCACCcTGcTtc |

| SEQ ID NO: | Isolate | | |
|---|---|---|---|
| 43 | Z7 | 489 | taTCCTTaTcGGGgTGGCaTACTTCtGCATGCAAGCTAATTGGGCCAAGGTCATtCTGGTC |
| 42 | Z6 | 489 | CgTCCTTGTTGGGtTGGCGTACTTCAGtATGCAAGCTAATGCAAGCTAAtGTCATCCTGGTC |
| 42-43 consensus (Z6) | | | cgTCCTTgTtGGGtTGGCgTACTTCaGtATGCAAGCTAATtGGGCCAAaGTCATcCTGGTC |

| SEQ ID NO: | Isolate | | |
|---|---|---|---|
| 43 | Z7 | 550 | CTTTTCCTCTaCGCTGGAGTTGATGCC |
| 42 | Z6 | 550 | CTTTTCCTCTTCGCTGGAGTTGATGCC |
| 42-43 consensus (Z6) | | | CTTTTCCTCTtCGCTGGAGTTGATGCC |

FIGURE 1G-1

| SEQ ID NO: | Isolate | | |
|---|---|---|---|
| 45 | SA1 | 1 | GTtCCCTACCGgAATGCCTCTGGGGTTTAcCATGTCACCAATGAcTGCCCAAACTCcTCCA |
| 47 | SA5 | 1 | GTCCCCTACCGgAAATGCCTCTGGGGTTTATCATGTCACCAATGATTGCCCAAACTCTTCCA |
| 49 | SA7 | 1 | GTCCCCTACCGgAAATGCCTCTCcGGGGTTTATCATGTCACCAATGATTGCCCgAACTCTTCCA |
| 46 | SA4 | 1 | GTTCCCTACCGgAAAcGCCTCTGGGGTTTATCATGTCACCAATGATTGCCCAAACTCTTCCA |
| 50 | SA13 | 1 | GTTCCCTACCGgAAATGCCTCTGGGGTTTATCATGTCACCAATGATTGCCCAAACTCTTCCA |
| 48 | SA6 | 1 | GTTCCtTACCGgAATGCCTCTGGGGTgTATCATGTtACCAATGATTGCCCAAACTCTTCCA |
| 45-50 | consensus | | GTtCCcTACCGaAAtGCCTCtGGGGTtTAtCATGTcACCAATGAtTGCCcAaACTCTTCCA |

| SEQ ID NO: | Isolate | | |
|---|---|---|---|
| 45 | SA1 | 62 | TAGTCTACGAGGCTGATAgCCTGATCtTGCACGCACCTGGCTGCGTGCCCTGTGTCAGgCA |
| 47 | SA5 | 62 | TAGTCTACGAGGCTGATAACCTGATtCTGCACGCACCTGGTTGCGTGCCCTGTGTCAaGgA |
| 49 | SA7 | 62 | TAGTCTAtGAGGCTGAcAACCTGATCCTGCACGCACCTGGTTGCGTGCCCTGTGTCAGaCA |
| 46 | SA4 | 62 | TAGTCTAtTACGAGGCTGATAACCTGATCTTGCACGCAtGCACCTGGTTGCGTGCCCtTGTGTCAGGCA |
| 50 | SA13 | 62 | TcGTCTACGAGGCTGATGACCTGATCTTACACGCACCTGGTTGCGTGCCCTGTGTtAGGCA |
| 48 | SA6 | 62 | TaGTCTAtGAGGCTGATGACCTGATCCTACACGCACCTGGCTGCGTGCCCTGTGTccGGaA |
| 45-50 | consensus | | TaGTcTAcGAGGCTGAtaaCCTGATc-TgCAcGcACCTGGtTGCGTGCCcTGTGTcaggcA |

FIGURE 1G-2

| SEQ ID NO: | Isolate | | |
|---|---|---|---|
| 45 | SA1 | 123 | AGaTAATGTCAGTAGGTGCTGGGTCCAAATCACCCCCACAcTGTCAGCCCCGAcTTCGGA |
| 47 | SA5 | 123 | AGgTAATGTCAGTAGGTGCTGGGTCCAAATCACCCCCACATTGTCAGCCCGAACCTCGGA |
| 49 | SA7 | 123 | AaATAATGTCAGTAGGTGCTGGGTCCAAATCACCCCCACATTGTCAGCCCCGAACCTCGGA |
| 46 | SA4 | 123 | AGATAATGTCAGTAAGTGCTGGGTCCAAATCACCCCCACgTTGTCAGCCCCGAAtCTCGGA |
| 50 | SA13 | 123 | GGgTAATGTCAGTAGGTGCTGGGTCCAgATCACCCCCACACTGTCAGCCCCGAGCCTCGGA |
| 48 | SA6 | 123 | GGaTAATGTCAGTAGaTGCTGGGTtCAtATCACCCCCACACTaTCAGCCCCGAGCCTCGGA |
| 45-50 | consensus | | agaTAATGTCAGTAggTGCTGGGTcCAaATCACCCCCACa-TgTCAGCCCCGAaccTCGGA |

| SEQ ID NO: | Isolate | | |
|---|---|---|---|
| 45 | SA1 | 184 | GCGGTCACGGCTCCTCTTCGGAGGGcCGTTGACTACTTAGCGGGaGCTGCtCTCTGCT |
| 47 | SA5 | 184 | GCGGTCACGGCTCCTCTTCCTCTTCGGAGGGtCGTTGACTACTTAGCGGGAGGGGCTGCCCTCTGCT |
| 49 | SA7 | 184 | GCGGTCACGGCTCCTCTCTTCGGAGGGCCGTTGACTACcTAGCGGGAGGGGCTGCCCTCTGCT |
| 46 | SA4 | 184 | GCGGTCACGGCTCCTCTCTTCGGAGGGCCGTTGACTACTTAGCGGGAGGGGCTGCCCTCTGCT |
| 50 | SA13 | 184 | GCGGTCACGGCTCCTCTCTTCGGAGGGCCGTTGACTACTTAGCGGGAGGGGCTGCCCTTTGCT |
| 48 | SA6 | 184 | GCGGTCACGGCTCCTCTCTTCGGAGGGCCGTTGAtTACTTgCGGGaGGGGCCGCCCTgTGCT |
| 45-50 | consensus | | GCGGTCACGGCTCCTCTTCGGAGGCcGTTGAcTACTTaGCGGGaGGGGCtGCcCTcTGCT |

FIGURE 1G-3

| SEQ ID NO: | Isolate | | |
|---|---|---|---|
| 45 | SA1 | 245 | CCGCACTATACGTCGGcGACGCGTGCGCGGGGCAGTGTTcTGGTAGGCCAAATGTTCACCTA |
| 47 | SA5 | 245 | CCGCACTATACGTCGGGGACGCGTGCGCGGGGCAGTGTTcTTGGTAGGCCAAATGTTCACCTA |
| 49 | SA7 | 245 | CCGCgCTATACGTCGGGGACGCGTGCGCGGGGCAGTGTTTTTGGTAGGCCAgATGTTCAgCTA |
| 46 | SA4 | 245 | CCGCaCTATACGTCGGGGACGCGTGCGCGGGGCAGTGTTTTTTGGTAGGCCAAATGTTCACCTA |
| 50 | SA13 | 245 | CCGCGTTATACGTCGGGGAGACGCGTGCGCGGGGCAGTGTTTTTGGTAGtCAAATGTTCACCTA |
| 48 | SA6 | 245 | CCGCGTTATACGTCGGGGAGACGtGTGCGGGGCAtTGTTTTTTGGTAGGcCAAATGTTCACCTA |
| 45-50 | consensus | | CCGC-cTATACGTCGGgGACGCGTGCGGGGCAgTGTTtTGGTAGGcCAaATGTTCAcCTA |

| SEQ ID NO: | Isolate | | |
|---|---|---|---|
| 45 | SA1 | 306 | TAGGCCTTCGCCAGCATACcACAGTGCAGGACTGTTCCATTTACAGtGGCCATATC |
| 47 | SA5 | 306 | TAGGCCCTTCGCCAGCATACTACGGTGCAGGACTGTCCAACTGTTCCATTTACAGCGGCCATATC |
| 49 | SA7 | 306 | TAGGCCCTTCGCCAGCACACTACGGTGCAGGACTGCAACTGTTCCATTTACAGTGGCCATATC |
| 46 | SA4 | 306 | TAGGCCCTTCGCCAGCACACTACGGTGCAGGACTGCAACTGTTCCATTTACAGTGGCCATATC |
| 50 | SA13 | 306 | TAGcCCCTTCGCCAGCACACTACGGTGCAaGACTGCAAtTGcTCtATTTACAGTGGCCATATC |
| 48 | SA6 | 306 | TAGcCCCTTCGCCgGCATAaTgttGTGCAGGACTGCAACTGtTCCATTTACAGTGGCCACATC |
| 45-50 | consensus | | TAGGcCCTTCGCCaGCATactacgGTgCAgGACTGCAAcTGtTCcATTTACAGTGGCCAtATC |

FIGURE 1G-4

| SEQ ID NO: | Isolate | | |
|---|---|---|---|
| 45 | SA1 | 367 | ACCGGCCACCGgATGGCtTGGGACATGATGATGAATTGGTCACCTACGACAGCCTTGcTGA |
| 47 | SA5 | 367 | ACCGGCCACCGgAATGGCATGGACATGATGATGAATTGGTCACCTACGACAGCCTTGGTGA |
| 49 | SA7 | 367 | ACCGGCCACCGgAATGGCATGGACATGATGATGAATTGGTCACCTACGACAGCCTTGGTGA |
| 46 | SA4 | 367 | ACCGGCCACCGGATGGCATGGACATGATGATGAATTGGTCACCTACGACAGCCTTGcTGA |
| 50 | SA13 | 367 | ACCGGCCACCGGATGGCATGGACATGATGATGAATTGGTCACCTACGACAGCtTTGGTGA |
| 48 | SA6 | 367 | ACtGGCCACCGGATGGCATGGACATGATGATGAATTGGTCACCTACaACAGCcTTGGTGA |
| 45-50 | consensus | | ACcGGCCACCGgATGGCaTGGGACATGATGATGAATTGGTCACCtaCgACaGCcTTGgTGA |

| SEQ ID NO: | Isolate | | |
|---|---|---|---|
| 45 | SA1 | 428 | TGGCCCAGaTGCTACGGATcCCCCAgTGGTCATaGACATCATaGCCGGGGCCACTGGGG |
| 47 | SA5 | 428 | TGGCCCAGgTGCTACGGATTCCCCAaGTGGTCATtGACATCATTGCCGGGGCCACTGGGG |
| 49 | SA7 | 428 | TGGCCCAGTTGCTACGGATTCCCCAGTGGTCATCGACATCATTGCCGGGGCCACTGGGG |
| 46 | SA4 | 428 | TGGCCCAGTTGCTACGGATTCCCCAGTGGTCATCGACATCATTGCCGGGGCCACTGGGG |
| 50 | SA13 | 428 | TGGCCCAGTTGtTACGGATTCCCCAGTGGTCATTGACATCATTGCCGGGcCCACTGGGG |
| 48 | SA6 | 428 | TGGCCCAaaTGCTACGGATTCCCCAGTGGTCATTGACATCATTGCCGGGgCCACTGGGG |
| 45-50 | consensus | | TGGCCCAgtTGcTACGGATtCCCCAgtGGTCATtGACATCATtGCCGGGgCCACTGGGG |

FIGURE 1G-5

| SEQ ID NO: | Isolate | | |
|---|---|---|---|
| 45 | SA1 | 489 | GGTCTTGTTgCCGcCGCATACTTtGCGTCggCCGCCAACTGGGCTAAGGTaGTGCTGGTt |
| 47 | SA5 | 489 | GGTCTTGTTCGCCGtCGCATACTTCGCGTCggCCGtCAGCGGCTAAGGCTAAGGTTGTGCTGGTC |
| 49 | SA7 | 489 | GGTCTTGTTCGCCGCCGCATATTTCGCGTCCAGCGGCTAACTGGGCTAAGGTTGTGCTGGTC |
| 46 | SA4 | 489 | GGTCTTGTTtGCCGCCGCATATTTCGCGTCCAGCGGCTAACTGGGCTAAGGTTGTGCTGGTC |
| 50 | SA13 | 489 | GGTCTTGTTCGCCGCCGCATACTaCGCGTCGGCGGCTAACTGGGCTAAGGTTGTGCTGGTC |
| 48 | SA6 | 489 | GGTCTTGTTCGCCGCtGCATACTtCGCGTCGGCGGCTAACTGGGCTAAGGTTGTGCTGGTC |
| 45-50 | consensus | | GGTCTTGTTcGCCGccGCATAcTtcGCGTC-GCgGCtAACTGGGCtAAGGTtgTgCTGGTc |

| SEQ ID NO: | Isolate | | |
|---|---|---|---|
| 45 | SA1 | 550 | CTGTTccCTGTTTGCGGGGGTCGATGGC |
| 47 | SA5 | 550 | CTGTTTCTGTTTGCGGGGGTCGATGGC |
| 49 | SA7 | 550 | TTGTTTCTGTTTGCGGGGGTCGATGCC |
| 46 | SA4 | 550 | TTGTTTCTGTTTGCGGGGGTCGATGCC |
| 50 | SA13 | 550 | cTGTTTCTGTTTGCGGGGGTCGATGCC |
| 48 | SA6 | 550 | tTGTTTCTGTTTGCGGGGGTtGATGCC |
| 45-50 | consensus | | -TGTTtCTGTTTGCGGGGGTCGATGcC |

FIGURE 1H-1

| SEQ ID NO: | Genotype | |
|---|---|---|
| 30-33 | (IV/2b) | 1 GTGGAAGTcAGgAACAtCAGTTctAGcTACTAcGCCACCAATGATTGCTCaAACAaCAGCA |
| 34 | (2c) | 1 GTGGAGGTcAAGGAACACCGGCGACTCCTACAGTGCCGACCAACGATTGCTCCAACTCTAGTA |
| 26-29 | (III/2a) | 1 GcccAAGTGAagAACAACACCAgtacCagcTacAGTGGTGACcAAcGACTGtTCcAAtGAcAGCA |
| 35-39 | (V/3a) | 1 cTAGAGTGGCCGAATAcGTCtGGCCTCTAtgTCCTtACCAACGACTGTtCCAATAGCAGTA |
| 9-25 | (II/1b) | 1 tAtGAaGTGCgCAACGTgTCCGGGgtgTAccAtGTCAcgAAcGACTGcTCCAACTcaAGca |
| 1-8 | (I/1a) | 1 tACCAAGTgCGCAACTCcaCgGGgCTTtACCATGCTtACCATGtCACCAATGAtTGCCCTAAcTCGAGtA |
| 40 | (4a) | 1 GAGCACTACCGGAATGCTTCGGGCATCTATCACATCACCAATGATTGTCCCGAACTCCAGTA |
| 42-43 | (4c) | 1 GTtAACTATCgCAATGCCTCGGGCGTCTATCACgTCACCAATGACTCCCGAACTCGAGCA |
| 44 | (4d) | 1 TACAACTATCGCAACAGTCGGCTCGGGCGTCTATCAGTCACCAATGATTGCCCGAACTCGAGCA |
| 41 | (4b) | 1 GTGCACTACCGGAATGCTTCGGGCGTCTATCAGTCACCAATGATTGCCCTAACACCAGCA |
| 45-50 | (5a) | 1 GTtCCcTACCGGAaAtGCCTCtGGGGTTtAtCAtGTCACCAATGAtTGCCaAACTCtTCCA |
| 51 | (6a) | 1 CTTACCTACGGCAACTCCAGTGGCTATACCATCCACAAATGATTGCCCAACTCCAGCA |

1-51 consensus                 A                TA        AC  AA  GA  TG     C    AA

| SEQ ID NO: | Genotype | |
|---|---|---|
| 30-33 | (IV/2b) | 62 TCACCTGGCAaCTCACCaACGCCAGTtCTCCACCTTCCCGGATGCGTCCCaTGTGAGAATGA |
| 34 | (2c) | 62 TCGTTTGGCAGCTTGAAGGAGCAGCAGTGCTTCATACTCCTGGATGCGTCCTTGTGAGCGTAC |
| 26-29 | (III/2a) | 62 TCAcCTGGCAaCTccAgGCCcGGCCGATGACGTcATTCTGCACACACCTGGCTGTGTACCTTGTTCAGGA |
| 35-39 | (V/3a) | 62 TtGTGTATGAGGCCGATGACGTcATTCTGCACACACCTGGCTGTGTACCTTGTTCAGGA |
| 9-25 | (II/1b) | 62 TtGTGTatGAggCAgCGGACATGATcATGACACAcCCCCGGGTGCCCTGCGTtCgGGA |
| 1-8 | (I/1a) | 62 TtGTGTACGAGGCGGCCGATGCCCATcCTgCAcaCtCCgGGGTGTGTcCCTTGCGTTCGcGA |
| 40 | (4a) | 62 TAGTCTATGAAGCTGACCGAAGCTGACCATCACACTGCCGGGGTGCGTACCCTGTGTGATGAC |
| 42-43 | (4c) | 62 TAgTGTATGAGGCCGAACATCTTACACCTCCAGGGTGCTtGCCCTGTGTGAGGGt |
| 44 | (4d) | 62 TAGTCTATGAAACCGATTACCACATCTTACACCTCCCCGGATGCGTTCTTGCGTGAGGGA |
| 41 | (4b) | 62 TAGTGTACGAGACGGAGCACCACACCATCATGCACTTGCCAGGGTGTGTCCCCGTGTGCGGAC |
| 45-50 | (5a) | 62 TaGTcTAcGAGGCTGAtaaCCTGATcttGCAcGCACCTGGtTGCcGCACCTGTGCCtGTGTcaggcA |
| 51 | (6a) | 62 TCGTGCTGGAGGCGGATGCTATGATCTTGCATTGCCTGGATGCTTGCCTGGATGCTTGCCTTGTGAGGGT |

1-51 consensus                T    A                  T  T  CA      CC  GG  TG    T  CC  TG  G

FIGURE 1H-2

| SEQ ID NO: | Genotype | |
|---|---|---|
| 30-33 | (IV/2b) | 123 CAATGGCACCCTGCGCTGCTGGATACAAGTgACACCTAATGTGGCTGTGAAACACCGcGGC |
| 34 | (2c) | 123 CGCCAACGTCTCTCGATGTTGGGTGCCGGTTGCCCCAATCTCGCCATAAGTCAACCTGGC |
| 26-29 | (III/2a) | 123 gGGAAAtaCaTCtCGgTGTGCTGGATACCGGTctCaCCAAAcGTgCCgTGCaGcaGCCcGGC |
| 35-39 | (V/3a) | 123 CGGCAATACATCcACGTGCTGACCCCaGTGACaCCTAcAGTGGCAGTCAGTTAcGTCGGA |
| 9-25 | (II/1b) | 123 gaacAActcCTCccgcTGcTGGGTAgGCGCTcacTcCCACGCTCgCgCACCAGGAAcgccAgC |
| 1-8 | (I/1a) | 123 GGgTaaCgcctCGAggTGTTGGGTGCcGgTGaCCCCCACGgTGCCACcAGGgACGGCAAa |
| 40 | (4a) | 123 TGGGAACACATGCGTTGCTGGACGCCGGTGACGCCTACAGTGGCTGTCGCACACCCGGGC |
| 42-43 | (4c) | 123 tGGGAAtCAGTCACGCTGCTGGGTGCCCTTACTCCACCGTGCGGtGtCTTATATCGGT |
| 44 | (4d) | 123 AGGGAACAAGTCTACATGCTGGGTGTCTCTCACCCCACCGTGCCAACATCTGAAT |
| 41 | (4b) | 123 GGAGAATACTTCTCGCTGCTGGGTCCAaATCACCCCACatTgTCAGcCCCGAaccTCGA |
| 45-50 | (5a) | 123 agaTAATGTCAGTAggTGCTGGGTCCAaATCACCCCACatTgTCAGcCCCGAaccTCGA |
| 51 | (6a) | 123 CGATGATCGGTCCACCTGTTGGCATGCTGTGACCCCCACCCTGGCCATACCAAATGCTTCC |

1-51 consensus                                    TG TGG        T  CCC A   T  C

| SEQ ID NO: | Genotype | |
|---|---|---|
| 30-33 | (IV/2b) | 184 GCaCTCACTCACAACCTGCGAaCaCAtgTcGAcaTGATcGTAATGGCAGCTACGGTCTGCT |
| 34 | (2c) | 184 GCTCTCACTCAGTCCTGCGCTGCGAGCACACATCGATATCATCGTGATGTCTGTACGGTCTGTT |
| 26-29 | (III/2a) | 184 GCcCTcACGCAGGGCTTGCGGACgCACATCGACATGGTtGTGATGTCCGCCACGCTCCTGCT |
| 35-39 | (V/3a) | 184 GCAACCACCGCTTCGATACGCAGTCAGTCGACATGTGGACCTatTAgTGGGCGGCCACgaTGTGCT |
| 9-25 | (II/1b) | 184 gTCcCCACTAcGaCaATACGACgcCAcGTCGATcACATCGATcTGCTCGTTGGGCGGCTgctTTCTGCT |
| 1-8 | (I/1a) | 184 CTCCCCCgCAACGCAGCTtCGACGTcACATCGATCTGCTTgTCgGGaAGcGCCACCCTCTGCT |
| 40 | (4a) | 184 GCTCCGCTTGAGTCGTTCCGGCGACATGTGGACTTAAGTGGTAGGCGCGGCCACTTTGTGTT |
| 42-43 | (4c) | 184 GCtCCGCTTGACTCCcTCCGGAGACATGTGGACCTGATGGTgGGCGCCGCTACTgTaTGCT |
| 44 | (4d) | 184 GCTCCGCTTGAGTCTTTGAGACGTCACGTGGATCTGGATCGAGACCTGATGGCCACTCTCTGCT |
| 41 | (4b) | 184 GCACCGTTAGAGTCCATGCCAGGCATGTAGACCATGAGCCATGGGCGGCTACTATGTGTT |
| 45-50 | (5a) | 184 GCGGTCACGGCTCCTCTTCGGAGGGCCGTTGACTACTtAgGCGCGGGGCtGcCctCTGCT |
| 51 | (6a) | 184 ACGCCCGCAACGGGATTCTTCTTGCGCCGCAGTGGTTTGCT |

1-51 consensus             T   G       T  GA       T  GA       T  G    GC      T TG  T

FIGURE 1H-3

| SEQ ID NO: | Genotype | | |
|---|---|---|---|
| 30-33 | (IV/2b) | 245 | CGGCCCTTGTATGTGGGaGACgTgTGCGGGGCCCGTGATGATCgtGTGCGCAGGCTtTCATAaT |
| 34 | (2c) | 245 | CTGCCCTTTATGTGGGGGACGTGTGTGTGGCGCGCTGATGCTGGCCGCTCAGGTGCTCGTCGT |
| 26-29 | (III/2a) | 245 | CgGCtCTtTACGTGGGGGGACcTCTGCGGcGGGTgATGCTCGCAGcCcAgATGTTCATtgT |
| 35-39 | (V/3a) | 245 | CTGCGCTTACGTGGGtGATaTGTGTGGGGCCCGTCTgTCCTcgTcTCcCAGCTGTTCACGTT |
| 9-25 | (II/1b) | 245 | CCGctATGTACgTGGGGGATCTCTGCGGAtCTcGTtTCCtcgTcTCcCAGCTGTTCACctT |
| 1-8 | (I/1a) | 245 | CGGCCCTCTACGTGGGGGACTGTGCGGGTCTGTCTtCTtGTCgGtCAaCTGTTCACctT |
| 40 | (4a) | 245 | CTGCCCCTCTATGTTGGGGACCTCTGCGAGTTGCCTTCCTGATGGGCAGATGATCACTTT |
| 42-43 | (4c) | 245 | CtGCCCTCTACgTTGGaGAtCTGTGGTgGtGCATTCTTGGTTGGCCAGATGTTcTCcTT |
| 44 | (4d) | 245 | CCGCCCTCTACATCGGAGACGTGTGTGTGGtGTGTCTTGGTCGGTCAACTGTTCACCTT |
| 41 | (4b) | 245 | CCGCCCTTCTACATTGGAGATCTGTGTGTGGAGGCGTCTCTTCCTAGTGGGCCAGCTGTTCGACTT |
| 45-50 | (5a) | 245 | CCGCgCTATACGTCGGGACGCGTGTGTGTGCGGGCAGtGTTtTTGGTAGGCCAaATGTTCAcCTA |
| 51 | (6a) | 245 | CATCCCTGTACATCGGGGACCTGTGTCTCTCTCTTTTTGGCGGGACAACTATTCACCTT |

| 1-51 | consensus | | C T TA T GG GA TG GG T T CA T |

| SEQ ID NO: | Genotype | | |
|---|---|---|---|
| 30-33 | (IV/2b) | 306 | ATCGCCaGaAACgCCACaACTTtACCCAagAGTGCAACTGTTCCATCTACCAAGGTCatATC |
| 34 | (2c) | 306 | GTCGCCACACAACCATACACTGTTTGTCCAGGAATGCAACTGTTCCATATACCCGGGCCGCATT |
| 26-29 | (III/2a) | 306 | CTCGCCGCaaCaCacCACTgGTTTGTGCAagAaTGCAAtTGCTCCATCTACCCtGGtACCATC |
| 35-39 | (V/3a) | 306 | CAGACCtCGTCGCCATCAAAACggTCCAGACAGACCTGTAACTGCTGTAACTGCTACCAGGCCAtCTT |
| 9-25 | (II/1b) | 306 | cTCgCCtCGcCggcAtgaGAaCagtaCAgtaCAaCGCAaGaCTGACAACTGCTCaaTCTATCCCggCacgTa |
| 1-8 | (I/1a) | 306 | cTCtCCCAAGgCgCCaCTGGACaCTGGACAAGaCTGCAAtTGTTCtATCTAtCCCggCCATATa |
| 40 | (4a) | 306 | TCGGCCGCGTCGCGCTGGACCACTGGACCAGGAGTGCAATTGTTCCATCTACACTGGCCATATC |
| 42-43 | (4c) | 306 | CCAGCCGCGACGCGCCACTCGCCGCCACTACGCCACCACCCAAGACTGCAATTGTCCATCTATCAcGCaGGCCAtaTc |
| 44 | (4d) | 306 | CCAACCTCGCCGCCGCCACTGGACAACTGACACCACCCCCAAGACTGCAATTGTCCATCTACACAGGACATATC |
| 41 | (4b) | 306 | CCGACCGCGCCGGCCAGGCCACTGGACTGGACCAGGATTGCAAACTGCTCAAcTGTCCATCTATCCTGGTCAGTC |
| 45-50 | (5a) | 306 | TAGgCCTCGCCaGCAtactacgGTgCAggACTGTgCAGgACTGCAAcTGTTCCATTTACAGtGGCCATATC |
| 51 | (6a) | 306 | TCAGCCCCGCCGTCATTGGACTGTGCAAGACTGCAAGACTGCAACTGCTCCATCTATACAGGCCACGTC T |

| 1-51 | consensus | | CC C CA TG AA TG TC T TA GG T |

FIGURE 1H-4

| SEQ ID NO: | Genotype | | |
|---|---|---|---|
| 30-33 | (IV/2b) | 367 | ACCGGCCACCGCATGGCATGGGACATGATGCTaAACTGGTCACCAACTCTtACCATGATCC |
| 34 | (2c) | 367 | ACGGGACACCGCCATGGCTTGGATATGATGATGATGAACTGGTCGCCCACTACCACCATGCTCC |
| 26-29 | (III/2a) | 367 | ActGGaCACCGTATGGCATGGGaCATGATGATGATGATGAACTGGTCGCCCACcaTGATCc |
| 35-39 | (V/3a) | 367 | TCAGGACATCGaATGGCTTGGATATGATGATGATGATGAATTGGTCCCCCGCTGTGGGTATGGTGG |
| 9-25 | (II/1b) | 367 | tCAGGTCAcCGCATGGCTTGGaTATGGCATGATGATGATGATGAACTGGTCaCCtACAgCaGCccTaGTgg |
| 1-8 | (I/1a) | 367 | ACGGGtCAcCGCATGGCaTGGGaCATGATGATGATGATGAACTGGTCCCCtACgaCgGCgcTGGTag |
| 40 | (4a) | 367 | ACCGGCCACAGGATGGCGTGGaCATGATGATGATGATGAACTGGAGACCCTACCACCACCTCTGCTCC |
| 42-43 | (4c) | 367 | ACgGGCCACAGaGGATGGCTTGGaCATGATGATGATGATGAACTGGAGTCCCaCAACCACCcTGcTtC |
| 44 | (4d) | 367 | ACAGGACACAGAGAATGGCTTGGaCATGATGATGATGATGAATTGGAGAGCCCACTGCGAGCGCTGGTCC |
| 41 | (4b) | 367 | TCGGGCCACAGGATGGCCTGGaCATGGGaCATGATGATGATGAACTGGAGAGCCCTACCAGCGCGCTGATTA |
| 45-50 | (5a) | 367 | ACcGGCCACCGgATGGaCATGGGCTTGGaCATGATGATGATGAACTGGTCACCtaCgACaGCcTTGgTGA |
| 51 | (6a) | 367 | ACCGGCCACAGAGGATGGCTTGGaCATGATGATGATGATGAACTGGTCACCCACAACCACTCTGGTCC |

| 1-51 | consensus | | C GG CA G ATGGC TGGGA ATGATG T AA TGG CC C T T |

| SEQ ID NO: | Genotype | | |
|---|---|---|---|
| 30-33 | (IV/2b) | 428 | TcGCCTAtGCcGCtCGTGTtCCTGaGCTAGtCCTgAaGTtGTCTTCGgCgCATTGGGG |
| 34 | (2c) | 428 | TGGCGTACTTGGTGCGCATCCCGGAAGTCATCTTGGATATTGTTACAGGAGGTCATTGGGG |
| 26-29 | (III/2a) | 428 | TGGCGTACGGCGATGCGCGTTCCCGAGGTCATCATAGACATCATtaGCCGgGCtCACTGGGG |
| 35-39 | (V/3a) | 428 | TgGCCGCACGTCCTGCGTtTGCCCAGACCtTGTTcGACATGATTaGCcGGCCCATTGGGG |
| 9-25 | (II/1b) | 428 | TaTCGCAgtTaCTCCGgaTCCCaCAAGCTgTCgTGGAcaTGGTggCgGGGCCCATTGGGG |
| 1-8 | (I/1a) | 428 | TaGCtCAGCTGCTCCgGaTCCCgCAaGCCaTCTTGGACATGATGGTCgTGCcCACTGGGG |
| 40 | (4a) | 428 | TCGCCCAGATCATGAGGGTCCCCACAGCACTCTGGTaGAtCTACTCgTCTGGAGGCCACTGGGG |
| 42-43 | (4c) | 428 | TCGCCCAGTCATGAGGATCCCCAGCTGCCATGGTCGACCTGCTTGCTCAGGCGCCACTGGGG |
| 44 | (4d) | 428 | TCGCCCAACTTATGAGGATCCCCAGGCGCCATGGTCGACCTGCTTGCTCACCGGGGTCACTGGGG |
| 41 | (4b) | 428 | TGGCTCAGATCTTACGATCCGATCCCTCTATCCAGGTCATtCCCCAGTGGTCATtGACATCATtGCCGGGCCACTGGGG |
| 45-50 | (5a) | 428 | TGGCCCAGtTGCTACGGATtCCCCAGGTCATtGACATCATtGCCGGGCCACTGGGG |
| 51 | (6a) | 428 | TATCTAGCATCTTGAGGGTACCTGAGATTTGTGCGAGTGTGATATTTGGTGGCCATTGGGG |

| 1-51 | consensus | | T C G T CC T T GG G CA TGGGG |

FIGURE 1H-5

```
SEQ ID NO:  Genotype
30-33       (IV/2b)    489 CGTGGTGTGTTTGGCCTTGGCCTATTTCTCCATGCAggGAGCGTGGGCCAAaGTtCATtGCCATC
34          (2c)       489 TGTAATGTTTGGCCCTCGCTTaCTTCTTCTCTATTCCATGCAGGGATCGTGGGCGAAGGTCATCGTTATC
26-29       (III/2a)   489 CGTCaTGTTCGGCTTaGCCTAGCCTACTTCTCTATGCAGGGAGCGTGGGCCAAaGTCGTTGTCATC
35-39       (V/3a)     489 CATCtTGGCGGCGGCCTTGCCTAGCCTATTAcTCCATGCAGGGCAGGCAACTGGGCAAGGTCGCTATcaTC
9-25        (II/1b)    489 agTCCTGGCGGGCCTtGCCTACTATTCCCATGGtGGGGAACTGGGCTAAGGTttTgATTGTg
1-8         (I/1a)     489 AGTCCTaGCGGGCATAGCGTATTTCtCCATGGtGGGAACTGGGCGAAGGTCcTggTaGTg
40          (4a)       489 CGTCCTCGCGGGCTTGGCGTtGGGtTGGCGtGGCGtTAGTTCAGCATGCTACTTCAgtAGCTAATTGGGCCAAGGTAGTCCTGGTC
42-43       (4c)       489 cgTCCTTgTTGGGtTGGCGtGGCGtTAGTTCAgTAGCTACTTCAgtATGCAAGCTAATTGGGCCAAaGTCATCCTGGTC
44          (4d)       489 CATTCTGGTTGGCATAGCGTACTTCAGCATGCTACTTCAGCAGCTAATTGGCCAAGTAATTGGCCAAGGTTATCCTGGTC
41          (4b)       489 AGTTCTTGCTGGTCTAGCTTTCTTCAGCATGCTAACTGGGCGAAGGTCATCCTGGTC
45-50       (5a)       489 GGTCTTGTTcGCCGCcGCATACTtcGCGTCGGCGCtAACTGGGCtAACTGGGCtAAGGTtGtCGTGGTc
51          (6a)       489 GATACTACTAGCCGTTGCCTACTTTGCCATGGCTGGCAATCTGGCAACTGGCTAAAAGTTCTGGCTGTT 1-51        consensus        T       T     G       GC T  T                   T SEQ ID NO:  Genotype
30-33       (IV/2b)    550 CTCCCTtCTTGTcGCAGGAGTGGAtGCA
34          (2c)       550 CTCCTGCTGACTGCTGGGGTGGAGGCG
26-29       (III/2a)   550 CTttTGCTggCcGCTGGGGTGGACGCG
35-39       (V/3a)     550 ATGgTTATGTTTTCAGGGGTCGAtGCC
9-25        (II/1b)    550 aTGCTACTcTTTGCcGGcGTtGAcGGg
1-8         (I/1a)     550 CTGtTGCTgTTTgCCGGCGTcGAtGCG
40          (4a)       550 CTTTTCCTCTTtGCTCGCTGGGTAGACGCC
42-43       (4c)       550 CTTTTCCTCTTTGCTCGCTGGAGTTGATGCC
44          (4d)       550 CTGTTTCTCTTTGCTCGCTGGAGTCGACGCT
41          (4b)       550 CTATTCCTCTTTGCCGGGGTCGAGGGA
45-50       (5a)       550 tTGTTtCTGTTTGCGGGGGTcGATGcC
51          (6a)       550 CTGTTCCTATTTGCAGGGGTTGAAGCA 1-51        consensus        T   T    T      C  GG GT GA G
```

FIGURE 2A-1

| SEQ ID NO: | Isolate | | |
|---|---|---|---|
| 56 | S14 | 1 | YQVRNSTGLYHVTNDCPNSSIVYEtADAILHaPGCVPCVREGNtSRCWVAMTPTVATRDGK------------ |
| 52 | DK7 | 1 | YQVRNSTGLYHVTNDCPNSSIVYEAADAILHTPGCVPCVREGNvSRCWVAMTPTVATRDGK------------ |
| 59 | US11 | 1 | YQVRNSTGLYHVTNDCPNSSIVYEAADAILHTPGCVPCVREGNaSRCWVAMTPTVATRDGK------------ |
| 55 | DR4 | 1 | YQVRNSTGLYHVTNDCPNSSIVYEAADAILHTPGCVPCVREGNtSRCWVAVTPTVATRDGK------------ |
| 54 | DR1 | 1 | HQVRNSTGLYHVTNDCPNSSIVYEAADAILHaPGCVPCVREGNASRCWVAVTPTVATRDGK------------ |
| 53 | DK9 | 1 | HQVRNSSGLYHVTNDCPNSSIVYEAADAILHSPGCVPCVREGNASKCWVAVAPTVATRDGK------------ |
| 58 | SW1 | 1 | YQVRNSSGLYHVTNDCPNSSIVYETADAILHSPGCVPCVREdgApKCWVAVAPTVATRDGK------------ |
| 57 | S18 | 1 | YQVRNStgLYHVTNDCPNSSIVYETAdtILHSPGCVPCVREgnAsrCWvpVAPTVATRDGK------------ |
| 52-59 | consensus | | yQVRNStGLYHVTNDCPNSSIVYEaADaILH-PGCVPCVREgnasrCWvavtPTVATRDGK |

| SEQ ID NO: | Isolate | | |
|---|---|---|---|
| 56 | S14 | 62 | LPatQLRRyIDLLVGSATLCSALYVGDLCGSVFLVGQLFTFSPRRlWTTQdCNCSIYPGHI------------ |
| 52 | DK7 | 62 | LPTaQLRRHIDLLVGSATLCSALYVGDLCGSVFLVGQLFTFSPRRHWTTQGCNCSIYPGHI------------ |
| 59 | US11 | 62 | LPTTQLRRHIDLLVGSATLCSALYVGDLCGSVFLVGQLFTFSPRRHWTTQGCNCSIYPGHI------------ |
| 55 | DR4 | 62 | LPTTQLRRHIDLLVGSATLCSALYVGDLCGSVFLVGQLFTFSPRRHWTTQDCNCSIYPGHI------------ |
| 54 | DR1 | 62 | LPTTQLRRHIDLLVGSATLCSALYVGDLCGSVFLVGQLFTFSPRRHWTTQDCNCSIYPGHI------------ |
| 53 | DK9 | 62 | LPATQLRRHIDLLVGSATLCSALYVGDLCGSVFLVGQLFTFSPRRHWTTQDCNCSIYPGHI------------ |
| 58 | SW1 | 62 | LPATQLRRHIDLLVGSATLCSALYVGDLCGSVFLVSQLFTFSPRRHWTTQDCNCSIYPGHI------------ |
| 57 | S18 | 62 | LPATQLRRHIDLLVGSATLCSALYVGDLCGSVFLVSQLFTiSPRRHWTTQDCNCSIYPGHI------------ |
| 52-59 | consensus | | LP-tQLRRhIDLLVGSATLCSALYVGDLCGSVFLVgQLFTfSPRrhwTTQdCNCSIYPGHI |

FIGURE 2A-2

| SEQ ID NO: | Isolate | | |
|---|---|---|---|
| 56 | S14 | 123 | TGHRMAWDMMMNWSPTTALVVAQLLRIPQAILDMIAGAHWGVLAGIAYFSMVGNWAKVLVV |
| 52 | DK7 | 123 | TGHRMAWDMMMNWSPTTALVVAQLLRIPQAILDMIAGAHWGVLAGIAYFSMVGNWAKVLVV |
| 59 | US11 | 123 | TGHRMAWDMMMNWSPTTaALVVAQLLRIPQAILDMIAGAHWGVLAGIAYFSMVGNWAKVLVV |
| 55 | DR4 | 123 | TGHRMAWDMMMNWSPTTALVVAQLLRIPQAILDMIAGAHWGVLAGIAYFSMVGNWAKVLVV |
| 54 | DR1 | 123 | TGHRMAWDMMMNWSPTTALVMAQLLRIPQAILDMIAGAHWGVLAGIAYFSMVGNWAKVLVV |
| 53 | DK9 | 123 | TGHRMAWDMMMNWSPTTaALVMAQLLRIPQAILDMIAGAHWGVLAGIAYFSMVGNWAKVVVV |
| 58 | SW1 | 123 | TGHRMAWDMMMNWSPTTALVvAQLLRIPQAVLDMIAGAHWGVLAGIAYFSMVGNWAKVLiV |
| 57 | S18 | 123 | TGHRMAWDMMMNWSPTTALViAQLLRvPQAVLDMIAGAHWGVLAGIAYFSMaGNWAKVLlV |
| 52-59 | consensus | | TGHRMAWDMMMNWSPTTALVvAQLLRIPQAiLDMIAGAHWGVLAGIAYFSMvGNWAKVlvV |

| SEQ ID NO: | Isolate | | |
|---|---|---|---|
| 56 | S14 | 184 | LLLFAGVDA |
| 52 | DK7 | 184 | LLLFAGVDA |
| 59 | US11 | 184 | LLLFAGVDA |
| 55 | DR4 | 184 | LLLFAGVDA |
| 54 | DR1 | 184 | LLLFAGVDA |
| 53 | DK9 | 184 | LLLFAGVDA |
| 58 | SW1 | 184 | LLLFtGVDA |
| 57 | S18 | 184 | LLLFsGVDA |
| 52-59 | consensus | | LLLFaGVDA |

FIGURE 2B-1

| SEQ ID NO: | Isolate | | |
|---|---|---|---|
| 75 | T10 | 1 | YEVRNVSGmYHVTNDCSNSSIVfEAaDlIMHTPGCVPCVREgNsSRCWVALTPTLAARNtS |
| 62 | DK1 | 1 | YEVRNVSGvYHVTNDCSNSSIVYEAvDvIMHTPGCVPCVRENNhSRCWVALTPTLAARNAS |
| 64 | HK4 | 1 | hEVhNVSGiYHVTNDCSNSSIVYEAADMIMHTPGCVPCVRENNSSRCWVALTPTLAARNAS |
| 76 | US6 | 1 | YEVRNVSGmYHVTNDCSNSSIVYEAADMIMHTPGCVPCVRENNSSRCWVALTPTLAARNAS |
| 68 | IND8 | 1 | YEVRNVSGVYHVTNDCSNSSIVYEAADMIMHTPGCVPCVREGNfSsCWVALTPTLAARNAS |
| 67 | IND5 | 1 | YEVRNVSGVYHVTNDCSNSSIVYEAADMIMHTPGCVPCVREGNSSRCWVALTPTLAARNAS |
| 73 | SW2 | 1 | YEVRNVSGVYHVTNDCSNSSIVYETADMIMHTPGCVPCVREaNSSRCWVALTPTLAARNtS |
| 63 | HK3 | 1 | YEVRNVSGIYHVTNDCSNSSvVYETADMIMHTPGCVPCVRENNSSRCWVALTPTLAARNVS |
| 66 | HK8 | 1 | YEVRNVSGIYHVTNDCSNSSIVYETADMIMHTPGCmPCVRENNSSRCWVALTPTLAARNVS |
| 61 | D3 | 1 | YEVRNVSGVVyqVTNDCSNSSIVYETADMIMHTPGCVPCVREdNSSRCWVALTPTLAARNsS |
| 74 | T3 | 1 | YEVRNVSGVVyYTNDCSNSSIVYETADMIMHTPGCVPCVREsNSSRCWVALTPTLAARNAS |
| 65 | HK5 | 1 | YEVRNVSGVYHVTNDCSN1SIVYETtDMIMHTPGCVPCVREsNSSRCWVAlaPTLAARNAS |
| 71 | S45 | 1 | YEVRNVSGaYHVTNDCSNSSIVYEAvDvIlHTPGCVPCVRENNSSRCWVALTPTLAARNSS |
| 72 | SA10 | 1 | YEVRNVSGmYHVTNDCSNSSIVYEAADMIMHTPGCVPCVRENNSSRCWVALTPTLAARNSS |
| 69 | P10 | 1 | YEVRNVSGVYHVTNDCSNSSIVYEAADMIMHTPGCVPCVRENNSSRCWVALTPTLAARNSS |
| 60 | D1 | 1 | YEVRNVSGVYHVTNDCSNSSIVYEtADMIMHTPGCVPCVREdNSSRCWVALTPTLAARNgn |
| 70 | S9 | 1 | YEVRNVSGaYHVTNDCSNSSIVYEaADvIMHTPGCVPCVqEgNSSqCWVALtPTLAARNat |
| 60-76 | consensus | | yEVrNVSGvYhVTNDCSNsSiVyEaaDmImHTPGCvPCVrEnNsSrCWVALtPTLAARNas |

FIGURE 2B-2

| SEQ ID NO: | Isolate | | |
|---|---|---|---|
| 75 | T10 | 62 | vPTTTIRRHVDLLVGAAAFCSAMYVGDLCGSVFLVSQLFTFSPRRHET1QDCNCSIYPGH1 |
| 62 | DK1 | 62 | IPTTTIRRHVDLLVGAAAFCSAMYVGDLCGSVFLVSQLFTFSPRRHETaQDCNCSIYPGHV |
| 64 | HK4 | 62 | IPTTTIRRHVDLLVGAAAFCSAMYVGDLCGSVFLVSQLFTFSPRRHETVQDCNCSIYPGHV |
| 76 | US6 | 62 | VPTTTIRRHVDLLVGAAtFCSAMYVGDLCGSVFLiSQLFTFSPRqHETVQDCNCSIYPGHV |
| 68 | IND8 | 62 | VPTTTIRRHVDLLVGAAAFCSAMYVGDLCGSVFLVSQLFTFSPRRHETVQDCNCSIYPGHV |
| 67 | IND5 | 62 | VsTTTIRhHVDLLVGAAAFCSvMYVGDLCGSVFLVSQLFTFSPRRHETVQDCNCSlYPGHV |
| 73 | SW2 | 62 | VPTTTIRRHVDLLVGAAAFCSAMYVGDLCGSVFLVSQLFTFSPRRHETVQDCNCSIYPGHV |
| 63 | HK3 | 62 | VPTTTIRRHVDLLVGAAAFCSAMYVGDLCGSVFLVSQLFTFSPRRHETVQDCNCSIYPGHV |
| 66 | HK8 | 62 | VPTTTIRRHVDLLVGAAAFCSAMYVGDLCGSVFLVSQLFTFSPRRHETVQeCNCSIYPGHV |
| 61 | D3 | 62 | VPTkTIRRHVDLLVGAAAFCSAMYVGDLCGSVFLVSQLFTFSPRRHETVQDCNCSIYPGHV |
| 74 | T3 | 62 | VPTTTIRRHVDLLVGAAAFCSAMYVGDLCGSV1LVSQLFTFSPRRyETVQDCNCSIYPGrV |
| 65 | HK5 | 62 | VPTTaIRRHVDLLVGAAAFCSAMYVGDLCGSVFLVSQLFTFSPRRHETVQDCNCSIYPGHV |
| 71 | S45 | 62 | VPTTTIRRHVDLLVGAAAFCSAMYVGDLCGSVFLVSQLFTFSPRRHETVQDCNCSIYPGHV |
| 72 | SA10 | 62 | VPTTTIRRHVDLLVGAAAFCSAMYVGDLCGSVFLVSQLFTFSPRRHETVQDCNCSIYPGHV |
| 69 | P10 | 62 | VPTTTAIRRHVDLLVGAAAFCSAMYVGDLCGSVFLVSQLFTFSPRRHwTVQDCNCSIYPGHV |
| 60 | D1 | 62 | VPTTAIRRHVDLLVGAAAFCSAMYVGDLCGSVFLISQLFT1SPRRHETVQeCNCSIYPGHV |
| 70 | S9 | 62 | VPTtTIRRHVDLLVGAAvFCSAMYVGDLCGSVFLISQLFTiSPRRHETVQnCNCSIYPGHV |
| 60-76 | consensus | | vpTtTIRrHVDLLVGAAaFCSaMYVGDLCGSVfLvSQLFTfSPRrheTvQdCNCSiYPGhv |

FIGURE 2B-3

| SEQ ID NO: | Isolate | | |
|---|---|---|---|
| 75 | T10 | 123 | SGHRMAWDMMMNWSPTTALVvSQLLRIPQAVmDMVtGAHWGVLAGLAYYSMAGNWAKVLIV |
| 62 | DK1 | 123 | SGHRMAWDMMMNWSPTTALV1SQLLRIPQAVvDMVAGAHWGVLAGLAYYSMAGNWAKVLIV |
| 64 | HK4 | 123 | SGHRMAWDMMMNWSPTTAALVVSQLLRIPQAVMDMVAGAHWGVLAGLAYYSMVGNWAKVLIV |
| 76 | US6 | 123 | SGHRMAWDMMMNWSPTAALVVSQLLRIPQAVMDMVAGAHWGVLAGLAYYSMVGNWAKVLIV |
| 68 | IND8 | 123 | SGHRMAWDMMMNWSPTTAALVVSQLLRIPQAVMDMVAGAHWGILAGLAYYSMVGNWAKVLIV |
| 67 | IND5 | 123 | SGHRMAWDMMMNWSPTTAALVVSQLLRIPQAVVDMVAGAHWGILAGLAYYSMVGNWAKVLIV |
| 73 | SW2 | 123 | SGHRMAWDMMMNWSPTAALVVSQLLRIPQAVMDMVAGAHWGVLAGLAYYSMVGNWAKVLIV |
| 63 | HK3 | 123 | SGHRMAWDMMMNWSPTAALVVSQLLRIPQAVVDMVAGAHWGVLAGLAYYSMVGNWAKVLIV |
| 66 | HK8 | 123 | SGHRMAWDMMMNWSPTTALVVSQLLRIPQAVVDMVAGAHWGVLAGLAYYSMVGNWAKVLIV |
| 61 | D3 | 123 | SGHRMAWDMMMNWSPTtALVVSQLLRIPQAiVDMVAGAHWGVLAGLAYYSMVGNWAKVLIV |
| 74 | T3 | 123 | TGHRMAWDMMMNWSPTaALVVSQLLRIPQAVVDMVAGAHWGVLAGLAYYSMVGNWAKVLIV |
| 65 | HK5 | 123 | TGHRMAWDMMMNWSPTTALVVSQLLRIPQAVVDMVAGAHWGVLAGLAYYSMVGNWAKVLIV |
| 71 | S45 | 123 | TGHRMAWDMMMNWSPTaALVVSQLLRIPQAVVDMVAGAHWGVLAGLAYYSMVGNWAKVLIV |
| 72 | SA10 | 123 | TGHRMAWDMMMNWSPTTALVVSQLLRIPQAIVDMVAGAHWGVLAGLAYYSMVGNWAKVLIV |
| 69 | P10 | 123 | sGHRMAWDMMMNWSPTTAALVVSQLLRIPQAIlDvVAGAHWGVLAGLAYYSMVGNWAKVLIV |
| 60 | D1 | 123 | TGHRMAWDMMMNWSPTTALVVSQLLRIPQAVMDMVAGAHWGVLAGLAYYSMVGNWAKVLIV |
| 70 | S9 | 123 | TGHRMAWDMMMNWSPTTALVVSQLLRIPQAVMDMVAGAHWGVLAGLAYYSMvGNWAKVLIV |
| 60-76 | consensus | | sGHRMAWDMMMNWSPTaALVvSQLLRiPQAvvDmVaGAHWGvLAGLAYYSMvGNWAKVLIV |

FIGURE 2B-4

| SEQ ID NO: | Isolate | | |
|---|---|---|---|
| 75 | T10 | 184 | mLLFAGVDG |
| 62 | DK1 | 184 | lLLFAGVDG |
| 64 | HK4 | 184 | mLLFAGVDG |
| 76 | US6 | 184 | lLLFAGVDG |
| 68 | IND8 | 184 | MLLFAGVDG |
| 67 | IND5 | 184 | MLLFAGVDG |
| 73 | SW2 | 184 | MLLFAGVDG |
| 63 | HK3 | 184 | MLLFAGVDG |
| 66 | HK8 | 184 | MLLFAGVDG |
| 61 | D3 | 184 | MLLFAGVDG |
| 74 | T3 | 184 | lLLFAGVDG |
| 65 | HK5 | 184 | MLLFAGVDG |
| 71 | S45 | 184 | MLLFAGVDG |
| 72 | SA10 | 184 | MLLFAGVDG |
| 69 | P10 | 184 | MLLFAGVDG |
| 60 | D1 | 184 | MLLFAGVDG |
| 70 | S9 | 184 | MLLFAGVDG |
| 60-76 | consensus | | mLLFAGVDG |

FIGURE 2C-1

| SEQ ID NO: | Isolate | | |
|---|---|---|---|
| 77 | T2 | 1 | AQVrNTsrgYMVTNDCSNeSITWQLQAAVLHVPGCiPCErlGNTSRCWIPVtPNVAVRQPG |
| 78 | T4 | 1 | AQVKNTtnSYMVTNDCSNDSITWQLQAAVLHVPGCVPCEktGNTSRCWIPVSPNVAVRQPG |
| 79 | T9 | 1 | AeVKNTSTSYMVTNDCSNDSITWQLQAAVLHVPGCVPCErVGNaSRCWIPVSPNVAVQRPG |
| 80 | US10 | 1 | vqVKNTSTSYMVTNDCSNDSITWQLeAAVLHVPGCVPCEkvSRCWIPVSPNVAVQRPG |
| 77-80 | consensus | | aqVKNTstsYMVTNDCSNdSITWQLqAAVLHVPGCvPCE-vGNtSRCWIPVsPNVAV--PG |

| SEQ ID NO: | Isolate | | |
|---|---|---|---|
| 77 | T2 | 62 | ALTQGLRTHIDMVVMSATLCSALYVGDLCGGVMLAAQMFIVSPrrHWFVQeCNCSIYPGTI |
| 78 | T4 | 62 | ALTQGLRTHIDMVVMSATLCSALYVGDLCGGVMLAAQMFIVSPQHHWFVQdCNCSIYPGTI |
| 79 | T9 | 62 | ALTQGLRTHIDMVVMSATLCSALYVGDLCGGVMLAAQMFIiSPQHHWFVQECNCSIYPGTI |
| 80 | US10 | 62 | ALTQGLRTHIDMVVMSATLCSALYVGDfCGGmMLAAQMFIvSPrHHsFVQECNCSIYPGTI |
| 77-80 | consensus | | ALTQGLRTHIDMVVMSATLCSALYVGDlCGGVMLAAQMFIvSP-hHwFVQeCNCSIYPGTI |

| SEQ ID NO: | Isolate | | |
|---|---|---|---|
| 77 | T2 | 123 | TGHRMAWDMMMNWSPTATMILAYAMRVPEVIiDIigGAHWGVMFGLAYFSMQGAWAKViVI |
| 78 | T4 | 123 | TGHRMAWDMMMNWSPTATMILAYAMRVPEVIlDIvSGAHWGVMFGLAYFSMQGAWAKVVVI |
| 79 | T9 | 123 | TGHRMAWDMMMNWSPTtTMILAYAMRVPEVIIDIISGAHWGVMFGLAYFSMQGAWAKVVVI |
| 80 | US10 | 123 | TGHRMAWDMMMNWSPTaTlILAYvMRVPEVIIDIISGAHWGVlFGLAYFSMQGAWAKVVVI |
| 77-80 | consensus | | TGHRMAWDMMMNWSPTaTmILAYaMRVPEVIiDIisGAHWGVmFGLAYFSMQGAWAKVvVI |

FIGURE 2C-2

| SEQ ID NO: | Isolate | | |
|---|---|---|---|
| 77 | T2 | 184 | LLLAAGVDA |
| 78 | T4 | 184 | LLLAAGVDA |
| 79 | T9 | 184 | LLLtAGVDA |
| 80 | US10 | 184 | LLLaAGVDA |
| 77-80 | consensus | | LLLaAGVDA |

FIGURE 2D-1

| SEQ ID NO: | Isolate | | |
|---|---|---|---|
| 82 | DK11 | 1 | VEVRNtSSSYYATNDCSNnSITWQLTNAVLHLPGCVPCENDNGTLHCWIQVTPNVAVKHRG |
| 83 | SW3 | 1 | VEVRNiSSSYYATNDCSNsSITWQLTNAVLHLPGCVPCENDNGTLHCWIQVTPNVAVKHRG |
| 84 | T8 | 1 | VEVRNtSfSYYATNDCSNNSITWQLTNAVLHLPGCVPCENDNGTLRCWIQVTPNVAVKHRG |
| 81 | DK8 | 1 | VEVRNiSsSYYATNDCSNNSITWQLTdAVLHLPGCVPCENDNGTLRCWIQVTPNVAVKHRG |
| 81-84 | consensus | | VEVRN-SsSYYATNDCSNnSITWQLTnAVLHLPGCVPCENDNGTL-CWIQVTPNVAVKHRG |

| SEQ ID NO: | Isolate | | |
|---|---|---|---|
| 82 | DK11 | 62 | ALTHNLRAHiDMIVMAATVCSALYVGDvCGAVMIVSQAFIvSPEhHhFTQECNCSIYQGhI |
| 83 | SW3 | 62 | ALTHNLRAHVDMIVMAATVCSALYVGDmCGAVMIVSQAFIISPERHNFTQECNCSIYQGrI |
| 84 | T8 | 62 | ALTHNLRTHVDVIVMAATVCSALYVGDVCGAVMIVSQAFIISPERHNFTQECNCSIYQGHI |
| 81 | DK8 | 62 | ALTHNLRTHVDVIVMAATVCSALYVGDVCGAVMIaSQAFIISPERHNFTQECNCSIYQGHI |
| 81-84 | consensus | | ALTHNLR-HvD-IVMAATVCSALYVGDvCGAVMIvSQAFIiSPErHnFTQECNCSIYQGhI |

| SEQ ID NO: | Isolate | | |
|---|---|---|---|
| 82 | DK11 | 123 | TGHRMAWDMMLNWSPTLTMILAYAARVPELVLEVVFGGHWGVVFGLAYFSMQGAWAKVIAI |
| 83 | SW3 | 123 | TGHRMAWDMMLNWSPTLTMILAYAARVPELVLEVVFGGHWGVVFGLAYFSMQGAWAKVIAI |
| 84 | T8 | 123 | TGHRMAWDMMLNWSPTLTMILAYAARVPELVLEVVFGGHWGVVFGLAYFSMQGAWAKVIAI |
| 81 | DK8 | 123 | TGHRMAWDMMLNWSPTLTMILAYAARVPELaQVVFGGHWGVVFGLAYFSMQGAWAKVIAI |
| 81-84 | consensus | | TGHRMAWDMMLNWSPTLTMILAYAARVPELvLeVVFGGHWGVVFGLAYFSMQGAWAKVIAI |

FIGURE 2D-2

| SEQ ID NO: | Isolate | | |
|---|---|---|---|
| 82 | DK11 | 184 | LLLVAGVDA |
| 83 | SW3 | 184 | LLLVAGVDA |
| 84 | T8 | 184 | LLLVAGVDA |
| 81 | DK8 | 184 | LLLVAGVDA |
| 81-84 | consensus | | LLLVAGVDA |

FIGURE 2E-1

| SEQ ID NO: | Isolate | | |
|---|---|---|---|
| 86 | DK12 | 1 | LEWRNVSGLYVLTNDCsNSSIVYEADDVILHTPGCVPCVQDGNTSTCWTSVTPTVAVRYVG |
| 87 | HK10 | 1 | LEWRNVSGLYVLTNDCpNSSIVYEADDVILHTPGCVPCVQDGNTSTCWTSVTPTVAVRYVG |
| 88 | S2 | 1 | LEWRNTSGLYVLTNDCSNSSIVYEADDVILHTPGCVPCVQDGNTSTCWTPVTPTVAVRYVG |
| 90 | S54 | 1 | LEWRNTSGLYiLTNDCSNSSIVYEADDVILHTPGCVPCVQDGNTSTCWTPVTPTVAVRYVG |
| 89 | S52 | 1 | LEWRNTSGLYvLTNDCSNSSIVYEADDVILHTPGCVPCVQDGNTSmCWTPVTPTVAVRYVG |
| 86-90 | consensus | | LEWRNtSGLYvLTNDCsNSSIVYEADDVILHTPGCVPCVQDGNTStCWTpVTPTVAVRYVG |

| SEQ ID NO: | Isolate | | |
|---|---|---|---|
| 86 | DK12 | 62 | ATTASIRSHVDLLVGAATMCSALYVGDvCGAVFLVGQAFTFRPRRHQTVQTCNCSLYPGHL |
| 87 | HK10 | 62 | ATTASIRSHVDLLVGAATMCSALYVGDMCGAVFLVGQAFTFRPRRHQTVQTCNCSLYPGHL |
| 88 | S2 | 62 | ATTASIRSHVDLLVGAATMCSALYVGDMCGAVFLVGQAFTFRPRRHQTVQTCNCSLYPGHL |
| 90 | S54 | 62 | ATTASIRSHVDLLVGAATLCSALYVGDMCGAVFLVGQAFTFRPRRHQTVQTCNCSLYPGHL |
| 89 | S52 | 62 | ATTASIRSHVDLLVGAATLCSALYVGDMCGAVFLVGQAFTFRPRRHQTVQTCNCSLYPGHv |
| 86-90 | consensus | | ATTASIRSHVDLLVGAATmCSALYVGDmCGAVFLVGQAFTFRPRRHQTVQTCNCSLYPGHl |

FIGURE 2E-2

| SEQ ID NO: | Isolate | | |
|---|---|---|---|
| 86 | DK12 | 123 | SGHRMAWDMMMNWSPAVGMVVAHVLRLPQTLFDIIAGAHWGImAGLAYYSMQGNWAKVAII |
| 87 | HK10 | 123 | SGHRMAWDMMMNWSPAVGMVVAHVLRLPQTLFDIIAGAHWGILAGLAYYSMQGNWAKVAII |
| 88 | S2 | 123 | SGHRMAWDMMMNWSPAVGMVVAHVLRLPQTLFDIIAGAHWGILAGLAYYSMQGNWAKVAII |
| 90 | S54 | 123 | SGHRMAWDMMMNWSPAVGMVVAHVLRLPQTvFDIIAGAHWGILAGLAYYSMQGNWAKVAII |
| 89 | S52 | 123 | SGHRMAWDMMMNWSPAVGMVVAHILRLPQTLFDILAGAHWGILAGLAYYSMQGNWAKVAII |
| 86-90 | consensus | | SGHRMAWDMMMNWSPAVGMVVAHvLRLPQTlFDiiAGAHWGIlAGLAYYSMQGNWAKVAIv |

| SEQ ID NO: | Isolate | | |
|---|---|---|---|
| 86 | DK12 | 184 | MVMFSGVDA |
| 87 | HK10 | 184 | MVMFSGVDA |
| 88 | S2 | 184 | MVMFSGVDA |
| 90 | S54 | 184 | MIMFSGVDA |
| 89 | S52 | 184 | MIMFSGVDA |
| 86-90 | consensus | | MvMFSGVDA |

FIGURE 2F

```
SEQ ID NO:    Isolate
    94          Z7      1   VNYhNASGVYHiTNDCPNSSImYEAEHHILHLPGCVPCVReGNQSRCWVALTPTVAAPYIG
                            ||| |||||||| |||||||||| ||||||| ||||||| || |||||||||||| ||||
    93          Z6      1   VNYRNASGVYHVTNDCPNSSIVYEAEHqILHLPGCILHLPGCVRVGNQSRCWVALTPTVAvsYIG
93-94 consensus (Z6)       VNYrNASGVYHvTNDCPNSSIvYEAEHqILHLPGClPCVRvGNQSRCWVALTPTVAvsYIG SEQ ID NO:    Isolate
    94          Z7     62   APLESiRRHVDLMVGAATVCSALYIGDLCGGVFLVGQMFSFQPRRHWTTQDCNCSIYAGHV
                            |||  ||||||||||||||||||| |||||||||||||||||||||||||||||||||
    93          Z6     62   APLdSLRRHVDLMVGAATVCSALYvGDLCGGaFLVGQMFSFQPRRHWTTQDCNCSIYAGHI
93-94 consensus (Z6)       APLdSlRRHVDLMVGAATVCSALYvGDLCGGaFLVGQMFSFQPRRHWTTQDCNCSIYAGHi SEQ ID NO:    Isolate
    94          Z7    123   TGHRMAWDMMMNWSPTTTLvLAQVMRIPSTLVDLLTGGHWGiLiGvAYFCMQANWAKVILV
                            |||||||||||||||||||| |||||||||||||| |||||| | ||||| |||||||||
    93          Z6    123   TGHRMAWDMMMNWSPTTTLLLAQVMRIPSTLVDLLaGGHWGvLvGLAYFSMQANWAKVILV
93-94 consensus (Z6)       TGHRMAWDMMMNWSPTTTLlLAQVMRIPSTLVDLLaGGHWGvLvGlAYFsMQANWAKVILV SEQ ID NO:    Isolate
    94          Z7    184   LFLyAGVDA
                            ||| |||||
    93          Z6    184   LFLFAGVDA
93-94 consensus (Z6)       LFLfAGVDA
```

FIGURE 2G-1

| SEQ ID NO: | Isolate | | |
|---|---|---|---|
| 98 | SA5 | 1 | VPYRNASGVYHVTNDCPNSSIVYEADNLILHAPGCVPCVkegNVSRCWVQITPTLSAPNLG |
| 100 | SA7 | 1 | VPYRNASGVYHVTNDCPNSSIVYEADNLILHAPGCVPCVRQnNVSRCWVQITPTLSAPNLG |
| 97 | SA4 | 1 | VPYRNASGVYHVTNDCPNSSIVYEADNLILHAPGCVPCVRQDNVSkCWVQITPTLSAPNLG |
| 96 | SA1 | 1 | VPYRNASGVYHVTNDCPNSSIVYEADNLILHAPGCVPCVRQDNVSRCWVQITPTLSAPtfG |
| 99 | SA6 | 1 | VPYRNASGVYHVTNDCPNSSIVYEAD sLILHAPGCVPCVRkDNVSRCWVhITPTLSAPSLG |
| 101 | SA13 | 1 | VPYRNASGVYHVTNDCPNSSIVYEADDLILHAPGCVPCVRggNVSRCWVqITPTLSAPSLG |
| 96-101 | consensus | | VPYRNASGVYHVTNDCPNSSIVYEADnLILHAPGCVPCVrqdNVSrCWVqITPTLSAPnlG |

| SEQ ID NO: | Isolate | | |
|---|---|---|---|
| 98 | SA5 | 62 | AVTAPLRRvVDYLAGGAALCSALYVGDACGAVFLVGQMFtYRPRQHTTVQDCNCSIYSGHI |
| 100 | SA7 | 62 | AVTAPLRRRAVDYLAGGAALCSALYVGDACGAVFLVGQMFsYRPRQHTTVQDCNCSIYSGHI |
| 97 | SA4 | 62 | AVTAPLRRRAVDYLAGGAALCSALYVGDACGAVFLVGQMFTYRPRQHTTVQDCNCSIYSGHI |
| 96 | SA1 | 62 | AVTAPLRRRAVDYLAGGAALCSALYVGDACGAVFLVGQMFTYRPRQHTTVQDCNCSIYSGHI |
| 99 | SA6 | 62 | AVTAPLRRRAVDYLAGGAALCSALYVGDvCGAlFLVGQMFTYRPRQHaTVQDCNCSIYSGHI |
| 101 | SA13 | 62 | AVTAPLRRRAVDYLAGGAALCSALYVGDaCGAvFLVGQMFTYsPRrHnvVQDCNCSIYSGHI |
| 96-101 | consensus | | AVTAPLRRaVDYLAGGAALCSALYVGDaCGAvFLVGQMFtYrPRqHttVQDCNCSIYSGHI |

FIGURE 2G-2

| SEQ ID NO: | Isolate | | |
|---|---|---|---|
| 98 | SA5 | 123 | TGHRMAWDMMMNWSPTTALVMAQvLRIPQVVIDIIAGGHWGVLFAVAYFASAANWAKVVLV |
| 100 | SA7 | 123 | TGHRMAWDMMMNWSPTTALVMAQLLRIPQVVIDIIAGGHWGVLFAAAYFASAANWAKVVLV |
| 97 | SA4 | 123 | TGHRMAWDMMMNWSPTTALLMAQLLRIPQVVIDIIAGGHWGVLFAAAYFASAANWAKViLV |
| 96 | SA1 | 123 | TGHRMAWDMMMNWSPTTALLMAQMLRIPQVVIDIIAGGHWGVLFAAAYFASAANWAKVVLV |
| 99 | SA6 | 123 | TGHRMAWDMMMNWSPaTALVMAQMLRIPQVVIDIIAGGHWGVLFAAAYFASAANWAKVVLV |
| 101 | SA13 | 123 | TGHRMAWDMMMNWSPtTALVMAQlLRIPQVVIDIIAGaHWGVLFAAAYyASAANWAKVVLV |
| 96-101 | consensus | | TGHRMAWDMMMNWSPtTALvMAQlLRIPQVVIDIIAGgHWGVLFAaAYfASAANWAKVvLV |

| SEQ ID NO: | Isolate | | |
|---|---|---|---|
| 98 | SA5 | 184 | LFLFAGVDg |
| 100 | SA7 | 184 | LFLFAGVDA |
| 97 | SA4 | 184 | LFLFAGVDA |
| 96 | SA1 | 184 | LFLFAGVDg |
| 99 | SA6 | 184 | LFLFAGVDA |
| 101 | SA13 | 184 | LFLFAGVDA |
| 96-101 | consensus | | LFLFAGVDa |

FIGURE 2H-1

| SEQ ID NO: | Genotype | |
|---|---|---|
| 81-84 | (IV/2b) | 1 VEVRNiSsSYYATNDCSNnSITWQLTnAVLHLPGCVPCENDNGTLrCWIQVTPNVAVKHRG |
| 85 | (2c) | 1 VEVKDTGDSYMPTNDCSNSSIVWQLEGAVLHTPGCVPCERTANVSRCWVPVAPNLAISQPG |
| 77-80 | (III/2a) | 1 aqVkNTstsYMVTNDCSNdSITWQLqAAVLHVPGCvPCEkvGNtSRCWIPVsPNVAVqqPG |
| 86-90 | (V/3a) | 1 LEWRNtSGLYvLTNDCsNSSIVYEADDVILHTPGCVPCVQDGNTStCWTpVTPTVAVRYVG |
| 60-76 | (II/1b) | 1 yEVrNVSGvYhVTNDCSNsSiVyEaaDmImHTPGCvPCVrEnNsSrCWVALtPTLAARNas |
| 52-59 | (I/1a) | 1 yQVRNStGLYHVTNDCPNSSIVYEaADaILHsPGCVPCVREgnasrCWVavtPTVATRDGK |
| 91 | (4a) | 1 EHYRNASGIYHITNDCPNSSIVYEADHHILHLPGCVPCVMTGNTSRCWTPVTPTVAVAHPG |
| 93-94 | (4c) | 1 VNYrNASGVYHvTNDCPNSSIVYEAEHqILHLPGClPCVRvGNQSRCWVALTPTVAvsYIG |
| 95 | (4d) | 1 YNYRNSSGVYHVTNDCPNSSIVYETDYHILHLPGCVPCVREGNKSTCWVSLTPTVAAQHLN |
| 92 | (4b) | 1 VHYRNASGVYHVTNDCPNTSIVYETEHHIMHLPGCVPCVRTENTSRCWVPLTPTVAAPYPN |
| 96-101 | (5a) | 1 VPYRNASGVYHVTNDCPNSSIVYEADnLILHAPGCVPCVrqdNVSrCWVqITPTLSAPnlG |
| 102 | (6a) | 1 LTYGNSSGLYHLTNDCPNSSIVLEADAMILHLPGCLPCVRVDDRSTCWHAVTPTLAIPNAS |
| 52-102 | consensus | Y TNDC N S H PGC PC CW P |

| SEQ ID NO: | Genotype | |
|---|---|---|
| 81-84 | (IV/2b) | 62 ALTHNLRtHvDmIVMAATVCSALYVGDvCGAVMIvSQAfIiSPErHnFTQECNCSIYQGhI |
| 85 | (2c) | 62 ALTKGLRAHIDIIVMSATVCSALYVGDVCGALMLAAQVVVVSPQHHTFVQECNCSIYPGRI |
| 77-80 | (III/2a) | 62 ALTQGLRTHIDMVVMSATLCSALYVGDlCGGvMLAAQMFIvSPqhHwFVQeCNCSIYPGTI |
| 86-90 | (V/3a) | 62 ATTASIRSHVDLLVGAATmCSALYVGDmCGAVFLVGQAFTFRPRRHQTVQTCNCSLYPGH1 |
| 60-76 | (II/1b) | 62 vpTttIRrHVDLLVGAAaFCSAMYVGDLCGSVfLvSQLFTfSPRrheTvQdCNCSIYPGhv |
| 52-59 | (I/1a) | 62 LPatQLRRhIDLLVGSATLCSALYVGDLCGSVFLVgQLFTfSPRrhWTTQdCNCSIYPGHI |
| 91 | (4a) | 62 APLESFRRHVDLMVGAATLCSALYVGDLCGGAFLMGQMITFRPRRHWTTQECNCSIYTGHI |
| 93-94 | (4c) | 62 APLdSlRRHVDLMVGAATVCSALvGDLCGGAFLVGQMFSFQPRRHWTTQDCNCSIYAGHi |
| 95 | (4d) | 62 APLESLRRHVDLMVGGATLCSALYIGDVCGCGGVFLVGQLFTFQPRRHWTTQDCNCSIYTGHI |
| 92 | (4b) | 62 APLESMRRHVDLMVGAATMCSAFYIGDLCGGVFLVGQLFDFRPRRHWTTQDCNCSIYPGHV |
| 96-101 | (5a) | 62 AVTAPLRRavDYLAGGAALCSALYVGDaCGAvFLVGQMFtYrPRqHttVQDCNCSIYSGHI |
| 102 | (6a) | 62 TPATGFRRHVDLLAGAAVCSSLYIGDLCGSLFLAGQLFTFQPRRHWTVQDCNCSIYTGHV |
| 52-102 | consensus | R D A CS Y GD CG Q P Q CNCS Y G |

FIGURE 2H-2

| SEQ ID NO: | Genotype | | |
|---|---|---|---|
| 81-84 | (IV/2b) | 123 | TGHRMAWDMMLNWSPTLTMILAYAARVPELvLeVVFGGHWGVVFGLAYFSMQGAWAKVIAI |
| 85 | (2c) | 123 | TGHRMAWDMMMNWSPTTTMLLAYLVRIPEVILDIVTGGHWGVMFGLAYFSMQGSWAKVIVI |
| 77-80 | (III/2a) | 123 | TGHRMAWDMMMNWSPTaTmILAYaMRVPEVIiDIisGAHWGVmFGLAYFSMQGAWAKVvVI |
| 86-90 | (V/3a) | 123 | SGHRMAWDMMMNWSPAVGMVVAHvLRLPQT1FDIiAGAHWGIiAGLAYYSMQGNWAKVAIi |
| 60-76 | (II/1b) | 123 | sGHRMAWDMMMNWSPTaALVvSQLLRiPQAvvDmVaGAHWGvLAGLAYYSMvGNWAKVLIV |
| 52-59 | (I/1a) | 123 | TGHRMAWDMMMNWSPTtALVvAQLLRiPQAiLDMIAGAHWGVLAGIAYFSMvGNWAKV1vV |
| 91 | (4a) | 123 | TGHRMAWDMMMNWSPTTLLLAQIMRVPTAFLDMVAGGHWGVLAGLAYFSMQGNWAKVVLV |
| 93-94 | (4c) | 123 | TGHRMAWDMMMNWSPTTLlLAQVMRIPSTLVDLLaGGHWGvLvG1AYFsMQANWAKVI1v |
| 95 | (4d) | 123 | TGHRMAWDMMMNWSPTATLVLAQLMRIPGAMVDLLAGGHWGILvGIAYFSMQANWAKVILv |
| 92 | (4b) | 123 | SGHRMAWDMMMNWSPTSALIMAQILRIPSILGDLLTGGHWGVLAGLAFFSMQSNWAKVILV |
| 96-101 | (5a) | 123 | TGHRMAWDMMMNWSPtTALvMAQ11RIPQVVIDIIAGghHWGVLFAaAYfASAANWAKVvLv |
| 102 | (6a) | 123 | TGHRMAWDMMMNWSPTTTLVLSSILRVPEICASVIFGGHWGILLAVAYFGMAGNWLKVLAV |

| 52-102 | consensus | GHRMAWDMM NWSP | R P | G HWG | A | W KV |

| SEQ ID NO: | Genotype | | |
|---|---|---|---|
| 81-84 | (IV/2b) | 184 | LLLVAGVDA |
| 85 | (2c) | 184 | LLLTAGVEA |
| 77-80 | (III/2a) | 184 | LLLaAGVDA |
| 86-90 | (V/3a) | 184 | MvMFSGVDA |
| 60-76 | (II/1b) | 184 | mLLFAGVDG |
| 52-59 | (I/1a) | 184 | LLLFaGVDA |
| 91 | (4a) | 184 | LFLFAGVDA |
| 93-94 | (4c) | 184 | LFLFAGVDA |
| 95 | (4d) | 184 | LFLFAGVDA |
| 92 | (4b) | 184 | LFLFAGVEG |
| 96-101 | (5a) | 184 | LFLFAGVDa |
| 102 | (6a) | 184 | LFLFAGVEA |

| 52-102 | consensus | GV |

| SEQ ID NO: | ISOLATE | | |
|---|---|---|---|
| 108 | DR4 | 1 | ATGAGCACGAATCCTAAACCTCAAAGAAAAAACCAAACGTAACACCAACCGTCGCCCACAGG |
| 103 | DK7 | 1 | ATGAGCACGAATCCTAAACCTCAAAGAAAAAACCAAACGTAACACCAACCGTCGCCCACAGG |
| 104 | US11 | 1 | ATGAGCACGAATCCTAAACCTCAAAGAAAAAACCAAACGTAACACCAACCGTCGCCCACAGG |
| 105 | S14 | 1 | ATGAGCACGAATCCTAAACCTCAAAGAAAAAACCAAACGTAACACCAACCGTCGCCCACAGG |
| 106 | SW1 | 1 | ATGAGCACGAATCCTAAACCTCAAAGAAAAAACCAAACGTAACACCAACCGTCGCCCACAGG |
| 107 | S18 | 1 | ATGAGCACGAATCCTAAACCTCAAAGAAAAAACCAAACGTAACACCAACCGTCGCCCACAGG |
| 103-108 | consensus | | ATGAGCACgAATCCTAAACCTCAAAGAAAAAACCAAACGTAACACCAACCGTCGCCCACAGG |

| SEQ ID NO: | ISOLATE | | |
|---|---|---|---|
| 108 | DR4 | 62 | ACGTCAAGTTCCCGGGTGCGGTCAGATCGTTGGTGGAGTTTACTTGTTGCCGCGCAGGGG |
| 103 | DK7 | 62 | ACGTCAAGTTCCCGGGTGCGGTCAGATCGTTGGTGGAGTTTACTTGTTGCCGCGCAGGGG |
| 104 | US11 | 62 | ACGTCAAGTTCCCGGGTGCGGTCAGATCGTTGGTGGAGTTTACTTGTTGCCGCGCAGGGG |
| 105 | S14 | 62 | ACGTCAAGTTCCCGGGTGCGGTCAGATCGTTGGTGGAGTTTACTTGTTGCCGCGCAGGGG |
| 106 | SW1 | 62 | ACGTCAAGTTCCCGGGTGCGGTCAGATCGTTGGTGGAGTTTACTTGTTGCCGCGCAGGGG |
| 107 | S18 | 62 | ACGTtAAGTTCCCGGGTGCGGTCAGATCGTTGGTGGAGTTTACTTGTTGCCGCGCAGGGG |
| 103-108 | consensus | | ACGTcAAGTTCCCGGGTGCGGTCAGATCGTTGGTGGAGTTTACTTGTTGCCGCGCAGGGG |

| SEQ ID NO: | ISOLATE | | |
|---|---|---|---|
| 108 | DR4 | 123 | CCCTAGATTGGGTGTGCGCGCGaCGAGGAAGAGACTTCCGAGCGGTCGCAACCTCGAGGTAGA |
| 103 | DK7 | 123 | CCCTAGATTGGGTGTGCGCGCGCGACGAGGAAGAGACTTCCGAGCGGTCGCAACCTCGAGGTAGA |
| 104 | US11 | 123 | CCCTAGATTGGGTGTGCGCGCGCGACGAGGAAGAGACTTCCGAGCGGTCGCAACCTCGAGGTAGA |
| 105 | S14 | 123 | CCCTAGATTGGGTGTGCGCGCGCGACGAGGAAGAGACTTCCGAGCGGTCGCAACCTCGAGGTAGA |
| 106 | SW1 | 123 | CCCTAGATTGGGTGTGCGCGCGCGACGAGGAAGAGACTTCCGAGCGGTCGCAACCTCGAGGTAGA |
| 107 | S18 | 123 | CCCTAGATTGGGTGTGCGCGCGCGACGAGGAAGAGACTTCCGCGGTCGCAACCTCGaGGTAGA |
| 103-108 | consensus | | CCCTAGATTGGGTGTGCGCGCGCGaCGAGGAAGAGACTTCCGAGCGGTCGCAACCTCGaGGTAGA |

FIGURE 6A-2

| SEQ ID NO: | ISOLATE | | |
|---|---|---|---|
| 108 | DR4 | 184 | CGTCAGCCTATCCCCAAGGCgCGTCGGCTCGGCCCGAGGGCAGGACCTGGGCTCAGCCCGGGTACC |
| 103 | DK7 | 184 | CGTCAGCCTATCCCCAAGGCACGTCGGCTCGGCCCGAGGGCAGGACCTGGGCTCAGCCCGGGTACC |
| 104 | US11 | 184 | CGTCAGCCTATCCCCAAGGCACGTCGGCTCGGCCCGAGGGCAGGACCTGGGCTCAGCCCGGGTACC |
| 105 | S14 | 184 | CGTCAGCCTATCCCCAAGGCACGTCGGCTCGGCCCGAGGGCAGGACCTGGGCTCAGCCCGGGTATC |
| 106 | SW1 | 184 | CGTCAGCCTATCCCCAAGGCGCGTCGGCGTCGGCCCGAGGGCAGGACCTGGGCTCAGCCCGGGTATC |
| 107 | S18 | 184 | CGTCAGCCTATCCCCAAGGCGCGTCGGCGTCGGCCCGAGGGCAGGACCTGGGCTCAGCCCGGGTACC |

103-108 consensus  CGTCAGCCTATCCCCAAGGC-CGTCGGCCCGAGGGCAGGACCTGGGCTCAGCCCGGGTACC

| SEQ ID NO: | ISOLATE | | |
|---|---|---|---|
| 108 | DR4 | 245 | CTTGGCCCCTCTATGGCAATGAGGGCTGCGGGTGGGCGGGATGGCTCCTGTCcCCCCGTGG |
| 103 | DK7 | 245 | CTTGGCCCCTCTATGGCAATGAGGGCTGCGGGTGGGCGGGATGGCTCGTGTCTCCCCGTGG |
| 104 | US11 | 245 | CTTGGCCCCTCTATGGCAATGAGGGCTGCGGGTGGGCGGGATGGCTCGTGTCTCCCCGTGG |
| 105 | S14 | 245 | CTTGGCCCCTCTATGGCAATGAGGGCTGCGGGTGGGCGGGATGGCTCTCCGTGTCTCCCCGTGG |
| 106 | SW1 | 245 | CTTGGCCCCTCTATGGCAATGAGGGCTGCGGGTGGGCGGaTGGCGGGTGGGCGGGATGGCTCCTGTCTCCCCGTGG |
| 107 | S18 | 245 | CTTGGCCCCTCTATGGCAATGAGGGCTGCGGgTGGGCGGGTGGGCGGGATGGCTCCTGTCTCCCCGTGG |

103-108 consensus  CTTGGCCCCTCTATGGCAATGAGGGCTGCGGGTGGGCGGGATGGCTCCTGTC-CCCCGTGG

| SEQ ID NO: | ISOLATE | | |
|---|---|---|---|
| 108 | DR4 | 306 | CTCTCGGCCTAGCTGGGGCCCCACAGACCCCCGGCGtAGGTCGCGCAATTTGGGTAAgGTC |
| 103 | DK7 | 306 | CTCTCGGCCTAGCTGGGGCCCCACAGACCCCCGGCGCAGGTCGCGCAATTTGGGTAAaGTC |
| 104 | US11 | 306 | CTCTCGGCCTAGCTGGGGCCCCACAGACCCCCGGCGTAGGTCGCGCAATTTGGGTAAGGTC |
| 105 | S14 | 306 | CTCTCGGCCTAGCTGGGGCCCCACAGgCCCCCGGCGTAGGTCGCGCAATTTGGGTAAGGTC |
| 106 | SW1 | 306 | CTCTCGGCCTAGCTGGGGCCCTACAGACCCCCGGCGTAGGTCGCGCAATTTGGGTAAGGTC |
| 107 | S18 | 306 | CTCTCGGCCTAGCTGGGGCCCTACAGACCCCCGGCGTAGGTCGCGCAATTTGGGTAAGGTC |

103-108 consensus  CTCtCGGCCTAGCTGGGGCCCcACaGACCCCCGGCGtAGGTCGCGCAATTTGGGtAAgGTC

FIGURE 6A-3

| SEQ ID NO: | ISOLATE | | |
|---|---|---|---|
| 108 | DR4 | 367 | ATCGAcACCCTcACGTGCGGCTTCGCCGACCTCATGGGTACATcCCGCTCGTCGGCCCC |
| 103 | DK7 | 367 | ATCGATACCCTtACGTGCGGCTTCGCCGACCTCATGGGTACATACCGCTCGTCGGCGCCC |
| 104 | US11 | 367 | ATCGATACCCTtACGTGCGGCTTCGCCGACCTCATGGGTACATACCGCTCGTCGGCGCCC |
| 105 | S14 | 367 | ATCGATACCCTCACGTGCGGCTTCGCCGACCTCATGGGTACATACCGCTCGTCGGCGCCC |
| 106 | SW1 | 367 | ATCGATACCCTCACGTGCGGCTTCGCCGACCTCATGGGTACATTCCGCTCGTCGGCGCCC |
| 107 | S18 | 367 | ATCGATACCCTCACGTGCGGCTTCGCCGACCTCATGGGTACATTCCGCTCGTCGGCGCCC |
| 103-108 | consensus | | ATCGAtACCCTcACGTGCGGCTTCGCCGACCTCATGGGTACATaCCGCTCGTCGGCGCCC |

| SEQ ID NO: | ISOLATE | | |
|---|---|---|---|
| 108 | DR4 | 428 | CcCCTTGGGgGCGTGCCAGGGCCCTGGCGCGTCCGaGTTCTGGAAGACGGCGTGAA |
| 103 | DK7 | 428 | CTCTTGGAGGCGTGCCAGGCGCCCTGGCGCATGGCGTCCGGTTCTGGAAGACGGCGTGAA |
| 104 | US11 | 428 | CTCTCGGAGGCGTGCCAGGCGCCCTGGCGCATGGCGTCCGGTTCTGGAAGACGGCGTGAA |
| 105 | S14 | 428 | CTCTCGGGGGCGTGCCAGGCGCCCTGGCGCATGGCGTCCGGTTCTGGAAGACGGCGTGAA |
| 106 | SW1 | 428 | CcCCTCGGAGGCGTGCCAGGCGCCCTGGCGCATGGCGTCCGGTTCTGGAAGACGGCGTGAA |
| 107 | S18 | 428 | CTCTtGGAGGCGTGCCAGGCGCCCTGGCGCATGGCGTCCGGTTCTGGAAGACGGCGTGAA |
| 103-108 | consensus | | CtCT-GGaGGCGTGCCAGGGCCCTGGCGCATGGCGTCCGgTTCTGGAAGACGGCGTGAA |

| SEQ ID NO: | ISOLATE | | |
|---|---|---|---|
| 108 | DR4 | 489 | CTATGCAACAGGGAAtCTTCCTGGTTGCTCTTTCTCTATCTTCCTTTGGCttTGCTCTCT |
| 103 | DK7 | 489 | CTATGCAACAGGAACCTTCCTGGTTGCTCTCTCTTCTCTATCTTCCTTTTGGCCCTGCTCTCT |
| 104 | US11 | 489 | CTATGCAACAGGAACCTTCCTGGTTGCTCTCTCTTCTCTATCTTCCTTCTGCCCTGCTCTCT |
| 105 | S14 | 489 | CTATGCAACAGGAACCTTCCTGGTTGCTCTTTCTCTTCTCTATCTTCCTCCTaGCCCTGCTTTCT |
| 106 | SW1 | 489 | CTATGCAACAGGAACCTTCCTGGTTGCTCTCTCTCTCTCTATCTTCCTTCTGCCCTGCTTCT |
| 107 | S18 | 489 | CTATGCAACAGGGAACCTTCCTGGTTGCTCTCTCTCTCTCTATCTTCCTTCTGCCCTGCTCTCT |
| 103-108 | consensus | | CTATGCAACAGGGAAcCTTCCTGGTTGCTCTCTTTCTCTtCTCTATCTtCCTtcTgCccTGCTcTCT |

FIGURE 6A-4

| SEQ ID NO: | ISOLATE | | |
|---|---|---|---|
| 108 | DR4 | 550 | TGCtTGACCGTGCCCGCaTCGGCC |
| 103 | DK7 | 550 | TGCCTGACCGTGCCCGCTTCGGCC |
| 104 | US11 | 550 | TGCCTGACTGTGCCCGCTTCAGCC |
| 105 | S14 | 550 | TGCCTGACTGTGCCCGCTTCAGCC |
| 106 | SW1 | 550 | TGCCTGACaGTGCCCGCGTCAGCC |
| 107 | S18 | 550 | TGtCTGACtGTGCCCGCGTCAGCt |

103-108  consensus          TGccTGActGTGCCCGCtTCaGCc

FIGURE 6B-1

| SEQ ID NO: | ISOLATE | | |
|---|---|---|---|
| 119 | S9 | 1 | ATGAGCACGAATCCTAAACCTCAAAGAAAAACCAAACGTAACACCAACCGCCGCCCACAGG |
| 117 | IND3 | 1 | ATGAGCACGAATCCTAAACCTCAAAGAAAAACCAAACGTAACACCAACCGCCGCCCACAGG |
| 118 | IND8 | 1 | ATGAGCACGAATCCTAAACCTCAAAGAAAAACCAAACGTAACACCAACCGCCGCCCACAGG |
| 111 | D1 | 1 | ATGAGCACGAATCCTAAACCTCAAAGAAAAACCAAACGTAACACCAACCGCCGCCCACAGG |
| 112 | US6 | 1 | ATGAGCACGAATCCTAAACCTCAAAGAAAAACCAAACGTAACACCAACCGCCGCCCACAGG |
| 113 | P10 | 1 | ATGAGCACGAATCCTAAACCTCAAAGAAAAACCAAACGTAACACCAACCGCCGCCCACAGG |
| 114 | DK1 | 1 | ATGAGCACGAATCCTAAACCTCAAAGAAAAACCAAACGTAACACCAACCGCCGCCCACAGG |
| 115 | T10 | 1 | ATGAGCACGAATCCTAAACCTCAAAGAAAAACCAAACGTAACACCAACCGCCGCCCACAGG |
| 116 | SW2 | 1 | ATGAGCACGAATCCTAAACCTCAAAGAAAAACCAAACGTAACACCAACCGCCGCCCACAGG |
| 122 | HK4 | 1 | ATGAGCACGAATCCTAAACCTCAAAGAAAGACCAAACGTAACACCAACCGCCGCCCACAGG |
| 109 | SA10 | 1 | ATGAGCACGAATCCTAAACCTCAAAGAAAAACCAAACGTAACACCAACCGCCGCCCACAGG |
| 110 | S45 | 1 | ATGAGCACGAATCCTAAACCTCAAAGACAAAACCAAACGTAACACCAACCGCCGCCCACAGG |
| 123 | P8 | 1 | ATGAGCACGACTCCTAAACCTCAAAGAAAAACCAAACGTAACACCAACCGCCGCCCACAGG |
| 124 | T3 | 1 | ATGAGCACGAATCCTAAACCTCAAAGAAAAACCAAACGTAACACCAgCCGCCGCCCACAGG |
| 120 | HK3 | 1 | ATGAGCACGAATCCTAAACCTCAAAGAAAAACCAAACGTAACACCAACCGCCGCCCACAGG |
| 121 | HK5 | 1 | ATGAGCACGAATCCTAAACCTCAAAGAAAAACCAAACGTAACACCAACCGCCGCCCACAGG |

109-124 consensus    ATGAGCACGAaTCCTAAACCTCAAAGAaAaACCAAACGTAACACCAaCCGCCGCCCACAGG

FIGURE 6B-2

| SEQ ID NO: | ISOLATE | | |
|---|---|---|---|
| 119 | S9 | 62 | ACGTtAAGTTCCCGGGCGGTGGtCAGATCGTCGGTGGAGTTTACCTGTTGCCGCGCAGGGG |
| 117 | IND3 | 62 | ACGTCAAGTTCCCGGGCGGTGGCGGTGGCCAGATCGTCGGTGGAGTTTACCTGTTGCCGCGCAGGGG |
| 118 | IND8 | 62 | ACGTCAAGTTCCCGGGCGGTGGCGGTGGCCAGATCGTCGGTGGAGTTTACCTGTTGCCGCGCAGGGG |
| 111 | D1 | 62 | ACGTCAAGTTCCCGGGCGGTGGCGGTGGTCAGATCGTCGGTGGAGTTTACCTGTTGCCGCGCAGGGG |
| 112 | US6 | 62 | ACGTCAAGTTCCCGGGCGGTGGCGGTGGTCAGATCGTCGGTGGAGTTTACCTGTTGCCGCGCAGGGG |
| 113 | P10 | 62 | ACGTCAAGTTCCCGGGCGGTGGCGGTGGTCAGATCGTCGGTGGAGTTTACCTGTTGCCGCGCAGGGG |
| 114 | DK1 | 62 | ACGTCAAGTTCCCGGGCGGTGGCGGTGGTCAGATCGTCGGTGGAGTTTACCTGTTGCCGCGCAGGGG |
| 115 | T10 | 62 | ACGTCAAGTTCCCGGGCGGTGGCGGTGGTCAGATCGTCGGTGGAGTTTACCTGTTGCCGCGCAGGGG |
| 116 | SW2 | 62 | ACGTCAAGTTCCCGGGCGGTGGCGGTGGCCAGATCGTCGGTGGAGTTTACCTGTTGCCGCGCAGGGG |
| 122 | HK4 | 62 | ACGTtAAGTTCCCGGGCGGTGGCGGTGGCCAGATCGTCGGTGGAGTTTACCTGTTGCCGCGCAGGGG |
| 109 | SA10 | 62 | ACGTCAAGTTCCCGGGCGGTGGCGGTGGTCAGATCGTCGGTGGAGTCTAtCTGTTGCCGCGCAGGGG |
| 110 | S45 | 62 | ACGTCAAGTTCCCGGGtGGcGGTGGCGGTGGTCAGATCGTCGGTGGAGTTTACCTGTTGCCGCGCAGGGG |
| 123 | P8 | 62 | ACGTtAAGTTCCCGGGCGGTGGCGGTGGTCAGATCGTCGGTGGAGTTTACCTGTTGCCGCGCAGGGG |
| 124 | T3 | 62 | ACGTtAAGTTCCCGGGCGGTGGCGGTGGTCAGATCGTCGGTGGAGTTTACCTGTTGCCGCGCAGGGG |
| 120 | HK3 | 62 | ACGTCAAGTTCCCGGGCGGTGGCGGTGGTCAGATCGTCGGTGGAGTTTACCTGTTGCCGCGCAGGGG |
| 121 | HK5 | 62 | ACGTCAAGTTCCCGGGCGGTGGCGGTGGTCAGATCGTCGGTGGAGTTTACCTGTTGCCGCGCAGGGG |
| 109-124 | consensus | | ACGTcAAGTTCCCGGGcGGtGGtCAGATCGTtGGTGGAGTTtACCTGTTGCCGCGCAGGGG |

FIGURE 6B-3

| SEQ ID NO: | ISOLATE | |
|---|---|---|
| 119 | S9 | 123 CCCCAGGTTGGGTGTGCGCGCaACTAGGAAGAGACTTCCGAGCGGTCGCAACCTCGTGGAAGG |
| 117 | IND3 | 123 CCCCAGGTTGGGTGTGCGCGCGACTAGGAAGAGACTTCCGAGCGGTCGCAACCTCGTGGAAGG |
| 118 | IND8 | 123 CCCCAGGTTGGGTGTGCGCGCGACTAGGAAGAGACTTCCGAGCGGTCGCAACCTCGTGGAAGG |
| 111 | D1 | 123 CCCCAGGTTGGGTGTGCGCGCGACTAGGAAGAGACTTCCGAGCGGTCGCAACCTCGTGGAAGG |
| 112 | US6 | 123 CCCCAGGTTGGGTGTGCGCGCGACTAGGAAGAGACTTCCGAGCGGTCGCAACCTCGTGGAAGG |
| 113 | P10 | 123 CCCCAGGTTGGGTGTGCGCGCGACTAGGAAGAGACTTCCGAGCGGTCGCAACCTCGTGGAAGG |
| 114 | DK1 | 123 CCCCAGGTTGGGTGTGCGCGCGACTAGGAAGAGACTTCCGAGCGGTCGCAACCTCGTGGAAGG |
| 115 | T10 | 123 CCCCAGGTTGGGTGTGCGCGCGACTAGGAAGAGACTTCCGAGCGGTCGCAACCTCGTGGAAGG |
| 116 | SW2 | 123 CCCCAGGTTGGGTGTGCGCGCGACTAGGAAGAGACTTCCGAGCGGTCGCAACCTCGTGGAAGG |
| 122 | HK4 | 123 CCCCcGGTTGGGTGTGCGCGCGACTAGGAAGAGACTTCCGAGCGGTCGCAACCTCGTGGAAGG |
| 109 | SA10 | 123 CCCCAGGTTGGGTGTGCGCGCGACgAGGAAGAGACTTCCGAGCGGTCGCAACCTCGTGGAAGG |
| 110 | S45 | 123 CCCCAGGTTGGGTGTGCGCGCGACTAGGAAGAGACTTCCGAGCGGTCaCAACCTCGTGGACGG |
| 123 | P8 | 123 CCCCAGGTTGGGTGTGCGCGCGACTAGGAAGAGACTTCCGAGCGGTCGaTCGCAACCTCGTGGcCAGG |
| 124 | T3 | 123 CCCCAGGTTGGGTGTGCGCGCGACTAGGAAGAGACTTCCGAGCGGTCGCAACCTCGTGGAAGG |
| 120 | HK3 | 123 CCCCAGGTTGGGTGTGCGCGCGACCAGGAAGAGACTTCaGAGCGGTCGCAACCTCGTGGAAGG |
| 121 | HK5 | 123 CCCCAGGTTGGGTGTGCGCGCGACCAGGAAGAGACTTCCGAGCGGTCGCAACCTCGTGGAAGG |

109-124 consensus  CCCCaGgTTGGGTGTGCGCGCGgACTAGGAAGAGACTTCCGAGCGGtTCgCAACCTCGTGGaaGG

FIGURE 6B-4

| SEQ ID NO: | ISOLATE | | |
|---|---|---|---|
| 119 | S9 | 184 | CGACAACCTATCCCCAAGGCTCGCCatCCCGAGGGCAGGGCCTGGGCTCAGCCCGGTACC |
| 117 | IND3 | 184 | CGACAACCTATCCCCAAGGCTCGCCGGCCCGAGGGTAGGGCCTGGGCTCAGCCCGGTACC |
| 118 | IND8 | 184 | CGACAACCTATCCCCAAGGCTCGCCGGCCCGAGGGTAGGGCCTGGGCTCAGCCCGGCACC |
| 111 | D1 | 184 | CGACAACCTATCCCCAAGGCTCGCCGGCCCGAGGGTAGGGCCTGGGCTCAGCCCGGTACC |
| 112 | US6 | 184 | CGACAACCTATCCCCAAGGCTCGCCGGCCCGAGGGCAGGGCCTGGGCTCAGCCCGGTACC |
| 113 | P10 | 184 | CGACAACCTATCCCCAAGGCTCGCCGGCCCGAGGGCAGGGCCTGGGCTCAGCCCGGTACC |
| 114 | DK1 | 184 | CGACAACCTATCCCCAAGGCTCGCCGGCCCGAGGGCAGGGCCTGGGCTCAGCCCGGTACC |
| 115 | T10 | 184 | CGACAgCCTATCCCCAAGGCTCGCCAGCCCGAGGGCAGGGCCTGGGCTCAGCCCGGTACC |
| 116 | SW2 | 184 | CGACAACCTATCCCCAAGGCTCGCCAGCCCGAGGGCAGGGCCTGGGCTCAGCCCGGTACC |
| 122 | HK4 | 184 | CGACAACCTATCCCCAAGGCTCGCCAaCCCGAGGGCAGGACCTGGGCTCAGCCCGGTACC |
| 109 | SA10 | 184 | CGACAACCTATCCCCAAGGCTCGCCAGCCCGAGGGCAGGACCTGGGCCCAGCCCGGTACC |
| 110 | S45 | 184 | CGACAACCTATCCCCAAGGCTCGCCGGCCCGAGGGCAGGGCCTGGGCCCAGCCCGGCAtC |
| 123 | P8 | 184 | CGACAACCTATCCCCAAGGCTCGCCGGCCCGAGGGCAGGGCCTGGGCCCAGCCCGGCACC |
| 124 | T3 | 184 | CGACAACCTATCCCCAAGGCTCGCCGGCCCGAGGGTAGGGCCTGGGCTCAGCCCGGTACC |
| 120 | HK3 | 184 | CGACAACCTATCCCCAAGGCTCGCCaACCCGAGGGCAGGACCTGGGCTCAGCCCGGTATC |
| 121 | HK5 | 184 | CGACAACCTATCCCCAAGGCTCGCgACCCGAGGGCAGGACCTGGGCTCAGCCCGGTATC |

| 109-124 | consensus | CGACAaCCTATCCCCAAGGCTCGCCggCCCGAGGGCAGGgCCTGGGCtCAGCCCGGtAcC |
|---|---|---|

FIGURE 6B-5

| SEQ ID NO: | ISOLATE | | |
|---|---|---|---|
| 119 | S9 | 245 | CTTGGCCCCTCTAcGGCAATGAGGGCTTGGGGTGGGCAGGATGGCTCCTGTCACCCGtGG |
| 117 | IND3 | 245 | CTTGGCCCCTCTATGGCAATGAGGGCTTGGGGTGGGCAGGATGGCTCCTGTCACCCGCGG |
| 118 | IND8 | 245 | CTTGGCCCCTCTATGGCAATGAGGGCTTGGGGTGGGCAGGATGGCTCCTGTCACCCGCGG |
| 111 | D1 | 245 | CTTGGCCCCTCTATGGCAACGAGGGCTTGGGGTGGGCAGGATGGCTCCTGTCACCCGCGG |
| 112 | US6 | 245 | CTTGGCCCCTCTATGGCAACGAGGGCaTGGGGTGGGCAGGATGGCTCCTGTCACCCGTGG |
| 113 | P10 | 245 | CTTGGCCCCTCTATGGCAATGAGGGCTtGGGGTGGGCAGGATGGCTCCTGTCACCCGTGG |
| 114 | DK1 | 245 | CTTGGCCCCTCTATGGCAATGAGGGCATGGGGTGGGCAGGATGGCTCCTGTCACCCGcGG |
| 115 | T10 | 245 | CTTGGCCCCTCTATGGCAATGAGGGCATGGGGTGGGCAGGATGGCTCCTGTCACCCGtGG |
| 116 | SW2 | 245 | CcTGGCCCCTCTATGGCAATGAGGGCATGGGaTGGGCAGGATGGCTCCTGTCcCCCGCGG |
| 122 | HK4 | 245 | CTTGGCCCCTCTATGGCAATGAGGGCATGGGGTGGGCAGGATGGCTCCTGTCACCCGCGG |
| 109 | SA10 | 245 | CTTGGCCCCTCTATGGCAATGAGGGCTTGGGGTGGGCAGGATGGCTCCTGTCACCCGTGG |
| 110 | S45 | 245 | CTTGGCCCCTCTATGGCAATGAGGGCTTGGGGTGGGCAGGATGGCTCCTGTCACCCGCGG |
| 123 | P8 | 245 | CTTGGCCCCTCTATGCCAATGAGGGCTTGGGGTGGGCgGGATGGCTCCTGTCACCCGCGG |
| 124 | T3 | 245 | CTTGGCCCCTCTATGGCgACGAGGGCATGGGGTGGGCAGGATGGCTCCTGTCACCCGCGG |
| 120 | HK3 | 245 | CTTGGCCCCTCTATGGCAACGAGGGCATGGGGTGGGCAGGATGGCTCCTGTCACCCGCGG |
| 121 | HK5 | 245 | CTTGGCCCCTCTATGGCAATGAGGGCATGGGGTGGGCAGGATGGCTCCTGTCACCCatGG |

109-124 consensus CtTGGCCCCTCTAtGgCaAtGAGGGC-TGGGgTGGGCaGGATGGCTCCTGTCaCCCGgcGG

FIGURE 6B-6

| SEQ ID NO: | ISOLATE | | |
|---|---|---|---|
| 119 | S9 | 306 | cTCTCGGCCTAGTTGGGGCCCCAatGACCCCCGGCGTAGGTCGCGTAAgTTTGGGTAAgGTC |
| 117 | IND3 | 306 | tTCTCGGCCTAGTTGGGGCCCCCACAGACCCCCGGCGTAGGTCGCGTAATTTGGGTAAaGTC |
| 118 | IND8 | 306 | CTCTCGGCCTAGTTGGGGCCCCCACAGACCCCCGGCGTAGGTCGCGTAATTTGGGTAAGGTC |
| 111 | D1 | 306 | CTCCCGGCCTAGTTGGGGCCCCCACcGACCCCCGGCGTAGGTCGCGTAATTTGGGTAAGGTC |
| 112 | US6 | 306 | CTCCCGGCCTAGTTGGGGCCCCCACGGACCCCCGGCGTAGGTCGCGTAATTTGGGTAAGGTC |
| 113 | P10 | 306 | CTCTCGGCCTAGTTGGGGCCCCCACGGACCCCCGGCGTAGGTCGCGTAATTTGGGTAAGGTC |
| 114 | DK1 | 306 | CTCTCGGCCTAGTTGGGGCCCCCAacGACCCCCGGCGTAGGTCGCGTAATTTGGGTAAGGTC |
| 115 | T10 | 306 | CTCcCGGCCTAGTTGGGGCCCCCACaGACCCCCGGCGTAGGTCGCGTAATTTGGGTAAGGTC |
| 116 | SW2 | 306 | CTCTCGGCCTAGTTGGGGCCCCCACtGACCCCCGGCGTAGGTCGCGTAATTTGGGTAAGGTC |
| 122 | HK4 | 306 | CTCTCGGCCTAGTTGGGGCCCCCACGGACCCCCGGCGTAGGTCGCGcAATTTGGGTAAGGTC |
| 109 | SA10 | 306 | CTCTCGGCCTAGTTGGGGCCCCCACGGACCCCCGGCGTAGGTCGCGTAATTTGGGTAAGGTC |
| 110 | S45 | 306 | CTCCCGGCCTAGTTGGGGCCCCCACGGACCCCCGGCGTAGGTCGCGtAATTTGGGTAAGGTC |
| 123 | P8 | 306 | CTCCCGGCCTAGTTGGGGCCCCCACGGACCCCCGGCGTAGGTCGCGCAATTTGGGTAAGGTC |
| 124 | T3 | 306 | CTCCCGGCCTAGTTGGGGCCCCCACAGACCCCCGGCGTAGGTCGCGCAATTTGGGTAAGGTC |
| 120 | HK3 | 306 | CTCTCGGCCTAATTGGGGCCCCCACGGACCCCCGGCGTAGGTCGCGtAAtCTGGGTAAGGTC |
| 121 | HK5 | 306 | CTCTCGGCCTAgTTGGGGCCCCCACGGACCCCCGGCGTAGGTCGCGtAATTTGGGTAAGGTC |

| 109-124 | consensus | | cTCtCGGCCTAgTTGGGGCCCCAcgGACCCCCGGCGTAGGTCGCtAATtTGGGTAAgGTC |

FIGURE 6B-7

| SEQ ID NO: | ISOLATE | | |
|---|---|---|---|
| 119 | S9 | 367 | ATCGATACCCTCACATGCGGCTTtGCCGACCTCATGGGTACATtCCGCTCGTCGGCGCCC |
| 117 | IND3 | 367 | ATCGATACCCTCACATGCGGCTTCGCCGACCTCATGGGTACATCCCGCTCGTCGGCGCCC |
| 118 | IND8 | 367 | ATCGATACCCTCACATGCGGCTTCGCCGACCTCATGGGTACATCCCGCTCGTCGGCGCCC |
| 111 | D1 | 367 | ATCGATACCCTCACATGCGGCTTCGCCGACCTCATGGGTACATCCCGCTCGTCGGCGCCC |
| 112 | US6 | 367 | ATCGATACCCTCACATGCGGCTTCGCCGACCTCATGGGTACATTCCGCTCGTCGGCGCCC |
| 113 | P10 | 367 | ATCGATACCCTCACATGCGGCTTCGCCGACCTCATGGGTACATTCCGCTCGTCGGCGCCC |
| 114 | DK1 | 367 | ATCGATACCCTCACATGCGGCTTCGCCGACCTCATGGGTACATTCCGCTCGTCGGCGCCC |
| 115 | T10 | 367 | ATCGATACCCTCACATGCGGCTTCGCCGACCTCATGGGTACATTCCGCTCGTCGGCGCCC |
| 116 | SW2 | 367 | ATCGATACCCTCACATGCGGCTTCGCCGACCTCATGGGTACATTCCGCTCGTCGGCGCCC |
| 122 | HK4 | 367 | ATCGATACCCTCACATGCGGCTTCGCCGACCTCATGGGTACATTCCGCTCGTCGGCGCCC |
| 109 | SA10 | 367 | ATCGATACCCTCACATGCGGCTTCGCCGACCTCATGGGTACATTCCGCTCGTCGGCGCCC |
| 110 | S45 | 367 | ATCGATACCCTCACgTGCGGCTTCGCCGACCTCATGGGTACATTCCGCTCGTCGGCGCCC |
| 123 | P8 | 367 | ATCGATACCCTCACATGCGGCTTCGCCGACCTCATGGGTACATTCCGCTCGTCGGCGgCC |
| 124 | T3 | 367 | ATCGATACCCTCACATGCGGCTTCGCCGACCTCATGGGTACATTCCGCTCGTCGGCGCtC |
| 120 | HK3 | 367 | ATCGATACCCTCACgTGCGGCTTCGCCGACCTCATGGGTACATCCCGCTCGTCGGtGCCC |
| 121 | HK5 | 367 | ATCGATACCCTCACgTGCGGCTTCGCCGACCTCATGGGTACATCCCGCTCGTCGGCGCCC |

| 109-124 | consensus | ATCGATACCCTCACaTGCGGCTTcGCCGACCTCATGGGTACATtCCGCTCGTCGGcGcccC |

FIGURE 6B-8

| SEQ ID NO: | ISOLATE | | |
|---|---|---|---|
| 119 | S9 | 428 | CCCTAGGGGGCGCTGCCAGGCtCTGGCGCATGGCGTCCGGGTtCTGGAGGACGGCGTGAA |
| 117 | IND3 | 428 | CCCTAGGGGGCGCTGCCAGGCCCTGGCGCATGGCGTCCGGGTCCTGGAGGACGGCGTGAA |
| 118 | IND8 | 428 | CCCTAGGGGGTGCTGCTGCCAGGCCCTGGCGCATGGCGTCCGGGTCCTGGAGGACGGCGTGAA |
| 111 | D1 | 428 | CCCTAGGGGGTGCTGCTGCCAGGCCCTGGCGCATGGCGTCCGGGTTCTGGAGGACGGCGTGAA |
| 112 | US6 | 428 | CCCTAGGGGGCGCTGCTGCCAGGCCCTGGCGCATGGCGTCCGGGTTCTGGAGGACGGCGTGAA |
| 113 | P10 | 428 | CCCTAGGGGGCGCTGCTGCCAGGCCCtTGGCGCATGGCGTCCGGGTTCTGGAGGACGGCGTGAA |
| 114 | DK1 | 428 | CCCTAGGGGGCGCTGCTGCCAGGCCCTGGCGCATGGCGTCCGGGTTCTGGAGGACGGCGTGAA |
| 115 | T10 | 428 | CCCTAGGGGGCGCTGCTGCCAGGCCCTGGCGCATGGCGTCCGGGTTCTGGAGGACGGCGTGAA |
| 116 | SW2 | 428 | CCCTAGGGGGCGCTGCCAGGCCCTGGCaCATGGCtCTGGCGTCCGGGTTCTGGAGGACGGCGTGAA |
| 122 | HK4 | 428 | CCCTAGGGGGCGCTGCCAGGCCCCTGGCgCATGGCGTCCGGGTGTCCGGGTTCTGGAGGACGGCGTGAA |
| 109 | SA10 | 428 | CCTTAGGGGCGtTGCCAGaGCCCTGGCaCATGGCGCATGGCGTCCGGGTGTCCGGGTTCTGGAaGACGGCGTGAA |
| 110 | S45 | 428 | CtTTAGGGGGCGCTGCGCGCTGCCAGgGCCTTGGCGCATGGCGTCCGGGTTCTGGAGGACGGCGTGAA |
| 123 | P8 | 428 | CCCTAGGGGGCGCGTTGCCAGaGCCTTGGCGCATGGCGTCCGGGTTGTGGAGGACGGCGTGAA |
| 124 | T3 | 428 | CCtTAGGGGGCGCGTTGCCAGGCCCTGGCGCATGGCGTCCGGGTTCTGGAGGACGGCGTGAA |
| 120 | HK3 | 428 | CCCTAGGGGGCGCGTTGCCAGGCCCTTGGCACATGGTGTCCGGGTTCTGGAGGACGGCGTGAA |
| 121 | HK5 | 428 | CCCTAGGGGGCGCGTTGCCAGAGCCCTGGCACACGGTGTCCGGGTTCTGGAGGACGGCGTGAA |

| 109-124 | consensus | CccTAGGGGCGcGCTGCCAGgGCccTGGCgCAtGGCGTCCGGGTcTGgAGgACGGCGTGAA |

FIGURE 6B-9

| SEQ ID NO: | ISOLATE | | |
|---|---|---|---|
| 119 | S9 | 489 | CTATGCAACAGGGAACCTcCCCGGTTGCTCTCTTTCTCTATCTTCCTTcTgGCTTTGCTgTCC |
| 117 | IND3 | 489 | CTATGCAACAGGGAACTTGCCCGGTTGCTCTCTTTCTCTATCTTCCTTTTaGCTTTGCTATCC |
| 118 | IND8 | 489 | CTATGCAACAGGGAACTTGCCCGGTTGCTCTCTTTCTCTATCTTCCTTTCCTTTGCTTATCC |
| 111 | D1 | 489 | tTATGCAACAGGGAAtTTGCCCGGTTGCTCTCTTTCTCTATCTTCCTTGGCTTTGCTGTCC |
| 112 | US6 | 489 | CTATGCAACAGGGAAcTTGCCCGGTTGCTCTCTTTCTCTATCTTCCTTGGCTTTGCTGTCC |
| 113 | P10 | 489 | CTATGCAACAGGGAATcTGCCCGGTTGCTCTCTTCTCTATCTTCCTTGGCTTTGCTGTCC |
| 114 | DK1 | 489 | CTACGCAACAGGGAATTGCCCGGTTGCTCTCTTCTCTATCTTCCTTGGCTCTgTtGTCC |
| 115 | T10 | 489 | CTATGCAACAGGGAATTGCCCGGTTGCTCTCTTTCTCTATCTTCCTTGGCTCTGCTgTCt |
| 116 | SW2 | 489 | CTATGCAACAGGGAATcTGCCCGGTTGCTCTCTTcCTTTCTCTATCTTCCTTGGCTtTGCTGTCC |
| 122 | HK4 | 489 | CTATGCAACAGGGAATTGCCCGGTTGCTCTCTTTCTCTATCTTCCTTGGCTtTGCTGTCC |
| 109 | SA10 | 489 | CTATGCAACAGGGAATTGCCCGGTTGCCcCTTTCTCTTCTCTATCTcGCTcTGCTGTCC |
| 110 | S45 | 489 | CTATGCAACAGGGAATcTGCCCGGTTGCCTGGTTGCTCTCTTTCTCTATCTTCCTTGGCTcTGCTGTCC |
| 123 | P8 | 489 | CTATGCAACAGGGAATcTGCCCGGTTGCCTGGTTGCTCTCTTTCTCTATCTTCCTTtTTGGCTTTGCTGTCC |
| 124 | T3 | 489 | tTAcGCAACAGGGAATTGCCCGGTTGCTCTCTTCTCTATCTTCCTTGGCTTTGCTGTCC |
| 120 | HK3 | 489 | CTAtGCAACAGGGAATTtACCCGGTTGCTCTCTTTCTCTATCTTCCTTGGCTTTGCTGTCC |
| 121 | HK5 | 489 | CTAcGCAACAGGGAATaTACCCGGTTGCTCTCTTTCTCTATCTTCCTtTTGGCTTTGCTGTCC |

109-124 consensus    cTAtGCAACAGGGAAttTgCCcGGTTGCtCtTTcTCTATCTTCCTctTgGCTtGcTgTCc

FIGURE 6B-10

```
SEQ ID NO:  ISOLATE
119         S9      550  TGTTTGACCATCCCAGCTTCCGCT
117         IND3    550  TGTTTGACCATCCCAGCTTCCGCT
118         IND8    550  TGTTTGACCgTCCCAGCTTCCGCT
111         D1      550  TGTTTGACCATCCCAGCTTCCGCT
112         US6     550  TGTTTGACCATtCCAGCTTCCGCT
113         P10     550  TGccTGACCATCCCAGCgTCCGCT
114         DK1     550  TGTtTGACCATCCCAGCTTCCGCc
115         T10     550  TGTCTGACCATCCCAGCTTCCGCT
116         SW2     550  TGTCTGACCATCCCAGCTTCCGCT
122         HK4     550  TGTTTGACCATCCCAGCTTCCGCT
109         SA10    550  TGTTTaACCATCCCAGCTTCCGCT
110         S45     550  TGcTGACCATCCCAGCTTCCGCT
123         P8      550  TGtcTGACCATCCCAGCTTCCGCT
124         T3      550  TGCTTGACCATCCCAGCTTCCGCT
120         HK3     550  TGCTTGACCACCCCAGCTTCCGCT
121         HK5     550  TGtcTGACCACCCCAGtTTCCGCT 109-124     consensus      TGttTgACCatcCCAGctTCCGct
```

FIGURE 6C-1

| SEQ ID NO: | ISOLATE | |
|---|---|---|
| 119 | S9 | 1 ATGAGCACGAATCCTAAACCTCAAAGAAAAACCAAACGTAACACCAACCGCCGCCCACAGG |
| 117 | IND3 | 1 ATGAGCACGAATCCTAAACCTCAAAGAAAAACCAAACGTAACACCAACCGCCGCCCACAGG |
| 118 | IND8 | 1 ATGAGCACGAATCCTAAACCTCAAAGAAAAACCAAACGTAACACCAACCGCCGCCCACAGG |
| 111 | D1 | 1 ATGAGCACGAATCCTAAACCTCAAAGAAAAACCAAACGTAACACCAACCGCCGCCCACAGG |
| 112 | US6 | 1 ATGAGCACGAATCCTAAACCTCAAAGAAAAACCAAACGTAACACCAACCGCCGCCCACAGG |
| 113 | P10 | 1 ATGAGCACGAATCCTAAACCTCAAAGAAAAACCAAACGTAACACCAACCGCCGCCCACAGG |
| 114 | DK1 | 1 ATGAGCACGAATCCTAAACCTCAAAGAAAAACCAAACGTAACACCAACCGCCGCCCACAGG |
| 115 | T10 | 1 ATGAGCACGAATCCTAAACCTCAAAGAAAAACCAAACGTAACACCAACCGCCGCCCACAGG |
| 116 | SW2 | 1 ATGAGCACGAATCCTAAACCTCAAAGAAAAACCAAACGTAACACCAACCGCCGCCCACAGG |
| 122 | HK4 | 1 ATGAGCACGAATCCTAAACCTCAAAGAAAGACCAAACGTAACACCAACCGCCGCCCACAGG |
| 109 | SA10 | 1 ATGAGCACGAATCCTAAACCTCAAAGAAAAACCAAACGTAACACCAACCGCCGCCCACAGG |
| 110 | S45 | 1 ATGAGCACGAATCCTAAACCTCAAAGAAAGACAAACGTAACACCAACCGCCGCCCACAGG |
| 123 | P8 | 1 ATGAGCACGACTCCTAAACCTCAAAGAAAAACCAAACGTAACACCAACCGCCGCCCACAGG |
| 124 | T3 | 1 ATGAGCACGAATCCTAAACCTCAAAGAAAAACCAAACGTAACACCAgCCGCCGCCCACAGG |
| 120 | HK3 | 1 ATGAGCACGAATCCTAAACCTCAAAGAAAAACCAAACGTAACACCAACCGCCGCCCACAGG |
| 121 | HK5 | 1 ATGAGCACGAATCCTAAACCTCAAAGAAAAACCAAACGTAACACCAACCGCCGCCCACAGG |
| 108 | DR4 | 1 ATGAGCACGAATCCTAAACCTCAAAGAAAAACCAAACGTAACACCAACCGTCGCCCACAGG |
| 104 | US11 | 1 ATGAGCACGAATCCTAAACCTCAAAGAAAAACCAAACGTAACACCAACCGTCGCCCACAGG |
| 105 | S14 | 1 ATGAGCACGAATCCTAAACCTCAAAGAAAAACCAAACGTAACACCAACCGTCGCCCACAGG |
| 106 | SW1 | 1 ATGAGCACGAATCCTAAACCTCAAAGAAAAACCAAACGTAACACCAACCGTCGCCCACAGG |
| 107 | S18 | 1 ATGAGCACACaAATCCTAAACCTCAAAGAAAAACCAAACGTAACACCAACCGTCGCCCACAGG |
| 103 | DK7 | 1 ATGAGCACgAATCCTAAACCTCAAAGAAAAACCAAACGTAACACCAACCGTCGCCCACAGG |

103-124 consensus ATGAGCACgAaTCCTAAACCTCAAAGAaAaACCAAACGTAACACCAaCCGcCGCCCACAGG

FIGURE 6C-2

| SEQ ID NO: | ISOLATE | | |
|---|---|---|---|
| 119 | S9 | 62 | ACGTtAAGTTCCCGGGCGGTGGtCAGATCGTcGGTGGAGTTTACCTGTTGCCGCGCAGGGG |
| 117 | IND3 | 62 | ACGTCAAGTTCCCGGGCGGTGGTGGCCAGATCGTTGGTGGAGTTTACCTGTTGCCGCGCAGGGG |
| 118 | IND8 | 62 | ACGTCAAGTTCCCGGGCGGTGGCCAGATCGTTGGTGGAGTTTACCTGTTGCCGCGCAGGGG |
| 111 | D1 | 62 | ACGTCAAGTTCCCGGGCGGTGGTCAGATCGTTGGTGGAGTTTACCTGTTGCCGCGCAGGGG |
| 112 | US6 | 62 | ACGTCAAGTTCCCGGGCGGTGGTCAGATCGTTGGTGGAGTTTACCTGTTGCCGCGCAGGGG |
| 113 | P10 | 62 | ACGTCAAGTTCCCGGGCGGTGGTCAGATCGTTGGTGGAGTTTACCTGTTGCCGCGCAGGGG |
| 114 | DK1 | 62 | ACGTCAAGTTCCCGGGCGGTGGTCAGATCGTTGGTGGAGTTTACCTGTTGCCGCGCAGGGG |
| 115 | T10 | 62 | ACGTCAAGTTCCCGGGCGGTGGTCAGATCGTTGGTGGAGTTTACCTGTTGCCGCGCAGGGG |
| 116 | SW2 | 62 | ACGTCAAGTTCCCGGGCGGTGGCCAGATCGTTGGTGGAGTTTACCTGTTGCCGCGCAGGGG |
| 122 | HK4 | 62 | ACGTCAAGTTCCCGGGCGGTGGCCAGATCGTcGGTGGAGTTTACCTGTTGCCGCGCAGGGG |
| 109 | SA10 | 62 | ACGTtAAGTTCCCGGGCGGTGGTCAGATCGTTGGTGGAGTcTAtCTGTTGCCGCGCAGGGG |
| 110 | S45 | 62 | ACGTCAAGTTCCCGGGtGGcGGTGGTCAGATCGTTGGTGGAGTTTACCTGTTGCCGCGCAGGGG |
| 123 | P8 | 62 | ACGTtAAGTTCCCGGGCGGTGGTCAGATCGTTGGTGGAGTTTACCTGTTGCCGCGCAGGGG |
| 124 | T3 | 62 | ACGTtAAGTTCCCGGGCGGTGGTCAGATCGTTGGTGGAGTTTACCTGTTGCCGCGCAGGGG |
| 120 | HK3 | 62 | ACGTCAAGTTCCCGGGTGGCGGTGGTCAGATCGTTGGTGGAGTTTACTTGTTGCCGCGCAGGGG |
| 121 | HK5 | 62 | ACGTCAAGTTCCCGGGTGGCGGTGGTCAGATCGTTGGTGGAGTTTACTTGTTGCCGCGCAGGGG |
| 108 | DR4 | 62 | ACGTCAAGTTCCCGGGTGGCGGTGGTCAGATCGTTGGTGGAGTTTACTTGTTGCCGCGCAGGGG |
| 104 | US11 | 62 | ACGTCAAGTTCCCGGGTGGCGGTGGTCAGATCGTTGGTGGAGTTTACTTGTTGCCGCGCAGGGG |
| 105 | S14 | 62 | ACGTCAAGTTCCCGGGTGGCGGTGGTCAGATCGTTGGTGGAGTTTACTTGTTGCCGCGCAGGGG |
| 106 | SW1 | 62 | ACGTCAAGTTCCCGGGTGGCGGTGGTCAGATCGTTGGTGGAGTTTACTTGTTGCCGCGCAGGGG |
| 107 | S18 | 62 | ACGTtAAGTTCCCGGGTGGCGGTGGTCAGATCGTTGGTGGAGTTTACTTGTTGCCGCGCAGGGG |
| 103 | DK7 | 62 | ACGTcAAGTTCCCGGGTGGCGGTGGTCAGATCGTTGGTGGAGTTTACTTGTTGCCGCGCAGGGG |

103-124 consensus  ACGTcAAGTTCCCGGGcGGtGGtCAGATCGTtGGTGGAGTtTAccTGTTGCCGCGCAGGGG

FIGURE 6C-3

| SEQ ID NO: | ISOLATE | | |
|---|---|---|---|
| 119 | S9 | 123 | CCCCAGGTTGGGTGTGCGCGCaACTAGGAAGACTTCCGAGCGGTCGCAACCTCGTGGAAGG |
| 117 | IND3 | 123 | CCCCAGGTTGGGTGTGCGCGCGCGACTAGGAAGACTTCCGAGCGGTCGCAACCTCGTGGAAGG |
| 118 | IND8 | 123 | CCCCAGGTTGGGTGTGCGCGCGCGACTAGGAAGACTTCCGAGCGGTCGCAACCTCGTGGAAGG |
| 111 | D1 | 123 | CCCCAGGTTGGGTGTGCGCGCGCGACTAGGAAGACTTCCGAGCGGTCGCAACCTCGTGGAAGG |
| 112 | US6 | 123 | CCCCAGGTTGGGTGTGCGCGCGCGACTAGGAAGACTTCCGAGCGGTCGCAACCTCGTGGAAGG |
| 113 | P10 | 123 | CCCCAGGTTGGGTGTGCGCGCGCGACTAGGAAGACTTCCGAGCGGTCGCAACCTCGTGGAAGG |
| 114 | DK1 | 123 | CCCCAGGTTGGGTGTGCGCGCGCGACTAGGAAGACTTCCGAGCGGTCGCAACCTCGTGGAAGG |
| 115 | T10 | 123 | CCCCAGGTTGGGTGTGCGCGCGCGACTAGGAAGACTTCCGAGCGGTCGCAACCTCGTGGAAGG |
| 116 | SW2 | 123 | CCCCcGGTTGGGTGTGCGCGCGCGACTAGGAAGACTTCCGAGCGGTCGCAACCTCGTGGAAGG |
| 122 | HK4 | 123 | CCCCAGGTTGGGTGTGCGCGCGCGACTAGGAAGACTTCCGAGCGGTCGCAACCTCGTGGAAGG |
| 109 | SA10 | 123 | CCCCAGGTTGGGTGTGCGCGCGCGACgAGGAAGACTTCCGAGCGGTCaCAACCTCGTGGACGG |
| 110 | S45 | 123 | CCCCAGGTTGGGTGTGCGCGCGCGACTAGGAAGACTTCCGAGCGGTCGaTCGCAACCTCGTGGcAGG |
| 123 | P8 | 123 | CCCCAGGTTGGGTGTGCGCGCGCGACTAGGAAGACTTCCGAGCGGTCGCAACCTCGTGGAAGG |
| 124 | T3 | 123 | CCCCAGGTTGGGTGTGCGCGCGCGACTAGGAAGACTTCaGAGCGGTCGCAACCTCGTGGAAGG |
| 120 | HK3 | 123 | CCCCAGGTTGGGTGTGCGCGCGCGACCAGGAAGACTTCCGAGCGGTCGCAACCTCGTGGAAGG |
| 121 | HK5 | 123 | CCCCAGGTTGGGTGTGCGCGCGCGACCAGGAAGACTTCCGAGCGGTCGCAACCTCGAGGTAGA |
| 108 | DR4 | 123 | CCCTAGATTGGGTGTGCGCGCGCGACGAGGAAGAAGACTTCCGAGCGGTCGCAACCTCGAGGTAGA |
| 104 | US11 | 123 | CCCTAGATTGGGTGTGCGCGCGCGACGAGGAAGAAGACTTCCGAGCGGTCGCAACCTCGAGGTAGA |
| 105 | S14 | 123 | CCCTAGATTGGGTGTGCGCGCGCGACGAGGAAGAAGACTTCCGAGCGGTCGCAACCTCGAGGTAGA |
| 106 | SW1 | 123 | CCCTAGATTGGGTGTGCGCGCGCGACGAGGAAGAAGACTTCCGAGCGGTCGCAACCTCGAGGTAGA |
| 107 | S18 | 123 | CCCTAGATTGGGTGTGCGCGCGCGACGAGGAAGAAGACTTCCGAGCGGTCGCAACCTCGcGGTAGA |
| 103 | DK7 | 123 | CCCTAGATTGGGTGTGCGCGCGCGccGAGGAAGAAGACTTCCGAGCGGTCGCAACCTCGaGGTAGA |

103-124 consensus CCCcaGgTTGGGTGTGCGCGCGcgaCtAGGAAGACTTCcGAGCGGtCGCAACCTCGtGGaaGg

FIGURE 6C-4

| SEQ ID NO: | ISOLATE | | |
|---|---|---|---|
| 119 | S9 | 184 | CGACAACCTATCCCCAAGGCTCGCCatCCCGAGGGCAGGGCCTGGGCTCAGCCCGGGTACC |
| 117 | IND3 | 184 | CGACAACCTATCCCCAAGGCTCGCCGCCGGCCCGAGGGTAGGGCCTGGGCTCAGCCCGGGTACC |
| 118 | IND8 | 184 | CGACAACCTATCCCCAAGGCTCGCCGCCGGCCCGAGGGTAGGGCCTGGGCTCAGCCCGGcACC |
| 111 | D1 | 184 | CGACAACCTATCCCCAAGGCTCGCCGCCGGCCCGAGGGTAGGGCCTGGGCTCAGCCCGGGTACC |
| 112 | US6 | 184 | CGACAACCTATCCCCAAGGCTCGCCGCCGGCCCGAGGGCAGGGCCTGGGCTCAGCCCGGGTACC |
| 113 | P10 | 184 | CGACAACCTATCCCCAAGGCTCGCCGCCGGCCCGAGGGCAGGGCCTGGGCTCAGCCCGGGTACC |
| 114 | DK1 | 184 | CGACAACCTATCCCCAAGGCTCGCCGCCAGCCCGAGGGCAGGGCCTGGGCTCAGCCCGGGTACC |
| 115 | T10 | 184 | CGACAgCCTATCCCCAAGGCTCGCCGCCAGCCCGAGGGCAGGGCCTGGGCTCAGCCCGGGTACC |
| 116 | SW2 | 184 | CGACAACCTATCCCCAAGGCTCGCCGCCAaCCCGAGGGCAGGACAGGACCTGGGCTCAGCtGGGTACC |
| 122 | HK4 | 184 | CGACAACCTATCCCCAAGGCTCGCCGCCAGCCCGAGGGCAGGACCTGGGCTCAGCCCGGGTACC |
| 109 | SA10 | 184 | CGACAACCTATCCCCAAGGCTCGCCGCCAGCCCGAGGGCAGGACCTGGCCCAGCCCGGGTACC |
| 110 | S45 | 184 | CGACAACCTATCCCCAAGGCTCGCCGCCGGCCCGAGGGCAGGACCTGGGCCCAGCCCGGGCAtC |
| 123 | P8 | 184 | CGACAACCTATCCCCAAGGCTCGCCGCCGGCCCGAGGGTAGGGCCTGGGCTCAGCCCGGCACC |
| 124 | T3 | 184 | CGACAACCTATCCCCAAGGCTCGCCGCCGGCCCGAGGGTAGGGCCTGGGCTCAGCCCGGGTACC |
| 120 | HK3 | 184 | CGACAACCTATCCCCAAGGCTCGCCGCCaACCCGAGGGCAGGACCTGGGCTCAGCCCGGTATC |
| 121 | HK5 | 184 | CGACAACCTATCCCCAAGGCTCGCCGCCAGCCCGAGGGCAGGACCTGGGCTCAGCCCGGTATC |
| 108 | DR4 | 184 | CGTCAGCCTATCCCCAAGGCgCGTCGGCCGTCGGCCCGAGGGCAGGACCTGGGCTCAGCCCGGGTACC |
| 104 | US11 | 184 | CGTCAGCCTATCCCCAAGGCACGTCGGCCCGAGGGCAGGACCTGGGCTCAGCCCGGGTACC |
| 105 | S14 | 184 | CGTCAGCCTATCCCCAAGGCACGTCGGCCCGAGGGCAGGACCTGGGCTCAGCCCGGGTATC |
| 106 | SW1 | 184 | CGTCAGCCTATCCCCAAGGCGCGTCGGCCCGAGGGCAGGACCTGGGCTCAGCCCGGGTACC |
| 107 | S18 | 184 | CGTCAGCCTATCCCCAAGGCGCGTCGGCCCGAGGGCAGGACCTGGGCTCAGCCCGGGTACC |
| 103 | DK7 | 184 | CGTCAGCCTATCCCCAAGGCaCGTCGGCCCGAGGGCAGGACCTGGGCTCAGCCCGGGTACC |

103-124  consensus  CGaCAaCCTATCCCCAAGGCtCGcCggCCCGAGGGcAGGgCCTGGGCtCAGCCCGGGtAcC

FIGURE 6C-5

| SEQ ID NO: | ISOLATE | | |
|---|---|---|---|
| 119 | S9 | 245 | CTTGGCCCCTCTACgCAATGAGGGCTTGGGGTGGGCAGGATGGCTCCTGTCACCCGtGG |
| 117 | IND3 | 245 | CTTGGCCCCTCTATGGCAATGAGGGCTTGGGGTGGGCAGGATGGCTCCTGTCCTGCGCGG |
| 118 | IND8 | 245 | CTTGGCCCCTCTATGGCAATGAGGGCTTGGGGTGGGCAGGATGGCTCCTGTCACCCGCGG |
| 111 | D1 | 245 | CTTGGCCCCTCTATGGCAACGAGGGCTTGGGGTGGGCAGGATGGCTCCTGTCACCCGCGG |
| 112 | US6 | 245 | CTTGGCCCCTCTATGGCAATGAGGGCaTGGGGTGGGCAGGATGGCTCCTGTCACCCGTGG |
| 113 | P10 | 245 | CTTGGCCCCTCTATGGCAATGAGGGCTtGGGGTGGGCAGGATGGCTCCTGTCACCCGTGG |
| 114 | DK1 | 245 | CTTGGCCCCTCTATGGCAATGAGGGCATGGGGTGGGCAGGATGGCTCCTGTCACCCGcGG |
| 115 | T10 | 245 | CTTGGCCCCTCTATGGCAATGAGGGCATGGGGTGGGCAGGATGGCTCCTGTCACCCGtGG |
| 116 | SW2 | 245 | CcTGGCCCCTCTATGGCAATGAGGGCATGGGGaTGGGCAGGATGGCTCCTGTCcCCCGCGG |
| 122 | HK4 | 245 | CTTGGCCCCTCTATGGCAATGAGGGCATGGGGTGGGCAGGATGGCTCCTGTCACCCGCGG |
| 109 | SA10 | 245 | CTTGGCCCCTCTATGGCAATGAGGGCTTGGGGTGGGCAGGATGGCTCCTGTCACCCGTGG |
| 110 | S45 | 245 | CTTGGCCCCTCTATGGCAATGAGGGCTTGGGGTGGGCgGGATGGCTCCTGTCACCCGTGG |
| 123 | P8 | 245 | CTTGGCCCCTCTATGcCAATGAGGGCTTGGGGTGGGCAGGATGGCTCCTGTCACCCGCGG |
| 124 | T3 | 245 | CTTGGCCCCTCTATGGCgACGAGGAGGGCTTGGGGTGGGCAGGATGGCTCCTGTCACCCGCGG |
| 120 | HK3 | 245 | CTTGGCCCCTCTATGGCAATGAGGGCTTGGGGTGGGCAGGATGGCTCCTGTCACCCGCGG |
| 121 | HK5 | 245 | CTTGGCCCCTCTATGGCAATGAGGGCTTGGGGTGGGCAGGATGGCTCCTGTCACCCaTGG |
| 108 | DR4 | 245 | CTTGGCCCCTCTATGGCAATGAGGGCTGCGGGGCTGCGGGGATGGCTCCTGTCcCCCGTGG |
| 104 | US11 | 245 | CTTGGCCCCTCTATGGCAATGAGGGCTGCGGGGCTGCGGGGATGGCTCCTGTCTCCCGTGG |
| 105 | S14 | 245 | CTTGGCCCCTCTATGGCAATGAGGGCTGCGGGGCTGCGGGGATGGCTCCTGTCTCCCGTGG |
| 106 | SW1 | 245 | CTTGGCCCCTCTATGGCAATGAGGGCTGCGGGaTGGGGCTGCGGaTGGCTCCTGTCCCCCGTGG |
| 107 | S18 | 245 | CTTGGCCCCTCTATGGCAATGAGGGCTGCGGGGCTGCGGGGATGGCTCCTGTCTCCCCGTGG |
| 103 | DK7 | 245 | CTTGGCCCCTCTATGGCAATGAGGGCTGCGGGGCTGCGGGGATGGCTCCTGTCtCCCCGTGG |

103-124 consensus    CtTGGCCCCTCTATgGCaAtGAGGGCttgGGGTGGGCaGGATGGCTCCTGTCaCCCCGtGG

FIGURE 6C-6

| SEQ ID NO: | ISOLATE | | |
|---|---|---|---|
| 119 | S9 | 306 | cTCTCGGCCTAGTTGGGGCCCCAatGACCCCCGGCGTAGGTCGCGTAATTGGGTAAgGTC |
| 117 | IND3 | 306 | tTCTCGGCCTAGTTGGGGCCCCACAGACCCCCGGCGTAGGTCGCGTAATTTGGGTAAaGTC |
| 118 | IND8 | 306 | CTCTCGGCCTAGTTGGGGCCCCACAGACCCCCGGCGTAGGTCGCGTAATTTGGGTAAGGTC |
| 111 | D1 | 306 | CTCCCGGCCTAGTTGGGGCCCCACCGACCCCCGGCGTAGGTCGCGTAATTTGGGTAAGGTC |
| 112 | US6 | 306 | CTCCCGGCCTAGTTGGGGCCCCACGGACCCCCGGCGTAGGTCGCGTAATTTGGGTAAGGTC |
| 110 | P10 | 306 | CTCTCGGCCTAGTTGGGGCCCCACGGACCCCCGGCGTAGGTCGCGTAATTTGGGTAAGGTC |
| 113 | DK1 | 306 | CTCTCGGCCTAGTTGGGGCCCCAacGACCCCCGGCGTAGGTCGCGTAATTTGGGTAAGGTC |
| 114 | T10 | 306 | CTCcCGGCCTAGTTGGGGCCCCACaGACCCCCGGCGTAGGTCGCGTAATTTGGGTAAGGTC |
| 115 | SW2 | 306 | CTCTCGGCCTAGTTGGGGCCCCACtGACCCCCGGCGTAGGTCGCGTAATTTGGGTAAGGTC |
| 116 | HK4 | 306 | CTCTCGGCCTAGTTGGGGCCCCACGGACCCCCGGCGTAGGTCGCGTAATTTGGGTAAGGTC |
| 122 | SA10 | 306 | CTCTCGGCCTAGTTGGGGCCCCACGGACCCCCGGCGTAGGTCGCGTAATTTGGGTAAGGTC |
| 109 | S45 | 306 | CTCTCGGCCTAGTTGGGGCCCCACGGACCCCCGGCGTAGGTCGCGtAATTTGGGTAAGGTC |
| 110 | P8 | 306 | CTCCCGGCCTAGTTGGGGCCCCACGGACCCCCGGCGTAGGTCGCGTAATTTGGGTAAGGTC |
| 123 | T3 | 306 | CTCCCGGCCTAATTGGGGCCCCACGGACCCCCGGCGTAGGTCGCGtAATcTGGGTAAGGTC |
| 124 | HK3 | 306 | CTCTCGGCCTAATTGGGGCCCCACGGACCCCCGGCGTAGGTCGCGCAATTTGGGTAAGGTC |
| 120 | HK5 | 306 | CTCTCGGCCTAGCTGGGGCCCCACGGACCCCCGGCGTAGGTCGCGtAATTTGGGTAAGGTC |
| 121 | DR4 | 306 | CTCTCGGCCTAGCTGGGGCCCCACaGACCCCCGGCGTAGGTCGCGCAATTTGGGTAAGGTC |
| 108 | US11 | 306 | CTCTCGGCCTAGCTGGGGCCCCACGGACCCCCGGCGTAGGTCGCGCAATTTGGGTAAGGTC |
| 104 | S14 | 306 | CTCTCGGCCTAGCTGGGGCCCCACAGACCCCCGGCGTAGGTCGCGCAATTTGGGTAAGGTC |
| 105 | SW1 | 306 | CTCTCGGCCTAGCTGGGGCCCCCTACAGACCCCCGGCGTAGGTCGCGCAATTTGGGTAAGGTC |
| 106 | S18 | 306 | CTCcCGGCCTAGCTGGGGCCCCACAGACCCCCGGCGTAGGTCGCGCAATTTGGGcAAAGTC |
| 107 | DK7 | 306 | CTCtCGGCCTAGCTGGGGCCCCCACAGACCCCCGGCGCAGGTCGCGCAATTTGGGTAAAGTC |

103-124 consensus    cTCtCGGCCTAgtTGGGGCCCCcAc-GACCCCCGGCGtAGGTCGCGtAAtTGGGtAAgGTC

FIGURE 6C-7

| SEQ ID NO: | ISOLATE | | |
|---|---|---|---|
| 119 | S9 | 367 | ATCGATACCCTCACATGCGGCTTtGCCGACCTCATGGGGTACATtCCGCTCGTCGGCGCCC |
| 117 | IND3 | 367 | ATCGATACCCTCACATGCGGCTTCGCCGACCTCATGGGGTACATCCCGCTCGTCGGCGCCC |
| 118 | IND8 | 367 | ATCGATACCCTCACATGCGGCTTCGCCGACCTCATGGGGTACATCCCGCTCGTCGGCGCCC |
| 111 | D1 | 367 | ATCGATACCCTCACATGCGGCTTCGCCGACCTCATGGGGTACATCCCGCTCGTCGGCGCCC |
| 112 | US6 | 367 | ATCGATACCCTCACATGCGGCTTCGCCGACCTCATGGGGTACATTCCGCTCGTCGGCGCCC |
| 113 | P10 | 367 | ATCGATACCCTCACATGCGGCTTCGCCGACCTCATGGGGTACATTCCGCTCGTCGGCGCCC |
| 114 | DK1 | 367 | ATCGATACCCTCACATGCGGCTTCGCCGACCTCATGGGGTACATTCCGCTCGTCGGCGCCC |
| 115 | T10 | 367 | ATCGATACCCTCACATGCGGCTTCGCCGACCTCATGGGGTACATTCCGCTCGTCGGCGCCC |
| 116 | SW2 | 367 | ATCGATACCCTCACATGCGGCTTCGCCGACCTCATGGGGTACATTCCGCTCGTCGGCGCCC |
| 122 | HK4 | 367 | ATCGATACCCTCACATGCGGCTTCGCCGACCTCATGGGGTACATTCCGCTCGTCGGCGCCC |
| 109 | SA10 | 367 | ATCGATACCCTCACATGCGGCTTCGCCGACCTCATGGGGTACATTCCGCTCGTCGGCGCCC |
| 110 | S45 | 367 | ATCGATACCCTCACgTGCGGCTTCGCCGACCTCATGGGGTACATTCCGCTCGTCGGCGCCC |
| 123 | P8 | 367 | ATCGATACCCTCACATGCGGCTTCGCCGACCTCATGGGGTACATTCCGCTCGTCGGCGCtC |
| 124 | T3 | 367 | ATCGATACCCTCACATGCGgCTTCGCCGACCTCATGGGGTACATTCCGCTCGTCGGCGCCC |
| 120 | HK3 | 367 | ATCGATACCCTCACATGCGGCTTCGCCGACCTCATGGGGTACATCCCGCTCGTCGGtGCCC |
| 121 | HK5 | 367 | ATCGATACCCTCACATGCGGCTTCGCCGACCTCATGGGGTACATCCCGCTCGTCGGCGCCC |
| 108 | DR4 | 367 | ATCGAcACACCCTCACgTGCGGCTTCGCCGACCTCATGGGGTACATCCCGCTCGTCGGCGCCC |
| 104 | US11 | 367 | ATCGATACCCTCACCTtACgTGCGGCTTCGCCGACCTCATGGGGTACATaCCGCTCGTCGGCGCCC |
| 105 | S14 | 367 | ATCGATACCCTCACgTGCGGCTTCGCCGACCTCATGGGGTACATaCCGCTCGTCGGCGCCC |
| 106 | SW1 | 367 | ATCGATACCCTCACgTGCGGCTTCGCCGACCTCATGGGGTACATTCCGCTCGTCGGCGCCC |
| 107 | S18 | 367 | ATCGATACCCTCACgTGCGGCTTCGCCGACCTCATGGGGTACATTCCGCTCGTCGGCGCCC |
| 103 | DK7 | 367 | ATCGATACCCTtACgTGCGGCTTCGCCGACCTCATGGGGTACATaCCGCTCGTCGGCGCCC |

103-124 consensus ATCGAtACCCTcACaTGCGGCTTcGCCGACCTCATGGGGTACAttCCGCTCGTCGGCGccC

FIGURE 6C-8

| SEQ ID NO: | ISOLATE | | |
|---|---|---|---|
| 119 | S9 | 428 | CCCTAGGGGCGCTGCCAGGGCtCTGGCGCATGGCGTCCGGTtCTGGAGGACGGCGTGAA |
| 117 | IND3 | 428 | CCCTAGGGGGCGCTGCCAGGGCCCTGGCGCATGGCGTCCGGTCCTGGAGGACGGCGTGAA |
| 118 | IND8 | 428 | CCCTAGGGGGTGCTGCCAGGGCCCTGGCGCATGGCGTCCGGTCCTGGAGGACGGCGTGAA |
| 111 | D1 | 428 | CCCTAGGGGGTGCTGCCAGGGCCCTGGCGCATGGCGTCCGGTTCTGGAGGACGGCGTGAA |
| 112 | US6 | 428 | CCCTAGGGGGCGCTGCCAGGGCCtTGGCGCATGGCGTCCGGTTCTGGAGGACGGCGTGAA |
| 113 | P10 | 428 | CCCTAGGGGGCGCTGCCAGGGCCCTGGCGCATGGCGTCCGGTTCTGGAGGACGGCGTGAA |
| 114 | DK1 | 428 | CCCTAGGGGGCGCTGCCAGGGCCCTGGCGCATGGCGTCCGGTTCTGGAGGACGGCGTGAA |
| 115 | T10 | 428 | CCCTAGGGGCGCTGCCAGGGCtCTGGCaCATGGCGTCCGGTTCTGGAGGACGGCGTGAA |
| 116 | SW2 | 428 | CCCTAGGGGCGCTGCCAGGGCCCTGGCgCATGGCGTCCGGTcCTGGAGGACGGCGTGAA |
| 122 | HK4 | 428 | CCTTAGGGGCGtGCCAGaGCCTGGCaCATGGCGTCCGGTgTGGAGGACGGCGTGAA |
| 109 | SA10 | 428 | CtTTAGGGGCGCTGCCAGgCCTTGGCGCATGGCGTCCGGTTCTGGAaGACGGCGTGAA |
| 110 | S45 | 428 | CCCTAGGGGGCGCTGCCAGaGCCTGGCGCATGGCGTCCGGTTCTGGAGGACGGCGTGAA |
| 123 | P8 | 428 | CCCTAGGGGGCGTTGCCAGGGCCTGGCGCATGGCGTCCGGTgTGGAGGACGGCGTGAA |
| 124 | T3 | 428 | CCtTAGGGGCGCTGCCAGGGCCTGGCGCATGGCGTCCGGTTCTGGAGGACGGCGTGAA |
| 120 | HK3 | 428 | CCCTAGGGGGCGTTGCCAGAGCCTTGGCACATGGTGTCCGGTTCTGGAGGACGGCGTGAA |
| 121 | HK5 | 428 | CCCTAGGGGGCGTTGCCAGAGCCTGGCACACGGTGTCCGGTTCTGGAGGACGGCGTGAA |
| 108 | DR4 | 428 | CCCTtGGGGCGCGCTGCCAGGGCCTGGCGCATGGCGTCCGaGTTCTGGAAGACGGCGTGAA |
| 104 | US11 | 428 | CtCTCGGaGGCGCGCTGCCAGGGCCTGGCGCATGGCGTCCGGTTCTGGAAGACGGCGTGAA |
| 105 | S14 | 428 | CcCTCGGgGGCGCGCTGCCAGGGCCTGGCGCATGGCGTCCGGTTCTGGAAGACGGCGTGAA |
| 106 | SW1 | 428 | CTCTtGGAGGCGCTGCCAGGGCCTGGCGCATGGCGTCCGGTTCTGGAAGACGGCGTGAA |
| 107 | S18 | 428 | CTCTcGGAGGCGCTGCCAGGGCCTGGCGCATGGCGTCCGGTTCTGGAAGACGGCGTGAA |
| 103 | DK7 | 428 | CTCTtGGAGGCGCTGCCAGGGCCTGGCGCATGGCGTCCGGTTCTGGAAGACGGCGTGAA |
| 103-124 | consensus | | CccTaGGgGGcGcTGCCAggGCCccTGGCgCAtGGcGTCCGgTcCTGGAgGACGGCGTGAA |

FIGURE 6C-9

| SEQ ID NO: | ISOLATE | | |
|---|---|---|---|
| 119 | S9 | 489 | CTATGCAACAGGGAACcTcCCCGGTTGCTCTTTCTCTATCTTCCTTcTgGCTTTGCTgTCC |
| 117 | IND3 | 489 | CTATGCAACAGGGAACTTGCCCGGTTGCTCTTTCTCTATCTTCCTTTTagCTTTGCTATCC |
| 118 | IND8 | 489 | CTATGCAACAGGGAACTTGCCCGGTTGCTCTTTCTCTATCTTCCTTTTGGCTTTGCTATCC |
| 111 | D1 | 489 | tTATGCAACAGGGAAtTTGCCCGGTTGCTCTTTCTCTATCTTCCTCTTGGCTTTGCTGTCC |
| 112 | US6 | 489 | CTATGCAACAGGGAACTTGCCCGGTTGCTCTTTCTCTATCTTCCTCTTGGCTTTGCTGTCC |
| 113 | P10 | 489 | CTATGCAACAGGGAATCTGCCCGGTTGCTCTTTCTCTATCTTCCTCTTGGCTTTGCTGTCC |
| 114 | DK1 | 489 | CTAcGCAACAGGGAATTTGCCCGGTTGCTCTTTCTCTATCTTCCTCTTGGCTTTGCTGTCC |
| 115 | T10 | 489 | CTATGCAACAGGGAATTTGCCCGGTTGCTCTTTCTCTATCTTCCTCTTGGCTGtGCTGTCC |
| 116 | SW2 | 489 | CTATGCAACAGGGAATcTGCCCGGTTGCTCTTTCTCTATCTTCCTCTTGGCTCTGCTGTCt |
| 122 | HK4 | 489 | CTATGCAACAGGGAATTTGCCCGGTTGCTCTTTCTCTATCTTCCTCTTGGCTCTGCTGTCC |
| 109 | SA10 | 489 | CTATGCAACAGGGAATTTGCCCGGTTGCcCTTTCTCTATCTTCCTCTTGGCTcTGCTGTCC |
| 110 | S45 | 489 | CTATGCAACAGGGAATCTGCCCGGTTGCTCTTTCTCTATCTTCCTCTTGGCTcTGCTGTCC |
| 123 | P8 | 489 | CTATGCAACAGGGAATTTGCCCGGTCGGTTGCTCTTTCTCTATCTTCCTtTTGGCTTTGCTGTCt |
| 124 | T3 | 489 | tTAcGCAACAGGGAATTTGCCCGGTTGCTCTTTCTCTATCTTCCTCTTGGCTTTGCTGTCC |
| 120 | HK3 | 489 | CTAtGCAACAGGGAATTTACCCGGTTGCTCTTTCTCTATCTTCCTCTTGGCTTTGCTGTCC |
| 121 | HK5 | 489 | CTAcGCAACAGGGAATaTaCCCGGTTGCTCTTTCTCTATCTTCCTTTTGGCTTTGCTGTCC |
| 108 | DR4 | 489 | CTATGCAACAGGGAATCTTCCTGGTTGCTCTTTCTCTATCTTCCTTTTGGCTTTGCTCTCT |
| 104 | US11 | 489 | CTATGCAACAGGGAACCTTCCTGGTTGCTCTTTCTCTATCTTCCTCTTGGCCCTGCTCTCT |
| 105 | S14 | 489 | CTATGCAACAGGGAACCTTCCTGGTTGCTCTTTCTCTATCTTCCTcCTaGCCCTGCTTTCT |
| 106 | SW1 | 489 | CTATGCAACAGGGAACCTTCCTGGTTGCTCTTTCTCTATCTTCCTCTTGGCCCTGCTTTCT |
| 107 | S18 | 489 | CTATGCAACAGGGAACCTTCCTGGTTGCTCTTTCTCTATCTTCCTCTTGGCCCTGCTCTCT |
| 103 | DK7 | 489 | CTATGCAACAGGGAACCTTCCTGGTTGCTCTTTCTCTATCTTCCTCTTGGCCCTGCTCTCT |

103-124 consensus cTAtGCAAcAGGGAAtcTgCCcGGTTGctCtTTcTCTATcTTCCtCtTgGCttTgCTgTCc

FIGURE 6C-10

| SEQ ID NO: | ISOLATE | | |
|---|---|---|---|
| 119 | S9 | 550 | TGTTTGACCATCCCAGCTTCCGCT |
| 117 | IND3 | 550 | TGTTTGACCATCCCAGCTTCCGCT |
| 118 | IND8 | 550 | TGTTTGACCgTCCCAGCTTCCGCT |
| 111 | D1 | 550 | TGTTTGACCATCCCAGCTTCCGCT |
| 112 | US6 | 550 | TGTTTGACCATtCCAGCTTCCGCT |
| 113 | P10 | 550 | TGccTGACCATCCCAGCgTCCGCT |
| 114 | DK1 | 550 | TGTtTGACCATCCCAGCTTCCGCT |
| 115 | T10 | 550 | TGTCTGACCATCCCAGCTTCCGCc |
| 116 | SW2 | 550 | TGTCTGACCATCCCAGCTTCCGCT |
| 122 | HK4 | 550 | TGTTTGACCATCCCAGCTTCCGCT |
| 109 | SA10 | 550 | TGTTTaACCATCCCAGCTTCCGCT |
| 110 | S45 | 550 | TGcTTGACCATCCCAGCTTCCGCT |
| 123 | P8 | 550 | TGtcTGACCATCCCAGCTTCCGCT |
| 124 | T3 | 550 | TGCTTGACCATCCCAGCTTCCGCT |
| 120 | HK3 | 550 | TGCTTGACCACCCCAGCTTCCGCT |
| 121 | HK5 | 550 | TGtcTGACCACCCCAGtTTCCGCT |
| 108 | DR4 | 550 | TGCtTGACCGTGCCCGCaTCgGCC |
| 104 | US11 | 550 | TGCCTGACTGTGCCCGCTTCAGCC |
| 105 | S14 | 550 | TGCCTGACTGTGCCCGCTTCAGCC |
| 106 | SW1 | 550 | TGCCTGACaGTGCCCGCGTCAGCC |
| 107 | S18 | 550 | TGtCTGACtGTGCCCGCGTCAGCt |
| 103 | DK7 | 550 | TGcCTGACcGTGCCCGCtTCgGCc |

103-124 consensus    TGtTTgACcatcCCaGctTCcGCt

FIGURE 6D-1

```
SEQ ID NO:   ISOLATE
    128           T2      1  ATGAGCACAAtTCCTAAACCTCAAAGAAAAACCAAAGAAAACACTAACCGTCGCCCACAaG
    125           T4      1  ATGAGCACAAATCCTAAACCTCAAAGAAAAACCAAAGAAAACACCAACCGTCGCCCACAgG
    126          US10     1  ATGAGCACAAATCCTAAACCTCAAAGAAAAACCAAAGAAAACACtAACCGTCGCCCACAaG
    127           T9      1  ATGAGCACAAATCCaAAACCCAAAGAAAAACCAtAAGAAAACACCAACCGTCGCCCACAgG 125-128      consensus      ATGAGCACAAaTCCtAAACCtCAAAGAAAAACCAaAAGAAAACAC-AACCGTCGCCCACA-G SEQ ID NO:   ISOLATE
    128           T2     62  ACGTTAAGTTtCCGGGCGGCGGCGGCCAGATCGTTGGCGGAGTATACTTGcTGCCGCGCAGGGG
    125           T4     62  ACGTTAAGTTcCCGGGCGGCGGCGGCCAGATCGTTGGCGGAGTATACTTGTTGCCGCGCAGGGG
    126          US10    62  ACGTTAAGTTtCCGGGCGGCGGCGGCCAGATCGTTGGCGGAGTATACTTGTTGCCGCGCAGGGG
    127           T9     62  ACGTTAAGTTcCCGGGCGGCGGCGGCCAGATCGTTGGCGGAGTATACTTGTTGCCGCGCAGGGG 125-128      consensus      ACGTTAAGTT-CCGGGCGGCGGCGGCCAGATCGTTGGCGGAGTATACTTGtTGCCGCGCAGGGG SEQ ID NO:   ISOLATE
    128           T2    123  CCCCAGGTTGGGTGTGCGCGCGACAAGGAAGAGACTTCGGAGCGGtTCCCAGCCtCGTGGaAGG
    125           T4    123  CCCCAGGTTGGGTGTGCGCGCGACAAGGAAGAGACTTCGGAGCGaTCCCAGCCACGTGGGAGG
    126          US10   123  CCCCAGGTTGGGTGTGCGCGCGACAAGGAAGAGACTTCGGAGCGGTCCCAGCCACGTGGAGG
    127           T9    123  CCCtAGGTTGGGTGTGCGCGCaCGACAAGGAAGAGACTTCGGAGCGGTCCCAGCCACGTGGGAGG 125-128      consensus      CCCCAGGTTGGGTGTGCGCGCGACAAGGAAGAGACTTCGGAGCGGtCCCAGCCaCGTGGGAGG SEQ ID NO:   ISOLATE
    128           T2    184  CGCCAGCCCATCCCtAAAGATCGGCGCTCCACTGGCAAGTCCTGGGGAAAACCAGGATAcC
    125           T4    184  CGCCAGCCCATCCCCAAAGATCGGCGCTCCACTGGCAAGTCCTGGGGAAAACCAGGATAtC
    126          US10   184  CGCCAGCCCATCCCCAAAGATCGGCGCCCCACTGGCAAGTCCTGGGGAAAACCAGGATACC
    127           T9    184  CGCCAGCCCATCCCCAAAGATCGGCGCtCCACTGGCAAGTCCTGGGGAAAACCAGGATACC 125-128      consensus      CGCCAGCCCATCCCcAAAGATCGGCGCtCCACTGGCAAGTCCTGGGGAAAACCAGGATACC
```

FIGURE 6D-2

| SEQ ID NO: | ISOLATE | | |
|---|---|---|---|
| 128 | T2 | 245 | CCTGGCCCCCTGTATGGGAATGAGGGgCTCGGCTGGGCTGGCAGGATGGCTCCTGTCCCCCGAGG |
| 125 | T4 | 245 | CCTGGCCCCCTGTATGGGAATGAGGGACTCGGCTGGGCTGGCAGGATGGCTCCTGTCCCCCGAGG |
| 126 | US10 | 245 | CtTGGCCCCCTATATGGGAATGAGGGACTCGGCTGGGCTGGCAGGATGGCTCCTGTCCCCCGAGG |
| 127 | T9 | 245 | CcTGGCCtCTATATGGGAATGAGGGACTCGGCTGGGCgGGATGGCTCCTGTCCCCCGAGG |

125-128 consensus          CcTGGCCcCT-TATGGGAATGAGGGaCTCGGCTGGGCaGGATGGCTCCTGTCCCCCGAGG

| SEQ ID NO: | ISOLATE | | |
|---|---|---|---|
| 128 | T2 | 306 | TTCtCGTCCCTCtTGGGGCCCCAATGACCCCCGGCATAGGTCGCGCAAtGTGGGTAAaGTC |
| 125 | T4 | 306 | TTCCCGTCCCTCCTGGGGCCCCAATGACCCCCGGCATAGGTCGCGCAACGTGGGTAAGGTC |
| 126 | US10 | 306 | TTCCCGTCCCCTCTTGGGGCCCCACTGAtCCCCGGCATAGGTCGCGCAACGTGGGTAAGGTC |
| 127 | T9 | 306 | TTCCCGTCCCTCTTGGGGCCCCAGTGAcCCCCGGCATAGGTCGCGCAACGTGGGTAAGGTC |

125-128 consensus          TTCcCGTCCCTCtTGGGGCCCCAaTGAcCCCCGGCATAGGTCGCGCAAcGTGGGTAAgGTC

| SEQ ID NO: | ISOLATE | | |
|---|---|---|---|
| 128 | T2 | 367 | ATCGATACCCTAAACGTGCgGCtTTGCCGACCTCATGGGGTACaTCCCCGTCGTAGGCGCcC |
| 125 | T4 | 367 | ATCGATACCCTAAACGTGCaGCCTTGCCGACCTCATGGGGTACGTCCCCGTCGTAGGCGgCC |
| 126 | US10 | 367 | ATCGATACCCTAAACGTGCGGCTTGCCGACCTCATGGGGGaTACATCCCCGTCGTgGGCGCtC |
| 127 | T9 | 367 | ATCGATACCCTAAACGTGCGGCTTTGCCGACCTCATGGGGTACATCCCCGTCGTaGGCGCcC |

125-128 consensus          ATCGATACCCTAAACGTGCgGCtTTGCCGACCTCATGGGGTACaTCCCCGTCGTaGGCGcC

| SEQ ID NO: | ISOLATE | | |
|---|---|---|---|
| 128 | T2 | 428 | CGcTtGGTtGGtGTCgCCAGAGCTCTtGCCGCATGGCCGTGAGAGTCCTGGAGGACGGaGTTAA |
| 125 | T4 | 428 | CGtTgGGTGGCGTCGCCAGAGCTCTCGCCGCATGGCCGTGAGAGTCCTGGAGGACGGGGTTAA |
| 126 | US10 | 428 | CGCTTGGTGGCGTCGCCAGAGCTCTCGCCGCATGGgCCGTGAGgGTCCTGGAGGACGGGGTTAA |
| 127 | T9 | 428 | CGCTTGGTGGCGTtGCCAGAGCTCTCGCCGCAcGGCCGTGAGaGTCCTGGAGaCGGGGTTAA |

125-128 consensus          CGcTtGGtGGcGTcGCCAGAGCTCTcGCCGCATGGCCGTGAGaGTCCTGGAGGACGGgGTTAA

FIGURE 6D-3

| SEQ ID NO: | ISOLATE | | |
|---|---|---|---|
| 128 | T2 | 489 | TTATGCAACAGGtAACTTACCcGGTTGCTCCTTTTCTATcTTCTTTGCTaGCCCTgCTGTCC |
| 125 | T4 | 489 | TTATGCAACAGGgAACTTACCtGGTTGCTCCTCCTTTTCTATtTTCTTGCTGGCCCTACTGTCC |
| 126 | US10 | 489 | TTATGCAACAGGaAACTTACCcGGTTGCTCCTCCTTTTCTATCTTCTTTGCTGGCCtTACTGTCC |
| 127 | T9 | 489 | TTATGCAACAGGaAACcTACCtGGTTGCTGGTTTTTTCTATCTTCTTTGCTGGCCcTACTGTCC |

125-128 consensus TTATGCAACAGGgAACtTACC-GGTTGCTCCcTTTCTATcTTCTTTGCTgGCCcTaCTGTCC

| SEQ ID NO: | ISOLATE | | |
|---|---|---|---|
| 128 | T2 | 550 | TGCATCACTATTCCgGTtTCaGCT |
| 125 | T4 | 550 | TGCATCACCATTCCAGTCTCCGCT |
| 126 | US10 | 550 | TGCATCACCATTCCAGTCTCTGCT |
| 127 | T9 | 550 | TGCATCACCAcTCCgGcCTCTGCT |

125-128 consensus TGCATCACcAtTCC-GtcTCtGCT

FIGURE 6E-1

| SEQ ID NO: | ISOLATE | | |
|---|---|---|---|
| 131 | DK11 | 1 | ATGAGCACAAATCCTAAACCTCAAAGAAAAACCAAAGAAATACAAACCGCCGCCCACAGG |
| 132 | SW3 | 1 | ATGAGCACAAATCCTAAACCTCAAAGAAAAACCAAAGAAATACAAACCGCCGCCCACAGG |
| 133 | DK8 | 1 | ATGAGCACAAATCCTAAACCTCAAAGAAAAACCAAAGACACAAACCGCCGCCCACAGG |
| 129 | T8 | 1 | ATGAGCACAAATCCTAAACCTCAAAGAAAAACCAAAGAAACAAACCGCCGCCCACAGG |
| 130 | US1 | 1 | ATGAGCACAAATCCTAAACCTCAAAGAAAAACCAAAGAAACACAAACCGCCGCCCACAGG |

129-133 consensus ATGAGCACAAATCCTAAACCTCAAAGAAAAACCAAAGAAACACAAACCGCCGCCCACAGG

| SEQ ID NO: | ISOLATE | | |
|---|---|---|---|
| 131 | DK11 | 62 | ACGTTAAGTTCCCGGGTGGCGGCCAGATCGTTGGCGGAGTTTACTTGCTGCCGCAGGGG |
| 132 | SW3 | 62 | ACGTTAAGTTCCCGGGTGGCGGCCAGATCGTTGGCGGAGTTTACTTGCTGCCGCAGGGG |
| 133 | DK8 | 62 | ACGTTAAGTTCCCGGGTGGCGGCCAGATCGTTGGCGGAGTTTACTTGCTGCCGCAGGGG |
| 129 | T8 | 62 | ACGTCAAGTTCCCGGGTGGCGGCCAGATCGTTGGCGGAGTTTACTTGCTGCCGCAGGGG |
| 130 | US1 | 62 | ACGTCAAGTTCCCGGGTGGCGGtCAGATCGTTGGCGGccAGATCGTTGCCGCAGGGG |

129-133 consensus ACGTtAAGTTCCCGGGTGGCGGcCAGATCGTTGGCGGAGTTtACTTGCTGCCGCAGGGG

| SEQ ID NO: | ISOLATE | | |
|---|---|---|---|
| 131 | DK11 | 123 | CCCCAGGTTGGGTGTGCGCaCGACAAGGAAGACTTCCGAGCGATCCCAGCCGCGTGGGAGA |
| 132 | SW3 | 123 | CCCCAGGTTGGGTGTGCGCGCGACAAGGAAGACTTCCGAGCGATCCCAGCCGCGTGGGAGA |
| 133 | DK8 | 123 | CCCCAGGTTGGGTGTGCGCGCGACAAGGAAGAAGtCTTCCGAGCGATCCCAGCCGCGTGGGAGg |
| 129 | T8 | 123 | CCCtAGGTTGGGTGTGCGCGCGACAAGGAAGACTTCCGAGCGATCCCAGCCGCGTGGGAGA |
| 130 | US1 | 123 | CCCcAGGTTGGGTGTGCGCGCGACAAGGAAGaCTTCCGAGCGATCCCAGCCGCGTGGGAGA |

129-133 consensus CCCcAGGTTGGGTGTGCGCgCGACAAGGAAGaCTTCCGAGCGATCCCAGCCGCGTGGGAGa

FIGURE 6E-2

| SEQ ID NO: | ISOLATE | | |
|---|---|---|---|
| 131 | DK11 | 184 | CGCCAGCCCATCCCGAAAGATCGGCGCTCCACCGGCAAGCCCTGGGGAAAGCCAGGATATC |
| 132 | SW3 | 184 | CGCCAGCCCATCCCGAAAGATCGGCGCTCCACCGGCAAGTCCTGGGGAAAGCCAGGATATC |
| 133 | DK8 | 184 | CGCCAGCCCATCCCGAAAGATCGGCGCTCCACCGGCAAGTCCTGGGGAAAACGGATATC |
| 129 | T8 | 184 | CGCCAGCCCATCCCGAAAGATCGGCGCTCCACCGGCAAGTCCTGGGGAAAACCAGGATATC |
| 130 | US1 | 184 | CGCCAGCCCATCCCGAAAGATCGGCGCTCCACCGGCAAGTCCTGGGGAAAgCCAGGATATC |
| 129-133 | consensus | | CGCCAGCCCATCCCGAAAGATCGGCGCTCCACCGGCAAGtCCTGGGGAAAgCCaGGATATC |

| SEQ ID NO: | ISOLATE | | |
|---|---|---|---|
| 131 | DK11 | 245 | CTTGGCCCCTGTATGGAAACGAGGGCTGGGCAGGTTGGCTCCTGTCCCCCGCGG |
| 132 | SW3 | 245 | CTTGGCCCCTGTATGGAAACGAGGGCTGGGCAGGTTGGCTCCTGTCCCCCGCGG |
| 133 | DK8 | 245 | CTTGGCCCCTGTATGGAAACGAGGGCTGGGCAGGTTGGCTCCTGTCCCCCGCGG |
| 129 | T8 | 245 | CTTGGCCTCTtTACGGAAACGAGGGCTGGGtTGGGCAGGTTGGCTCCTGTCCCCCGCGG |
| 130 | US1 | 245 | CTTGGCCTCTgTATGGAAACGAGGGCTGGGcTGGGCAGGTTGGCTCCTGTCCCCCGCGG |
| 129-133 | consensus | | CTTGGCccCTgTAtGGAAACGAGGGCTGGGcTGGGCAGGTTGGCTCCTGTCCCCCGCGG |

| SEQ ID NO: | ISOLATE | | |
|---|---|---|---|
| 131 | DK11 | 306 | GTCTCATCCTAATTGGGGCCCCACTGACCCCCGGCATAaATCACGCAATTTGGtAAAGTC |
| 132 | SW3 | 306 | GTCTCATCCTAATTGGGGCCCCACTGACCCCCGGCATAGATCACGCAATTTGGCAAAGTC |
| 133 | DK8 | 306 | GTCTCGTCCTACTTGGGGCCCCACTGACCCCCGGCATAGATCACGCAATTTGGCAAAGTC |
| 129 | T8 | 306 | GTCTCGTCCTACTTGGGGCCCCACTGACCCCCGGCATAGATCACGTAATTGGGCAgAGTC |
| 130 | US1 | 306 | GTCTCGTCCTACTTGGGGCCCCACTGACCCCCGGCAcAGATCACGTAACTTGGGCAagGTC |
| 129-133 | consensus | | GTCTCgTCCTAcTTGGGGCCCCACTGACCCCCGGCAtAgATCACGcAAtTTGGGCAaaGTC |

FIGURE 6E-3

| SEQ ID NO: | ISOLATE | | |
|---|---|---|---|
| 131 | DK11 | 367 | ATCGACACCATTACGTGTGGTTTTGCCGACCTCATGGGTACATCCCTGTCGTCGGCGCCC |
| 132 | SW3 | 367 | ATCGACACCATTACGTGTGGTTTTGCCGACCTCATGGGTACATCCCTGTCGTTGGCGCCC |
| 133 | DK8 | 367 | ATCGACACCATTACGTGTGGTTTTGCCGACCTCATGGGTACATCCCTGTCGTTGGCGCCC |
| 129 | T8 | 367 | ATCGATACCATTACaTGTGGTTTTGCCGACCTCATGGGTACATCCCTGTCGTTGGCGCCC |
| 130 | US1 | 367 | ATCGATACCATTACGTGTGGTTTTGCCGACCTCATGGGTACATCCCTGTCGTTGGCGCCC |

129-133 consensus ATCGAcACACCATTACgTGTGGTTTTGCCGACCTCATGGGTACATCCCTGTCGTtGGCGCCC

| SEQ ID NO: | ISOLATE | | |
|---|---|---|---|
| 131 | DK11 | 428 | CGGTCGGAGGCGTCGCCAGAGCTCTGGCACACGGTGTTAGAGTCCTGGAAGACGGGATAAA |
| 132 | SW3 | 428 | CGGTCGGAGGCGTCGCCAGAGCTCTGGCACACGGTGTTAGAGTCCTGGAAGACGGGATAAA |
| 133 | DK8 | 428 | CGGTtGGAGGCGTCGCCAGAGCTCTGGCACACGGTGTTAGGGTCCTGGAAGACGGGATAAA |
| 129 | T8 | 428 | CGGTCGGAGGCGTCGCCAGAGCTCTGGCACAtGGTGTTAGGGTCCTGGAAGACGGGATAAA |
| 130 | US1 | 428 | CGGTCGGAGGCGTCGCCAGAGCTCTGGCACAcGGTGTTAGgGTCCTGGAAGACGGGATAAA |

129-133 consensus CGGTCGGAGGCGTCGCCAGAGCTCTGGCACAcGGTGTTAGgGTCCTGGAAGACGGGATAAA

| SEQ ID NO: | ISOLATE | | |
|---|---|---|---|
| 131 | DK11 | 489 | TTACGCAACAGGGAATCTGCCTGGTTGCTCTTTTCTATCTTCTTACTTGCTCTTCTGTCa |
| 132 | SW3 | 489 | TTACGCAACAGGGAATCTGCCTGGTTGCTCTTTTTCTATCTTCTTACTTGCTCTTCTGTCG |
| 133 | DK8 | 489 | TTACGCAACAGGGAATTTGCCTGGTTGCTCTTTTCTATCTTCTTGCTTGCTCTTCTGTCG |
| 129 | T8 | 489 | cTAtGCAACAGGGAATCTGCCTGGTTGCTCCTTTTCTATCTTCTTGCTTGCTCTTCTGTCa |
| 130 | US1 | 489 | tTAcGCAACAGGGAATCTGCCTGGTTGCTCTTTCTATCTTCTTaCTTGCTCTTCTGTCg |

129-133 consensus tTAcGCAACAGGGAATCTGCCTGGTTGCTCtTTTTCTATCTTCTTaCTTGCTCTTCTGTCg

| SEQ ID NO: | ISOLATE | | |
|---|---|---|---|
| 131 | DK11 | 550 | TGCTgCACAGTGCCAGTGTCTGCG |
| 132 | SW3 | 550 | TGCTtCACAGTGCCAGTGTCTGCG |
| 133 | DK8 | 550 | TGCTgCACAGTGCCAGTGTCTGCG |
| 129 | T8 | 550 | TGCTtCACAGTGCCAGTGTCTGCA |
| 130 | US1 | 550 | TGCgcCACggTGCCggTGTCTGCA |
| 129-133 | consensus | | TGCt-CACaGTGCCagTGTCTGCg |

```
SEQ ID NO:  ISOLATE
131         DK11    1   ATGAGCACAAATCCTAAACCTCAAAGAAAAACCAAAGAAATACAAACCGCCGCCCACAGG
132         SW3     1   ATGAGCACAAATCCTAAACCTCAAAGAAAAACCAAAGAAATACAAACCGCCGCCCACAGG
133         DK8     1   ATGAGCACAAATCCTAAACCTCAAAGAAAAACCAAAGAAACACAAACCGCCGCCCACAGG
129         T8C     1   ATGAGCACAAATCCTAAACCTCAAAGAAAAACCAAAGAAACACAAACCGCCGCCCACAGG
130         US1     1   ATGAGCACAAATCCTAAACCTCAAAGAAAAACCAAAGAAACACAAACCGCCGCCCACAGG
125         T4      1   ATGAGCACAAATCCTAAACCTCAAAGAAAAACCAAAGAAACACCAACCGTCGCCCACAGG
126         US10    1   ATGAGCACAAATCCTAAACCTCAAAGAAAAACCAAAGAAACACtAACCGTCGCCCACAaG
127         T9      1   ATGAGCACAAATCCAAAACCcCAAAGAAAAACCAtAAGAAACACAAACCGTCGCCCACAgG
128         T2      1   ATGAGCACAAAtCCTAAACCTCAAAGAAAAACCAAAGAAACACTAACCGTCGCCCACAaG
134         S83     1   ATGAGCACAAAaCCTAAACCTCAAAGAAAAACCAAAGAAACACTAACCGcCGCCCACAgG 125-134     consensus    ATGAGCACAAaTCCtAAACCtCAAAGAAAAACCAaAGAAAcACaAACCGcCGCCCACAgG SEQ ID NO:  ISOLATE
131         DK11    62  ACGTTAAGTTCCCGGGTGGCGGCCAGATCGTTGGCGGAGTTTACTTGCTGCCGCGCAGGGG
132         SW3     62  ACGTTAAGTTCCCGGGTGGCGGCCAGATCGTTGGCGGAGTTTACTTGCTGCCGCGCAGGGG
133         DK8     62  ACGTTAAGTTCCCGGGTGGCGGCCAGATCGTTGGCGGAGTTTACTTGCTGCCGCGCAGGGG
129         T8      62  ACGTCAAGTTCCCGGGTGGCGGCCAGATCGTTGGCGGAGTTTACTTGCTGCCGCGCAGGGG
130         US1     62  ACGTCAAGTTCCCGGGTGGCGGCCAGATCGTTGGCGGAGTTTACTTGCTGCCGCGCAGGGG
125         T4      62  ACGTCAAGTTCCCGGGCGGCGGCGGtCAGATCGTTGGCGGAGTATACTTGTTGCCGCAGGGG
126         US10    62  ACGTCAAGTTCCCGGGCGGCGGCGGCCAGATCGTTGGCGGAGTATACTTGTTGCCGCAGGGG
127         T9      62  ACGTTAAGTTtCCGGGCGGCGGCGGCCAGATCGTTGGCGGAGTATACTTGTTGCCGCAGGGG
128         T2      62  ACGTTAAGTTtCCGGGCGGCGGCGGCCAGATCGTTGGCGGAGTATACTTGCTGCCGCAGGGG
134         S83     62  ACGTcAAGTTcCCGGGCGGCGGCGGCGGtGGCCAGATCGTTGGCGGAGTATACTTGCTGCCGCAGGGG 125-134     consensus    ACGTtAAGTTcCCGGG-GGcGGcCAGATCGTTGGCGGAGT-TACTTGcTGCCGCAGGGG
```

FIGURE 6F-2

| SEQ ID NO: | ISOLATE | | |
|---|---|---|---|
| 131 | DK11 | 123 | CCCCAGGTTGGGTGTGCGCaCGACAAGGAAGACTTCCGAGCGATCCCAGCCGCGTGGGAGA |
| 132 | SW3 | 123 | CCCCAGGTTGGGTGTGCGCGCGACAAGGAAGACTTCCGAGCGATCCCAGCCGCGTGGGAGA |
| 133 | DK8 | 123 | CCCCAGGTTGGGTGTGCGCGCGACAAGGAAGAAGtCTTCCGAGCGATCCCAGCCGCGTGGGAGg |
| 129 | T8 | 123 | CCCtAGGTTGGGTGTGCGCGCGACAAGGAAGACTTCCGAGCGATCCCAGCCGCGTGGGAGA |
| 130 | US1 | 123 | CCCCAGGTTGGGTGTGCGCGCGACAAGGAAGACTTCCGAGCGATCCCAGCCGCGTGGGAGA |
| 125 | T4 | 123 | CCCCAGGTTGGGTGTGCGCGCGACAAGGAAGACTTCGGAGCGATCCAGCCACGTGGGAGG |
| 126 | US10 | 123 | CCCCAGGTTGGGTGTGCGCGCGACAAGGAAGACTTCGGAGCGGTCCCAGCCACGTGGGAGG |
| 127 | T9 | 123 | CCCtAGGTTGGGTGTGCGCaCGACAAGGAAGACTTCGGAGCGGTCCCAGCCACGTGGGAGG |
| 128 | T2 | 123 | CCCcAGGTTGGGTGTGCGCGCGACAAGGAAGACTTCGGAGCGGTCCCAGCCtCGTGGaAGG |
| 134 | S83 | 123 | CCCgAGaTTGGGTGTGCGCGCGACGAGGAAAaACTTCcGAaCGGTCCGAaCGGTCCAGCCaCGTGGGAGG |
| 125-134 | consensus | | CCCcAGgTTGGGTGTGCGCGCgACaAGGAAGaCTTCcGAgCgATCCCAGCCgCGTGGgAGg |

| SEQ ID NO: | ISOLATE | | |
|---|---|---|---|
| 131 | DK11 | 184 | CGCCAGCCCCATCCCGAAAGATCGGCGCTCCACCGGCAAGcCCTGGGAAAGCCAGGATATC |
| 132 | SW3 | 184 | CGCCAGCCCCATCCCGAAAGATCGGCGCTCCACCGGCAAGTCCTGGGAAAGCCAGGATATC |
| 133 | DK8 | 184 | CGCCAGCCCCATCCCGAAAGATCGGCGCTCCACCGGCAAGTCCTGGGAAAACCAGGATATC |
| 129 | T8 | 184 | CGCCAGCCCCATCCCGAAAGATCGGCGCTCCACCGGCAAGTCCTGGGAAAACCgGGATATC |
| 130 | US1 | 184 | CGCCAGCCCCATCCCGAAAGATCGGCGCTCCACCGGCAAGTCCTGGGAAAgCCAGGATATC |
| 125 | T4 | 184 | CGCCAGCCCCATCCCAAAAGATCGGCGCTCCACTGGCAAGTCCTGGGAAAACCAGGATATC |
| 126 | US10 | 184 | CGCCAGCCCCATCCCCAAAGATCGGCGCTCCACTGGCAAGTCCTGGGAAAACCAGGATACC |
| 127 | T9 | 184 | CGCCAGCCCCATCCCCAAAGATCGGCGCcCCACTGGCAAGTCCTGGGAAAACCAGGATACC |
| 128 | T2 | 184 | CGCCAGCCCCATCCCTAAAGATCGGCGCTCCACTGGCAAGTCCTGGGAAAACCAGGATACC |
| 134 | S83 | 184 | CGCCAGCCCCATCCCTAAAGATCGGCGCaCCACTGGCAAGTCCTGCCAAGTCCAGGATACC |
| 125-134 | consensus | | CGCCAGCCCCATCCCgAAAGATCGGCGCtCCAC-GGCAAGtCCTGGGAAAaCCaGGATAtC |

FIGURE 6F-3

| SEQ ID NO: | ISOLATE | | |
|---|---|---|---|
| 131 | DK11 | 245 | CTTGGCCCCTGTATGGAAACGAGGGCTGCGGCTGGGCAGGTTGGCTCCTGTCCCCCGCGG |
| 132 | SW3 | 245 | CTTGGCCCCTGTATGGAAACGAGGGCTGCGGCTGGGCAGGTTGGCTCCTGTCCCCCGCGG |
| 133 | DK8 | 245 | CTTGGCCCCTGTATGGAAACGAGAGGCTGCGGCTGGGCAGGTTGGCTCCTGTCCCCCGCGG |
| 129 | T8 | 245 | CTTGGCCCTCTCTtTACGGAAACGAGAGGCTGCGGCTGGGCAGGTTGGCTCCTGTCCCCCGCGG |
| 130 | US1 | 245 | CTTGGCCTCTGTACGGAAACGAGGGCTGCGGCTGGGCAGGTTGGCTCCTGTCCCCCGCGG |
| 125 | T4 | 245 | CcTGGCCCCTGTATGGAATGGAATGAGGGACTCGGCTGGGCAGGATGGCTCCTGTCCCCCGAGG |
| 126 | US10 | 245 | CtTGGCCCCTATATGGAATGGAATGAGGGACTCGGCTGGGCAGGATGGCTCCTGTCCCCCGAGG |
| 127 | T9 | 245 | CCTGGCCtCTATATGGAATGGAATGAGGGACTCGGCTGGGCAGGATGGCTCCTGTCCCCCGAGG |
| 128 | T2 | 245 | CCTGGCCCCTGTATGGAATGGAATGAGGGCTCGGCTGGGCAGGATGGCTCCTGTCCCCCGAGG |
| 134 | S83 | 245 | CtTGGCCCCTGTATGGAATGAGGGCCTTGGCTGGCAGGgTGGCTCCTGTCCCCCGcGG |
| 125-134 | consensus | | CtTGGCCcCTgTAtGG-AA-GAGGGc--CGGcTGGGCaGGtTGGCTCCTGTCCCCCGcGG |

| SEQ ID NO: | ISOLATE | | |
|---|---|---|---|
| 131 | DK11 | 306 | GTCTCATCCTAATTGGGGCCCCACTGACCCCCGGCATAaATCACGCAATTTGGGtAAAGTC |
| 132 | SW3 | 306 | GTCTCATCCTAATTGGGGCCCCACTGACCCCCGGCATAGATCACGCAATTTGGGCAAAGTC |
| 133 | DK8 | 306 | GTCTCGTTCCTACTTGGGGCCCCACTGACCCCCGGCATAGATCACGCAATTTGGGCAAAGTC |
| 129 | T8 | 306 | GTCTCGTCCTACTTGGGGCCCCACTGACCCCCGGCATAGATCACGTAATTTGGGCAgAGTC |
| 130 | US1 | 306 | GTCTCGTCCTACTTGGGGCCCCACTGACCCCCGGCACAGATCACGTAACTTGGGCAAGGTC |
| 125 | T4 | 306 | TTCCCGTCCCTCCTGGGGCCCCAaTGACCCCACTGAtCCCCGGCATAGGTCGCGCAACGTGGGTAAGGTC |
| 126 | US10 | 306 | TTCCCGTCCCTCTTGGGGCCCCACTGAtCCCCGGCATAGGTCGCGCAACGTGGGTAAGGTC |
| 127 | T9 | 306 | TTCCCGTCCCTCTTGGGGCCCCACTGACCCCCGGCATAGGTCGCGCAACGTGGGTAAGGTC |
| 128 | T2 | 306 | TTCCCGTCCCTCTTGGGGCCCCAGTGACCCCCGGCATAGGTCGCGCAAtGTGGGTAAaGTC |
| 134 | S83 | 306 | TTCTCGcCTTCaTGGGGCCCACcGACCGACCCCCGGCATAaaTCGCGCAACtTGGGTAAGGTC |
| 125-134 | consensus | | -TCtCgtCCt-ctTGGGGCCCCActGAcCCCCGGCATAgaTC-CGcAA-tTGGGtAa-GTC |

FIGURE 6F-4

| SEQ ID NO: | ISOLATE | | |
|---|---|---|---|
| 131 | DK11 | 367 | ATCGACACCATTACGTGTGGTTTTGCCGACCTCATGGGTACATCCCTGTCGTcGGCGCCC |
| 132 | SW3 | 367 | ATCGACACCATTACGTGTGGTTTTGCCGACCTCATGGGTACATCCCTGTCCTGTTGGCGCCC |
| 133 | DK8 | 367 | ATCGACACCATTACGTGTGGTTTTGCCGACCTCATGGGTACATCCCTGTCCTGTTGGCGCCC |
| 129 | T8 | 367 | ATCGATACCATTACaTGTGGTTTTGCCGACCTCATGGGTACATCCCTGTCGTTGGCGCCC |
| 130 | US1 | 367 | ATCGATACCATTACGTGTGGTTGTTTGCCGACCTCATGGGTACATCCCTGTCGTTGGCGCCC |
| 125 | T4 | 367 | ATCGATACCCTAACGTGCAGCCTTGCCGACCTCATGGGTACGTCCCCGTCGTaGGCGgCC |
| 126 | US10 | 367 | ATCGATACCCTAACGTGCGGCTTTGCCGACCTCATGGGaTACATCCCCGTCGTgGGGCGtC |
| 127 | T9 | 367 | ATCGATACCCTAACGTGCGGCTTTGCCGACCTCATGGGTACATCCCCGTCGTAGGCGCCC |
| 128 | T2 | 367 | ATCGATACCCTAACGTGCGGCTTTGCCGACCTCATGGGTACATCCCCGTCGTAGGCGCCC |
| 134 | S83 | 367 | ATCGATACCCTAACGTGCGGtTTTGCCGACCTCATGGGTACATaCCCGTCGTtGGCGCtC |

125-134 consensus ATCGAtACC-T-ACgTG-gGtTTTGCCGACCTCATGGGtACaTcCC-GTCGTtGGCGCcC

| SEQ ID NO: | ISOLATE | | |
|---|---|---|---|
| 131 | DK11 | 428 | CGGTCGGAGGCGTCGCCCAGAGCTCTGGCACACGGTGTTAGAGTCCTGGAAGACGGATAAA |
| 132 | SW3 | 428 | CGGTCGGAGGCGTCGCCCAGAGCTCTGGCACACGGTGTTAGAGTCCTGGAAGACGGATAAA |
| 133 | DK8 | 428 | CGGTtGGAGGCGTCGCCCAGAGCTCTGGCACACGGTGTTAGGGTCCTGGAAGACGGATAAA |
| 129 | T8 | 428 | CGGTCGGAGGCGTCGCCCAGAGCTCTGGCACACGGTGTTAGGGTCCTGGAAGACGGATAAA |
| 130 | US1 | 428 | CGGTCGGAGGCGTCGCCCAGAGCTCTGGCACACAtGGTGTTAGGGTCCTGGAAGACGGATAAA |
| 125 | T4 | 428 | CGtTgGGTGGCGTCGCCCAGAGCTCTGCGCATGGCGTGAGaGTCCTGAGgACGGGGTTAA |
| 126 | US10 | 428 | CGCTTGGTGGCGTCGCCCAGAGCTCTCGCGCATGGCGTGAGgGTCCTGGAGGACGGGGTTAA |
| 127 | T9 | 428 | CGCTTGGTGGCGTtGCCGAGAGCTCTCGCCGCACGGCGTGAGAGTCCTGGAGGACGGGGTTAA |
| 128 | T2 | 428 | CGCTTGGTGGTGTcGCCGAGAGCTCTtGCGCATGGCGTGAGAGTCCTGGAGGACGGaGTTAA |
| 134 | S83 | 428 | CCgTTGGCGGCGTtGCCAGAGAGCCCTGCGCcCATGGGGTtCTGGAGGACGGgaTaAA |

125-134 consensus CggTtGGaGGCGTcGCCAGAGCtCTggCaCA-GgtGT-AG-GTcCTGGA-GACGGgaTaAA

FIGURE 6F-5

| SEQ ID NO: | ISOLATE | | |
|---|---|---|---|
| 131 | DK11 | 489 | TTACGCAACAGGGAATCTGCCTGGTTGCTCTCTTTTCTATCTTCTTACTTGCTCTTCTGTCa |
| 132 | SW3 | 489 | TTACGCAACAGGGAATCTGCCTGGTTGCTCTCTTTCTTTCTATCTTCTTACTTGCTCTTCTGTCG |
| 133 | DK8 | 489 | TTACGCAACAGGGAATTTGCCTGGTTGCCTCTCTTTTCTATCTTCTTGCTGCTCTTCTGTCG |
| 129 | T8 | 489 | cTAtGCAACAGGGAATTTGCCTGGTTGCCTCTCTTTTCTATCTTCTTGCTGCTCTTCTGTCa |
| 130 | US1 | 489 | TTAcGCAACAGGGAATcTGCCTGGTTGCCTCCTTTTCTTTCTATCTTCTTaCTTGCTCTTCTGTCg |
| 125 | T4 | 489 | TTATGCAACAGGGAACTTACCTGGTTGCCTCCTTTCTATTTTCTTGCTTGCTTGGCCCTACTGTCC |
| 126 | US10 | 489 | TTATGCAACAGGGAACTTACCcGGTTGCCTCTCTTTTCTATCTTCTTGCTGCTTACTGTCC |
| 127 | T9 | 489 | TTATGCAACAGGGAACcTACCtGGTTGCCTCTCTTTTCTATCTTCTTGCTGCCCTACTGTCC |
| 128 | T2 | 489 | TTATGCAACAGGtAACTTACCCGGTTGCCTCTCTTTTCCTTTCTATCTTCTTGCTaGCCCTGTCC |
| 134 | S83 | 489 | TTATGCAACgGGgAATTgCCCGGTTGCTCTCTATCTTTcTCTATCTTTcTcTTGGCCCTctTGTCt |

125-134 consensus tTAtGCAACaGGgAAtTgCCTGGTTGCTCTCTTTTCTATcTTcTTgcTTgC-cTtcTGTCc

| SEQ ID NO: | ISOLATE | | |
|---|---|---|---|
| 131 | DK11 | 550 | TGCTgCACAGTGCCAGTGTCTGCG |
| 132 | SW3 | 550 | TGCTtCACAGTGCCAGTGTCTGCG |
| 133 | DK8 | 550 | TGCTgCACAGTGCCAGTGTCTGCG |
| 129 | T8 | 550 | TGCTtCACAGTGCCAGTGTCTGCA |
| 130 | US1 | 550 | TGCgcCACgGTGCCgGTGTCTGCA |
| 125 | T4 | 550 | TGCATCACCATTCCAGTCTCCGCT |
| 126 | US10 | 550 | TGCATCACCATTCCAGTCTCTGCT |
| 127 | T9 | 550 | TGCATCACCAcTCCGGcCTTCTGCT |
| 128 | T2 | 550 | TGCATCACTATTCCGGTTTCaGCT |
| 134 | S83 | 550 | TGCATCtCTgTgCCaGTTTCCGCc |

125-134 consensus TGCatCaCagtgCCaGtgTCtGCt

FIGURE 6G-1

| SEQ ID NO: | ISOLATE | | |
|---|---|---|---|
| 138 | DK12 | 1 | ATGAGCACACTTCCTAAACCTCAAAGAAAAACCAAAAGAAAACACCATCCGTCGCCCACAGG |
| 135 | HK10 | 1 | ATGAGCACACTTCCTAAACCTCAAAGAAAAACCAAAAGAAAACACCATCCGTCGCCCACAGG |
| 136 | S52 | 1 | ATGAGCACACTTCCTAAACCTCAAAGAAAAACCAAAAGAAAACACCATCCGTCGCCCACAGG |
| 137 | S2 | 1 | ATGAGCACACTTCCTAAACCTCAAAGAAAAACCAAAAGAAAACACCATCCGTCGCCCACAGG |

135-138 consensus ATGAGCACACTTCCTAAACCTCAAAGAAAAACCAAAAGAAAACACCATCCGTCGCCCACAGG

| SEQ ID NO: | ISOLATE | | |
|---|---|---|---|
| 138 | DK12 | 62 | ACGTCAAGTTCCCGGGTGGCGGACAGATCGTTGGTGGTGGAGTATACGTGTTGCCGCAGGGG |
| 135 | HK10 | 62 | ACGTTAAGTTCCCGGGTGGCGGACAGATCGTTGGTGGTGGAGTATACGTGTTGCCGCAGGGG |
| 136 | S52 | 62 | ACGTTAAGTTCCCGGGTGGCGGACAGATCGTTGGTGGTGGAGTATACGTGTTGCCGCAGGGG |
| 137 | S2 | 62 | ACaTcAAGTTCCCGGGTGGCGGACAGATCGTTGGTGGTGGAGTATACGTGTTGCCGCAGGGG |

135-138 consensus ACgT-AAGTTCCCGGGTGGCGGACAGATCGTTGGTGGTGGAGTATACGTGTTGCCGCAGGGG

| SEQ ID NO: | ISOLATE | | |
|---|---|---|---|
| 138 | DK12 | 123 | CCCACGATTGGGTGTGCGCGCGACGCGTAAAACTTCTGAACGGTCaCAGCCTCGCGGACGg |
| 135 | HK10 | 123 | CCCACGATTGGGTGTGCGCGCGACGCGTAAAACTTCTGAACGGTCgCAGCCTCGCGGACGA |
| 136 | S52 | 123 | CCCACGATTGGGTGTGCGCGCGACGCGTAAAACTTCTGAACGGTCACAGCCTCGCGGACGA |
| 137 | S2 | 123 | CCCACGATTGGGTGTGCGCGCGACGCGTAAAACTTCTGAACGGTCACAGCCTCGCGGACGg |

135-138 consensus CCCACGATTGGGTGTGCGCGCGACGCGTAAAACTTCTGAACGGTCaCAGCCTCGCGGACG-

| SEQ ID NO: | ISOLATE | | |
|---|---|---|---|
| 138 | DK12 | 184 | CGACAGCCTATCCCCAAGGCGCGTCGGAGCGAAGGCCGGTCCTGGGCTCAGCCtGGGTACC |
| 135 | HK10 | 184 | CGACAGCCTATCCCCAAGGCGCGTCGGAGCGAAGGCCGGTCCTGGGCTCAGCCCGGGTACC |
| 136 | S52 | 184 | CGACAGCCTATCCCCAAGGCGCGTCGGAGCGAAGGCCGGTCCTGGGCTCAGCCCGGGTACC |
| 137 | S2 | 184 | CGACAGCCTATCCCCAAGGCGCGTCGGAGCGAAGGCCGGaTCCTGGGCTCAGCCGGGTACC |

135-138 consensus CGACAGCCTATCCCCAAGGCGCGTCGGAGCGAAGGCCGgTCCTGGGCTCAGCCgGGTACC

FIGURE 6G-2

| SEQ ID NO: | ISOLATE | | |
|---|---|---|---|
| 138 | DK12 | 245 | CTTGGCCCCTCTATGGTAACGAGGGCTGCGGGTGGGCAGGGTGGCTCCTGTCCCCACGCGG |
| 135 | HK10 | 245 | CTTGGCCCCTCTATGGTAACGAGGGCTGCGGGTGGGCAGGaTGGCTCCTGTCCCCACGCGG |
| 136 | S52 | 245 | CTTGGCCCCTCTATGGTAAtGAGGGCTGCGGGTGGGCAGGGTGGCTCCTGTCCCCACGCGG |
| 137 | S2 | 245 | CTTGGCCCCTCTATGGTAACGAGGGCTGCGGGTGGGCAGGGTGGCTCCTGTCCCCACGCGG |
| 135-138 | consensus | | CTTGGCCCCTCTATGGTAACGAGGGCTGCGGGTGGGCAGGGTGGCTCCTGTCCCCACGCGG |

| SEQ ID NO: | ISOLATE | | |
|---|---|---|---|
| 138 | DK12 | 306 | CTCCCGTCCATCTTGGGGCCCAAACGACCCCCGGCCGgaGGTCCCGCAATTTGGGTAAgGTC |
| 135 | HK10 | 306 | CTCCCGTCCATCTTGGGGCCCAAACGACCCCCGGCCGCGacGGTCCCGCAATTTGGGTAAAGTC |
| 136 | S52 | 306 | CTCCCGTCCATCTTGGGGCCCAAACGACCCCCGGCCGGAGTCCCGCAATTTGGGTAAAGTC |
| 137 | S2 | 306 | CTCCCGTCCATCTTGGGGCCCAAAtGACCCCCGGCCGGAGTCCCGCAATTTGGGTAAAGTC |
| 135-138 | consensus | | CTCCCGTCCATCTTGGGGCCCAAACGACCCCCGGCCGgaGGTCCCGCAATTTGGGTAAgGTC |

| SEQ ID NO: | ISOLATE | | |
|---|---|---|---|
| 138 | DK12 | 367 | ATCGATACCCTcACGTGCGGATTCGCCGACCTCATGGGGTACATCCCGCTCGTCGGCGCTC |
| 135 | HK10 | 367 | ATCGATACCCTTACGTGCGGATTCGCCGACCTCATGGGTACATCCCGCTCGTCGGCGCTC |
| 136 | S52 | 367 | ATCGATACCCTTACGTGCGGATTCGCCGACCTCATGGGTACATCCCGCTCGTCGGCGCTC |
| 137 | S2 | 367 | ATCGATACCCTTACGTGCGGCTTCGCCGACCTCATGGGTACATCCCGCTCGTCGGCGCTC |
| 135-138 | consensus | | ATCGATACCCTtACGTGCGGATTCGCCGACCTCATGGGTACATCCCGCTCGTCGGCGCTC |

| SEQ ID NO: | ISOLATE | | |
|---|---|---|---|
| 138 | DK12 | 428 | CtGTAGGgGGCGTCGCAAGAGCCCTCGCGCGTGAGGGCCCTTGAAGACGGGATAAA |
| 135 | HK10 | 428 | CCGTAGGAGGCGTCGCAAGAGCCCTCGCGCATGGCCGTGAGGGCCCTTGAAGACGGGATAAA |
| 136 | S52 | 428 | CCGTAGGAGGCGTCGCAAGAGCCCTCGCGCATGGCCGTGAGGGCCCTTGAAGACGGGATAAA |
| 137 | S2 | 428 | CCGTAGGAGGCGTCGCAAGAGCCCTCGCGCATGGCCGTGAGGGCCCTTGAAGACGGGATAAA |
| 135-138 | consensus | | CCGTAGGaGGCGTCGCAAGAGCCCTCGCGCATGGCCGTGAGGGCCCTTGAAGACGGGATAAA |

FIGURE 6G-3

| SEQ ID NO: | ISOLATE | | |
|---|---|---|---|
| 138 | DK12 | 489 | TTTCGCAACAGGGAACTTGCCCGGTTGCTCCTTTCTATCTTCCTTCTTGCTCTGTTCTCT |
| 135 | HK10 | 489 | TTTCGCAACAGGGAACTTGCCCGGTTGCTCCTCCTTTCTATCTTCCTTCTTGCTCTGTTCTCT |
| 136 | S52 | 489 | TTTTGCAACAGGGAACTTGCCCGGTTGCTCCTCCTTTCTATCTTCCTTCTTGCTCTGTTCTCT |
| 137 | S2 | 489 | TTTTGCAACAGGGAACTTGCCCGGTTGCTCTCTTTTCTATCTTCCTTCTTGCcCTGTTCTCt |

135-138 consensus  TTT-GCAACAGGGAACTTGCCCGGTTGCTCcTTTTCTATCTTCCTTCTTGCtCTGTTCTCt

| SEQ ID NO: | ISOLATE | | |
|---|---|---|---|
| 138 | DK12 | 550 | TGCcTAATTCATCCAGCAGCAGCTAGT |
| 135 | HK10 | 550 | TGCTTAATTCATCCAGCAGCAGCTAGT |
| 136 | S52 | 550 | TGCTTAgTTCATCCtGCAGCTAGT |
| 137 | S2 | 550 | TGCTTAaTTCATCCaGCAGCAGCTAGT |

135-138 consensus  TGCtTAaTTCATCCaGCAGCAGCTAGT

FIGURE 6H-1

| SEQ ID NO: | ISOLATE | | |
|---|---|---|---|
| 145 | DK13 | 1 | ATGAGCACGAATCCTAAACCTCAAAGAAAAACCAAACGTAACACCAACCGCCGCCCaATGG |
| 143 | Z6 | 1 | ATGAGCACGAATCCTAAACCTCAAAGAAAAACCAAACGTAACACCAACCGCCGCCCCATGG |
| 144 | Z7 | 1 | ATGAGCACGAATCCTAAACCTCAAAGAAAAACCAAACGTAACACCAACCGCCGCCCCATGG |
| 140 | Z8 | 1 | ATGAGCACGAATCCTAAACCTCAAAGAAAAACCAAACGTAACACCAACCGCCGCCCtATGG |
| 139 | Z4 | 1 | ATGAGCACGAATCCTAAACCTCAAAGAAAAACCAAACGTAACACCAACCGCCGCCCCATGG |
| 142 | Z5 | 1 | ATGAGCACGAATCCTAAACCTCAAAGAAAAACCAAACGTAACACCAACCGCCGCCCCATGG |
| 141 | Z1 | 1 | ATGAGCACACAAATCCTAAACCTCAAAGAAAAACCAAACGTAACACCAACCGtCGCCGCCCATGG |
| 139-145 | consensus | | ATGAGCACgAATCCTAAACCTCAAAGAAAAACCAAACGTAACACCAACCGcGCCCCATGG |

| SEQ ID NO: | ISOLATE | | |
|---|---|---|---|
| 145 | DK13 | 62 | ACGTTAAGTTCCCGGGTGGCGGCCAGATCGTTGGCGGAGTTTACTTGTTGCCGCGCAGGGG |
| 143 | Z6 | 62 | ACGTTAAGTTCCCGGGTGGTGCGCGGTGGCCAGATCGTTGGCGGAGTTTACTTGTTGCCGCGCAGGGG |
| 144 | Z7 | 62 | ACGTTAAGTTCCCGGGCGGTGGCCaGGCGGCCAGATCGTTGGCGGAGTTTACTTGTTGCCGCGCAGGGG |
| 140 | Z8 | 62 | AtGTAAAaTTCCCGGGTGGTGGCCAGATCGTTGGCGGAGTTTACTTGTTGCCGCGCAGGGG |
| 139 | Z4 | 62 | AcGTAAAgTTCCCGGGTGGTGGtCAGATCGTTGGCGGAGTTTACTTGTTGCCGCGCAGGGG |
| 142 | Z5 | 62 | ATGTAAAATTCCCGGGCGGCCAGATCGTTGGCGGAGTTTACTTGTTGCCGCGCAGGGG |
| 141 | Z1 | 62 | ATGTgAAATTCCCGGGCGGCCAGATCGTTGGCGGAGTTTACTTGcTGCCGCGCAGGGG |
| 139-145 | consensus | | AcGT-AAgTTCCCgGGtGGtGGCCAGATCGTTGGCGGAGTTTACTTGtTGcCGCGCAGGGG |

| SEQ ID NO: | ISOLATE | | |
|---|---|---|---|
| 145 | DK13 | 123 | CCCtAGaTTGGGTGTGCGCGCGGACTAGGAAGAGACTTCGGAGCGGTCGCAACCTCGTGGGAGg |
| 143 | Z6 | 123 | CCCCAGgTTGGGTGTGCGCGCGGACTAGGAAGAGACTTCGGAGCGGTCGCAACCTCGTGGGAGA |
| 144 | Z7 | 123 | CCCCAGaTTGGGTGTGCGCGCaCAaACTAGGAAGAGACTTCGGAGCGGTCGCAACCTCGTGGGAGA |
| 140 | Z8 | 123 | CCCCAGgTTGGGTGTGCGCGCGGACTCGGAAGAGACTTCGGAGCGGTCGCAACCTCGTGGCAGG |
| 139 | Z4 | 123 | CCCCAGgTTGGGTGTGCGCGCGGACTCGGAaAGAGACTTCGGAGCGGTCGCAACCTCGTGGCAGG |
| 142 | Z5 | 123 | CCCCAGgTTGGGTGTGCGCGCGGACTCGGAAGAGACTTCGGAGCGGTCGCAACCTCGCGGCAGG |
| 141 | Z1 | 123 | CCCcGGTTGGGTGTGCGCGCCagCTCGGAAGACTTCGGAGCGGTCaCAACCTCGtGGCAGG |
| 139-145 | consensus | | CCCcaGgTTGGGTGTGCGCgCGgaCTcGgAAGACTTCGGAGCGGTCgCAACCTCGtGGCAGg |

FIGURE 6H-2

```
SEQ ID NO:   ISOLATE
    145        DK13    184 CGCCAGCCTATCCCCAAGGCgCGcCaActcGAGGGtAGGTCCTGGGCTCAGCCtGGGTATC
    143         Z6     184 CGCCAGCCTATCCCCAAGGCACGTCGATCTGAGGGAAGGTCCTGGGCTCAGCCGGGTATC
    144         Z7     184 CGTCAGCCTATCCCCAAGGCACGTCGATCTGAGGGAAGGTCCTGGGCTCAaCCCGGGTACC
    140         Z8     184 CGTCAGCCTATCCCCAAGGCACGTCGGTCGAGGGCAGGTAGGTCCTGGGCTCAGCCGGGTACC
    139         Z4     184 CGTCAaCCTATCCCCAAGGCGCGcCaGcCaGAGAGGGCAGaTCCTGGGCgCAGCCCGGGTACC
    142         Z5     184 CGTCAGCCTATCCCCaGGCaCGtCGGTCCGAGGGCAGGTCCTGGGCTCAGCCGGGTACC
    141         Z1     184 CGTCAGCCTATCCCCaAGGCgCGcCGGTCCGAGGGCAGGTCCTGGGCTCAGCCGGGTACC 139-145       consensus     CGtCAgCCTATCCCCaAGGCaCGtCggtccGAGGGCAGgTCCTGGGCtCAgCCcGGGTAcC SEQ ID NO:   ISOLATE
    145        DK13    245 CtTGGCCcCTTTACGGCAATGAGGGcTGCGGGTGGGCGGATGGCTCCTGTCACCCCGTGG
    143         Z6     245 CATGGCCTCTTTACGGTAATGAGGGTTGCGGGTTGCGGGATGGCTCCTGTCACCCCGTGG
    144         Z7     245 CATGGCCTCTTTACGGTAAcGAGGGTTGCGGGTTGCGGGCAGGATGGCTCtTGTCACCCCGTGG
    140         Z8     245 CATGGCCTCTTTACGGTAATGAaGGCTTGGGTGGCGGGCAGGTTGGCTCCTGTCCCCCGCGG
    139         Z4     245 CTTGGCCcCTCtATGGCAATGAGGGCTGCGGGTGGGCAGGGTTGCAGGTGGCTCCTGTCCTCCGCGG
    142         Z5     245 CTTGGCCtCTTTATGGCAATGAGGGCTGTGGGTGGGCAGGGTGTGCAGGTGGCTCCTGTCCCCCCGGG
    141         Z1     245 CTTGGCCcCTTTACGGCAATGAGGGCTGTGGGTGGGCAGGGTGTGCAGGTGGCTCCTGTCCCCCCGCGG 139-145       consensus     CtTGGCCtCTtTAcGGcAAtGAgGGcTGcGGGTGGGCaGG-TGGCTCCTGTC-CCcGcGG SEQ ID NO:   ISOLATE
    145        DK13    306 CTCTCGgCCGTCTTGGGGcCCGAATGATCCCCGGCGAGGTCCCGCAACTTGGGTAAGGTC
    143         Z6     306 CTCTCGACCGTCTTGGGGtCCAAATGATCCCGGCGAAGGTCCCGCAACTTGGGTAAGGTC
    144         Z7     306 CTCTCGACCGTCTTGGGGCCCAAATGATCCCCGGCGAAGGTCCCGCAACTTGGGTAAGGTC
    140         Z8     306 CTCTCGACCGTCTTGGGGCCCAAATGATCCCCGGCGAGTCGCGCAATTTGGGTAAGGTC
    139         Z4     306 CTCTCGGCCATCTTGGGGCCCAAATGATCCCCGGCGGAGATCGCAATCTGGGTAAGGTC
    142         Z5     306 aTCTCGGCCATCTTGGGGCCCaAAATGATCCCCGGCGTAGTCCCGCAATCTGGGTAAGGTC
    141         Z1     306 tTCCaGGCCGTCTTGGGGCCCcAATGATCCCCGGCGTAGTCCCGCAATCTGGGTAAaGTC 139-145       consensus     cTCtcGgCCGTCTTGGGGcCCaAATGATCCCCGGCGAGTCCGcAAttGGGTAAGTC
```

FIGURE 6H-3

| SEQ ID NO: | ISOLATE | | |
|---|---|---|---|
| 145 | DK13 | 367 | ATCGATACcCCTAACTTGCGGcTTCGCCGAcCTCATGGGATACATCCCGgTCGTAGGCGCCC |
| 143 | Z6 | 367 | ATCGATACtCTAACTTGCGGtTTCGCCGAtCTCATGGGATACATCCCGCTCGTAGGCGCCC |
| 144 | Z7 | 367 | ATCGATACCCTAACcTGCGGCTTtGCCGACCTCATGGGATACATCCCGCTCGTAGGCGCCC |
| 140 | Z8 | 367 | ATCGATACCCTcACGTGCGGCTTCGCCGACCTCATGGGATACATCCCGCTCGTGGGCGCCC |
| 139 | Z4 | 367 | ATCGATACCCTGACGTGCGCGCTTCGCCGACCTCATGGGATACATCCCGCTCGTGGGCGCCC |
| 142 | Z5 | 367 | ATCGATACCCTGACGTGGCTTCGCCGACCTCATGGGATACATTCCGCTCGTcGGCGCCC |
| 141 | Z1 | 367 | ATCGATACCCTGACGTGTGGCTTCGCCGACCTCATGGGATACATTCCGCTCGTCGGCGCCC |

139-145 consensus ATCGATACcCT-ACgTGcGGcTTcGCCGAcCTCATGGGATACATcCCGcTCGTaGGCGCCC

| SEQ ID NO: | ISOLATE | | |
|---|---|---|---|
| 145 | DK13 | 428 | CCGTGGGtGGCGTCGCCGCAGaGCCCTGGCgCATGGCgTcAGGctTcTGGAGGACGGGTCAA |
| 143 | Z6 | 428 | CCGTGGGCGGCGTCGCCGCCAGGGCCCTGGCaCATGGCTGTTAGGGCTGTGGAGGACGGGATCAA |
| 144 | Z7 | 428 | CCGTGGGCGGCGTCGCCGCCAGGGCCCTaGCCGCTTAGGGCTCTGGAGGACGGGATCAA |
| 140 | Z8 | 428 | CaGTaGGaGGCGTCGCCAGaGCCCTGGCCGTCAGGGCCGTGGAGGACGGGATCAA |
| 139 | Z4 | 428 | CcGTgGGGGGCGTCGCCAGGGCCCTcTGGCGCATGGCCGTCAGGGCCGTGGAGGACGGGATCAA |
| 142 | Z5 | 428 | CaGTaGGTGGCGTCGCCAGGGCCCTTGGCGCATGGCCGTCAGGGCCCTGGAGGACGGAATCAA |
| 141 | Z1 | 428 | CtGTgGGTGGCGTCGCCAGGGCCCTGGCGCATGGCCGTCAGGGCCGTGGAGGACGGAATtAA |

139-145 consensus CcGTgGGtGGCGTCGCCAGGGCccTgGCgCATGGCgTcAGGgctgTGGAGGACGGgaTcAA

| SEQ ID NO: | ISOLATE | | |
|---|---|---|---|
| 145 | DK13 | 489 | TTATGCAACAGGGAATCTTCCCGGTTGCTCTTTCTCTATCTTCCTCTTGGCACTgCTcTCG |
| 143 | Z6 | 489 | TTATGCAACAGGGAATCTTCCCGGTTGCTCTCTTCTCTATCTTCCTCTTGGCACTTCTTTCG |
| 144 | Z7 | 489 | TTATGCAACAGGGAATCTTCCCGGTTGCTCTTTCTCTATCTTCCTCTTGGCACTTCTTTCG |
| 140 | Z8 | 489 | CTATGCAACAGGGAACCTTCCCGGTTGCTCTCTTTTCTCTATCTTCCTCTTGGCACTTCTTTCG |
| 139 | Z4 | 489 | CTATGCAACAGGGAATCTTCCCGGTTCCtGTTGCTCTCTTCTCTTCTCTATCTTCCTCTTGGCACTTCTTTCG |
| 142 | Z5 | 489 | CTATGCAACAGGGAATCTTCCCGGTTGCTCTCTTCCTTTCTCTATCTTCCTaCTTGCACTTtCTTCG |
| 141 | Z1 | 489 | CTAcGCAACAGGGAACCTTCCGGTTGCTCTCTTCTCTTCTCTATCTTCCTTCTTGCACTTtCTCTCG |

139-145 consensus cTAtGCAACAGGGAAtCTTCCcGGTTGCTcTCTTcTCtCTATCTTCcTctTggCACTtcTCTCG

FIGURE 6H-4

| SEQ ID NO: | ISOLATE | | |
|---|---|---|---|
| 145 | DK13 | 550 | TGCCTgACTGTTCCCgCtTCGGCC |
| 143 | Z6 | 550 | TGCCTaACTGTTCCCaCCTCGGCC |
| 144 | Z7 | 550 | TGCCTgACTGTTCCCGCCTCGGCC |
| 140 | Z8 | 550 | TGCCTaACcGTcCCAGCGTCtGCT |
| 139 | Z4 | 550 | TGCCTcACtGTtCCAGCGTCgGCT |
| 142 | Z5 | 550 | TGCtTGACAACACCgGCATCCGCT |
| 141 | Z1 | 550 | TGCcTGACAACACCaGCATCtGCc |

139-145  consensus     TGCcTgACtgttCC-gC-TCgGCc

FIGURE 6I-1

```
SEQ ID NO:   ISOLATE
153          SA11     1  ATGAGCACGAATCCTAAACCTCAAAGAAAACCaAAAGAAAACACCAACCGCCCACAGG
152          SA6      1  ATGAGCACGAATCCTAAACCTCAAAGAAAACCAAAAGAAAACACCAACCGCCCACAGG
146          SA4      1  ATGAGCACGAATCCTAAACCTCAAAGAAAACCAAAAGAAAACACCAACCGCCCACAGG
147          SA5      1  ATGAGCACGAATCCTAAACCTCAAAGAAAACCAAAAGAAAACACCAACCGCCCACAGG
148          SA7      1  ATGAGCACGAATCCTAAACCTCAAAGAAAACCAAAAGAAAACACCAACCGCCCACAGG
149          SA1      1  ATGAGCACGAATCCTAAACCTCAAAGAAAACCAAAAGAAAACACCAACCtCCGCCACAGG
150          SA3      1  ATGAGCACGAATCCTAAACCTCAAAGAAAACCAAAAGAAAACACCAACCGCCCACAGG
151          SA13     1  ATGAGCACGAATCCTAAACCTCAAAGAAAACCAAAAGAAAACACCAACCGCCCACAGG 146-153      consensus    ATGAGCACGAATCCTAAACCTCAAAGAAAACCaAAAGAAAACACCAACCgCCGCCCACAGG SEQ ID NO:   ISOLATE
153          SA11    62  ACGTCAAGTTCCCGGGCGGTGGTCAGATCGTTGGTGGAGTTTACTTGTTGCCGCGCAGGGG
152          SA6     62  ACGTCAAGTTCCCGGGCGGTGGTCAGATCGTTGGTGGAGTTTACTTGTTGCCGCGCAGGGG
146          SA4     62  ACGTtAAGTTCCCGGGCGGTGGTCAGATCGTTGGTGGAGTCTACTTGTTGCCGCGCAGGGG
147          SA5     62  ACGTCAAGTTCCCGGGCGGTGGTCAGATCGTTGGTGGAGTTTACTTGTTGCCGCGCAGGGG
148          SA7     62  ACGTCAAGTTCCCGGGCGGTGGTCAGATCGTTGGTGGAGTTTACTTGTTGCCGCGCAGGGG
149          SA1     62  ACGTCAAGTTCCCGGGCGGTGGTCAGATCGTTGGTGGAGTTTACTTGTTGCCGCGCAGGGG
150          SA3     62  ACGTCAAGTTCCCGGGCGGTGGTCAGATCGTTGGTGGAGTTTACTTGTTGCCGCGCAGGGG
151          SA13    62  ACGTCAAGTTCCCGGGCGGTGGTCAGATCGTTGGTGGAGTTTACTTGTTGCCGCGCAGGGG 146-153      consensus    ACGTcAAGTTCCCGGGCGGTGGTCAGATCGTTGGTGGAGTtTACTTGTTGCCGCGCAGGGG SEQ ID NO:   ISOLATE
153          SA11   123  CCCTaGgtTGGGTGTGCGCGCGACTCGGAAGACTTCaGAACGGTCGCAACCCCGTGGcCGG
152          SA6    123  CCCTcGtaTGGGTGTGCGCGCGACTCGGAAGACTTCgGAACGGTCGCAACCCCGTGGaCGG
146          SA4    123  CCCTAGgTTGGGTGTGCGCGCGACTCGGAAGACTTCAGAACGGTCGCAACCCCGTGGCCGG
147          SA5    123  CCCTAGaTTGGGTGTGCGCGCGACTCGGAAGACTTCAGAACGGTCGCAACCCCGTGGCCGG
148          SA7    123  CCCTAGGTTGGGTGTGCGCGCGACTCGGAAGACTTCAGAACGGTCGCAACCCCGTGGCCGG
149          SA1    123  CCCAGGTTGGGTGTGCGCGCGACTCGGAAGACTTCgGAACGGTCGCAACCCCGTGGCCGG
150          SA3    123  CCCAGGTTGGGTGTGCGCGCGACTCGGAAGACTTCAGAACGGTCGCAACCCCGTGACGG
151          SA13   123  CCCtAGGTTGGGTGTGCGCGCGCaACTCGGAAGACTTCAGAACGGTCGCAACCCCGTGACGG 146-153      consensus    CCCtaGgtTGGGTGTGCGCGCGACTCGGAAGACTTCaGAACGGTCGCAACCCCGTGGcCGG
```

FIGURE 6I-2

```
SEQ ID NO:   ISOLATE
153          SA11      184  CGTCAGCCTATTCCCAAGGCGCGCCAAcCCaCGGGcCGGTCCTGGGGTCAACCCGGGTACC
152          SA6       184  CGTCAGCCTATTCCCAAGGCGCGCCAAtCCgCGGGtCGGTCCTGGGGTCAACCCGGGTACC
146          SA4       184  CGCCAGCCTATTCCCAAGGCGCGCCAACCCACGGGCCGGTCCTGGGGTCAACCCGGGTACC
147          SA5       184  CGCCAGCCTATTCCCAAGGCGCGCCAACCCACGGGCCGGTCCTGGGGTCAACCCGGGTACC
148          SA7       184  CGCCAGCCTATTCCCAAGGCGCGCCAACCCACGGGCCGGTCCTGGGGTCAACCCGGGTACC
149          SA1       184  CGCCAGCCTATTCCCAAGGCGCGCCAACCCACGGGCCGGTCCTGGGGTCAACCCGGGTACC
150          SA3       184  CGCCAGCCTATTCCCAAGGCtCGCCAGCCCACGGGCCGGTCCTGGGGTCAACCCGGGTACC
151          SA13      184  CGtCAGCCTATcCCCAAGGCgCGCCAGCCCACGGGCCGGTCCTGGGGTCAACCCGGGTACC 146-153      consensus       CGcCAGCCTATtCCCAAGGCgCGCCAacCCaCGGGcCGGTCCTGGGGTCAACCCGGGTACC SEQ ID NO:   ISOLATE
153          SA11      245  CTTGGCCCCtTTTACGCCAATGAGGGCCTCGGGTGGGCAGGGTGGcTGCTCTCCCCtCGAGG
152          SA6       245  CTTGGCCCCCTTTACGCCAATGAGGGCCTCGGGTGGGCAGGGTGGTTGCTCTCCCCCCGAGG
146          SA4       245  CTTGGCCCCCTTTACGCCAATGAGGGCCTCGGGTGGGCAGGGTGGTTGCTCTCCCCCCGAGG
147          SA5       245  CTTGGCCCCCTTTACGCCAATGAGGGCCTCGGGTGGGCAGGGTGGTTGCTCTCCCCCCGAGG
148          SA7       245  CTTGGCCCCCTTTACGCCAATGAGGGCCTCGGGTGGGCAGGGTGGTTGCTCTCCCCCCGAGG
149          SA1       245  CTTGGCCCCCTTTACGCCAATGAGGGCCTCGGGTGGGCAGGGTGGTTGCTCTCCCCCCGAGG
150          SA3       245  CTTGGCCCCCCTTTACGCCAATGAGGGCCTCGaGTGGGTGGGCAGGGTGGTTGCTCTCCCCCCGAGG
151          SA13      245  CTTGGCCCCCCTTTAtGCCAATGAGGGCCTCGgGTGGGTGGGCAGGGTGGtTGCTCTCCCCCCGAGG 146-153      consensus       CTTGGCCCCCTTTACGCCAATGAGGGCCTCGGGtGGGCAGGGTGGtTGCTCTCCCCcCGAGG SEQ ID NO:   ISOLATE
153          SA11      306  CTCTCGGCCTAAcTGGGGCCCCAATGACCCCCGGCGAAGATCGCGGCAAGTTTGGCAAGGTC
152          SA6       306  CTCTCGGCCTAATTGGGGCCCCAATGACCCCCGGCGAAAATCGCGCAATTTGGTAAGGTC
146          SA4       306  CTCTCGGCCTAATTGGGGCCCCAATGACCCCCGGCGAAATCGCGCAATTTGGTAAGGTC
147          SA5       306  CTCTCGGCCTAATTGGGGCCCCAATGACCCCCGGCGAAAAgTCGCGCAATTTGGTAAGGTC
148          SA7       306  CTCTCGGCCTAATTGGGGCCCCAATGACCCCCGGCGAAAaTCGCGCAATTTGGTAAGGTC
149          SA1       306  CTCTCGGCCTAATTGGGGCCCCAATGACCCCCGGCGAAAGTCGCGCAATTTGGTAAGGTC
150          SA3       306  CTCTCGGCCTAgTTGGGGCCCCAACgACCCCCGGCGGAAATCGCGGAAATCGCGGAAATTTGGTAAGGTC
151          SA13      306  CTCTCGGCCTAaTTGGGGCCCCAAtGACCCCCGGCGAAATCGCGAAATCGCGCAAcTTGGTAAGGTC 146-153      consensus       CTCTCGGCCTAatTGGGGCCCCAAtGACCCCCGGCGaAaaTCGCGCAAtTTGGtAAGGTC
```

FIGURE 6I-3

| SEQ ID NO: | ISOLATE | | |
|---|---|---|---|
| 153 | SA11 | 367 | ATCGATACCCTAACGTGCGGATTCGCCGACCTCATGGGTACATCCCGCTCGTAGGCGCC |
| 152 | SA6 | 367 | ATCGATACCCTAACGTGCGGATTCGCCGACCTCATGGGTACATCCCGCTCGTAGGCGCC |
| 146 | SA4 | 367 | ATCGATACCCTAACGTGCGGATTCGCCGACCTCATGGGTACATCCCGCTCGTAGGCGCC |
| 147 | SA5 | 367 | ATCGATACCCTAACGTGCGGATTCGCCGACCTCATGGGTACATCCCGCTCGTAGGCGCC |
| 148 | SA7 | 367 | ATCGATACCCTAACGTGCGGATTCGCCGACCTCATGGGTACATCCCGCTCGTAGGCGCC |
| 149 | SA1 | 367 | ATCGAcACCCTAACaTGCGGATTCGCCGACCTCATGGGTACATCCCGCTCGTAGGCGCC |
| 150 | SA3 | 367 | ATCGATACCCTAACGTGCGGATTCGCCGATCTCATGGGTACATCCCGCTCGTAGGCGCC |
| 151 | SA13 | 367 | ATCGATACCCTgACGTGCGGATTCGCCGACCTCATGGGTACATCCCGCTCGTAGGCGCC |
| 146-153 | consensus | | ATCGAtACCCTaACgTGCGGATTCGCCGAcCTCATGGGTACATCCCGCTCGTAGGCGCC |

| SEQ ID NO: | ISOLATE | | |
|---|---|---|---|
| 153 | SA11 | 428 | CCGTTGGGGGCGTCGCAAGGGCcCTCGCACACGGTGTGAGaGcTCTTGAGGACGGGTAAA |
| 152 | SA6 | 428 | CCGTTGGGGGCGTCGCAAGGGCtCTCGCACACGGTGTGAGGGTTCTTGAGGACGGGTAAA |
| 146 | SA4 | 428 | CCGTTGGGGGCGTCGCAAGGGCCCTtGCACATGGTGTGAGGGTTCTTGAGGACGGGTAAA |
| 147 | SA5 | 428 | CCGTTGGGGGCGTCGCAAGGGCCCTCGCACATGGTGTGAGGGTTCTTGAGGACGGGTAAA |
| 148 | SA7 | 428 | CCGTTGGGGGCGTCGCAAGGGCTCTCGCACACGGTGTGAGGGTTCTTGAGGACGGGTAAA |
| 149 | SA1 | 428 | CCGTTGGGGGCGTCGCAAGGGCTCTCGCACACGGTGTGAGGGTTCTTGAGGACGGGTAAA |
| 150 | SA3 | 428 | CCGTTGGGGGCGTCGCAAGGGCTCTCGCACAtGGTGTGAGGGTTCTTGAGGACGGGTAAA |
| 151 | SA13 | 428 | CCGTTGGGGGCGTCGCAAGGGCTCTCGCACAcGGTGTGAGggttCTTGAGGACGGGTAAA |
| 146-153 | consensus | | CCGTTGGGGGCGTCGCAAGGGCtCTcGCACAcGGTGTGAGGGTTCTTGAGGACGGGTAAA |

| SEQ ID NO: | ISOLATE | | |
|---|---|---|---|
| 153 | SA11 | 489 | tTATGCAACAGGGAATcTtCCCGGTTGCTCTTTCTCcATCTTTaTCCTTGCACTTCTCTCG |
| 152 | SA6 | 489 | CTATGCAACAGGGAATTTGCCCGGTTGCTCTTTCTCTATCTTTgTCCTTGCACTTCTCTCG |
| 146 | SA4 | 489 | CTATGCAACgGGGAATTTGCCCGGTTGCTCTTTCTCTATCTTTATCCTTGCACTTCTCTCG |
| 147 | SA5 | 489 | CTATGCAACAGGGAATTTGCCCGGTTGCTCTTTCTCTATCTTTATCCTTGCACTTCTCTCG |
| 148 | SA7 | 489 | tTACGCAACAGGGAATcTGCCCGGTTGCTCTTTCTCTATCTTTATCCTTGCACTTCTCTCG |
| 149 | SA1 | 489 | CTACGCAACAGGGAATTTGCCCGGTTGCTCTTTCTCTATCTTTATCCTTGCACTTCTTTCc |
| 150 | SA3 | 489 | CTACGCAACAGGGAATTTACCCGGTTGCTCTTTCTCTATCTTTATCCTTGCACTTCTTTCA |
| 151 | SA13 | 489 | CTAtGCAACAGGGAATTTACCCGGTTGCTCTTTCTCTATCTTTATCCTTGCACTTCTTTCA |
| 146-153 | consensus | | cTAtGCAACaGGGAATTgCCCGGTTGCTCTTTCTCtATCTTTaTCCTTGCACTTCTcTCg |

FIGURE 6I-4

| SEQ ID NO: | ISOLATE | | |
|---|---|---|---|
| 153 | SA11 | 550 | TGCtTgACCGTCCCgGCCaCTGCA |
| 152 | SA6  | 550 | TGCCTaACCGTCCCtGCCTCTGCA |
| 146 | SA4  | 550 | TGCCTGACCGTCCCgGCCTCTGCA |
| 147 | SA5  | 550 | TGCtTGACCGTCCCAGCCTCTGCA |
| 148 | SA7  | 550 | TGCCTGACCGTCCCAGCCTCCGCA |
| 149 | SA1  | 550 | TGtCTGAtCaTCCCGGCCTCTGCA |
| 150 | SA3  | 550 | TGCCTGACCGTCCCGGCCTCTGCA |
| 151 | SA13 | 550 | TGCCTGACtGTCCCGaCCTCTGCc |

146-153    consensus           TGccTgAccgTCCCggCCtCtGCa

FIGURE 6J-1

```
SEQ ID NO:    Genotype
103-154       cons.      1   ATGAGCACGaaTCCtAAACCtCAAAGAaAaACCaaAcGtAaCaCCaaCCgcCgCgCCCacagG 103-124         1        1   ATGAGCACGAaTCCTAAACCTCAAAGAaAaACCAAACGTAACACCAaCCGcCGCGCCCACAGG
125-134         2        1   ATGAGCACAAaTCCTAAACCTCAAAGAaAaACCAAACGTAACACCAaCCGcCGCGCCCACAGG
135-138         3        1   ATGAGCACACTTCCTAAACCTCAAAGAAAAACCAAACCAAAGAAACACCATCCGTCGCCCACAGG
139-145         4        1   ATGAGCACGaATCCTAAACCTCAAAGAAAAACCAAACGTAACACCAACCGcCGCCCATGG
146-153         5        1   ATGAGCACGAATCCTAAACCTCAAAGAAAAACCAaAAGAAACaCCAACCGCCCACAGG
154             6        1   ATGAGCACACTTCCAAAACCCCAAAGAAAAACCAAAGAAACACCAACCGTCGCCCAACGG SEQ ID NO:    Genotype
103-154       cons.     62   AcgTcAAgTTCCCgGgCgGtGtCAGATCGTtGGtGGAGTtTActTGtTGCCGCGCAGGGG 103-124         1       62   ACGTCAAGTTCCCGGGCgGTGGTCAGATCGTCGGTGGAGTtTAccTGTTGCCGCGCAGGGG
125-134         2       62   ACGTtAAGTTCCCGGGCgGGCGGCCAGATCGTTGGCGGAGTaTACTTGCTGCCGCGCAGGGG
135-138         3       62   ACgTCAAGTTCCCGGGTGGCGGACAGATCGTTGGTGGAGTATACGTGTTGCCGCGCAGGGG
139-145         4       62   AcGTaAAgTTCCCGgGtGGtGGCCAGATCGTTGGCGGAGTTTACTTGtTGCCGCGCAGGGG
146-153         5       62   ACGTCAAGTTCCCGGCGGTGGTCGTCAGATCGTCAGATCGTTGGTGGAGTtTACTTGTTGCCGCGCAGGGG
154             6       62   ACGTCAAGTTCCCGGGTGGCGGTCAGATCGTCAGATCGTTGGCGGAGTTTACTTGTTGCCGCGCAGGGG SEQ ID NO:    Genotype
103-154       cons.    123   CCCcaGgTTGGGTGTGCGCgCgaCtaGgAAgaCTTCCGAgCGgTCgCAaCCtcGtGGaaGg 103-124         1      123   CCCcaGgTTGGGTGTGCGCGCGCGgaCTAGGAAGAAGACTTCCGAGAAGACTTCGAGCGGTCGCAACCTCGAGCGGTCGCAACCTCGTGGaaGg
125-134         2      123   CCCcAGgTTGGGTGTGCGCGCGCGACAaGGAaGaCTTCCGAgCGaTCCCAGCCGCGTGGGAGg
135-138         3      123   CCCACGATTGGGTGTGCGCGCGACGGCGTAAACTTCTGAACGTCaCAGCCTCGCGGACGa
139-145         4      123   CCCcaGgTTGGGTGTGCGCGCGgaCTCgGAGACTTCGGAGCGTCgCAACCTCGtGGcAGg
146-153         5      123   CCCtaGgTTGGGTGTGCGCGCGACTCGGAAGACTTCaGAACGTCGAGAACGGTCGCAACCCCGTGGgCGG
154             6      123   CCCCGGTTGGGTGTGCGCGCGACGAGAAAGACTTCCGAGCGATCCCAGCCCAGAGGCAGG
```

FIGURE 6J-2

| SEQ ID NO: | Genotype | | |
|---|---|---|---|
| 103-154 | cons. | 184 | CGaCAgCCtATcCCcaAgGctCGcCggcccgagGGcaggtcCTGGGctcagCCcGGgtAcC |
| 103-124 | 1 | 184 | CGaCAaCCTATCCCaAGGCtCGcCggCCCGAGGgCAGGgCCTGGGCtCAGCCCGGtAcC |
| 125-134 | 2 | 184 | CGCCAGCCCATCCCgAAAgATCGGCGCtCCACtGGCAAGtCCTGGGGAAAaCCaGGATAtC |
| 135-138 | 3 | 184 | CGACAGCCTATCCCCAAGGCGCGTCGGAGCGAAGGCCGgTCCTGGGCTCAGCCCGGTACC |
| 139-145 | 4 | 184 | CGtCAgCCTATCCCCaAGGCaCGtCggtccGAGGGCAgGTCCTGGGCtCAgCCCGGGTAcC |
| 146-153 | 5 | 184 | CGcCAGCCTATtCCCAAGGCgCGCCAaccCaCGGGcCGgTCCTGGGTCAACCCGGGTACC |
| 154 | 6 | 184 | CGCCAACCTATACCCAAAAGGCGCGCCAGCCCAGGCAGGCACTGGGCTCAGCCCGGATACC |

| SEQ ID NO: | Genotype | | |
|---|---|---|---|
| 103-154 | cons. | 245 | CtTGGCCcCTcTAtGgcaAtGAGGGCagGaTGGCTccTgTCcCCgcGG |
| 103-124 | 1 | 245 | CtTGGCCCCCTCTATgCaAtGAGGGCTtgGGgTGGGCagGATGGCTCCTgTCaCCCCgtGG |
| 125-134 | 2 | 245 | CtTGGCCCCCTgTAtGGgAAtGAGGGcctCGGCGTGGCTGGCTCCTgTCCCCCCGCGG |
| 135-138 | 3 | 245 | CTTGGCCCCCTCTATGGTAACGAGGGCTGCGGGGTGGGCAGGGTGGCTCCTGTCCCCACGCGG |
| 139-145 | 4 | 245 | CtTGGCCtCTtTAcGCaAtGAGtGAGGGCTGCGGGTGGCTGGCTCCTgTCCTCCcCGCGG |
| 146-153 | 5 | 245 | CTTGGCCCCCTTTAcGCCAATGAGGGCCTCGgGTGGGCAGGGTGGtTGCTCTCCCGAGG |
| 154 | 6 | 245 | CTTGGCCTCTTTATGGAAACGAGGGCTGTGGGTGGGCAGGTTGGCTCCTgTCCTCCCCGCGG |

| SEQ ID NO: | Genotype | | |
|---|---|---|---|
| 103-153 | cons. | 306 | cTTcTcggCCtagtTGGGGCCccActgACCCCCCGGCgtaggTCgCGcAAttTGGGtAagGTC |
| 103-124 | 1 | 306 | cTCtCGGCCTAgtTGGGGCCCCAcaGACCCCCGGCCTAGGTCGCGtAGTTCGGtAAgGTC |
| 125-134 | 2 | 306 | tTTCtCgtCCtctTGGGGCCCCACtGACCCCGGCCATaGaTCGCaACtTGGGtAAgGTC |
| 135-138 | 3 | 306 | CTCCCGTCCATCTTGGGCCCAAAcGACCCCGGaGGTCCCGCAATTTGGGTAAaGTC |
| 139-145 | 4 | 306 | cTCtCggCCgTCTTGGGCCcaAATGATCCCCGGCCgAAGtTCCCGcAAttTGGGTAAgGTC |
| 146-153 | 5 | 306 | CTCTCGGCCTAatTGGGCCCCAATGACCCCCGGCGaAaaTCGCGAATTGGGtAAGGTC |
| 154 | 6 | 306 | CTCCCGGCCACATTGGGCGCCCAATGACCCCCGGCCGTCGATCCCGAATTGGGTAAGGTC |

FIGURE 6J-3

| SEQ ID NO: | Genotype | | |
|---|---|---|---|
| 103-154 | cons. | 367 | ATCGAtACccTcACgTGcggCtTcGCCgAccTCATGGGTACaTcCCgcTCgTCggCgcCC |
| 103-124 | 1 | 367 | ATCGAtACCCTcACaTGCGGCTTcGCCgACCTCATGGGTACATcCCGCTCGTCGGCgcCC |
| 125-134 | 2 | 367 | ATCGAtACCCTcTaACgTGcggTtTTGCCgACCTCATGGGaTACaTcCCCGCTCGTtGGCgcCC |
| 135-138 | 3 | 367 | ATCGATACCCTtACgTGCggaTTCgCCgACCTCATGGGTACATCCCGCTCGTCGGCGCTC |
| 139-145 | 4 | 367 | ATCGATACCcTgACgTGCgGCTTcGCCgACCTCATGGGATACATcCCgCTCGTaGGCGCCC |
| 146-153 | 5 | 367 | ATCGAtACCCTaACgTGCGGATTCGCCgACCTCATGGGTACATCCCGCTCGTAGGCGGCC |
| 154 | 6 | 367 | ATCGATACCCTAACGTGTGGGTTCgCCgATCTCATGGGTACATTCCCGTCGTGGGCGCGC |

| SEQ ID NO: | Genotype | | |
|---|---|---|---|
| 103-154 | cons. | 428 | CcgTaGGgGGcGtcGCcaggGCccTgGCgCATgGCgTcaGggttcTgGAgGACGggTgAA |
| 103-124 | 1 | 428 | CccTaGGGGcGCTGCCAGgGCccTGGCgCATgGCgTCCgGTtcTGGAgGACGGCGTGAA |
| 125-134 | 2 | 428 | CggTtGGaGGCcGTcGCCAGAGCtCTgGCaCATgGtGTgAGgGTcCTGGAgGAGGACGGgaTaAAA |
| 135-138 | 3 | 428 | CCgTAGGaGGCGTCGCAAGAGCCCTgGCCATgGCgTGAGGCCCTTGAAGACGGGATAAA |
| 139-145 | 4 | 428 | CcgTgGGtGGCGTCGCCAGgGCccTgGCgCATgGCgTCAGGgctgTGGAGGACGGgaTcAA |
| 146-153 | 5 | 428 | CCGTTGGGGGCGTCGCCAAGgGCtCTcGCAGGGCTgTGAGgGttCTTGAGGACGGGTAAA |
| 154 | 6 | 428 | CTTTGGGGCGGCGTCGGCGCTCGCACATGGCGTCGCAATCGAGGACGGGATCAA |

| SEQ ID NO: | Genotype | | |
|---|---|---|---|
| 103-154 | cons. | 489 | cTatGCAACaGggAAttTgCCcGGTTGCtCtTTcTCtAtCTTccTtcTggCtCTgcTgTCc |
| 103-124 | 1 | 489 | cTAtGCAACaGggAAAtTgCCgGTTGCtCtTTTCtCtTTtCtTATcTTccTATcTTcCtTTgcTTgCTgTTCc |
| 125-134 | 2 | 489 | tTATGCAACaGggAAAtTgCCtGGTTGCtCtTTTCtTATcTTccTATcTTTcTtGCCtTcTgTTCc |
| 135-138 | 3 | 489 | TTTcGCAACAGGGAACTTGCCCgGTTGCCcTTTTCtTTTCtCtTTGCtCTGTTCTCt |
| 139-145 | 4 | 489 | cTAtGCAACaGGgAAtCTTCCcGGTTGCtCtTTCtCtTTCctTgGCACTTCtCTCG |
| 146-153 | 5 | 489 | cTAtGCAACaGGGAATTgCcCGGTTGCtCtTTcTCtAtCTTTaTCCTTGCACTTCTcTCg |
| 154 | 6 | 489 | TTATGCAACAGGgAATCTCCCCGGTTGCtCtTTcTCtAtCTTcTCCTTTTGGCACTACTCTCG |

FIGURE 6J-4

| SEQ ID NO: | Genotype | | |
|---|---|---|---|
| 103-154 | cons. | 550 | TGcctgaccgtcCCagcttCtgct |
| 103-124 | 1 | 550 | TGttTgACcatcCCaGctTCcGCt |
| 125-134 | 2 | 550 | TGCatCaCagtgCCaGtgTCtGCt |
| 135-138 | 3 | 550 | TGCtTAaTTCATCCagCAGCTAGT |
| 139-145 | 4 | 550 | TGCcTgACtgttCCagCgTCgGCc |
| 146-153 | 5 | 550 | TGCcTgAccgTCCggCCtCtGCa |
| 154 | 6 | 550 | TGCCTCACAACGCCAGCTTCGGCT |

| SEQ ID NO: | ISOLATE | | |
|---|---|---|---|
| 156 | US11 | 1 | MSTNPKPQRKTKRNTNRRPQDVKFPGGGQIVGGVYLLPRRGPRLGVRATRKTSERSQPRGR |
| 157 | S14 | 1 | MSTNPKPQRKTKRNTNRRPQDVKFPGGGQIVGGVYLLPRRGPRLGVRATRKTSERSQPRGR |
| 158 | SW1 | 1 | MSTNPKPQRKTKRNTNRRPQDVKFPGGGQIVGGVYLLPRRGPRLGVRATRKTSERSQPRGR |
| 159 | S18 | 1 | MSTNPKPQRKTKRNTNRRPQDVKFPGGGQIVGGVYLLPRRGPRLGVRATRKTSERSQPRGR |
| 160 | DR4 | 1 | MSTNPKPQRKTKRNTNRRPQDVKFPGGGQIVGGVYLLPRRGPRLGVRATRKTSERSQPRGR |
| 155 | DK7 | 1 | MSTNPKPQRKTKRNTNRRPQDVKFPGGGQIVGGVYLLPRRGPRLGVRApRKTSERSQPRGR |

155-160 consensus  MSTNPKPQRKTKRNTNRRPQDVKFPGGGQIVGGVYLLPRRGPRLGVRAtRKTSERSQPRGR

| SEQ ID NO: | ISOLATE | | |
|---|---|---|---|
| 156 | US11 | 62 | RQPIPKARRPEGRTWAQPGYPWPLYGNEGCGWAGWLLSPRGSRPSWGPTDPRRRSRNLGKV |
| 157 | S14 | 62 | RQPIPKARRPEGRTWAQPGYPWPLYGNEGCGWAGWLLSPRGSRPSWGPTDPRRRSRNLGKV |
| 158 | SW1 | 62 | RQPIPKARRPEGRTWAQPGYPWPLYGNEGCGWAGWLLSPRGSRPSWGPTDPRRRSRNLGKV |
| 159 | S18 | 62 | RQPIPKARRPEGRTWAQPGYPWPLYGNEGCGWAGWLLSPRGSRPSWGPTDPRRRSRNLGKV |
| 160 | DR4 | 62 | RQPIPKARRPEGRTWAQPGYPWPLYGNEGCGWAGWLLSPRGSRPSWGPTDPRRRSRNLGKV |
| 155 | DK7 | 62 | RQPIPKARRPEGRTWAQPGYPWPLYGNEGCGWAGWLLSPRGSRPSWGPTDPRRRSRNLGKV |

155-160 consensus  RQPIPKARRPEGRTWAQPGYPWPLYGNEGCGWAGWLLSPRGSRPSWGPTDPRRRSRNLGKV

| SEQ ID NO: | ISOLATE | | |
|---|---|---|---|
| 156 | US11 | 123 | IDTLTCGFADLMGYIPLVGAPLGGAARALAHGVRVLEDGVNYATGNLPGCSFSIFLLALLS |
| 157 | S14 | 123 | IDTLTCGFADLMGYIPLVGAPLGGAARALAHGVRVLEDGVNYATGNLPGCSFSIFLLALLS |
| 158 | SW1 | 123 | IDTLTCGFADLMGYIPLVGAPLGGAARALAHGVRVLEDGVNYATGNLPGCSFSIFLLALLS |
| 159 | S18 | 123 | IDTLTCGFADLMGYIPLVGAPLGGAARALAHGVRVLEDGVNYATGNLPGCSFSIFLLALLS |
| 160 | DR4 | 123 | IDTLTCGFADLMGYIPLVGAPLGGAARALAHGVRVLEDGVNYATGNLPGCSFSIFLLALLS |
| 155 | DK7 | 123 | IDTLTCGFADLMGYIPLVGAPLGGAARALAHGVRVLEDGVNYATGNLPGCSFSIFLLALLS |

155-160 consensus  IDTLTCGFADLMGYIPLVGAPLGGAARALAHGVRVLEDGVNYATGNLPGCSFSIFLLALLS

| SEQ ID NO: | ISOLATE | | |
|---|---|---|---|
| 156 | US11 | 184 | CLTVPASA |
| 157 | S14 | 184 | CLTVPASA |
| 158 | SW1 | 184 | CLTVPASA |
| 159 | S18 | 184 | CLTVPASA |
| 160 | DR4 | 184 | CLTVPASA |
| 155 | DK7 | 184 | CLTVPASA |
| 155-160 | consensus | | CLTVPASA |

| SEQ ID NO: | ISOLATE | |
|---|---|---|
| 175 | P8 | 1 MSTtPKPQRKTKRNTsRRPQDVKFPGGGQIVGGVYLLPRRGPRLGVRATRKTSERSQPRGR |
| 170 | IND8 | 1 MSTNPKPQRKTKRNTNRRPQDVKFPGGGQIVGGVYLLPRRGPRLGVRATRKTSERSQPRGR |
| 162 | S45 | 1 MSTNPKPQRqTKRNTNRRPQDVKFPGGGQIVGGVYLLPRRGPRLGVRATRKTSERSQPRGR |
| 171 | S9 | 1 MSTNPKPQRKTKRNTNRRPQDVKFPGGGQIVGGVYLLPRRGPRLGVRATRKTSERSQPRGR |
| 163 | D1 | 1 MSTNPKPQRKTKRNTNRRPQDVKFPGGGQIVGGVYLLPRRGPRLGVRATRKTSERSQPRGR |
| 165 | P10 | 1 MSTNPKPQRKTKRNTNRRPQDVKFPGGGQIVGGVYLLPRRGPRLGVRATRKTSERSQPRGR |
| 169 | IND3 | 1 MSTNPKPQRKTKRNTNRRPQDVKFPGGGQIVGGVYLLPRRGPRLGVRATRKTSERSQPRGR |
| 164 | US6 | 1 MSTNPKPQRKTKRNTNRRPQDVKFPGGGQIVGGVYLLPRRGPRLGVRATRKTSERSQPRGR |
| 166 | DK1 | 1 MSTNPKPQRKTKRNTNRRPQDVKFPGGGQIVGGVYLLPRRGPRLGVRATRKTSERSQPRGR |
| 167 | T10 | 1 MSTNPKPQRKTKRNTNRRPQDVKFPGGGQIVGGVYLLPRRGPRLGVRATRKTSERSQPRGR |
| 168 | SW2 | 1 MSTNPKPQRKTKRNTNRRPQDVKFPGGGQIVGGVYLLPRRGPRLGVRATRKTSERSQPRGR |
| 161 | SA10 | 1 MSTNPKPQRKTKRNTNRRPQDVKFPGGGQIVGGVYLLPRRGPRLGVRATRKTSERSQPRGR |
| 174 | HK4 | 1 MSTNPKPQRKTKRNTNRRPQDVKFPGGGQIVGGVYLLPRRGPRLGVRATRKTSERSQPRGR |
| 172 | HK3 | 1 MSTNPKPQRKTKRNTNRRPQDVKFPGGGQIVGGVYLLPRRGPRLGVRATRKTSERSQPRGR |
| 176 | T3 | 1 MSTNPKPQRKTKRNTNRRPQDVKFPGGGQIVGGVYLLPRRGPRLGVRATRKTSERSQPRGR |
| 173 | HK5 | 1 MSTNPKPQRKTKRNTNRRPQDVKFPGGGQIVGGVYLLPRRGPRLGVRATRKTSERSQPRGR |

161-176 consensus MSTnPKPQRkTKRNTnRRPQDVKFPGGGQIVGGVYLLPRRGPRLGVRATRKTSERSQPRGR

| SEQ ID NO: | ISOLATE | |
|---|---|---|
| 175 | P8 | 62 RQPIPKARRPEGRAWAQPGHPWPLYaNEGLGWAGWLLSPRGSRPSWGPTDPRRRSRNLGKV |
| 170 | IND8 | 62 RQPIPKARRPEGRAWAQPGHPWPLYGNEGLGWAGWLLSPRGSRPSWGPTDPRRRSRNLGKV |
| 162 | S45 | 62 RQPIPKARRPEGRAWAQPGHPWPLYGNEGLGWAGWLLSPRGSRPSWGPTDPRRRSRNLGKV |
| 171 | S9 | 62 RQPIPKARhPEGRAWAQPGYPWPLYGNEGLGWAGWLLSPRGSRPSWGPnDPRRRSRNLGKV |
| 163 | D1 | 62 RQPIPKARRPEGRAWAQPGYPWPLYGNEGLGWAGWLLSPRGSRPSWGPTDPRRRSRNLGKV |
| 165 | P10 | 62 RQPIPKARRPEGRAWAQPGYPWPLYGNEGLGWAGWLLSPRGSRPSWGPTDPRRRSRNLGKV |
| 169 | IND3 | 62 RQPIPKARRPEGRAWAQPGYPWPLYGNEGLGWAGWLLSPRGSRPSWGPTDPRRRSRNLGKV |
| 164 | US6 | 62 RQPIPKARRPEGRAWAQPGYPWPLYGNEGMGWAGWLLSPRGSRPSWGPTDPRRRSRNLGKV |
| 166 | DK1 | 62 RQPIPKARRPEGRAWAQPGYPWPLYGNEGMGWAGWLLSPRGSRPSWGPTDPRRRSRNLGKV |
| 167 | T10 | 62 RQPIPKARRPEGRAWAQPGYPWPLYGNEGMGWAGWLLSPRGSRPSWGPnDPRRRSRNLGKV |
| 168 | SW2 | 62 RQPIPKARQPEGRAWAQPGYPWPLYGNEGMGWAGWLLSPRGSRPSWGPTDPRRRSRNLGKV |
| 161 | SA10 | 62 RQPIPKARQPEGRTWAQPGYPWPLYGNEGlGWAGWLLSPRGSRPSWGPTDPRRRSRNLGKV |
| 174 | HK4 | 62 RQPIPKARhPEGRAWAQPGYPWPLYGNEGMGWAGWLLSPRGSRPSWGPTDPRRRSRNLGKV |
| 172 | HK3 | 62 RQPIPKARQPEGRTWAQPGYPWPLYGNEGMGWAGWLLSPRGSRPNWGPTDPRRRSRNLGKV |
| 176 | T3 | 62 RQPIPKARQPEGRTWAQPGYPWPLYGdEGMGWAGWLLSPRGSRPNWGPTDPRRRSRNLGKV |
| 173 | HK5 | 62 RQPIPKARRPEGRAWAQPGYPWPLYGnEGMGWAGWLLSPhGSRPsWGPTDPRRRSRNLGKV |

161-176 consensus RQPIPKARrPEGRaWAQPGyPWPLYgnEG-GWAGWLLSPrGSRPsWGPtDPRRRSRNLGKV

FIGURE 7B-2

| SEQ ID NO: | ISOLATE | | |
|---|---|---|---|
| 175 | P8 | IDTLTCGFADLMGYIPLVGgPLGGvARALAHGVRVvEDGVNYATGNLPGCSFSIFLLALLS | 123 |
| 170 | IND8 | IDTLTCGFADLMGYIPLVGAPLGGAARALAHGVRVLEDGVNYATGNLPGCSFSIFLLALLS | 123 |
| 162 | S45 | IDTLTCGFADLMGYIPLVGAPLGGAARALAHGVRVLEDGVNYATGNLPGCSFSIFLLALLS | 123 |
| 171 | S9 | IDTLTCGFADLMGYIPLVGAPLGGAARALAHGVRVLEDGVNYATGNLPGCSFSIFLLALLS | 123 |
| 163 | D1 | IDTLTCGFADLMGYIPLVGAPLGGAARALAHGVRVLEDGVNYATGNLPGCSFSIFLLALLS | 123 |
| 165 | P10 | IDTLTCGFADLMGYIPLVGAPLGGAARALAHGVRVLEDGVNYATGNLPGCSFSIFLLALLS | 123 |
| 169 | IND3 | IDTLTCGFADLMGYIPLVGAPLGGAARALAHGVRVLEDGVNYATGNLPGCSFSIFLLALLS | 123 |
| 164 | US6 | IDTLTCGFADLMGYIPLVGAPLGGAARALAHGVRVLEDGVNYATGNLPGCSFSIFLLALLS | 123 |
| 166 | DK1 | IDTLTCGFADLMGYIPLVGAPLGGAARALAHGVRVLEDGVNYATGNLPGCSFSIFLLALLS | 123 |
| 167 | T10 | IDTLTCGFADLMGYIPLVGAPLGGAARALAHGVRVLEDGVNYATGNLPGCSFSIFLLALLS | 123 |
| 168 | SW2 | IDTLTCGFADLMGYIPLVGAPLGGVARALAHGVRVLEDGVNYATGNLPGCSFSIFLLALLS | 123 |
| 161 | SA10 | IDTLTCGFADLMGYIPLVGAPLGGVARALAHGVRVLEDGVNYATGNLPGCpFSIFLLALLS | 123 |
| 174 | HK4 | IDTLTCGFADLMGYIPLVGAPLGGVARALAHGVRVvEDGVNYATGNLPGCSFSIFLLALLS | 123 |
| 172 | HK3 | IDTLTCGFADLMGYIPLVGAPLGGVARALAHGVRVLEDGVNYATGNLPGCSFSIFLLALLS | 123 |
| 176 | T3 | IDTLTCGFADLMGYIPLVGAPLGGVARALAHGVRVLEDGVNYATGNLPGCSFSIFLLALLS | 123 |
| 173 | HK5 | IDTLTCGFADLMGYIPLVGAPLGGVARALAHGVRVLEDGVNYATGNiPGCSFSIFLLALLS | 123 |

| 161-176 | consensus | IDTLTCGFADLMGYIPLVGaPLGGaARALAHGVRVLEDGVNYATGNLPGCsFSIFLLALLS | |

| SEQ ID NO: | ISOLATE | | |
|---|---|---|---|
| 175 | P8 | CLTiPASA | 184 |
| 170 | IND8 | CLTvPASA | 184 |
| 162 | S45 | CLTIPASA | 184 |
| 171 | S9 | CLTIPASA | 184 |
| 163 | D1 | CLTIPASA | 184 |
| 165 | P10 | CLTIPASA | 184 |
| 169 | IND3 | CLTIPASA | 184 |
| 164 | US6 | CLTIPASA | 184 |
| 166 | DK1 | CLTIPASA | 184 |
| 167 | T10 | CLTIPASA | 184 |
| 168 | SW2 | CLTIPASA | 184 |
| 161 | SA10 | CLTIPASA | 184 |
| 174 | HK4 | CLTIPASA | 184 |
| 172 | HK3 | CLTtPASA | 184 |
| 176 | T3 | CLTIPASA | 184 |
| 173 | HK5 | CLTtPvSA | 184 |

| 161-176 | consensus | CLTiPaSA | |

FIGURE 7C-1

| SEQ ID NO: | ISOLATE | | |
|---|---|---|---|
| 173 | HK5 | 1 | MSTNPKPQRKTKRNTNRRPQDVKFPGGGQIVGGVYLLPRRGPRLGVRATRKTSERSQPRGR |
| 176 | T3 | 1 | MSTNPKPQRKTKRNTNRRPQDVKFPGGGQIVGGVYLLPRRGPRLGVRATRKTSERSQPRGR |
| 172 | HK3 | 1 | MSTNPKPQRKTKRNTNRRPQDVKFPGGGQIVGGVYLLPRRGPRLGVRATRKTSERSQPRGR |
| 174 | HK4 | 1 | MSTNPKPQRKTKRNTNRRPQDVKFPGGGQIVGGVYLLPRRGPRLGVRATRKTSERSQPRGR |
| 161 | SA10 | 1 | MSTNPKPQRKTKRNTNRRPQDVKFPGGGQIVGGVYLLPRRGPRLGVRATRKTSERSQPRGR |
| 168 | SW2 | 1 | MSTNPKPQRKTKRNTNRRPQDVKFPGGGQIVGGVYLLPRRGPRLGVRATRKTSERSQPRGR |
| 167 | T10 | 1 | MSTNPKPQRKTKRNTNRRPQDVKFPGGGQIVGGVYLLPRRGPRLGVRATRKTSERSQPRGR |
| 166 | DK1 | 1 | MSTNPKPQRKTKRNTNRRPQDVKFPGGGQIVGGVYLLPRRGPRLGVRATRKTSERSQPRGR |
| 164 | US6 | 1 | MSTNPKPQRKTKRNTNRRPQDVKFPGGGQIVGGVYLLPRRGPRLGVRATRKTSERSQPRGR |
| 169 | IND3 | 1 | MSTNPKPQRKTKRNTNRRPQDVKFPGGGQIVGGVYLLPRRGPRLGVRATRKTSERSQPRGR |
| 165 | P10 | 1 | MSTNPKPQRKTKRNTNRRPQDVKFPGGGQIVGGVYLLPRRGPRLGVRATRKTSERSQPRGR |
| 163 | D1 | 1 | MSTNPKPQRKTKRNTNRRPQDVKFPGGGQIVGGVYLLPRRGPRLGVRATRKTSERSQPRGR |
| 156 | US11 | 1 | MSTNPKPQRKTKRNTNRRPQDVKFPGGGQIVGGVYLLPRRGPRLGVRATRKTSERSQPRGR |
| 157 | S14 | 1 | MSTNPKPQRKTKRNTNRRPQDVKFPGGGQIVGGVYLLPRRGPRLGVRATRKTSERSQPRGR |
| 158 | SW1 | 1 | MSTNPKPQRKTKRNTNRRPQDVKFPGGGQIVGGVYLLPRRGPRLGVRATRKTSERSQPRGR |
| 159 | S18 | 1 | MSTNPKPQRKTKRNTNRRPQDVKFPGGGQIVGGVYLLPRRGPRLGVRATRKTSERSQPRGR |
| 160 | DR4 | 1 | MSTNPKPQRKTKRNTNRRPQDVKFPGGGQIVGGVYLLPRRGPRLGVRATRKTSERSQPRGR |
| 155 | DK7 | 1 | MSTNPKPQRKTKRNTNRRPQDVKFPGGGQIVGGVYLLPRRGPRLGVRApRKTSERSQPRGR |
| 170 | IND8 | 1 | MSTNPKPQRKTKRNTNRRPQDVKFPGGGQIVGGVYLLPRRGPRLGVRATRKTSERSQPRGR |
| 162 | S45 | 1 | MSTNPKPQRKTKRNTsRRPQDVKFPGGGQIVGGVYLLPRRGPRLGVRATRKTSERSQPRGR |
| 171 | S9 | 1 | MSTNPKPQRKTKRNTNRRPQDVKFPGGGQIVGGVYLLPRRGPRLGVRATRKTSERSQPRGR |
| 175 | P8 | 1 | MSTtPKPQRKTKRNTNRRPQDVKFPGGGQIVGGVYLLPRRGPRLGVRATRKTSERSQPRGR |

155-176 consensus    MSTnPkPQRkTKRNTnRRPQDVKFPGGGQIVGGVYLLPRRGPRLGVRAtRKTSERSQPRGR

FIGURE 7C-2

| SEQ ID NO: | ISOLATE | | |
|---|---|---|---|
| 173 | HK5 | 62 | RQPIPKARRPEGRtWAQPGYPWPLYGnEGMGWAGWLLSPhGSRPsWGPTDPRRRSRNLGKV |
| 176 | T3 | 62 | RQPIPKARRPEGRaWAQPGYPWPLYGdEGMGWAGWLLSPRGSRPNWGPTDPRRRSRNLGKV |
| 172 | HK3 | 62 | RQPIPKARQPEGRTWAQPGYPWPLYGNEGMGWAGWLLSPRGSRPNWGPTDPRRRSRNLGKV |
| 174 | HK4 | 62 | RQPIPKARQPEGRTWAQPGYPWPLYGNEGMGWAGWLLSPRGSRPSWGPTDPRRRSRNLGKV |
| 161 | SA10 | 62 | RQPIPKARQPEGRTWAQPGYPWPLYGNEGMGWAGWLLSPRGSRPSWGPTDPRRRSRNLGKV |
| 168 | SW2 | 62 | RQPIPKARQPEGRAWAQPGYPWPLYGNEGl GWAGWLLSPRGSRPSWGPTDPRRRSRNLGKV |
| 167 | T10 | 62 | RQPIPKARQPEGRAWAQPGYPWPLYGNEGMGWAGWLLSPRGSRPSWGPTDPRRRSRNLGKV |
| 166 | DK1 | 62 | RQPIPKARQPEGRAWAQPGYPWPLYGNEGMGWAGWLLSPRGSRPSWGPTDPRRRSRNLGKV |
| 164 | US6 | 62 | RQPIPKARRPEGRAWAQPGYPWPLYGNEGMGWAGWLLSPRGSRPSWGPTDPRRRSRNLGKV |
| 169 | IND3 | 62 | RQPIPKARRPEGRAWAQPGYPWPLYGNEGMGWAGWLLSPRGSRPSWGPnDPRRRSRNLGKV |
| 165 | P10 | 62 | RQPIPKARRPEGRAWAQPGYPWPLYGNEGMGWAGWLLSPRGSRPSWGPTDPRRRSRNLGKV |
| 163 | D1 | 62 | RQPIPKARRPEGRAWAQPGYPWPLYGNEGLGWAGWLLSPRGSRPSWGPTDPRRRSRNLGKV |
| 156 | US11 | 62 | RQPIPKARRPEGRTWAQPGYPWPLYGNEGLGWAGWLLSPRGSRPSWGPTDPRRRSRNLGKV |
| 157 | S14 | 62 | RQPIPKARRPEGRTWAQPGYPWPLYGNEGCGWAGWLLSPRGSRPSWGPTDPRRRSRNLGKV |
| 158 | SW1 | 62 | RQPIPKARRPEGRTWAQPGYPWPLYGNEGCGWAGWLLSPRGSRPSWGPTDPRRRSRNLGKV |
| 159 | S18 | 62 | RQPIPKARRPEGRTWAQPGYPWPLYGNEGCGWAGWLLSPRGSRPSWGPTDPRRRSRNLGKV |
| 160 | DR4 | 62 | RQPIPKARRPEGRTWAQPGYPWPLYGNEGCGWAGWLLSPRGSRPSWGPTDPRRRSRNLGKV |
| 155 | DK7 | 62 | RQPIPKARRPEGRTWAQPGYPWPLYGNEGLGWAGWLLSPRGSRPSWGPTDPRRRSRNLGKV |
| 170 | IND8 | 62 | RQPIPKARRPEGRAWAQPGHPWPLYGNEGLGWAGWLLSPRGSRPSWGPTDPRRRSRNLGKV |
| 162 | S45 | 62 | RQPIPKARhPEGRAWAQPGHPWPLYGNEGLGWAGWLLSPRGSRPSWGPTDPRRRSRNLGKV |
| 171 | S9 | 62 | RQPIPKARrPEGRAWAQPGyPWPLYGNEGLGWAGWLLSPRGSRPSWGPnDPRRRSRNLGKV |
| 175 | P8 | 62 | RQPIPKARrPEGRAWAQPGhPWPLYaNEGLGWAGWLLSPRGSRPSWGPTDPRRRSRNLGKV |

155-176 consensus RQPIPKARrPEGRaWAQPGyPWPLYgnEG-GWAGWLLSPrGSRPsWGPTDPRRRSRNLGKV

FIGURE 7C-3

| SEQ ID NO: | ISOLATE | | |
|---|---|---|---|
| 173 | HK5 | 123 | IDTLTCGFADLMGYIPLVGAPLGGVARARALAHGVRVLEDGVNYATGNiPGCSFSIFLLALLS |
| 176 | T3 | 123 | IDTLTCGFADLMGYIPLVGAPLGGVARARALAHGVRVLEDGVNYATGNLPGCSFSIFLLALLS |
| 172 | HK3 | 123 | IDTLTCGFADLMGYIPLVGAPLGGVARARALAHGVRVLEDGVNYATGNLPGCSFSIFLLALLS |
| 174 | HK4 | 123 | IDTLTCGFADLMGYIPLVGAPLGGVARARALAHGVRVLEDGVNYATGNLPGCSFSIFLLALLS |
| 161 | SA10 | 123 | IDTLTCGFADLMGYIPLVGAPLGGVARARALAHGVRVvEDGVNYATGNLPGCSFSIFLLALLS |
| 168 | SW2 | 123 | IDTLTCGFADLMGYIPLVGAPLGGAARARALAHGVRVLEDGVNYATGNLPGCpFSIFLLALLS |
| 167 | T10 | 123 | IDTLTCGFADLMGYIPLVGAPLGGAARARALAHGVRVLEDGVNYATGNLPGCSFSIFLLALLS |
| 166 | DK1 | 123 | IDTLTCGFADLMGYIPLVGAPLGGAARARALAHGVRVLEDGVNYATGNLPGCSFSIFLLALLS |
| 164 | US6 | 123 | IDTLTCGFADLMGYIPLVGAPLGGAARARALAHGVRVLEDGVNYATGNLPGCSFSIFLLALLS |
| 169 | IND3 | 123 | IDTLTCGFADLMGYIPLVGAPLGGAARARALAHGVRVLEDGVNYATGNLPGCSFSIFLLALLS |
| 165 | P10 | 123 | IDTLTCGFADLMGYIPLVGAPLGGAARARALAHGVRVLEDGVNYATGNLPGCSFSIFLLALLS |
| 163 | D1 | 123 | IDTLTCGFADLMGYIPLVGAPLGGAARARALAHGVRVLEDGVNYATGNLPGCSFSIFLLALLS |
| 156 | US11 | 123 | IDTLTCGFADLMGYIPLVGAPLGGAARARALAHGVRVLEDGVNYATGNLPGCSFSIFLLALLS |
| 157 | S14 | 123 | IDTLTCGFADLMGYIPLVGAPLGGAARARALAHGVRVLEDGVNYATGNLPGCSFSIFLLALLS |
| 158 | SW1 | 123 | IDTLTCGFADLMGYIPLVGAPLGGAARARALAHGVRVLEDGVNYATGNLPGCSFSIFLLALLS |
| 159 | S18 | 123 | IDTLTCGFADLMGYIPLVGAPLGGAARARALAHGVRVLEDGVNYATGNLPGCSFSIFLLALLS |
| 160 | DR4 | 123 | IDTLTCGFADLMGYIPLVGAPLGGAARARALAHGVRVLEDGVNYATGNLPGCSFSIFLLALLS |
| 155 | DK7 | 123 | IDTLTCGFADLMGYIPLVGAPLGGAARARALAHGVRVLEDGVNYATGNLPGCSFSIFLLALLS |
| 170 | IND8 | 123 | IDTLTCGFADLMGYIPLVGAPLGGAARARALAHGVRVLEDGVNYATGNLPGCSFSIFLLALLS |
| 162 | S45 | 123 | IDTLTCGFADLMGYIPLVGAPLGGAARARALAHGVRVLEDGVNYATGNLPGCSFSIFLLALLS |
| 171 | S9 | 123 | IDTLTCGFADLMGYIPLVGgPLGGvARARALAHGVRVvEDGVNYATGNLPGCSFSIFLLALLS |
| 175 | P8 | 123 | IDTLTCGFADLMGYIPLVGgPLGGvARARALAHGVRVLEDGVNYATGNLPGCSFSIFLLALLS |

155-176 consensus IDTLTCGFADLMGYIPLVGaPLGGaARARALAHGVRVlEDGVNYATGNlPGCsFSIFLLALLS

FIGURE 7C-4

| SEQ ID NO: | ISOLATE | | |
|---|---|---|---|
| 173 | HK5 | 184 | CLTtPvSA |
| 176 | T3 | 184 | CLTiPASA |
| 172 | HK3 | 184 | CLTtPASA |
| 174 | HK4 | 184 | CLTIPASA |
| 161 | SA10 | 184 | CLTIPASA |
| 168 | SW2 | 184 | CLTIPASA |
| 167 | T10 | 184 | CLTIPASA |
| 166 | DK1 | 184 | CLTIPASA |
| 164 | US6 | 184 | CLTIPASA |
| 169 | IND3 | 184 | CLTIPASA |
| 165 | P10 | 184 | CLTIPASA |
| 163 | D1 | 184 | CLTVPASA |
| 156 | US11 | 184 | CLTVPASA |
| 157 | S14 | 184 | CLTVPASA |
| 158 | SW1 | 184 | CLTVPASA |
| 159 | S18 | 184 | CLTVPASA |
| 160 | DR4 | 184 | CLTVPASA |
| 155 | DK7 | 184 | CLTVPASA |
| 170 | IND8 | 184 | CLTIPASA |
| 162 | S45 | 184 | CLTIPASA |
| 171 | S9 | 184 | CLTIPASA |
| 175 | P8 | 184 | CLTIPASA |

155-176    consensus    CLTiPaSA

FIGURE 7D

```
SEQ ID NO:  ISOLATE
179         T9      1  MSTNPKPQRKTiRNTNRRPQDVKFPGGGQIVGGVYLLPRRGPRLGVRtTRKTSERSQPRGR
178         US10    1  MSTNPKPQRKTKRNTNRRPQDVKFPGGGQIVGGVYLLPRRGPRLGVRATRKTSERSQPRGR
180         T2      1  MSTiPKPQRKTKRNTNRRPQDVKFPGGGQIVGGVYLLPRRGPRLGVRATRKTSERSQPRGR
177         T4      1  MSTnPKPQRKTKRNTNRRPQDVKFPGGGQIVGGVYLLPRRGPRLGVRATRKTSERSQPRGR 177-180  consensus      MSTnPKPQRKTkRNTNRRPQDVKFPGGGQIVGGVYLLPRRGPRLGVRaTRKTSERSQPRGR SEQ ID NO:  ISOLATE
179         T9      62 RQPIPKDRRsTGKSWGKPGYPWPLYGNEGLGWAGWLLSPRGSRPSWGPsDPRHRSRNVGKV
178         US10    62 RQPIPKDRRpTGKSWGKPGYPWPLYGNEGLGWAGWLLSPRGSRPSWGPtDPRHRSRNVGKV
180         T2      62 RQPIPKDRRSTGKSWGKPGYPWPLYGNEGLGWAGWLLSPRGSRPSWGPNDPRHRSRNVGKV
177         T4      62 RQPIPKDRRSTGKSWGKPGYPWPLYGNEGLGWAGWLLSPRGSRPSWGPNDPRHRSRNVGKV 177-180  consensus      RQPIPKDRRsTGKSWGKPGYPWPLYGNEGLGWAGWLLSPRGSRPSWGPnDPRHRSRNVGKV SEQ ID NO:  ISOLATE
179         T9     123 IDTLTCGFADLMGYIPVVGAPLGGVARALAHGVRVLEDGVNYATGNLPGCSFSIFLLALLS
178         US10   123 IDTLTCGFADLMGYIPVVGAPLGGVARALAHGVRVLEDGVNYATGNLPGCSFSIFLLALLS
180         T2     123 IDTLTCGFADLMGYvPVVGgPLGGVARALAHGVRVLEDGVNYATGNLPGCSFSIFLLALLS
177         T4     123 IDTLTCslADLMGYIPVVGAPLGGVARALAHGVRVLEDGVNYATGNLPGCSFSIFLLALLS 177-180  consensus      IDTLTCgfADLMGYiPVVGaPLGGVARALAHGVRVLEDGVNYATGNLPGCSFSIFLLALLS SEQ ID NO:  ISOLATE
179         T9     184 CITtPaSA
178         US10   184 CITIPVSA
180         T2     184 CITIPVSA
177         T4     184 CITIPVSA 177-180  consensus      CITiPvSA
```

FIGURE 7E

| SEQ ID NO: | ISOLATE | | |
|---|---|---|---|
| 183 | DK11 | 1 | MSTNPKPQRKTKRNTNRRPQDVKFPGGGQIVGGVYLLPRRGPRLGVRtTRKTSERSQPRGR |
| 184 | SW3 | 1 | MSTNPKPQRKTKRNTNRRPQDVKFPGGGQIVGGVYLLPRRGPRLGVRATRKTSERSQPRGR |
| 181 | T8 | 1 | MSTNPKPQRKTKRNTNRRPQDVKFPGGGQIVGGVYLLPRRGPRLGVRATRKTSERSQPRGR |
| 182 | US1 | 1 | MSTNPKPQRKTKRNTNRRPQDVKFPGGGQIVGGVYLLPRRGPRLGVRATRKTSERSQPRGR |
| 185 | DK8 | 1 | MSTNPKPQRKTKRNTNRRPQDVKFPGGGQIVGGVYLLPRRGPRLGVRATRKsSERSQPRGR |
| 181-185 | consensus | | MSTNPKPQRKTKRNTNRRPQDVKFPGGGQIVGGVYLLPRRGPRLGVRaTRKtSERSQPRGR |

| SEQ ID NO: | ISOLATE | | |
|---|---|---|---|
| 183 | DK11 | 62 | RQPIPKDRRSTGKpWGKPGYPWPLYGNEGCGWAGWLLSPRGSHPNWGPTDPRHkSRNLGKV |
| 184 | SW3 | 62 | RQPIPKDRRSTGKSWGKPGYPWPLYGNEGCGWAGWLLSPRGSHPNWGPTDPRHRSRNLGKV |
| 181 | T8 | 62 | RQPIPKDRRSTGKSWGKPGYPWPLYGNEGCGWAGWLLSPRGSRPTWGPTDPRHRSRNLGrV |
| 182 | US1 | 62 | RQPIPKDRRSTGKSWGKPGYPWPLYGNEGCGWAGWLLSPRGSRPTWGPTDPRHRSRNLGKV |
| 185 | DK8 | 62 | RQPIPKDRRSTGKSWGKPGYPWPLYGNEGCGWAGWLLSPRGSRPTWGPTDPRHRSRNLGKV |
| 181-185 | consensus | | RQPIPKDRRSTGKsWGKPGYPWPLYGNEGCGWAGWLLSPRGSrPtWGPTDPRHrSRNLGkV |

| SEQ ID NO: | ISOLATE | | |
|---|---|---|---|
| 183 | DK11 | 123 | IDTITCGFADLMGYIPVVGAPVGGVARALAHGVRVLEDGINYATGNLPGCSFSIFLLALLS |
| 184 | SW3 | 123 | IDTITCGFADLMGYIPVVGAPVGGVARALAHGVRVLEDGINYATGNLPGCSFSIFLLALLS |
| 181 | T8 | 123 | IDTITCGFADLMGYIPVVGAPVGGVARALAHGVRVLEDGINYATGNLPGCSFSIFLLALLS |
| 182 | US1 | 123 | IDTITCGFADLMGYIPVVGAPVGGVARALAHGVRVLEDGINYATGNLPGCSFSIFLLALLS |
| 185 | DK8 | 123 | IDTITCGFADLMGYIPVVGAPVGGVARALAHGVRVLEDGINYATGNLPGCSFSIFLLALLS |
| 181-185 | consensus | | IDTITCGFADLMGYIPVVGAPVGGVARALAHGVRVLEDGINYATGNLPGCSFSIFLLALLS |

| SEQ ID NO: | ISOLATE | | |
|---|---|---|---|
| 183 | DK11 | 184 | CcTVPVSA |
| 184 | SW3 | 184 | CFTVPVSA |
| 181 | T8 | 184 | CFTVPVSA |
| 182 | US1 | 184 | CaTVPVSA |
| 185 | DK8 | 184 | CcTVPVSA |
| 181-185 | consensus | | C-TVPVSA |

FIGURE 7F-1

| SEQ ID NO: | ISOLATE | | |
|---|---|---|---|
| 183 | DK11 | 1 | MSTNPKPQRKTKRNTNRRPQDVKFPGGGQIVGGVYLLPRRGPRLGVRtTRKTSERSQPRGR |
| 184 | SW3 | 1 | MSTNPKPQRKTKRNTNRRPQDVKFPGGGQIVGGVYLLPRRGPRLGVRATRKTSERSQPRGR |
| 181 | T8 | 1 | MSTNPKPQRKTKRNTNRRPQDVKFPGGGQIVGGVYLLPRRGPRLGVRATRKTSERSQPRGR |
| 182 | US1 | 1 | MSTNPKPQRKTKRNTNRRPQDVKFPGGGQIVGGVYLLPRRGPRLGVRATRKTSERSQPRGR |
| 185 | DK8 | 1 | MSTNPKPQRKTKRNTNRRPQDVKFPGGGQIVGGVYLLPRRGPRLGVRATRKsSERSQPRGR |
| 186 | S83 | 1 | MSTNPKPQRKTKRNTNRRPQDVKFPGGGQIVGGVYLLPRRGPRLGVRATRKTSERSQPRGR |
| 178 | US10 | 1 | MSTNPKPQRKTKRNTNRRPQDVKFPGGGQIVGGVYLLPRRGPRLGVRATRKTSERSQPRGR |
| 180 | T2 | 1 | MSTiPKPQRKTKRNTNRRPQDVKFPGGGQIVGGVYLLPRRGPRLGVRtTRKTSERSQPRGR |
| 179 | T9 | 1 | MSTNPKPQRKTiRNTNRRPQDVKFPGGGQIVGGVYLLPRRGPRLGVRtTRKTSERSQPRGR |
| 177 | T4 | 1 | MSTNPKPQRKTKRNTNRRPQDVKFPGGGQIVGGVYLLPRRGPRLGVRaTRKTSERSQPRGR |
| 177-186 | consensus | | MSTnPKPQRKTkRNTNRRPQDVKFPGGGQIVGGVYLLPRRGPRLGVRaTRKtSERSQPRGR |

| SEQ ID NO: | ISOLATE | | |
|---|---|---|---|
| 183 | DK11 | 62 | RQPIPKDRRSTGKpWGKPGYPWPLYGNEGCGWAGWLLSPRGSHPNWGPTDPRHkSRNLGKV |
| 184 | SW3 | 62 | RQPIPKDRRSTGKSWGKPGYPWPLYGNEGCGWAGWLLSPRGSHPNWGPTDPRHRSRNLGKV |
| 181 | T8 | 62 | RQPIPKDRRSWGKSWGKPGYPWPLYGNEGCGWAGWLLSPRGSRPTWGPTDPRHRSRNLGrV |
| 182 | US1 | 62 | RQPIPKDRRSTGKSWGKPGYPWPLYGNEGCGWAGWLLSPRGSRPTWGPTDPRHRSRNLGKV |
| 185 | DK8 | 62 | RQPIPKDRRSTGKSWGKPGYPWPLYGNEGCGWAGWLLSPRGSRPSWGPTDPRHRSRNLGKV |
| 186 | S83 | 62 | RQPIPKDRRSWGrPGYPWPLYGNEGLGWAGWLLSPRGSRPSWGPTDPRHkSRNLGKV |
| 178 | US10 | 62 | RQPIPKDRRpTGKSWGKPGYPWPLYGNEGLGWAGWLLSPRGSRPSWGPTDPRHRSRNVGKV |
| 180 | T2 | 62 | RQPIPKDRRSTGKSWGKPGYPWPLYGNEGLGWAGWLLSPRGSRPSWGPnDPRHRSRNVGKV |
| 179 | T9 | 62 | RQPIPKDRRSTGKSWGKPGYPWPLYGNEGLGWAGWLLSPRGSRPSWGPsDPRHRSRNVGKV |
| 177 | T4 | 62 | RQPIPKDRRSTGKSWGKPGYPWPLYGNEGLGWAGWLLSPRGSRPSWGPnDPRHRSRNVGKV |
| 177-186 | consensus | | RQPIPKDRRsTGKsWGkPGYPWPLYGNEG-GWAGWLLSPRGSrPsWGPtDPRHrSRNlGkV |

FIGURE 7F-2

| SEQ ID NO: | ISOLATE | | |
|---|---|---|---|
| 183 | DK11 | 123 | IDTITCGFADLMGYIPVVGAPVGGVARALAHGVRVLEDGINYATGNLPGCSFSIFLLALLS |
| 184 | SW3 | 123 | IDTITCGFADLMGYIPVVGAPVGGVARALAHGVRVLEDGINYATGNLPGCSFSIFLLALLS |
| 181 | T8 | 123 | IDTITCGFADLMGYIPVVGAPVGGVARALAHGVRVLEDGINYATGNLPGCSFSIFLLALLS |
| 182 | US1 | 123 | IDTITCGFADLMGYIPVVGAPVGGVARALAHGVRVLEDGINYATGNLPGCSFSIFLLALLS |
| 185 | DK8 | 123 | IDTITCGFADLMGYIPVVGAPVGGVARALAHGVRVLEDGINYATGNLPGCSFSIFLLALLS |
| 186 | S83 | 123 | IDTLTCGFADLMGYIPVVGAPVGGVARALAHGVRVLEDGINYATGNLPGCSFSIFLLALLS |
| 178 | US10 | 123 | IDTLTCGFADLMGYIPVVGAPVGGVARALAHGVRVLEDGVNYATGNLPGCSFSIFLLALLS |
| 180 | T2 | 123 | IDTLTCGFADLMGYIPVVGAPLGGVARALAHGVRVLEDGVNYATGNLPGCSFSIFLLALLS |
| 179 | T9 | 123 | IDTLTCGFADLMGYIPVVGAPLGGVARALAHGVRVLEDGVNYATGNLPGCSFSIFLLALLS |
| 177 | T4 | 123 | IDTLTCsLADLMGYvPVVGgPLGGVARALAHGVRVLEDGVNYATGNLPGCSFSIFLLALLS |

177-186 consensus     IDT-TCgfADLMGYiPVVGaPvGGVARALAHGVRVLEDGiNYATGNLPGCSFSIFLLALLS

| SEQ ID NO: | ISOLATE | | |
|---|---|---|---|
| 183 | DK11 | 184 | CcTVPVSA |
| 184 | SW3 | 184 | CFTVPVSA |
| 181 | T8 | 184 | CFTVPVSA |
| 182 | US1 | 184 | CaTVPVSA |
| 185 | DK8 | 184 | CcTVPVSA |
| 186 | S83 | 184 | CIsVPVSA |
| 178 | US10 | 184 | CITIPVSA |
| 180 | T2 | 184 | CITIPVSA |
| 179 | T9 | 184 | CITtPaSA |
| 177 | T4 | 184 | CITiPvSA |

177-186 consensus     CitvPvSA

FIGURE 7G

| SEQ ID NO: | ISOLATE | | |
|---|---|---|---|
| 189 | S2 | 1 | MSTLPKPQRKTKRNTIRRPQDiKFPGGGQIVGGVYVLPRRGPRLGVRATRKTSERSQPRGR |
| 187 | HK10 | 1 | MSTLPKPQRKTKRNTIRRPQDVKFPGGGQIVGGVYVLPRRGPRLGVRATRKTSERSQPRGR |
| 190 | DK12 | 1 | MSTLPKPQRKTKRNTIRRPQDVKFPGGGQIVGGVYVLPRRGPRLGVRATRKTSERSQPRGR |
| 188 | S52 | 1 | MSTLPKPQRKTKRNTIRRPQDVKFPGGGQIVGGVYVLPRRGPRLGVRATRKTSERSQPRGR |
| 187-190 | consensus | | MSTLPKPQRKTKRNTIRRPQDvKFPGGGQIVGGVYVLPRRGPRLGVRATRKTSERSQPRGR |

| SEQ ID NO: | ISOLATE | | |
|---|---|---|---|
| 189 | S2 | 62 | RQPIPKARRSEGRSWAQPGYPWPLYGNEGCGWAGWLLSPRGSRPSWGPNDPRRRSRNLGKV |
| 187 | HK10 | 62 | RQPIPKARRSEGRSWAQPGYPWPLYGNEGCGWAGWLLSPRGSRPSWGPNDPRRRSRNLGKV |
| 190 | DK12 | 62 | RQPIPKARRSEGRSWAQPGYPWPLYGNEGCGWAGWLLSPRGSRPSWGPNDPRRRSRNLGKV |
| 188 | S52 | 62 | RQPIPKARRSEGRSWAQPGYPWPLYGNEGCGWAGWLLSPRGSRPSWGPNDPRRRSRNLGKV |
| 187-190 | consensus | | RQPIPKARRSEGRSWAQPGYPWPLYGNEGCGWAGWLLSPRGSRPSWGPNDPRRRSRNLGKV |

| SEQ ID NO: | ISOLATE | | |
|---|---|---|---|
| 189 | S2 | 123 | IDTLTCGFADLMGYIPLVGAPVGGVARALAHGVRALEDGINFATGNLPGCSFSIFLLALFS |
| 187 | HK10 | 123 | IDTLTCGFADLMGYIPLVGAPVGGVARALAHGVRALEDGINFATGNLPGCSFSIFLLALFS |
| 190 | DK12 | 123 | IDTLTCGFADLMGYIPLVGAPVGGVARALAHGVRALEDGINFATGNLPGCSFSIFLLALFS |
| 188 | S52 | 123 | IDTLTCGFADLMGYIPLVGAPVGGVARALAHGVRALEDGINFATGNLPGCSFSIFLLALFS |
| 187-190 | consensus | | IDTLTCGFADLMGYIPLVGAPVGGVARALAHGVRALEDGINFATGNLPGCSFSIFLLALFS |

| SEQ ID NO: | ISOLATE | | |
|---|---|---|---|
| 189 | S2 | 184 | CLiHPAAS |
| 187 | HK10 | 184 | CLIHPAAS |
| 190 | DK12 | 184 | CLIHPAAS |
| 188 | S52 | 184 | CLvHPAAS |
| 187-190 | consensus | | CLiHPAAS |

FIGURE 7H-1

| SEQ ID NO: | ISOLATE | | |
|---|---|---|---|
| 194 | Z5 | 1 | MSTNPKPQRKTKRNTNRRPMDVKFPGGGQIVGGVYLLPRRGPRLGVRAtRKTSERSQPRGR |
| 193 | Z1 | 1 | MSTNPKPQRKTKRNTNRRPMDVKFPGGGQIVGGVYLLPRRGPRLGVRAaRKTSERSQPRGR |
| 192 | Z8 | 1 | MSTNPKPQRKTKRNTNRRPMDVKFPGGGQIVGGVYLLPRRGPRLGVRATRKTSERSQPRGR |
| 195 | Z6 | 1 | MSTNPKPQRKTKRNTNRRPMDVKFPGGGQIVGGVYLLPRRGPRLGVRATRKTSERSQPRGR |
| 196 | Z7 | 1 | MSTNPKPQRKTKRNTNRRPMDVKFPGGGQIVGGVYLLPRRGPRLGVRtTRKTSERSQPRGR |
| 191 | Z4 | 1 | MSTNPKPQRKTKRNTNRRPMDVKFPGGGQIVGGVYLLPRRGPRLGVRATRKTSERSQPRGR |
| 197 | DK13 | 1 | MSTNPKPQRKTKRNTNRRPMDVKFPGGGQIVGGVYLLPRRGPRLGVRATRKTSERSQPRGR |

191-197 consensus    MSTNPKPQRKTKRNTNRRPMDVKFPGGGQIVGGVYLLPRRGPRLGVRatRKTSERSQPRGR

| SEQ ID NO: | ISOLATE | | |
|---|---|---|---|
| 194 | Z5 | 62 | RQPIPqARRSEGRSWAQPGYPWPLYGNEGCGWAGWLLSPRGSRPSWGqNDPRRRSRNLGKV |
| 193 | Z1 | 62 | RQPIPKARRSEGRSWAQPGYPWPLYGNEGCGWAGWLLSPRGSRPSWGPNDPRRRSRNLGKV |
| 192 | Z8 | 62 | RQPIPKARRSEGRSWAQPGYPWPLYGNEGCGWAGWLLSPRGSRPSWGPNDPRRRSRNLGKV |
| 195 | Z6 | 62 | RQPIPKARRSEGRSWAQPGYPWPLYGNEGCGWAGWLLSPRGSRPSWGPNDPRRRSRNLGKV |
| 196 | Z7 | 62 | RQPIPKARRSEGRSWAQPGYPWPLYGNEGCGWAGWLLSPRGSRPSWGPNDPRRRSRNLGKV |
| 191 | Z4 | 62 | RQPIPKARQpEGRSWAQPGYPWPLYGNEGCGWAGWLLSPRGSRPSWGPNDPRRRSRNLGKV |
| 197 | DK13 | 62 | RQPIPKARQlEGRSWAQPGYPWPLYGNEGCGWAGWLLSPRGSRPSWGPNDPRRRSRNLGKV |

191-197 consensus    RQPIPkARrsEGRSWAQPGYPWPLYGNEGCGWAGWLLSPRGSRPSWGpNDPRRRSRNLGKV

FIGURE 7H-2

| SEQ ID NO: | ISOLATE | | |
|---|---|---|---|
| 194 | Z5 | 123 | IDTLTCGFADLMGYIPLVGAPVGGVARALAHGVRAlEDGINYATGNLPGCSFSIFLLALfS |
| 193 | Z1 | 123 | IDTLTCGFADLMGYIPLVGAPVGGVARALAHGVRAVEDGINYATGNLPGCSFSIFLLALLS |
| 192 | Z8 | 123 | IDTLTCGFADLMGYIPLVGAPVGGVARALAHGVRAVEDGINYATGNLPGCSFSIFLLALLS |
| 195 | Z6 | 123 | IDTLTCGFADLMGYIPLVGAPVGGVARALAHGVRAVEDGINYATGNLPGCSFSIFLLALLS |
| 196 | Z7 | 123 | IDTLTCGFADLMGYIPLVGAPVGGVARALAHGVRAlEDGINYATGNLPGCSFSIFLLALLS |
| 191 | Z4 | 123 | IDTLTCGFADLMGYIPiVGAPVGGVARALAHGVRAvEDGINYATGNLPGCSFSIFLLALLS |
| 197 | DK13 | 123 | IDTLTCGFADLMGYIPvVGAPVGGVARALAHGVRRl1EDGvNYATGNLPGCSFSIFLLALLS |

191-197 consensus    IDTLTCGFADLMGYIPlVGAPVGGVARALAHGVRavEDGiNYATGNLPGCSFSIFLLAlLS

| SEQ ID NO: | ISOLATE | | |
|---|---|---|---|
| 194 | Z5 | 184 | CLTTPASA |
| 193 | Z1 | 184 | CLTTPASA |
| 192 | Z8 | 184 | CLTVPASA |
| 195 | Z6 | 184 | CLTVPtSA |
| 196 | Z7 | 184 | CLTVPASA |
| 191 | Z4 | 184 | CLTVPASA |
| 197 | DK13 | 184 | CLTVPASA |

191-197 consensus    CLTvPaSA

FIGURE 71-1

| SEQ ID NO: | ISOLATE | | |
|---|---|---|---|
| 205 | SA11 | 1 | MSTNPKPQRKTKRNTNRRPQDVKFPGGGQIVGGVYLLPRRGPRLGVRATRKTSERSQPRGR |
| 202 | SA3 | 1 | MSTNPKPQRKTKRNTNRRPQDVKFPGGGQIVGGVYLLPRRGPRLGVRATRKTSERSQPRGR |
| 198 | SA4 | 1 | MSTNPKPQRKTKRNTNRRPQDVKFPGGGQIVGGVYLLPRRGPRLGVRATRKTSERSQPRGR |
| 199 | SA5 | 1 | MSTNPKPQRKTKRNTNRRPQDVKFPGGGQIVGGVYLLPRRGPRLGVRATRKTSERSQPRGR |
| 200 | SA7 | 1 | MSTNPKPQRKTKRNTNRRPQDVKFPGGGQIVGGVYLLPRRGPRLGVRATRKTSERSQPRGR |
| 203 | SA13 | 1 | MSTNPKPQRKTKRNTN1RPQDVKFPGGGQIVGGVYLLPRRGPRLGVRATRKTSERSQPRGR |
| 201 | SA1 | 1 | MSTNPKPQRKTqRNTNrRPQDVKFPGGGQIVGGVYLLPRRGPRLGVRATRKTSERSQPRGR |
| 204 | SA6 | 1 | MSTNPKPQRKTqRNTNrRPQDVKFPGGGQIVGGVYLLPRRGPRmGVRATRKTSERSQPRGR |

198-205 consensus    MSTNPKPQRKTkRNTNrRPQDVKFPGGGQIVGGVYLLPRRGPRLGVRATRKTSERSQPRGR

| SEQ ID NO: | ISOLATE | | |
|---|---|---|---|
| 205 | SA11 | 62 | RQPIPKARQPTGRSWGQPGYPWPfYANEGLgWAGWLLSPRGSRPnWGPNDPRRrSRNLGKV |
| 202 | SA3 | 62 | RQPIPKARQPTGRSWGQPGYPWPLYANEGLGWAGWLLSPRGSRPsWGPNDPRRKSRNLGKV |
| 198 | SA4 | 62 | RQPIPKARQPTGRSWGQPGYPWPLYANEGLGWAGWLLSPRGSRPNWGPNDPRRKSRNLGKV |
| 199 | SA5 | 62 | RQPIPKARQPTGRSWGQPGYPWPLYANEGLGWAGWLLSPRGSRPNWGPNDPRRKSRNLGKV |
| 200 | SA7 | 62 | RQPIPKARQPTGRSWGQPGYPWPLYANEGLGWAGWLLSPRGSRPNWGPNDPRRKSRNLGKV |
| 203 | SA13 | 62 | RQPIPKARQPTGRSWGQPGYPWPLYANEGLGWAGWLLSPRGSRPNWGPNDPRRKSRNLGKV |
| 201 | SA1 | 62 | RQPIPKARQPTGRSWGQPGYPWPLYANEGLGWAGWLLSPRGSRPNWGPNDPRRKSRNLGKV |
| 204 | SA6 | 62 | RQPIPKARQsaGRSWGQPGYPWPLYANEGLGWAGWLLSPRGSRPNWGPNDPRRKSRNLGKV |

198-205 consensus    RQPIPKARQptGRSWGQPGYPWPlYANEGLgWAGWLLSPRGSRPnWGPNDPRRkSRNLGKV

FIGURE 7I-2

| SEQ ID NO: | ISOLATE | | |
|---|---|---|---|
| 205 | SA11 | 123 | IDTLTCGFADLMGYIPLVGGPVGGVARALAHGVRaLEDGVNYATGNLPGCSFSIFILALLS |
| 202 | SA3 | 123 | IDTLTCGFADLMGYIPLVGGPVGGVARALAHGVRVLEDGVNYATGNLPGCSFSIFILALLS |
| 198 | SA4 | 123 | IDTLTCGFADLMGYIPLVGGPVGGVARALAHGVRVLEDGVNYATGNLPGCSFSIFILALLS |
| 199 | SA5 | 123 | IDTLTCGFADLMGYIPLVGGPVGGVARALAHGVRVLEDGVNYATGNLPGCSFSIFILALLS |
| 200 | SA7 | 123 | IDTLTCGFADLMGYIPLVGGPVGGVARALAHGVRVLEDGVNYATGNLPGCSFSIFILALLS |
| 203 | SA13 | 123 | IDTLTCGFADLMGYIPLVGGPVGGVARALAHGVRVLEDGVNYATGNLPGCSFSIFILALLS |
| 201 | SA1 | 123 | IDTLTCGFADLMGYIPLVGGPVGGVARALAHGVRVLEDGVNYATGNLPGCSFSIFILALLS |
| 204 | SA6 | 123 | IDTLTCGFADLMGYIPLVGGPVGGVARALAHGVRVLEDGVNYATGNLPGCSFSIFvLALLS |

198-205 consensus  IDTLTCGFADLMGYIPLVGGPVGGVARALAHGVRvLEDGVNYATGNLPGCSFSIFiLALLS

| SEQ ID NO: | ISOLATE | | |
|---|---|---|---|
| 205 | SA11 | 184 | CLTVPAtA |
| 202 | SA3 | 184 | CLTVPASA |
| 198 | SA4 | 184 | CLTVPASA |
| 199 | SA5 | 184 | CLTVPASA |
| 200 | SA7 | 184 | CLTVPASA |
| 203 | SA13 | 184 | CLTVPtSA |
| 201 | SA1 | 184 | CLiiPASA |
| 204 | SA6 | 184 | CLtvPASA |

198-205 consensus  CLtvPasA

FIGURE 7J

```
SEQ ID NO:   Genotype
155-206      cons.      1    MSTnPKPQRkTkRNTnrRpqDvkFPGGGQIVGGVYllPRRGPRlGVRatRKtSERSQPRGRRQPIPkaRrpeGrswaqPGyPWPlYgnEGcgWAGW 155-176      type 1          MSTnPKPQRKTKRNThRRPQDVKFPGGGQIVGGVYLLPRRGPRLGVRAtRKTSERSQPRGRRQPIPKARrPEGRaWAQPGyPWPLYgnEG-GWAGW
177-186      type 2          MSTnPKPQRKTkRNTNRRPQDVKFPGGGQIVGGVYLLPRRGPRLGVRaTRKTSERSQPRGRRQPIPKDRRsTGKsWGkPGYPWPLYGNEGlGWAGW
187-190      type 3          MSTLPKPQRKTKRNTIRRPQDVKFPGGGQIVGGVYLLPRRGPRLGVRATRKTSERSQPRGRRQPIPKARRsEGRSWAQPGYPWPLYGNEGCGWAGW
191-197      type 4          MSTNPKPQRKTKRNTNRRPMDVKFPGGGQIVGGVYLLPRRGPRLGVRatRKTSERSQPRGRRQPIPKARrsEGRSWGQPGYPWPLYGNEGCGWAGW
198-205      type 5          MSTNPKPQRKTkRNTnrRPQDVKFPGGGQIVGGVYLLPRRGPRLGVRATRKTSERSQPRGRRQPIPKARQptGRSWGQPGYPWPlYANEGlgWAGW
206          type 6          MSTLPKPQRKTKRNTNRRPTDVKFPGGGQIVGGVYLLPRRGPRLGVRATRKTSERSQPRGRRQPIPKARQPQGRHWAQPGYPWPLYGNEGCGWAGW SEQ ID NO:   Genotype
155-206      cons.      97   LLSPrGSrPsWGptDPRrrsRNlGkVIDTlTCgfADLMGYiPlVGaPlGGvArALAHGVRvlEDGvNyATGNlPGCsFSIFlLAllSCLtvPasa 155-176      type 1          LLSPrGSRPsWGPtDPRRRSRNLGKVIDTLTCGFADLMGYIPLVGaPLGGaARALAHGVRVlEDGVNYATGNlPGCsFSIFLLALLSCLTiPaSA
177-186      type 2          LLSPRGSrPsWGPtDPRHrSRNLGkVIDTlTCgfADLMGYiPvVGaPvGGVARALAHGVRVLEDGiNYATGNLPGCSFSIFLLALLSCitvPvSA
187-190      type 3          LLSPRGSRPSWGPNDPRRRSRNLGKVIDTLTCGFADLMGYIPLVGAPLGGVARALAHGVRALEDGINFATGNLPGCSFSIFLLALFSCLiHPAAS
191-197      type 4          LLSPRGSRPSWGpNDPRRRSRNLGKVIDTLTCGFADLMGYiPlVGAPVGGVARALAHGVRaVEDGiNYATGNLPGCSFSIFLLAlLSCLTvPaSA
198-205      type 5          LLSPRGSRPnWGPNDPRRkSRNLGkVIDTLTCGFADLMGYIPLVGGPVGGPVGGVARALAHGVRvLEDGVNYATGNLPGCSFSIFiLALLSCLtvPasA
206          type 6          LLSPRGSRPHWGPNDPRRRSRNLGKVIDTLTCGFADLMGYIPVVGAPLGVAAALAHGVRAIEDGINYATGNLPGCSFSIFLLALLSCLTTPASA
```

FIGURE 7K

| SEQ ID NO: | Genotype |
|---|---|
| 155-160 | I/1a |
| 161-176 | II/1b |
| 177-180 | III/2a |
| 181-185 | IV/2b |
| 186 | 2c |
| 187-190 | (V)/3a |
| 191 | 4a |
| 193 | 4b |
| 195 | 4c |
| 197 | 4d |
| 194 | 4e |
| 192 | 4f |
| 198-205 | 5a |
| 206 | 6a |

```
                   10        20        30        40        50        60        70        80        90
        MSTnPKPQRKTKRNTnrRPqDvKFPGGGQIVGGVYlLPRRGPRlGVRatRKtSERSQPRGRRQPIPkaRrpeGrsWaqPGyPWPlYgnEGgWAGW
155-160 ----N-----K-K---NR---Q-V-------------L------------------At--T-----------KA-RPE-RT-AQ--Y---L--GN---CG---
161-176 ----n-----k-k---nR---Q-V-------------L------------------AT--T-----------KA-rPE-Ra-AQ--y---L--gn---mG---
177-180 ----n-----K-k---NR---Q-V-------------L------------------aT--t-----------KD-RsT-KS-GK--Y---L--GN---LG---
181-185 ----N-----K-K---NR---Q-V-------------L------------------aT--t-----------KD-RST-Ks-GK--Y---L--GN---CG---
186     ----N-----K-K---NR---Q-V-------------L------------------AT--T-----------KD-RTT-KS-GR--Y---L--GN---LG---
187-190 ----L-----K-K---IR---Q-v----------V--L------------------AT--T-----------KA-RSE-RS-AQ--Y---L--GN---CG---
191     ----N-----K-K---NR---M-V-------------L------------------AA--T-----------KA-QPE-RS-AQ--Y---L--GN---CG---
193     ----N-----K-K---NR---M-V-------------L------------------AT--T-----------KA-RSE-RS-AQ--Y---L--GN---CG---
195     ----N-----K-K---NR---M-V-------------L------------------aT--T-----------KA-RSE-RS-AQ--Y---L--GN---CG---
197     ----N-----K-K---NR---M-V-------------L------------------AT--T-----------QA-RSE-RS-AQ--Y---L--GN---CG---
194     ----N-----K-K---NR---M-V-------------L------------------AT--T-----------KA-QLE-RS-AQ--Y---L--GN---CG---
192     ----N-----K-K---NR---M-V-------------L------------------AT--T-----------KA-RSE-RS-AQ--Y---L--GN---CG---
198-205 ----N-----K-K---Nr---Q-V-------------L------------------AT--T-----------KA-Qpt-RS-GQ--Y---I--AN---Lg---
206     ----L-----K-K---NR---T-V-------------L------------------AT--T-----------KA-QPQ-RH-AQ--Y---L--GN---CG---

100       110       120       130       140       150       160       170       180       190
        LLSPrGSrPsWGptDPRrrSRNlGkVIDTlTCgfADLMGYIPlVGaPlGGVArALAHGVRvlEDGvNyATGNlPGCsFSIFlLAlISClTvPasa
155-160 ----R-R-S--PT---RR-----L--K-----------GF-----I--L---A-L---A-R-----------VL------V-Y-----L---S-----L---LTV-ASA
161-176 ----r-R-s--Pt---RR-----L--K-----------gF----------L---a-R-----------Vl------v-y-----l---s-----l---LTi-aSA
177-180 ----R-R-S--Pn---HR-----V--K-----------gf-----I--------V-R-----------Vl------V-Y-----L---s-----L---ITi-vSA
181-185 ----R-r-t--PT---Hr-----L--K-----------GF--------V-a-L-V-R-----------VL------V-Y-----L---s-----L---fTv-VSA
186     ----R-R-S--PT---HK-----L--K-----------GF--------V---V-R-----------VL------V-Y-----L---S-----L---ISV-VSA
187-190 ----R-R-S--PN---RR-----L--K-----------GF-----I--A-V-V-R-----------AL------I-F-----L---S-----F---LiH-AAS
191     ----R-R-S--PN---RR-----L--K-----------GF-----I--L-A-V-V-R-----------AV------I-Y-----L---S-----L---LTV-ASA
193     ----R-R-S--PN---RR-----L--K-----------GF-----I--L-A-V-V-R-----------AV------V-Y-----L---S-----L---LTV-tSA
195     ----R-R-S--PN---RR-----L--K-----------GF-----I--L-A-V-V-R-----------AV------I-Y-----L---S-----L---LTV-ASA
197     ----R-R-S--QN---RR-----L--K-----------GF-----I--L-A-V-V-R-----------LL------V-Y-----L---S-----F---LTT-ASA
194     ----R-R-S--PN---RR-----L--K-----------GF-----I--L-A-V-V-R-----------AL------I-Y-----L---s-----L---LTV-ASA
192     ----R-R-S--PN---RR-----L--K-----------GF-----I--L-A-V-V-R-----------AV------V-Y-----L---S-----L---LtV-asA
198-205 ----R-r-n--PN---RK-----L--K-----------GF-----I--L-G-V-V-R-----------VL------V-Y-----L---S-----i---ltv-asA
206     ----R-H-H--PN---RR-----L--K-----------GF-----I--V-A-L-V-A-----------Al------I-Y-----L---S-----l---LTT-ASA
```

HEPATITIC C VIRUS (HCV) CORE GENE NUCLEOTIDE SEQUENCES AND RELATED METHODS OF DETECTING MAJOR AND MINOR GENOTYPES OF HCV ISOLATES

The present application is a continuation-in-part of U.S. application Ser. No. 08/086,428, filed on Jun. 29, 1993, now issued as U.S. Pat. No. 5,514,539 on May 7, 1996.

FIELD OF INVENTION

The present invention is in the field of hepatitis virology. The invention relates to the complete nucleotide and deduced amino acid sequences of the envelope 1 (E1) and core genes of hepatitis C virus (HCV) isolates from around the world and the grouping of these isolates into fourteen distinct HCV genotypes. More specifically, this invention relates to oligonucleotides, peptides and recombinant proteins derived from the envelope 1 and core gene sequences of these isolates of hepatitis C virus and to diagnostic methods and vaccines which employ these reagents.

BACKGROUND OF INVENTION

Hepatitis C, originally called non-A, non-B hepatitis, was first described in 1975 as a disease serologically distinct from hepatitis A and hepatitis B (Feinstone, S. M. et al. (1975) N. Engl. J. Med. 292:767–770). Although hepatitis C was (and is) the leading type of transfusion-associated hepatitis as well as an important part of community-acquired hepatitis, little progress was made in understanding the disease until the recent identification of hepatitis C virus (HCV) as the causative agent of hepatitis C via the cloning and sequencing of the HCV genome (Choo, A. L. et al. (1989) Science 288:359–362). The sequence information generated by this study resulted in the characterization of HCV as a small, enveloped, positive-stranded RNA virus and led to the demonstration that HCV is a major cause of both acute and chronic hepatitis worldwide (Weiner, A. J. et al. (1990) Lancet 335:1–3). These observations, combined with studies showing that over 50% of acute cases of hepatitis C progress to chronicity with 20% of these resulting in cirrhosis and an undetermined proportion progressing to liver cancer, have led to tremendous efforts by investigators within the hepatitis C field to develop diagnostic assays and vaccines which can detect and prevent hepatitis C infection.

The cloning and sequencing of the HCV genome by Choo et al. (1989) has permitted the development of serologic tests which can detect HCV or antibody to HCV (Kuo, G. et al. (1989) Science 244:362–364). In addition, the work of Choo et al. has also allowed the development of methods for detecting HCV infection via amplification of HCV RNA sequences by reverse transcription and cDNA polymerase chain reaction (RT-PCR) using primers derived from the HCV genomic sequence (Weiner, A. J. et al.). However, although the development of these diagnostic methods has resulted in improved diagnosis of HCV infection, only approximately 60% of cases of hepatitis C are associated with a factor identified as contributing to transmission of HCV (Alter, M. J. et al. (1989) JAMA 262:1201–1205). This observation suggests that effective control of hepatitis C transmission is likely to occur only via universal pediatric vaccination as has been initiated recently for hepatitis B virus. Unfortunately, attempts to date to protect chimpanzees from hepatitis C infection via administration of recombinant vaccines have had only limited success. Moreover, the apparent genetic heterogeneity of HCV, as indicated by the recent assignment of all available HCV isolates to one of four genotypes, I–IV (Okamoto, H. et al. (1992) J. Gen. Virol; 73:673–679), presents additional hurdles which must be overcome in order to develop accurate and effective diagnostic assays and vaccines.

For example, one possible obstacle to the development of effective hepatitis C vaccines would arise if the observed genetic heterogeneity of HCV reflects serologic heterogeneity. In such a case, the most genetically diverse strains of HCV may then represent different serotypes of HCV with the result being that infection with one strain may not protect against infection with another. Indeed, the inability of one strain to protect against infection with another strain was recently noted by both Farci et al. (Farci, P. et al. (1992) Science 258:135–140) and Prince et al. (Prince, A. M. et al. (1992) J. Infect. Dis. 165:438–443), each of whom presented evidence that while infection with one strain of HCV does modify the degree of the hepatitis C associated with the reinfection, it does not protect against reinfection with a closely related strain. The genetic heterogeneity among different HCV strains also increases the difficulty encountered in developing RT-PCR assays to detect HCV infection since such heterogeneity often results in false-negative results because of primer and template mismatch. In addition, currently used serologic tests for detection of HCV or for detection of antibody to HCV are not sufficiently well developed to detect all of the HCV genotypes which might exist in a given blood sample. Finally, in terms of choosing the proper treatment modality to combat hepatitis infection, the inability of presently available serologic assays to distinguish among the various genotypes of HCV represents a significant shortcoming in that recent reports suggest that an HCV-infected patient's response to therapy might be related to the genotype of the infectious virus (Yoshioka, K. et al. (1992) Hepatology 16:293–299; Kanai, K. et al. (1992) Lancet 339:1543; Lan, J. Y. N. et al. (1992) Hepatology 16:209A). Indeed, the data presented in the above studies suggest that the closely related genotypes I and II are less responsive to interferon therapy than are the closely related genotypes III and IV. Moreover, preliminary data by Pozzato et al. (Pozzato, G. et al. (1991) Lancet 338:509) suggests that different genotypes may be associated with different types or degrees of clinical disease. Taken together, these studies suggest that before effective vaccines against HCV infection can be developed, and indeed, before more accurate and effective methods for diagnosis and treatment of HCV infection can be produced, one must obtain a greater knowledge about the genetic and serologic diversity of HCV isolates.

In a recent attempt to gain an understanding of the extent of genetic heterogeneity among HCV strains, Bukh et al. carried out a detailed analysis of HCV isolates via the use of PCR technology to amplify different regions of the HCV genome (Bukh, J. et al. (1992a) Proc. Natl. Acad. Sci. 89:187–191). Following PCR amplification, the 5'-noncoding (5' NC) portion of the genomes of various HCV isolates were sequenced and it was found that primer pairs designed from conserved regions of the 5' NC region of the HCV genome were more sensitive for detecting the presence of HCV than were primer pairs representing other portions of the genome (Bukh, J. et al. (1992b) Proc. Natl. Acad. Sci. U.S.A. 89:4942–4946). In addition, the authors noted that although many of the HCV isolates examined could be classified into the four genotypes described by Okamoto et al. (1992), other previously undescribed genotypes emerged based on genetic heterogeneity observed in the 5' NC region of the various isolates. One of the most prominent of these newly noted genotypes comprised a group of related viruses that contained the most genetically divergent 5' NC regions of those studied. This group of viruses, tentatively classified as a fifth genotype, are very similar to strains recently described by others (Cha, T.-A et al. (1992) Proc. Natl. Acad. Sci. U.S.A. 89:7144–7148; Chan, S-W. et al. (1992) J. Gen. Virol., 73:1131–1141 and Lee, C-H et al. (1992) J. Clin. Microbio. 30:1602–1604). In addition, at least four more putative genotypes were identified thereby providing evidence that the genetic heterogeneity of HCV was more extensive than previously appreciated.

However, while the studies of Bukh et al. (1992a and b) provided new and useful information on the genetic heterogeneity of HCV, it is widely appreciated by those skilled in the art that the three structural genes of HCV, core (C), envelope (E1) and envelope 2/nonstructural 1 (E2/NS1) are the most important for the development of serologic diagnostics and vaccines since it is the product of these genes that constitutes the hepatitis C virion. Thus, a determination of the nucleotide sequence of one or all of the structural genes of a variety of HCV isolates would be useful in designing reagents for use in diagnostic assays and vaccines since a demonstration of genetic heterogeneity in a structural gene(s) of HCV isolates might suggest that some of the HCV genotypes represent distinct serotypes of HCV based upon the previously observed relationship between genetic heterogeneity and serologic heterogeneity among another group of single-stranded, positive-sense RNA viruses, the picornaviruses (Ruechert, R. R. "Picornaviridae and their replication", in Fields, B. N. et al., eds. Virology, New York: Raven Press, Ltd. (1990) 507–548).

SUMMARY OF INVENTION

The present invention relates to cDNAs encoding the complete nucleotide sequence of either the envelope 1 (E1) gene or the core (C) gene of an isolate of human hepatitis C virus (HCV).

The present invention also relates to the nucleic acid and deduced amino acid sequences of these E1 and core cDNAs.

It is an object of this invention to provide synthetic nucleic acid sequences capable of directing production of recombinant E1 and core proteins, as well as equivalent natural nucleic acid sequences. Such natural nucleic acid sequences may be isolated from a cDNA or genomic library from which the gene capable of directing synthesis of the E1 or core proteins may be identified and isolated. For purposes of this application, nucleic acid sequence refers to RNA, DNA, cDNA or any synthetic variant thereof which encodes for peptides.

The invention also relates to the method of preparing recombinant E1 and core proteins derived from E1 and core cDNA sequences respectively by cloning the nucleic acid encoding either the recombinant E1 or core protein and inserting the cDNA into an expression vector and expressing the recombinant protein in a host cell.

The invention also relates to isolated and substantially purified recombinant E1 and core proteins and analogs thereof encoded by E1 and core cDNAs respectively.

The invention further relates to the use of recombinant E1 and core proteins, either alone, or in combination with each other, as diagnostic agents and as vaccines.

The present invention also relates to the recombinant production of the core protein of the present invention to contain a second protein on its surface and therefore serve as a carrier in a multivalent vaccine preparation. Further, the present invention relates to the use of the self aggregating core or envelope proteins as a drug delivery system for anti-virals.

The invention also relates to the use of single-stranded antisense poly- or oligonucleotides derived from E1 or core cDNAs, or from both E1 and core cDNAs, to inhibit expression of hepatitis C E1 and/or core genes.

The invention further relates to multiple computer-generated alignments of the nucleotide and deduced amino acid sequences of the E1 and core cDNAs. These multiple sequence alignments produce consensus sequences which serve to highlight regions of homology and non-homology between sequences found within the same genotype or in different genotypes and hence, these alignments can be used by one skilled in the art to design peptides and oligonucleotides useful as reagents in diagnostic assays and vaccines.

The invention therefore also relates to purified and isolated peptides and analogs thereof derived from E1 and core cDNA sequences.

The invention further relates to the use of these peptides as diagnostic agents and vaccines.

The present invention also encompasses methods of detecting antibodies specific for hepatitis C virus in biological samples. The methods of detecting HCV or antibodies to HCV disclosed in the present invention are useful for diagnosis of infection and disease caused by HCV and for monitoring the progression of such disease. Such methods are also useful for monitoring the efficacy of therapeutic agents during the course of treatment of HCV infection and disease in a mammal.

The invention also provides a kit for the detection of antibodies specific for HCV in a biological sample where said kit contains at least one purified and isolated peptide derived from the E1 or core cDNA sequences. In addition, the invention provides for a kit containing at least one purified and isolated peptide derived from the E1 cDNA sequences and at least one purified and isolated peptide derived from the core cDNA sequences.

The invention further provides isolated and purified genotype-specific oligonucleotides and analogs thereof derived from E1 and core cDNA sequences.

The invention also relates to methods for detecting the presence of hepatitis C virus in a mammal, said methods comprising analyzing the RNA of a mammal for the presence of hepatitis C virus. The invention further relates to methods for determining the genotype of hepatitis C virus present in a mammal. This method is useful in determining the proper course of treatment for an HCV-infected patient.

The invention also provides a diagnostic kit for the detection of hepatitis C virus in a biological sample. The kit comprises purified and isolated nucleic acid sequences useful as primers for reverse-transcription polymerase chain reaction (RT-PCR) analysis of RNA for the presence of hepatitis C virus genomic RNA.

The invention further provides a diagnostic kit for the determination of the genotype of a hepatitis C virus present in a mammal. The kit comprises purified and isolated nucleic acid sequences useful as primers for RT-PCR analysis of RNA for the presence of HCV in a biological sample and purified and isolated nucleic acid sequences useful as hybridization probes in determining the genotype of the HCV isolate detected in PCR analysis.

This invention also relates to pharmaceutical compositions useful in prevention or treatment of hepatitis C in a mammal.

DESCRIPTION OF FIGURES

FIGS. 1A-1 to 1H-5 show computer generated sequence alignments of the nucleotide sequences of 51 HCV E1 cDNAs. The single letter abbreviations used for the nucleotides shown in FIGS. 1A-1 to 1A-5 are those standardly used in the art. FIGS. 1A-1 to 1A-4 show the alignment of SEQ ID NOs: 1–8 to produce a consensus sequence for genotype I/1a. FIGS. 1A-1 to 1A-4 show the alignment of SEQ ID NOs: 9–25 to produce a consensus sequence for genotype II/1b. FIGS. 1C-1 to 1C-2 show the alignment of SEQ ID NOs: 26–29 to produce a consensus sequence for genotype III/2a. FIGS. 1D-1 to 1D-2 show the alignment of SEQ ID NOs: 30–33 to produce a consensus sequence for genotype IV/2b. FIGS. 1E-1 to 1E-3 show the alignment of SEQ ID NOs: 35–39 to produce a consensus sequence for genotype V/3a. FIGS. 1F-1 to 1F-2 show the computer alignment of SEQ ID NOs: 42–43 to produce a "consensus" sequence for genotype 4C where the "consensus" sequence given is that of SEQ ID NO: 42. FIGS. 1G-1 to 1G-3 show the alignment of SEQ ID NOs: 45–50 to produce a consensus sequence for genotype 5a. The nucleotides shown in capital letters in the consensus sequences of FIGS. 1A-1 to 1G-3 are those conserved within a genotype while nucleotides shown in lower case letters in the consensus sequences are those variable within a genotype. In addition, in FIGS. 1A-1 to 1E-3 and 1G-1 to 1G-3, when the lower case letter is shown in a consensus sequence, the lower case letter represents the nucleotide found most frequently in the sequences aligned to produce the consensus sequence. In FIG. 1F, the lower case letters shown in the consensus sequence are nucleotides in SEQ ID NO: 42 which differ from nucleotides found in the same positions in SEQ ID NO: 43. Finally, a hyphen at a nucleotide position in the consensus sequences in FIGS. 1A-1 to 1G-3 indicates that two nucleotides were found in equal numbers at that position in the aligned sequences. In the aligned sequences, nucleotides are shown in lower case letters if they differed from the nucleotides of both adjacent isolates. FIGS. 1H-1 to 1H-5 show the alignment of the consensus sequences of FIGS. 1A-1 to 1G-3 with SEQ ID NO: 34 (genotype 2c), SEQ ID NO: 40 (genotype 4a), SEQ ID NO: 41 (genotype 4b), SEQ ID NO: 44 (genotype 4d) and SEQ ID NO: 51 (genotype 6a) to produce a consensus sequence for all twelve genotypes. This consensus sequence is shown as the bottom line of FIGS. 1H-1 to 1H-5 where the nucleotides shown in capital letters are conserved among all genotypes and a blank space indicates that the nucleotide at that position is not conserved among all genotypes.

FIGS. 2A-1 to 2H-2 show computer alignments of the deduced amino acid sequences of 51 HCV E1 cDNAs. The single letter abbreviations used for the amino acids shown in FIGS. 2A–H follow the conventional amino acid shorthand for the twenty naturally occurring amino acids. FIGS. 2A-1 to 2A-2 show the alignment of SEQ ID NOs: 52–59 to produce a consensus sequence for genotype I/1a. FIGS. 2B-1 to 2B-4 show the alignment of SEQ ID NOs: 60–76 to produce a consensus sequence for genotype II/1b. FIG. 2C shows the alignment of SEQ ID NOs: 77–80 to produce a consensus sequence for genotype III/2a. FIG. 2D shows the alignment of SEQ ID NOs: 81–84 to produce a consensus sequence for genotype IV/2b. FIG. 2E shows the alignment of SEQ ID NOs: 86–90 to produce a consensus sequence for genotype V/3a. FIG. 2F shows the computer alignment of SEQ ID NOs: 93–94 to produce a consensus sequence for genotype 4c. FIG. 2G shows the alignment of SEQ ID NOs: 96–101 to produce a consensus sequence for genotype 5a. The amino acids shown in capital letters in the consensus sequences of FIGS. 2A-1 to 2G are those conserved within a genotype while amino acids shown in lower case letters in the consensus sequences are those variable within a genotype. In addition, in FIGS. 2A-1 to 2E and 2G when the lower case letter is shown in a consensus sequence, the letter represents the amino acid found most frequently in the sequences aligned to produce the consensus sequence. In FIG. 2F, the lower case letters shown in the consensus sequence are amino acids in SEQ ID NO: 93 which differ from amino acids found in the same positions in SEQ ID NO: 94. Finally, a hyphen at an amino acid position in the consensus sequences of FIGS. 2A-1 to 2G indicates that two amino acids were found in equal numbers at that position in the aligned sequences. In the aligned sequences, amino acids are shown in lower case letters if they differed from the amino acids of both adjacent isolates. FIGS. 2H-1 and 2H-2 show the alignment of the consensus sequences of FIGS. 2A-1 to 2G with SEQ ID NO: 85 (genotype 2c), SEQ ID NO: 91 (genotype 4a), SEQ ID NO: 92 (genotype 4b), SEQ ID NO: 95 (genotype 4d) and SEQ ID NO: 102 (genotype 6a) to produce a consensus sequence for all twelve genotypes. This consensus sequence is shown as the bottom line of FIGS. 2H-1 and 2H-2 show where the amino acids shown in capital letters are conserved among all genotypes and a blank space indicates that the amino acid at that position is not conserved among all genotypes.

FIGS. 3A and 3B show multiple sequence alignment of the deduced amino acid sequence of the E1 gene of 51 HCV isolates collected worldwide. The consensus sequence of the E1 protein is shown in boldface (top). In the consensus sequence cysteine residues are highlighted with stars, potential N-linked glycosylation sites are underlined, and invariant amino acids are capitalized, whereas variable amino acids are shown in lower case letters. In the alignment, amino acids are shown in lower case letters if they differed from the amino acid of both adjacent isolates. Amino acid residues shown in bold print in the alignment represent residues which at that position in the amino acid sequence are genotype-specific. Amino acids that were invariant among all HCV isolates are shown as hyphens (–) in the alignment. Amino acid positions correspond to those of the HCV prototype sequence (HCV-1, Choo, L. et al. (1991) Proc. Natl. Acad. Sci. USA 88:2451–2455) with the first amino acid of the E1 protein at position 192. The grouping of isolates into 12 genotypes (I/1a, II/1b, III/2a, IV/2b, V/3a, 2c, 4a, 4b, 4c, 4d, 5a and 6a) is indicated.

FIG. 4 shows a dendrogram of the genetic relatedness of the twelve genotypes of HCV based on the percent amino acid identity of the E1 gene of the HCV genome. The twelve genotypes shown are designated as I/1a, II/1b, III/2a, IV/2b, V/3a, 2c, 4a, 4b, 4c, 4d, 5a and 6a. The shaded bars represent a range showing the maximum and minimum homology between the amino acid sequence of any one isolate of the genotype indicated and the amino acid sequence of any other isolate.

FIG. 5 shows the distribution of the complete E1 gene sequence of 74 HCV isolates into the twelve HCV genotypes in the 12 countries studied. For 51 of these HCV isolates, including 8 isolates of genotype I/1a, 17 isolates of genotype II/1b and 26 isolates comprising the additional 10 genotypes, the complete E1 gene sequence was determined. In the remaining 23 isolates, all of genotypes I/1a and II/1b, the genotype assignment was based on only a partial E1 gene sequence. The partially sequenced isolates did not represent additional genotypes in any of the 12 countries. The number of isolates of a particular genotype is given in each of the 12 countries studied. For ease of viewing, those genotypes designated by two terms (e.g., I/1a) are indicated by the latter term (e.g. 1a). The designations used for each country are: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z). National borders depicted in this figure represent those existing at the time of sampling.

FIGS. 6A-1 to 6K-2 show computer generated sequence alignments of the nucleotide sequences of 52 HCV core cDNAs. Single letter abbreviations used for the nucleotides shown in FIGS. 6A-1 to 6J-4 are those standardly used in the art. FIGS. 6A-1 to 6A-4 show the alignment of SEQ ID NOs: 103–108 to produce a consensus sequence for genotype I/Ia. FIGS. 6B-1 to 6B-10 show the alignment of SEQ ID NOs: 109–124 to produce a consensus sequence for genotype II/1b. FIGS. 6C-1 to 6C-10 show the alignments of the sequences comprising minor genotypes I/1a (SEQ ID NOS: 103–108) and II/1b (SEQ ID NOs: 109–124) to produce a consensus sequence for the major genotype, genotype 1. FIGS. 6D-1 to 6D-3 show the alignment of SEQ ID NOs: 125–128 to produce a consensus sequence for genotype III/2a. FIGS. 6E-1 to 6E-4 show the alignment of SEQ ID NOs: 129–133 to produce a consensus sequence for genotype IV/2b. FIGS. 6F-1 to 6F-4 show the alignment of the sequences of minor genotypes III/2a (SEQ ID NOs: 125–128), IV/2b (SEQ ID NOs: 129–133) and 2c (SEQ ID NO: 134) to produce a consensus sequence for the major genotype, genotype 2. FIGS. 6G-1 to 6G-3 show the alignment of SEQ ID NOs: 135–138 to produce a consensus sequence for genotype V/3a. FIGS. 6H-1 to 6H-4 show the computer alignment of the sequences of minor genotypes 4a–4f (SEQ ID NOs: 139–145) to produce a consensus sequence for the major genotype, genotype 4. FIG. 6I shows the alignment of SEQ ID NOs: 146–153 to produce a consensus sequence for genotype 5a. The nucleotides shown in capital letters in the consensus sequences in FIGS. 6A-1 to 6I-4 show are those conserved within the genotype while nucleotides shown in lower case letters in the consensus sequences are those variable within a genotype. In addition, when the lower case letter is shown in the consensus sequence, the lower case letter represents the nucleotide found most frequently in the sequences aligned to produce that consensus sequence. Moreover, a hyphen at a nucleotide position in the consensus sequences in FIGS. 6A-1 to 6I-4 indicates that two nucleotides were found in equal numbers at that position in the sequences aligned to produce the consensus sequence. Finally, nucleotides are shown in lower case letters in the sequences aligned to produce each consensus sequence shown in FIGS. 6A-1 to 6I-4, if they differed from the nucleotides of both adjacent isolates. FIGS. 6J-1 to 6J-4 show the alignment of the consensus sequences of major genotypes 1 (FIGS. 6C-1 to 6C-10), 2 (FIGS. 6F-1 to 6F-5), 3 (FIGS. 6G-1 to 6G-3), 4 (FIGS. 6H-1 to 6H-4), 5 (FIGS. 6I-1 to 6I-4) and 6 (SEQ ID NO: 154) to produce a consensus sequence for all genotypes and FIGS. 6K-1 to 6K-2 show the alignment of consensus sequences of FIGS. 6A-1 to 6A-4, 6B-1 to 6B-10, 6D-1 to 6D-3, 6E-1 to 6E-4, 6G-1 to 6G-3, and 6I-1 to 6I-4 with SEQ ID NO: 134 (genotype 2c), SEQ ID NO: 139 (genotype 4a), SEQ ID NO: 141 (genotype 4b), SEQ ID NO: 143 (genotype 4c), SEQ ID NO: 145 (genotype 4d), SEQ ID NO: 142 (genotype 4e), SEQ ID NO: 140 (genotype 4f) and SEQ ID NO: 154 (genotype 6a) to produce a consensus sequence for all fourteen genotypes. The nucleotides shown in capital letters in the consensus sequences of FIGS. 6J-4 and 6K-1 are conserved among all genotypes and the nucleotide shown in lower case letter represent the nucleotides found most frequently in the sequences aligned to produce this consensus sequence. In addition, the presence of a hyphen at a nucleotide position in all fourteen sequences aligned in FIGS. 6K-1 to 6K-2 indicates that the nucleotide found at that position in the aligned sequences is the same as nucleotide shown at the corresponding position in the consensus sequences of FIG. 6K.

FIGS. 7A-1 to 7J show computer alignments of the deduced amino acid sequences of the 52 HCV core cDNAs. The single letter abbreviations used for the amino acids shown in FIGS. 7A-1 to 7J follow the conventional amino acid short hand for the twenty natural occurring amino acids. FIGS. 7A-1 to 7A-2 show the alignment of SEQ ID NOs: 155–160 to produce a consensus sequence for genotype I/1a. FIGS. 7B-1 to 7B-2 the alignment of SEQ ID NOs: 161–176 to produce a consensus sequence for genotype II/1b. FIGS. 7C-1 to 7C-4 show the alignment of the sequences comprising minor genotypes I/a (SEQ ID NOS: 155–160) and II/1b (SEQ ID NOS: 161–176) to produce a consensus sequence for the major genotype, genotype 1. FIG. 7D shows the alignment of SEQ ID NOs: 177–180 to produce a consensus sequence for genotype III/2a. FIG. 7E shows the alignment of SEQ ID NOs: 181–185 to produce a consensus sequence for genotype IV/2b. FIGS. 7F-1 and 7F-2 show the alignment of the sequences of minor genotypes III/2a (SEQ ID NOS: 177–180), IV/2b (SEQ ID NOS: 181–185) and 2c (SEQ ID NO: 186) to produce a consensus sequence for the major genotype, genotype 2. FIG. 7G shows the alignment of SEQ ID NOs: 187–190 to produce a consensus sequence for genotype V/3a. FIGS. 7H-1 to 7H-2 show the computer alignment of the sequences of minor genotypes 4a–4f (SEQ ID NOs: 191–197) to produce a consensus sequence for the major genotype, genotype 4. FIGS. 7I-1 and 7I-2 the alignment of SEQ ID NOs: 198–205 to produce a consensus sequence for genotype 5a. The amino acids shown in capital letters in the consensus sequences of FIGS. 7A-1 to 7I-2 are those conserved within the genotype while amino acids shown in lower case letters in the consensus sequences are those variable within the genotype. In addition, when a lower case letter is found in the consensus sequences shown in FIG. 7A-1 to 7I-2, the letter represents the amino acid found most frequently in the sequences aligned to produce that consensus sequence. Moreover, a hyphen in an amino acid position in the consensus sequences of FIGS. 7A-14 7I indicates that two amino acids were found in equal numbers at that position in the sequences aligned to produce that consensus sequence. Finally, amino acids are shown in lower case letters in the sequences aligned to produce the consensus sequences shown in FIGS. 7A-14 7I if these amino acids differed from the amino acids of both adjacent isolates. FIG. 7J shows the alignment of the consensus sequences of major genotypes 1 (FIGS. 7C-1 to 7C-4), 2 (FIGS. 7F-1 and 7F-2), 3 (FIG. 7G), 4 (FIGS. 7H-1 and 7H-2), 5 (FIG. 7I-1 and 7I-2) and 6 (SEQ ID NO: 154) to produce a consensus sequence for all genotypes and FIG. 7K shows the alignment of the consensus sequences of FIGS. 7A-1 to 7A-2, 7B-1 to 7B-2, 7D, 7E, 7G and 7I-1 to 7I-2 with SEQ ID NO: 186 (genotype 2c), SEQ ID NO: 191 (genotype 4a), SEQ ID NO: 193 (genotype 4b), SEQ ID NO: 195 (genotype 4c), SEQ ID NO: 197 (genotype 4d), SEQ ID NO: 194 (genotype 4e), SEQ ID NO: 192 (genotype 4f) and SEQ ID NO: 206 (genotype 6a) to produce a consensus sequence for all fourteen genotypes. The amino acids shown in capital letters in the consensus sequences shown in FIGS. 7J and 7K are conserved among all genotypes while the amino acids shown in lower case letters represent amino acids found most frequently in the sequences aligned to produce this consensus sequence. In addition, the presence of a hyphen at an amino acid position in all fourteen sequences aligned in FIG. 7K indicates that the amino acid found at that position in the aligned sequences is the same as the amino acid shown at the corresponding position in the consensus sequence of FIG. 7K.

DETAILED DESCRIPTION OF INVENTION

Figure 4:
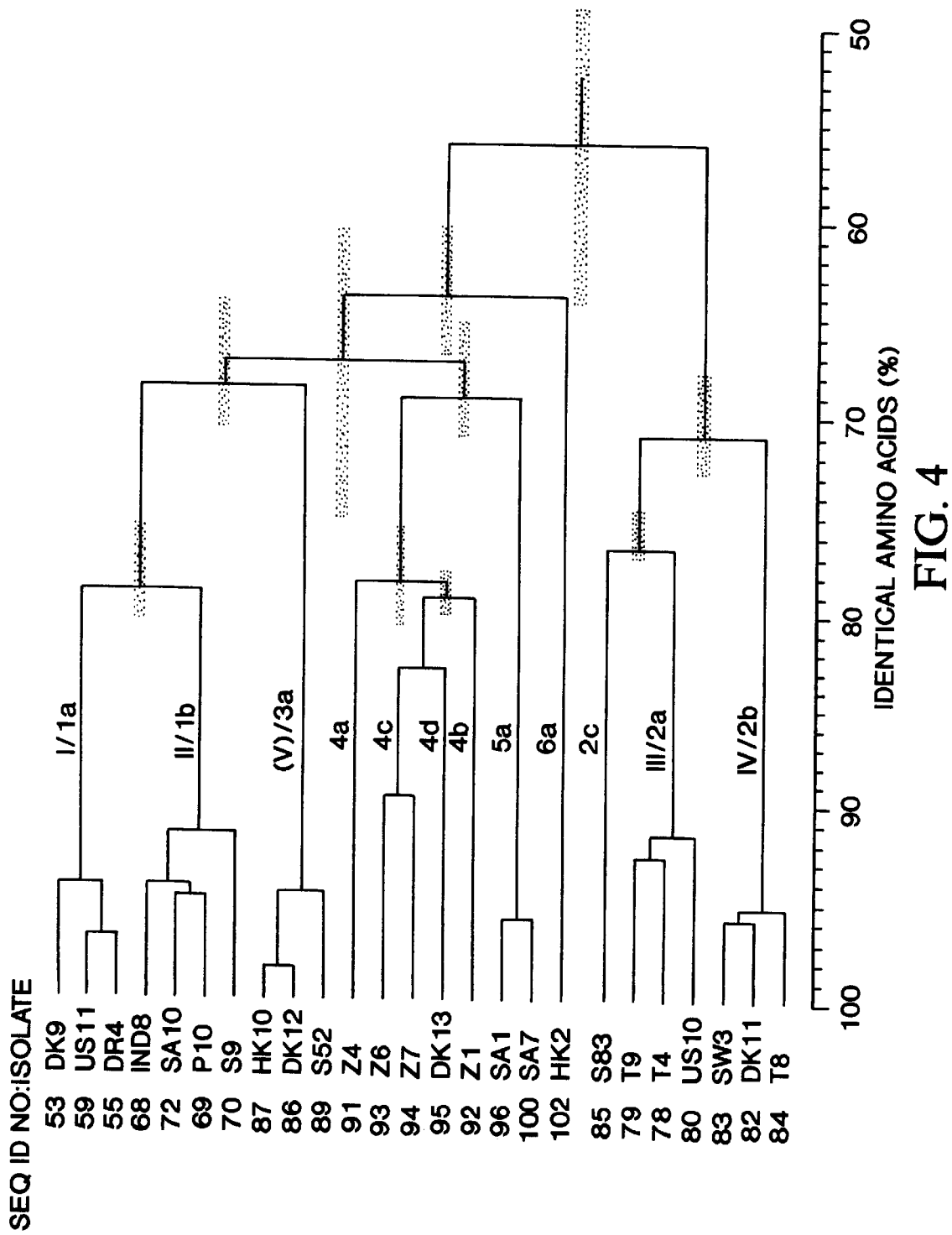

The present invention relates to cDNAs encoding the complete nucleotide sequence of the envelope 1 (E1) and core genes of isolates of human hepatitis C virus (HCV). The E1 cDNAs of the present invention were obtained as follows. Viral RNA was extracted from serum collected from humans infected with hepatitis C virus and the viral RNA was then reverse transcribed and amplified by polymerase chain reaction using primers deduced from the sequence of the HCV strain H-77 (Ogata, N. et al. (1991) Proc. Natl. Acad. Sci. U.S.A. 88:3392–3396). The amplified cDNA was then isolated by gel electrophoresis and sequenced.

The present invention further relates to the nucleotide sequences of the cDNAs encoding the E1 gene of 51 HCV isolates. These nucleotide sequences are shown in the sequence listing as SEQ ID NO: 1 through SEQ ID NO: 51.

The abbreviations used for the nucleotides are those standardly used in the art.

The deduced amino acid sequence of each of SEQ ID NO: 1 through SEQ ID NO: 51 are presented in the sequence listing as SEQ ID NO: 52 through SEQ ID NO: 102 where the amino acid sequence in SEQ ID NO: 52 is deduced from the nucleotide sequence shown in SEQ ID NO: 1, the amino acid sequence shown in SEQ ID NO: 53 is deduced from the nucleotide sequence shown in SEQ ID NO: 2 and so on. The deduced amino acid sequence of each of SEQ ID NOs: 52–102 starts at nucleotide 1 of the corresponding nucleic acid sequence shown in SEQ ID NOs: 1–51 and extends 575 nucleotides to a total length of 576 nucleotides.

The three letter abbreviations used in SEQ ID Nos: 52–102 follow the conventional amino acid shorthand for the twenty naturally occurring amino acids.

The present invention also relates to the nucleotide sequences of the cDNAs encoding the core gene of 52 HCV isolates. These nucleotide sequences are shown in the sequence listing as SEQ ID NO: 103 through SEQ ID NO: 154.

The core cDNAs of the present invention were obtained as follows. Viral RNA was extracted from serum and reversed transcribed as described above for cloning of the E1 cDNAs. The core cDNAs of the present invention were then amplified by polymerase chain reaction using primers deduced from previously determined sequences that flank the core gene (Bukh et al. (1992)) *Proc. Natl. Acad. Sci. U.S.A.*, 89: 4942–4946; Bukh et al. (1993) *Proc. Natl. Acad. Sci. U.S.A.*, 90: 8234–8238).

The deduced amino acid sequence of each of SEQ ID NO: 103 through SEQ ID NO: 154 are presented in the sequence listing as SEQ ID NO: 155 through SEQ ID NO: 206 where the amino acid sequence in SEQ ID NO: 155 is deduced from the nucleotide sequence shown in SEQ ID NO: 103, the amino acid sequence shown in SEQ ID NO: 156 is deduced from the nucleotide sequence shown in SEQ ID NO: 104 and so on. The deduced amino acid sequence of each of SEQ ID NOs: 155–206 starts at nucleotide 1 of the corresponding nucleotide sequence shown in SEQ ID NOs: 103–154 and extends 572 nucleotides to a total length of 573 nucleotides.

Preferably, the E1 and core proteins and peptides of the present invention are substantially homologous to, and most preferably biologically equivalent to, native HCV E1 and core proteins and peptides. By "biologically equivalent" as used throughout the specification and claims, it is meant that the compositions are immunogenically equivalent to the native E1 and core proteins and peptides. The E1 and core proteins and peptides of the present invention may also stimulate the production of protective antibodies upon injection into a mammal that would serve to protect the mammal upon challenge with HCV. By "substantially homologous" as used throughout the ensuing specification and claims to describe E1 and core proteins and peptides, it is meant a degree of homology in the amino acid sequence of the E1 and core proteins and peptides to the native E1 and core proteins and peptides respectively. Preferably the degree of homology is in excess of 90, preferably in excess of 95, with a particularly preferred group of proteins being in excess of 99 homologous with the native E1 or core proteins and peptides.

Variations are contemplated in the cDNA sequences shown in SEQ ID NO: 1 through SEQ ID NO: 51 and in SEQ ID NO: 103 through SEQ ID NO: 154 which will result in a nucleic acid sequence that is capable of directing production of analogs of the corresponding protein shown in SEQ ID NO: 52 through SEQ ID NO: 102 and in SEQ ID NO: 155 through SEQ ID NO: 206. It should be noted that the cDNA sequences set forth above represent a preferred embodiment of the present invention. Due to the degeneracy of the genetic code, it is to be understood that numerous choices of nucleotides may be made that will lead to a DNA sequence capable of directing production of the instant protein or its analogs. As such, DNA sequences which are functionally equivalent to the sequence set forth above or which are functionally equivalent to sequences that would direct production of analogs of the E1 and core proteins produced pursuant to the amino acid sequences set forth above, are intended to be encompassed within the present invention.

The term analog as used throughout the specification or claims to describe the E1 and core proteins and peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the native E1 or core protein or peptide.

"Chemical derivative" refers to an E1 or core protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The E1 and core proteins and peptide of the present invention also includes any protein or peptide having one or more additions and/or deletions of residues relative to the sequence of a peptide whose sequence is shown herein, so long as the peptide is biologically equivalent to the native E1 or core protein or peptide.

The present invention also includes a recombinant DNA method for the manufacture of HCV E1 and core proteins. In this method, natural or synthetic nucleic acid sequences may be used to direct the production of E1 and core proteins.

In one embodiment of the invention, the method comprises:

(a) preparation of a nucleic acid sequence capable of directing a host organism to produce HCV E1 or core protein;

(b) cloning the nucleic acid sequence into a vector capable of being transferred into and replicated in a host organism, such vector containing operational elements for the nucleic acid sequence;

(c) transferring the vector containing the nucleic acid and operational elements into a host organism capable of expressing the protein;

(d) culturing the host organism under conditions appropriate for amplification of the vector and expression of the protein; and (e) harvesting the protein.

In another embodiment of the invention, the method for the recombinant DNA synthesis of an HCV E1 protein encoded by any one of the nucleic acid sequences shown in SEQ ID NOs: 1–51 comprises:

(a) culturing a transformed or transfected host organism containing a nucleic acid sequence capable of directing the host organism to produce a protein, under conditions such that the protein is produced, said protein exhibiting substantial homology to a native E1 protein isolated from HCV having the amino acid sequence according to any one of the amino acid sequences shown in SEQ ID NOs: 52–102 or combinations thereof.

In one embodiment, the RNA sequence of an HCV isolate was isolated and converted to cDNA as follows. Viral RNA is extracted from a biological sample collected from human subjects infected with hepatitis C and the viral RNA is then reverse transcribed and amplified by polymerase chain reaction using primers deduced from the sequence of HCV strain H-77 (Ogata et al. (1991)). Preferred primer sequences are shown as SEQ ID NOs: 207–212 in the sequence listing. Once amplified, the PCR fragments are isolated by gel electrophoresis and sequenced.

In an alternative embodiment, the above method may be utilized for the recombinant DNA synthesis of an HCV core protein encoded by any one of the nucleic acid sequences shown in SEQ ID NOS: 103–154, where the protein produced by this method exhibits substantial homology to a native core protein isolated from HCV having amino acid sequence according to any one of the amino acid sequences shown in SEQ ID NOS: 155–206 or combinations thereof.

The vectors contemplated for use in the present invention include any vectors into which a nucleic acid sequence as described above can be inserted, along with any preferred or required operational elements, and which vector can then be subsequently transferred into a host organism and replicated in such organisms. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

In construction of the recombinant expression vectors of the present invention, it should additionally be noted that multiple copies of the nucleic acid sequence of interest (either E1 or core) and its attendant operational elements may be inserted into each vector. In such an embodiment, the host organism would produce greater amounts per vector of the desired E1 or core protein. The number of multiple copies of the nucleic acid sequence which may be inserted into the vector is limited only by the ability of the resultant vector due to its size, to be transferred into and replicated and transcribed in an appropriate host microorganism.

Of course, those skilled in the art would readily understand that copies of both core and E1 nucleic acid sequence may be inserted into single vector such that a host organism transformed or transfected with said vector would produce both the desired E1 and core proteins. For example, a polysistronic vector in which multiple different E1 and/or core proteins may be expressed from a single vector is created by placing expression of each protein under control of an internal ribosomal entry site (IRES) (Molla, A. et al. *Nature*, 356:255–257 (1992); Gong, S. K. et al. *J. of Virol.*, 263:1651–1660 (1989)).

In another embodiment, restriction digest fragments containing a coding sequence for E1 or core proteins can be inserted into a suitable expression vector that functions in prokaryotic or eukaryotic cells. By suitable is meant that the vector is capable of carrying and expressing a complete nucleic acid sequence coding for an E1 or core protein. Preferred expression vectors are those that function in a eukaryotic cell. Examples of such vectors include but are not limited to vaccinia virus vectors, adenovirus or herpes viruses. A preferred vector is the baculovirus transfer vector, pBlueBac.

In yet another embodiment, the selected recombinant expression vector may then be transfected into a suitable eukaryotic cell system for purposes of expressing the recombinant protein. Such eukaryotic cell systems include but are not limited to cell lines such as HeLa, MRC-5 or CV-1. A preferred eukaryotic cell system is SF9 insect cells.

The expressed recombinant protein may be detected by methods known in the art including, but not limited to, Coomassie blue staining and Western blotting.

The present invention also relates to substantially purified and isolated recombinant E1 and core proteins. In one embodiment, the recombinant protein expressed by the SF9 cells can be obtained as a crude lysate or it can be purified by standard protein purification procedures known in the art which may include differential precipitation, molecular sieve chromatography, ion-exchange chromatography, isoelectric focusing, gel electrophoresis and affinity and immunoaffinity chromatography. The recombinant protein may be purified by passage through a column containing a resin which has bound thereto antibodies specific for the open reading frame (ORF) protein.

The present invention further relates to the use of recombinant E1 and core proteins as diagnostic agents and vaccines. In one embodiment, the expressed recombinant proteins of this invention can be used in immunoassays for diagnosing or prognosing hepatitis C in a mammal. For the purposes of the present invention, "mammal" as used throughout the specification and claims, includes, but is not limited to humans, chimpanzees, other primates and the like. In a preferred embodiment, the immunoassay is useful in diagnosing hepatitis C infection in humans.

Immunoassays of the present invention may be those commonly used by those skilled in the art including, but not limited to, radioimmunoassay, Western blot assay, immunofluorescent assay, enzyme immunoassay, chemiluminescent assay, immunohistochemical assay, immunoprecipitation and the like. Standard techniques known in the art for ELISA are described in *Methods in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art (Oellerich, M. 1984. *J. Clin. Chem. Clin.* BioChem 22:895–904) Biological samples appropriate for such detection assays include, but are not limited to serum, liver, saliva, lymphocytes or other mononuclear cells.

In a preferred embodiment, test serum is reacted with a solid phase reagent having surface-bound recombinant HCV E1 and/or core protein(s) as antigen(s). The solid surface reagent can be prepared by known techniques for attaching protein to solid support material. These attachment methods include non-specific adsorption of the protein to the support or covalent attachment of the protein to a reactive group on the support. After reaction of the antigen with anti-HCV antibody, unbound serum components are removed by washing and the antigen-antibody complex is reacted with a secondary antibody such as labelled anti-human antibody. The label may be an enzyme which is detected by incubating the solid support in the presence of a suitable fluorimetric or calorimetric reagent. Other detectable labels may also be used, such as radiolabels or colloidal gold, and the like.

The HCV E1 and/or core proteins and analogs thereof may be prepared in the form of a kit, alone, or in combinations with other reagents such as secondary antibodies, for use in immunoassays.

In yet another embodiment the recombinant E1 and core proteins or analogs thereof can be used as a vaccine to protect mammals against challenge with hepatitis C. The vaccine, which acts as an immunogen, may be a cell, cell lysate from cells transfected with a recombinant expression vector or a culture supernatant containing the expressed protein. Alternatively, the immunogen is a partially or substantially purified recombinant protein. In yet another embodiment, the immunogen may be a fusion protein comprising core protein and a second, non-core protein joined together such that the core portion of the fusion protein will aggregate and "trap" the second protein on the surface of the particle produced by aggregation of the core protein. (Molecular Biology of the Hepatitis B Virus", McLachlan, A. (1991) CRC Press, Boca Raton, Fla.). Alternatively, the core protein could be mixed with the second protein in vitro to produce particles in which all or part of the second protein was exposed on the surface of the particle. Such particles would then serve as a carrier in a multi-valent vaccine preparation. Second proteins or parts thereof which could be mixed with or fused to the core protein include, but are not limited to, HCV E1 and hepatitis B surface antigen.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving the solid active ingredient in water containing physiologically compatible substances such as sodium chloride (e.g. 0.1–2.0 m), glycine, and the like, and having a buffered pH compatible with physiological conditions to produce an aqueous solution, and rendering said solution sterile. These may be present in unit or multi-dose containers, for example, sealed ampules or vials.

The formulations of the present invention may incorporate a stabilizer. Illustrative stabilizers are preferably incorporated in an amount of 0.10–10,000 parts by weight per part by weight of immunogens. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, an anti-adsorption agent may be used.

Additional pharmaceutical methods may be employed to control the duration of action. Controlled release preparations may be achieved through the use of polymer to complex or adsorb the proteins or their derivatives. The controlled delivery may be exercised by selecting appropriate macromolecules (for example polyester, polyamino acids, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

The E1 and core proteins of the present invention may also be used as a delivery system for anti-virals to prevent or attenuate HCV infection in a mammal by utilizing the property of both proteins to self-aggregate in vitro to "trap" the antiviral within the particles produced via aggregation of the core and E1 proteins. Examples of anti-virals which could be delivered by such a system include, but are not limited to antisense DNA or RNAs.

Vaccination can be conducted by conventional methods. For example, the immunogen or immunogens (e.g. the E1 protein may be administered alone or in combination with the E1 proteins derived from other isolates of HCV) can be used in a suitable diluent such as saline or water, or complete or incomplete adjuvants. Further, the immunogen(s) may or may not be bound to a carrier to make the protein(s) immunogenic. Examples of such carrier molecules include but are not limited to bovine serum albumin (BSA), keyhole limpet hemocyanin (KLH), tetanus toxoid, and the like. The immunogen(s) can be administered by any route appropriate for antibody production such as intravenous, intraperitoneal, intramuscular, subcutaneous, and the like. The immunogen (s) may be administered once or at periodic intervals until a significant titer of anti-HCV antibody is produced. The antibody may be detected in the serum using an immunoassay.

In yet another embodiment, the immunogen may be nucleic acid sequence capable of directing host organism synthesis of E1 and/or core protein(s). Such nucleic acid sequence may be inserted into a suitable expression vector by methods known to those skilled in the art. Expression vectors suitable for producing high efficiency gene transfer in vivo include retroviral, adenoviral and vaccinia viral vectors. Operational elements of such expression vectors are disclosed previously in the present specification and are known to one skilled in the art. Such expression vectors can be administered intravenously, intramuscularly, subcutaneously, intraperitoneally or orally.

In an alternative embodiment, direct gene transfer may be accomplished via intramuscular injection of, for example, plasmid-based eukaryotic expression vectors containing a nucleic acid sequence capable of directing host organism synthesis of E1 and/or core protein(s). Such an approach has previously been utilized to produce the hepatitis B surface antigen in vivo and resulted in an antibody response to the surface antigen (Davis, H. L. et al. (1993) *Human molecular Genetics*, 2:1847–1851; see also Davis et al. (1993) *Human Gene Therapy*, 4:151–159 and 733–740).

Doses of E1 and/or core protein(s)-encoding nucleic acid sequence effective to elicit a protective antibody response against HCV infection range from about 1 to about 500 $\mu$g. A more preferred range being about 1 to about 500 $\mu$g.

The E1 and/or core proteins and expression vectors containing a nucleic acid sequence capable of directing host organism synthesis of E1 and/or core protein(s) may be supplied in the form of a kit, alone, or in the form of a pharmaceutical composition as described above.

The administration of the immunogen(s) of the present invention may be for either a prophylactic or therapeutic purpose. When provided prophylactically, the immunogen (s) is provided in advance of any exposure to HCV or in advance of any symptom of any symptoms due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV. The therapeutic administration of the immunogen(s) serves to attenuate the infection or disease.

In addition to use as a vaccine, the compositions can be used to prepare antibodies to HCV E1 and core proteins. The antibodies can be used directly as antiviral agents or they may be used in immunoassays disclosed herein to detect HCV E1 and core proteins present in patient sera. To prepare antibodies, a host animal is immunized using the E1 and/or core proteins native to the virus particle bound to a carrier as described above for vaccines. The host serum or plasma is collected following an appropriate time interval to provide a composition comprising antibodies reactive with the E1 or core protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen-binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl.

Acad. Sci. USA 84:3439; Nishimura et al., 1987 Canc. Res. 47:999; Wood et al., 1985 Nature 314:446; Shaw et al., 1988 J. Natl. Cancer Inst. 80:15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedler al. 1988 J. Immunol. 141:4053, all incorporated herein by reference).

The antibodies or antigen binding fragments may also be produced by genetic engineering. The technology for expression of both heavy and light cain genes in E. coli is the subject of the PCT patent applications; publication number WO 901443, WO901443, and WO 9014424 and in Huse et al., 1989 Science 246:1275–1281.

The antibodies can also be used as a means of enhancing the immune response. The antibodies can be administered in amount similar to those used for other therapeutic administrations of antibody. For example, normal immune globulin is administered at 0.02–0.1 ml/1b body weight during the early incubation period of other viral diseases such as rabies, measles, and hepatitis B to interfere with viral entry into cells. Thus, antibodies reactive with the HCV E1 and/or core proteins can be passively administered alone or in conjunction with another anti-viral agent to a host infected with an HCV to enhance the immune response and/or the effectiveness of an antiviral drug.

Alternatively, anti-HCV E1 antibodies and anti-HCV core antibodies can be induced by administered anti-idiotype antibodies as immunogens. Conveniently, a purified anti-HCV E1 or anti-HCV core antibody preparation prepared as described above is used to induce anti-idiotype antibody in a host animal, the composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-HCV E1 and anti-HCV core antibodies, or by affinity chromatography using anti-HCV E1 or anti-HCV core antibodies bound to the affinity matrix. The anti-idiotype antibodies produced are similar in conformation to the authentic HCV E1 or core protein and may be used to prepare an HCV vaccine rather than using an HCV E1 or core protein.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

The HCV E1 and core proteins of the invention are also intended for use in producing antiserum designed for pre- or post-exposure prophylaxis. Here an E1 or core protein, or mixture of E1 and/or core proteins is formulated with a suitable adjuvant and administered by injection to human volunteers, according to known methods for producing human antisera. Antibody response to the injected proteins is monitored, during a several-week period following immunization, by periodic serum sampling to detect the presence of anti-HCV E1 and/or anti-HCV core serum antibodies, using an immunoassay as described herein.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

For both in vivo use of antibodies to HCV virus-like particles and proteins and anti-idiotype antibodies and diagnostic use, it may be preferable to use monoclonal antibodies. Monoclonal anti-HCV E1 and anti-HCV core protein antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., New York, N.Y., pp. 56–97). To produce a human-human hybridoma, a human lymphocyte donor is selected. A donor known to be infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-E1 and anti-core antibodies, the antibodies must bind to HCV E1 and core proteins respectively. For monoclonal anti-idiotype antibodies, the antibodies must bind to anti-E1 and anti-core protein antibodies respectively. Cells producing antibodies of the desired specificity are selected.

The present invention also relates to the use of single-stranded antisense poly- or oligonucleotides derived from nucleotide sequences substantially homologous to those shown in SEQ ID NOs: 1–51 to inhibit the expression of hepatitis C E1 genes. The present invention further relates to the use of single-stranded anti-sense poly- or oligo-nucleotides derived from nucleotide sequences substantially homologous to those shown in SEQ ID NOs: 103–154 to inhibit the expression of hepatitis C core genes. Alternatively, the anti-sense poly- or oligo-nucleotides may be complementary to both the E1 and core genes and hence, inhibit the expression of both hepatitis C E1 and core genes. By substantially homologous as used throughout the specification and claims to describe the nucleic acid sequences of the present invention, is meant a level of homology between the nucleic acid sequence and the SEQ ID NOs. referred to in the above sentence. Preferably, the level of homology is in excess of 80%, more preferably in excess of 90%, with a preferred nucleic acid sequence being in excess of 95% homologous with the DNA sequence shown in the indicated SEQ ID NO. These anti-sense poly- or oligonucleotides can be either DNA or RNA. The targeted sequence is typically messenger RNA and more preferably, a single sequence required for processing or translation of the RNA. The anti-sense poly- or oligonucleotides can be conjugated to a polycation such as polylysine as disclosed in Lemaitre, M. et al. ((1989) Proc. Natl. Acad. Sci. USA 84:648–652) and this conjugate can be administrated to a mammal in an amount sufficient to hybridize to and inhibit the function of the messenger RNA.

The present invention further relates to multiple computer-generated alignments of the nucleotide and deduced amino acid sequences shown in SEQ ID NOs: 1–206. Computer analysis of the nucleotide sequences shown in SEQ ID NOs: 1–51 and 103–154 and of the deduced amino acid sequences shown in SEQ ID NOs: 52–102 and 155–206 can be carried out using commercially available computer programs known to one skilled in the art.

In one embodiment, computer analysis of SEQ ID NOs: 1–51 by the program GENALIGN (Intelligenetics, Inc. Mountainview, Calif.) results in distribution of the 51 HCV E1 sequences into twelve genotypes based upon the degree of variation of the sequences. For the purposes of the present invention, the nucleotide sequence identity of E1 cDNAs of HCV isolates of the same genotype is in the range of about 85% to about 100% whereas the identity of E1 cDNA sequences of different genotypes is in the range of about 50% to about 80%.

The grouping of SEQ ID NOs: 1–51 into twelve HCV genotypes is shown below.

| SEQ ID NOs: | Genotypes |
| --- | --- |
| 1–8 | I/1a |
| 9–25 | II/1b |
| 26–29 | III/2a |
| 30–33 | IV/2b |
| 34 | 2c |
| 35–39 | V/3a |
| 40 | 4a |
| 41 | 4b |
| 42–43 | 4c |
| 44 | 4d |
| 45–50 | 5a |
| 51 | 6a |

Figure 1B-4:
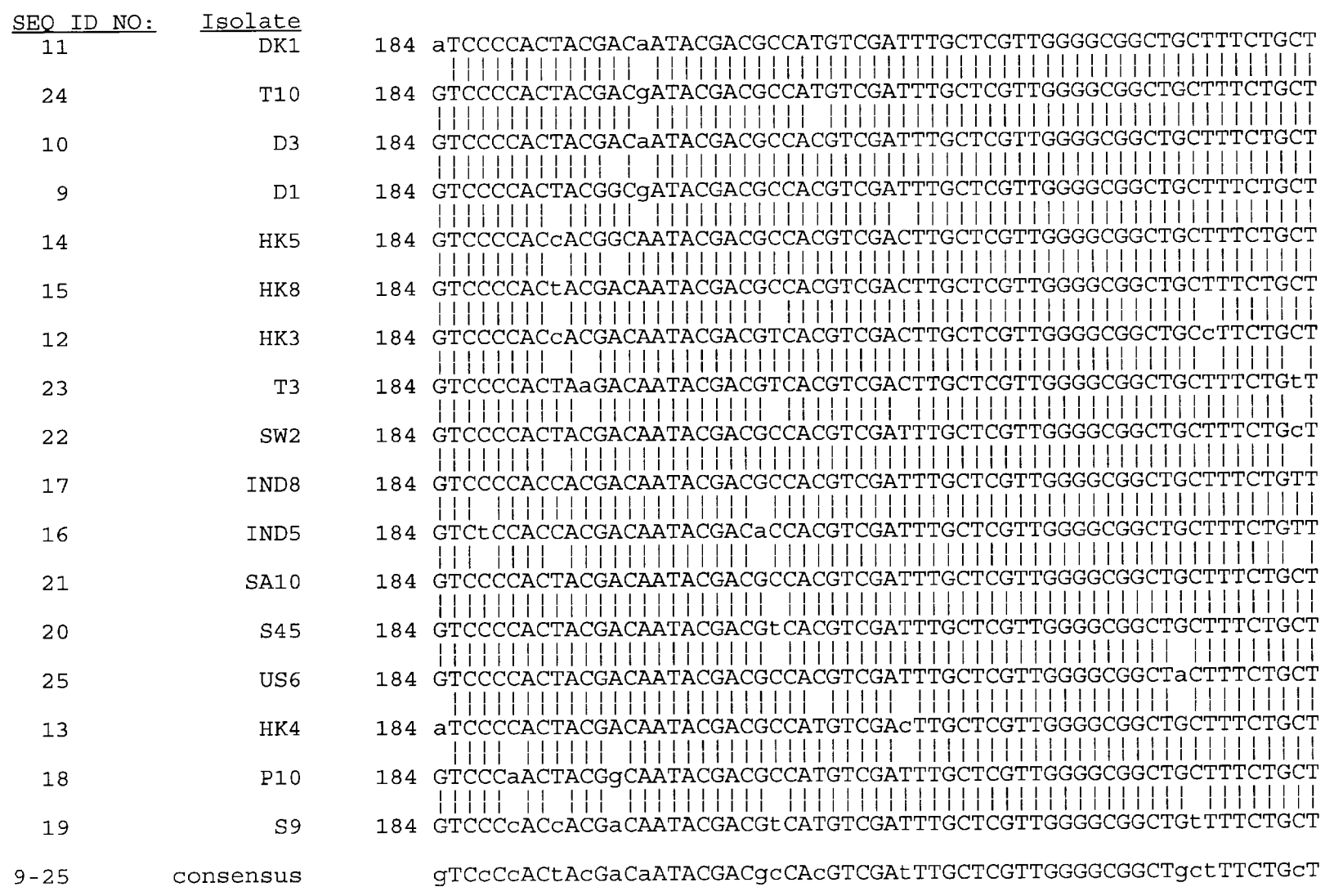

For those genotypes containing more than one E1 nucleotide sequence, computer alignment of the constituent nucleotide sequences of the genotype was conducted using GENALIGN in order to produce a consensus sequence for each genotype. These alignments and their resultant consensus sequences are shown in FIGS. 1A-1 to 1G-3 for the seven genotypes (I/1a, II/1b, III/2a, IV/2b, V/3a, 4c and 5a) which comprise more than one nucleotide sequence. Further alignment of the consensus sequences of FIG. 1A–G with SEQ ID NO: 34 (genotype 2c), SEQ ID NO: 40 (genotype 4a), SEQ ID NO: 41 (genotype 4b), SEQ ID NO: 44 (genotype 4d) and SEQ ID NO: 51 (genotype 6a) produces a consensus sequence for all twelve genotypes as shown in FIGS. 1H-1 to 1H-3. The multiple alignments of nucleotide sequences shown in FIGS. 1A-1 to 1H-5 produce consensus sequences which serve to highlight regions of homology and non-homology between sequences found within the same genotype or in different genotypes and hence, these alignments can be used by one skilled in the art to design oligonucleotides useful as reagents in diagnostic assays for HCV.

Examples of purified and isolated oligonucleotide sequences derived from the consensus sequences shown in FIGS. 1A–H include, but are not limited to, SEQ ID NOs: 213–239 where these oligonucleotides are useful as "genotype-specific" primers and probes since these oligonucleotides can hybridize specifically to the nucleotide sequence of the E1 gene of HCV isolates belonging to a single genotype. The genotype-specificity of the oligonucleotides shown in SEQ ID NOs: 213–239 is as follows: SEQ ID NOs: 213–214 are specific for genotype I/1a; SEQ ID NOs: 215–216 are specific for genotype II/1b; SEQ ID NOs: 217–218 are specific for genotype III/2a; SEQ ID NOs: 219–220 are specific for genotype IV/2b; SEQ ID NOs: 221–223 are specific for genotype 2c; SEQ ID NOs: 224–226 are specific for genotype V/3a; SEQ ID NOs: 227–228 are specific for genotype 4a; SEQ ID NOs: 229–230 are specific for genotype 4b; SEQ ID NOs: 231–232 are specific for genotype 4c; SEQ ID NOs: 233–234 are specific for genotype 4d; SEQ ID NOs: 235–236 are specific for genotype 5a and SEQ ID NOs: 237–239 are specific for genotype 6a.

In another embodiment, the computer analysis of SEQ ID NOs: 103–154 by the program GENALIGN results in distribution of the 52 HCV core sequences into 14 genotypes based upon the degree of variation of the sequences.

The grouping of SEQ ID NOs: 103–154 into 14 HCV genotypes is shown below.

| SEQ ID NOs: | Genotypes |
| --- | --- |
| 103–108 | I/1a |
| 109–124 | II/1b |
| 125–128 | III/2a |
| 129–133 | IV/2b |
| 134 | 2c |
| 135–138 | V/3a |
| 139 | 4a |
| 141 | 4b |
| 143 | 4c |
| 144 | 4c |
| 145 | 4d |
| 142 | 4e |
| 140 | 4f |
| 146–153 | 5a |
| 154 | 6a |

Figure 5:
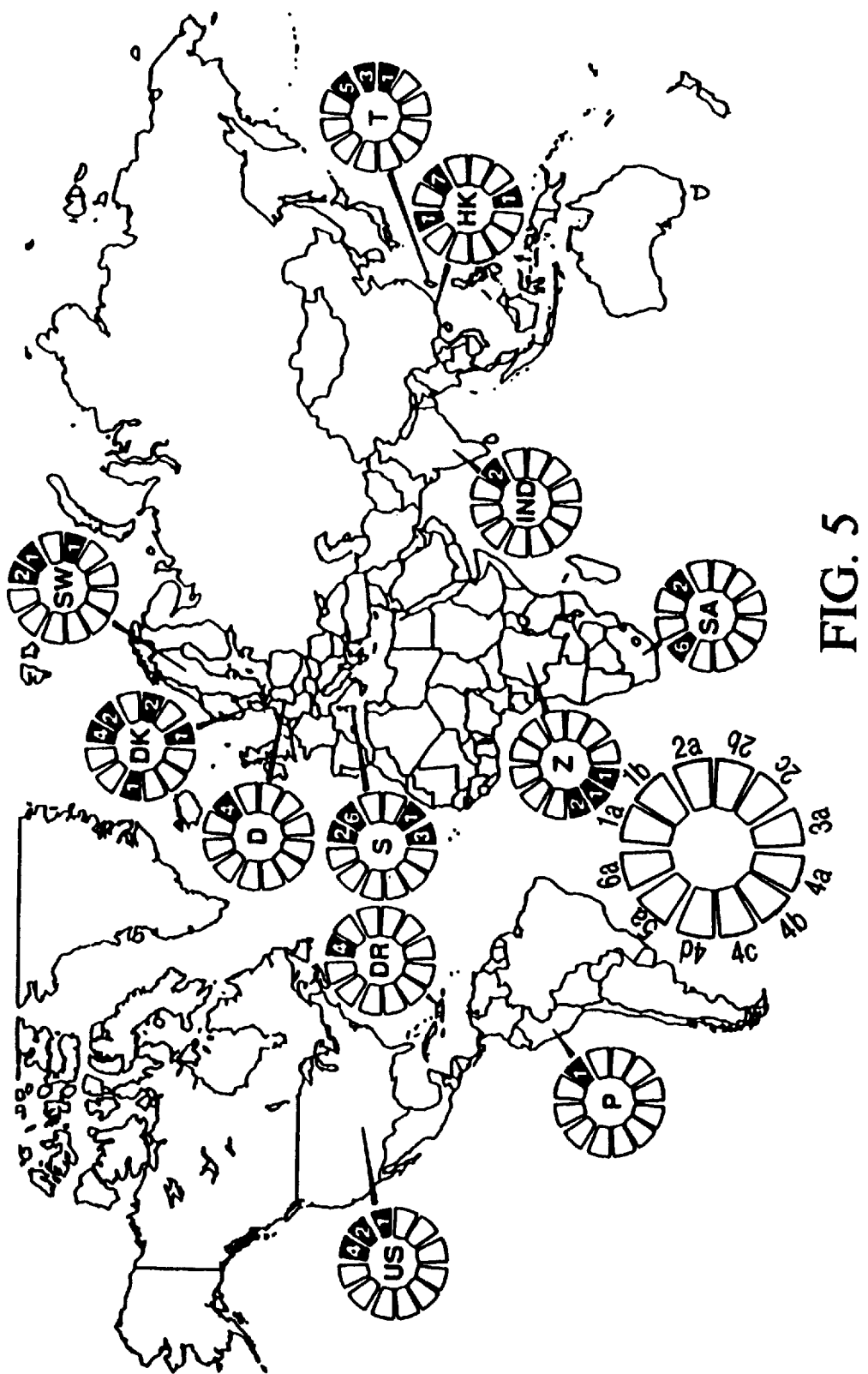
Figure 6K-1:
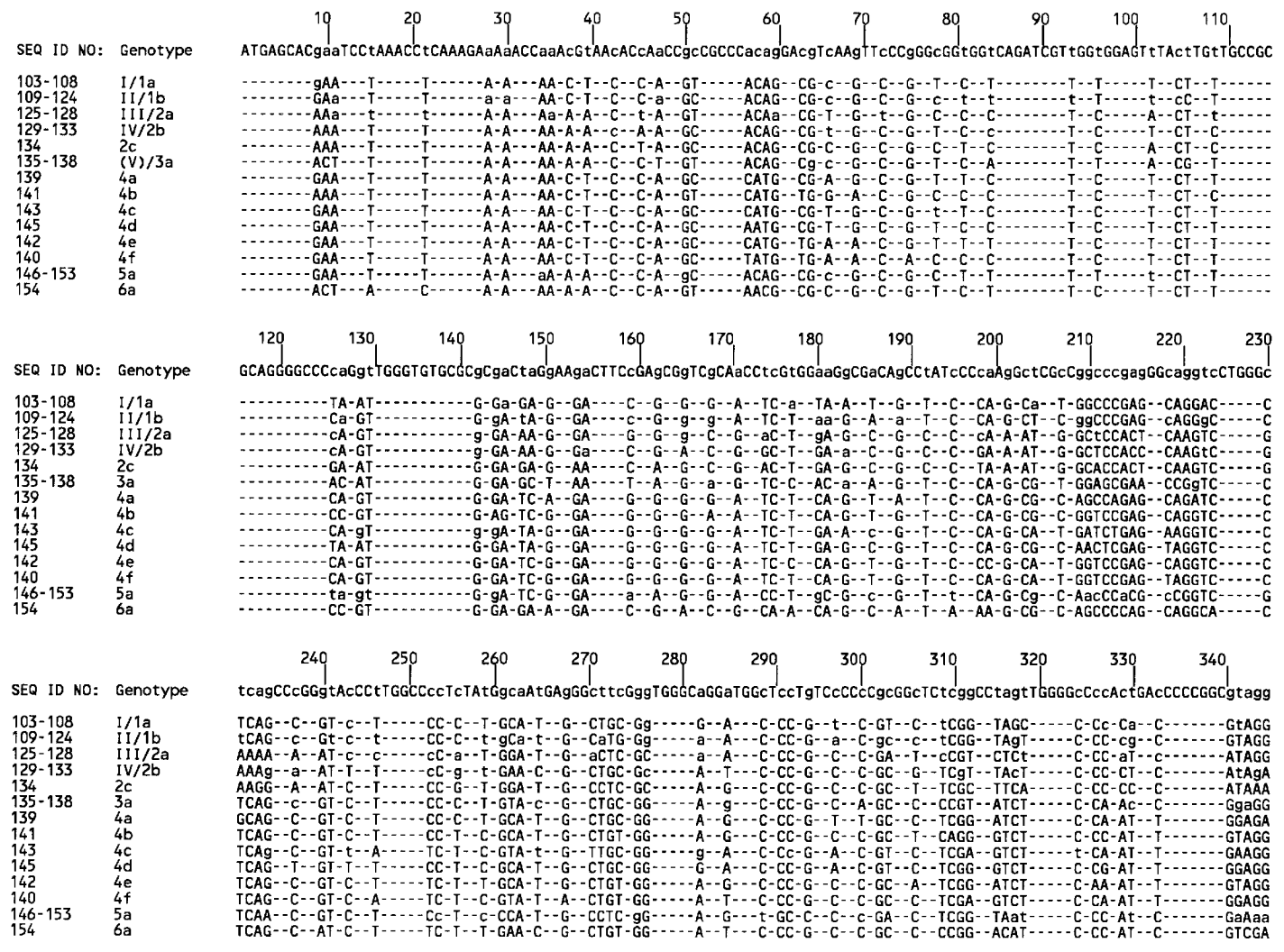
Figure 6K-2:
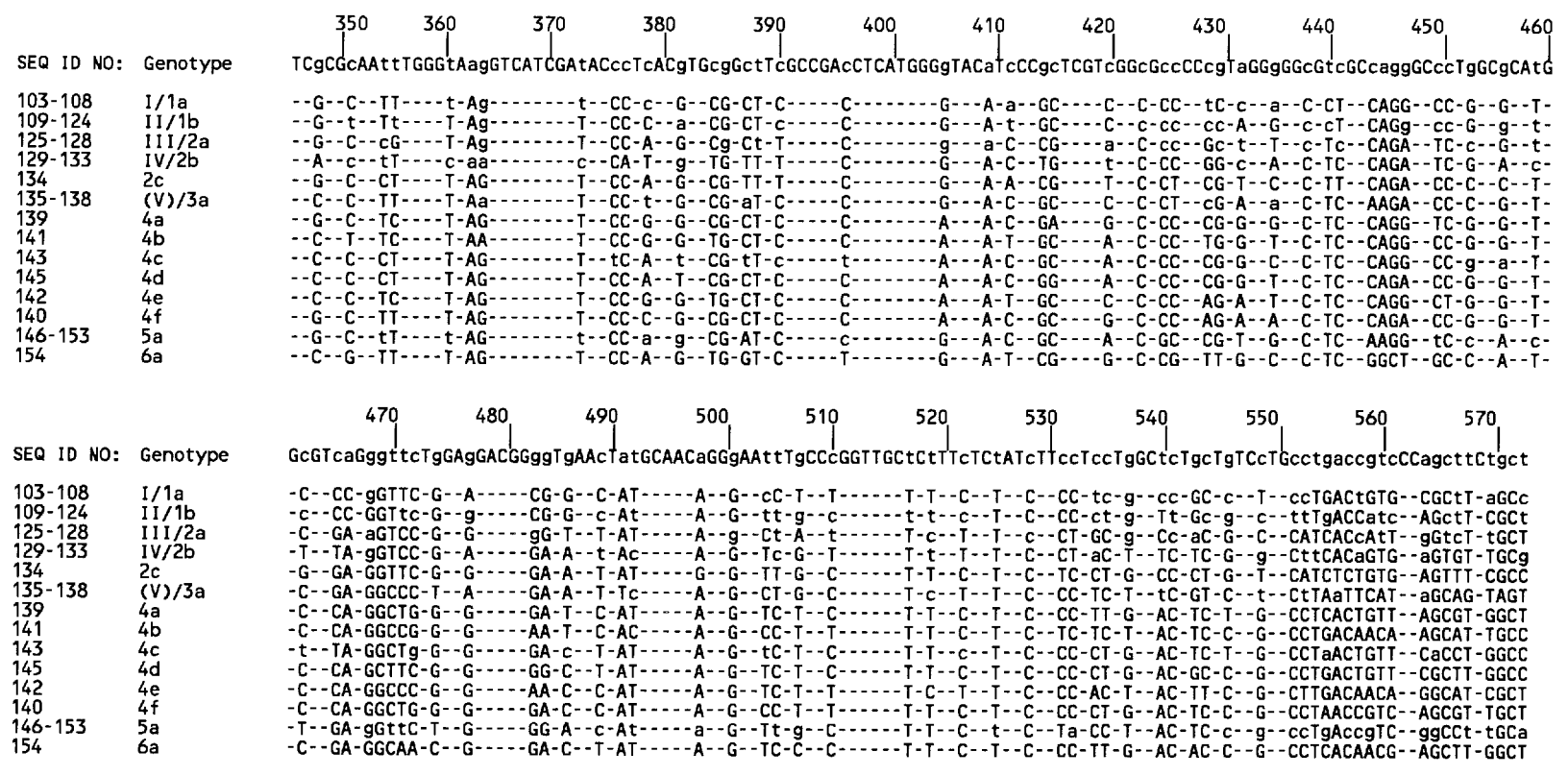

These 14 genotypes can be further grouped into 6 major genotypes designated genotypes 1–6 where genotype 1 comprises the sequences contained in minor genotypes I/1a and II/1b; genotype 2 comprises the sequences contained in minor genotypes III/2a, IV/2b and 2c; genotype 3 comprises sequences contained in genotype V/3a; genotype 4 comprises sequences contained in minor genotypes 4a–4f; genotype 5 comprises the sequences contained in genotype 5a and genotype 6 comprises the sequence contained in genotype 6a. Computer alignment of the constituent nucleotide sequences of the core cDNAs falling within genotypes I/1a, II/1b, III/2a, IV/2b, V/3a and 5a, to produce a consensus sequence for each of these genotypes is shown in FIGS. 6F-1 to 6A-4 (I/1a), 6B-1 to 6B-10 (II/1b), 6D-1 to 6D-3 (III/2a), 6E-1 to 6E-4 (IV/2b), 6G-1 to 6G-3 (V/3a), and 6I-1 to 6I-4 (VI/5a). The alignment of the sequences found in minor genotypes I/1a and II/1b to produce a consensus sequence for major genotype 1 is shown in FIGS. 6C-1 to 6C-10. The alignment of the sequences contained in minor genotypes III/2a, IV/2b and 2c to produce a consensus sequence for major genotype 2 is shown in FIGS. 6F-1 to 6F-5. The alignment of the nucleotide sequences contained in minor genotypes 4a–4f to produce a consensus sequence for major genotype 4 is shown in FIGS. 6H-1 to 6H-9. Further alignment of the consensus sequences shown in FIGS. 6C-1 to 6C-10, 6F-1 to 6F-5, 6G-1 to 6G-3, 6H-1 to 6H-4, and 6I-1 to 6I-4 with SEQ ID NO: 154 (genotype 6a/major genotype 6) to produce a consensus sequence for all genotypes is shown in FIGS. 6J-1 to 6J-4 and alignment of the consensus sequences shown in FIGS. 6A-1 to 6A-4, 6B-1 to 6B-10, 6D-1 to 6D-3, 6E-1 to 6E-4, 6G-1 to 6G-3, and 6I-1 to 6I-4 with 4a), SEQ ID NO: 141 (genotype 4b), SEQ ID NO: 143 (genotype 4c), SEQ ID NO: 145 (genotype 4d), SEQ ID NO: 142 (genotype 4e), SEQ ID NO: 140 (genotype 4f) and SEQ ID NO: 154 (genotype 6a) to produce a consensus sequence for all fourteen genotypes is shown in FIGS. 6K-1 and 6K-2. As with the alignments of the envelope (E1) nucleotide sequences, the consensus sequences shown in FIGS. 6A-1 to 6K-2 serve to highlight regions of homology and non-homology between sequences found within the same genotype or in different genotypes and hence, can be used by one skilled in the art to design oligonucleotides useful as reagents in diagnostic assays for HCV.

For example, purified and isolated oligonucleotide sequences derived from the consensus sequences shown in FIGS. 6A-1 to 6K-2 may be useful as genotype-specific primers and probes since these oligonucleotides can hybridize specifically to the nucleotide sequence of the core gene of HCV isolates belonging to a given genotype. Examples of regions of the consensus sequence of the core gene of a given genotype from which primers specific for that genotype may be deduced include but are not limited to, the nucleotide domains shown below for each genotype. The sequence in which the indicated nucleotide domains are found are indicated in parentheses to the right of each genotype.

Genotype 1 (Consensus Sequence of FIGS. 6C-1 to 6C-10)
427–466, 444–483, 447–486 (5'-3', sense)
505–466, 522–483, 525–486 (5'-3', antisense)

Genotype 1a (Consensus Sequence of FIGS. 6A-1 t0 6A-4)
141–180, 279–318 (5'-3', sense)
219–180, 246–207 (5'-3', antisense)

Genotype 1b (Consensus Sequence of FIGS. 6B-1 to 6B-10)
67–106, 127–186, 234–273 (5'-3', sense)
144–106, 225–186, 311–272, 312–273 (5'-3', antisense)

Genotype 2 (Consensus Sequence of FIGS. 6F-1 to 6F-5)
153–192, 162–201, 164–203, 168–207, 171–210, 182–221, 19214 231, 193–232, 302–341 (5'-3', sense)
231–192, 240–201, 242–203, 246–207, 249–210, 260–221, 270–231, 271–232, 380–341 (5'-3', antisense)

Genotype III/2a (Consensus Secuence of FIGS. 6D-1 to 6D-3)
276–315, 306–355 (5'-3', sense)
309–270, 354–315, 394–355, 571–532 (5'-3', antisense)

Genotype IV/2b (Consensus Sequence of FIGS. 6E-1 to 6E-4)
6–45, 135–174, 177–216, 309–348, 337–376, 375–414, 501–540 (5'-3', sense)
84–45, 213–174, 255–216, 387–348, 415–376, 453–414, 571–532, 573–540 (5'-3', antisense)

Genotype 2c (SEQ ID NO: 134)
194–233, 273–312, 279–318, 417–456, 423–462, 504–543, 505–544, 517–556 (5'-3', sense)
272–233, 351–312, 354–315, 357–318, 450–411, 495–456, 501–462, 573–543, 556–573 (5'-3', antisense)

Genotype 3 or Genotype V/3a (Consensus Sequence of FIGS. 6G-1 to 6G-3)
8–47, 45–84, 68–107, 87–126, 88–127, 90–129, 111–150, 142–181, 173–212, 177–216, 261–300, 276–315, 452–491, 520–559, 521–560, 529–568, 532–571, 533–572. (5'-3', sense)
86–47, 123–84, 146–107, 165–126, 186–147, 189–150, 219–180, 250–211, 251–212, 255–216, 339–300, 530–491, 573–543, 573–557, 573–559, 573–560. (5'-3', antisense)

Genotype 4 (Consensus Sequence of FIGS. 6H-1 to 6H-4)
20–59 (5'-3', sense)
97–58, 98–59 (5'-3', antisense)

Genotype 4a (SEQ ID NO: 139)
111–150, 150–189, 174–213, 183–222, 192–231, 261–300, 376–415, 396–435, 531–570 (5'-3', sense)
186–147, 252–213, 270 –231, 339–300, 454–415 (5'-3', antisense)

Genotype 4b (SEQ ID NO: 141)
27–66, 30–69, 106–145, 271–310, 433–472, 447–486, 453–492 (5'-3', sense)
105–66, 183–144, 184–145, 345–306, 348–309, 349–310, 468–429, 510–471, 522–483, 570–531 (5'-3', antisense)

Genotype 4c (SEQ ID NO: 143
174–213, 180–219, 207–246, 231–270 (5'-3', sense)
249–210, 252–213, 258–219, 309–270, 504–465 (5'-3', antisense)

Genotype 4d (SEQ ID NO: 145)
173–212, 188–327, 430–469 (5'-3', sense)
248–209, 249–210, 250–211, 251–212, 366–327, 508–469 (5'-3', antisense)

Genotype 4e (SEQ ID NO: 142)
160–199, 267–306, 287–326, 288–327, 524–564 (5'-3', sense)
238–199, 345–306, 365–326, 216–177, 522–483 (5'-3', antisense)

Genotype 4f (SEQ ID NO: 140)
18–57, 36–75, 228–267, 396–435 (5'-3', sense)
96–57, 114–75, 306–267 (5'-3', antisense)

Genotype 5 or 5a (Consensus Sequence of FIGS. 6I-1 to 6I-4)
176–215, 177–216, 181–220, 195–234, 221–260, 252–291, 255–294, 396–435, 435–474, 447–486, 498–537 (5'-3', sense)
254–215, 299–260, 310–271, 330–291, 333–294, 354–315, 464–425, 471–432, 483–444, 570–531 (5'-3', antisense)

Genotype 6 or 6a (SEQ ID NO: 154)
20–59, 136–175, 156–195, 159–198, 175–214, 185–224, 277–316, 278–317, 312–351, 348–387,405–444, 406–445, 407–446, 408–447, 411–450, 432–471, 433–472, 435–474, 522–561 ( 5'-3', sense).
98–59, 214–175, 234–195, 237–198, 253–214, 262–223, 263–224, 354–315, 355–316, 382–343, 390–351, 426–387, 468–429, 483–444, 484–445, 485–446, 486–447, 489–450, 510–471, 511–472, 513–474 (5'-3', antisense)

Such nucleotide domains may range from about 15 to about 100 bases in length with a more preferred range being about 30 to about 60 bases in length.

In an alternative embodiment, universal primers able to hybridize to the nucleotide sequences of the core gene of HCV isolates belonging to all of the genotypes disclosed herein may be deduced from universally conserved nucleotide domains of the consensus sequence shown in FIGS. 6J-1 to 6J-4 and 6K-1 to 6K-2. Examples of such nucleotide domains include, but are not limited to, those shown below:

nucleotides 1–20, 1–25, 1–26, 1–27, 1–33, 50–89, 51–90, 52–91, 53–92, 61–100, 62–101, 77–116, 78–117, 79–118, 80–119, 81–120, 82–121, 83–122, 84–123, 85–124, 86–125, 97–136, 98–137, 99–138, 100–139, 101–140, 102–141, 329–368, 330–369, 331–370, 332–371, 354–393, 355–394, 356–395, 362–401, 363–402, 364–403, 365–404, 369–408, 442–481, 443–482, 457–496, 458–497, 475–514, 476–515, 477–516 (5'-3, sense); and nucleotides 40–1, 41–2, 42–3, 43–4, 51–12, 52–13, 55–16, 56–17, 57–18, 58–19, 61–22, 62–23, 63–24, 64–25, 70–31, 124–85, 125–86, 126–87, 127–88, 128–89, 129–90, 136–97, 137–98, 138–99, 149–110, 150–111, 151–112, 152–113, 153–114, 154–115, 155–116, 156–117, 157–118, 158–119, 159–120, 170–131, 171–132, 172–133, 173–134, 174–135, 175–136, 403–364, 405–365, 406–366, 406–367, 430–391, 431–392, 432–393, 436–397, 437–398, 438–399, 439–400, 517–478, 518–479, 519–480, 532–493, 533–494, 550–511, 551–512 (5'-3', antisense)

Those skilled in the art would readily understand that the term "antisense" as used herein refers to primer sequences which are the complementary sequence of the indicated consensus sequence or SEQ ID NO:. Further, provided with the above examples of regions of the consensus sequences or indicated SEQ ID NOS: from which to deduce universal and genotype-specific primers, those skilled in the art would readily be able to select pairs of primers, one sense and one antisense, which would be useful in the detection of HCV genotypes via the PCR methods described herein.

In yet another embodiment, the sequences shown in SEQ ID NO.: 103–154 and the resultant consensus sequences produced by alignment of these SEQ ID NOs as shown in FIGS. 6A–6K may also be useful in the design of hybridization probes specific for a given HCV genotype. Examples of nucleotide domains of the consensus sequence or SEQ ID NO of a given genotype from which genotype-specific hybridization probes may be deduced include, but are not limited to, those shown below where the sequence from which the domains are found is indicated in parentheses to the right of each genotype.

| Genotype | Position |
|---|---|
| 1a (Consensus sequence of Figures 6A-1 to Figure 6A-4) | 50–85 |
| | 155–205 |
| | 207–277 |
| | 281–333 |
| | 429–477 |
| | 530–573 |
| 1b (Consensus sequence of Figures 6B-1 to Figure 6B-10) | 81–131 |
| | 159–225 |
| | 252–318 |
| | 411–472 |
| | 530–573 |
| 2a (Consensus sequence of Figures 6D-1 to Figure 6D-3) | 35–75 |
| | 200–276 |
| | 290–340 |
| | 330–380 |
| | 410–472 |
| | 530–573 |
| 2b (Consensus sequence of Figures 6E-1 to Figure 6E-4) | 20–70 |
| | 149–199 |
| | 191–241 |
| | 240–285 |
| | 261–318 |
| | 323–373 |
| | 351–401 |
| | 389–439 |
| | 429–477 |
| | 530–573 |
| 2c (SEQ ID NO:134) | 208–258 |
| | 230–276 |
| | 290–345 |
| | 411–460 |
| | 430–490 |
| | 530–573 |
| 3a (Consensus sequence of Figures 6G-1 to 6G-3) | 1–50 |
| | 40–100 |
| | 100–160 |
| | 145–190 |
| | 190–240 |
| | 275–325 |
| | 411–455 |
| | 466–516 |
| | 530–573 |
| 4a (SEQ ID NO:139) | 35–85 |
| | 145–195 |
| | 200–250 |
| | 255–305 |
| | 341–390 |
| | 390–440 |
| | 530–573 |
| 4b (SEQ ID NO:141) | 35–85 |
| | 120–170 |
| | 180–225 |
| | 230–275 |
| | 285–335 |
| | 405–455 |
| | 462–492 |
| | 530–573 |
| 4c (SEQ ID NO:143) | 35–85 |
| | 190–246 |
| | 245–295 |
| | 282–318 |
| | 372–415 |
| | 440–480 |
| | 530–573 |
| 4d (SEQ ID NO:145) | 35–85 |
| | 187–237 |
| | 302–352 |
| | 405–455 |
| | 444–494 |
| | 530–573 |
| 4e (SEQ ID NO:142) | 35–85 |
| | 57–84 |
| | 174–224 |
| | 230–275 |
| | 290–340 |
| | 422–472 |
| | 530–573 |
| 4f (SEQ ID NO:140) | 35–85 |
| | 174–224 |
| | 242–292 |
| | 290–340 |
| | 422–472 |
| | 530–573 |
| 5a (Consensus sequence of Figures 6I-1 to 6I-4) | 180–234 |
| | 265–315 |
| | 315–355 |
| | 420–486 |
| | 530–573 |
| 6a (SEQ ID NO:154) | 34–84 |
| | 150–200 |
| | 180–230 |
| | 230–290 |
| | 291–333 |
| | 341–395 |
| | 429–490 |
| | 530–573 |
| 1 (Consensus sequence of Figures 6C-1 to 6C-10) | 192–241 |
| | 435–495 |
| 2 (Consensus sequence of Figures 6F-1 to 6F-5) | 186–240 |
| | 320–360 |
| | 440–475 |
| 4 (Consensus sequence of Figures 6H-1 to 6H-4) | 40–80 |

In yet another embodiment, universal hybridization probes may be derived from the consensus sequences shown in FIGS. 6J-1 to 6J-4 and 6K-1 to 6K-2. Examples of nucleotide domains of the consensus sequences shown in FIGS. 6J-1 to 6J-4 and 6K-1 to 6K-2 from which universal hybridization probes may be derived include, but are not limited to, 1–33; 85–141; 364–408; 478–516.

The oligonucleotides of this invention can be synthesized using any of the known methods of oligonucleotide synthesis (e.g., the phosphodiester method of Agarwal et al. 1972, Agnew. Chem. Int. Ed. Engl. 11:451, the phosphotriester method of Hsiung et al. 1979, Nucleic Acids Res 6:1371, or the automated diethylphosphoramidite method of Baeucage et al. 1981, Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In a preferred embodiment, the oligonucleotides of the present invention are synthetic oligonucleotides. The oligonucleotides of the present invention may range from about 15 to about 100 nucleotides; with the preferred sizes being about 20 to about 60 nucleotides; a more preferred size being about 25 to about 50 nucleotides; and a most preferred size being about 30 to about 40 nucleotides.

The present invention also relates to methods for detecting the presence of HCV in a mammal, said methods comprising analyzing the RNA of a mammal for the presence of hepatitis C virus.

The RNA to be analyzed can be isolated from serum, liver, saliva, lymphocytes or other mononuclear cells as viral RNA, whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412). A preferred method of isolating RNA is extraction of viral RNA by the guanidinium-phenol-chloroform method of Bukh et al. (1992a).

The methods for analyzing the RNA for the presence of HCV include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W. H. Freeman and Company, New York).

A preferred method for analyzing the RNA is RT-PCR. In this method, the RNA can be reverse transcribed to first strand cDNA using a primer or primers derived from the nucleotide sequences shown in SEQ ID NOs: 1–51 or SEQ ID NOs: 103–154 or sequences complementary to those described. Once the cDNAs are synthesized, PCR amplification is carried out using pairs of primers designed to hybridize with sequences in the HCV E1 or core cDNA which are an appropriate distance apart (at least about 50 nucleotides) to permit amplification of the cDNA and subsequent detection of the amplification product. Alternatively, one can amplify both E1 and core cDNA sequences by using a primer pair where one primer hybridizes with the E1 cDNA sequence and the other primer hybridizes with the core cDNA sequence. Each primer of a pair is a single-stranded oligonucleotide of about 20 to about 60 bases in length with a more preferred range being about 30 to about 50 bases in length where one primer (the "upstream" primer) is complementary to the original RNA and the second primer (the "downstream" primer) is complementary to the first strand of cDNA generated by reverse transcription of the RNA. The target sequence is generally about 100 to about 300 base pairs long but can be as large as 500–1500 base pairs. Optimization of the amplification reaction to obtain sufficiently specific hybridization to the nucleotide sequence of interest (either E1 or core or both E1 and core) is well within the skill in the art and is preferably achieved by adjusting the annealing temperature.

In one embodiment, the primer pairs selected to amplify E1 and core cDNAs are universal primers. By "universal", as used to describe primers throughout the claims and specification, is meant those primer pairs which can amplify E1 and/or core gene fragments derived from an HCV isolate belonging to any one of the genotypes of HCV described herein. Purified and isolated universal primers for E1 cDNAs are used in Example 1 of the present invention and are shown as SEQ ID NOs: 207–212 where SEQ ID NOs: 207 and 208 represent one pair of primers, SEQ ID NOs: 209 and 210 represent a second pair of primers and SEQ ID NOs: 211–212 represent a third pair of primers. Nucleotide domains of the consensus sequence shown in FIGS. 6J-1 to 6J-4 from which universal primers for core cDNAs may be deduced have previously been disclosed within the present specification. Alternatively, a universal primer for E1 cDNA sequence and a universal primer for core cDNA sequence may be used as a universal primer pair to amplify both E1 and core cDNAs.

In an alternative embodiment, primer pairs selected to amplify E1 and/or core cDNAs are genotype-specific primers. In the present invention, genotype-specific primer pairs can readily be derived from the following genotype-specific E1 nucleotide domains: nucleotides 197–238 and 450–480 of the consensus sequence of genotype I/1a shown in FIGS. 1A-1 to 1A-4; nucleotides 197–238 and 450–480 of the consensus sequence of genotype II/1b shown in FIGS. 1B-1 to 1B-10; nucleotides 199–238 and 438–480 of the consensus sequence of genotype III/2a shown in FIGS. 1C-1 to 1C-2; nucleotides 124–177 and 450–480 of the consensus sequence of genotype IV/2b shown in FIGS. 1D-1 to 1D-2; nucleotides 124–177, 193–238 and 436–480 of SEQ ID NO: 34 (genotype 2C); nucleotides 168–207, 294–339 and 406–480 of the consensus sequence of genotype V/3a shown in FIGS. 1E-1 to 1E-3; nucleotides 145–183 and 439–480 of SEQ ID NO: 40 (genotype 4a); nucleotides 168–207 and 432–480 of SEQ ID NO: 41 (genotype 4b); nucleotides 130–183 and 450–480 of the consensus sequence of genotype 4c shown in FIGS. 1F-1 to 1F-2; nucleotides 130–183 and 450–480 of SEQ ID NO: 44 (genotype 4d); nucleotides 166–208 and 437–480 of the consensus sequence of genotype 5a shown in FIG. 1b and nucleotides 168–207, 216–252 and 429–480 of SEQ ID NO: 51 (genotype 6a). Genotype-specific HCV core nucleotide domains from which genotype-specific primers may be deduced have previously been described herein. Those skilled in the art would readily appreciate that in a pair of genotype-specific primers, each primer is derived from different nucleotide domains specific for a given genotype. Also, it is understood by those skilled in the art that each pair of primers comprises one primer which is complementary to the original viral RNA and the other which is complementary to the first strand of cDNA generated by reverse transcription of the viral RNA. For example, in a pair of genotype-specific primers for genotype 4b, one primer would have a nucleotide sequence derived from region 168–207 of SEQ ID NO: 40 and the other primer would have a nucleotide sequence which is the complement of region 432–480 of SEQ ID NO: 40. One skilled in the art would readily recognize that such genotype-specific domains would also be useful in designing oligonucleotides for use as genotype-specific hybridization probes. Indeed, genotype-specific hybridization probes deduced from the E1 and core sequences of the present invention have been previously disclosed herein.

The amplification products of PCR can be detected either directly or indirectly. In one embodiment, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be detected by agarose gel electrophoresis followed by ethidum bromide staining and visualization under ultraviolet light or via direct sequencing of the PCR-products. Thus, in one embodiment, the present invention relates to a method for determining the genotype of a hepatitis C virus present in a mammal where said method comprises: amplifying RNA of a mammal via RT-PCR using labelled genotype-specific primers for the amplification step of the cDNA produced by reverse transcription.

In yet another embodiment, unlabelled amplification products can be detected via hybridization with labelled nucleic acid probes radioactively labelled or, labelled with biotin, in methods known to one skilled in the art such as dot and slot blot hybridization (Kafatos, F. C. et al. (1979) or filter hybridization (Hollander, M. C. et al. (1990)).

In one embodiment, the nucleic acid sequences used as probes are selected from, and substantially homologous to, SEQ ID NOs: 1–51 and/or SEQ ID NOs: 103–154. Such probes are useful as universal probes in that they can detect PCR-amplification products of E1 and/or core cDNAs of an HCV isolate belonging to any of the HCV genotypes disclosed herein. The size of these probes can range from about 200 to about 500 nucleotides. In an alternative embodiment, the sequence alignments shown in FIGS. 1A–1H and 6A–6J may be used to design oligonucleotides useful as universal hybridization probes. Examples of core and envelope nucleotide domains from which such universal oligonucleotides may be deduced are disclosed herein.

In yet another embodiment, the present invention relates to a method for determining the genotype of a hepatitis C virus present in a mammal where said method comprises:

(a) amplifying RNA of a mammal via RT-PCR to produce amplification products;

(b) contacting said products with at least one genotype-specific oligonucleotide; and (c) detecting complexes of said products which bind to said oligonucleotide(s).

In this method, one embodiment of said amplification step is carried out using the universal primers for E1 or core cDNAs as disclosed above. In step (b) of this method, the genotype-specific sequences used as probes may be deduced from the genotype-specific E1 and core nucleotide domains disclosed herein. These probes are useful in specifically detecting PCR-amplification products of E1 or core cDNAs of HCV isolates belonging to one of the HCV genotypes disclosed herein. In a preferred embodiment, these probes are used alone or in combination with other probes specific to the same genotype.

For example, a probe having a sequence according to SEQ ID NO: 213 can be used alone or in combination with a probe having a sequence according to SEQ ID NO: 214. The probes used in this method can range in size from about 15 to about 100 nucleotides with a more preferred range being about 30 to about 70 nucleotides. Such probes can be synthesized as described earlier.

In an alternative embodiment, the genotype of the amplification product of step (a) may be determined by using the nucleic acid sequences shown in SEQ ID NOs: 1–51 and 103–154 as probes (Delwart, E. et al. (1993)) Science, 262: 1257–1261). Probes utilized in the method of Delwart et al. may range in size from about 100 to about 1,000 nucleotides with a more preferred probe size being about 200 to about 800 base pairs and a most preferred probe size being about 300 to about 700 nucleotides.

The nucleic acid sequence used as a probe to detect PCR amplification products of the present invention can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, New York). In addition, there are known non-radioactive techniques for signal amplification including methods for attaching chemical moieties to pyrimidine and purine rings (Dale, R. N. K. et al. (1973) Proc. Natl. Acad. Sci., 70:2238–2242; Heck, R. F. (1968) S. Am. Chem. Soc., 90:5518–5523), methods which allow detection by chemiluminescence (Barton, S. K. et al. (1992) J. Am. Chem. Soc., 114:8736–8740) and methods utilizing biotinylated nucleic acid probes (Johnson, T. K. et al. (1983) Anal. Biochem., 133:126–131; Erickson, P. F. et al. (1982) J. of Immunology Methods, 51:241–249; Matthaei, F. S. et al. (1986) Anal. Biochem., 157:123–128) and methods which allow detection by fluorescence using commercially available products.

The present invention also relates to computer analysis of the amino acid sequences shown in SEQ ID NOs: 52–102 by the program GENALIGN. This analysis groups the 51 amino acid sequences shown in SEQ ID NOs: 52–102 into twelve genotypes based upon the degree of variation of the amino acid sequences. For the purposes of the present invention, the amino acid sequence identity of E1 amino acid sequences of the same genotype ranges from about 85% to about 100% whereas the identity of E1 amino acid sequences of different genotypes ranges from about 45% to about 80%.

The grouping of SEQ ID NOs: 52–102 into twelve HCV genotypes is shown below:

| SEQ ID NOs: | Genotypes |
| --- | --- |
| 52–59 | I/1a |
| 60–76 | II/1b |
| 77–80 | III/2a |
| 81–84 | IV/2b |
| 85 | 2c |
| 86–90 | V/3a |
| 91 | 4a |
| 92 | 4b |
| 93–94 | 4c |
| 95 | 4d |
| 96–101 | 5a |
| 102 | 6a |

For those genotypes containing more than one E1 amino acid sequence, computer alignment of the constituent sequences of each genotype was conducted using the computer program GENALIGN in order to produce a consensus sequence for each genotype. These alignments and their resultant consensus sequences are shown in FIGS. 2A-1 to 2G for the seven genotypes (I/1a, II/1b, III/2a, IV/2b, V/3a, 4c and 5a) which comprise more than one sequence. Further alignment of the consensus sequences shown in FIGS. 2A-1 to 2G with the amino acid sequences of SEQ ID NO: 85 (genotype 2c); SEQ ID NO: 91 (genotype 4a); SEQ ID NO: 92 (genotype 4b); SEQ ID NO: 95 (genotype 4d) and SEQ ID NO: 102 (genotype 6a) to produce a consensus amino acid sequence for all twelve genotypes is shown in FIGS. 2H-1 to 2H-2. The multiple alignment of E1 amino acid sequences shown in FIGS. 2A–H produces consensus sequences which serve to highlight regions of homology and non-homology between E1 amino acid sequences of the same genotype and of different genotypes and hence, these alignments can readily be used by those skilled in the art to design peptides useful in assays and vaccines for the diagnosis and prevention of HCV infection.

In another embodiment, the computer analysis of SEQ ID NOS: 155–206 by the probe genome results in distribution of the 52 HCV core sequences into 14 genotypes based upon identification of genotype-specific amino acid sequences.

The grouping of SEQ ID NOS: 155–206 into 14 HCV genotypes is shown below:

| SEQ ID NOs: | Genotypes |
| --- | --- |
| 155–160 | I/1a |
| 161–176 | II/1b |
| 177–180 | III/2a |
| 181–185 | IV/2b |
| 186 | 2c |
| 187–190 | V/3a |
| 191 | 4a |
| 193 | 4b |
| 195 | 4c |
| 196 | 4c |
| 197 | 4d |
| 194 | 4e |
| 192 | 4f |
| 198–205 | 5a |
| 206 | 6a |

These fourteen genotypes can be further grouped into six major genotypes designated genotypes 1–6 as described earlier for the core nucleotide sequences of the present application. Computer alignment of the amino acid sequences disclosed in SEQ ID NOS: 155–206 are shown in FIGS. 7A-1 to 7J. As with the multiple alignments of the E-1 amino acid sequences, the consensus sequences shown in FIGS. 7A-1 to 7J serve to highlight regions of homology and nonhomology between core amino acid sequences of the same genotype and of different genotypes and hence, these alignments can readily be used by those skilled in the art to design peptides useful in assays and vaccines for the diagnosis and prevention of HCV infection.

Examples of purified and isolated peptides deduced from the alignments shown in FIG. 2A-1 to 2H-2 include, but are not limited to, SEQ ID NOs: 240–263 wherein these peptides are derived from two regions of the amino acid sequences shown in FIGS. 2A-1 to 2H-2, amino acids 48–80 and amino acids 138–160. The peptides shown in SEQ ID NOs. 240–263 are useful as genotype-specific diagnostic reagents since they are capable of detecting an immune response specific to HCV isolates belonging to a single genotype. The genotype-specificity of the peptides shown in SEQ ID NOs: 240–263 are as follows: SEQ ID NOs: 240 and 252 are specific for genotype IV/2b; SEQ ID NOs: 241 and 253 are specific for genotype 2c; SEQ ID NOs: 242 and 254 are specific for genotype III/2a; SEQ ID NOs: 243 and 255 are specific for genotype V/a; SEQ ID NOs: 244 and 256 are specific for genotype II/1b; SEQ ID NOs: 245 and 257 are specific for genotype I/1a; SEQ ID NOs: 246 and 258 are specific for genotype 4a; SEQ ID NOs: 247 and 259 are specific for genotype 4c; SEQ ID NOs: 248 and 260 are specific for genotype 4d; SEQ ID NOs: 249 and 261 are specific for genotype 4b; SEQ ID NOs: 250 and 262 are specific for genotype 5a and SEQ ID NOs: 251 and 263 are specific for genotype 6a. In SEQ ID NO: 240, Xaa at position 22 is a residue of Ala or Thr, Xaa at position 24 is a residue of Val or Ile, Xaa at position 26 is a residue of Val or Met; in SEQ ID NO: 242, Xaa at position 5 is a Ser or Thr residue, Xaa at position 11 is an Arg or Gln residue, Xaa at position 12 is an Arg or Gln residue; in SEQ ID NO: 243, Xaa at position 3 is a Pro or Ser residue, Xaa at position 33 is a Leu or Met residue; in SEQ ID NO: 244, Xaa at position 5 is a Thr or Ala residue, Xaa at position 13 is a Gly, Ala, Ser, Val or Thr residue, Xaa at position 14 is a Ser, Thr or Asn residue, Xaa at position 15 is a Val or Ile residue, Xaa at position 16 is a Pro or Ser residue, Xaa at position 18 is a Thr or Lys residue, Xaa at position 19 is a Thr or Ala residue, Xaa at position 22 is an Arg or His residue, Xaa at position 32 is an Ala, Val or Thr residue; in SEQ ID NO: 245, Xaa at position 3 is an Ala or Pro residue, Xaa at position 4 is a Val or Met residue, Xaa at position 5 is a Thr or Ala residue, Xaa at position 17 is a Thr or Ala residue, Xaa at position 18 is a Thr or Ala residue, Xaa at position 23 is a His or Tyr residue; in SEQ ID NO: 247, Xaa at position 10 is a Val or Ala residue, Xaa at position 11 is a Ser or Pro residue, Xaa at position 18 is an Asp or Glu residue Xaa at position 20 is a Leu or Ile residue; in SEQ ID NO: 250, Xaa at position 3 is a Gln or His residue, Xaa at position 12 is an Asn, Ser or Thr residue, Xaa at position 13 is a Leu or Phe residue, Xaa at position 23 is an Ala or Val residue; in SEQ ID NO: 252, Xaa at position 16 is a Val or Ala residue, Xaa at position 18 is a Glu or Gln residue; in SEQ ID NO: 254, Xaa at position 2 is an Ala or Thr residue, Xaa at position 4 is a Met or Leu residue, Xaa at position 9 is an Ala or Val residue, Xaa at position 17 is an Ile or Leu residue, Xaa at position 20 is an Ile or Val residue, Xaa at position 21 is a Ser or Gly residue; in SEQ ID NO: 151, Xaa at position 9 is a Val or Ile residue, Xaa at position 16 is a Leu or Val residue, Xaa at position 20 is an Ile or Leu residue; in SEQ ID NO: 256, Xaa at position 2 is an Ala or Thr residue, Xaa at position 6 is a Val or Leu residue, Xaa at position 12 is an Ile or Leu residue, Xaa at position 16 is a Val or Ile residue, Xaa at position 17 is a Val, Leu or Met residue, Xaa at position 19 is a Met or Val residue, Xaa at position 21 is an Ala or Thr residue; in SEQ ID NO: 257, Xaa at position 2 is a Thr or Ala residue, Xaa at position 6 is a Val, Ile or Met residue, Xaa at position 12 is an Ile or Val residue, Xaa at position 16 is a Ile or Val residue; in SEQ ID NO: 155, Xaa at position 5 is a Leu or Val residue, Xaa at position 21 is a Thr or Ala residue; in SEQ ID NO: 262, Xaa at position 1 is a Thr or Ala residue, Xaa at position 5 is a Val or Leu residue, Xaa at position 9 is a Leu, Met or Val residue, Xaa at position 23 is a Gly or Ala residue.

Examples of core amino acid domains from which genotype-specific peptides may be deduced, include but are not limited to, those shown below where the sequence in which the indicated domains are found is given in parentheses to the right of each genotype:

| Genotype | Amino Acid Domains |
| --- | --- |
| 1a (consensus sequence of Figures 7A-1 to 7A-2) | 67–78 |
| 1b (consensus sequence of Figures 7B-1 to 7B-2) | 67–78 |
| 2 (consensus sequence of Figures 7F-1 to 7F-2) | 66–81 |
| | 110–119 |
| 2a (consensus sequence of Figure 7D) | 67–78 |
| | 115–125 |
| 2b (consensus sequence of Figure 7E) | 67–78 |
| | 123–133 |

| Genotype | Amino Acid Domains |
| --- | --- |
| 2c (SEQ ID NO:186) | 67–78 |
| | 75–81 |
| | 184–191 |
| 3a (consensus sequence of Figure 7G) | 8–22 |
| | 32–46 |
| | 67–78 |
| | 158–170 |
| | 180–191 |
| 4 (consensus sequence of Figures 7H-1 to 7H-2) | 14–23 |
| 4a (SEQ ID NO:191) | 67–78 |
| 4b (SEQ ID NO:193) | 45–57 |
| | 67–78 |
| 4c (SEQ ID NO:195) | 67–78 |
| 4d (SEQ ID NO:197) | 67–78 |
| 4e (SEQ ID NO:194) | 67–78 |
| 4f (SEQ ID NO:192) | 67–78 |
| 5a (consensus sequence of Figure 7J) | 67–78 |
| 6a (SEQ ID NO:206) | 67–78 |
| | 101–108 |
| | 144–155 |
| | 157–163 |

Those skilled in the art would be aware that the peptides of the present invention or analogs thereof can be synthesized by automated instruments sold by a variety of manufacturers or can be commercially custom-ordered and prepared. The term analog has been described earlier in the specification and for purposes of describing the peptides of the present invention, analogs can further include branched, cyclic or other non-linear arrangements of the peptide sequences of the present invention.

Alternatively, peptides can be expressed from nucleic acid sequences where such sequences can be DNA, cDNA, RNA or any variant thereof which is capable of directing protein synthesis. In one embodiment, restriction digest fragments containing a coding sequence for a peptide can be inserted into a suitable expression vector that functions in prokaryotic or eukaryotic cells. Such restriction digest fragments may be obtained from clones isolated from prokaryotic or eukaryotic sources which encode the peptide sequence.

Suitable expression vectors and methods of isolating clones encoding the peptide sequences of the present invention have previously been described. In yet another embodiment, an oligonucleotide capable of directing host organism synthesis of the given peptide may be synthesized and inserted into the expression vector.

The preferred size of the peptides of the present invention is from about 8 to about 100 amino acids in length when the peptides are chemically synthesized with a more preferred size being about 8 to about 30 amino acids and a most preferred size being about 10 to about 20 amino acids in length. For recombinantly expressed peptides, the size may range from about 20 to about 190 amino acids in length with a more preferred size being about 70 amino acids.

The present invention further relates to the use of genotype-specific peptides in methods of detecting antibodies against a specific genotype of HCV in biological samples. In one embodiment, at least one genotype-specific peptide deduced from a genotype-specific core or E1 amino acid domain may be used in any of immunoassays described herein to detect antibodies specific for a single genotype of HCV. In another embodiment, at least one genotype-specific peptide deduced from a genotype-specific core nucleotide domain and at least one genotype-specific peptide deduced from an E1 amino acid domain may be used in an immunoassay to detect antibodies against a single genotype of HCV. A preferred immunoassay is ELISA.

It is understood by those skilled in the art that the diagnostic assays described herein using genotype-specific oligonucleotides or genotype-specific peptides can be useful in assisting one skilled in the art to choose a course of therapy for the HCV-infected individual.

In an alternative embodiment, a mixture of genotype-specific peptides can be used in an immunoassay to detect antibodies against multiple genotypes of HCV disclosed herein. For example, a mixture of genotype-specific peptides deduced from E1 amino acid sequences may comprise at least one peptide selected from SEQ ID NOs: 244–245 and 256–257; one peptide selected from SEQ ID NOs: 240, 242, 252 and 254; one peptide selected from SEQ ID NOs: 246–249 and 258–261; one peptide selected from SEQ ID NOs: 250 and 262; one peptide selected from SEQ ID NOs: 243 and 255; one peptide selected from SEQ ID NOs: 242 and 254 and one peptide selected from SEQ ID NOs: 244 and 263. In a preferred embodiment, the peptides of the present invention can be used in an ELISA assay as described previously for recombinant E1 and core proteins.

In an alternative embodiment, the peptide(s) utilized in an immunoassay to detect all the genotypes of HCV disclosed herein may be a universal peptide deduced from universally conserved amino acid domains of the E1 or core proteins disclosed herein.

Examples of universally conserved core amino acid domains within the consensus sequence shown in FIG. 7J from which universal peptides may be deduced include, but are not limited to amino acid domains 23–35, 53–66, 93–108, 122–138, 150–156, and 165–181 of the consensus sequence. Examples of universally conserved E1 amino acid domains within the HCV E1 protein are located within the consensus sequence for the 51 HCV E1 proteins shown in FIG. 2H of the present application. Examples of universally conserved domains within the consensus sequence shown in FIGS. 2H-1 to 2H-2 include, but are not limited to, amino acid domains 10–20, 111–120, and 124–137 of the consensus sequence. The universal peptides of the present invention may be used in an immunoassay to detect antibodies in patient sera specific for any of the genotypes of HCV disclosed herein.

The peptides of the present invention or analogs thereof may be prepared in the form of a kit, alone or in combinations with other reagents such as secondary antibodies, for use in immunoassay.

In another embodiment, the genotype-specific and universal peptides of the present invention may be used to produce antibodies that will react against HCV E1 or core proteins in immunoassays. In one embodiment, a genotype-specific E1 or core peptide can be used alone or in combination with other E1 or core peptides specific to the same genotype as immunogens to produce antibodies specific to HCV proteins of a single genotype.

In another embodiment, a mixture of peptides specific for different genotypes may be used to produce antibodies that will react with HCV proteins of any genotype disclosed herein. More preferably, antibodies reactive with HCV proteins of any genotype may be produced by immunizing an animal with universal peptide(s) of the present invention. Examples of immunoassays in which such antibodies could be utilized to detect HCV E1 and core proteins in biological samples include, but are not limited to, radioimmunoassays and ELISAs. Examples of biological samples in which HCV E1 and core proteins could be detected includes, but it is not limited to, serum, saliva and liver.

Of course, those skilled in the art would readily understand that the genotype-specific and universal peptides of the present invention and expression vectors containing nucleic acid sequence capable of directing host organism synthesis of these peptides could also be used as vaccines against hepatitis C. Formulations suitable for administering the peptide(s) and expression vectors of the present invention as immunogen, routes of administration, pharmaceutical compositions comprising the peptides expression vectors and so forth are the same as those previously described for recombinant E1 and core proteins.

The genotype-specific and universal peptides of the present invention and expression vectors containing nucleic acid sequence capable of direct host organism synthesis of these peptides may also be supplied in the form of a kit, alone, or in the form of a pharmaceutical composition as described above for recombinant E1 and core proteins.

Any articles or patents referenced herein are incorporated by reference. The following examples illustrate various aspects of the invention but are in no way intended to limit the scope thereof.

MATERIALS

Serum used in these examples was obtained from 84 anti-HCV positive individuals who were previously found to be positive for HCV RNA in a cDNA PCR assay with primer set a from the 5' NC region of the HCV genome (Bukh, J. et al. (1992 (b)) Proc. Natl. Acad. Sci. USA 89:4942–4946). These samples were from 12 countries: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z).

EXAMPLE 1

Identification of the cDNA Sequence of the E1 Gene of 51 Isolates of HCV Via RT-PCR Analysis of Viral RNA Using Universal Primers Viral RNA was extracted from 100 µl of serum by the guanidinium-phenol-chloroform method and the final RNA solution was divided into 10 equal aliquots and stored at −80° C. as described (Bukh, et al. (1992 (a)). The sequences of the synthetic oligonucleotides used in the RT-PCR assay, deduced from the sequence of HCV strain H-77 (Ogata, N. et al. (1991) Proc. Natl. Acad. Sci. USA 88:3392–3396), are shown as SEQ ID NOs: 207–212. One aliquot of the final RNA solution, equivalent to 10 µl of serum, was used for cDNA synthesis that was performed in a 20 µl reaction mixture using avian myeloblastosis virus reverse transcriptase (Promega, Madison, Wis.) and SEQ ID NO: 208 as a primer. The resulting cDNA was amplified in a "nested" PCR assay by Taq DNA polymerase (Amplitaq, Perkin-Elmer/Cetus) as described previously (Bukh et al. (1992a)) with primer set e (SEQ ID NOs: 207–210). Precautions were taken to avoid contamination with exogenous HCV nucleic acid (Bukh et al. 1992a)), and negative controls (normal, uninfected serum) were interspersed between every test sample in both the RNA extraction and cDNA PCR procedures. No false positive results were observed in the analysis. In most instances, amplified DNA (first or second PCR products) was reamplified with primers SEQ ID NO: 211 and SEQ ID NO: 212 prior to sequencing since these two primers contained EcoR1 sites which would facilitate future cloning of the E1 gene. Amplified DNA was purified by gel electrophoresis followed by glass-milk extraction (Geneclean, BIO 101, LaJolla, Calif.) and both strands were sequenced directly by the dideoxy-nucleotide chain termination method (Bachman, B. et al. (1990) Nucl. Acids Res. 18:1309)) with phage T7 DNA polymerase (Sequenase, United States Biochemicals, Cleveland, Ohio), [alpha $^{35}$S] dATP (Amersham, Arlington Heights, Ill.) or [alpha $^{33}$P] DATP (Amersham or DuPont, Wilmington, Del.) and sequencing primers. RNA extracted from serum containing HCV strain H-77, previously sequenced by Ogata, N. et al. (1991), was amplified with primer set e (SEQ ID NOs: 207–210) and sequenced in parallel as a control. The nucleotide sequences of the envelope 1 (E1) gene of all 51 HCV isolates are shown as SEQ ID NOs: 1–51. In all 51 HCV isolates, the E1 gene was exactly 576 nucleotides in length and did not have any in-frame stop codons.

EXAMPLE 2

Computer Analysis of the Nucleotide and Deduced Amino Acid Sequences of the E1 Gene of 51 HCV Isolates Multiple computer-generated alignments of the nucleotide (SEQ ID NOs: 1–51, FIGS. 1A-1 to 1H-3) and deduced amino acid sequences (SEQ ID NOs: 52–102, FIGS. 2A-1 to 2H-2) of the cDNAs of the 51 HCV isolates constructed using the computer program GENALIGN (Miller, R. H. et al. (1990) Proc. Natl. Acad. Sci. USA 87:2057–2061) resulted in the 51 HCV isolates being divided into twelve genotypes based upon the degree of variation of the E1 gene sequence as shown in table 1.

Biochemistry: Bukh et al.

TABLE 1

Percent nucleotide (nt) and amino acid (aa) sequence identify of the E1 gene among the 12 HCV genotypes.

|       | I/1a | II/1b | III/2a | IV/2b | 2c | (V)/3a | 4a | 4b | 4c | 4d | 5a | 6a | nt: |
|---|---|---|---|---|---|---|---|---|---|---|---|---|---|
|       | 89.9–97.6 | 72.0–76.2 | 59.2–63.7 | 56.1–58.3 | 60.8–62.8 | 63.0–66.3 | 63.9–67.2 | 64.9–66.8 | 62.7–64.4 | 67.7–69.4 | 62.3–67.2 | 62.2–63.9 | I/1a |
| aa:   |      | 88.9–97.9 | 58.3–62.2 | 53.8–57.5 | 60.1–61.5 | 63.9–67.2 | 60.9–63.7 | 63.4–65.8 | 61.6–65.1 | 63.0–65.5 | 62.2–66.5 | 61.6–63.0 | II/1b |
| I/1a  | 91.1–98.4 |  | 88.0–91.3 | 69.1–71.0 | 72.7–73.6 | 58.0–60.8 | 61.5–62.7 | 58.9–60.4 | 59.7–63.4 | 58.7–61.3 | 56.6–60.8 | 55.0–56.8 | III/2a |
| II/1b | 75.5–80.7 | 90.1–97.9 |  | 92.7–95.0 | 67.5–68.9 | 56.3–58.3 | 58.9–60.8 | 56.4–57.6 | 57.1–59.9 | 57.5–59.0 | 53.5–56.6 | 53.6–55.2 | IV/2b |
| III/2a | 58.3–64.6 | 52.6–56.8 | 89.1–92.7 | — |  | 57.5–58.2 | 59.2 | 58.5 | 58.0–58.3 | 58.9 | 56.9–57.1 | 57.6 | 2c |
| IV/2b | 54.2–56.8 | 51.0–54.2 | 69.3–72.9 | 93.8–96.4 |  | 93.8–99.1 | 64.4–65.3 | 62.7–64.1 | 60.9–62.5 | 62.3–63.9 | 61.8–64.4 | 58.0–58.9 | (V)/3a |
| 2c    | 56.3–60.4 | 52.6–55.7 | 74.5–77.1 | 67.7–69.8 | — |  | — | 74.8 | 75.5–78.0 | 74.8 | 62.8–64.6 | 62.0 | 4a |

TABLE 1-continued

Percent nucleotide (nt) and amino acid (aa) sequence identify of the E1 gene among the 12 HCV genotypes.

| | I/1a | II/1b | III/2a | IV/2b | 2c | (V)/3a | 4a | 4b | 4c | 4d | 5a | 6a | nt: |
|---|---|---|---|---|---|---|---|---|---|---|---|---|---|
| (V)/3a | 64.1–68.8 | 66.7–70.8 | 54.7–58.9 | 54.2–56.8 | 52.1–53.6 | 94.3–98.4 | | — | 74.0–74.8 | 72.0 | 63.9–64.6 | 62.7 | 4b |
| 4a | 69.3–73.4 | 64.6–67.2 | 62.0–63.0 | 58.9–60.4 | 58.3 | 66.1–68.8 | — | | 90.1 | 77.6–78.6 | 62.7–64.8 | 63.0–64.4 | 4c |
| 4b | 66.7–69.3 | 66.1–70.3 | 53.6–56.3 | 52.1–53.1 | 53.6 | 62.0–64.6 | 76.0 | — | | | 64.4–66.1 | 64.1 | 4d |
| 4c | 66.1–72.9 | 64.6–69.3 | 55.2–61.5 | 54.1–58.3 | 54.7–58.3 | 63.0–65.6 | 77.1–81.3 | 79.2–80.2 | 89.6 | | 90.1–95.7 | 60.6–63.2 | 5a |
| 4d | 73.4–75.5 | 66.7–70.3 | 56.3–58.9 | 55.2–55.7 | 54.2 | 63.,5–64.6 | 78.1 | 77.6 | 82.8 | — | | — | 6a |
| 5a | 66.1–73.4 | 64.1–70.3 | 52.6–57.3 | 50.5–53.1 | 54.2–56.3 | 60.4–64.1 | 67.2–68.2 | 65.1–67.2 | 67.7–71.4 | 69.3–71.4 | 92.7–97.4 | | |
| 6a | 64.6–65.6 | 62.5–65.6 | 49.0–51.0 | 49.0–50.5 | 50.5 | 57.8–58.9 | 66.1 | 62.5 | 66.1–67.2 | 66.7 | 62.0–63.5 | — | |

Nucleotide sequences analyzed in compiling the above table are shown in SEQ ID NOs:1–51 while the amino acid sequences analyzed are shown in SEQ ID NOs:52–102.
The grouping of SEQ ID NOs: into gentoypes is previously described in the specification.

The nucleotide and amino acid sequence identity of HCV isolates of the same genotype was in the range of 88.0–99.1% and 89.1–98.4%, respectively, whereas that of HCV isolates of different genotypes was in the range of 53.5–78.6% and 49.0–82.8%, respectively. The latter differences are similar to those found when comparing the envelope gene sequences of the various serotypes of the related flaviviruses, as well as other RNA viruses. When microheterogeneity in a sequence was observed, defined as more than one prominent nucleotide at a specific position, the nucleotide that was identical to that of the HCV prototype (HCV1, Choo et al. (1989)) was reported if possible. Alternatively, the nucleotide that was identical to the most closely related isolate is shown.

Figure 3A:
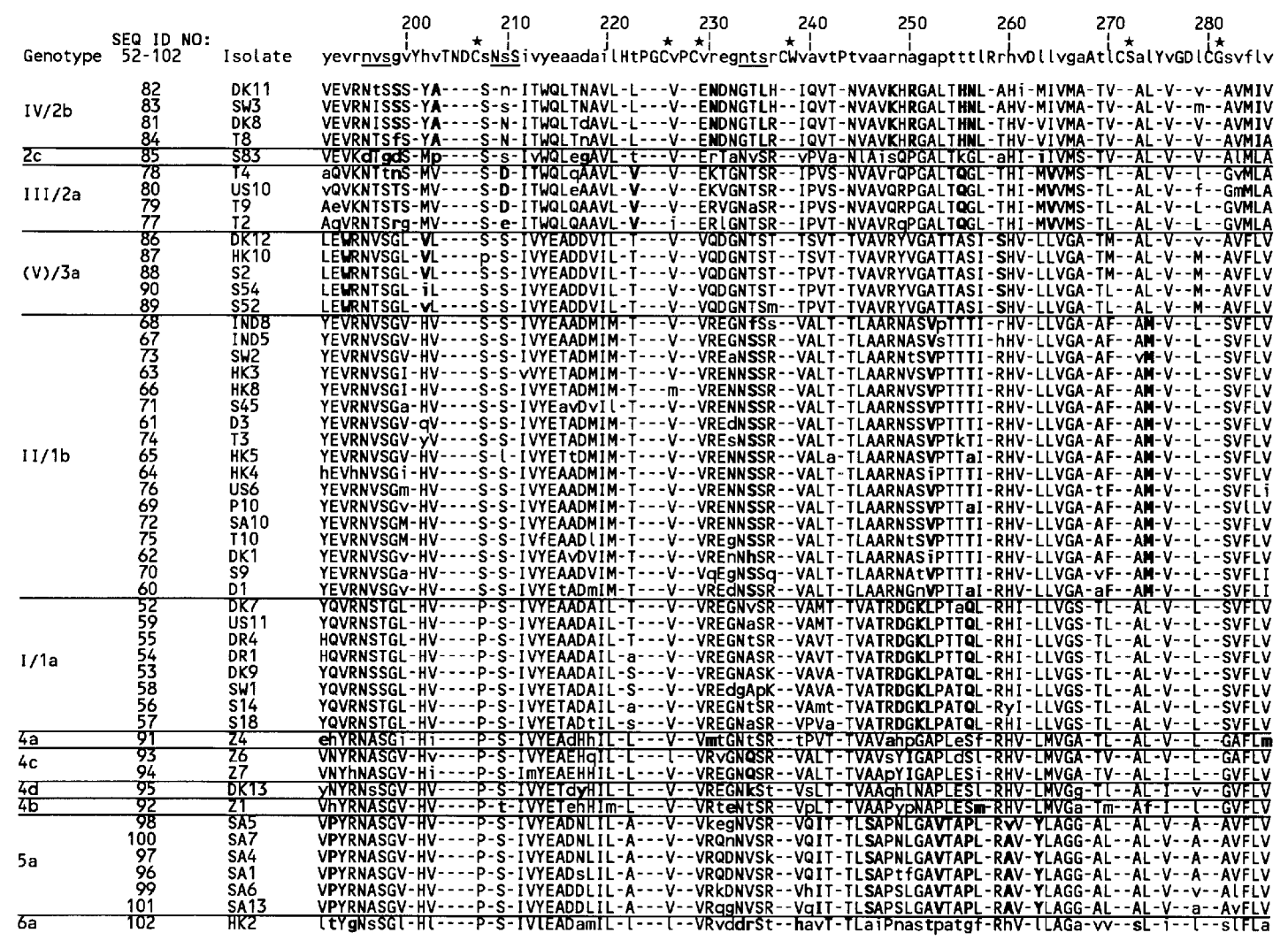
Figure 3B:
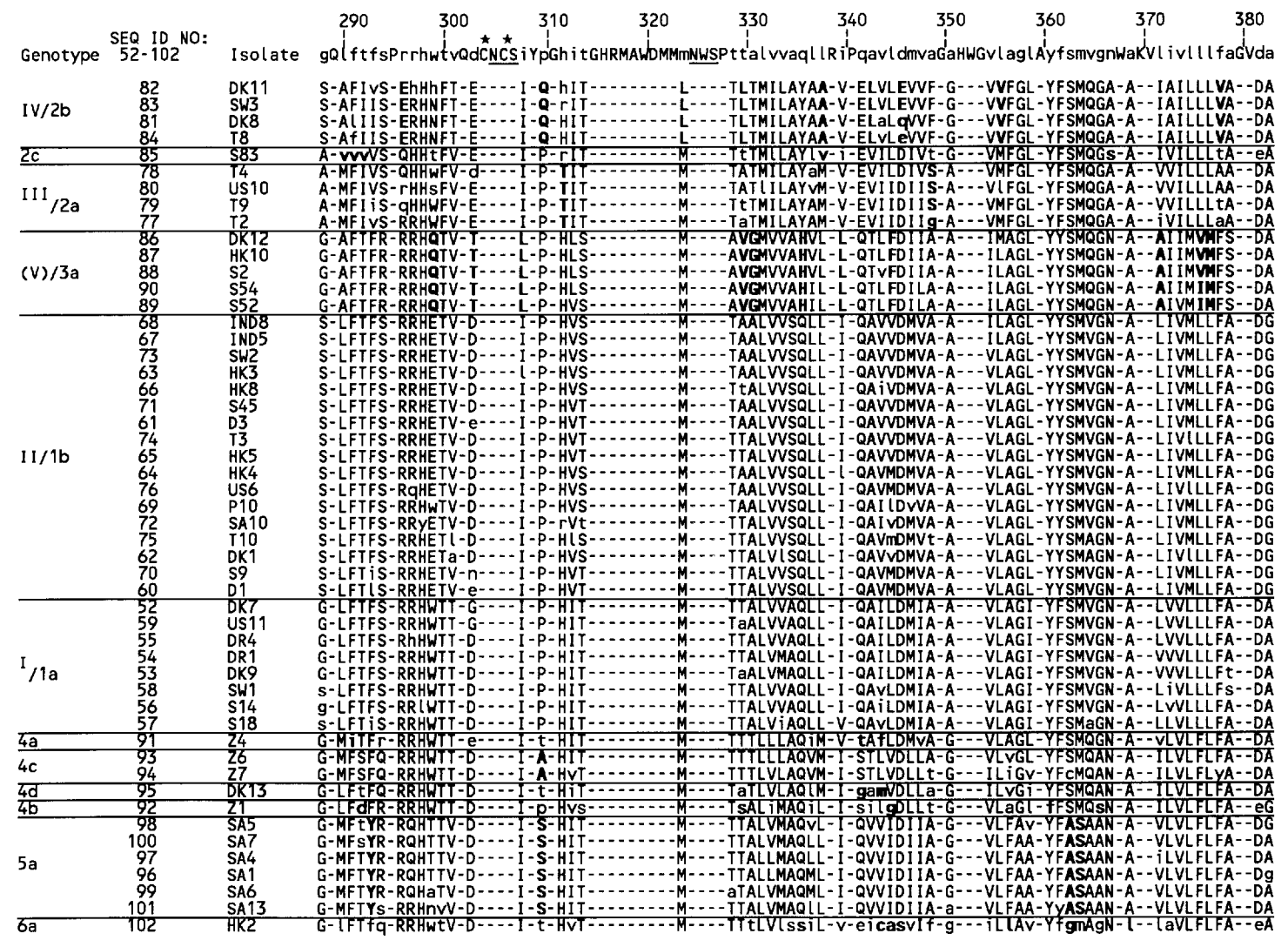

Analysis of the consensus sequence of the E1 protein of the 51 HCV isolates from this study demonstrated that a total of 60 (30.3%) of the 192 amino acids of the E1 protein were invariant among these isolates (FIGS. 3A and 3B). Most impressive, all 8 cysteine residues as well as 6 of 8 proline residues were invariant. The most abundant amino acids (e.g. alanine, valine and leucine) showed a very low degree of conservation. The consensus sequence of the E1 protein contained 5 potential N-linked glycosylation sites. Three sites at positions 209, 305 and 325 were maintained in all 51 HCV isolates. A site at position 196 was maintained in all isolates except the sole isolate of genotype 2c. Also, a site at position 234 was maintained in all isolates except one isolate of genotype I/1a, all four isolates of genotype IV/2b and the sole isolate of genotype 6a. Conversely, only genotype IV/2b isolates had a potential glycosylation site at position 233. Further analysis revealed a highly conserved amino acid domain (aa 302–328) in the E1 protein with 20 (74.1%) of 27 amino acids invariant among all 51 HCV isolates. It is possible that the 5' and 3' ends of this domain are conserved due to important cysteine residues and N-linked glycosylation sites. The central sequence, 5'-GHRMAWDMM-3' (aa 315–323), may be conserved due to additional functional constraints on the protein structure. Finally, although the amino acid sequence surrounding the putative E1 protein cleavage site was variable, an amino acid doublet (GV) at position 380 was invariant among all HCV isolates.

A dendrogram of the genetic relatedness of the E1 protein of selected HCV isolates representing the 12 genotypes is shown in FIG. 4. This dendrogram was constructed using the program CLUSTAL (Higgins, D. G. et al. (1988) Gene, 73:237–244) and had a limit of 25 sequences. The scale showing percent identity was added based upon manual calculation. From the 51 HCV isolates for which the complete sequence of the E1 gene region was obtained, 25 isolates representing the twelve genotypes were selected for analysis. This dendrogram in combination with the analysis of the E1 gene sequence of 51 HCV isolates in Table 1 demonstrates extensive heterogeneity of this important gene.

The worldwide distribution of the 12 genotypes among 74 HCV isolates is depicted in FIG. 5. The complete E1 gene sequence was determined in 51 of these HCV isolates (SEQ ID NOs: 1–51), including 8 isolates of genotype I/1a, 17 isolates of genotype II/1b and 26 isolates comprising genotypes III/2a, IV/2b, 2c, 3a, 4a–4d, 5a and 6a. In the remaining 23 isolates, all of genotypes I/1a and II/1b, the genotype assignment was based on a partial E1 gene sequence since they did not represent additional genotypes in any of the 12 countries. The number of isolates of a particular genotype is given in each of the 12 countries studied. Of the twelve genotypes, genotypes I/1a and II/1b were the most common accounting for 48 (65%) of the 74 isolates. Analysis of the E1 gene sequences available in the GenBank data base at the time of this study revealed that all 44 such sequences were of genotypes I/1a, II/1b, III/2a and IV/2b. Thus, based upon E1 gene analysis, 8 new genotypes of HCV have been identified.

Also of interest, different HCV genotypes were frequently found in the same country, with the highest number of genotypes (five) being detected in Denmark. Of the twelve genotypes, genotypes I/1a, II/1b, III/2a, IV/2b and V/3a were widely distributed with genotype II/1b being identified in 11 of 12 countries studied (Zaire was the only exception). In addition, while genotypes I/1a and II/1b were predominant in the Americas, Europe and Asia, several new genotypes were predominant in Africa.

It was also found that genotypes I/1a, II/1b, III/2a, IV/2b and V/3a of HCV were widely distributed around the world, whereas genotypes 2c, 4a, 4b, 4d, 5a and 6a were identified only in discreet geographical regions. For example, the majority of isolates in South Africa comprised a new genotype (5a) and all isolates in Zaire comprised 3 new closely related genotypes (4a, 4b, 4c). These genotypes were not identified outside Africa.

EXAMPLE 3

Identification of the cDNA Sequence of the Core Gene of 52 Isolates of HCV

Viral RNA extraction, cDNA synthesis and "nested" PCR were carried out as in Example 1. For the cDNA PCR assay HCV-specific synthetic oligonucleotides deduced from previously determined sequences that flank the C gene were used. Amplified DNA was purified by gel electrophoresis followed by glass-milk extraction as described in Example 1 or by electroelution and both strands were sequenced directly. In 44 of the 52 HCV isolates studied the procedures for direct sequencing described in Example 1 were utilized. For a number of the HCV isolates confirmatory sequencing was performed with the Applied Biosystems 373A automated DNA sequencer and 8 HCV isolates of genotype I/1a or II/1b were sequenced exclusively by this method. All 73 negative control samples interspersed among the test samples were negative for HCV RNA.

The amplified DNA fragment obtained in 50 of the 52 HCV isolates was specifically designed to overlap with previously obtained 5' NC sequences (Bukh et al. (1992b) Proc. Natl. Acad. Sci. U.S.A. 89:4942–4946) and with the E1 sequences disclosed herein at approximately 80 nucleotide positions each. A complete match was observed in 6033 of 6035 overlapping nucleotides. Two discrepancies were observed in isolate US6 at nt 552 (C and T) and nt 561 (C and T) respectively. This may have been due to microheterogeneity at these nucleotide positions, since the remaining overlapping sequence was unique for isolate US6. In addition, there were 3 confirmed instances of microheterogeneity: nt 33 in isolate SA11 (C,T and T), nt 36 in isolate S45 (A,C and A), and nt 552 in isolate P10 (C,T and T). Overall, the excellent agreement in these overlapping sequences in this study with the NC sequences disclosed in Bukh et al. and with the E1 sequences disclosed herein definitively ruled out contamination as a source of non-authentic HCV sequences. Furthermore, this analysis proved that the sequences obtained were from a single population, and not from different populations as could happen in mixed infections.

Figure 8A:
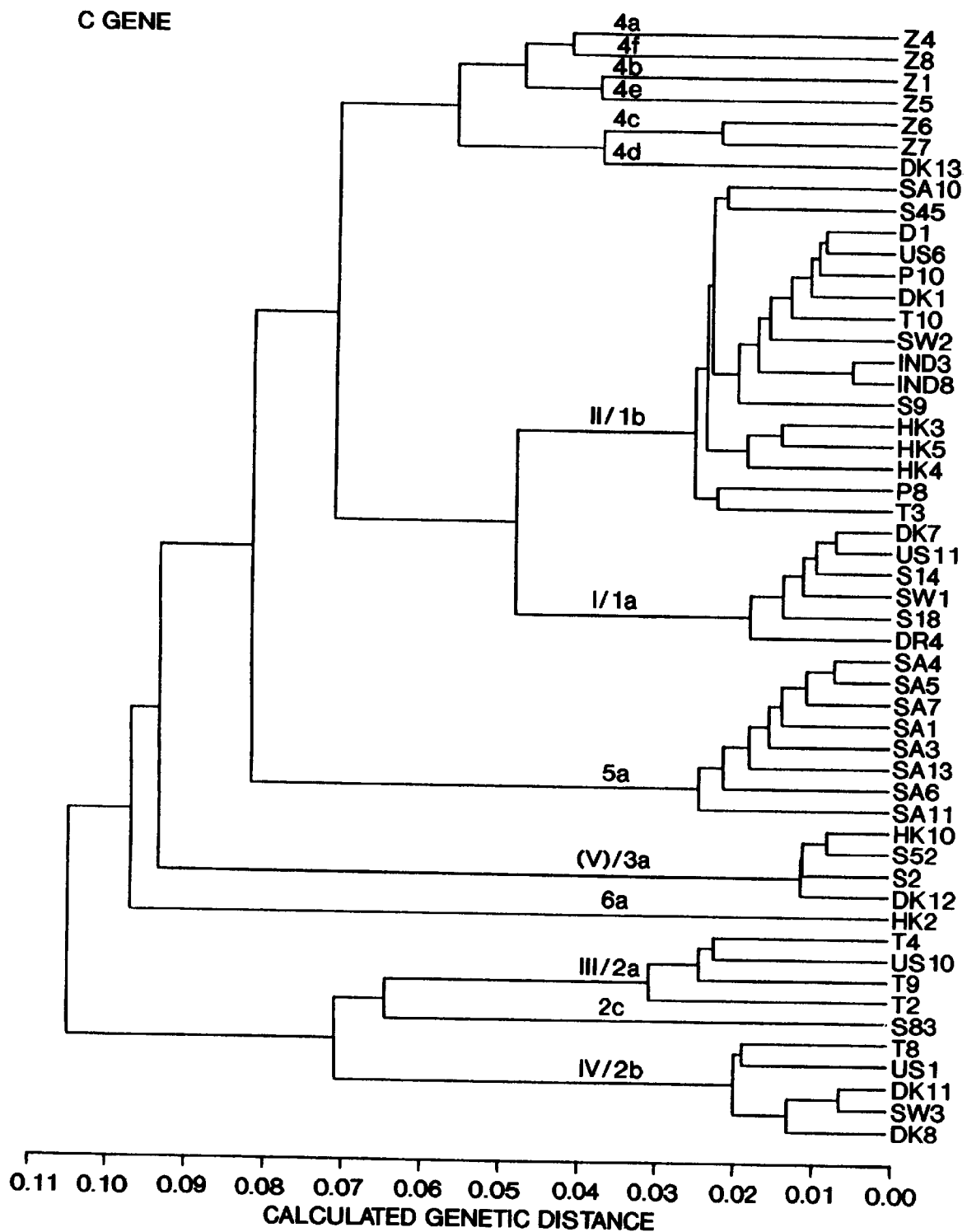
FIGS. 8A and 8B show phylogenetic trees illustrating the calculated evolutionary relationships of the different HCV isolates based upon the C gene sequence of 52 HCV isolates and the E1 gene sequence of 51 HCV isolates, respectively. The phylogenetic trees were constructed by the unweighted pair-group method with arithmetic mean (Nei, M. (1987) *Molecular Evolutionary Genetics* (Columbia University Press, New York, N.Y.), pp 287–326) using the computer software package "Gene Works" from IntelliGenetics. The lengths of the horizontal lines connecting the sequences, given in absolute values from 0 to 1, are proportional to the estimated genetic distances between the sequences. Genotype designations of HCV isolates are indicated. In 45 HCV isolates, both the C and the E1 gene sequences were determined.
Figure 8B:
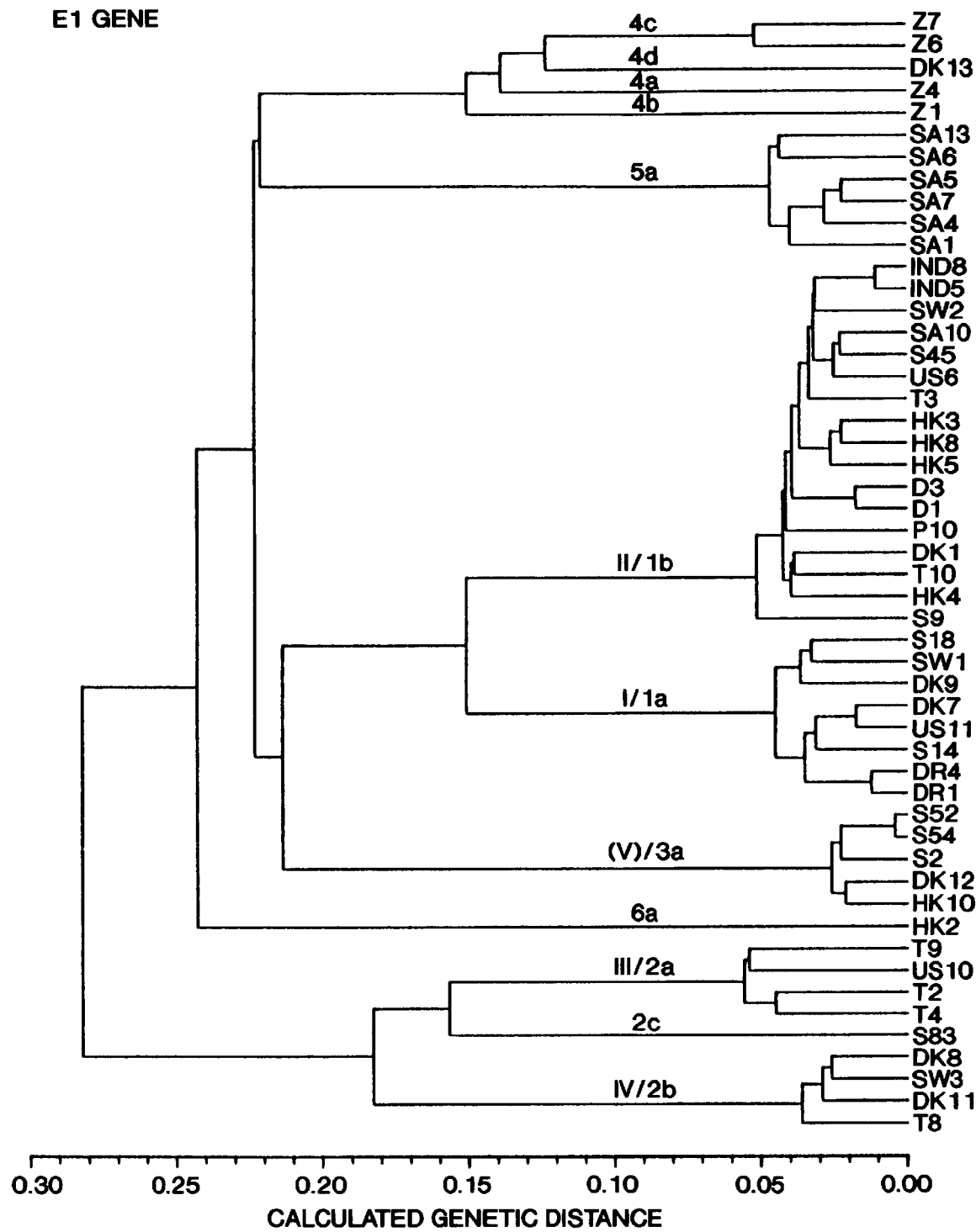

The core (C) gene was exactly 573 nucleotides in length in all 52 HCV isolates with an amino terminal start codon and no in-frame stop codons. Microheterogeneity was observed in 26 of the 52 HCV isolates at 0.2–1.4% of the 573 nucleotide positions of the C gene, and resulted in changes in 0.5–1.0% of the 191 predicted amino acids in 12 of these isolates. A multiple sequence alignment was performed and it showed that the nucleotide identities of the C gene among these HCV isolates were in the range of 79.4–99.0%. In order to compare the genetic relatedness of HCV isolates in different gene regions, phylogenetic trees of the C gene of all 52 HCV isolates and the E1 gene of 51 HCV isolates were constructed using the unweighted pair-group method with arithmetic mean (Nei, M. (1987) Molecular Evolutionary Genetics (Columbia University Press, New York, N.Y., pp. 287–326) (FIGS. 8A and 8B). In both dendrograms a division of the 45 HCV isolates from which C and E1 genes had been cloned into at least six major genetic groups (genotypes 1–6) and 12 minor genetic groups (genotypes I/1a, II/1b, III/2a, IV/2b, 2c, V/3a, 4a–4d, 5a, and 6a) was observed. It is noteworthy that a major division in genetic distance between HCV isolates of genotype 2 and those of the other genotypes in the phylogenetic analyses of both gene sequences was observed. Furthermore, the divergence of the minor genotypes within genotype 2 exhibited a degree of heterogeneity that is equivalent to that observed among the major genotypes. Analysis of the C gene from isolates Z5 and Z8, which had a unique 5' NC sequence (Bukh et al. (1992)) but from which the E1 gene could not be amplified, revealed that these isolates represented two additional genotypes. The designations 4e and 4f are assigned to these genotypes that have not been described previously. Overall, the present specification demonstrates that the genetic relatedness of HCV isolates is equivalent when analyzing the most conserved gene (C) and one of the most variable genes (E1) of the HCV genome, thereby providing strong evidence for the suggested division into major and minor genotypes.

EXAMPLE 4

Computer Analysis of the Nucleotide and Deduced Amino Acid Sequences of the Core Gene of 52 HCV Isolates In order to study further the heterogeneity of the C gene, a consensus sequence of the core gene from the 52 HCV isolates (FIGS. 6J-1 to 6J-4) was obtained. A total of 335 (58.5%) of the 573 nucleotides of the C gene were invariant among these HCV isolates. Nucleotides at the 1st and 2nd codon positions were invariant at 70.7% and 81.7% of these positions, respectively, while nucleotides at the 3rd position were invariant at only 23.0% of such positions. Stretches of 6 or more invariant nucleotides were observed from nucleotides 1–8, 22–27, 85–92, 110–125, 131–141, 334–340, 364–371, 397–404, and 511–516 and may be suitable for anchoring primers for amplification of HCV RNA in cDNA PCR assays.

Genotype-specific nucleotide positions of the core gene of hepatitis C virus were also noted for each of the genotypes. These genotype-specific nucleotides are shown below where each genotype-specific nucleotide is given in parentheses next to the nucleotide position in which it is found.

Genotype 1: 460 (C), 466 (C), 483 (C), 486 (G).
Genotype I/1a: 180 (T).
Genotype II/1b: 106 (C), 273 (G).
Genotype 2: 192 (C), 201 (A), 203 (A), 207 (G), 210 (C), 221 (A), 231 (A), 232 (A), 341(A).
Genotype III/2a: 315 (C), 355 (G).
Genotype IV/2b: 45 (A), 174 (G), 216 (C), 348 (A), 376 (A), 414 (T).
Genotype 2c: 233 (G), 312 (C), 318 (A), 456 (C), 462 (G), 543 (C), 556 (T).
Genotype V/3a: 47 (T), 84 (A), 106 (G), 126 (A), 150 (T), 212 (G), 216 (A), 300 (A), 491 (T), 559 (C), 560 (A), 568 (G), 571 (A), 572 (G)
Genotype 4: 59 (T).
Genotype 4a: 213 (A), 231 (G), 415 (A).
Genotype 4b: 66 (G), 145 (G), 310 (A).
Genotype 4c: 213 (T), 219 (A), 270 (T).
Genotype 4d: 212 (T) , 327 (G) , 469 (C)
Genotype 4e: 199 (C), 306 (A), 326 (A).
Genotype 4f: 57 (T), 75 (A), 267 (A).
Genotype 5a: 291 (G), 294 (C).
Genotype 6a: 59 (C), 175 (A), 195 (A), 198 (A), 214 (C), 224 (A), 316 (C), 351 (G), 387 (G), 444–447 (GGCT), 450 (G), 471–472 (AA), 474 (C).

These genotype-specific nucleotides are of utility in designing the genotype-specific PCR primers and hybridization probes.

Finally, although the full length nucleic acid sequence of the C gene of isolates representing genotypes I/1a, II/1b, III/2a, IV/2b and V/3a have been reported by others, those of 9 of the 14 genotypes (i.e., 2c, 4a–4f, 5a and 6a) have not been reported previously. In sum, by aligning the consensus sequences of the major genotypes, the present application enables those skilled in the art to map universally conserved sequences as well as genotype-specific sequences of the C gene among 14 genotypes of HCV.

In order to study the heterogeneity of the deduced C protein, a multiple sequence alignment of the predicted amino acids for all 52 HCV isolates was performed, and a consensus sequence was obtained (FIG. 7J). The identities of the predicted 191 amino acids of the C protein among these HCV isolates were in the range of 85.3–100.0%. A total of 132 (69.1%) of the 191 amino acids of the C protein were invariant. The most prevalent amino acids in the consensus sequence were glycine (13.6%), arginine (12.6%), proline (11.0%), and leucine (9.9%). The most conserved amino acids were tryptophan (5 of 5 amino acids invariant), aspartic acid (5 of 5 amino acids invariant), proline (19 of 21 amino acids invariant) and glycine (23 of 26 amino acids invariant). Previous analyses indicated that HCV is evolutionarily related to pestiviruses (Miller et al. (1990) *Proc. Natl. Acad. Sci. U.S.A.* 87:2057–2061). In this regard, it is of interest to note that the C proteins of both viruses have a high content of proline residues (Collette M. S. et al. (1988) *Virology* 165:200–208), which are likely to be important in maintaining the structure of this protein. As is characteristic for a protein that binds to nucleic acid, the C protein has conserved amino acids that are basic and positively charged, and these are capable of neutralizing the negative charge of the HCV RNA encapsidated by this protein (Rice, C. M. et al. (1986) in Togaviridae and Flaviviridae, eds Schleinger, S. & Schlensinger, M. J. (Plenum Press, New York, N.Y.) pp. 279–326). Specifically, over 16% of the amino acids in the consensus sequence of the C protein of HCV are arginine and lysine that are located primarily in three clusters (i.e., from amino acids 6–23, 39–74 and 101–121) (Shih, C. M. et al. (1993) *J. Gen. Virol.* 67:5823–5832) (FIG. 7J). The 10 arginine and lysine residues within amino acids 39–62 are invariant among all 52 HCV isolates, suggesting that this domain may represent an important RNA-binding site. The capsid proteins of the related flavi-and pestiviruses (Miller et al. (1990)) also have a high content of arginine and lysine (Rice et al. (1986); Collette et al. (1988). Although there are three major hydrophilic regions (i.e., amino acids 2–23, 39–74 and 101–121) that are conserved in all 52 HCV isolates, the remainder of the C protein is hydrophobic. Interestingly, one such highly conserved hydrophobic domain from aa 24–39 is flanked by proline residues. The hydrophobic domains are likely to be involved in protein-protein and/or protein-RNA interactions during assembly of the nucleocapsid, as well as in interaction with the lipoprotein envelope, as has been suggested for flaviviruses (Rice et al. (1986)). Other significant observations are: (i) a cluster of 5 invariant tryptophan residues from aa 76–107; (ii) the lack of an N-linked glycosylation site (N-X-T/S); (iii) two potential nuclear localization signals (i.e., PRRGPR at amino acids 38–43 and PRGRRQP at amino acids 58–64) that are present in all 52 HCV isolates (Shih et al. (1993)); and (iv) a putative DNA-binding motif SPRG at amino acids 99–102, found in 51 of the 52 HCV isolates, with SP present in all 52 isolates. This study demonstrates that the C protein has features that are highly conserved among the various genotypes of HCV, and that are known to be characteristic of capsid proteins of other related viruses.

It should also be noted that the phylogenetic analysis of the amino acid sequence of the C proteins was not capable of resolving the minor groups within genotypes 1 and 4 because of the conservation of this protein (data not shown). Indeed, only a few type-specific amino acids were identified. One striking example was that isolates of genotype 4 have an additional methionine at position 20 that is specific for this major genetic group. Finally, the conservation of the sequences surrounding the cleavage site between the C and the E1 proteins of the different genotypes, which has been determined to be between amino acid 191 (alanine) and aa 192 (tyrosine) in HCV isolates of genotype 1 was analyzed (Hijikata, M., et al. (1991) *Proc. Natl. Acad. Sci. USA* 88:5547–5551). The C-terminal sequence of C is serine-alanine in all but one of the 48 HCV isolates comprising genotypes 1, 2, 4, 5 and 6. However, all 4 HCV isolates of genotype 3 in this study, as well as isolates of genotype 3 published previously (Okamoto, H., et al. (1993) *J. Gen. Virol.* 74:2385–2390, Stuyver, L., et al. (1993) *Biochem. Biophys. Res. Comm.* 192:635–641), contain alanine-serine at this position. Thus, studies will be needed to determine the C/E1 cleavage site in genotype 3 isolates. Overall, the present invention application discloses the mapping of universally conserved sequences, as well as genotype-specific sequences, of the C protein among 14 genotypes of HCV. Implications of the mapping of universally conserved and genotype-specific core nucleotide and amino acid core sequences for diagnosis of HCV infection and for determination of HCV genotypes Detection of antibodies directed against the HCV core protein is important in the diagnosis of HCV infection. The recombinant C22-3 protein, spanning amino acids 2–120 of the C gene, is a major component of the commercially available second-generation anti-HCV tests. Several studies have indicated that the three major hydrophilic regions of the C protein contain linear immunogenic epitopes (summarized in *J. Clin. Microbiol*, 30:1989–1994) (Sallberg, M. et al. (1992). For example, antibodies against synthetic peptides from amino acids 1–18, 51–68 and 101–118 were detected in infected patients (Sällberg, M. et al. (1992)). The present application demonstrates that, while these immunogenic regions are highly conserved, genotype-specific differences are observed at several amino acid positions that may influence the specificity and sensitivity of the serological tests. One such example is that a single amino acid substitution at amino acid 110 has been demonstrated to affect sero-reactivity (Sällberg, et al. (1992)). Despite the high degree of conservation in the immunodominant regions of the C protein among the different genotypes, it is possible that genetic heterogeneity of the C protein could lead to false negative results in current serological tests.

With respect to genotype analysis, several methods have been used to determine the genotype of HCV isolates without resorting to sequence analysis. These include PCR followed by: (i) amplification with type-specific primers (Okamoto, H. et al. (1992) *J. Gen. Virol.*, 73:673–679); (ii) determination of restriction-length polymorphism (Simmons, P. et al. (1993) *J. Gen. Virol.*, 74:661–668); and (iii) specific hybridization (Stuyver, L. (1993) *J. Gen. Virol.*, 74:1093–1102). The proposed methods have primarily been based on 5' NC and C sequences. Previous studies suggested that 5' NC-based genotyping systems would only be predictive of the major genetic groups of HCV (Bukh, J., et al. (1992) *Proc. Natl. Acad. Sci. USA* 89:4942–4946, Bukh, J., et al. (1993) *Proc. Natl. Acad. Sci. USA* 90:8234–8238). The most widely used C-based genotype system has been the PCR assay with type-specific primers that was designed for distinguishing HCV isolates of genotypes I/1a, II/1b, III/2a, IV/2b and V/3a (Okamoto, H., et al. (1993) *J. Gen. Virol.* 74:2385–2390, Okamoto, H. et al. (1992) *J. Gen. Virol.* 73:673–679). Since this system was developed prior to the identification of genotypes 2c, 4a–4f, 5a and 6a there are significant limitations to this typing system. For example, the primers specific for genotype IV/2b (nt 270–251) are as highly conserved within isolates of genotype 4c and 6a as within the isolates of genotype IV/2b. Thus, this assay probably can not distinguish among these genotypes. Another C-based approach involves distinguishing between genotypes 1 and 2 by type-specific antibody responses (Machida et al (1992) *Hepotology*, 16:886–891). Synthetic peptides composed of amino acids 65–81 were found to be genotype-specific for genotypes 1 and 2 in ELISA assays. The present analysis of amino acid sequences demonstrated significant variation within isolates of genotypes 1 and 2. Thus it is likely that these peptides will not identify all isolates of genotypes 1 and 2. Furthermore, the peptide for genotype 1 was highly conserved within isolates of genotypes 3 and 4 and might detect antibodies against these genotypes as well. Finally, it should be pointed out that most isolates of genotypes 3 and 4 had an identical amino acid sequence at positions 65–81.

EXAMPLE 5

Detection by ELISA Based on Antigen from Insect Cells Expressing Complete E1 or Core Protein Expression of E1 or Core protein in SF9 cells. A cDNA (eg SEQ ID NO: 1) encoding a complete E1 protein (eg SEQ ID NO: 52) or a cDNA (eg SEQ ID NO: 103) encoding a complete core protein (e.g. SEQ ID NO: 155) is subcloned into pBlueBac—Transfer vector (Invitrogen) using standard subcloning procedures. The resultant recombinant expression vector is cotransfected into SF9 insect cells (Invitrogen) by the Ca precipitation method according to the Invitrogen protocol.

ELISA Based on Infected SF9 cells. $5 \times 10^6$ SF9 cells infected with the above-described recombinant expression vector are resuspended in 1 ml of 10 mM Tris-HCl, pH 7.5, 0.15M NaCl and are then frozen and thawed 3 times. 10 ul of this suspension is dissolved in 10 ml of carbonate buffer (pH 9.6) and used to cover one flexible microtiter assay plate (Falcon). Serum samples are diluted 1:20, 1:400 and 1:8000, or 1:100, 1:1000 and 1:10000. Blocking and washing solutions for use in the ELISA assay are PBS containing 10% fetal calf serum and 0.5% gelatin (blocking solution) and PBS with 0.05% Tween –20 (Sigma, St.Louis, Mo.) (washing solution). As a secondary antibody, peroxidase-conjugated goat IgG fraction to human IgG or horse radish peroxidase-labelled goat anti-Old or anti-New World monkey immunoglobulin is used. The results are determined by measuring the optical density (O.D.) at 405 nm.

To determine if insect cells-derived E1 or core protein representing genotype I/a of HCV could detect anti-HCV antibody in chimpanzees infected with genotype I/1a of HCV, three infected chimpanzees are examined. The serum of all 3 chimpanzees are found to seroconvert to anti-HCV.

EXAMPLE 6

Use of the Complete E1 Protein as a Vaccine

Mammals are immunized with purified or partially purified E1 protein in an amount sufficient to stimulate the production of protective antibodies. The immunized mammals challenged with various genotypes of HCV are protected.

It is understood by one skilled in the art that the recombinant E1 protein used in the above vaccine can also be used in combination with other recombinant E1 proteins having an amino acid sequence shown in SEQ ID NOs: 52–102. In addition, recombinant core proteins having an amino acid sequence shown in SEQ ID NOs: 155–206 could also be used in the above vaccine, either alone, in combination with other recombinant core proteins of the present invention, or in combination with recombinant E1 proteins having an amino acid sequence shown in SEQ ID NOs: 52–102.

EXAMPLE 7

Determination of the Genotype of an HCV Isolate Via Hybridization of Genotype-Specific Oligonucleotides to RT-PCR Amplification Products Viral RNA is isolated from serum obtained from a mammal and is subjected to RT-PCR as in Example 1 or Example 3. Following amplification, the amplified DNA is purified as described in Example 1 or Example 3 and aliquots of 100 ul of amplification product are applied to dots on a nitrocellulose filter set in a dot blot apparatus. The dots are then cut into separate dots and each dot is hybridized to a $^{32}P$-labelled oligonucleotide specific for a single genotype of HCV. The oligonucleotides to be used as hybridization probes are deduced from the consensus sequences shown in FIGS. 1A-1 to 1H-3 or 6A-1 to 6J-4 or from the SEQ ID NOs: representing E1 or core sequences comprising genotypes 4a–4f, 2c and 6a.

EXAMPLE 8

ELISA Based on Synthetic Peptides Derived From E1 cDNA Sequences

E1 peptide(s) specific for genotype I/1a is placed in 0.1% PBS buffer and 50 ul of a 1mg/ml solution of peptide is used to cover each well of the microtiter assay plate. Serum samples from two mammals infected with genotype I/1a HCV and from one mammal infected with genotype 5a HCV are diluted as in Example 3 and the ELISA is carried out as in Example 3. Both mammals infected with genotype I HCV react positively with peptides while the mammal infected with genotype 5a HCV exhibits no reactivity. One skilled in the art would readily understand that in the above experiment, core peptides specific for genotype I/1a could be used in place of, or in combination with the E1 genotype-specific peptide(s).

EXAMPLE 9

Use of E1 Peptides as a Vaccine

Since the E1 genotype-specific peptides of the present invention are derived from two variable regions in the complete E1 protein, there exists support for the use of these peptides as a vaccine to protect against a variety of HCV genotypes. Mammals are immunized with peptide(s) selected from SEQ ID NOs: 136–159 in an amount sufficient to stimulate production of protective antibodies. The immunized mammals challenged with various genotypes of HCV are protected. One skilled in the art would readily understand that genotype-specific core peptides of the present invention could also be used either alone, in combination with each other, or in combination with the genotype-specific E1 peptides, as a vaccine to protect against a variety of HCV genotypes. In addition, the above vaccines may also be formulated using the universal core and/or E1 peptides of the present invention.

We claim:

1. A method for detecting the presence of a hepatitis C virus in a biological sample comprising:
   (a) amplifying reverse transcription products of RNA via polymerase chain reaction using universal primers consisting of at least 15 contiguous nucleotides selected from the following regions of SEQ ID NOs: 103–154:
      (i) sense nucleotide regions 1–33, 50–89, 51–90, 52–91, 53–92, 61–100, 62–101, 77–116, 78–117, 79–118, 80–119, 81–120, 82–121, 83–122, 84–123, 85–124, 86–125, 329–368, 330–369, 331–370, 332–371, 354–393, 355–394, 356–395, 442–481, 443–482, 457–496, 458–497, 475–514, 476–515, 477–516 and,
      (ii) antisense nucleotide regions 40–1, 41–2, 42–3, 43–4, 51–12, 52–13, 55–16, 56–17, 57–18, 58–19, 61–22, 62–23, 63–24, 64–25, 70–31, 124–85, 125–86, 126–87, 127–88, 128–89, 129–90, 517–478, 518–479, 519–480, 532–493, 533–494, 550–511, 551–512; and
   (b) detecting said amplification products, wherein detection of said product indicates the presence of hepatitis C virus in the biological sample.

2. A method for determining the major genotype of a hepatitis C virus isolate comprising:
   (a) amplifying reverse transcription products of RNA via polymerase chain reaction using amplification primers consisting of at least 15 contiguous nucleotides selected from the following major genotype-specific nucleotide domains:
      (i) major genotype 1-specific nucleotide domains located in sense nucleotide regions 427–466, 444–483, 447–486 and antisense nucleotide regions 505–466, 522–483 and 525–486 of SEQ ID NOs: 103–124;
      (ii) major genotype 2-specific nucleotide domains located in sense nucleotide regions 153–192, 162–201, 164–203, 168–207, 171–210, 182–221, 192–231, 197–242 and antisense nucleotide regions 231–192, 240–201, 242–203, 246–207, 249–210 and 380–341 of SEQ ID NOs: 125–134;
      (iii) major genotype 3-specific nucleotide domains located in SEQ ID NOs: 135–138;
      (iv) major genotype 4-specific nucleotide domains located in SEQ ID NOs: 139–145;
      (v) major genotype 5-specific nucleotide domains located in SEQ ID NOs: 146–153; and
      (vi) major genotype 6-specific nucleotide domains located in SEQ ID NO: 154; and
   (b) detecting said amplification products, where the detection of said products indicates that the hepatitis C virus belongs to a single major genotype selected from major genotypes 1–6.

3. A method for detecting the presence of hepatitis C virus in a biological sample comprising:
   (a) amplifying reverse transcription products of RNA via polymerase chain reaction to produce amplification products;
   (b) contacting said products with a probe having at least one nucleic acid sequence shown in SEQ ID NO: 103 through SEQ ID NO: 154 under conditions which permit the formation of complexes between said products and said nucleic acid sequence; and
   (c) detecting sail complexes, where the detection of said complexes indicates the presence of hepatitis C virus in the biological sample.

4. The method of claim 3, wherein said amplification of step (a) uses universal primers consisting of at least 15 contiguous nucleotides selected from the following regions of SEQ ID Nos: 103–154:
   (i) sense nucleotide regions 1–33, 50–89, 51–90, 52–91, 53–92, 61–100, 62–101, 77–116, 78–117, 79–118, 80–119, 81–120, 82–121, 83–122, 84–123, 85–124, 86–125, 329–368, 330–369, 331–370, 332–371, 354–393, 355–394, 356–395, 442–481, 443–482, 457–496, 458–497, 475–514, 476–515, 477–516 and
   (ii) antisense nucleotide regions 40–1, 41–2, 42–3, 43–4, 51–12, 52–13, 55–16, 56–17, 57–18, 58–19, 61–22, 62–23, 63–24, 64–25, 70–31, 124–85, 125–86, 126–87, 127–88, 128–89, 129–90, 517–478, 518–479, 519–480, 532–493, 533–494, 550–511, 551–512.

5. A method for determining the major genotype of a hepatitis C virus isolate comprising:
(a) amplifying reverse transcription products of RNA via polymerase chain reaction to produce amplification products;
(b) contacting said products with at least one oligonucleotide consisting of at least 15 contiguous nucleotides selected from the following major genotype specific nucleotide domains:
  (i) major genotype 1-specific nucleotide domains located in sense nucleotide regions 427–466, 444–483, 447–486 and antisense nucleotide regions 505–466, 522–483 and 525–486 of SEQ ID NOs: 103–124;
  (ii) major genotype 2-specific nucleotide domains located in sense nucleotide regions 153–192, 162–201, 164–203, 168–207, 171–210, 182–221, 192–231, 197–242 and antisense nucleotide regions 231–192, 240–201, 242–203, 246–207, 249–210 and 380–341 of SEQ ID NOs: 125–134;
  (iii) major genotype 3-specific nucleotide domains located in SEQ ID NOs: 135–138;
  (iv) major genotype 4-specific nucleotide domain located in SEQ ID NOs: 139–145;
  (v) major genotype 5-specific nucleotide domain located in SEQ ID NOs: 146–153; and
  (vi) major genotype 6-specific nucleotide domains located in SEQ ID NO: 154; and
(c) detecting complexes of said products and said oligonucleotide(s), the detection of said complexes indicating that the hepatitis C virus belongs to a single major genotype selected from major genotypes 1–6.

6. A method for determining the minor genotype of a hepatitis C virus isolate comprising:
(a) amplifying reverse transcription products of RNA via polymerase chain reaction using amplification primers consisting of at least 15 contiguous nucleotides selected from the following minor genotype-specific domains:
  (i) minor genotype I/1a-specific nucleotide domains located in sense nucleotide regions 141–180, 279–318 and antisense nucleotide regions 246–207 of SEQ ID NOs: 103–108;
  (ii) minor genotype II/1b-specific nucleotide domains located in sense nucleotide regions 67–106, 127–186, 234–273 and antisense nucleotide regions 144–106 and 225–186 of SEQ ID NOs: 109–124;
  (iii) minor genotype III/2a-specific nucleotide domains located in antisense nucleotide regions 354–315, 394–355 and 571–532 of SEQ ID NOs: 125–128;
  (iv) minor genotype IV/2b-specific nucleotide domains located in sense nucleotide regions 6–45, 135–174, 177–216, 309–348, 337–376, 375–414, 501–540 and antisense nucleotide regions 84–45, 213–174, 255–216, 387–348, 415–376, 453–414, 571–532 and 573–540 of SEQ ID NOs: 129–133;
  (v) minor genotype 2c-specific nucleotide domains located in SEQ ID NO: 134;
  (vi) minor genotype V/3a-specific nucleotide domains located in SEQ ID NOs;
  (vii) minor genotype 4a-specific nucleotide domains located in SEQ ID NO: 139;
  (viii) minor genotype 4b-specific nucleotide domains located in SEQ ID NO: 141;
  (ix) minor genotype 4c-specific nucleotide domains located in SEQ ID NO: 143;
  (x) minor genotype 4d-specific nucleotide domains located in SEQ ID NO: 145;
  (xi) minor genotype 4e-specific nucleotide domains located in SEQ ID NO: 142;
  (xii) minor genotype 4f-specific nucleotide domains located in SEQ ID NO: 140;
  (xiii) minor genotype 5a-specific nucleotide domains located in SEQ ID NOs: 146–153; and
  (xiv) minor genotype 6a-specific nucleotide domains located in SEQ ID NO: 154; and
(b) detecting complexes of said products and said oligonucleotides where the detection of said complexes indicates that the hepatitis C virus belongs to a single minor genotype selected from minor genotypes I/1a, II/1b, III/2a, IV/2b, 2c, V/3a, 4a, 4b, 4c, 4d, 4e, 4f, 5a and 6a.

7. A method for determining the minor genotype of a hepatitis C virus isolate comprising:
(a) amplifying reverse transcription products of RNA via -polymerase chain reaction to produce amplification products;
(b) contacting said products with at least one oligonucleotide consisting of at least 15 contiguous nucleotides selected from one of the following minor genotype-specific nucleotide domains:
  (i) minor genotype I/1a-specific nucleotide domains located in sense nucleotide regions 141–180, 279–318 and antisense nucleotide regions 246–207 of SEQ ID NOs: 193–108;
  (ii) minor genotype II/1b-specific nucleotide domains located in sense nucleotide region 67–106, 127–186, 234–273 and antisense nucleotide regions 144–106 and 225–186 of SEQ ID NOs: 109–124;
  (iii) minor genotype III/2a-specific nucleotide domains located in antisense nucleotide regions 354–315, 394–355 and 571–532 of SEQ ID NOs: 125–128;
  (iv) minor genotype IV/2b-specific nucleotide domains located in sense nucleotide regions 6–45, 135–174, 177–216, 309–348, 337–376, 375–414, 501–540 and antisense nucleotide regions 84–45, 213–174, 255–216, 387–348, 415–376, 453–414, 571–532 and 573–540 of SEQ ID NOs: 129–133;
  (v) minor genotype 2c-specific nucleotide domains located in SEQ ID NO: 134;
  (vi) minor genotype V/3a-specific nucleotide domains located in SEQ ID NOs: ;
  (vii) minor genotype 4a-specific nucleotide domains located in SEQ ID NO: 139;
  (viii) minor genotype 4b-specific nucleotide domains located in SEQ ID NO: 141;
  (ix) minor genotype 4c-specific nucleotide domains located in SEQ ID NO: 143;
  (x) minor genotype 4d-specific nucleotide domains located in SEQ ID NO: 145;
  (xi) minor genotype 4e-specific nucleotide domains located in SEQ ID NO: 142;
  (Xii) minor genotype 4f-specific nucleotide domains located in SEQ ID NO: 140;
  (xiii) minor genotype 5a-specific nucleotide domains located in SEQ ID NOs: 146–153; and
  (xiv) minor genotype 6a-specific nucleotide domains located in SEQ ID NO: 154; and
(c) detecting complexes of said products and said oligonucleotide(s), the detection of said complexes indicating that the hepatitis C virus belongs to a single major genotype selected from mayor genotypes 1–6.

8. An isolated oligonucleotide consisting of at least 15 contiguous nucleotides selected from the following regions of SEQ ID Nos: 103–154:

(i) sense nucleotide regions 1–20, 1–25, 1–26, 1–27, 1–33, 50–89, 51–90, 52–91, 53–92, 61–100, 62–101, 77–116, 78–117, 79–118, 80–119, 81–120, 82–121, 83–122, 84–123, 85–124, 86–125, 329–368, 330–369, 331–370, 332–371, 354–393, 355–394, 356–395, 442–481, 443–482, 457–496, 458–497, 475–514, 476–515, 477–516 and (ii) antisense nucleotide regions 40–1, 41–2, 42–3, 43–4, 51–12, 52–13, 55–16, 56–17, 57–18, 58–19, 61–22, 62–23, 63–24, 64–25, 70–31, 124–85, 125–86, 126–87, 127–88, 128–89, 129–90, 517–478, 518–479, 519–480, 532–493, 533–494, 550–511, 551–512.

9. A diagnostic kit for use in detecting the presence of hepatitis C virus in a biological sample, said kit comprising at least one oligonucleotide according to claim 8.

10. A diagnostic kit for use in detecting the presence of hepatitis C virus in a biological sample, said kit comprising at least one nucleic acid sequence selected from the group consisting of SEQ ID NO: 103–154.

11. An isolated oligonucleotide consisting of at least 15 contiguous nucleotides selected from the following major genotype-specific nucleotide domains:

(a) major genotype 1-specific nucleotide domains located in sense nucleotide regions 427–466, 435–495, 444–483, 447–486 and antisense nucleotide regions 505–466, 522–483 and 525–486 of SEQ ID NOs: 103–124;

(b) major genotype 2-specific nucleotide domains located in sense nucleotide regions 153–192, 162–201, 164–203, 168–207, 171–210, 182–221, 186–240, 192–231, 197–242, 320–360, 440–475 and antisense nucleotide regions 231–192, 240–201, 242–203, 246–207, 249–210 and 380–341 of SEQ ID NOs: 125–134;

(c) major genotype 3-specific nucleotide domains located in SEQ ID NOs: 135–138;

(d) major genotype 4-specific nucleotide domains located in SEQ ID NOs: 139–145;

(e) major genotype 5-specific nucleotide domains located in SEQ ID NOs: 146–153; and (f) major genotype 6-specific nucleotide domains located in SEQ ID NO: 154.

12. A diagnostic kit for determining which major genotype a hepatitis C virus isolate belongs to, said kit comprising at least one oligonucleotide according to claim 11.

13. An isolated oligonucleotide consisting of at least 15 contiguous nucleotides selected from the following minor genotype-specific nucleotide regions:

(a) minor genotype I/1a-specific nucleotide domains located in sense nucleotide regions 141–180, 207–277, 279–318 and antisense nucleotide region 246–207 of SEQ ID NOS: 103–108;

(b) minor genotype II/1b-specific nucleotide domains located in sense nucleotide regions 67–106, 81–131, 127–186, 159–225, 411–472, 530–573 and antisense nucleotide regions 144–106 and 225–186 of SEQ ID NOS: 109–124:

(c) minor genotype III/2a-specific nucleotide domains located in sense nucleotide regions 35–75, 200–276, 330–380, 410–472, 530–573 and antisense nucleotide regions 354–315, 394–355 and 571–532 of SEQ ID NOs: 125–128;

(d) minor genotype IV/2b-specific nucleotide domains located in sense nucleotide regions 6–45, 20–70, 135–174, 149–199, 177–216, 191–241, 309–348, 323–373, 337–376, 351–401, 375–414, 389–439, 429–477, 530–573, 501–540 and antisense nucleotide regions 84–45, 213–174, 255–216, 387–348, 415–376, 453–414, 571–532 and 573–540 of SEQ ID NOs: 129–133;

(e) minor genotype 2c-specific nucleotide domains located in SEQ ID NO: 134;

(f) minor genotype V/3a-specific nucleotide domains located in SEQ ID NOs: 135–138;

(g) minor genotype 4a-specific nucleotide domains located in SEQ ID NO: 139;

(h) minor genotype 4b-specific nucleotide domains located in SEQ ID NO: 141;

(i) minor genotype 4c-specific nucleotide domains located in SEQ ID NO: 143;

(j) minor genotype 4d-specific nucleotide domains located in SEQ ID NO: 145;

(k) minor genotype 4e-specific nucleotide domains located in SEQ ID NO: 142;

(l) minor genotype 4f-specific nucleotide domains located in SEQ ID NO: 140;

(m) minor genotype 5a-specific nucleotide domains located in SEQ ID NOs: 146–153; and (n) minor genotype 6a-specific nucleotide domains located in SEQ ID NO: 154.

14. A diagnostic kit for determining the minor genotype of a hepatitis C virus isolate, said kit comprising at least one oligonucleotide according to claim 13.

* * * * *

UNITED STATES PATENT AND TRADEMARK OFFICE
CERTIFICATE OF CORRECTION

PATENT NO.      :   5,882,852

DATED           :   March 16, 1999

INVENTOR(S)     :   Jens BUKH, Roger H. MILLER, and Robert H. PURCELL

It is certified that errors appear in the above-identified patent and that said Letters Patent is hereby corrected as shown below:

In the Claims

In claim 1, line 50, please change the word "product" to "products";

In claim 3, line 53, please change the word "sail" to "said";

In claim 4, line 59, please change the word "Nos" to "NOs";

In claim 6, line 63, after the word "NOs:" please add "135-138", to read "NOs: 135-138";

In claim 7, line 21, please delete the hyphen (-) before the word "polymerase";

In claim 7, line 30, please change "193-108" to "103-108";

In claim 7, line 32, please change the word "region" to "regions";

In claim 7, line 47, after the word "NOs:" please add "135-138", to read "NOs: 135-138";

In claim 7, line 58, please change the roman numeral "(Xii)" to "(xii)";

In claim 7, line 67, please change the word "mayor" to "major";

In claim 8, line 3, please change the word "Nos" to "NOs";

In claim 13, line 7, please change the word "NOS" to "NOs";

UNITED STATES PATENT AND TRADEMARK OFFICE
CERTIFICATE OF CORRECTION

PATENT NO. : 5,882,852
DATED : March 16, 1999
INVENTOR(S) : Jens Bukh, et al

It is certified that error appears in the above-identified patent and that said Letters Patent is hereby corrected as shown below:

In claim 13 line 12, please change the word "NOS" to "NOs";

Signed and Sealed this

Twenty-first Day of March, 2000

Attest:

Q. TODD DICKINSON

Attesting Officer     *Commissioner of Patents and Trademarks*

SEQUENCE LISTING ( 1 ) GENERAL INFORMATION:

( i i i ) NUMBER OF SEQUENCES: 263

( 2 ) INFORMATION FOR SEQ ID NO:1:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK7

( x i ) SEQUENCE DESCRIPTION: SEQ ID NO:1:

| | | | | | | | | | | | | |
|---|---|---|---|---|---|---|---|---|---|---|---|---|
| TAC | CAA | GTG | CGC | AAC | TCC | ACG | GGG | CTT | TAC | CAT | GTC | ACC | 39 |
| AAT | GAT | TGC | CCT | AAC | TCG | AGT | ATC | GTG | TAC | GAG | GCG | GCC | 78 |
| GAT | GCC | ATC | CTG | CAC | ACT | CCG | GGG | TGT | GTC | CCT | TGC | GTT | 117 |
| CGC | GAG | GGT | AAC | GTC | TCG | AGG | TGT | TGG | GTG | GCG | ATG | ACC | 156 |
| CCC | ACG | GTG | GCC | ACC | AGG | GAT | GGC | AAA | CTC | CCC | ACA | GCG | 195 |
| CAG | CTT | CGA | CGT | CAC | ATC | GAT | CTG | CTC | GTC | GGG | AGT | GCC | 234 |
| ACC | CTC | TGT | TCG | GCC | CTC | TAC | GTG | GGG | GAC | CTG | TGC | GGG | 273 |
| TCT | GTC | TTT | CTT | GTC | GGT | CAA | CTG | TTT | ACC | TTC | TCT | CCC | 312 |
| AGG | CGC | CAC | TGG | ACG | ACG | CAA | GGC | TGC | AAT | TGT | TCT | ATC | 351 |
| TAT | CCT | GGC | CAT | ATA | ACG | GGT | CAC | CGC | ATG | GCG | TGG | GAT | 390 |
| ATG | ATG | ATG | AAC | TGG | TCC | CCT | ACC | ACG | GCG | TTG | GTA | GTA | 429 |
| GCT | CAG | CTG | CTC | CGG | ATC | CCG | CAA | GCC | ATC | TTG | GAC | ATG | 468 |
| ATC | GCT | GGT | GCT | CAC | TGG | GGA | GTC | CTG | GCG | GGC | ATA | GCG | 507 |
| TAT | TTT | TCC | ATG | GTG | GGG | AAC | TGG | GCG | AAG | GTC | CTG | GTA | 546 |
| GTG | CTG | CTG | CTA | TTT | GCC | GGC | GTC | GAC | GCG | | | | 576 |

( 2 ) INFORMATION FOR SEQ ID NO:2:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK9

( x i ) SEQUENCE DESCRIPTION: SEQ ID NO:2:

| | | | | | | | | | | | | |
|---|---|---|---|---|---|---|---|---|---|---|---|---|
| TAC | CAA | GTA | CGC | AAC | TCC | TCG | GGC | CTC | TAC | CAT | GTC | ACC | 39 |
| AAT | GAT | TGC | CCT | AAC | TCG | AGT | ATT | GTG | TAC | GAG | GCG | GCC | 78 |
| GAT | GCC | ATC | CTG | CAT | TCT | CCA | GGG | TGT | GTC | CCT | TGC | GTT | 117 |
| CGC | GAG | GGT | AAC | GCC | TCG | AAA | TGT | TGG | GTG | GCG | GTG | GCC | 156 |
| CCC | ACG | GTG | GCC | ACC | AGG | GAC | GGC | AAG | CTC | CCC | GCA | ACG | 195 |
| CAG | CTT | CGA | CGT | CAC | ATC | GAT | CTG | CTT | GTC | GGG | AGC | GCC | 234 |
| ACC | CTC | TGC | TCG | GCC | CTC | TAT | GTG | GGG | GAC | TTG | TGC | GGG | 273 |

```
TCT  GTC  TTC  CTT  GTC  GGC  CAA  CTG  TTC  ACC  TTC  TCC  CCC                    312
AGA  CGC  CAC  TGG  ACA  ACG  CAA  GAC  TGC  AAC  TGT  TCT  ATC                    351
TAC  CCC  GGC  CAT  ATT  ACG  GGT  CAT  CGC  ATG  GCG  TGG  GAT                    390
ATG  ATG  ATG  AAC  TGG  TCC  CCT  ACA  GCA  GCG  CTG  GTA  ATG                    429
GCG  CAG  CTG  CTC  AGG  ATC  CCG  CAG  GCC  ATC  TTG  GAC  ATG                    468
ATC  GCT  GGT  GCC  CAC  TGG  GGA  GTC  CTA  GCG  GGC  ATA  GCG                    507
TAT  TTC  TCC  ATG  GTG  GGG  AAC  TGG  GCG  AAG  GTC  GTG  GTG                    546
GTA  CTG  TTG  CTG  TTT  ACC  GGC  GTC  GAT  GCG                                   576
```

(2) INFORMATION FOR SEQ ID NO:3:

(i) SEQUENCE CHARACTERISTICS:
    (A) LENGTH: 576 base pairs
    (B) TYPE: nucleic acid
    (C) STRANDEDNESS: single
    (D) TOPOLOGY: linear (vi) ORIGINAL SOURCE:
    (A) ORGANISM: homosapiens
    (C) INDIVIDUAL ISOLATE: DR1

(xi) SEQUENCE DESCRIPTION: SEQ ID NO:3:

```
CAC  CAA  GTG  CGC  AAC  TCT  ACA  GGG  CTT  TAC  CAT  GTC  ACC                    39
AAT  GAT  TGC  CCT  AAT  TCG  AGT  ATT  GTG  TAC  GAG  GCG  GCC                    78
GAT  GCC  ATC  CTG  CAC  GCG  CCG  GGG  TGT  GTC  CCT  TGC  GTT                    117
CGC  GAG  GGT  AAC  GCC  TCG  AGG  TGT  TGG  GTG  GCG  GTG  ACC                    156
CCC  ACG  GTG  GCC  ACC  AGG  GAC  GGC  AAA  CTC  CCC  ACA  ACG                    195
CAG  CTT  CGA  CGT  CAC  ATC  GAC  CTG  CTT  GTC  GGG  AGC  GCC                    234
ACC  CTC  TGC  TCG  GCC  CTC  TAC  GTG  GGG  GAC  CTG  TGC  GGG                    273
TCT  GTC  TTC  CTT  GTC  GGT  CAA  CTG  TTC  ACC  TTT  TCT  CCC                    312
AGG  CGC  CAC  TGG  ACA  ACG  CAA  GAC  TGC  AAT  TGT  TCT  ATC                    351
TAT  CCC  GGC  CAT  ATA  ACG  GGA  CAC  CGT  ATG  GCA  TGG  GAT                    390
ATG  ATG  ATG  AAC  TGG  TCC  CCT  ACG  ACA  GCG  CTG  GTA  ATG                    429
GCT  CAG  CTG  CTC  CGG  ATC  CCA  CAA  GCC  ATC  TTG  GAC  ATG                    468
ATC  GCT  GGA  GCC  CAC  TGG  GGA  GTC  CTA  GCG  GGC  ATA  GCG                    507
TAT  TTC  TCC  ATG  GTG  GGG  AAC  TGG  GCG  AAG  GTC  GTG  GTA                    546
GTG  CTG  TTG  CTG  TTT  GCC  GGC  GTT  GAT  GCG                                   576
```

(2) INFORMATION FOR SEQ ID NO:4:

(i) SEQUENCE CHARACTERISTICS:
    (A) LENGTH: 576 base pairs
    (B) TYPE: nucleic acid
    (C) STRANDEDNESS: single
    (D) TOPOLOGY: linear (vi) ORIGINAL SOURCE:
    (A) ORGANISM: homosapiens
    (C) INDIVIDUAL ISOLATE: DR4

(xi) SEQUENCE DESCRIPTION: SEQ ID NO:4:

```
CAC  CAA  GTG  CGC  AAC  TCT  ACA  GGG  CTT  TAC  CAT  GTC  ACC                    39
AAT  GAT  TGC  CCT  AAT  TCG  AGT  ATT  GTG  TAC  GAG  GCG  GCC                    78
```

```
GAT  GCC  ATC  CTG  CAC  ACG  CCG  GGG  TGT  GTC  CCT  TGC  GTT              117

CGC  GAG  GGT  AAC  ACC  TCG  AGG  TGT  TGG  GTG  GCG  GTG  ACC              156

CCC  ACG  GTG  GCC  ACC  AGG  GAC  GGC  AAA  CTC  CCC  ACA  ACG              195

CAG  CTC  CGA  CGT  CAC  ATC  GAC  CTG  CTT  GTC  GGG  AGC  GCC              234

ACC  CTC  TGC  TCG  GCC  CTC  TAC  GTG  GGG  GAC  TTG  TGC  GGG              273

TCT  GTC  TTC  CTT  GTC  GGT  CAA  CTG  TTC  ACC  TTC  TCT  CCC              312

AGG  CAC  CAC  TGG  ACA  ACG  CAA  GAC  TGC  AAT  TGT  TCC  ATC              351

TAT  CCC  GGC  CAT  ATA  ACG  GGC  CAC  CGC  ATG  GCG  TGG  GAT              390

ATG  ATG  ATG  AAC  TGG  TCC  CCT  ACG  ACA  GCG  CTG  GTA  GTA              429

GCT  CAG  CTG  CTC  CGG  ATC  CCA  CAA  GCC  ATC  TTG  GAC  ATG              468

ATC  GCT  GGT  GCC  CAC  TGG  GGA  GTC  CTA  GCG  GGC  ATA  GCG              507

TAT  TTC  TCC  ATG  GTG  GGG  AAC  TGG  GCG  AAG  GTC  CTG  GTA              546

GTG  CTG  TTG  CTG  TTT  GCC  GGC  GTT  GAT  GCG                             576
```

( 2 ) INFORMATION FOR SEQ ID NO:5:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S14

( x i ) SEQUENCE DESCRIPTION: SEQ ID NO:5:

```
TAC  CAA  GTG  CGC  AAC  TCC  ACG  GGG  CTT  TAC  CAT  GTT  ACC              39

AAT  GAT  TGC  CCT  AAC  TCG  AGT  ATT  GTG  TAC  GAG  ACA  GCT              78

GAT  GCT  ATC  CTA  CAC  GCT  CCG  GGA  TGT  GTC  CCT  TGC  GTT              117

CGT  GAG  GGT  AAC  ACC  TCG  AGG  TGT  TGG  GTG  GCG  ATG  ACC              156

CCC  ACG  GTG  GCC  ACC  AGG  GAC  GGC  AAA  CTC  CCC  GCA  ACG              195

CAG  CTT  CGA  CGT  TAC  ATC  GAT  CTG  CTT  GTC  GGG  AGC  GCC              234

ACC  CTC  TGT  TCG  GCC  CTC  TAC  GTG  GGG  GAC  TTG  TGC  GGG              273

TCT  GTC  TTT  CTT  GTC  GGT  CAG  CTG  TTT  ACC  TTC  TCT  CCC              312

AGG  CGC  CTC  TGG  ACG  ACG  CAA  GAC  TGC  AAT  TGT  TCT  ATC              351

TAT  CCC  GGC  CAT  ATA  ACG  GGT  CAT  CGC  ATG  GCA  TGG  GAT              390

ATG  ATG  ATG  AAC  TGG  TCC  CCT  ACG  ACG  GCA  CTG  GTA  GTA              429

GCT  CAG  CTG  CTC  CGG  ATC  CCA  CAA  GCC  ATC  TTG  GAT  ATG              468

ATC  GCT  GGT  GCT  CAC  TGG  GGA  GTC  CTA  GCG  GGC  ATA  GCG              507

TAT  TTC  TCC  ATG  GTG  GGA  AAC  TGG  GCG  AAG  GTC  CTA  GTG              546

GTG  CTG  CTG  CTA  TTC  GCC  GGC  GTT  GAC  GCG                             576
```

( 2 ) INFORMATION FOR SEQ ID NO:6:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
   ( A ) ORGANISM: homosapiens
   ( C ) INDIVIDUAL ISOLATE: S18

( x i ) SEQUENCE DESCRIPTION: SEQ ID NO:6:

| | | | | | | | | | | | | |
|---|---|---|---|---|---|---|---|---|---|---|---|---|
| TAC | CAA | GTA | CGC | AAC | TCC | ACG | GGC | CTT | TAC | CAT | GTC | ACC | 39 |
| AAT | GAC | TGC | CCT | AAC | TCG | AGC | ATT | GTG | TAC | GAG | ACG | GCC | 78 |
| GAT | ACC | ATC | CTA | CAC | TCT | CCG | GGG | TGT | GTC | CCT | TGC | GTT | 117 |
| CGC | GAG | GGT | AAC | GCC | TCG | AGA | TGT | TGG | GTG | CCG | GTG | GCC | 156 |
| CCC | ACA | GTT | GCC | ACC | AGG | GAC | GGC | AAA | CTC | CCC | GCA | ACG | 195 |
| CAG | CTT | CGA | CGT | CAC | ATC | GAT | CTG | CTT | GTT | GGG | AGC | GCC | 234 |
| ACC | CTC | TGC | TCG | GCC | CTC | TAT | GTG | GGG | GAC | CTG | TGC | GGG | 273 |
| TCT | GTC | TTT | CTT | GTC | AGC | CAG | CTG | TTC | ACT | ATC | TCC | CCC | 312 |
| AGG | CGC | CAC | TGG | ACA | ACG | CAA | GAC | TGC | AAC | TGT | TCT | ATC | 351 |
| TAC | CCC | GGC | CAT | ATA | ACG | GGT | CAC | CGT | ATG | GCA | TGG | GAT | 390 |
| ATG | ATG | ATG | AAC | TGG | TCC | CCT | ACA | ACG | GCG | TTG | GTA | ATA | 429 |
| GCT | CAG | CTG | CTC | AGG | GTC | CCG | CAA | GCC | GTC | TTG | GAC | ATG | 468 |
| ATC | GCT | GGT | GCC | CAC | TGG | GGA | GTC | CTA | GCG | GGC | ATA | GCG | 507 |
| TAT | TTC | TCC | ATG | GCG | GGG | AAC | TGG | GCG | AAG | GTC | CTG | CTA | 546 |
| GTG | CTG | TTG | CTG | TTT | GCC | GGC | GTC | GAT | GCG | | | | 576 |

( 2 ) INFORMATION FOR SEQ ID NO:7:

( i ) SEQUENCE CHARACTERISTICS:
      ( A ) LENGTH: 576 base pairs
      ( B ) TYPE: nucleic acid
      ( C ) STRANDEDNESS: single
      ( D ) TOPOLOGY: linear ( v i ) ORIGINAL SOURCE:
      ( A ) ORGANISM: homosapiens
      ( C ) INDIVIDUAL ISOLATE: SW1

( x i ) SEQUENCE DESCRIPTION: SEQ ID NO:7:

| | | | | | | | | | | | | |
|---|---|---|---|---|---|---|---|---|---|---|---|---|
| TAC | CAA | GTA | CGC | AAC | TCC | TCG | GGC | CTT | TAC | CAT | GTC | ACC | 39 |
| AAT | GAT | TGC | CCT | AAC | TCG | AGT | ATT | GTG | TAC | GAG | ACG | GCC | 78 |
| GAT | GCC | ATT | CTA | CAC | TCT | CCA | GGG | TGT | GTC | CCT | TGC | GTT | 117 |
| CGC | GAG | GAT | GGC | GCC | CCG | AAG | TGT | TGG | GTG | GCG | GTG | GCC | 156 |
| CCC | ACA | GTC | GCC | ACT | AGG | GAC | GGC | AAA | CTC | CCT | GCA | ACG | 195 |
| CAG | CTT | CGA | CGT | CAC | ATC | GAT | CTG | CTT | GTC | GGA | AGC | GCC | 234 |
| ACC | CTC | TGC | TCG | GCC | CTC | TAC | GTG | GGG | GAC | TTG | TGC | GGG | 273 |
| TCT | GTC | TTT | CTC | GTC | AGT | CAA | CTG | TTC | ACG | TTC | TCC | CCC | 312 |
| AGG | CGC | CAC | TGG | ACA | ACG | CAA | GAC | TGT | AAC | TGT | TCT | ATC | 351 |
| TAT | CCC | GGC | CAC | ATA | ACG | GGT | CAC | CGC | ATG | GCA | TGG | GAT | 390 |
| ATG | ATG | ATG | AAC | TGG | TCC | CCC | ACA | ACA | GCG | CTG | GTA | GTA | 429 |
| GCT | CAG | CTG | CTC | AGG | ATC | CCG | CAA | GCC | GTC | TTG | GAC | ATG | 468 |
| ATC | GCT | GGT | GCC | CAC | TGG | GGA | GTC | CTA | GCG | GGC | ATA | GCG | 507 |
| TAT | TTC | TCC | ATG | GTG | GGG | AAC | TGG | GCG | AAG | GTC | CTG | ATA | 546 |

| | | | | | | | | | | |
|---|---|---|---|---|---|---|---|---|---|---|
| GTG | CTG | TTG | CTG | TTT | TCC | GGC | GTC | GAT | GCG | 576 |

( 2 ) INFORMATION FOR SEQ ID NO:8:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US11

( x i ) SEQUENCE DESCRIPTION: SEQ ID NO:8:

| | | | | | | | | | | |
|---|---|---|---|---|---|---|---|---|---|---|
| TAC | CAA | GTA | CGC | AAC | TCC | ACG | GGG | CTT | TAC | CAT | GTC | ACC | 39 |
| AAT | GAT | TGC | CCT | AAC | TCG | AGT | ATT | GTG | TAC | GAG | GCG | GCC | 78 |
| GAT | GCC | ATC | CTG | CAC | ACT | CCG | GGG | TGT | GTT | CCT | TGC | GTT | 117 |
| CGC | GAG | GGT | AAC | GCT | TCG | AGG | TGT | TGG | GTG | GCG | ATG | ACC | 156 |
| CCC | ACG | GTG | GCC | ACC | AGG | GAC | GGC | AAA | CTC | CCC | ACA | ACG | 195 |
| CAA | CTT | CGA | CGT | CAC | ATC | GAT | CTG | CTT | GTC | GGG | AGC | GCC | 234 |
| ACC | CTC | TGT | TCG | GCC | CTC | TAC | GTG | GGG | GAC | CTG | TGC | GGG | 273 |
| TCT | GTC | TTT | CTT | GTC | GGT | CAA | CTG | TTT | ACC | TTC | TCT | CCC | 312 |
| AGA | CGC | CAC | TGG | ACG | ACG | CAG | GGC | TGC | AAT | TGT | TCT | ATC | 351 |
| TAT | CCC | GGC | CAT | ATA | ACG | GGT | CAC | CGC | ATG | GCA | TGG | GAT | 390 |
| ATG | ATG | ATG | AAC | TGG | TCC | CCT | ACG | GCG | GCG | TTG | GTG | GTA | 429 |
| GCT | CAG | CTG | CTC | CGG | ATC | CCA | CAA | GCC | ATC | TTG | GAC | ATG | 468 |
| ATC | GCT | GGT | GCT | CAC | TGG | GGA | GTC | CTA | GCG | GGC | ATA | GCG | 507 |
| TAT | TTC | TCC | ATG | GTG | GGG | AAC | TGG | GCG | AAG | GTC | CTG | GTA | 546 |
| GTG | CTG | CTG | CTA | TTT | GCC | GGC | GTC | GAC | GCG | | | | 576 |

( 2 ) INFORMATION FOR SEQ ID NO:9:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: D1

( x i ) SEQUENCE DESCRIPTION: SEQ ID NO:9:

| | | | | | | | | | | | | | |
|---|---|---|---|---|---|---|---|---|---|---|---|---|---|
| TAT | GAA | GTG | CGC | AAC | GTG | TCC | GGG | GTG | TAC | CAT | GTC | ACG | 39 |
| AAC | GAC | TGT | TCC | AAC | TCG | AGC | ATT | GTG | TAT | GAG | ACA | GCG | 78 |
| GAC | ATG | ATC | ATG | CAC | ACC | CCC | GGG | TGC | GTG | CCC | TGC | GTT | 117 |
| CGG | GAG | GAC | AAC | TCC | TCT | CGC | TGC | TGG | GTA | GCG | CTC | ACC | 156 |
| CCC | ACG | CTC | GCG | GCT | AGG | AAT | GGC | AAC | GTC | CCC | ACT | ACG | 195 |
| GCG | ATA | CGA | CGC | CAC | GTC | GAT | TTG | CTC | GTT | GGG | GCG | GCT | 234 |
| GCT | TTC | TGC | TCC | GCC | ATG | TAC | GTG | GGG | GAT | CTC | TGC | GGA | 273 |
| TCT | GTT | TTC | CTC | ATC | TCC | CAG | CTG | TTC | ACC | CTC | TCG | CCT | 312 |
| CGC | CGG | CAT | GAG | ACG | GTA | CAG | GAG | TGT | AAT | TGC | TCA | ATC | 351 |

| | |
|---|---:|
| TAT CCC GGC CAC GTG ACA GGT CAC CGT ATG GCT TGG GAT | 390 |
| ATG ATG ATG AAC TGG TCA CCT ACA ACA GCC TTA GTG GTA | 429 |
| TCG CAG TTA CTC CGG ATC CCA CAA GCT GTC ATG GAC ATG | 468 |
| GTG GCG GGG GCC CAC TGG GGG GTC CTG GCG GGC CTC GCC | 507 |
| TAC TAT TCC ATG GTG GGG AAC TGG GCT AAG GTT TTG ATT | 546 |
| GTG ATG CTA CTC TTT GCT GGC GTT GAC GGC | 576 |

( 2 ) INFORMATION FOR SEQ ID NO:10:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: D3

( x i ) SEQUENCE DESCRIPTION: SEQ ID NO:10:

| | |
|---|---:|
| TAT GAA GTG CGC AAC GTG TCC GGG GTG TAC CAA GTC ACC | 39 |
| AAT GAC TGT TCC AAC TCG AGC ATC GTG TAT GAG ACA GCG | 78 |
| GAC ATG ATC ATG CAC ACC CCC GGG TGC GTG CCC TGC GTT | 117 |
| CGG GAG GAC AAC TCC TCT CGC TGC TGG GTA GCG CTC ACC | 156 |
| CCC ACG CTC GCG GCT AGG AAT AGC AGC GTC CCC ACT ACG | 195 |
| ACA ATA CGA CGC CAC GTC GAT TTG CTC GTT GGG GCG GCT | 234 |
| GCT TTC TGC TCC GCC ATG TAC GTG GGG GAT CTT TGC GGA | 273 |
| TCT GTT TTC CTC GTC TCC CAG CTG TTC ACC TTC TCG CCT | 312 |
| CGC CGG CAT GAG ACA GTA CAG GAA TGT AAC TGC TCA ATC | 351 |
| TAT CCC GGC CAC GTG ACA GGT CAC CGC ATG GCT TGG GAT | 390 |
| ATG ATG ATG AAC TGG TCG CCT ACA GCA GCC CTA GTG GTA | 429 |
| TCG CAG TTA CTC CGG ATC CCA CAA GCT GTC GTG GAC ATG | 468 |
| GTG GCG GGG GCC CAC TGG GGG GTC CTG GCG GGC CTC GCC | 507 |
| TAC TAT TCC ATG GTG GGG AAC TGG GCT AAG GTT TTG ATT | 546 |
| GTG ATG CTA CTC TTT GCT GGC GTC GAC GGC | 576 |

( 2 ) INFORMATION FOR SEQ ID NO:11:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK1

( x i ) SEQUENCE DESCRIPTION: SEQ ID NO:11:

| | |
|---|---:|
| TAT GAA GTG CGC AAC GTG TCC GGG GTG TAC CAC GTC ACA | 39 |
| AAC GAC TGC TCC AAC TCA AGC ATC GTG TAT GAG GCA GTG | 78 |
| GAC GTG ATC ATG CAT ACC CCA GGG TGC GTG CCC TGC GTT | 117 |
| CGG GAG AAC AAC CAC TCC CGT TGC TGG GTA GCG CTC ACC | 156 |

| | | | | | | | | | | | | | |
|---|---|---|---|---|---|---|---|---|---|---|---|---|---|
| CCC | ACG | CTC | GCG | GCC | AGG | AAC | GCC | AGC | ATC | CCC | ACT | ACG | 195 |
| ACA | ATA | CGA | CGC | CAT | GTC | GAT | TTG | CTC | GTT | GGG | GCG | GCT | 234 |
| GCT | TTC | TGC | TCC | GCT | ATG | TAC | GTG | GGG | GAC | CTC | TGC | GGA | 273 |
| TCC | GTT | TTC | CTC | GTC | TCT | CAG | CTG | TTC | ACC | TTT | TCA | CCT | 312 |
| CGC | CGG | CAT | GAG | ACA | GCA | CAG | GAC | TGC | AAC | TGC | TCA | ATC | 351 |
| TAT | CCC | GGC | CAC | GTT | TCA | GGT | CAC | CGC | ATG | GCT | TGG | GAT | 390 |
| ATG | ATG | ATG | AAC | TGG | TCA | CCT | ACA | ACA | GCC | CTA | GTG | CTA | 429 |
| TCG | CAG | TTA | CTC | CGA | ATC | CCA | CAA | GCT | GTC | GTG | GAC | ATG | 468 |
| GTG | GCG | GGG | GCC | CAC | TGG | GGA | GTC | CTG | GCG | GGC | CTC | GCC | 507 |
| TAC | TAC | TCC | ATG | GCG | GGG | AAC | TGG | GCC | AAG | GTT | TTA | ATT | 546 |
| GTG | TTG | CTA | CTC | TTT | GCC | GGC | GTT | GAT | GGG | | | | 576 |

( 2 ) INFORMATION FOR SEQ ID NO:12:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK3

( x i ) SEQUENCE DESCRIPTION: SEQ ID NO:12:

| | | | | | | | | | | | | | |
|---|---|---|---|---|---|---|---|---|---|---|---|---|---|
| TAT | GAA | GTG | CGC | AAC | GTG | TCC | GGG | ATA | TAC | CAT | GTC | ACG | 39 |
| AAC | GAC | TGC | TCC | AAC | TCA | AGC | GTC | GTG | TAT | GAG | ACA | GCA | 78 |
| GAC | ATG | ATC | ATG | CAT | ACC | CCT | GGA | TGC | GTG | CCC | TGC | GTA | 117 |
| CGG | GAG | AAC | AAC | TCC | TCC | CGC | TGT | TGG | GTA | GCG | CTC | ACT | 156 |
| CCC | ACG | CTC | GCG | GCC | AGG | AAC | GTC | AGC | GTC | CCC | ACC | ACG | 195 |
| ACA | ATA | CGA | CGT | CAC | GTC | GAC | TTG | CTC | GTT | GGG | GCG | GCT | 234 |
| GCC | TTC | TGC | TCC | GCT | ATG | TAC | GTG | GGG | GAT | CTC | TGC | GGA | 273 |
| TCT | GTT | TTC | CTT | GTC | TCC | CAG | CTG | TTC | ACC | TTC | TCG | CCT | 312 |
| CGC | CGA | CAC | GAG | ACA | GTA | CAG | GAC | TGC | AAC | TGC | TCA | CTC | 351 |
| TAT | CCC | GGC | CAC | GTA | TCA | GGT | CAC | CGC | ATG | GCT | TGG | GAT | 390 |
| ATG | ATG | ATG | AAC | TGG | TCC | CCT | ACA | GCA | GCC | CTA | GTG | GTG | 429 |
| TCG | CAA | TTA | CTC | CGG | ATC | CCG | CAA | GCT | GTC | GTG | GAC | ATG | 468 |
| GTG | GCG | GGG | GCC | CAC | TGG | GGA | GTC | CTA | GCG | GGC | CTT | GCC | 507 |
| TAC | TAT | TCC | ATG | GTG | GGA | AAC | TGG | GCT | AAG | GTT | TTG | ATT | 546 |
| GTG | ATG | CTA | CTT | TTT | GCC | GGC | GTT | GAT | GGG | | | | 576 |

( 2 ) INFORMATION FOR SEQ ID NO:13:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK4

( x i ) SEQUENCE DESCRIPTION: SEQ ID NO:13:

| | | | | | | | | | | | | | |
|---|---|---|---|---|---|---|---|---|---|---|---|---|---|
| CAT | GAA | GTG | CAC | AAC | GTA | TCC | GGG | ATC | TAC | CAT | GTC | ACG | 39 |
| AAC | GAC | TGC | TCC | AAC | TCA | AGT | ATT | GTG | TAT | GAG | GCA | GCG | 78 |
| GAC | ATG | ATC | ATG | CAT | ACC | CCC | GGG | TGC | GTG | CCC | TGC | GTC | 117 |
| CGG | GAG | AAC | AAC | TCC | TCC | CGT | TGC | TGG | GTA | GCG | CTC | ACT | 156 |
| CCC | ACG | CTC | GCG | GCC | AGG | AAC | GCC | AGC | ATC | CCC | ACT | ACG | 195 |
| ACA | ATA | CGA | CGC | CAT | GTC | GAC | TTG | CTC | GTT | GGG | GCG | GCT | 234 |
| GCT | TTC | TGC | TCC | GCC | ATG | TAC | GTG | GGA | GAT | CTC | TGC | GGA | 273 |
| TCT | GTC | TTC | CTC | GTC | TCC | CAG | TTG | TTC | ACC | TTC | TCG | CCT | 312 |
| CGC | CGG | CAT | GAG | ACG | GTA | CAG | GAC | TGC | AAT | TGC | TCA | ATC | 351 |
| TAT | CCC | GGC | CAC | GTA | TCA | GGT | CAC | CGC | ATG | GCT | TGG | GAT | 390 |
| ATG | ATG | ATG | AAC | TGG | TCA | CCT | ACA | GCA | GCC | CTA | GTG | GTA | 429 |
| TCG | CAG | TTA | CTC | CGA | CTC | CCA | CAA | GCT | GTC | ATG | GAC | ATG | 468 |
| GTG | GCG | GGA | GCC | CAC | TGG | GGA | GTC | CTA | GCG | GGC | CTT | GCT | 507 |
| TAC | TAT | TCC | ATG | GTG | GGG | AAC | TGG | GCC | AAG | GTT | TTG | ATT | 546 |
| GTG | ATG | CTA | CTC | TTT | GCC | GGC | GTT | GAC | GGG | | | | 576 |

( 2 ) INFORMATION FOR SEQ ID NO:14:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK5

( x i ) SEQUENCE DESCRIPTION: SEQ ID NO:14:

| | | | | | | | | | | | | | |
|---|---|---|---|---|---|---|---|---|---|---|---|---|---|
| TAT | GAA | GTG | CGC | AAC | GTG | TCC | GGG | GTA | TAC | CAT | GTC | ACG | 39 |
| AAC | GAC | TGC | TCC | AAC | TTA | AGC | ATC | GTG | TAC | GAG | ACA | ACG | 78 |
| GAC | ATG | ATC | ATG | CAC | ACC | CCT | GGG | TGC | GTG | CCC | TGC | GTT | 117 |
| CGG | GAA | AAC | AAC | TCC | TCC | CGT | TGT | TGG | GTA | GCG | CTC | GCC | 156 |
| CCC | ACG | CTC | GCG | GCC | AGG | AAC | GCC | AGC | GTC | CCC | ACC | ACG | 195 |
| GCA | ATA | CGA | CGC | CAC | GTC | GAC | TTG | CTC | GTT | GGG | GCG | GCT | 234 |
| GCT | TTC | TGC | TCC | GCT | ATG | TAC | GTG | GGG | GAT | CTT | TGC | GGA | 273 |
| TCT | GTT | TTC | CTC | GTC | TCC | CAG | CTG | TTC | ACC | TTC | TCG | CCT | 312 |
| CGC | CGA | CAC | GAG | ACG | GTA | CAG | GAC | TGC | AAC | TGC | TCA | ATC | 351 |
| TAT | CCC | GGC | CAC | GTA | ACA | GGT | CAC | CGC | ATG | GCT | TGG | GAT | 390 |
| ATG | ATG | ATG | AAC | TGG | TCA | CCT | ACA | ACA | GCC | CTA | GTG | GTG | 429 |
| TCG | CAG | TTA | CTC | CGG | ATC | CCG | CAA | GCT | GTC | GTG | GAC | ATG | 468 |
| GTA | GCG | GGG | GCC | CAC | TGG | GGG | GTC | CTG | GCG | GGC | CTT | GCC | 507 |
| TAC | TAT | TCC | ATG | GTG | GGA | AAC | TGG | GCT | AAG | GTT | TTG | ATT | 546 |
| GTG | ATG | CTA | CTT | TTT | GCC | GGC | GTT | GAT | GGG | | | | 576 |

( 2 ) INFORMATION FOR SEQ ID NO:15:

( i ) SEQUENCE CHARACTERISTICS:
    ( A ) LENGTH: 576 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: HK8

( x i ) SEQUENCE DESCRIPTION: SEQ ID NO:15:

| | | | | | | | | | | | | | |
|---|---|---|---|---|---|---|---|---|---|---|---|---|---|
| TAT | GAA | GTG | CGC | AAC | GTG | TCC | GGG | ATA | TAC | CAT | GTC | ACG | 39 |
| AAC | GAC | TGC | TCC | AAC | TCA | AGC | ATC | GTG | TAT | GAA | ACA | GCG | 78 |
| GAC | ATG | ATT | ATG | CAT | ACC | CCT | GGA | TGC | ATG | CCC | TGC | GTT | 117 |
| CGG | GAG | AAC | AAC | TCC | TCC | CGT | TGC | TGG | GTG | GCG | CTC | ACT | 156 |
| CCC | ACG | CTC | GCG | GCT | AGG | AAT | GTC | AGC | GTC | CCC | ACT | ACG | 195 |
| ACA | ATA | CGA | CGC | CAC | GTC | GAC | TTG | CTC | GTT | GGG | GCG | GCT | 234 |
| GCT | TTC | TGC | TCC | GCT | ATG | TAC | GTG | GGG | GAT | CTC | TGC | GGA | 273 |
| TCT | GTT | TTC | CTC | GTC | TCC | CAG | CTG | TTC | ACC | TTT | TCG | CCT | 312 |
| CGC | CGA | CAC | GAG | ACG | GTA | CAG | GAC | TGC | AAC | TGC | TCA | ATC | 351 |
| TAT | CCC | GGC | CAC | GTA | TCA | GGT | CAC | CGC | ATG | GCT | TGG | GAT | 390 |
| ATG | ATG | ATG | AAC | TGG | TCG | CCC | ACA | ACA | GCC | CTA | GTG | GTG | 429 |
| TCG | CAG | TTA | CTC | CGG | ATC | CCG | CAA | GCT | ATC | GTG | GAC | ATG | 468 |
| GTG | GCG | GGG | GCC | CAC | TGG | GGA | GTC | CTA | GCG | GGC | CTT | GCC | 507 |
| TAC | TAT | TCC | ATG | GTG | GGC | AAC | TGG | GCT | AAG | GTT | TTG | ATT | 546 |
| GTG | ATG | CTA | CTG | TTT | GCC | GGC | GTT | GAT | GGG | | | | 576 |

( 2 ) INFORMATION FOR SEQ ID NO:16:

( i ) SEQUENCE CHARACTERISTICS:
    ( A ) LENGTH: 576 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: IND5

( x i ) SEQUENCE DESCRIPTION: SEQ ID NO:16:

| | | | | | | | | | | | | | |
|---|---|---|---|---|---|---|---|---|---|---|---|---|---|
| TAT | GAA | GTG | CGC | AAC | GTG | TCC | GGG | GTG | TAC | CAT | GTC | ACG | 39 |
| AAC | GAC | TGC | TCC | AAC | TCA | AGT | ATT | GTG | TAT | GAG | GCA | GCG | 78 |
| GAC | ATG | ATC | ATG | CAC | ACT | CCC | GGG | TGC | GTG | CCC | TGC | GTT | 117 |
| CGG | GAG | GGC | AAC | TCC | TCT | CGC | TGC | TGG | GTA | GCG | CTC | ACT | 156 |
| CCC | ACT | CTC | GCG | GCC | AGG | AAC | GCC | AGC | GTC | TCC | ACC | ACG | 195 |
| ACA | ATA | CGA | CAC | CAC | GTC | GAT | TTG | CTC | GTT | GGG | GCG | GCT | 234 |
| GCT | TTC | TGT | TCC | GCT | ATG | TAC | GTG | GGG | GAT | CTA | TGC | GGA | 273 |
| TCT | GTT | TTC | CTC | GTC | TCC | CAG | CTG | TTC | ACC | TTC | TCA | CCG | 312 |
| CGC | CGG | CAT | GAG | ACA | GTA | CAG | GAC | TGC | AAT | TGC | TCC | ATC | 351 |
| TAT | CCC | GGC | CAC | GTA | TCA | GGT | CAC | CGC | ATG | GCC | TGG | GAT | 390 |
| ATG | ATG | ATG | AAC | TGG | TCA | CCT | ACA | GCA | GCC | CTA | GTG | GTA | 429 |
| TCG | CAG | TTG | CTC | CGG | ATC | CCA | CAA | GCT | GTC | GTG | GAT | ATG | 468 |

5,882,852

-continued

| | | | | | | | | | | | | |
|---|---|---|---|---|---|---|---|---|---|---|---|---|
| GTG | GCG | GGG | GCC | CAC | TGG | GGA | ATC | CTG | GCG | GGC | CTT | GCC | 507 |
| TAC | TAT | TCC | ATG | GTA | GGG | AAC | TGG | GCT | AAG | GTT | TTG | ATT | 546 |
| GTG | ATG | CTA | CTC | TTT | GCC | GGC | GTT | GAC | GGG | | | | 576 |

( 2 ) INFORMATION FOR SEQ ID NO:17:

( i ) SEQUENCE CHARACTERISTICS:
           ( A ) LENGTH: 576 base pairs
           ( B ) TYPE: nucleic acid
           ( C ) STRANDEDNESS: single
           ( D ) TOPOLOGY: linear ( v i ) ORIGINAL SOURCE:
           ( A ) ORGANISM: homosapiens
           ( C ) INDIVIDUAL ISOLATE: IND8

( x i ) SEQUENCE DESCRIPTION: SEQ ID NO:17:

| | | | | | | | | | | | | |
|---|---|---|---|---|---|---|---|---|---|---|---|---|
| TAT | GAG | GTG | CGC | AAC | GTG | TCC | GGG | GTG | TAC | CAT | GTC | ACG | 39 |
| AAC | GAC | TGC | TCC | AAC | TCA | AGT | ATT | GTG | TAT | GAG | GCA | GCG | 78 |
| GAC | ATG | ATC | ATG | CAC | ACC | CCC | GGG | TGC | GTG | CCC | TGC | GTT | 117 |
| CGG | GAG | GGC | AAC | TTC | TCT | AGT | TGC | TGG | GTA | GCG | CTC | ACT | 156 |
| CCC | ACT | CTC | GCG | GCT | AGG | AAC | GCC | AGC | GTC | CCC | ACC | ACG | 195 |
| ACA | ATA | CGA | CGC | CAC | GTC | GAT | TTG | CTC | GTT | GGG | GCG | GCT | 234 |
| GCT | TTC | TGT | TCC | GCT | ATG | TAC | GTG | GGG | GAT | CTC | TGC | GGA | 273 |
| TCT | GTT | TTC | CTT | GTC | TCC | CAG | CTG | TTC | ACC | TTC | TCA | CCG | 312 |
| CGC | CGG | CAT | GAG | ACA | GTA | CAG | GAC | TGC | AAT | TGC | TCC | ATC | 351 |
| TAT | CCC | GGC | CAC | GTA | TCA | GGT | CAC | CGC | ATG | GCT | TGG | GAT | 390 |
| ATG | ATG | ATG | AAC | TGG | TCA | CCT | ACA | GCG | GCC | CTA | GTG | GTA | 429 |
| TCG | CAG | TTG | CTC | CGG | ATC | CCA | CAA | GCT | GTC | GTG | GAT | ATG | 468 |
| GTG | GCG | GGG | GCC | CAC | TGG | GGA | ATC | CTG | GCG | GGC | CTT | GCC | 507 |
| TAC | TAT | TCC | ATG | GTA | GGG | AAC | TGG | GCT | AAG | GTT | TTG | ATT | 546 |
| GTG | ATG | CTA | CTC | TTT | GCC | GGC | GTT | GAC | GGG | | | | 576 |

( 2 ) INFORMATION FOR SEQ ID NO:18:

( i ) SEQUENCE CHARACTERISTICS:
           ( A ) LENGTH: 576 base pairs
           ( B ) TYPE: nucleic acid
           ( C ) STRANDEDNESS: single
           ( D ) TOPOLOGY: linear ( v i ) ORIGINAL SOURCE:
           ( A ) ORGANISM: homosapiens
           ( C ) INDIVIDUAL ISOLATE: P10

( x i ) SEQUENCE DESCRIPTION: SEQ ID NO:18:

| | | | | | | | | | | | | |
|---|---|---|---|---|---|---|---|---|---|---|---|---|
| TAT | GAA | GTG | CGC | AAC | GTG | TCC | GGG | GTG | TAC | CAT | GTC | ACG | 39 |
| AAC | GAC | TGC | TCC | AAC | TCA | AGT | ATT | GTG | TAT | GAG | GCA | GCG | 78 |
| GAC | ATG | ATA | ATG | CAC | ACC | CCC | GGG | TGC | GTG | CCC | TGT | GTT | 117 |
| CGG | GAG | AAC | AAC | TCC | TCC | CGC | TGC | TGG | GTA | GCG | CTC | ACT | 156 |
| CCC | ACA | CTC | GCG | GCT | AGG | AAT | TCC | AGC | GTC | CCA | ACT | ACG | 195 |
| GCA | ATA | CGA | CGC | CAT | GTC | GAT | TTG | CTC | GTT | GGG | GCG | GCT | 234 |
| GCT | TTC | TGC | TCC | GCT | ATG | TAC | GTG | GGG | GAT | CTC | TGC | GGA | 273 |

```
TCT GTT CTC CTC GTC TCC CAG CTG TTC ACC TTC TCA CCT            312
CGC CGG CAT TGG ACA GTA CAG GAC TGC AAT TGT TCA ATC            351
TAT CCT GGC CAC GTA TCA GGT CAC CGC ATG GCT TGG GAT            390
ATG ATG ATG AAC TGG TCG CCC ACA GCA GCC CTA GTG GTG            429
TCG CAG CTA CTC CGG ATC CCA CAA GCT ATC TTG GAT GTG            468
GTG GCG GGG GCC CAC TGG GGA GTC CTG GCG GGC CTT GCC            507
TAC TAT TCC ATG GTG GGG AAC TGG GCT AAG GTC TTG ATT            546
GTG ATG CTA CTC TTT GCC GGC GTT GAC GGA                        576
```

( 2 ) INFORMATION FOR SEQ ID NO:19:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S9

( x i ) SEQUENCE DESCRIPTION: SEQ ID NO:19:

```
TAT GAA GTG CGC AAC GTA TCC GGG GCG TAC CAT GTC ACG            39
AAC GAC TGC TCC AAC TCA AGT ATT GTG TAC GAG GCA GCG            78
GAC GTG ATC ATG CAT ACC CCC GGG TGT GTA CCC TGC GTT            117
CAG GAG GGT AAC TCC TCC CAA TGC TGG GTG GCG CTC ACC            156
CCC ACG CTC GCG GCC AGG AAC GCT ACC GTC CCC ACC ACG            195
ACA ATA CGA CGT CAT GTC GAT TTG CTC GTT GGG GCG GCT            234
GTT TTC TGC TCC GCT ATG TAC GTG GGG GAC CTG TGC GGA            273
TCT GTT TTC CTC ATC TCC CAG CTG TTC ACC ATC TCG CCC            312
CGT CGG CAT GAG ACA GTA CAG AAC TGC AAT TGC TCA ATC            351
TAT CCC GGA CAC GTG ACA GGT CAT CGC ATG GCC TGG GAT            390
ATG ATG ATG AAC TGG TCG CCT ACA ACA GCC CTA GTG GTA            429
TCG CAG CTA CTC CGG ATC CCA CAA GCT GTC ATG GAT ATG            468
GTG GCG GGG GCC CAC TGG GGA GTC CTG GCG GGC CTC GCC            507
TAC TAT TCC ATG GTG GGG AAC TGG GCT AAG GTT TTG ATT            546
GTG ATG CTA CTT TTT GCT GGT GTT GAC GGG                        576
```

( 2 ) INFORMATION FOR SEQ ID NO:20:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S45

( x i ) SEQUENCE DESCRIPTION: SEQ ID NO:20:

```
TAT GAA GTG CGC AAC GTG TCC GGG GCG TAC CAT GTC ACG            39
AAC GAC TGC TCC AAC TCA AGC ATT GTG TAT GAG GCA GTG            78
```

| | | | | | | | | | | | | |
|---|---|---|---|---|---|---|---|---|---|---|---|---|
|GAC|GTG|ATC|CTG|CAC|ACC|CCT|GGG|TGC|GTG|CCC|TGC|GTT|117
|CGG|GAG|AAC|AAC|TCC|TCC|CGT|TGC|TGG|GTG|GCG|CTC|ACT|156
|CCC|ACG|CTC|GCG|GCC|AGG|AAC|TCC|AGC|GTC|CCC|ACT|ACG|195
|ACA|ATA|CGA|CGT|CAC|GTC|GAT|TTG|CTC|GTT|GGG|GCG|GCT|234
|GCT|TTC|TGC|TCC|GCT|ATG|TAC|GTG|GGG|GAT|CTC|TGC|GGA|273
|TCT|GTT|TTC|CTT|GTT|TCC|CAG|CTG|TTC|ACC|TTC|TCG|CCT|312
|CGT|CGG|CAT|GAG|ACA|GTA|CAG|GAC|TGC|AAC|TGT|TCA|ATC|351
|TAT|CCC|GGC|CAC|GTA|ACA|GGT|CAC|CGC|ATG|GCT|TGG|GAT|390
|ATG|ATG|ATG|AAC|TGG|TCG|CCT|ACA|GCA|GCC|TTA|GTG|GTA|429
|TCG|CAG|TTA|CTC|CGG|ATC|CCA|CAA|GCT|GTC|GTG|GAC|ATG|468
|GTG|GCG|GGG|GCC|CAC|TGG|GGA|GTC|CTG|GCG|GGC|CTT|GCC|507
|TAC|TAT|TCC|ATG|GTG|GGG|AAC|TGG|GCT|AAG|GTT|CTG|ATT|546
|GTG|ATG|CTA|CTC|TTT|GCC|GGC|GTT|GAC|GGG| | | |576

( 2 ) INFORMATION FOR SEQ ID NO:21:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA10

( x i ) SEQUENCE DESCRIPTION: SEQ ID NO:21:

| | | | | | | | | | | | | |
|---|---|---|---|---|---|---|---|---|---|---|---|---|
|TAT|GAA|GTG|CGC|AAC|GTG|TCC|GGG|ATG|TAC|CAT|GTC|ACG|39
|AAC|GAC|TGC|TCC|AAC|TCA|AGC|ATT|GTG|TAT|GAG|GCA|GCG|78
|GAC|ATG|ATC|ATG|CAC|ACC|CCC|GGG|TGC|GTG|CCC|TGC|GTT|117
|CGG|GAG|AAC|AAC|TCC|TCC|CGC|TGC|TGG|GTA|GCG|CTC|ACT|156
|CCC|ACG|CTC|GCG|GCC|AGG|AAC|TCC|AGC|GTC|CCC|ACT|ACG|195
|ACA|ATA|CGA|CGC|CAC|GTC|GAT|TTG|CTC|GTT|GGG|GCG|GCT|234
|GCT|TTC|TGC|TCC|GCC|ATG|TAC|GTG|GGG|GAC|CTC|TGC|GGA|273
|TCT|GTT|TTC|CTT|GTC|TCC|CAG|CTG|TTC|ACC|TTC|TCG|CCT|312
|CGC|CGG|TAT|GAG|ACA|GTA|CAG|GAC|TGC|AAT|TGC|TCA|ATC|351
|TAT|CCC|GGC|CGC|GTA|ACA|GGT|CAC|CGC|ATG|GCT|TGG|GAT|390
|ATG|ATG|ATG|AAC|TGG|TCA|CCT|ACA|ACA|GCT|CTA|GTA|GTA|429
|TCG|CAG|TTA|CTC|CGG|ATC|CCA|CAA|GCT|ATC|GTG|GAC|ATG|468
|GTG|GCG|GGG|GCC|CAC|TGG|GGA|GTC|CTA|GCG|GGC|CTT|GCC|507
|TAC|TAT|TCC|ATG|GTG|GGG|AAC|TGG|GCT|AAG|GTT|TTG|ATT|546
|GTT|ATG|CTA|CTC|TTT|GCC|GGC|GTT|GAC|GGG| | | |576

( 2 ) INFORMATION FOR SEQ ID NO:22:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
 ( A ) ORGANISM: homosapiens
 ( C ) INDIVIDUAL ISOLATE: SW2

( x i ) SEQUENCE DESCRIPTION: SEQ ID NO:22:

| | | | | | | | | | | | | |
|---|---|---|---|---|---|---|---|---|---|---|---|---|
| TAT | GAA | GTG | CGC | AAC | GTG | TCC | GGG | GTG | TAT | CAT | GTC | ACG | 39 |
| AAC | GAC | TGT | TCC | AAC | TCA | AGC | ATT | GTG | TAT | GAG | ACA | GCG | 78 |
| GAC | ATG | ATC | ATG | CAT | ACC | CCC | GGG | TGC | GTG | CCC | TGC | GTT | 117 |
| CGG | GAG | GCC | AAC | TCC | TCC | CGC | TGC | TGG | GTA | GCG | CTC | ACT | 156 |
| CCC | ACG | CTA | GCA | GCC | AGG | AAC | ACC | AGC | GTC | CCC | ACT | ACG | 195 |
| ACA | ATA | CGA | CGC | CAC | GTC | GAT | TTG | CTC | GTT | GGG | GCG | GCT | 234 |
| GCT | TTC | TGC | TCC | GTT | ATG | TAC | GTG | GGG | GAT | CTC | TGC | GGA | 273 |
| TCT | GTT | TTC | CTC | GTC | TCC | CAG | CTG | TTC | ACT | TTT | TCA | CCT | 312 |
| CGC | CGG | CAC | GAG | ACA | GTA | CAG | GAC | TGC | AAC | TGT | TCC | ATC | 351 |
| TAT | CCC | GGC | CAC | GTA | TCA | GGT | CAC | CGC | ATG | GCT | TGG | GAC | 390 |
| ATG | ATG | ATG | AAC | TGG | TCA | CCT | ACA | GCA | GCC | CTG | GTG | GTA | 429 |
| TCG | CAG | TTA | CTC | CGG | ATC | CCA | CAA | GCT | GTC | GTG | GAC | ATG | 468 |
| GTA | GCG | GGG | GCC | CAC | TGG | GGA | GTC | CTG | GCG | GGC | CTT | GCA | 507 |
| TAC | TAT | TCC | ATG | GTG | GGG | AAC | TGG | GCT | AAG | GTT | TTG | ATT | 546 |
| GTG | ATG | CTA | CTC | TTT | GCT | GGC | GTT | GAC | GGG | | | | 576 |

( 2 ) INFORMATION FOR SEQ ID NO:23:

( i ) SEQUENCE CHARACTERISTICS:
 ( A ) LENGTH: 576 base pairs
 ( B ) TYPE: nucleic acid
 ( C ) STRANDEDNESS: single
 ( D ) TOPOLOGY: linear ( v i ) ORIGINAL SOURCE:
 ( A ) ORGANISM: homosapiens
 ( C ) INDIVIDUAL ISOLATE: T3

( x i ) SEQUENCE DESCRIPTION: SEQ ID NO:23:

| | | | | | | | | | | | | |
|---|---|---|---|---|---|---|---|---|---|---|---|---|
| TAC | GAA | GTG | CGC | AAC | GTG | TCC | GGG | GTG | TAC | TAT | GTC | ACG | 39 |
| AAC | GAC | TGT | TCC | AAC | TCA | AGC | ATT | GTG | TAT | GAG | ACA | GCG | 78 |
| GAC | ATG | ATC | ATG | CAC | ACC | CCT | GGG | TGC | GTG | CCC | TGC | GTT | 117 |
| CGG | GAG | AGC | AAT | TCC | TCC | CGC | TGC | TGG | GTA | GCG | CTT | ACT | 156 |
| CCC | ACG | CTC | GCG | GCC | AGG | AAC | GCC | AGC | GTC | CCC | ACT | AAG | 195 |
| ACA | ATA | CGA | CGT | CAC | GTC | GAC | TTG | CTC | GTT | GGG | GCG | GCT | 234 |
| GCT | TTC | TGT | TCC | GCT | ATG | TAC | GTG | GGG | GAT | CTC | TGC | GGA | 273 |
| TCT | GTT | TTC | CTC | GTC | TCC | CAG | CTG | TTC | ACT | TTC | TCG | CCT | 312 |
| CGC | CGG | CAT | GAG | ACA | GTA | CAG | GAC | TGC | AAC | TGC | TCA | ATC | 351 |
| TAT | CCC | GGC | CAC | GTA | ACA | GGT | CAC | CGT | ATG | GCT | TGG | GAT | 390 |
| ATG | ATG | ATG | AAC | TGG | TCG | CCC | ACA | ACG | GCA | CTA | GTG | GTG | 429 |
| TCG | CAG | TTG | CTC | CGG | ATC | CCA | CAA | GCT | GTC | GTG | GAC | ATG | 468 |
| GTG | GCG | GGG | GCC | CAC | TGG | GGA | GTC | CTG | GCG | GGC | CTT | GCC | 507 |
| TAC | TAT | TCC | ATG | GTG | GGG | AAC | TGG | GCT | AAG | GTT | TTG | ATT | 546 |

```
GTG CTG CTA CTC TTT GCC GGC GTT GAT GGG                                    576
```

( 2 ) INFORMATION FOR SEQ ID NO:24:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T10

( x i ) SEQUENCE DESCRIPTION: SEQ ID NO:24:

```
TAT GAA GTG CGC AAC GTG TCC GGG ATG TAC CAT GTC ACG                         39
AAC GAC TGC TCC AAC TCA AGC ATT GTG TTT GAG GCA GCG                         78
GAC TTG ATC ATG CAC ACC CCC GGG TGC GTG CCC TGC GTT                        117
CGG GAG GGC AAC TCC TCC CGC TGC TGG GTA GCG CTC ACT                        156
CCC ACG CTC GCG GCC AGG AAC ACC AGC GTC CCC ACT ACG                        195
ACG ATA CGA CGC CAT GTC GAT TTG CTC GTT GGG GCG GCT                        234
GCT TTC TGC TCC GCT ATG TAT GTG GGA GAC CTC TGC GGA                        273
TCT GTT TTC CTC GTC TCT CAG CTG TTC ACC TTC TCG CCT                        312
CGC CGG CAT GAG ACT TTG CAG GAC TGC AAC TGC TCA ATC                        351
TAT CCC GGC CAT CTG TCA GGT CAC CGC ATG GCT TGG GAC                        390
ATG ATG ATG AAC TGG TCG CCT ACA ACA GCT CTA GTG GTG                        429
TCG CAG TTA CTC CGG ATC CCA CAA GCT GTC ATG GAC ATG                        468
GTG ACA GGG GCC CAC TGG GGA GTC CTG GCG GGC CTT GCC                        507
TAC TAT TCC ATG GCG GGG AAC TGG GCT AAG GTT TTA ATT                        546
GTG ATG CTA CTC TTT GCC GGC GTT GAT GGG                                    576
```

( 2 ) INFORMATION FOR SEQ ID NO:25:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US6

( x i ) SEQUENCE DESCRIPTION: SEQ ID NO:25:

```
TAT GAA GTG CGC AAC GTG TCC GGG ATG TAC CAT GTC ACG                         39
AAC GAC TGC TCC AAC TCA AGC ATT GTG TAT GAG GCA GCG                         78
GAC ATG ATC ATG CAC ACT CCC GGG TGC GTG CCC TGT GTT                        117
CGG GAG AAC AAT TCC TCC CGC TGC TGG GTA GCG CTC ACT                        156
CCC ACG CTC GCG GCC AGG AAC GCT AGC GTC CCC ACT ACG                        195
ACA ATA CGA CGC CAC GTC GAT TTG CTC GTT GGG GCG GCT                        234
ACT TTC TGC TCC GCT ATG TAC GTG GGG GAC CTC TGC GGG                        273
TCC GTT TTC CTC ATC TCC CAG CTG TTC ACC TTC TCG CCT                        312
CGT CAG CAT GAG ACA GTA CAG GAC TGC AAT TGT TCA ATC                        351
```

| | | | | | | | | | | | | | |
|---|---|---|---|---|---|---|---|---|---|---|---|---|---|
| TAT | CCC | GGC | CAC | GTA | TCA | GGT | CAC | CGC | ATG | GCT | TGG | GAT | 390 |
| ATG | ATG | ATG | AAT | TGG | TCA | CCT | ACA | GCA | GCC | CTA | GTG | GTA | 429 |
| TCG | CAG | TTA | CTC | CGG | ATC | CCA | CAA | GCT | GTC | ATG | GAC | ATG | 468 |
| GTG | GCG | GGG | GCC | CAC | TGG | GGA | GTC | CTG | GCG | GGC | CTT | GCC | 507 |
| TAC | TAT | TCC | ATG | GTG | GGG | AAC | TGG | GCT | AAG | GTT | CTG | ATT | 546 |
| GTG | TTG | CTA | CTC | TTT | GCC | GGC | GTT | GAC | GGG | | | | 576 |

(2) INFORMATION FOR SEQ ID NO:26:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T2

(xi) SEQUENCE DESCRIPTION: SEQ ID NO:26:

| | | | | | | | | | | | | | |
|---|---|---|---|---|---|---|---|---|---|---|---|---|---|
| GCC | CAA | GTG | AGG | AAC | ACC | AGC | CGC | GGT | TAC | ATG | GTG | ACT | 39 |
| AAC | GAC | TGT | TCC | AAT | GAG | AGC | ATC | ACC | TGG | CAG | CTC | CAA | 78 |
| GCC | GCG | GTT | CTC | CAC | GTC | CCC | GGG | TGT | ATC | CCG | TGT | GAG | 117 |
| AGG | CTG | GGA | AAT | ACA | TCC | CGA | TGC | TGG | ATA | CCG | GTC | ACA | 156 |
| CCA | AAC | GTG | GCC | GTG | CGG | CAG | CCC | GGC | GCT | CTT | ACG | CAG | 195 |
| GGC | TTG | CGG | ACG | CAC | ATC | GAC | ATG | GTT | GTG | ATG | TCC | GCC | 234 |
| ACG | CTC | TGC | TCT | GCC | CTC | TAC | GTG | GGG | GAC | CTC | TGC | GGC | 273 |
| GGG | GTG | ATG | CTC | GCA | GCC | CAG | ATG | TTC | ATT | GTC | TCG | CCG | 312 |
| CGA | CGC | CAC | TGG | TTT | GTG | CAA | GAA | TGC | AAT | TGC | TCC | ATC | 351 |
| TAC | CCC | GGT | ACC | ATC | ACT | GGA | CAC | CGT | ATG | GCA | TGG | GAC | 390 |
| ATG | ATG | ATG | AAC | TGG | TCG | CCC | ACA | GCC | ACC | ATG | ATC | CTG | 429 |
| GCG | TAC | GCG | ATG | CGC | GTT | CCC | GAG | GTC | ATC | ATA | GAC | ATC | 468 |
| ATC | GGC | GGG | GCT | CAC | TGG | GGC | GTC | ATG | TTT | GGC | TTG | GCC | 507 |
| TAC | TTC | TCT | ATG | CAG | GGA | GCG | TGG | GCG | AAG | GTC | ATT | GTC | 546 |
| ATC | CTC | TTG | CTG | GCT | GCT | GGG | GTG | GAC | GCG | | | | 576 |

(2) INFORMATION FOR SEQ ID NO:27:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T4

(xi) SEQUENCE DESCRIPTION: SEQ ID NO:27:

| | | | | | | | | | | | | | |
|---|---|---|---|---|---|---|---|---|---|---|---|---|---|
| GCA | CAA | GTG | AAG | AAC | ACC | ACT | AAC | AGC | TAC | ATG | GTG | ACC | 39 |
| AAC | GAC | TGT | TCT | AAT | GAC | AGC | ATC | ACT | TGG | CAG | CTC | CAG | 78 |
| GCC | GCG | GTC | CTC | CAC | GTC | CCC | GGG | TGT | GTC | CCG | TGC | GAG | 117 |
| AAA | ACG | GGA | AAT | ACA | TCT | CGG | TGC | TGG | ATA | CCG | GTT | TCA | 156 |

| | | | | | | | | | | | | |
|---|---|---|---|---|---|---|---|---|---|---|---|---|
|CCA|AAC|GTG|GCC|GTG|CGG|CAG|CCC|GGC|GCC|CTC|ACG|CAG|195|
|GGC|TTG|CGG|ACG|CAC|ATT|GAC|ATG|GTT|GTG|ATG|TCC|GCC|234|
|ACG|CTC|TGC|TCT|GCT|CTT|TAC|GTG|GGG|GAC|CTC|TGC|GGC|273|
|GGG|GTG|ATG|CTC|GCA|GCC|CAG|ATG|TTC|ATC|GTC|TCG|CCG|312|
|CAA|CAT|CAC|TGG|TTT|GTG|CAA|GAC|TGC|AAT|TGC|TCT|ATC|351|
|TAC|CCT|GGC|ACC|ATC|ACT|GGA|CAC|CGT|ATG|GCA|TGG|GAT|390|
|ATG|ATG|ATG|AAC|TGG|TCG|CCC|ACG|GCC|ACC|ATG|ATC|CTG|429|
|GCG|TAC|GCG|ATG|CGC|GTT|CCC|GAG|GTC|ATC|TTA|GAC|ATC|468|
|GTT|AGC|GGG|GCA|CAC|TGG|GGC|GTC|ATG|TTC|GGC|TTG|GCC|507|
|TAC|TTC|TCT|ATG|CAG|GGA|GCG|TGG|GCG|AAA|GTC|GTT|GTC|546|
|ATC|CTT|CTG|CTG|GCC|GCT|GGG|GTG|GAC|GCG| | | |576|

( 2 ) INFORMATION FOR SEQ ID NO:28:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T9

( x i ) SEQUENCE DESCRIPTION: SEQ ID NO:28:

| | | | | | | | | | | | | |
|---|---|---|---|---|---|---|---|---|---|---|---|---|
|GCC|GAA|GTG|AAG|AAC|ACC|AGT|ACC|AGC|TAC|ATG|GTG|ACA|39|
|AAT|GAC|TGT|TCC|AAC|GAC|AGC|ATC|ACC|TGG|CAA|CTC|CAG|78|
|GCC|GCG|GTC|CTC|CAC|GTC|CCC|GGG|TGC|GTC|CCG|TGC|GAG|117|
|AGA|GTT|GGA|AAC|GCG|TCG|CGG|TGC|TGG|ATA|CCG|GTC|TCG|156|
|CCA|AAC|GTA|GCT|GTG|CAG|CGG|CCT|GGC|GCC|CTC|ACG|CAG|195|
|GGC|TTG|CGG|ACG|CAC|ATC|GAC|ATG|GTT|GTG|ATG|TCC|GCC|234|
|ACG|CTC|TGC|TCC|GCT|CTC|TAC|GTG|GGG|GAT|CTC|TGC|GGC|273|
|GGG|GTA|ATG|CTC|GCC|GCT|CAG|ATG|TTC|ATT|ATC|TCG|CCG|312|
|CAG|CAC|CAC|TGG|TTT|GTG|CAG|GAA|TGC|AAC|TGC|TCC|ATT|351|
|TAC|CCT|GGT|ACC|ATC|ACT|GGA|CAC|CGT|ATG|GCA|TGG|GAC|390|
|ATG|ATG|ATG|AAC|TGG|TCG|CCC|ACA|ACC|ACC|ATG|ATC|TTG|429|
|GCG|TAC|GCG|ATG|CGC|GTT|CCC|GAG|GTC|ATC|ATA|GAC|ATC|468|
|ATC|AGC|GGA|GCT|CAC|TGG|GGC|GTC|ATG|TTC|GGC|CTA|GCC|507|
|TAC|TTC|TCT|ATG|CAG|GGA|GCG|TGG|GCG|AAG|GTC|GTT|GTC|546|
|ATC|CTG|TTG|CTC|ACC|GCT|GGC|GTG|GAC|GCG| | | |576|

( 2 ) INFORMATION FOR SEQ ID NO:29:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US10

( x i ) SEQUENCE DESCRIPTION: SEQ ID NO:29:

```
GTC CAA GTG AAA AAC ACC AGT ACC AGC TAT ATG GTG ACC         39
AAT GAC TGC TCC AAC GAC AGC ATC ACT TGG CAA CTT GAG         78
GCT GCG GTC CTC CAC GTT CCC GGG TGT GTC CCG TGC GAG        117
AAA GTG GGA AAT ACA TCT CGG TGC TGG ATA CCG GTC TCA        156
CCA AAT GTG GCC GTG CAG CGG CCT GGC GCC CTC ACG CAG        195
GGC TTG CGG ACT CAC ATC GAC ATG GTC GTG ATG TCC GCC        234
ACG CTC TGC TCC GCT CTT TAC GTG GGG GAC TTC TGC GGT        273
GGG ATG ATG CTC GCA GCC CAA ATG TTC ATT GTC TCG CCG        312
CGC CAC CAC TCG TTT GTG CAG GAA TGC AAC TGC TCC ATC        351
TAC CCC GGT ACC ATC ACC GGG CAC CGT ATG GCA TGG GAC        390
ATG ATG ATG AAC TGG TCG CCC ACG GCC ACT TTG ATC CTG        429
GCG TAC GTG ATG CGC GTT CCC GAG GTC ATC ATA GAC ATC        468
ATT AGC GGG GCG CAT TGG GGC GTC TTG TTC GGC TTA GCC        507
TAC TTC TCT ATG CAG GGA GCG TGG GCG AAA GTC GTT GTC        546
ATC CTT CTG CTA GCC GCT GGG GTG GAC GCG                    576
```

( 2 ) INFORMATION FOR SEQ ID NO:30:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK8

( x i ) SEQUENCE DESCRIPTION: SEQ ID NO:30:

```
GTG GAA GTC AGG AAC ATC AGT TCC AGC TAC TAC GCC ACC         39
AAT GAT TGC TCA AAC AAC AGC ATC ACC TGG CAA CTC ACC         78
GAC GCA GTT CTC CAC CTT CCC GGA TGC GTC CCA TGT GAG        117
AAT GAC AAT GGC ACC CTG CGC TGC TGG ATA CAA GTG ACA        156
CCT AAT GTG GCT GTG AAA CAC CGC GGC GCA CTT ACT CAT        195
AAC CTG CGA ACA CAC GTC GAC GTG ATC GTA ATG GCA GCT        234
ACG GTC TGC TCG GCC TTG TAT GTG GGA GAC GTA TGC GGG        273
GCC GTG ATG ATC GTG TCG CAG GCT CTC ATA ATA TCG CCT        312
GAA CGC CAC AAC TTT ACC CAG GAG TGC AAC TGT TCC ATC        351
TAC CAA GGT CAT ATC ACC GGC CAC CGC ATG GCA TGG GAC        390
ATG ATG CTA AAC TGG TCA CCA ACT CTT ACC ATG ATC CTC        429
GCC TAT GCC GCT CGT GTT CCT GAG CTA GCC CTC CAG GTT        468
GTC TTC GGC GGC CAT TGG GGC GTG GTG TTT GGC TTG GCC        507
TAT TTC TCC ATG CAG GGA GCG TGG GCC AAA GTC ATT GCC        546
ATC CTC CTT CTT GTC GCA GGA GTG GAT GCA                    576
```

( 2 ) INFORMATION FOR SEQ ID NO:31:

( i ) SEQUENCE CHARACTERISTICS:

(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK11

(xi) SEQUENCE DESCRIPTION: SEQ ID NO:31:

| | | | | | | | | | | | | | |
|---|---|---|---|---|---|---|---|---|---|---|---|---|---|
| GTG | GAA | GTC | AGG | AAC | ACC | AGT | TCT | AGT | TAC | TAC | GCC | ACC | 39 |
| AAT | GAT | TGC | TCA | AAC | AAC | AGC | ATC | ACC | TGG | CAA | CTC | ACC | 78 |
| AAC | GCA | GTT | CTC | CAC | CTT | CCC | GGA | TGC | GTC | CCA | TGT | GAG | 117 |
| AAT | GAC | AAT | GGC | ACC | CTG | CAC | TGC | TGG | ATA | CAA | GTG | ACA | 156 |
| CCT | AAT | GTG | GCT | GTG | AAA | CAC | CGC | GGC | GCA | CTC | ACT | CAC | 195 |
| AAC | CTG | CGA | GCA | CAT | ATA | GAT | ATG | ATT | GTA | ATG | GCA | GCT | 234 |
| ACG | GTC | TGC | TCG | GCC | TTG | TAT | GTG | GGA | GAC | GTG | TGC | GGG | 273 |
| GCC | GTG | ATG | ATC | GTG | TCG | CAG | GCT | TTC | ATA | GTA | TCG | CCA | 312 |
| GAA | CAC | CAC | CAC | TTT | ACC | CAA | GAG | TGC | AAC | TGT | TCC | ATC | 351 |
| TAC | CAA | GGT | CAC | ATC | ACC | GGC | CAC | CGC | ATG | GCA | TGG | GAC | 390 |
| ATG | ATG | CTT | AAC | TGG | TCA | CCA | ACT | CTC | ACC | ATG | ATC | CTC | 429 |
| GCC | TAT | GCC | GCC | CGT | GTT | CCT | GAG | CTA | GTC | CTT | GAA | GTC | 468 |
| GTC | TTC | GGT | GGT | CAT | TGG | GGT | GTG | GTG | TTT | GGC | TTG | GCC | 507 |
| TAT | TTC | TCC | ATG | CAG | GGA | GCG | TGG | GCC | AAG | GTC | ATT | GCC | 546 |
| ATC | CTC | CTT | CTT | GTA | GCA | GGA | GTG | GAT | GCA | | | | 576 |

(2) INFORMATION FOR SEQ ID NO:32:

(i) SEQUENCE CHARACTERISTICS:
(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SW3

(xi) SEQUENCE DESCRIPTION: SEQ ID NO:32:

| | | | | | | | | | | | | | |
|---|---|---|---|---|---|---|---|---|---|---|---|---|---|
| GTG | GAA | GTC | AGG | AAC | ATC | AGT | TCT | AGC | TAC | TAT | GCC | ACC | 39 |
| AAT | GAT | TGC | TCA | AAC | AGC | AGC | ATC | ACC | TGG | CAA | CTC | ACC | 78 |
| AAC | GCA | GTC | CTC | CAC | CTT | CCC | GGA | TGC | GTC | CCG | TGT | GAG | 117 |
| AAT | GAT | AAT | GGC | ACC | CTG | CAC | TGC | TGG | ATA | CAA | GTG | ACA | 156 |
| CCT | AAT | GTG | GCT | GTG | AAA | CAC | CGC | GGC | GCG | CTC | ACT | CAC | 195 |
| AAC | CTG | CGA | GCA | CAC | GTC | GAT | ATG | ATC | GTA | ATG | GCA | GCT | 234 |
| ACG | GTC | TGC | TCG | GCC | TTG | TAT | GTG | GGA | GAC | ATG | TGC | GGG | 273 |
| GCC | GTG | ATG | ATC | GTG | TCG | CAG | GCT | TTC | ATA | ATA | TCG | CCA | 312 |
| GAA | CGC | CAC | AAC | TTT | ACC | CAA | GAG | TGC | AAC | TGT | TCC | ATC | 351 |
| TAC | CAA | GGT | CGT | ATC | ACC | GGC | CAC | CGC | ATG | GCG | TGG | GAC | 390 |
| ATG | ATG | CTA | AAC | TGG | TCA | CCA | ACT | CTT | ACC | ATG | ATC | CTT | 429 |
| GCC | TAT | GCC | GCT | CGT | GTT | CCT | GAG | CTA | GTC | CTT | GAA | GTT | 468 |

| | |
|---|---|
| GTC TTC GGC GGC CAT TGG GGC GTG GTG TTT GGC TTG GCC | 5 0 7 |
| TAT TTC TCC ATG CAA GGA GCG TGG GCC AAG GTC ATT GCC | 5 4 6 |
| ATC CTC CTG CTT GTC GCA GGA GTG GAT GCA | 5 7 6 |

( 2 ) INFORMATION FOR SEQ ID NO:33:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T8

( x i ) SEQUENCE DESCRIPTION: SEQ ID NO:33:

| | |
|---|---|
| GTG GAA GTT AGA AAC ACC AGT TTT AGC TAC TAC GCC ACC | 3 9 |
| AAT GAT TGC TCG AAC AAC AGC ATC ACC TGG CAG CTC ACC | 7 8 |
| AAC GCA GTT CTC CAC CTT CCC GGA TGC GTC CCA TGT GAG | 1 1 7 |
| AAT GAC AAT GGC ACC TTG CGC TGC TGG ATA CAA GTA ACA | 1 5 6 |
| CCT AAT GTG GCT GTG AAA CAC CGT GGC GCA CTC ACT CAC | 1 9 5 |
| AAC CTG CGA ACG CAT GTC GAC GTG ATC GTA ATG GCA GCT | 2 3 4 |
| ACG GTC TGC TCG GCC TTG TAT GTG GGG GAC GTG TGC GGG | 2 7 3 |
| GCC GTG ATG ATA GCG TCG CAG GCT TTC ATA ATA TCG CCA | 3 1 2 |
| GAA CGC CAC AAC TTC ACC CAG GAG TGC AAC TGT TCC ATC | 3 5 1 |
| TAC CAA GGT CAT ATC ACC GGC CAC CGC ATG GCA TGG GAC | 3 9 0 |
| ATG ATG CTG AAC TGG TCA CCA ACT CTC ACC ATG ATC CTC | 4 2 9 |
| GCC TAC GCT GCT CGT GTG CCT GAA CTA GTC CTT GAA GTT | 4 6 8 |
| GTC TTC GGC GGC CAT TGG GGC GTG GTG TTT GGC TTG GCC | 5 0 7 |
| TAT TTC TCC ATG CAA GGA GCG TGG GCC AAA GTC ATC GCC | 5 4 6 |
| ATC CTC CTC CTT GTC GCA GGA GTG GAC GCA | 5 7 6 |

( 2 ) INFORMATION FOR SEQ ID NO:34:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S83

( x i ) SEQUENCE DESCRIPTION: SEQ ID NO:34:

| | |
|---|---|
| GTG GAG GTC AAG GAC ACC GGC GAC TCC TAC ATG CCG ACC | 3 9 |
| AAC GAT TGC TCC AAC TCT AGT ATC GTT TGG CAG CTT GAA | 7 8 |
| GGA GCA GTG CTT CAT ACT CCT GGA TGC GTC CCT TGT GAG | 1 1 7 |
| CGT ACC GCC AAC GTC TCT CGA TGT TGG GTG CCG GTT GCC | 1 5 6 |
| CCC AAT CTC GCC ATA AGT CAA CCT GGC GCT CTC ACT AAG | 1 9 5 |
| GGC CTG CGA GCA CAC ATC GAT ATC ATC GTG ATG TCT GCT | 2 3 4 |
| ACG GTC TGT TCT GCC CTT TAT GTG GGG GAC GTG TGT GGC | 2 7 3 |
| GCG CTG ATG CTG GCC GCT CAG GTC GTC GTC GTG TCG CCA | 3 1 2 |

| | | | | | | | | | | | | |
|---|---|---|---|---|---|---|---|---|---|---|---|---|
|CAA|CAC|CAT|ACG|TTT|GTC|CAG|GAA|TGC|AAC|TGT|TCC|ATA|351|
|TAC|CCG|GGC|CGC|ATT|ACG|GGA|CAC|CGC|ATG|GCT|TGG|GAT|390|
|ATG|ATG|ATG|AAC|TGG|TCG|CCC|ACT|ACC|ACC|ATG|CTC|CTG|429|
|GCG|TAC|TTG|GTG|CGC|ATC|CCG|GAA|GTC|ATC|TTG|GAT|ATT|468|
|GTT|ACA|GGA|GGT|CAT|TGG|GGT|GTA|ATG|TTT|GGC|CTC|GCT|507|
|TAC|TTC|TCC|ATG|CAG|GGA|TCG|TGG|GCG|AAG|GTC|ATC|GTT|546|
|ATC|CTC|CTG|CTG|ACT|GCT|GGG|GTG|GAG|GCG| | | |576|

( 2 ) INFORMATION FOR SEQ ID NO:35:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK12

( x i ) SEQUENCE DESCRIPTION: SEQ ID NO:35:

| | | | | | | | | | | | | |
|---|---|---|---|---|---|---|---|---|---|---|---|---|
|TTA|GAG|TGG|CGG|AAT|GTG|TCC|GGC|CTC|TAC|GTC|CTT|ACC|39|
|AAC|GAC|TGT|TCC|AAT|AGC|AGT|ATC|GTG|TAT|GAG|GCC|GAT|78|
|GAC|GTC|ATT|CTG|CAC|ACA|CCT|GGC|TGT|GTA|CCT|TGT|GTT|117|
|CAG|GAC|GGC|AAT|ACA|TCT|ACG|TGC|TGG|ACC|TCA|GTG|ACG|156|
|CCT|ACA|GTG|GCA|GTC|AGG|TAC|GTC|GGA|GCA|ACC|ACC|GCT|195|
|TCG|ATA|CGC|AGT|CAT|GTG|GAC|CTG|CTA|GTG|GGC|GCG|GCC|234|
|ACG|ATG|TGC|TCT|GCG|CTC|TAC|GTG|GGT|GAT|GTG|TGT|GGG|273|
|GCC|GTC|TTC|CTT|GTG|GGA|CAA|GCC|TTC|ACG|TTC|AGA|CCT|312|
|CGT|CGC|CAT|CAA|ACA|GTC|CAG|ACC|TGT|AAC|TGC|TCG|CTG|351|
|TAC|CCA|GGC|CAT|CTT|TCA|GGA|CAT|CGA|ATG|GCT|TGG|GAT|390|
|ATG|ATG|ATG|AAT|TGG|TCC|CCC|GCT|GTG|GGT|ATG|GTG|GTA|429|
|GCG|CAC|GTC|CTG|CGT|CTG|CCC|CAG|ACC|TTG|TTC|GAC|ATA|468|
|ATA|GCT|GGG|GCC|CAT|TGG|GGC|ATC|ATG|GCG|GGC|CTA|GCC|507|
|TAT|TAC|TCC|ATG|CAG|GGC|AAC|TGG|GCC|AAG|GTC|GCT|ATC|546|
|ATC|ATG|GTT|ATG|TTT|TCA|GGA|GTC|GAT|GCC| | | |576|

( 2 ) INFORMATION FOR SEQ ID NO:36:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK10

( x i ) SEQUENCE DESCRIPTION: SEQ ID NO:36:

| | | | | | | | | | | | | |
|---|---|---|---|---|---|---|---|---|---|---|---|---|
|CTA|GAG|TGG|CGG|AAT|GTG|TCT|GGC|CTC|TAT|GTC|CTT|ACC|39|
|AAC|GAC|TGT|CCC|AAT|AGC|AGT|ATT|GTG|TAT|GAG|GCC|GAT|78|
|GAC|GTC|ATT|CTG|CAC|ACA|CCT|GGC|TGT|GTA|CCT|TGT|GTT|117|

```
CAG  GAC  GGC  AAT  ACA  TCC  ACG  TGC  TGG  ACC  TCG  GTG  ACA              156
CCT  ACA  GTG  GCA  GTC  AGG  TAC  GTC  GGA  GCA  ACC  ACC  GCC              195
TCG  ATA  CGC  AGT  CAT  GTG  GAC  CTG  TTA  GTG  GGC  GCG  GCC              234
ACG  ATG  TGC  TCT  GCG  CTC  TAC  GTG  GGC  GAT  ATG  TGT  GGG              273
GCC  GTC  TTC  CTC  GTG  GGA  CAA  GCC  TTC  ACG  TTC  AGA  CCG              312
CGT  CGC  CAT  CAA  ACG  GTC  CAG  ACC  TGT  AAC  TGC  TCG  CTG              351
TAC  CCA  GGC  CAC  CTT  TCA  GGA  CAT  CGA  ATG  GCT  TGG  GAT              390
ATG  ATG  ATG  AAT  TGG  TCC  CCC  GCC  GTG  GGT  ATG  GTG  GTG              429
GCG  CAC  GTC  CTG  CGG  TTG  CCC  CAG  ACC  TTG  TTC  GAC  ATA              468
ATA  GCC  GGG  GCC  CAT  TGG  GGC  ATC  TTG  GCA  GGC  CTA  GCC              507
TAT  TAC  TCC  ATG  CAG  GGC  AAC  TGG  GCC  AAG  GTC  GCT  ATC              546
ATC  ATG  GTT  ATG  TTT  TCA  GGG  GTC  GAT  GCC                             576
```

( 2 ) INFORMATION FOR SEQ ID NO:37:

( i ) SEQUENCE CHARACTERISTICS:
       ( A ) LENGTH: 576 base pairs
       ( B ) TYPE: nucleic acid
       ( C ) STRANDEDNESS: single
       ( D ) TOPOLOGY: linear ( v i ) ORIGINAL SOURCE:
       ( A ) ORGANISM: homosapiens
       ( C ) INDIVIDUAL ISOLATE: S2

( x i ) SEQUENCE DESCRIPTION: SEQ ID NO:37:

```
CTA  GAG  TGG  CGG  AAT  ACG  TCT  GGC  CTC  TAT  GTC  CTC  ACC              39
AAC  GAC  TGT  TCC  AAT  AGC  AGT  ATT  GTG  TAT  GAG  GCC  GAT              78
GAC  GTT  ATT  CTG  CAC  ACA  CCT  GGC  TGT  GTA  CCT  TGT  GTT              117
CAG  GAC  GGT  AAT  ACA  TCC  ACG  TGC  TGG  ACC  CCA  GTG  ACA              156
CCT  ACA  GTG  GCA  GTC  AGG  TAT  GTC  GGA  GCA  ACC  ACC  GCT              195
TCG  ATA  CGC  AGT  CAT  GTG  GAC  CTA  TTG  GTG  GGC  GCG  GCC              234
ACT  ATG  TGC  TCT  GCG  CTC  TAC  GTG  GGT  GAT  ATG  TGT  GGG              273
GCC  GTC  TTT  CTC  GTG  GGA  CAA  GCC  TTC  ACG  TTC  AGA  CCT              312
CGT  CGC  CAT  CAA  ACG  GTC  CAG  ACC  TGT  AAC  TGC  TCG  CTG              351
TAC  CCA  GGC  CAT  CTT  TCA  GGA  CAT  CGC  ATG  GCT  TGG  GAT              390
ATG  ATG  ATG  AAT  TGG  TCC  CCC  GCT  GTG  GGT  ATG  GTG  GTG              429
GCG  CAC  GTT  CTG  CGT  TTG  CCC  CAG  ACC  GTG  TTC  GAC  ATA              468
ATA  GCC  GGG  GCC  CAT  TGG  GGC  ATC  TTG  GCG  GGC  CTA  GCC              507
TAT  TAC  TCC  ATG  CAA  GGC  AAC  TGG  GCC  AAG  GTC  GCT  ATC              546
ATC  ATG  GTT  ATG  TTT  TCA  GGG  GTC  GAC  GCC                             576
```

( 2 ) INFORMATION FOR SEQ ID NO:38:

( i ) SEQUENCE CHARACTERISTICS:
       ( A ) LENGTH: 576 base pairs
       ( B ) TYPE: nucleic acid
       ( C ) STRANDEDNESS: single
       ( D ) TOPOLOGY: linear ( v i ) ORIGINAL SOURCE:
    ( A ) ORGANISM: homosapiens
    ( C ) INDIVIDUAL ISOLATE: S52

( x i ) SEQUENCE DESCRIPTION: SEQ ID NO:38:

| | | | | | | | | | | | | |
|---|---|---|---|---|---|---|---|---|---|---|---|---|
| CTA | GAG | TGG | CGG | AAT | ACG | TCT | GGC | CTC | TAT | GTC | CTT | ACC | 39 |
| AAC | GAC | TGT | TCC | AAT | AGC | AGT | ATT | GTG | TAT | GAG | GCC | GAT | 78 |
| GAC | GTC | ATT | CTG | CAC | ACA | CCC | GGC | TGT | GTA | CCT | TGT | GTT | 117 |
| CAG | GAC | GGC | AAT | ACA | TCC | ATG | TGC | TGG | ACC | CCA | GTG | ACA | 156 |
| CCT | ACG | GTG | GCA | GTC | AGG | TAC | GTC | GGA | GCA | ACC | ACC | GCT | 195 |
| TCG | ATA | CGC | AGT | CAT | GTG | GAC | CTA | TTA | GTG | GGC | GCG | GCC | 234 |
| ACG | CTG | TGC | TCT | GCG | CTC | TAT | GTG | GGT | GAT | ATG | TGT | GGG | 273 |
| GCC | GTC | TTT | CTC | GTG | GGA | CAA | GCC | TTC | ACG | TTC | AGA | CCT | 312 |
| CGT | CGC | CAT | CAA | ACG | GTC | CAG | ACC | TGT | AAC | TGC | TCG | CTG | 351 |
| TAC | CCA | GGC | CAT | GTT | TCA | GGA | CAT | CGA | ATG | GCT | TGG | GAT | 390 |
| ATG | ATG | ATG | AAT | TGG | TCC | CCC | GCT | GTG | GGT | ATG | GTG | GTG | 429 |
| GCG | CAC | ATC | CTG | CGA | TTG | CCC | CAG | ACC | TTG | TTT | GAC | ATA | 468 |
| CTG | GCC | GGG | GCC | CAT | TGG | GGC | ATC | TTG | GCG | GGC | CTA | GCC | 507 |
| TAT | TAT | TCT | ATG | CAG | GGC | AAC | TGG | GCC | AAG | GTC | GCT | ATT | 546 |
| GTC | ATG | ATT | ATG | TTT | TCA | GGG | GTC | GAT | GCC | | | | 576 |

( 2 ) INFORMATION FOR SEQ ID NO:39:

( i ) SEQUENCE CHARACTERISTICS:
    ( A ) LENGTH: 576 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: S54

( x i ) SEQUENCE DESCRIPTION: SEQ ID NO:39:

| | | | | | | | | | | | | |
|---|---|---|---|---|---|---|---|---|---|---|---|---|
| CTA | GAG | TGG | CGG | AAT | ACG | TCT | GGC | CTC | TAT | ATC | CTT | ACC | 39 |
| AAC | GAC | TGT | TCC | AAT | AGC | AGT | ATT | GTG | TAT | GAG | GCC | GAT | 78 |
| GAC | GTC | ATT | CTG | CAC | ACA | CCC | GGC | TGT | GTA | CCT | TGT | GTT | 117 |
| CAG | GAC | GGC | AAT | ACA | TCC | ACG | TGC | TGG | ACC | CCA | GTG | ACA | 156 |
| CCT | ACG | GTG | GCA | GTC | AGG | TAC | GTC | GGA | GCA | ACC | ACC | GCT | 195 |
| TCG | ATA | CGC | AGT | CAT | GTG | GAC | CTA | TTA | GTG | GGC | GCG | GCC | 234 |
| ACG | CTG | TGC | TCT | GCG | CTC | TAT | GTG | GGT | GAT | ATG | TGT | GGG | 273 |
| GCC | GTC | TTT | CTC | GTG | GGA | CAA | GCC | TTC | ACG | TTC | AGA | CCT | 312 |
| CGT | CGC | CAT | CAA | ACG | GTC | CAG | ACC | TGT | AAC | TGC | TCG | CTG | 351 |
| TAC | CCA | GGC | CAT | CTT | TCA | GGA | CAT | CGA | ATG | GCT | TGG | GAT | 390 |
| ATG | ATG | ATG | AAT | TGG | TCC | CCC | GCT | GTG | GGT | ATG | GTG | GTG | 429 |
| GCG | CAC | ATC | CTG | CGA | TTG | CCC | CAG | ACC | TTG | TTT | GAC | ATA | 468 |
| CTG | GCC | GGG | GCC | CAT | TGG | GGC | ATC | TTG | GCG | GGC | CTA | GCC | 507 |
| TAT | TAT | TCT | ATG | CAG | GGC | AAC | TGG | GCC | AAG | GTC | GCT | ATC | 546 |
| ATC | ATG | ATT | ATG | TTT | TCA | GGG | GTC | GAT | GCC | | | | 576 |

( 2 ) INFORMATION FOR SEQ ID NO:40:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z4

( x i ) SEQUENCE DESCRIPTION: SEQ ID NO:40:

```
GAG  CAC  TAC  CGG  AAT  GCT  TCG  GGC  ATC  TAT  CAC  ATC  ACC                39
AAT  GAT  TGT  CCG  AAT  TCC  AGT  ATA  GTC  TAT  GAA  GCT  GAC                78
CAT  CAC  ATC  CTA  CAC  TTG  CCG  GGG  TGC  GTA  CCC  TGT  GTG               117
ATG  ACT  GGG  AAC  ACA  TCG  CGT  TGC  TGG  ACG  CCG  GTG  ACG               156
CCT  ACA  GTG  GCT  GTC  GCA  CAC  CCG  GGC  GCT  CCG  CTT  GAG               195
TCG  TTC  CGG  CGA  CAT  GTG  GAC  TTA  ATG  GTA  GGC  GCG  GCC               234
ACT  TTG  TGT  TCT  GCC  CTC  TAT  GTT  GGG  GAC  CTC  TGC  GGA               273
GGT  GCC  TTC  CTG  ATG  GGG  CAG  ATG  ATC  ACT  TTT  CGG  CCG               312
CGT  CGC  CAC  TGG  ACC  ACG  CAG  GAG  TGC  AAT  TGT  TCC  ATC               351
TAC  ACT  GGC  CAT  ATC  ACC  GGC  CAC  AGG  ATG  GCG  TGG  GAC               390
ATG  ATG  ATG  AAC  TGG  AGC  CCT  ACC  ACC  ACT  CTG  CTC  CTC               429
GCC  CAG  ATC  ATG  AGG  GTC  CCC  ACA  GCC  TTT  CTC  GAC  ATG               468
GTT  GCC  GGA  GGC  CAC  TGG  GGC  GTC  CTC  GCG  GGC  TTG  GCG               507
TAC  TTC  AGC  ATG  CAA  GGC  AAT  TGG  GCC  AAG  GTA  GTC  CTG               546
GTC  CTT  TTC  CTC  TTT  GCT  GGG  GTA  GAC  GCC                              576
```

( 2 ) INFORMATION FOR SEQ ID NO:41:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z1

( x i ) SEQUENCE DESCRIPTION: SEQ ID NO:41:

```
GTG  CAC  TAC  CGG  AAT  GCT  TCG  GGC  GTC  TAT  CAT  GTC  ACC                39
AAT  GAT  TGC  CCT  AAC  ACC  AGC  ATA  GTG  TAC  GAG  ACG  GAG                78
CAC  CAC  ATC  ATG  CAC  TTG  CCA  GGG  TGT  GTC  CCC  TGT  GTG               117
CGG  ACG  GAG  AAT  ACT  TCT  CGC  TGC  TGG  GTG  CCC  TTG  ACC               156
CCC  ACT  GTG  GCC  GCG  CCC  TAT  CCC  AAC  GCA  CCG  TTA  GAG               195
TCC  ATG  CGC  AGG  CAT  GTA  GAC  CTG  ATG  GTG  GGT  GCG  GCT               234
ACT  ATG  TGT  TCC  GCC  TTC  TAC  ATT  GGA  GAT  CTG  TGT  GGA               273
GGC  GTC  TTC  CTA  GTG  GGC  CAG  CTG  TTC  GAC  TTC  CGA  CCG               312
CGC  CGG  CAC  TGG  ACC  ACC  CAG  GAT  TGC  AAC  TGC  TCC  ATC               351
TAT  CCT  GGT  CAC  GTC  TCG  GGC  CAC  AGG  ATG  GCC  TGG  GAC               390
```

| | | | | | | | | | | | | |
|---|---|---|---|---|---|---|---|---|---|---|---|---|
|ATG|ATG|ATG|AAC|TGG|AGC|CCT|ACC|AGC|GCG|CTG|ATT|ATG|429|
|GCT|CAG|ATC|TTA|CGG|ATC|CCC|TCT|ATC|CTA|GGT|GAC|TTG|468|
|CTC|ACC|GGG|GGT|CAC|TGG|GGA|GTT|CTT|GCT|GGT|CTA|GCT|507|
|TTC|TTC|AGC|ATG|CAG|AGT|AAC|TGG|GCG|AAG|GTC|ATC|CTG|546|
|GTC|CTA|TTC|CTC|TTT|GCC|GGG|GTC|GAG|GGA| | | |576|

( 2 ) INFORMATION FOR SEQ ID NO:42:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z6

( x i ) SEQUENCE DESCRIPTION: SEQ ID NO:42:

| | | | | | | | | | | | | |
|---|---|---|---|---|---|---|---|---|---|---|---|---|
|GTT|AAC|TAT|CGC|AAT|GCC|TCG|GGC|GTC|TAT|CAC|GTC|ACC|39|
|AAC|GAC|TGC|CCG|AAC|TCG|AGC|ATA|GTG|TAT|GAG|GCC|GAA|78|
|CAC|CAG|ATC|TTA|CAC|CTC|CCA|GGG|TGC|TTG|CCC|TGT|GTG|117|
|AGG|GTT|GGG|AAT|CAG|TCA|CGC|TGC|TGG|GTG|GCC|CTT|ACT|156|
|CCC|ACC|GTG|GCG|GTG|TCT|TAT|ATC|GGT|GCT|CCG|CTT|GAC|195|
|TCC|CTC|CGG|AGA|CAT|GTG|GAC|CTG|ATG|GTG|GGC|GCC|GCT|234|
|ACT|GTA|TGC|TCT|GCC|CTC|TAC|GTT|GGA|GAT|CTG|TGC|GGT|273|
|GGT|GCA|TTC|TTG|GTT|GGC|CAG|ATG|TTC|TCC|TTC|CAG|CCG|312|
|CGA|CGC|CAC|TGG|ACT|ACG|CAG|GAC|TGC|AAT|TGT|TCT|ATC|351|
|TAC|GCA|GGG|CAT|ATC|ACG|GGC|CAC|AGG|ATG|GCA|TGG|GAC|390|
|ATG|ATG|ATG|AAC|TGG|AGT|CCC|ACA|ACC|ACC|TGC|TTC|CTC|429|
|GCC|CAG|GTC|ATG|AGG|ATC|CCT|AGC|ACT|CTG|GTA|GAT|CTA|468|
|CTC|GCT|GGA|GGG|CAC|TGG|GGC|GTC|CTT|GTT|GGG|TTG|GCG|507|
|TAC|TTC|AGT|ATG|CAA|GCT|AAT|TGG|GCC|AAA|GTC|ATC|CTG|546|
|GTC|CTT|TTC|CTC|TTC|GCT|GGA|GTT|GAT|GCC| | | |576|

( 2 ) INFORMATION FOR SEQ ID NO:43:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z7

( x i ) SEQUENCE DESCRIPTION: SEQ ID NO:43:

| | | | | | | | | | | | | |
|---|---|---|---|---|---|---|---|---|---|---|---|---|
|GTC|AAC|TAT|CAC|AAT|GCC|TCG|GGC|GTC|TAT|CAC|ATC|ACC|39|
|AAC|GAC|TGC|CCG|AAC|TCG|AGC|ATA|ATG|TAT|GAG|GCC|GAA|78|
|CAC|CAC|ATC|CTA|CAC|CTC|CCA|GGG|TGC|GTA|CCC|TGT|GTG|117|
|AGG|GAG|GGG|AAC|CAG|TCA|CGC|TGC|TGG|GTG|GCC|CTT|ACT|156|
|CCC|ACC|GTG|GCG|GCG|CCT|TAT|ATC|GGT|GCA|CCG|CTT|GAA|195|

| | | | | | | | | | | | | |
|---|---|---|---|---|---|---|---|---|---|---|---|---|
|TCC|ATC|CGG|AGA|CAT|GTG|GAC|CTG|ATG|GTA|GGC|GCT|GCT|234|
|ACA|GTG|TGC|TCC|GCT|CTC|TAC|ATT|GGG|GAC|CTG|TGC|GGT|273|
|GGC|GTA|TTT|TTG|GTT|GGT|CAG|ATG|TTT|TCT|TTC|CAG|CCG|312|
|CGA|CGC|CAC|TGG|ACT|ACG|CAG|GAC|TGC|AAT|TGT|TCC|ATC|351|
|TAT|GCG|GGG|CAC|GTT|ACA|GGC|CAC|AGA|ATG|GCA|TGG|GAC|390|
|ATG|ATG|ATG|AAC|TGG|AGT|CCC|ACA|ACC|ACC|TTG|GTC|CTC|429|
|GCC|CAG|GTT|ATG|AGG|ATC|CCT|AGC|ACT|CTG|GTG|GAC|CTA|468|
|CTC|ACT|GGA|GGG|CAC|TGG|GGT|ATC|CTT|ATC|GGG|GTG|GCA|507|
|TAC|TTC|TGC|ATG|CAA|GCT|AAT|TGG|GCC|AAG|GTC|ATT|CTG|546|
|GTC|CTT|TTC|CTC|TAC|GCT|GGA|GTT|GAT|GCC| | | |576|

(2) INFORMATION FOR SEQ ID NO:44:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DK13

(xi) SEQUENCE DESCRIPTION: SEQ ID NO:44:

| | | | | | | | | | | | | |
|---|---|---|---|---|---|---|---|---|---|---|---|---|
|TAC|AAC|TAT|CGC|AAC|AGC|TCG|GGT|GTC|TAC|CAT|GTC|ACC|39|
|AAC|GAT|TGC|CCG|AAC|TCG|AGC|ATA|GTC|TAT|GAA|ACC|GAT|78|
|TAC|CAC|ATC|TTA|CAC|CTC|CCG|GGA|TGC|GTT|CCT|TGC|GTG|117|
|AGG|GAA|GGG|AAC|AAG|TCT|ACA|TGC|TGG|GTG|TCT|CTC|ACC|156|
|CCC|ACC|GTG|GCT|GCG|CAA|CAT|CTG|AAT|GCT|CCG|CTT|GAG|195|
|TCT|TTG|AGA|CGT|CAC|GTG|GAT|CTG|ATG|GTG|GGC|GGC|GCC|234|
|ACT|CTC|TGC|TCC|GCC|CTC|TAC|ATC|GGA|GAC|GTG|TGT|GGG|273|
|GGT|GTG|TTC|TTG|GTC|GGT|CAA|CTG|TTC|ACC|TTC|CAA|CCT|312|
|CGC|CGC|CAC|TGG|ACC|ACC|CAA|GAC|TGC|AAT|TGT|TCC|ATC|351|
|TAC|ACA|GGA|CAT|ATC|ACA|GGA|CAC|AGA|ATG|GCT|TGG|GAC|390|
|ATG|ATG|ATG|AAT|TGG|AGC|CCC|ACT|GCG|ACG|CTG|GTC|CTC|429|
|GCC|CAA|CTT|ATG|AGG|ATC|CCA|GGC|GCC|ATG|GTC|GAC|CTG|468|
|CTT|GCA|GGC|GGC|CAC|TGG|GGC|ATT|CTG|GTT|GGC|ATA|GCG|507|
|TAC|TTC|AGC|ATG|CAA|GCT|AAT|TGG|GCC|AAG|GTT|ATC|CTG|546|
|GTC|CTG|TTT|CTC|TTT|GCT|GGA|GTC|GAC|GCT| | | |576|

(2) INFORMATION FOR SEQ ID NO:45:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SA1

(xi) SEQUENCE DESCRIPTION: SEQ ID NO:45:

-continued

| | | | | | | | | | | | | | |
|---|---|---|---|---|---|---|---|---|---|---|---|---|---|
| GTT | CCC | TAC | CGG | AAT | GCC | TCT | GGG | GTT | TAC | CAT | GTC | ACC | 39 |
| AAT | GAC | TGC | CCA | AAC | TCC | TCC | ATA | GTC | TAC | GAG | GCT | GAT | 78 |
| AGC | CTG | ATC | TTG | CAC | GCA | CCT | GGC | TGC | GTG | CCC | TGT | GTC | 117 |
| AGG | CAA | GAT | AAT | GTC | AGT | AGG | TGC | TGG | GTC | CAA | ATC | ACC | 156 |
| CCC | ACA | CTG | TCA | GCC | CCG | ACC | TTC | GGA | GCG | GTC | ACG | GCT | 195 |
| CCT | CTT | CGG | AGG | GCC | GTT | GAC | TAC | TTA | GCG | GGA | GGA | GCT | 234 |
| GCT | CTC | TGC | TCC | GCA | CTA | TAC | GTC | GGC | GAC | GCG | TGC | GGG | 273 |
| GCA | GTG | TTT | CTG | GTA | GGC | CAA | ATG | TTC | ACC | TAT | AGG | CCT | 312 |
| CGC | CAG | CAT | ACC | ACA | GTG | CAG | GAC | TGC | AAC | TGT | TCC | ATT | 351 |
| TAC | AGT | GGC | CAT | ATC | ACC | GGC | CAC | CGG | ATG | GCT | TGG | GAC | 390 |
| ATG | ATG | ATG | AAT | TGG | TCA | CCT | ACG | ACA | GCC | TTG | CTG | ATG | 429 |
| GCC | CAG | ATG | CTA | CGG | ATC | CCC | CAG | GTG | GTC | ATA | GAC | ATC | 468 |
| ATA | GCC | GGG | GGC | CAC | TGG | GGG | GTC | TTG | TTT | GCC | GCC | GCA | 507 |
| TAC | TTT | GCG | TCG | GCC | GCC | AAC | TGG | GCT | AAG | GTA | GTG | CTG | 546 |
| GTT | CTG | TTC | CTG | TTT | GCG | GGG | GTC | GAT | GGC | | | | 576 |

( 2 ) INFORMATION FOR SEQ ID NO:46:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA4

( x i ) SEQUENCE DESCRIPTION: SEQ ID NO:46:

| | | | | | | | | | | | | | |
|---|---|---|---|---|---|---|---|---|---|---|---|---|---|
| GTT | CCC | TAC | CGA | AAC | GCC | TCT | GGG | GTT | TAT | CAT | GTC | ACC | 39 |
| AAT | GAT | TGC | CCA | AAC | TCT | TCC | ATA | GTT | TAC | GAG | GCT | GAT | 78 |
| AAC | CTG | ATC | TTG | CAT | GCA | CCT | GGT | TGC | GTG | CCT | TGT | GTC | 117 |
| AGG | CAA | GAT | AAT | GTC | AGT | AAG | TGC | TGG | GTC | CAA | ATC | ACC | 156 |
| CCC | ACG | TTG | TCA | GCC | CCG | AAT | CTC | GGA | GCG | GTC | ACG | GCT | 195 |
| CCT | CTT | CGG | AGG | GCC | GTT | GAC | TAC | TTA | GCG | GGA | GGG | GCT | 234 |
| GCC | CTC | TGC | TCC | GCA | CTA | TAC | GTC | GGG | GAC | GCG | TGC | GGG | 273 |
| GCA | GTG | TTT | TTG | GTA | GGC | CAA | ATG | TTC | ACC | TAT | AGG | CCT | 312 |
| CGC | CAG | CAC | ACT | ACG | GTG | CAA | GAC | TGC | AAT | TGC | TCT | ATT | 351 |
| TAC | AGT | GGC | CAT | ATC | ACC | GGC | CAC | CGG | ATG | GCA | TGG | GAC | 390 |
| ATG | ATG | ATG | AAT | TGG | TCA | CCT | ACG | ACG | GCC | TTG | CTG | ATG | 429 |
| GCC | CAG | TTG | CTA | CGG | ATT | CCC | CAG | GTG | GTC | ATC | GAC | ATC | 468 |
| ATT | GCC | GGG | GGC | CAC | TGG | GGG | GTC | TTG | TTT | GCC | GCC | GCA | 507 |
| TAT | TTC | GCG | TCA | GCG | GCT | AAC | TGG | GCT | AAG | GTT | ATA | CTG | 546 |
| GTC | TTG | TTT | CTG | TTT | GCG | GGG | GTC | GAT | GCC | | | | 576 |

( 2 ) INFORMATION FOR SEQ ID NO:47:

( i ) SEQUENCE CHARACTERISTICS:

(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA5

(xi) SEQUENCE DESCRIPTION: SEQ ID NO:47:

| GTC | CCC | TAC | CGA | AAT | GCC | TCT | GGG | GTT | TAT | CAT | GTC | ACC | 39 |
| AAT | GAT | TGC | CCA | AAC | TCT | TCC | ATA | GTC | TAC | GAG | GCT | GAT | 78 |
| AAC | CTG | ATT | CTG | CAC | GCA | CCT | GGT | TGC | GTG | CCC | TGT | GTC | 117 |
| AAG | GAA | GGT | AAT | GTC | AGT | AGG | TGC | TGG | GTC | CAA | ATC | ACC | 156 |
| CCC | ACA | TTG | TCA | GCC | CCG | AAC | CTC | GGA | GCG | GTC | ACG | GCT | 195 |
| CCT | CTT | CGG | AGG | GTC | GTT | GAC | TAC | TTA | GCG | GGA | GGG | GCT | 234 |
| GCC | CTC | TGC | TCC | GCA | CTA | TAC | GTC | GGG | GAC | GCG | TGC | GGG | 273 |
| GCA | GTG | TTC | TTG | GTA | GGC | CAA | ATG | TTC | ACC | TAT | AGG | CCT | 312 |
| CGC | CAG | CAT | ACT | ACG | GTG | CAG | GAC | TGC | AAC | TGT | TCC | ATT | 351 |
| TAC | AGC | GGC | CAT | ATC | ACC | GGC | CAC | CGA | ATG | GCA | TGG | GAC | 390 |
| ATG | ATG | ATG | AAT | TGG | TCA | CCT | ACG | ACA | GCC | TTG | GTG | ATG | 429 |
| GCC | CAG | GTG | CTA | CGG | ATT | CCC | CAA | GTG | GTC | ATT | GAC | ATC | 468 |
| ATT | GCC | GGG | GGC | CAC | TGG | GGG | GTC | TTG | TTC | GCC | GTC | GCA | 507 |
| TAC | TTC | GCG | TCA | GCG | GCT | AAC | TGG | GCT | AAG | GTT | GTG | CTG | 546 |
| GTC | CTG | TTT | CTG | TTT | GCG | GGG | GTC | GAT | GGC | | | | 576 |

(2) INFORMATION FOR SEQ ID NO:48:

(i) SEQUENCE CHARACTERISTICS:
(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA6

(xi) SEQUENCE DESCRIPTION: SEQ ID NO:48:

| GTT | CCT | TAC | CGG | AAT | GCC | TCT | GGG | GTG | TAT | CAT | GTT | ACC | 39 |
| AAT | GAT | TGC | CCA | AAC | TCT | TCC | ATA | GTC | TAT | GAG | GCT | GAT | 78 |
| GAC | CTG | ATC | CTA | CAC | GCA | CCT | GGC | TGC | GTG | CCC | TGT | GTC | 117 |
| CGG | AAG | GAT | AAT | GTC | AGT | AGA | TGC | TGG | GTT | CAT | ATC | ACC | 156 |
| CCC | ACA | CTA | TCA | GCC | CCG | AGC | CTC | GGA | GCG | GTC | ACG | GCT | 195 |
| CCT | CTT | CGG | AGG | GCC | GTT | GAT | TAC | TTG | GCG | GGA | GGG | GCC | 234 |
| GCC | CTG | TGC | TCC | GCG | TTA | TAC | GTC | GGA | GAC | GTG | TGC | GGG | 273 |
| GCA | TTG | TTT | TTG | GTA | GGC | CAA | ATG | TTC | ACC | TAT | AGG | CCT | 312 |
| CGC | CAG | CAT | GCT | ACG | GTA | CAG | GAC | TGC | AAC | TGC | TCC | ATT | 351 |
| TAC | AGT | GGC | CAT | ATC | ACT | GGC | CAC | CGG | ATG | GCA | TGG | GAC | 390 |
| ATG | ATG | ATG | AAT | TGG | TCA | CCC | GCG | ACA | GCC | TTG | GTG | ATG | 429 |
| GCC | CAA | ATG | CTA | CGG | ATT | CCC | CAG | GTG | GTC | ATT | GAC | ATC | 468 |

| | | | | | | | | | | | | |
|---|---|---|---|---|---|---|---|---|---|---|---|---|
| ATT | GCC | GGG | GGC | CAC | TGG | GGG | GTC | TTG | TTC | GCC | GCT | GCA | 5 0 7 |
| TAC | TTC | GCG | TCG | GCG | GCT | AAC | TGG | GCT | AAG | GTT | GTG | CTG | 5 4 6 |
| GTC | TTG | TTT | CTG | TTT | GCG | GGG | GTT | GAT | GCC | | | | 5 7 6 |

( 2 ) INFORMATION FOR SEQ ID NO:49:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA7

( x i ) SEQUENCE DESCRIPTION: SEQ ID NO:49:

| | | | | | | | | | | | | |
|---|---|---|---|---|---|---|---|---|---|---|---|---|
| GTC | CCC | TAC | CGA | AAT | GCC | TCC | GGG | GTT | TAT | CAT | GTC | ACC | 3 9 |
| AAT | GAT | TGC | CCG | AAC | TCT | TCC | ATA | GTC | TAT | GAG | GCT | GAC | 7 8 |
| AAC | CTG | ATC | CTG | CAC | GCA | CCT | GGT | TGC | GTG | CCC | TGT | GTC | 1 1 7 |
| AGA | CAA | AAT | AAT | GTC | AGT | AGG | TGC | TGG | GTC | CAA | ATC | ACC | 1 5 6 |
| CCC | ACA | TTG | TCA | GCC | CCG | AAC | CTC | GGA | GCG | GTC | ACG | GCT | 1 9 5 |
| CCT | CTT | CGG | AGG | GCC | GTT | GAC | TAC | CTA | GCG | GGA | GGG | GCT | 2 3 4 |
| GCC | CTC | TGC | TCC | GCG | CTA | TAC | GTC | GGG | GAC | GCG | TGC | GGG | 2 7 3 |
| GCA | GTG | TTT | TTG | GTA | GGC | CAG | ATG | TTC | AGC | TAT | AGG | CCT | 3 1 2 |
| CGC | CAG | CAC | ACT | ACG | GTG | CAG | GAC | TGC | AAC | TGT | TCC | ATT | 3 5 1 |
| TAC | AGT | GGC | CAT | ATC | ACC | GGC | CAC | CGA | ATG | GCA | TGG | GAC | 3 9 0 |
| ATG | ATG | ATG | AAT | TGG | TCA | CCT | ACG | ACA | GCC | TTG | GTG | ATG | 4 2 9 |
| GCC | CAG | TTG | CTA | CGG | ATT | CCC | CAG | GTG | GTC | ATC | GAC | ATC | 4 6 8 |
| ATT | GCC | GGG | GGC | CAC | TGG | GGG | GTC | TTG | TTC | GCC | GCC | GCA | 5 0 7 |
| TAT | TTC | GCG | TCA | GCG | GCT | AAC | TGG | GCT | AAG | GTT | GTG | CTG | 5 4 |
| GTC | TTG | TTT | CTG | TTT | GCG | GGG | GTC | GAT | GCC | | | | 5 7 6 |

( 2 ) INFORMATION FOR SEQ ID NO:50:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA13

( x i ) SEQUENCE DESCRIPTION: SEQ ID NO:50:

| | | | | | | | | | | | | |
|---|---|---|---|---|---|---|---|---|---|---|---|---|
| GTT | CCC | TAC | CGA | AAT | GCC | TCT | GGG | GTT | TAT | CAT | GTC | ACC | 3 9 |
| AAT | GAT | TGC | CCA | AAC | TCT | TCC | ATC | GTC | TAC | GAG | GCT | GAT | 7 8 |
| GAC | CTG | ATC | TTA | CAC | GCA | CCT | GGT | TGC | GTG | CCC | TGT | GTT | 1 1 7 |
| AGG | CAG | GGT | AAT | GTC | AGT | AGG | TGC | TGG | GTC | CAG | ATC | ACC | 1 5 6 |
| CCC | ACA | CTG | TCA | GCC | CCG | AGC | CTC | GGA | GCG | GTC | ACG | GCT | 1 9 5 |
| CCT | CTT | CGG | AGG | GCC | GTT | GAC | TAC | TTA | GCG | GGG | GGG | GCT | 2 3 4 |
| GCC | CTT | TGC | TCC | GCG | TTA | TAC | GTC | GGA | GAC | GCG | TGC | GGG | 2 7 3 |

| | | | | | | | | | | | | |
|---|---|---|---|---|---|---|---|---|---|---|---|---|
| GCA | GTG | TTT | TTG | GTA | GGT | CAA | ATG | TTC | ACC | TAT | AGC | CCT | 312 |
| CGC | CGG | CAT | AAT | GTT | GTG | CAG | GAC | TGC | AAC | TGT | TCC | ATT | 351 |
| TAC | AGT | GGC | CAC | ATC | ACC | GGC | CAC | CGG | ATG | GCA | TGG | GAC | 390 |
| ATG | ATG | ATG | AAT | TGG | TCA | CCT | ACA | ACA | GCT | TTG | GTG | ATG | 429 |
| GCC | CAG | TTG | TTA | CGG | ATT | CCC | CAG | GTG | GTC | ATT | GAC | ATC | 468 |
| ATT | GCC | GGG | GCC | CAC | TGG | GGG | GTC | TTG | TTC | GCC | GCC | GCA | 507 |
| TAC | TAC | GCG | TCG | GCG | GCT | AAC | TGG | GCC | AAG | GTT | GTG | CTG | 546 |
| GTC | CTG | TTT | CTG | TTT | GCG | GGG | GTC | GAT | GCC | | | | 576 |

( 2 ) INFORMATION FOR SEQ ID NO:51:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK2

( x i ) SEQUENCE DESCRIPTION: SEQ ID NO:51:

| | | | | | | | | | | | | |
|---|---|---|---|---|---|---|---|---|---|---|---|---|
| CTT | ACC | TAC | GGC | AAC | TCC | AGT | GGG | CTA | TAC | CAT | CTC | ACA | 39 |
| AAT | GAT | TGC | CCC | AAC | TCC | AGC | ATC | GTG | CTG | GAG | GCG | GAT | 78 |
| GCT | ATG | ATC | TTG | CAT | TTG | CCT | GGA | TGC | TTG | CCT | TGT | GTG | 117 |
| AGG | GTC | GAT | GAT | CGG | TCC | ACC | TGT | TGG | CAT | GCT | GTG | ACC | 156 |
| CCC | ACC | CTG | GCC | ATA | CCA | AAT | GCT | TCC | ACG | CCC | GCA | ACG | 195 |
| GGA | TTC | CGC | AGG | CAT | GTG | GAT | CTT | CTT | GCG | GGC | GCC | GCA | 234 |
| GTG | GTT | TGC | TCA | TCC | CTG | TAC | ATC | GGG | GAC | CTG | TGT | GGC | 273 |
| TCT | CTC | TTT | TTG | GCG | GGA | CAA | CTA | TTC | ACC | TTT | CAG | CCC | 312 |
| CGC | CGT | CAT | TGG | ACT | GTG | CAA | GAC | TGC | AAC | TGC | TCC | ATC | 351 |
| TAT | ACA | GGC | CAC | GTC | ACC | GGC | CAC | AGG | ATG | GCT | TGG | GAC | 390 |
| ATG | ATG | ATG | AAC | TGG | TCA | CCC | ACA | ACC | ACT | CTG | GTC | CTA | 429 |
| TCT | AGC | ATC | TTG | AGG | GTA | CCT | GAG | ATT | TGT | GCG | AGT | GTG | 468 |
| ATA | TTT | GGT | GGC | CAT | TGG | GGG | ATA | CTA | CTA | GCC | GTT | GCC | 507 |
| TAC | TTT | GGC | ATG | GCT | GGC | AAC | TGG | CTA | AAA | GTT | CTG | GCT | 546 |
| GTT | CTG | TTC | CTA | TTT | GCA | GGG | GTT | GAA | GCA | | | | 576 |

( 2 ) INFORMATION FOR SEQ ID NO:52:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK7

( x i ) SEQUENCE DESCRIPTION: SEQ ID NO:52:

Tyr Gln Val Arg Asn Ser Thr Gly Leu Tyr His Val Thr Asn Asp
               5                     10                  15

Cys Pro Asn Ser Ser Ile Val Tyr Glu Ala Ala Asp Ala Ile Leu

|   |   |   |   |   | 20 |   |   |   |   | 25 |   |   |   |   | 30 |
|---|---|---|---|---|---|---|---|---|---|---|---|---|---|---|---|
| His | Thr | Pro | Gly | Cys<br>35 | Val | Pro | Cys | Val | Arg<br>40 | Glu | Gly | Asn | Val | Ser<br>45 |
| Arg | Cys | Trp | Val | Ala<br>50 | Met | Thr | Pro | Thr | Val<br>55 | Ala | Thr | Arg | Asp | Gly<br>60 |
| Lys | Leu | Pro | Thr | Ala<br>65 | Gln | Leu | Arg | Arg | His<br>70 | Ile | Asp | Leu | Leu | Val<br>75 |
| Gly | Ser | Ala | Thr | Leu<br>80 | Cys | Ser | Ala | Leu | Tyr<br>85 | Val | Gly | Asp | Leu | Cys<br>90 |
| Gly | Ser | Val | Phe | Leu<br>95 | Val | Gly | Gln | Leu | Phe<br>100 | Thr | Phe | Ser | Pro | Arg<br>105 |
| Arg | His | Trp | Thr | Thr<br>110 | Gln | Gly | Cys | Asn | Cys<br>115 | Ser | Ile | Tyr | Pro | Gly<br>120 |
| His | Ile | Thr | Gly | His<br>125 | Arg | Met | Ala | Trp | Asp<br>130 | Met | Met | Met | Asn | Trp<br>135 |
| Ser | Pro | Thr | Thr | Ala<br>140 | Leu | Val | Val | Ala | Gln<br>145 | Leu | Leu | Arg | Ile | Pro<br>150 |
| Gln | Ala | Ile | Leu | Asp<br>155 | Met | Ile | Ala | Gly | Ala<br>160 | His | Trp | Gly | Val | Leu<br>165 |
| Ala | Gly | Ile | Ala | Tyr<br>170 | Phe | Ser | Met | Val | Gly<br>175 | Asn | Trp | Ala | Lys | Val<br>180 |
| Leu | Val | Val | Leu | Leu<br>185 | Leu | Phe | Ala | Gly | Val<br>190 | Asp | Ala |   |   |   |

(2) INFORMATION FOR SEQ ID NO:53:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK9

(xi) SEQUENCE DESCRIPTION: SEQ ID NO:53:

|   |   |   |   |   |   |   |   |   |   |   |   |   |   |   |   |
|---|---|---|---|---|---|---|---|---|---|---|---|---|---|---|---|
| Tyr | Gln | Val | Arg | Asn<br>5 | Ser | Ser | Gly | Leu | Tyr<br>10 | His | Val | Thr | Asn | Asp<br>15 |
| Cys | Pro | Asn | Ser | Ser<br>20 | Ile | Val | Tyr | Glu | Ala<br>25 | Ala | Asp | Ala | Ile | Leu<br>30 |
| His | Ser | Pro | Gly | Cys<br>35 | Val | Pro | Cys | Val | Arg<br>40 | Glu | Gly | Asn | Ala | Ser<br>45 |
| Lys | Cys | Trp | Val | Ala<br>50 | Val | Ala | Pro | Thr | Val<br>55 | Ala | Thr | Arg | Asp | Gly<br>60 |
| Lys | Leu | Pro | Ala | Thr<br>65 | Gln | Leu | Arg | Arg | His<br>70 | Ile | Asp | Leu | Leu | Val<br>75 |
| Gly | Ser | Ala | Thr | Leu<br>80 | Cys | Ser | Ala | Leu | Tyr<br>85 | Val | Gly | Asp | Leu | Cys<br>90 |
| Gly | Ser | Val | Phe | Leu<br>95 | Val | Gly | Gln | Leu | Phe<br>100 | Thr | Phe | Ser | Pro | Arg<br>105 |
| Arg | His | Trp | Thr | Thr<br>110 | Gln | Asp | Cys | Asn | Cys<br>115 | Ser | Ile | Tyr | Pro | Gly<br>120 |
| His | Ile | Thr | Gly | His<br>125 | Arg | Met | Ala | Trp | Asp<br>130 | Met | Met | Met | Asn | Trp<br>135 |
| Ser | Pro | Thr | Ala | Ala<br>140 | Leu | Val | Met | Ala | Gln<br>145 | Leu | Leu | Arg | Ile | Pro<br>150 |

| Gln | Ala | Ile | Leu | Asp<br>155 | Met | Ile | Ala | Gly | Ala<br>160 | His | Trp | Gly | Val | Leu<br>165 |
|---|---|---|---|---|---|---|---|---|---|---|---|---|---|---|
| Ala | Gly | Ile | Ala | Tyr<br>170 | Phe | Ser | Met | Val | Gly<br>175 | Asn | Trp | Ala | Lys | Val<br>180 |
| Val | Val | Val | Leu | Leu<br>185 | Leu | Phe | Thr | Gly | Val<br>190 | Asp | Ala | | | |

( 2 ) INFORMATION FOR SEQ ID NO:54:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DR1

( x i ) SEQUENCE DESCRIPTION: SEQ ID NO:54:

| His | Gln | Val | Arg | Asn<br>5 | Ser | Thr | Gly | Leu | Tyr<br>10 | His | Val | Thr | Asn | Asp<br>15 |
|---|---|---|---|---|---|---|---|---|---|---|---|---|---|---|
| Cys | Pro | Asn | Ser | Ser<br>20 | Ile | Val | Tyr | Glu | Ala<br>25 | Ala | Asp | Ala | Ile | Leu<br>30 |
| His | Ala | Pro | Gly | Cys<br>35 | Val | Pro | Cys | Val | Arg<br>40 | Glu | Gly | Asn | Ala | Ser<br>45 |
| Arg | Cys | Trp | Val | Ala<br>50 | Val | Thr | Pro | Thr | Val<br>55 | Ala | Thr | Arg | Asp | Gly<br>60 |
| Lys | Leu | Pro | Thr | Thr<br>65 | Gln | Leu | Arg | Arg | His<br>70 | Ile | Asp | Leu | Leu | Val<br>75 |
| Gly | Ser | Ala | Thr | Leu<br>80 | Cys | Ser | Ala | Leu | Tyr<br>85 | Val | Gly | Asp | Leu | Cys<br>90 |
| Gly | Ser | Val | Phe | Leu<br>95 | Val | Gly | Gln | Leu | Phe<br>100 | Thr | Phe | Ser | Pro | Arg<br>105 |
| Arg | His | Trp | Thr | Thr<br>110 | Gln | Asp | Cys | Asn | Cys<br>115 | Ser | Ile | Tyr | Pro | Gly<br>120 |
| His | Ile | Thr | Gly | His<br>125 | Arg | Met | Ala | Trp | Asp<br>130 | Met | Met | Met | Asn | Trp<br>135 |
| Ser | Pro | Thr | Thr | Ala<br>140 | Leu | Val | Met | Ala | Gln<br>145 | Leu | Leu | Arg | Ile | Pro<br>150 |
| Gln | Ala | Ile | Leu | Asp<br>155 | Met | Ile | Ala | Gly | Ala<br>160 | His | Trp | Gly | Val | Leu<br>165 |
| Ala | Gly | Ile | Ala | Tyr<br>170 | Phe | Ser | Met | Val | Gly<br>175 | Asn | Trp | Ala | Lys | Val<br>180 |
| Val | Val | Val | Leu | Leu<br>185 | Leu | Phe | Ala | Gly | Val<br>190 | Asp | Ala | | | |

( 2 ) INFORMATION FOR SEQ ID NO:55:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DR4

( x i ) SEQUENCE DESCRIPTION: SEQ ID NO:55:

| His | Gln | Val | Arg | Asn<br>5 | Ser | Thr | Gly | Leu | Tyr<br>10 | His | Val | Thr | Asn | Asp<br>15 |
|---|---|---|---|---|---|---|---|---|---|---|---|---|---|---|

```
Cys  Pro  Asn  Ser  Ser  Ile  Val  Tyr  Glu  Ala  Ala  Asp  Ala  Ile  Leu
                    20                       25                           30

His  Thr  Pro  Gly  Cys  Val  Pro  Cys  Val  Arg  Glu  Gly  Asn  Thr  Ser
                    35                       40                           45

Arg  Cys  Trp  Val  Ala  Val  Thr  Pro  Thr  Val  Ala  Thr  Arg  Asp  Gly
                    50                       55                           60

Lys  Leu  Pro  Thr  Thr  Gln  Leu  Arg  Arg  His  Ile  Asp  Leu  Leu  Val
                    65                       70                           75

Gly  Ser  Ala  Thr  Leu  Cys  Ser  Ala  Leu  Tyr  Val  Gly  Asp  Leu  Cys
                    80                       85                           90

Gly  Ser  Val  Phe  Leu  Val  Gly  Gln  Leu  Phe  Thr  Phe  Ser  Pro  Arg
                    95                      100                          105

His  His  Trp  Thr  Thr  Gln  Asp  Cys  Asn  Cys  Ser  Ile  Tyr  Pro  Gly
                   110                      115                          120

His  Ile  Thr  Gly  His  Arg  Met  Ala  Trp  Asp  Met  Met  Met  Asn  Trp
                   125                      130                          135

Ser  Pro  Thr  Thr  Ala  Leu  Val  Val  Ala  Gln  Leu  Leu  Arg  Ile  Pro
                   140                      145                          150

Gln  Ala  Ile  Leu  Asp  Met  Ile  Ala  Gly  Ala  His  Trp  Gly  Val  Leu
                   155                      160                          165

Ala  Gly  Ile  Ala  Tyr  Phe  Ser  Met  Val  Gly  Asn  Trp  Ala  Lys  Val
                   170                      175                          180

Leu  Val  Val  Leu  Leu  Leu  Phe  Ala  Gly  Val  Asp  Ala
                   185                      190
```

( 2 ) INFORMATION FOR SEQ ID NO:56:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S14

( x i ) SEQUENCE DESCRIPTION: SEQ ID NO:56:

```
Tyr  Gln  Val  Arg  Asn  Ser  Thr  Gly  Leu  Tyr  His  Val  Thr  Asn  Asp
                     5                       10                           15

Cys  Pro  Asn  Ser  Ser  Ile  Val  Tyr  Glu  Thr  Ala  Asp  Ala  Ile  Leu
                    20                       25                           30

His  Ala  Pro  Gly  Cys  Val  Pro  Cys  Val  Arg  Glu  Gly  Asn  Thr  Ser
                    35                       40                           45

Arg  Cys  Trp  Val  Ala  Met  Thr  Pro  Thr  Val  Ala  Thr  Arg  Asp  Gly
                    50                       55                           60

Lys  Leu  Pro  Ala  Thr  Gln  Leu  Arg  Arg  Tyr  Ile  Asp  Leu  Leu  Val
                    65                       70                           75

Gly  Ser  Ala  Thr  Leu  Cys  Ser  Ala  Leu  Tyr  Val  Gly  Asp  Leu  Cys
                    80                       85                           90

Gly  Ser  Val  Phe  Leu  Val  Gly  Gln  Leu  Phe  Thr  Phe  Ser  Pro  Arg
                    95                      100                          105

Arg  Leu  Trp  Thr  Thr  Gln  Asp  Cys  Asn  Cys  Ser  Ile  Tyr  Pro  Gly
                   110                      115                          120

His  Ile  Thr  Gly  His  Arg  Met  Ala  Trp  Asp  Met  Met  Met  Asn  Trp
                   125                      130                          135

Ser  Pro  Thr  Thr  Ala  Leu  Val  Val  Ala  Gln  Leu  Leu  Arg  Ile  Pro
```

|     |     |     |     | 140 |     |     |     |     | 145 |     |     |     |     | 150 |
| --- | --- | --- | --- | --- | --- | --- | --- | --- | --- | --- | --- | --- | --- | --- |
| Gln | Ala | Ile | Leu | Asp | Met | Ile | Ala | Gly | Ala | His | Trp | Gly | Val | Leu |
|     |     |     |     | 155 |     |     |     |     | 160 |     |     |     |     | 165 |
| Ala | Gly | Ile | Ala | Tyr | Phe | Ser | Met | Val | Gly | Asn | Trp | Ala | Lys | Val |
|     |     |     |     | 170 |     |     |     |     | 175 |     |     |     |     | 180 |
| Leu | Val | Val | Leu | Leu | Leu | Phe | Ala | Gly | Val | Asp | Ala |     |     |     |
|     |     |     |     | 185 |     |     |     |     | 190 |     |     |     |     |     |

( 2 ) INFORMATION FOR SEQ ID NO:57:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S18

( x i ) SEQUENCE DESCRIPTION: SEQ ID NO:57:

|     |     |     |     |     |     |     |     |     |     |     |     |     |     |     |
| --- | --- | --- | --- | --- | --- | --- | --- | --- | --- | --- | --- | --- | --- | --- |
| Tyr | Gln | Val | Arg | Asn | Ser | Thr | Gly | Leu | Tyr | His | Val | Thr | Asn | Asp |
|     |     |     |     | 5   |     |     |     |     | 10  |     |     |     |     | 15  |
| Cys | Pro | Asn | Ser | Ser | Ile | Val | Tyr | Glu | Thr | Ala | Asp | Thr | Ile | Leu |
|     |     |     |     | 20  |     |     |     |     | 25  |     |     |     |     | 30  |
| His | Ser | Pro | Gly | Cys | Val | Pro | Cys | Val | Arg | Glu | Gly | Asn | Ala | Ser |
|     |     |     |     | 35  |     |     |     |     | 40  |     |     |     |     | 45  |
| Arg | Cys | Trp | Val | Pro | Val | Ala | Pro | Thr | Val | Ala | Thr | Arg | Asp | Gly |
|     |     |     |     | 50  |     |     |     |     | 55  |     |     |     |     | 60  |
| Lys | Leu | Pro | Ala | Thr | Gln | Leu | Arg | Arg | His | Ile | Asp | Leu | Leu | Val |
|     |     |     |     | 65  |     |     |     |     | 70  |     |     |     |     | 75  |
| Gly | Ser | Ala | Thr | Leu | Cys | Ser | Ala | Leu | Tyr | Val | Gly | Asp | Leu | Cys |
|     |     |     |     | 80  |     |     |     |     | 85  |     |     |     |     | 90  |
| Gly | Ser | Val | Phe | Leu | Val | Ser | Gln | Leu | Phe | Thr | Ile | Ser | Pro | Arg |
|     |     |     |     | 95  |     |     |     |     | 100 |     |     |     |     | 105 |
| Arg | His | Trp | Thr | Thr | Gln | Asp | Cys | Asn | Cys | Ser | Ile | Tyr | Pro | Gly |
|     |     |     |     | 110 |     |     |     |     | 115 |     |     |     |     | 120 |
| His | Ile | Thr | Gly | His | Arg | Met | Ala | Trp | Asp | Met | Met | Met | Asn | Trp |
|     |     |     |     | 125 |     |     |     |     | 130 |     |     |     |     | 135 |
| Ser | Pro | Thr | Thr | Ala | Leu | Val | Ile | Ala | Gln | Leu | Leu | Arg | Val | Pro |
|     |     |     |     | 140 |     |     |     |     | 145 |     |     |     |     | 150 |
| Gln | Ala | Val | Leu | Asp | Met | Ile | Ala | Gly | Ala | His | Trp | Gly | Val | Leu |
|     |     |     |     | 155 |     |     |     |     | 160 |     |     |     |     | 165 |
| Ala | Gly | Ile | Ala | Tyr | Phe | Ser | Met | Val | Gly | Asn | Trp | Ala | Lys | Val |
|     |     |     |     | 170 |     |     |     |     | 175 |     |     |     |     | 180 |
| Leu | Leu | Val | Leu | Leu | Leu | Phe | Ala | Gly | Val | Asp | Ala |     |     |     |
|     |     |     |     | 185 |     |     |     |     | 190 |     |     |     |     |     |

( 2 ) INFORMATION FOR SEQ ID NO:58:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SW1

( x i ) SEQUENCE DESCRIPTION: SEQ ID NO:58:

```
Tyr Gln Val Arg Asn Ser Ser Gly Leu Tyr His Val Thr Asn Asp
              5                  10                 15
Cys Pro Asn Ser Ser Ile Val Tyr Glu Thr Ala Asp Ala Ile Leu
             20                  25                 30
His Ser Pro Gly Cys Val Pro Cys Val Arg Glu Asp Gly Ala Pro
             35                  40                 45
Lys Cys Trp Val Ala Val Ala Pro Thr Val Ala Thr Arg Asp Gly
             50                  55                 60
Lys Leu Pro Ala Thr Gln Leu Arg Arg His Ile Asp Leu Leu Val
             65                  70                 75
Gly Ser Ala Thr Leu Cys Ser Ala Leu Tyr Val Gly Asp Leu Cys
             80                  85                 90
Gly Ser Val Phe Leu Val Ser Gln Leu Phe Thr Phe Ser Pro Arg
             95                 100                105
Arg His Trp Thr Thr Gln Asp Cys Asn Cys Ser Ile Tyr Pro Gly
            110                 115                120
His Ile Thr Gly His Arg Met Ala Trp Asp Met Met Met Asn Trp
            125                 130                135
Ser Pro Thr Thr Ala Leu Val Val Ala Gln Leu Leu Arg Ile Pro
            140                 145                150
Gln Ala Val Leu Asp Met Ile Ala Gly Ala His Trp Gly Val Leu
            155                 160                165
Ala Gly Ile Ala Tyr Phe Ser Met Val Gly Asn Trp Ala Lys Val
            170                 175                180
Leu Ile Val Leu Leu Leu Phe Ser Gly Val Asp Ala
            185                 190
```

(2) INFORMATION FOR SEQ ID NO:59:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: US11

(xi) SEQUENCE DESCRIPTION: SEQ ID NO:59:

```
Tyr Gln Val Arg Asn Ser Thr Gly Leu Tyr His Val Thr Asn Asp
              5                  10                 15
Cys Pro Asn Ser Ser Ile Val Tyr Glu Ala Ala Asp Ala Ile Leu
             20                  25                 30
His Thr Pro Gly Cys Val Pro Cys Val Arg Glu Gly Asn Ala Ser
             35                  40                 45
Arg Cys Trp Val Ala Met Thr Pro Thr Val Ala Thr Arg Asp Gly
             50                  55                 60
Lys Leu Pro Thr Thr Gln Leu Arg Arg His Ile Asp Leu Leu Val
             65                  70                 75
Gly Ser Ala Thr Leu Cys Ser Ala Leu Tyr Val Gly Asp Leu Cys
             80                  85                 90
Gly Ser Val Phe Leu Val Gly Gln Leu Phe Thr Phe Ser Pro Arg
             95                 100                105
Arg His Trp Thr Thr Gln Gly Cys Asn Cys Ser Ile Tyr Pro Gly
            110                 115                120
His Ile Thr Gly His Arg Met Ala Trp Asp Met Met Met Asn Trp
            125                 130                135
```

```
Ser  Pro  Thr  Ala  Ala  Leu  Val  Val  Ala  Gln  Leu  Leu  Arg  Ile  Pro
               140                      145                         150

Gln  Ala  Ile  Leu  Asp  Met  Ile  Ala  Gly  Ala  His  Trp  Gly  Val  Leu
               155                      160                         165

Ala  Gly  Ile  Ala  Tyr  Phe  Ser  Met  Val  Gly  Asn  Trp  Ala  Lys  Val
               170                      175                         180

Leu  Val  Val  Leu  Leu  Leu  Phe  Ala  Gly  Val  Asp  Ala
               185                      190
```

( 2 ) INFORMATION FOR SEQ ID NO:60:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: D1

( x i ) SEQUENCE DESCRIPTION: SEQ ID NO:60:

```
Tyr  Glu  Val  Arg  Asn  Val  Ser  Gly  Val  Tyr  His  Val  Thr  Asn  Asp
               5                        10                          15

Cys  Ser  Asn  Ser  Ser  Ile  Val  Tyr  Glu  Thr  Ala  Asp  Met  Ile  Met
               20                       25                          30

His  Thr  Pro  Gly  Cys  Val  Pro  Cys  Val  Arg  Glu  Asp  Asn  Ser  Ser
               35                       40                          45

Arg  Cys  Trp  Val  Ala  Leu  Thr  Pro  Thr  Leu  Ala  Ala  Arg  Asn  Gly
               50                       55                          60

Asn  Val  Pro  Thr  Thr  Ala  Ile  Arg  Arg  His  Val  Asp  Leu  Leu  Val
               65                       70                          75

Gly  Ala  Ala  Ala  Phe  Cys  Ser  Ala  Met  Tyr  Val  Gly  Asp  Leu  Cys
               80                       85                          90

Gly  Ser  Val  Phe  Leu  Ile  Ser  Gln  Leu  Phe  Thr  Leu  Ser  Pro  Arg
               95                       100                         105

Arg  His  Glu  Thr  Val  Gln  Glu  Cys  Asn  Cys  Ser  Ile  Tyr  Pro  Gly
               110                      115                         120

His  Val  Thr  Gly  His  Arg  Met  Ala  Trp  Asp  Met  Met  Met  Asn  Trp
               125                      130                         135

Ser  Pro  Thr  Thr  Ala  Leu  Val  Val  Ser  Gln  Leu  Leu  Arg  Ile  Pro
               140                      145                         150

Gln  Ala  Val  Met  Asp  Met  Val  Ala  Gly  Ala  His  Trp  Gly  Val  Leu
               155                      160                         165

Ala  Gly  Leu  Ala  Tyr  Tyr  Ser  Met  Val  Gly  Asn  Trp  Ala  Lys  Val
               170                      175                         180

Leu  Ile  Val  Met  Leu  Leu  Phe  Ala  Gly  Val  Asp  Gly
               185                      190
```

( 2 ) INFORMATION FOR SEQ ID NO:61:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: D3

-continued ( x i ) SEQUENCE DESCRIPTION: SEQ ID NO:61:

| Tyr | Glu | Val | Arg | Asn | Val | Ser | Gly | Val | Tyr | Gln | Val | Thr | Asn | Asp |
|---|---|---|---|---|---|---|---|---|---|---|---|---|---|---|
| | | | | 5 | | | | | 10 | | | | | 15 |

| Cys | Ser | Asn | Ser | Ser | Ile | Val | Tyr | Glu | Thr | Ala | Asp | Met | Ile | Met |
|---|---|---|---|---|---|---|---|---|---|---|---|---|---|---|
| | | | | 20 | | | | | 25 | | | | | 30 |

| His | Thr | Pro | Gly | Cys | Val | Pro | Cys | Val | Arg | Glu | Asp | Asn | Ser | Ser |
|---|---|---|---|---|---|---|---|---|---|---|---|---|---|---|
| | | | | 35 | | | | | 40 | | | | | 45 |

| Arg | Cys | Trp | Val | Ala | Leu | Thr | Pro | Thr | Leu | Ala | Ala | Arg | Asn | Ser |
|---|---|---|---|---|---|---|---|---|---|---|---|---|---|---|
| | | | | 50 | | | | | 55 | | | | | 60 |

| Ser | Val | Pro | Thr | Thr | Thr | Ile | Arg | Arg | His | Val | Asp | Leu | Leu | Val |
|---|---|---|---|---|---|---|---|---|---|---|---|---|---|---|
| | | | | 65 | | | | | 70 | | | | | 75 |

| Gly | Ala | Ala | Ala | Phe | Cys | Ser | Ala | Met | Tyr | Val | Gly | Asp | Leu | Cys |
|---|---|---|---|---|---|---|---|---|---|---|---|---|---|---|
| | | | | 80 | | | | | 85 | | | | | 90 |

| Gly | Ser | Val | Phe | Leu | Val | Ser | Gln | Leu | Phe | Thr | Phe | Ser | Pro | Arg |
|---|---|---|---|---|---|---|---|---|---|---|---|---|---|---|
| | | | | 95 | | | | | 100 | | | | | 105 |

| Arg | His | Glu | Thr | Val | Gln | Glu | Cys | Asn | Cys | Ser | Ile | Tyr | Pro | Gly |
|---|---|---|---|---|---|---|---|---|---|---|---|---|---|---|
| | | | | 110 | | | | | 115 | | | | | 120 |

| His | Val | Thr | Gly | His | Arg | Met | Ala | Trp | Asp | Met | Met | Met | Asn | Trp |
|---|---|---|---|---|---|---|---|---|---|---|---|---|---|---|
| | | | | 125 | | | | | 130 | | | | | 135 |

| Ser | Pro | Thr | Ala | Ala | Leu | Val | Val | Ser | Gln | Leu | Leu | Arg | Ile | Pro |
|---|---|---|---|---|---|---|---|---|---|---|---|---|---|---|
| | | | | 140 | | | | | 145 | | | | | 150 |

| Gln | Ala | Val | Val | Asp | Met | Val | Ala | Gly | Ala | His | Trp | Gly | Val | Leu |
|---|---|---|---|---|---|---|---|---|---|---|---|---|---|---|
| | | | | 155 | | | | | 160 | | | | | 165 |

| Ala | Gly | Leu | Ala | Tyr | Tyr | Ser | Met | Val | Gly | Asn | Trp | Ala | Lys | Val |
|---|---|---|---|---|---|---|---|---|---|---|---|---|---|---|
| | | | | 170 | | | | | 175 | | | | | 180 |

| Leu | Ile | Val | Met | Leu | Leu | Phe | Ala | Gly | Val | Asp | Gly | | | |
|---|---|---|---|---|---|---|---|---|---|---|---|---|---|---|
| | | | | 185 | | | | | 190 | | | | | |

( 2 ) INFORMATION FOR SEQ ID NO:62:

( i ) SEQUENCE CHARACTERISTICS:
    ( A ) LENGTH: 192 amino acids
    ( B ) TYPE: amino acid
    ( C ) STRANDEDNESS: unknown
    ( D ) TOPOLOGY: unknown ( v i ) ORIGINAL SOURCE:
    ( A ) ORGANISM: homosapiens
    ( C ) INDIVIDUAL ISOLATE: DK1

( x i ) SEQUENCE DESCRIPTION: SEQ ID NO:62:

| Tyr | Glu | Val | Arg | Asn | Val | Ser | Gly | Val | Tyr | His | Val | Thr | Asn | Asp |
|---|---|---|---|---|---|---|---|---|---|---|---|---|---|---|
| | | | | 5 | | | | | 10 | | | | | 15 |

| Cys | Ser | Asn | Ser | Ser | Ile | Val | Tyr | Glu | Ala | Val | Asp | Val | Ile | Met |
|---|---|---|---|---|---|---|---|---|---|---|---|---|---|---|
| | | | | 20 | | | | | 25 | | | | | 30 |

| His | Thr | Pro | Gly | Cys | Val | Pro | Cys | Val | Arg | Glu | Asn | Asn | His | Ser |
|---|---|---|---|---|---|---|---|---|---|---|---|---|---|---|
| | | | | 35 | | | | | 40 | | | | | 45 |

| Arg | Cys | Trp | Val | Ala | Leu | Thr | Pro | Thr | Leu | Ala | Ala | Arg | Asn | Ala |
|---|---|---|---|---|---|---|---|---|---|---|---|---|---|---|
| | | | | 50 | | | | | 55 | | | | | 60 |

| Ser | Ile | Pro | Thr | Thr | Thr | Ile | Arg | Arg | His | Val | Asp | Leu | Leu | Val |
|---|---|---|---|---|---|---|---|---|---|---|---|---|---|---|
| | | | | 65 | | | | | 70 | | | | | 75 |

| Gly | Ala | Ala | Ala | Phe | Cys | Ser | Ala | Met | Tyr | Val | Gly | Asp | Leu | Cys |
|---|---|---|---|---|---|---|---|---|---|---|---|---|---|---|
| | | | | 80 | | | | | 85 | | | | | 90 |

| Gly | Ser | Val | Phe | Leu | Val | Ser | Gln | Leu | Phe | Thr | Phe | Ser | Pro | Arg |
|---|---|---|---|---|---|---|---|---|---|---|---|---|---|---|
| | | | | 95 | | | | | 100 | | | | | 105 |

| Arg | His | Glu | Thr | Ala | Gln | Asp | Cys | Asn | Cys | Ser | Ile | Tyr | Pro | Gly |
|---|---|---|---|---|---|---|---|---|---|---|---|---|---|---|
| | | | | 110 | | | | | 115 | | | | | 120 |

| | | | | | | | | | | | | | | |
|---|---|---|---|---|---|---|---|---|---|---|---|---|---|---|
| His | Val | Ser | Gly | His 125 | Arg | Met | Ala | Trp | Asp 130 | Met | Met | Met | Asn | Trp 135 |
| Ser | Pro | Thr | Thr | Ala 140 | Leu | Val | Leu | Ser | Gln 145 | Leu | Leu | Arg | Ile | Pro 150 |
| Gln | Ala | Val | Val | Asp 155 | Met | Val | Ala | Gly | Ala 160 | His | Trp | Gly | Val | Leu 165 |
| Ala | Gly | Leu | Ala | Tyr 170 | Tyr | Ser | Met | Ala | Gly 175 | Asn | Trp | Ala | Lys | Val 180 |
| Leu | Ile | Val | Leu | Leu 185 | Leu | Phe | Ala | Gly | Val 190 | Asp | Gly | | | |

(2) INFORMATION FOR SEQ ID NO:63:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK3

(xi) SEQUENCE DESCRIPTION: SEQ ID NO:63:

| | | | | | | | | | | | | | | |
|---|---|---|---|---|---|---|---|---|---|---|---|---|---|---|
| Tyr | Glu | Val | Arg | Asn 5 | Val | Ser | Gly | Ile | Tyr 10 | His | Val | Thr | Asn | Asp 15 |
| Cys | Ser | Asn | Ser | Ser 20 | Val | Val | Tyr | Glu | Thr 25 | Ala | Asp | Met | Ile | Met 30 |
| His | Thr | Pro | Gly | Cys 35 | Val | Pro | Cys | Val | Arg 40 | Glu | Asn | Asn | Ser | Ser 45 |
| Arg | Cys | Trp | Val | Ala 50 | Leu | Thr | Pro | Thr | Leu 55 | Ala | Ala | Arg | Asn | Val 60 |
| Ser | Val | Pro | Thr | Thr 65 | Thr | Ile | Arg | Arg | His 70 | Val | Asp | Leu | Leu | Val 75 |
| Gly | Ala | Ala | Ala | Phe 80 | Cys | Ser | Ala | Met | Tyr 85 | Val | Gly | Asp | Leu | Cys 90 |
| Gly | Ser | Val | Phe | Leu 95 | Val | Ser | Gln | Leu | Phe 100 | Thr | Phe | Ser | Pro | Arg 105 |
| Arg | His | Glu | Thr | Val 110 | Gln | Asp | Cys | Asn | Cys 115 | Ser | Leu | Tyr | Pro | Gly 120 |
| His | Val | Ser | Gly | His 125 | Arg | Met | Ala | Trp | Asp 130 | Met | Met | Met | Asn | Trp 135 |
| Ser | Pro | Thr | Ala | Ala 140 | Leu | Val | Val | Ser | Gln 145 | Leu | Leu | Arg | Ile | Pro 150 |
| Gln | Ala | Val | Val | Asp 155 | Met | Val | Ala | Gly | Ala 160 | His | Trp | Gly | Val | Leu 165 |
| Ala | Gly | Leu | Ala | Tyr 170 | Tyr | Ser | Met | Val | Gly 175 | Asn | Trp | Ala | Lys | Val 180 |
| Leu | Ile | Val | Met | Leu 185 | Leu | Phe | Ala | Gly | Val 190 | Asp | Gly | | | |

(2) INFORMATION FOR SEQ ID NO:64:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens (C) INDIVIDUAL ISOLATE: HK4

(xi) SEQUENCE DESCRIPTION: SEQ ID NO:64:

```
His Glu Val His Asn Val Ser Gly Ile Tyr His Val Thr Asn Asp
                5                  10                      15
Cys Ser Asn Ser Ser Ile Val Tyr Glu Ala Ala Asp Met Ile Met
                20                 25                      30
His Thr Pro Gly Cys Val Pro Cys Val Arg Glu Asn Asn Ser Ser
                35                 40                      45
Arg Cys Trp Val Ala Leu Thr Pro Thr Leu Ala Ala Arg Asn Ala
                50                 55                      60
Ser Ile Pro Thr Thr Thr Ile Arg Arg His Val Asp Leu Leu Val
                65                 70                      75
Gly Ala Ala Ala Phe Cys Ser Ala Met Tyr Val Gly Asp Leu Cys
                80                 85                      90
Gly Ser Val Phe Leu Val Ser Gln Leu Phe Thr Phe Ser Pro Arg
                95                 100                     105
Arg His Glu Thr Val Gln Asp Cys Asn Cys Ser Ile Tyr Pro Gly
                110                115                     120
His Val Ser Gly His Arg Met Ala Trp Asp Met Met Met Asn Trp
                125                130                     135
Ser Pro Thr Ala Ala Leu Val Val Ser Gln Leu Leu Arg Leu Pro
                140                145                     150
Gln Ala Val Met Asp Met Val Ala Gly Ala His Trp Gly Val Leu
                155                160                     165
Ala Gly Leu Ala Tyr Tyr Ser Met Val Gly Asn Trp Ala Lys Val
                170                175                     180
Leu Ile Val Met Leu Leu Phe Ala Gly Val Asp Gly
                185                190
```

(2) INFORMATION FOR SEQ ID NO:65:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK5

(xi) SEQUENCE DESCRIPTION: SEQ ID NO:65:

```
Tyr Glu Val Arg Asn Val Ser Gly Val Tyr His Val Thr Asn Asp
                5                  10                      15
Cys Ser Asn Leu Ser Ile Val Tyr Glu Thr Thr Asp Met Ile Met
                20                 25                      30
His Thr Pro Gly Cys Val Pro Cys Val Arg Glu Asn Asn Ser Ser
                35                 40                      45
Arg Cys Trp Val Ala Leu Ala Pro Thr Leu Ala Ala Arg Asn Ala
                50                 55                      60
Ser Val Pro Thr Thr Ala Ile Arg Arg His Val Asp Leu Leu Val
                65                 70                      75
Gly Ala Ala Ala Phe Cys Ser Ala Met Tyr Val Gly Asp Leu Cys
                80                 85                      90
Gly Ser Val Phe Leu Val Ser Gln Leu Phe Thr Phe Ser Pro Arg
                95                 100                     105
Arg His Glu Thr Val Gln Asp Cys Asn Cys Ser Ile Tyr Pro Gly
```

|   |   |   |   |   | 110 |   |   |   |   | 115 |   |   |   |   | 120 |
|---|---|---|---|---|---|---|---|---|---|---|---|---|---|---|---|
| His | Val | Thr | Gly | His | Arg | Met | Ala | Trp | Asp | Met | Met | Met | Asn | Trp |
|   |   |   |   | 125 |   |   |   |   | 130 |   |   |   |   | 135 |
| Ser | Pro | Thr | Thr | Ala | Leu | Val | Val | Ser | Gln | Leu | Leu | Arg | Ile | Pro |
|   |   |   |   | 140 |   |   |   |   | 145 |   |   |   |   | 150 |
| Gln | Ala | Val | Val | Asp | Met | Val | Ala | Gly | Ala | His | Trp | Gly | Val | Leu |
|   |   |   |   | 155 |   |   |   |   | 160 |   |   |   |   | 165 |
| Ala | Gly | Leu | Ala | Tyr | Tyr | Ser | Met | Val | Gly | Asn | Trp | Ala | Lys | Val |
|   |   |   |   | 170 |   |   |   |   | 175 |   |   |   |   | 180 |
| Leu | Ile | Val | Met | Leu | Leu | Phe | Ala | Gly | Val | Asp | Gly |   |   |   |
|   |   |   |   | 185 |   |   |   |   | 190 |   |   |   |   |   |

( 2 ) INFORMATION FOR SEQ ID NO:66:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: HK8

( x i ) SEQUENCE DESCRIPTION: SEQ ID NO:66:

| Tyr | Glu | Val | Arg | Asn | Val | Ser | Gly | Ile | Tyr | His | Val | Thr | Asn | Asp |
|---|---|---|---|---|---|---|---|---|---|---|---|---|---|---|
|   |   |   |   | 5 |   |   |   |   | 10 |   |   |   |   | 15 |
| Cys | Ser | Asn | Ser | Ser | Ile | Val | Tyr | Glu | Thr | Ala | Asp | Met | Ile | Met |
|   |   |   |   | 20 |   |   |   |   | 25 |   |   |   |   | 30 |
| His | Thr | Pro | Gly | Cys | Met | Pro | Cys | Val | Arg | Glu | Asn | Asn | Ser | Ser |
|   |   |   |   | 35 |   |   |   |   | 40 |   |   |   |   | 45 |
| Arg | Cys | Trp | Val | Ala | Leu | Thr | Pro | Thr | Leu | Ala | Ala | Arg | Asn | Val |
|   |   |   |   | 50 |   |   |   |   | 55 |   |   |   |   | 60 |
| Ser | Val | Pro | Thr | Thr | Thr | Ile | Arg | Arg | His | Val | Asp | Leu | Leu | Val |
|   |   |   |   | 65 |   |   |   |   | 70 |   |   |   |   | 75 |
| Gly | Ala | Ala | Ala | Phe | Cys | Ser | Ala | Met | Tyr | Val | Gly | Asp | Leu | Cys |
|   |   |   |   | 80 |   |   |   |   | 85 |   |   |   |   | 90 |
| Gly | Ser | Val | Phe | Leu | Val | Ser | Gln | Leu | Phe | Thr | Phe | Ser | Pro | Arg |
|   |   |   |   | 95 |   |   |   |   | 100 |   |   |   |   | 105 |
| Arg | His | Glu | Thr | Val | Gln | Asp | Cys | Asn | Cys | Ser | Ile | Tyr | Pro | Gly |
|   |   |   |   | 110 |   |   |   |   | 115 |   |   |   |   | 120 |
| His | Val | Ser | Gly | His | Arg | Met | Ala | Trp | Asp | Met | Met | Met | Asn | Trp |
|   |   |   |   | 125 |   |   |   |   | 130 |   |   |   |   | 135 |
| Ser | Pro | Thr | Thr | Ala | Leu | Val | Val | Ser | Gln | Leu | Leu | Arg | Ile | Pro |
|   |   |   |   | 140 |   |   |   |   | 145 |   |   |   |   | 150 |
| Gln | Ala | Ile | Val | Asp | Met | Val | Ala | Gly | Ala | His | Trp | Gly | Val | Leu |
|   |   |   |   | 155 |   |   |   |   | 160 |   |   |   |   | 165 |
| Ala | Gly | Leu | Ala | Tyr | Tyr | Ser | Met | Val | Gly | Asn | Trp | Ala | Lys | Val |
|   |   |   |   | 170 |   |   |   |   | 175 |   |   |   |   | 180 |
| Leu | Ile | Val | Met | Leu | Leu | Phe | Ala | Gly | Val | Asp | Gly |   |   |   |
|   |   |   |   | 185 |   |   |   |   | 190 |   |   |   |   |   |

( 2 ) INFORMATION FOR SEQ ID NO:67:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown (v i) ORIGINAL SOURCE:
    (A) ORGANISM: homosapiens
    (C) INDIVIDUAL ISOLATE: IND5

(x i) SEQUENCE DESCRIPTION: SEQ ID NO:67:

| Tyr | Glu | Val | Arg | Asn | Val | Ser | Gly | Val | Tyr | His | Val | Thr | Asn | Asp |
|---|---|---|---|---|---|---|---|---|---|---|---|---|---|---|
|  |  |  |  | 5 |  |  |  |  | 10 |  |  |  |  | 15 |
| Cys | Ser | Asn | Ser | Ser | Ile | Val | Tyr | Glu | Ala | Ala | Asp | Met | Ile | Met |
|  |  |  |  | 20 |  |  |  |  | 25 |  |  |  |  | 30 |
| His | Thr | Pro | Gly | Cys | Val | Pro | Cys | Val | Arg | Glu | Gly | Asn | Ser | Ser |
|  |  |  |  | 35 |  |  |  |  | 40 |  |  |  |  | 45 |
| Arg | Cys | Trp | Val | Ala | Leu | Thr | Pro | Thr | Leu | Ala | Ala | Arg | Asn | Ala |
|  |  |  |  | 50 |  |  |  |  | 55 |  |  |  |  | 60 |
| Ser | Val | Ser | Thr | Thr | Thr | Ile | Arg | His | His | Val | Asp | Leu | Leu | Val |
|  |  |  |  | 65 |  |  |  |  | 70 |  |  |  |  | 75 |
| Gly | Ala | Ala | Ala | Phe | Cys | Ser | Ala | Met | Tyr | Val | Gly | Asp | Leu | Cys |
|  |  |  |  | 80 |  |  |  |  | 85 |  |  |  |  | 90 |
| Gly | Ser | Val | Phe | Leu | Val | Ser | Gln | Leu | Phe | Thr | Phe | Ser | Pro | Arg |
|  |  |  |  | 95 |  |  |  |  | 100 |  |  |  |  | 105 |
| Arg | His | Glu | Thr | Val | Gln | Asp | Cys | Asn | Cys | Ser | Ile | Tyr | Pro | Gly |
|  |  |  |  | 110 |  |  |  |  | 115 |  |  |  |  | 120 |
| His | Val | Ser | Gly | His | Arg | Met | Ala | Trp | Asp | Met | Met | Met | Asn | Trp |
|  |  |  |  | 125 |  |  |  |  | 130 |  |  |  |  | 135 |
| Ser | Pro | Thr | Ala | Ala | Leu | Val | Val | Ser | Gln | Leu | Leu | Arg | Ile | Pro |
|  |  |  |  | 140 |  |  |  |  | 145 |  |  |  |  | 150 |
| Gln | Ala | Val | Val | Asp | Met | Val | Ala | Gly | Ala | His | Trp | Gly | Ile | Leu |
|  |  |  |  | 155 |  |  |  |  | 160 |  |  |  |  | 165 |
| Ala | Gly | Leu | Ala | Tyr | Tyr | Ser | Met | Val | Gly | Asn | Trp | Ala | Lys | Val |
|  |  |  |  | 170 |  |  |  |  | 175 |  |  |  |  | 180 |
| Leu | Ile | Val | Met | Leu | Leu | Phe | Ala | Gly | Val | Asp | Gly |  |  |  |
|  |  |  |  | 185 |  |  |  |  | 190 |  |  |  |  |  |

(2) INFORMATION FOR SEQ ID NO:68:

(i) SEQUENCE CHARACTERISTICS:
    (A) LENGTH: 192 amino acids
    (B) TYPE: amino acid
    (C) STRANDEDNESS: unknown
    (D) TOPOLOGY: unknown (v i) ORIGINAL SOURCE:
    (A) ORGANISM: homosapiens
    (C) INDIVIDUAL ISOLATE: IND8

(x i) SEQUENCE DESCRIPTION: SEQ ID NO:68:

| Tyr | Glu | Val | Arg | Asn | Val | Ser | Gly | Val | Tyr | His | Val | Thr | Asn | Asp |
|---|---|---|---|---|---|---|---|---|---|---|---|---|---|---|
|  |  |  |  | 5 |  |  |  |  | 10 |  |  |  |  | 15 |
| Cys | Ser | Asn | Ser | Ser | Ile | Val | Tyr | Glu | Ala | Ala | Asp | Met | Ile | Met |
|  |  |  |  | 20 |  |  |  |  | 25 |  |  |  |  | 30 |
| His | Thr | Pro | Gly | Cys | Val | Pro | Cys | Val | Arg | Glu | Gly | Asn | Phe | Ser |
|  |  |  |  | 35 |  |  |  |  | 40 |  |  |  |  | 45 |
| Ser | Cys | Trp | Val | Ala | Leu | Thr | Pro | Thr | Leu | Ala | Ala | Arg | Asn | Ala |
|  |  |  |  | 50 |  |  |  |  | 55 |  |  |  |  | 60 |
| Ser | Val | Pro | Thr | Thr | Thr | Ile | Arg | Arg | His | Val | Asp | Leu | Leu | Val |
|  |  |  |  | 65 |  |  |  |  | 70 |  |  |  |  | 75 |
| Gly | Ala | Ala | Ala | Phe | Cys | Ser | Ala | Met | Tyr | Val | Gly | Asp | Leu | Cys |
|  |  |  |  | 80 |  |  |  |  | 85 |  |  |  |  | 90 |
| Gly | Ser | Val | Phe | Leu | Val | Ser | Gln | Leu | Phe | Thr | Phe | Ser | Pro | Arg |
|  |  |  |  | 95 |  |  |  |  | 100 |  |  |  |  | 105 |

Arg His Glu Thr Val Gln Asp Cys Asn Cys Ser Ile Tyr Pro Gly
            110                 115                 120

His Val Ser Gly His Arg Met Ala Trp Asp Met Met Met Asn Trp
            125                 130                 135

Ser Pro Thr Ala Ala Leu Val Val Ser Gln Leu Leu Arg Ile Pro
            140                 145                 150

Gln Ala Val Val Asp Met Val Ala Gly Ala His Trp Gly Ile Leu
            155                 160                 165

Ala Gly Leu Ala Tyr Tyr Ser Met Val Gly Asn Trp Ala Lys Val
            170                 175                 180

Leu Ile Val Met Leu Leu Phe Ala Gly Val Asp Gly
            185                 190

(2) INFORMATION FOR SEQ ID NO:69:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: P10

(xi) SEQUENCE DESCRIPTION: SEQ ID NO:69:

Tyr Glu Val Arg Asn Val Ser Gly Val Tyr His Val Thr Asn Asp
            5                   10                  15

Cys Ser Asn Ser Ser Ile Val Tyr Glu Ala Ala Asp Met Ile Met
            20                  25                  30

His Thr Pro Gly Cys Val Pro Cys Val Arg Glu Asn Asn Ser Ser
            35                  40                  45

Arg Cys Trp Val Ala Leu Thr Pro Thr Leu Ala Ala Arg Asn Ser
            50                  55                  60

Ser Val Pro Thr Thr Ala Ile Arg Arg His Val Asp Leu Leu Val
            65                  70                  75

Gly Ala Ala Ala Phe Cys Ser Ala Met Tyr Val Gly Asp Leu Cys
            80                  85                  90

Gly Ser Val Leu Leu Val Ser Gln Leu Phe Thr Phe Ser Pro Arg
            95                  100                 105

Arg His Trp Thr Val Gln Asp Cys Asn Cys Ser Ile Tyr Pro Gly
            110                 115                 120

His Val Ser Gly His Arg Met Ala Trp Asp Met Met Met Asn Trp
            125                 130                 135

Ser Pro Thr Ala Ala Leu Val Val Ser Gln Leu Leu Arg Ile Pro
            140                 145                 150

Gln Ala Ile Leu Asp Val Val Ala Gly Ala His Trp Gly Val Leu
            155                 160                 165

Ala Gly Leu Ala Tyr Tyr Ser Met Val Gly Asn Trp Ala Lys Val
            170                 175                 180

Leu Ile Val Met Leu Leu Phe Ala Gly Val Asp Gly
            185                 190

(2) INFORMATION FOR SEQ ID NO:70:

(i) SEQUENCE CHARACTERISTICS:
        (A) LENGTH: 192 amino acids
        (B) TYPE: amino acid
        (C) STRANDEDNESS: unknown (D) TOPOLOGY: unknown (vi) ORIGINAL SOURCE:
    (A) ORGANISM: homosapiens
    (C) INDIVIDUAL ISOLATE: S9

(xi) SEQUENCE DESCRIPTION: SEQ ID NO:70:

| Tyr | Glu | Val | Arg | Asn | Val | Ser | Gly | Ala | Tyr | His | Val | Thr | Asn | Asp |
|---|---|---|---|---|---|---|---|---|---|---|---|---|---|---|
|  |  |  |  | 5 |  |  |  |  | 10 |  |  |  |  | 15 |
| Cys | Ser | Asn | Ser | Ser | Ile | Val | Tyr | Glu | Ala | Ala | Asp | Val | Ile | Met |
|  |  |  |  | 20 |  |  |  |  | 25 |  |  |  |  | 30 |
| His | Thr | Pro | Gly | Cys | Val | Pro | Cys | Val | Gln | Glu | Gly | Asn | Ser | Ser |
|  |  |  |  | 35 |  |  |  |  | 40 |  |  |  |  | 45 |
| Gln | Cys | Trp | Val | Ala | Leu | Thr | Pro | Thr | Leu | Ala | Ala | Arg | Asn | Ala |
|  |  |  |  | 50 |  |  |  |  | 55 |  |  |  |  | 60 |
| Thr | Val | Pro | Thr | Thr | Thr | Ile | Arg | Arg | His | Val | Asp | Leu | Leu | Val |
|  |  |  |  | 65 |  |  |  |  | 70 |  |  |  |  | 75 |
| Gly | Ala | Ala | Val | Phe | Cys | Ser | Ala | Met | Tyr | Val | Gly | Asp | Leu | Cys |
|  |  |  |  | 80 |  |  |  |  | 85 |  |  |  |  | 90 |
| Gly | Ser | Val | Phe | Leu | Ile | Ser | Gln | Leu | Phe | Thr | Ile | Ser | Pro | Arg |
|  |  |  |  | 95 |  |  |  |  | 100 |  |  |  |  | 105 |
| Arg | His | Glu | Thr | Val | Gln | Asn | Cys | Asn | Cys | Ser | Ile | Tyr | Pro | Gly |
|  |  |  |  | 110 |  |  |  |  | 115 |  |  |  |  | 120 |
| His | Val | Thr | Gly | His | Arg | Met | Ala | Trp | Asp | Met | Met | Met | Asn | Trp |
|  |  |  |  | 125 |  |  |  |  | 130 |  |  |  |  | 135 |
| Ser | Pro | Thr | Thr | Ala | Leu | Val | Val | Ser | Gln | Leu | Leu | Arg | Ile | Pro |
|  |  |  |  | 140 |  |  |  |  | 145 |  |  |  |  | 150 |
| Gln | Ala | Val | Met | Asp | Met | Val | Ala | Gly | Ala | His | Trp | Gly | Val | Leu |
|  |  |  |  | 155 |  |  |  |  | 160 |  |  |  |  | 165 |
| Ala | Gly | Leu | Ala | Tyr | Tyr | Ser | Met | Val | Gly | Asn | Trp | Ala | Lys | Val |
|  |  |  |  | 170 |  |  |  |  | 175 |  |  |  |  | 180 |
| Leu | Ile | Val | Met | Leu | Leu | Phe | Ala | Gly | Val | Asp | Gly |  |  |  |
|  |  |  |  | 185 |  |  |  |  | 190 |  |  |  |  |  |

(2) INFORMATION FOR SEQ ID NO:71:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S45

(xi) SEQUENCE DESCRIPTION: SEQ ID NO:71:

| Tyr | Glu | Val | Arg | Asn | Val | Ser | Gly | Ala | Tyr | His | Val | Thr | Asn | Asp |
|---|---|---|---|---|---|---|---|---|---|---|---|---|---|---|
|  |  |  |  | 5 |  |  |  |  | 10 |  |  |  |  | 15 |
| Cys | Ser | Asn | Ser | Ser | Ile | Val | Tyr | Glu | Ala | Val | Asp | Val | Ile | Leu |
|  |  |  |  | 20 |  |  |  |  | 25 |  |  |  |  | 30 |
| His | Thr | Pro | Gly | Cys | Val | Pro | Cys | Val | Arg | Glu | Asn | Asn | Ser | Ser |
|  |  |  |  | 35 |  |  |  |  | 40 |  |  |  |  | 45 |
| Arg | Cys | Trp | Val | Ala | Leu | Thr | Pro | Thr | Leu | Ala | Ala | Arg | Asn | Ser |
|  |  |  |  | 50 |  |  |  |  | 55 |  |  |  |  | 60 |
| Ser | Val | Pro | Thr | Thr | Thr | Ile | Arg | Arg | His | Val | Asp | Leu | Leu | Val |
|  |  |  |  | 65 |  |  |  |  | 70 |  |  |  |  | 75 |
| Gly | Ala | Ala | Ala | Phe | Cys | Ser | Ala | Met | Tyr | Val | Gly | Asp | Leu | Cys |
|  |  |  |  | 80 |  |  |  |  | 85 |  |  |  |  | 90 |

Gly Ser Val Phe Leu Val Ser Gln Leu Phe Thr Phe Ser Pro Arg
                    95                 100                105

Arg His Glu Thr Val Gln Asp Cys Asn Cys Ser Ile Tyr Pro Gly
                110                 115                120

His Val Thr Gly His Arg Met Ala Trp Asp Met Met Met Asn Trp
                125                 130                135

Ser Pro Thr Ala Ala Leu Val Val Ser Gln Leu Leu Arg Ile Pro
                140                 145                150

Gln Ala Val Val Asp Met Val Ala Gly Ala His Trp Gly Val Leu
                155                 160                165

Ala Gly Leu Ala Tyr Tyr Ser Met Val Gly Asn Trp Ala Lys Val
                170                 175                180

Leu Ile Val Met Leu Leu Phe Ala Gly Val Asp Gly
                185                 190

( 2 ) INFORMATION FOR SEQ ID NO:72:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA10

( x i ) SEQUENCE DESCRIPTION: SEQ ID NO:72:

Tyr Glu Val Arg Asn Val Ser Gly Met Tyr His Val Thr Asn Asp
                 5                  10                 15

Cys Ser Asn Ser Ser Ile Val Tyr Glu Ala Ala Asp Met Ile Met
                20                  25                 30

His Thr Pro Gly Cys Val Pro Cys Val Arg Glu Asn Asn Ser Ser
                35                  40                 45

Arg Cys Trp Val Ala Leu Thr Pro Thr Leu Ala Ala Arg Asn Ser
                50                  55                 60

Ser Val Pro Thr Thr Thr Ile Arg Arg His Val Asp Leu Leu Val
                65                  70                 75

Gly Ala Ala Ala Phe Cys Ser Ala Met Tyr Val Gly Asp Leu Cys
                80                  85                 90

Gly Ser Val Phe Leu Val Ser Gln Leu Phe Thr Phe Ser Pro Arg
                95                 100                105

Arg Tyr Glu Thr Val Gln Asp Cys Asn Cys Ser Ile Tyr Pro Gly
                110                 115                120

Arg Val Thr Gly His Arg Met Ala Trp Asp Met Met Met Asn Trp
                125                 130                135

Ser Pro Thr Thr Ala Leu Val Val Ser Gln Leu Leu Arg Ile Pro
                140                 145                150

Gln Ala Ile Val Asp Met Val Ala Gly Ala His Trp Gly Val Leu
                155                 160                165

Ala Gly Leu Ala Tyr Tyr Ser Met Val Gly Asn Trp Ala Lys Val
                170                 175                180

Leu Ile Val Met Leu Leu Phe Ala Gly Val Asp Gly
                185                 190

( 2 ) INFORMATION FOR SEQ ID NO:73:

( i ) SEQUENCE CHARACTERISTICS:
        ( A ) LENGTH: 192 amino acids ( B ) TYPE: amino acid
( C ) STRANDEDNESS: unknown
( D ) TOPOLOGY: unknown ( v i ) ORIGINAL SOURCE:
( A ) ORGANISM: homosapiens
( C ) INDIVIDUAL ISOLATE: SW2

( x i ) SEQUENCE DESCRIPTION: SEQ ID NO:73:

```
Tyr Glu Val Arg Asn Val Ser Gly Val Tyr His Val Thr Asn Asp
                  5                  10                      15
Cys Ser Asn Ser Ser Ile Val Tyr Glu Thr Ala Asp Met Ile Met
                 20                  25                      30
His Thr Pro Gly Cys Val Pro Cys Val Arg Glu Ala Asn Ser Ser
                 35                  40                      45
Arg Cys Trp Val Ala Leu Thr Pro Thr Leu Ala Ala Arg Asn Thr
                 50                  55                      60
Ser Val Pro Thr Thr Thr Ile Arg Arg His Val Asp Leu Leu Val
                 65                  70                      75
Gly Ala Ala Ala Phe Cys Ser Val Met Tyr Val Gly Asp Leu Cys
                 80                  85                      90
Gly Ser Val Phe Leu Val Ser Gln Leu Phe Thr Phe Ser Pro Arg
                 95                 100                     105
Arg His Glu Thr Val Gln Asp Cys Asn Cys Ser Ile Tyr Pro Gly
                110                 115                     120
His Val Ser Gly His Arg Met Ala Trp Asp Met Met Met Asn Trp
                125                 130                     135
Ser Pro Thr Ala Ala Leu Val Val Ser Gln Leu Leu Arg Ile Pro
                140                 145                     150
Gln Ala Val Val Asp Met Val Ala Gly Ala His Trp Gly Val Leu
                155                 160                     165
Ala Gly Leu Ala Tyr Tyr Ser Met Val Gly Asn Trp Ala Lys Val
                170                 175                     180
Leu Ile Val Met Leu Leu Phe Ala Gly Val Asp Gly
                185                 190
```

( 2 ) INFORMATION FOR SEQ ID NO:74:

( i ) SEQUENCE CHARACTERISTICS:
( A ) LENGTH: 192 amino acids
( B ) TYPE: amino acid
( C ) STRANDEDNESS: unknown
( D ) TOPOLOGY: unknown ( v i ) ORIGINAL SOURCE:
( A ) ORGANISM: homosapiens
( C ) INDIVIDUAL ISOLATE: T3

( x i ) SEQUENCE DESCRIPTION: SEQ ID NO:74:

```
Tyr Glu Val Arg Asn Val Ser Gly Val Tyr Tyr Val Thr Asn Asp
                  5                  10                      15
Cys Ser Asn Ser Ser Ile Val Tyr Glu Thr Ala Asp Met Ile Met
                 20                  25                      30
His Thr Pro Gly Cys Val Pro Cys Val Arg Glu Ser Asn Ser Ser
                 35                  40                      45
Arg Cys Trp Val Ala Leu Thr Pro Thr Leu Ala Ala Arg Asn Ala
                 50                  55                      60
Ser Val Pro Thr Lys Thr Ile Arg Arg His Val Asp Leu Leu Val
                 65                  70                      75
Gly Ala Ala Ala Phe Cys Ser Ala Met Tyr Val Gly Asp Leu Cys
```

80                              85                              90
Gly Ser Val Phe Leu Val Ser Gln Leu Phe Thr Phe Ser Pro Arg
                 95                              100                             105

Arg His Glu Thr Val Gln Asp Cys Asn Cys Ser Ile Tyr Pro Gly
                110                             115                             120

His Val Thr Gly His Arg Met Ala Trp Asp Met Met Met Asn Trp
                125                             130                             135

Ser Pro Thr Thr Ala Leu Val Val Ser Gln Leu Leu Arg Ile Pro
                140                             145                             150

Gln Ala Val Val Asp Met Val Ala Gly Ala His Trp Gly Val Leu
                155                             160                             165

Ala Gly Leu Ala Tyr Tyr Ser Met Val Gly Asn Trp Ala Lys Val
                170                             175                             180

Leu Ile Val Leu Leu Leu Phe Ala Gly Val Asp Gly
                185                             190

( 2 ) INFORMATION FOR SEQ ID NO:75:

( i ) SEQUENCE CHARACTERISTICS:
       ( A ) LENGTH: 192 amino acids
       ( B ) TYPE: amino acid
       ( C ) STRANDEDNESS: unknown
       ( D ) TOPOLOGY: unknown ( v i ) ORIGINAL SOURCE:
       ( A ) ORGANISM: homosapiens
       ( C ) INDIVIDUAL ISOLATE: T10

( x i ) SEQUENCE DESCRIPTION: SEQ ID NO:75:

Tyr Glu Val Arg Asn Val Ser Gly Met Tyr His Val Thr Asn Asp
                 5                              10                              15

Cys Ser Asn Ser Ser Ile Val Phe Glu Ala Ala Asp Leu Ile Met
                20                              25                              30

His Thr Pro Gly Cys Val Pro Cys Val Arg Glu Gly Asn Ser Ser
                35                              40                              45

Arg Cys Trp Val Ala Leu Thr Pro Thr Leu Ala Ala Arg Asn Thr
                50                              55                              60

Ser Val Pro Thr Thr Thr Ile Arg Arg His Val Asp Leu Leu Val
                65                              70                              75

Gly Ala Ala Ala Phe Cys Ser Ala Met Tyr Val Gly Asp Leu Cys
                80                              85                              90

Gly Ser Val Phe Leu Val Ser Gln Leu Phe Thr Phe Ser Pro Arg
                95                              100                             105

Arg His Glu Thr Leu Gln Asp Cys Asn Cys Ser Ile Tyr Pro Gly
                110                             115                             120

His Leu Ser Gly His Arg Met Ala Trp Asp Met Met Met Asn Trp
                125                             130                             135

Ser Pro Thr Thr Ala Leu Val Val Ser Gln Leu Leu Arg Ile Pro
                140                             145                             150

Gln Ala Val Met Asp Met Val Thr Gly Ala His Trp Gly Val Leu
                155                             160                             165

Ala Gly Leu Ala Tyr Tyr Ser Met Ala Gly Asn Trp Ala Lys Val
                170                             175                             180

Leu Ile Val Met Leu Leu Phe Ala Gly Val Asp Gly
                185                             190

( 2 ) INFORMATION FOR SEQ ID NO:76:

( i ) SEQUENCE CHARACTERISTICS:
   ( A ) LENGTH: 192 amino acids
   ( B ) TYPE: amino acid
   ( C ) STRANDEDNESS: unknown
   ( D ) TOPOLOGY: unknown ( v i ) ORIGINAL SOURCE:
   ( A ) ORGANISM: homosapiens
   ( C ) INDIVIDUAL ISOLATE: US6

( x i ) SEQUENCE DESCRIPTION: SEQ ID NO:76:

```
Tyr Glu Val Arg Asn Val Ser Gly Met Tyr His Val Thr Asn Asp
                 5                  10                 15

Cys Ser Asn Ser Ser Ile Val Tyr Glu Ala Ala Asp Met Ile Met
                20                  25                 30

His Thr Pro Gly Cys Val Pro Cys Val Arg Glu Asn Asn Ser Ser
                35                  40                 45

Arg Cys Trp Val Ala Leu Thr Pro Thr Leu Ala Ala Arg Asn Ala
                50                  55                 60

Ser Val Pro Thr Thr Thr Ile Arg Arg His Val Asp Leu Leu Val
                65                  70                 75

Gly Ala Ala Thr Phe Cys Ser Ala Met Tyr Val Gly Asp Leu Cys
                80                  85                 90

Gly Ser Val Phe Leu Ile Ser Gln Leu Phe Thr Phe Ser Pro Arg
                95                 100                105

Gln His Glu Thr Val Gln Asp Cys Asn Cys Ser Ile Tyr Pro Gly
               110                 115                120

His Val Ser Gly His Arg Met Ala Trp Asp Met Met Met Asn Trp
               125                 130                135

Ser Pro Thr Ala Ala Leu Val Val Ser Gln Leu Leu Arg Ile Pro
               140                 145                150

Gln Ala Val Met Asp Met Val Ala Gly Ala His Trp Gly Val Leu
               155                 160                165

Ala Gly Leu Ala Tyr Tyr Ser Met Val Gly Asn Trp Ala Lys Val
               170                 175                180

Leu Ile Val Leu Leu Leu Phe Ala Gly Val Asp Gly
               185                 190
```

( 2 ) INFORMATION FOR SEQ ID NO:77:

( i ) SEQUENCE CHARACTERISTICS:
      ( A ) LENGTH: 192 amino acids
      ( B ) TYPE: amino acid
      ( C ) STRANDEDNESS: unknown
      ( D ) TOPOLOGY: unknown ( v i ) ORIGINAL SOURCE:
      ( A ) ORGANISM: homosapiens
      ( C ) INDIVIDUAL ISOLATE: T2

( x i ) SEQUENCE DESCRIPTION: SEQ ID NO:77:

```
Ala Gln Val Arg Asn Thr Ser Arg Gly Tyr Met Val Thr Asn Asp
                 5                  10                 15

Cys Ser Asn Glu Ser Ile Thr Trp Gln Leu Gln Ala Ala Val Leu
                20                  25                 30

His Val Pro Gly Cys Ile Pro Cys Glu Arg Leu Gly Asn Thr Ser
                35                  40                 45

Arg Cys Trp Ile Pro Val Thr Pro Asn Val Ala Val Arg Gln Pro
                50                  55                 60

Gly Ala Leu Thr Gln Gly Leu Arg Thr His Ile Asp Met Val Val
                65                  70                 75
```

Met Ser Ala Thr Leu Cys Ser Ala Leu Tyr Val Gly Asp Leu Cys
                80                          85                          90

Gly Gly Val Met Leu Ala Ala Gln Met Phe Ile Val Ser Pro Arg
                95                         100                         105

Arg His Trp Phe Val Gln Glu Cys Asn Cys Ser Ile Tyr Pro Gly
               110                         115                         120

Thr Ile Thr Gly His Arg Met Ala Trp Asp Met Met Met Asn Trp
               125                         130                         135

Ser Pro Thr Ala Thr Met Ile Leu Ala Tyr Ala Met Arg Val Pro
               140                         145                         150

Glu Val Ile Ile Asp Ile Ile Gly Gly Ala His Trp Gly Val Met
               155                         160                         165

Phe Gly Leu Ala Tyr Phe Ser Met Gln Gly Ala Trp Ala Lys Val
               170                         175                         180

Ile Val Ile Leu Leu Leu Ala Ala Gly Val Asp Ala
               185                         190

(2) INFORMATION FOR SEQ ID NO:78:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T4

(xi) SEQUENCE DESCRIPTION: SEQ ID NO:78:

Ala Gln Val Lys Asn Thr Thr Asn Ser Tyr Met Val Thr Asn Asp
                 5                          10                          15

Cys Ser Asn Asp Ser Ile Thr Trp Gln Leu Gln Ala Ala Val Leu
                20                          25                          30

His Val Pro Gly Cys Val Pro Cys Glu Lys Thr Gly Asn Thr Ser
                35                          40                          45

Arg Cys Trp Ile Pro Val Ser Pro Asn Val Ala Val Arg Gln Pro
                50                          55                          60

Gly Ala Leu Thr Gln Gly Leu Arg Thr His Ile Asp Met Val Val
                65                          70                          75

Met Ser Ala Thr Leu Cys Ser Ala Leu Tyr Val Gly Asp Leu Cys
                80                          85                          90

Gly Gly Val Met Leu Ala Ala Gln Met Phe Ile Val Ser Pro Gln
                95                         100                         105

His His Trp Phe Val Gln Asp Cys Asn Cys Ser Ile Tyr Pro Gly
               110                         115                         120

Thr Ile Thr Gly His Arg Met Ala Trp Asp Met Met Met Asn Trp
               125                         130                         135

Ser Pro Thr Ala Thr Met Ile Leu Ala Tyr Ala Met Arg Val Pro
               140                         145                         150

Glu Val Ile Leu Asp Ile Val Ser Gly Ala His Trp Gly Val Met
               155                         160                         165

Phe Gly Leu Ala Tyr Phe Ser Met Gln Gly Ala Trp Ala Lys Val
               170                         175                         180

Val Val Ile Leu Leu Leu Ala Ala Gly Val Asp Ala
               185                         190

( 2 ) INFORMATION FOR SEQ ID NO:79:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T9

( x i ) SEQUENCE DESCRIPTION: SEQ ID NO:79:

```
Ala  Glu  Val  Lys  Asn  Thr  Ser  Thr  Ser  Tyr  Met  Val  Thr  Asn  Asp
                    5                        10                        15

Cys  Ser  Asn  Asp  Ser  Ile  Thr  Trp  Gln  Leu  Gln  Ala  Ala  Val  Leu
                    20                       25                        30

His  Val  Pro  Gly  Cys  Val  Pro  Cys  Glu  Arg  Val  Gly  Asn  Ala  Ser
                    35                       40                        45

Arg  Cys  Trp  Ile  Pro  Val  Ser  Pro  Asn  Val  Ala  Val  Gln  Arg  Pro
                    50                       55                        60

Gly  Ala  Leu  Thr  Gln  Gly  Leu  Arg  Thr  His  Ile  Asp  Met  Val  Val
                    65                       70                        75

Met  Ser  Ala  Thr  Leu  Cys  Ser  Ala  Leu  Tyr  Val  Gly  Asp  Leu  Cys
                    80                       85                        90

Gly  Gly  Val  Met  Leu  Ala  Ala  Gln  Met  Phe  Ile  Ile  Ser  Pro  Gln
                    95                       100                       105

His  His  Trp  Phe  Val  Gln  Glu  Cys  Asn  Cys  Ser  Ile  Tyr  Pro  Gly
                    110                      115                       120

Thr  Ile  Thr  Gly  His  Arg  Met  Ala  Trp  Asp  Met  Met  Met  Asn  Trp
                    125                      130                       135

Ser  Pro  Thr  Thr  Thr  Met  Ile  Leu  Ala  Tyr  Ala  Met  Arg  Val  Pro
                    140                      145                       150

Glu  Val  Ile  Ile  Asp  Ile  Ile  Ser  Gly  Ala  His  Trp  Gly  Val  Met
                    155                      160                       165

Phe  Gly  Leu  Ala  Tyr  Phe  Ser  Met  Gln  Gly  Ala  Trp  Ala  Lys  Val
                    170                      175                       180

Val  Val  Ile  Leu  Leu  Leu  Thr  Ala  Gly  Val  Asp  Ala
                    185                      190
```

( 2 ) INFORMATION FOR SEQ ID NO:80:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: US10

( x i ) SEQUENCE DESCRIPTION: SEQ ID NO:80:

```
Val  Gln  Val  Lys  Asn  Thr  Ser  Thr  Ser  Tyr  Met  Val  Thr  Asn  Asp
                    5                        10                        15

Cys  Ser  Asn  Asp  Ser  Ile  Thr  Trp  Gln  Leu  Glu  Ala  Ala  Val  Leu
                    20                       25                        30

His  Val  Pro  Gly  Cys  Val  Pro  Cys  Glu  Lys  Val  Gly  Asn  Thr  Ser
                    35                       40                        45

Arg  Cys  Trp  Ile  Pro  Val  Ser  Pro  Asn  Val  Ala  Val  Gln  Arg  Pro
                    50                       55                        60
```

| | | | | | | | | | | | | | | |
|---|---|---|---|---|---|---|---|---|---|---|---|---|---|---|
| Gly | Ala | Leu | Thr | Gln<br>65 | Gly | Leu | Arg | Thr | His<br>70 | Ile | Asp | Met | Val | Val<br>75 |
| Met | Ser | Ala | Thr | Leu<br>80 | Cys | Ser | Ala | Leu | Tyr<br>85 | Val | Gly | Asp | Phe | Cys<br>90 |
| Gly | Gly | Met | Met | Leu<br>95 | Ala | Ala | Gln | Met | Phe<br>100 | Ile | Val | Ser | Pro | Arg<br>105 |
| His | His | Ser | Phe | Val<br>110 | Gln | Glu | Cys | Asn | Cys<br>115 | Ser | Ile | Tyr | Pro | Gly<br>120 |
| Thr | Ile | Thr | Gly | His<br>125 | Arg | Met | Ala | Trp | Asp<br>130 | Met | Met | Met | Asn | Trp<br>135 |
| Ser | Pro | Thr | Ala | Thr<br>140 | Leu | Ile | Leu | Ala | Tyr<br>145 | Val | Met | Arg | Val | Pro<br>150 |
| Glu | Val | Ile | Ile | Asp<br>155 | Ile | Ile | Ser | Gly | Ala<br>160 | His | Trp | Gly | Val | Leu<br>165 |
| Phe | Gly | Leu | Ala | Tyr<br>170 | Phe | Ser | Met | Gln | Gly<br>175 | Ala | Trp | Ala | Lys | Val<br>180 |
| Val | Val | Ile | Leu | Leu<br>185 | Leu | Ala | Ala | Gly | Val<br>190 | Asp | Ala | | | |

( 2 ) INFORMATION FOR SEQ ID NO:81:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK8

( x i ) SEQUENCE DESCRIPTION: SEQ ID NO:81:

| | | | | | | | | | | | | | | |
|---|---|---|---|---|---|---|---|---|---|---|---|---|---|---|
| Val | Glu | Val | Arg | Asn<br>5 | Ile | Ser | Ser | Ser | Tyr<br>10 | Tyr | Ala | Thr | Asn | Asp<br>15 |
| Cys | Ser | Asn | Asn | Ser<br>20 | Ile | Thr | Trp | Gln | Leu<br>25 | Thr | Asp | Ala | Val | Leu<br>30 |
| His | Leu | Pro | Gly | Cys<br>35 | Val | Pro | Cys | Glu | Asn<br>40 | Asp | Asn | Gly | Thr | Leu<br>45 |
| Arg | Cys | Trp | Ile | Gln<br>50 | Val | Thr | Pro | Asn | Val<br>55 | Ala | Val | Lys | His | Arg<br>60 |
| Gly | Ala | Leu | Thr | His<br>65 | Asn | Leu | Arg | Thr | His<br>70 | Val | Asp | Val | Ile | Val<br>75 |
| Met | Ala | Ala | Thr | Val<br>80 | Cys | Ser | Ala | Leu | Tyr<br>85 | Val | Gly | Asp | Val | Cys<br>90 |
| Gly | Ala | Val | Met | Ile<br>95 | Val | Ser | Gln | Ala | Leu<br>100 | Ile | Ile | Ser | Pro | Glu<br>105 |
| Arg | His | Asn | Phe | Thr<br>110 | Gln | Glu | Cys | Asn | Cys<br>115 | Ser | Ile | Tyr | Gln | Gly<br>120 |
| His | Ile | Thr | Gly | His<br>125 | Arg | Met | Ala | Trp | Asp<br>130 | Met | Met | Leu | Asn | Trp<br>135 |
| Ser | Pro | Thr | Leu | Thr<br>140 | Met | Ile | Leu | Ala | Tyr<br>145 | Ala | Ala | Arg | Val | Pro<br>150 |
| Glu | Leu | Ala | Leu | Gln<br>155 | Val | Val | Phe | Gly | Gly<br>160 | His | Trp | Gly | Val | Val<br>165 |
| Phe | Gly | Leu | Ala | Tyr<br>170 | Phe | Ser | Met | Gln | Gly<br>175 | Ala | Trp | Ala | Lys | Val<br>180 |
| Ile | Ala | Ile | Leu | Leu<br>185 | Leu | Val | Ala | Gly | Val<br>190 | Asp | Ala | | | |

( 2 ) INFORMATION FOR SEQ ID NO:82:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK11

( x i ) SEQUENCE DESCRIPTION: SEQ ID NO:82:

```
Val Glu Val Arg Asn Thr Ser Ser Ser Tyr Tyr Ala Thr Asn Asp
                 5                  10                 15
Cys Ser Asn Asn Ser Ile Thr Trp Gln Leu Thr Asn Ala Val Leu
                20                  25                 30
His Leu Pro Gly Cys Val Pro Cys Glu Asn Asp Asn Gly Thr Leu
                35                  40                 45
His Cys Trp Ile Gln Val Thr Pro Asn Val Ala Val Lys His Arg
                50                  55                 60
Gly Ala Leu Thr His Asn Leu Arg Ala His Ile Asp Met Ile Val
                65                  70                 75
Met Ala Ala Thr Val Cys Ser Ala Leu Tyr Val Gly Asp Val Cys
                80                  85                 90
Gly Ala Val Met Ile Val Ser Gln Ala Phe Ile Val Ser Pro Glu
                95                 100                105
His His His Phe Thr Gln Glu Cys Asn Cys Ser Ile Tyr Gln Gly
               110                 115                120
His Ile Thr Gly His Arg Met Ala Trp Asp Met Met Leu Asn Trp
               125                 130                135
Ser Pro Thr Leu Thr Met Ile Leu Ala Tyr Ala Ala Arg Val Pro
               140                 145                150
Glu Leu Val Leu Glu Val Val Phe Gly Gly His Trp Gly Val Val
               155                 160                165
Phe Gly Leu Ala Tyr Phe Ser Met Gln Gly Ala Trp Ala Lys Val
               170                 175                180
Ile Ala Ile Leu Leu Leu Val Ala Gly Val Asp Ala
               185                 190
```

( 2 ) INFORMATION FOR SEQ ID NO:83:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SW3

( x i ) SEQUENCE DESCRIPTION: SEQ ID NO:83:

```
Val Glu Val Arg Asn Ile Ser Ser Ser Tyr Tyr Ala Thr Asn Asp
                 5                  10                 15
Cys Ser Asn Ser Ser Ile Thr Trp Gln Leu Thr Asn Ala Val Leu
                20                  25                 30
His Leu Pro Gly Cys Val Pro Cys Glu Asn Asp Asn Gly Thr Leu
                35                  40                 45
His Cys Trp Ile Gln Val Thr Pro Asn Val Ala Val Lys His Arg
```

```
                         50                         55                         60
Gly  Ala  Leu  Thr  His  Asn  Leu  Arg  Ala  His  Val  Asp  Met  Ile  Val
                    65                        70                             75

Met  Ala  Ala  Thr  Val  Cys  Ser  Ala  Leu  Tyr  Val  Gly  Asp  Met  Cys
                    80                        85                             90

Gly  Ala  Val  Met  Ile  Val  Ser  Gln  Ala  Phe  Ile  Ile  Ser  Pro  Glu
                    95                        100                            105

Arg  His  Asn  Phe  Thr  Gln  Glu  Cys  Asn  Cys  Ser  Ile  Tyr  Gln  Gly
                    110                       115                            120

Arg  Ile  Thr  Gly  His  Arg  Met  Ala  Trp  Asp  Met  Met  Leu  Asn  Trp
                    125                       130                            135

Ser  Pro  Thr  Leu  Thr  Met  Ile  Leu  Ala  Tyr  Ala  Ala  Arg  Val  Pro
                    140                       145                            150

Glu  Leu  Val  Leu  Glu  Val  Val  Phe  Gly  Gly  His  Trp  Gly  Val  Val
                    155                       160                            165

Phe  Gly  Leu  Ala  Tyr  Phe  Ser  Met  Gln  Gly  Ala  Trp  Ala  Lys  Val
                    170                       175                            180

Ile  Ala  Ile  Leu  Leu  Leu  Val  Ala  Gly  Val  Asp  Ala
                    185                       190
```

( 2 ) INFORMATION FOR SEQ ID NO:84:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T8

( x i ) SEQUENCE DESCRIPTION: SEQ ID NO:84:

```
Val  Glu  Val  Arg  Asn  Thr  Ser  Phe  Ser  Tyr  Tyr  Ala  Thr  Asn  Asp
                    5                         10                             15

Cys  Ser  Asn  Asn  Ser  Ile  Thr  Trp  Gln  Leu  Thr  Asn  Ala  Val  Leu
                    20                        25                             30

His  Leu  Pro  Gly  Cys  Val  Pro  Cys  Glu  Asn  Asp  Asn  Gly  Thr  Leu
                    35                        40                             45

Arg  Cys  Trp  Ile  Gln  Val  Thr  Pro  Asn  Val  Ala  Val  Lys  His  Arg
                    50                        55                             60

Gly  Ala  Leu  Thr  His  Asn  Leu  Arg  Thr  His  Val  Asp  Val  Ile  Val
                    65                        70                             75

Met  Ala  Ala  Thr  Val  Cys  Ser  Ala  Leu  Tyr  Val  Gly  Asp  Val  Cys
                    80                        85                             90

Gly  Ala  Val  Met  Ile  Ala  Ser  Gln  Ala  Phe  Ile  Ile  Ser  Pro  Glu
                    95                        100                            105

Arg  His  Asn  Phe  Thr  Gln  Glu  Cys  Asn  Cys  Ser  Ile  Tyr  Gln  Gly
                    110                       115                            120

His  Ile  Thr  Gly  His  Arg  Met  Ala  Trp  Asp  Met  Met  Leu  Asn  Trp
                    125                       130                            135

Ser  Pro  Thr  Leu  Thr  Met  Ile  Leu  Ala  Tyr  Ala  Ala  Arg  Val  Pro
                    140                       145                            150

Glu  Leu  Val  Leu  Glu  Val  Val  Phe  Gly  Gly  His  Trp  Gly  Val  Val
                    155                       160                            165

Phe  Gly  Leu  Ala  Tyr  Phe  Ser  Met  Gln  Gly  Ala  Trp  Ala  Lys  Val
                    170                       175                            180
```

```
Ile Ala Ile Leu Leu Leu Val Ala Gly Val Asp Ala
                185                 190
```

( 2 ) INFORMATION FOR SEQ ID NO:85:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S83

( x i ) SEQUENCE DESCRIPTION: SEQ ID NO:85:

```
Val Glu Val Lys Asp Thr Gly Asp Ser Tyr Met Pro Thr Asn Asp
                5                   10                  15

Cys Ser Asn Ser Ser Ile Val Trp Gln Leu Glu Gly Ala Val Leu
                20                  25                  30

His Thr Pro Gly Cys Val Pro Cys Glu Arg Thr Ala Asn Val Ser
                35                  40                  45

Arg Cys Trp Val Pro Val Ala Pro Asn Leu Ala Ile Ser Gln Pro
                50                  55                  60

Gly Ala Leu Thr Lys Gly Leu Arg Ala His Ile Asp Ile Ile Val
                65                  70                  75

Met Ser Ala Thr Val Cys Ser Ala Leu Tyr Val Gly Asp Val Cys
                80                  85                  90

Gly Ala Leu Met Leu Ala Ala Gln Val Val Val Ser Pro Gln
                95                  100                 105

His His Thr Phe Val Gln Glu Cys Asn Cys Ser Ile Tyr Pro Gly
                110                 115                 120

Arg Ile Thr Gly His Arg Met Ala Trp Asp Met Met Met Asn Trp
                125                 130                 135

Ser Pro Thr Thr Thr Met Leu Leu Ala Tyr Leu Val Arg Ile Pro
                140                 145                 150

Glu Val Ile Leu Asp Ile Val Thr Gly Gly His Trp Gly Val Met
                155                 160                 165

Phe Gly Leu Ala Tyr Phe Ser Met Gln Gly Ser Trp Ala Lys Val
                170                 175                 180

Ile Val Ile Leu Leu Leu Thr Ala Gly Val Glu Ala
                185                 190
```

( 2 ) INFORMATION FOR SEQ ID NO:86:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK12

( x i ) SEQUENCE DESCRIPTION: SEQ ID NO:86:

```
Leu Glu Trp Arg Asn Val Ser Gly Leu Tyr Val Leu Thr Asn Asp
                5                   10                  15

Cys Ser Asn Ser Ser Ile Val Tyr Glu Ala Asp Asp Val Ile Leu
                20                  25                  30

His Thr Pro Gly Cys Val Pro Cys Val Gln Asp Gly Asn Thr Ser
                35                  40                  45
```

|       |       |       |       |       |       |       |       |       |       |       |       |
|-------|-------|-------|-------|-------|-------|-------|-------|-------|-------|-------|-------|
| Thr   | Cys   | Trp   | Thr   | Ser   | Val   | Thr   | Pro   | Thr   | Val   | Ala   | Val   | Arg   | Tyr   | Val   |

Thr Cys Trp Thr Ser Val Thr Pro Thr Val Ala Val Arg Tyr Val
                    50                  55                              60

Gly Ala Thr Thr Ala Ser Ile Arg Ser His Val Asp Leu Leu Val
                    65                  70                              75

Gly Ala Ala Thr Met Cys Ser Ala Leu Tyr Val Gly Asp Val Cys
                    80                  85                              90

Gly Ala Val Phe Leu Val Gly Gln Ala Phe Thr Phe Arg Pro Arg
                    95                 100                             105

Arg His Gln Thr Val Gln Thr Cys Asn Cys Ser Leu Tyr Pro Gly
                   110                 115                             120

His Leu Ser Gly His Arg Met Ala Trp Asp Met Met Met Asn Trp
                   125                 130                             135

Ser Pro Ala Val Gly Met Val Val Ala His Val Leu Arg Leu Pro
                   140                 145                             150

Gln Thr Leu Phe Asp Ile Ile Ala Gly Ala His Trp Gly Ile Met
                   155                 160                             165

Ala Gly Leu Ala Tyr Tyr Ser Met Gln Gly Asn Trp Ala Lys Val
                   170                 175                             180

Ala Ile Ile Met Val Met Phe Ser Gly Val Asp Ala
                   185                 190

(2) INFORMATION FOR SEQ ID NO:87:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK10

(xi) SEQUENCE DESCRIPTION: SEQ ID NO:87:

Leu Glu Trp Arg Asn Val Ser Gly Leu Tyr Val Leu Thr Asn Asp
                     5                  10                              15

Cys Pro Asn Ser Ser Ile Val Tyr Glu Ala Asp Asp Val Ile Leu
                    20                  25                              30

His Thr Pro Gly Cys Val Pro Cys Val Gln Asp Gly Asn Thr Ser
                    35                  40                              45

Thr Cys Trp Thr Ser Val Thr Pro Thr Val Ala Val Arg Tyr Val
                    50                  55                              60

Gly Ala Thr Thr Ala Ser Ile Arg Ser His Val Asp Leu Leu Val
                    65                  70                              75

Gly Ala Ala Thr Met Cys Ser Ala Leu Tyr Val Gly Asp Met Cys
                    80                  85                              90

Gly Ala Val Phe Leu Val Gly Gln Ala Phe Thr Phe Arg Pro Arg
                    95                 100                             105

Arg His Gln Thr Val Gln Thr Cys Asn Cys Ser Leu Tyr Pro Gly
                   110                 115                             120

His Leu Ser Gly His Arg Met Ala Trp Asp Met Met Met Asn Trp
                   125                 130                             135

Ser Pro Ala Val Gly Met Val Val Ala His Val Leu Arg Leu Pro
                   140                 145                             150

Gln Thr Leu Phe Asp Ile Ile Ala Gly Ala His Trp Gly Ile Leu
                   155                 160                             165

Ala Gly Leu Ala Tyr Tyr Ser Met Gln Gly Asn Trp Ala Lys Val

|     |     |     |     | 170 |     |     |     |     | 175 |     |     |     |     | 180 |
| --- | --- | --- | --- | --- | --- | --- | --- | --- | --- | --- | --- | --- | --- | --- |
| Ala | Ile | Ile | Met | Val | Met | Phe | Ser | Gly | Val | Asp | Ala |     |     |     |
|     |     |     |     | 185 |     |     |     |     | 190 |     |     |     |     |     |

( 2 ) INFORMATION FOR SEQ ID NO:88:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S2

( x i ) SEQUENCE DESCRIPTION: SEQ ID NO:88:

| Leu | Glu | Trp | Arg | Asn | Thr | Ser | Gly | Leu | Tyr | Val | Leu | Thr | Asn | Asp |
| --- | --- | --- | --- | --- | --- | --- | --- | --- | --- | --- | --- | --- | --- | --- |
|     |     |     |     | 5   |     |     |     |     | 10  |     |     |     |     | 15  |
| Cys | Ser | Asn | Ser | Ser | Ile | Val | Tyr | Glu | Ala | Asp | Asp | Val | Ile | Leu |
|     |     |     |     | 20  |     |     |     |     | 25  |     |     |     |     | 30  |
| His | Thr | Pro | Gly | Cys | Val | Pro | Cys | Val | Gln | Asp | Gly | Asn | Thr | Ser |
|     |     |     |     | 35  |     |     |     |     | 40  |     |     |     |     | 45  |
| Thr | Cys | Trp | Thr | Pro | Val | Thr | Pro | Thr | Val | Ala | Val | Arg | Tyr | Val |
|     |     |     |     | 50  |     |     |     |     | 55  |     |     |     |     | 60  |
| Gly | Ala | Thr | Thr | Ala | Ser | Ile | Arg | Ser | His | Val | Asp | Leu | Leu | Val |
|     |     |     |     | 65  |     |     |     |     | 70  |     |     |     |     | 75  |
| Gly | Ala | Ala | Thr | Met | Cys | Ser | Ala | Leu | Tyr | Val | Gly | Asp | Met | Cys |
|     |     |     |     | 80  |     |     |     |     | 85  |     |     |     |     | 90  |
| Gly | Ala | Val | Phe | Leu | Val | Gly | Gln | Ala | Phe | Thr | Phe | Arg | Pro | Arg |
|     |     |     |     | 95  |     |     |     |     | 100 |     |     |     |     | 105 |
| Arg | His | Gln | Thr | Val | Gln | Thr | Cys | Asn | Cys | Ser | Leu | Tyr | Pro | Gly |
|     |     |     |     | 110 |     |     |     |     | 115 |     |     |     |     | 120 |
| His | Leu | Ser | Gly | His | Arg | Met | Ala | Trp | Asp | Met | Met | Asn | Trp |
|     |     |     |     | 125 |     |     |     |     | 130 |     |     |     |     | 135 |
| Ser | Pro | Ala | Val | Gly | Met | Val | Val | Ala | His | Val | Leu | Arg | Leu | Pro |
|     |     |     |     | 140 |     |     |     |     | 145 |     |     |     |     | 150 |
| Gln | Thr | Val | Phe | Asp | Ile | Ile | Ala | Gly | Ala | His | Trp | Gly | Ile | Leu |
|     |     |     |     | 155 |     |     |     |     | 160 |     |     |     |     | 165 |
| Ala | Gly | Leu | Ala | Tyr | Tyr | Ser | Met | Gln | Gly | Asn | Trp | Ala | Lys | Val |
|     |     |     |     | 170 |     |     |     |     | 175 |     |     |     |     | 180 |
| Ala | Ile | Ile | Met | Val | Met | Phe | Ser | Gly | Val | Asp | Ala |     |     |     |
|     |     |     |     | 185 |     |     |     |     | 190 |     |     |     |     |     |

( 2 ) INFORMATION FOR SEQ ID NO:89:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S52

( x i ) SEQUENCE DESCRIPTION: SEQ ID NO:89:

| Leu | Glu | Trp | Arg | Asn | Thr | Ser | Gly | Leu | Tyr | Val | Leu | Thr | Asn | Asp |
| --- | --- | --- | --- | --- | --- | --- | --- | --- | --- | --- | --- | --- | --- | --- |
|     |     |     |     | 5   |     |     |     |     | 10  |     |     |     |     | 15  |
| Cys | Ser | Asn | Ser | Ser | Ile | Val | Tyr | Glu | Ala | Asp | Asp | Val | Ile | Leu |
|     |     |     |     | 20  |     |     |     |     | 25  |     |     |     |     | 30  |

| His | Thr | Pro | Gly | Cys | Val | Pro | Cys | Val | Gln | Asp | Gly | Asn | Thr | Ser |
|     |     |     |     | 35  |     |     |     |     | 40  |     |     |     |     | 45  |

| Met | Cys | Trp | Thr | Pro | Val | Thr | Pro | Thr | Val | Ala | Val | Arg | Tyr | Val |
|     |     |     |     | 50  |     |     |     |     | 55  |     |     |     |     | 60  |

| Gly | Ala | Thr | Thr | Ala | Ser | Ile | Arg | Ser | His | Val | Asp | Leu | Leu | Val |
|     |     |     |     | 65  |     |     |     |     | 70  |     |     |     |     | 75  |

| Gly | Ala | Ala | Thr | Leu | Cys | Ser | Ala | Leu | Tyr | Val | Gly | Asp | Met | Cys |
|     |     |     |     | 80  |     |     |     |     | 85  |     |     |     |     | 90  |

| Gly | Ala | Val | Phe | Leu | Val | Gly | Gln | Ala | Phe | Thr | Phe | Arg | Pro | Arg |
|     |     |     |     | 95  |     |     |     |     | 100 |     |     |     |     | 105 |

| Arg | His | Gln | Thr | Val | Gln | Thr | Cys | Asn | Cys | Ser | Leu | Tyr | Pro | Gly |
|     |     |     |     | 110 |     |     |     |     | 115 |     |     |     |     | 120 |

| His | Val | Ser | Gly | His | Arg | Met | Ala | Trp | Asp | Met | Met | Met | Asn | Trp |
|     |     |     |     | 125 |     |     |     |     | 130 |     |     |     |     | 135 |

| Ser | Pro | Ala | Val | Gly | Met | Val | Val | Ala | His | Ile | Leu | Arg | Leu | Pro |
|     |     |     |     | 140 |     |     |     |     | 145 |     |     |     |     | 150 |

| Gln | Thr | Leu | Phe | Asp | Ile | Leu | Ala | Gly | Ala | His | Trp | Gly | Ile | Leu |
|     |     |     |     | 155 |     |     |     |     | 160 |     |     |     |     | 165 |

| Ala | Gly | Leu | Ala | Tyr | Tyr | Ser | Met | Gln | Gly | Asn | Trp | Ala | Lys | Val |
|     |     |     |     | 170 |     |     |     |     | 175 |     |     |     |     | 180 |

| Ala | Ile | Val | Met | Ile | Met | Phe | Ser | Gly | Val | Asp | Ala |
|     |     |     |     | 185 |     |     |     |     | 190 |     |     |

(2) INFORMATION FOR SEQ ID NO:90:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S54

(xi) SEQUENCE DESCRIPTION: SEQ ID NO:90:

| Leu | Glu | Trp | Arg | Asn | Thr | Ser | Gly | Leu | Tyr | Ile | Leu | Thr | Asn | Asp |
|     |     |     |     | 5   |     |     |     |     | 10  |     |     |     |     | 15  |

| Cys | Ser | Asn | Ser | Ser | Ile | Val | Tyr | Glu | Ala | Asp | Asp | Val | Ile | Leu |
|     |     |     |     | 20  |     |     |     |     | 25  |     |     |     |     | 30  |

| His | Thr | Pro | Gly | Cys | Val | Pro | Cys | Val | Gln | Asp | Gly | Asn | Thr | Ser |
|     |     |     |     | 35  |     |     |     |     | 40  |     |     |     |     | 45  |

| Thr | Cys | Trp | Thr | Pro | Val | Thr | Pro | Thr | Val | Ala | Val | Arg | Tyr | Val |
|     |     |     |     | 50  |     |     |     |     | 55  |     |     |     |     | 60  |

| Gly | Ala | Thr | Thr | Ala | Ser | Ile | Arg | Ser | His | Val | Asp | Leu | Leu | Val |
|     |     |     |     | 65  |     |     |     |     | 70  |     |     |     |     | 75  |

| Gly | Ala | Ala | Thr | Leu | Cys | Ser | Ala | Leu | Tyr | Val | Gly | Asp | Met | Cys |
|     |     |     |     | 80  |     |     |     |     | 85  |     |     |     |     | 90  |

| Gly | Ala | Val | Phe | Leu | Val | Gly | Gln | Ala | Phe | Thr | Phe | Arg | Pro | Arg |
|     |     |     |     | 95  |     |     |     |     | 100 |     |     |     |     | 105 |

| Arg | His | Gln | Thr | Val | Gln | Thr | Cys | Asn | Cys | Ser | Leu | Tyr | Pro | Gly |
|     |     |     |     | 110 |     |     |     |     | 115 |     |     |     |     | 120 |

| His | Leu | Ser | Gly | His | Arg | Met | Ala | Trp | Asp | Met | Met | Met | Asn | Trp |
|     |     |     |     | 125 |     |     |     |     | 130 |     |     |     |     | 135 |

| Ser | Pro | Ala | Val | Gly | Met | Val | Val | Ala | His | Ile | Leu | Arg | Leu | Pro |
|     |     |     |     | 140 |     |     |     |     | 145 |     |     |     |     | 150 |

| Gln | Thr | Leu | Phe | Asp | Ile | Leu | Ala | Gly | Ala | His | Trp | Gly | Ile | Leu |
|     |     |     |     | 155 |     |     |     |     | 160 |     |     |     |     | 165 |

```
Ala  Gly  Leu  Ala  Tyr  Tyr  Ser  Met  Gln  Gly  Asn  Trp  Ala  Lys  Val
               170                      175                           180

Ala  Ile  Ile  Met  Ile  Met  Phe  Ser  Gly  Val  Asp  Ala
               185                      190
```

( 2 ) INFORMATION FOR SEQ ID NO:91:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z4

( x i ) SEQUENCE DESCRIPTION: SEQ ID NO:91:

```
Glu  His  Tyr  Arg  Asn  Ala  Ser  Gly  Ile  Tyr  His  Ile  Thr  Asn  Asp
                    5                        10                       15

Cys  Pro  Asn  Ser  Ser  Ile  Val  Tyr  Glu  Ala  Asp  His  His  Ile  Leu
                    20                       25                       30

His  Leu  Pro  Gly  Cys  Val  Pro  Cys  Val  Met  Thr  Gly  Asn  Thr  Ser
                    35                       40                       45

Arg  Cys  Trp  Thr  Pro  Val  Thr  Pro  Thr  Val  Ala  Val  Ala  His  Pro
                    50                       55                       60

Gly  Ala  Pro  Leu  Glu  Ser  Phe  Arg  Arg  His  Val  Asp  Leu  Met  Val
                    65                       70                       75

Gly  Ala  Ala  Thr  Leu  Cys  Ser  Ala  Leu  Tyr  Val  Gly  Asp  Leu  Cys
                    80                       85                       90

Gly  Gly  Ala  Phe  Leu  Met  Gly  Gln  Met  Ile  Thr  Phe  Arg  Pro  Arg
                    95                       100                      105

Arg  His  Trp  Thr  Thr  Gln  Glu  Cys  Asn  Cys  Ser  Ile  Tyr  Thr  Gly
                    110                      115                      120

His  Ile  Thr  Gly  His  Arg  Met  Ala  Trp  Asp  Met  Met  Met  Asn  Trp
                    125                      130                      135

Ser  Pro  Thr  Thr  Thr  Leu  Leu  Leu  Ala  Gln  Ile  Met  Arg  Val  Pro
                    140                      145                      150

Thr  Ala  Phe  Leu  Asp  Met  Val  Ala  Gly  Gly  His  Trp  Gly  Val  Leu
                    155                      160                      165

Ala  Gly  Leu  Ala  Tyr  Phe  Ser  Met  Gln  Gly  Asn  Trp  Ala  Lys  Val
                    170                      175                      180

Val  Leu  Val  Leu  Phe  Leu  Phe  Ala  Gly  Val  Asp  Ala
                    185                      190
```

( 2 ) INFORMATION FOR SEQ ID NO:92:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z1

( x i ) SEQUENCE DESCRIPTION: SEQ ID NO:92:

```
Val  His  Tyr  Arg  Asn  Ala  Ser  Gly  Val  Tyr  His  Val  Thr  Asn  Asp
                    5                        10                       15

Cys  Pro  Asn  Thr  Ser  Ile  Val  Tyr  Glu  Thr  Glu  His  His  Ile  Met
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 20  |     |     |     |     | 25  |     |     |     |     | 30  |
| His | Leu | Pro | Gly | Cys<br>35 | Val | Pro | Cys | Val | Arg<br>40 | Thr | Glu | Asn | Thr | Ser<br>45 |
| Arg | Cys | Trp | Val | Pro<br>50 | Leu | Thr | Pro | Thr | Val<br>55 | Ala | Ala | Pro | Tyr | Pro<br>60 |
| Asn | Ala | Pro | Leu | Glu<br>65 | Ser | Met | Arg | Arg | His<br>70 | Val | Asp | Leu | Met | Val<br>75 |
| Gly | Ala | Ala | Thr | Met<br>80 | Cys | Ser | Ala | Phe | Tyr<br>85 | Ile | Gly | Asp | Leu | Cys<br>90 |
| Gly | Gly | Val | Phe | Leu<br>95 | Val | Gly | Gln | Leu | Phe<br>100 | Asp | Phe | Arg | Pro | Arg<br>105 |
| Arg | His | Trp | Thr | Thr<br>110 | Gln | Asp | Cys | Asn | Cys<br>115 | Ser | Ile | Tyr | Pro | Gly<br>120 |
| His | Val | Ser | Gly | His<br>125 | Arg | Met | Ala | Trp | Asp<br>130 | Met | Met | Met | Asn | Trp<br>135 |
| Ser | Pro | Thr | Ser | Ala<br>140 | Leu | Ile | Met | Ala | Gln<br>145 | Ile | Leu | Arg | Ile | Pro<br>150 |
| Ser | Ile | Leu | Gly | Asp<br>155 | Leu | Leu | Thr | Gly | Gly<br>160 | His | Trp | Gly | Val | Leu<br>165 |
| Ala | Gly | Leu | Ala | Phe<br>170 | Phe | Ser | Met | Gln | Ser<br>175 | Asn | Trp | Ala | Lys | Val<br>180 |
| Ile | Leu | Val | Leu | Phe<br>185 | Leu | Phe | Ala | Gly | Val<br>190 | Glu | Gly |     |     |     |

( 2 ) INFORMATION FOR SEQ ID NO:93:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z6

( x i ) SEQUENCE DESCRIPTION: SEQ ID NO:93:

|     |     |     |     |     |     |     |     |     |     |     |     |     |     |     |
| --- | --- | --- | --- | --- | --- | --- | --- | --- | --- | --- | --- | --- | --- | --- |
| Val | Asn | Tyr | Arg | Asn<br>5 | Ala | Ser | Gly | Val | Tyr<br>10 | His | Val | Thr | Asn | Asp<br>15 |
| Cys | Pro | Asn | Ser | Ser<br>20 | Ile | Val | Tyr | Glu | Ala<br>25 | Glu | His | Gln | Ile | Leu<br>30 |
| His | Leu | Pro | Gly | Cys<br>35 | Leu | Pro | Cys | Val | Arg<br>40 | Val | Gly | Asn | Gln | Ser<br>45 |
| Arg | Cys | Trp | Val | Ala<br>50 | Leu | Thr | Pro | Thr | Val<br>55 | Ala | Val | Ser | Tyr | Ile<br>60 |
| Gly | Ala | Pro | Leu | Asp<br>65 | Ser | Leu | Arg | Arg | His<br>70 | Val | Asp | Leu | Met | Val<br>75 |
| Gly | Ala | Ala | Thr | Val<br>80 | Cys | Ser | Ala | Leu | Tyr<br>85 | Val | Gly | Asp | Leu | Cys<br>90 |
| Gly | Gly | Ala | Phe | Leu<br>95 | Val | Gly | Gln | Met | Phe<br>100 | Ser | Phe | Gln | Pro | Arg<br>105 |
| Arg | His | Trp | Thr | Thr<br>110 | Gln | Asp | Cys | Asn | Cys<br>115 | Ser | Ile | Tyr | Ala | Gly<br>120 |
| His | Ile | Thr | Gly | His<br>125 | Arg | Met | Ala | Trp | Asp<br>130 | Met | Met | Met | Asn | Trp<br>135 |
| Ser | Pro | Thr | Thr | Thr<br>140 | Leu | Leu | Leu | Ala | Gln<br>145 | Val | Met | Arg | Ile | Pro<br>150 |

| | | | | | | | | | | | | | | |
|---|---|---|---|---|---|---|---|---|---|---|---|---|---|---|
| Ser | Thr | Leu | Val | Asp<br>155 | Leu | Leu | Ala | Gly | Gly<br>160 | His | Trp | Gly | Val | Leu<br>165 |
| Val | Gly | Leu | Ala | Tyr<br>170 | Phe | Ser | Met | Gln | Ala<br>175 | Asn | Trp | Ala | Lys | Val<br>180 |
| Ile | Leu | Val | Leu | Phe<br>185 | Leu | Phe | Ala | Gly | Val<br>190 | Asp | Ala | | | |

( 2 ) INFORMATION FOR SEQ ID NO:94:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z7

( x i ) SEQUENCE DESCRIPTION: SEQ ID NO:94:

| | | | | | | | | | | | | | | |
|---|---|---|---|---|---|---|---|---|---|---|---|---|---|---|
| Val | Asn | Tyr | His | Asn<br>5 | Ala | Ser | Gly | Val | Tyr<br>10 | His | Ile | Thr | Asn | Asp<br>15 |
| Cys | Pro | Asn | Ser | Ser<br>20 | Ile | Met | Tyr | Glu | Ala<br>25 | Glu | His | His | Ile | Leu<br>30 |
| His | Leu | Pro | Gly | Cys<br>35 | Val | Pro | Cys | Val | Arg<br>40 | Glu | Gly | Asn | Gln | Ser<br>45 |
| Arg | Cys | Trp | Val | Ala<br>50 | Leu | Thr | Pro | Thr | Val<br>55 | Ala | Ala | Pro | Tyr | Ile<br>60 |
| Gly | Ala | Pro | Leu | Glu<br>65 | Ser | Ile | Arg | Arg | His<br>70 | Val | Asp | Leu | Met | Val<br>75 |
| Gly | Ala | Ala | Thr | Val<br>80 | Cys | Ser | Ala | Leu | Tyr<br>85 | Ile | Gly | Asp | Leu | Cys<br>90 |
| Gly | Gly | Val | Phe | Leu<br>95 | Val | Gly | Gln | Met | Phe<br>100 | Ser | Phe | Gln | Pro | Arg<br>105 |
| Arg | His | Trp | Thr | Thr<br>110 | Gln | Asp | Cys | Asn | Cys<br>115 | Ser | Ile | Tyr | Ala | Gly<br>120 |
| His | Val | Thr | Gly | His<br>125 | Arg | Met | Ala | Trp | Asp<br>130 | Met | Met | Met | Asn | Trp<br>135 |
| Ser | Pro | Thr | Thr | Thr<br>140 | Leu | Val | Leu | Ala | Gln<br>145 | Val | Met | Arg | Ile | Pro<br>150 |
| Ser | Thr | Leu | Val | Asp<br>155 | Leu | Leu | Thr | Gly | Gly<br>160 | His | Trp | Gly | Ile | Leu<br>165 |
| Ile | Gly | Val | Ala | Tyr<br>170 | Phe | Cys | Met | Gln | Ala<br>175 | Asn | Trp | Ala | Lys | Val<br>180 |
| Ile | Leu | Val | Leu | Phe<br>185 | Leu | Tyr | Ala | Gly | Val<br>190 | Asp | Ala | | | |

( 2 ) INFORMATION FOR SEQ ID NO:95:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK13

( x i ) SEQUENCE DESCRIPTION: SEQ ID NO:95:

| | | | | | | | | | | | | | | |
|---|---|---|---|---|---|---|---|---|---|---|---|---|---|---|
| Tyr | Asn | Tyr | Arg | Asn<br>5 | Ser | Ser | Gly | Val | Tyr<br>10 | His | Val | Thr | Asn | Asp<br>15 |

```
Cys  Pro  Asn  Ser  Ser  Ile  Val  Tyr  Glu  Thr  Asp  Tyr  His  Ile  Leu
                    20                      25                          30

His  Leu  Pro  Gly  Cys  Val  Pro  Cys  Val  Arg  Glu  Gly  Asn  Lys  Ser
                    35                      40                          45

Thr  Cys  Trp  Val  Ser  Leu  Thr  Pro  Thr  Val  Ala  Ala  Gln  His  Leu
                    50                      55                          60

Asn  Ala  Pro  Leu  Glu  Ser  Leu  Arg  Arg  His  Val  Asp  Leu  Met  Val
                    65                      70                          75

Gly  Gly  Ala  Thr  Leu  Cys  Ser  Ala  Leu  Tyr  Ile  Gly  Asp  Val  Cys
                    80                      85                          90

Gly  Gly  Val  Phe  Leu  Val  Gly  Gln  Leu  Phe  Thr  Phe  Gln  Pro  Arg
                    95                      100                         105

Arg  His  Trp  Thr  Thr  Gln  Asp  Cys  Asn  Cys  Ser  Ile  Tyr  Thr  Gly
                    110                     115                         120

His  Ile  Thr  Gly  His  Arg  Met  Ala  Trp  Asp  Met  Met  Met  Asn  Trp
                    125                     130                         135

Ser  Pro  Thr  Ala  Thr  Leu  Val  Leu  Ala  Gln  Leu  Met  Arg  Ile  Pro
                    140                     145                         150

Gly  Ala  Met  Val  Asp  Leu  Leu  Ala  Gly  Gly  His  Trp  Gly  Ile  Leu
                    155                     160                         165

Val  Gly  Ile  Ala  Tyr  Phe  Ser  Met  Gln  Ala  Asn  Trp  Ala  Lys  Val
                    170                     175                         180

Ile  Leu  Val  Leu  Phe  Leu  Phe  Ala  Gly  Val  Asp  Ala
                    185                     190
```

( 2 ) INFORMATION FOR SEQ ID NO:96:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA1

( x i ) SEQUENCE DESCRIPTION: SEQ ID NO:96:

```
Val  Pro  Tyr  Arg  Asn  Ala  Ser  Gly  Val  Tyr  His  Val  Thr  Asn  Asp
                    5                       10                          15

Cys  Pro  Asn  Ser  Ser  Ile  Val  Tyr  Glu  Ala  Asp  Ser  Leu  Ile  Leu
                    20                      25                          30

His  Ala  Pro  Gly  Cys  Val  Pro  Cys  Val  Arg  Gln  Asp  Asn  Val  Ser
                    35                      40                          45

Arg  Cys  Trp  Val  Gln  Ile  Thr  Pro  Thr  Leu  Ser  Ala  Pro  Thr  Phe
                    50                      55                          60

Gly  Ala  Val  Thr  Ala  Pro  Leu  Arg  Arg  Ala  Val  Asp  Tyr  Leu  Ala
                    65                      70                          75

Gly  Gly  Ala  Ala  Leu  Cys  Ser  Ala  Leu  Tyr  Val  Gly  Asp  Ala  Cys
                    80                      85                          90

Gly  Ala  Val  Phe  Leu  Val  Gly  Gln  Met  Phe  Thr  Tyr  Arg  Pro  Arg
                    95                      100                         105

Gln  His  Thr  Thr  Val  Gln  Asp  Cys  Asn  Cys  Ser  Ile  Tyr  Ser  Gly
                    110                     115                         120

His  Ile  Thr  Gly  His  Arg  Met  Ala  Trp  Asp  Met  Met  Met  Asn  Trp
                    125                     130                         135

Ser  Pro  Thr  Thr  Ala  Leu  Leu  Met  Ala  Gln  Met  Leu  Arg  Ile  Pro
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 140 |     |     |     |     | 145 |     |     |     |     | 150 |
| Gln | Val | Val | Ile | Asp | Ile | Ile | Ala | Gly | Gly | His | Trp | Gly | Val | Leu |
|     |     |     |     | 155 |     |     |     |     | 160 |     |     |     |     | 165 |
| Phe | Ala | Ala | Ala | Tyr | Phe | Ala | Ser | Ala | Ala | Asn | Trp | Ala | Lys | Val |
|     |     |     |     | 170 |     |     |     |     | 175 |     |     |     |     | 180 |
| Val | Leu | Val | Leu | Phe | Leu | Phe | Ala | Gly | Val | Asp | Gly |     |     |     |
|     |     |     |     | 185 |     |     |     |     | 190 |     |     |     |     |     |

(2) INFORMATION FOR SEQ ID NO:97:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA4

(xi) SEQUENCE DESCRIPTION: SEQ ID NO:97:

|     |     |     |     |     |     |     |     |     |     |     |     |     |     |     |
| --- | --- | --- | --- | --- | --- | --- | --- | --- | --- | --- | --- | --- | --- | --- |
| Val | Pro | Tyr | Arg | Asn | Ala | Ser | Gly | Val | Tyr | His | Val | Thr | Asn | Asp |
|     |     |     |     | 5   |     |     |     |     | 10  |     |     |     |     | 15  |
| Cys | Pro | Asn | Ser | Ser | Ile | Val | Tyr | Glu | Ala | Asp | Asn | Leu | Ile | Leu |
|     |     |     |     | 20  |     |     |     |     | 25  |     |     |     |     | 30  |
| His | Ala | Pro | Gly | Cys | Val | Pro | Cys | Val | Arg | Gln | Asp | Asn | Val | Ser |
|     |     |     |     | 35  |     |     |     |     | 40  |     |     |     |     | 45  |
| Lys | Cys | Trp | Val | Gln | Ile | Thr | Pro | Thr | Leu | Ser | Ala | Pro | Asn | Leu |
|     |     |     |     | 50  |     |     |     |     | 55  |     |     |     |     | 60  |
| Gly | Ala | Val | Thr | Ala | Pro | Leu | Arg | Arg | Ala | Val | Asp | Tyr | Leu | Ala |
|     |     |     |     | 65  |     |     |     |     | 70  |     |     |     |     | 75  |
| Gly | Gly | Ala | Ala | Leu | Cys | Ser | Ala | Leu | Tyr | Val | Gly | Asp | Ala | Cys |
|     |     |     |     | 80  |     |     |     |     | 85  |     |     |     |     | 90  |
| Gly | Ala | Val | Phe | Leu | Val | Gly | Gln | Met | Phe | Thr | Tyr | Arg | Pro | Arg |
|     |     |     |     | 95  |     |     |     |     | 100 |     |     |     |     | 105 |
| Gln | His | Thr | Thr | Val | Gln | Asp | Cys | Asn | Cys | Ser | Ile | Tyr | Ser | Gly |
|     |     |     |     | 110 |     |     |     |     | 115 |     |     |     |     | 120 |
| His | Ile | Thr | Gly | His | Arg | Met | Ala | Trp | Asp | Met | Met | Asn | Trp |
|     |     |     |     | 125 |     |     |     |     | 130 |     |     |     |     | 135 |
| Ser | Pro | Thr | Thr | Ala | Leu | Leu | Met | Ala | Gln | Leu | Leu | Arg | Ile | Pro |
|     |     |     |     | 140 |     |     |     |     | 145 |     |     |     |     | 150 |
| Gln | Val | Val | Ile | Asp | Ile | Ile | Ala | Gly | Gly | His | Trp | Gly | Val | Leu |
|     |     |     |     | 155 |     |     |     |     | 160 |     |     |     |     | 165 |
| Phe | Ala | Ala | Ala | Tyr | Phe | Ala | Ser | Ala | Ala | Asn | Trp | Ala | Lys | Val |
|     |     |     |     | 170 |     |     |     |     | 175 |     |     |     |     | 180 |
| Ile | Leu | Val | Leu | Phe | Leu | Phe | Ala | Gly | Val | Asp | Ala |     |     |     |
|     |     |     |     | 185 |     |     |     |     | 190 |     |     |     |     |     |

(2) INFORMATION FOR SEQ ID NO:98:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA5

(xi) SEQUENCE DESCRIPTION: SEQ ID NO:98:

| Val | Pro | Tyr | Arg | Asn<br>5 | Ala | Ser | Gly | Val | Tyr<br>10 | His | Val | Thr | Asn | Asp<br>15 |
|---|---|---|---|---|---|---|---|---|---|---|---|---|---|---|
| Cys | Pro | Asn | Ser | Ser<br>20 | Ile | Val | Tyr | Glu | Ala<br>25 | Asp | Asn | Leu | Ile | Leu<br>30 |
| His | Ala | Pro | Gly | Cys<br>35 | Val | Pro | Cys | Val | Lys<br>40 | Glu | Gly | Asn | Val | Ser<br>45 |
| Arg | Cys | Trp | Val | Gln<br>50 | Ile | Thr | Pro | Thr | Leu<br>55 | Ser | Ala | Pro | Asn | Leu<br>60 |
| Gly | Ala | Val | Thr | Ala<br>65 | Pro | Leu | Arg | Arg | Val<br>70 | Val | Asp | Tyr | Leu | Ala<br>75 |
| Gly | Gly | Ala | Ala | Leu<br>80 | Cys | Ser | Ala | Leu | Tyr<br>85 | Val | Gly | Asp | Ala | Cys<br>90 |
| Gly | Ala | Val | Phe | Leu<br>95 | Val | Gly | Gln | Met | Phe<br>100 | Thr | Tyr | Arg | Pro | Arg<br>105 |
| Gln | His | Thr | Thr | Val<br>110 | Gln | Asp | Cys | Asn | Cys<br>115 | Ser | Ile | Tyr | Ser | Gly<br>120 |
| His | Ile | Thr | Gly | His<br>125 | Arg | Met | Ala | Trp | Asp<br>130 | Met | Met | Met | Asn | Trp<br>135 |
| Ser | Pro | Thr | Thr | Ala<br>140 | Leu | Val | Met | Ala | Gln<br>145 | Val | Leu | Arg | Ile | Pro<br>150 |
| Gln | Val | Val | Ile | Asp<br>155 | Ile | Ile | Ala | Gly | Gly<br>160 | His | Trp | Gly | Val | Leu<br>165 |
| Phe | Ala | Val | Ala | Tyr<br>170 | Phe | Ala | Ser | Ala | Ala<br>175 | Asn | Trp | Ala | Lys | Val<br>180 |
| Val | Leu | Val | Leu | Phe<br>185 | Leu | Phe | Ala | Gly | Val<br>190 | Asp | Gly | | | |

( 2 ) INFORMATION FOR SEQ ID NO:99:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA6

( x i ) SEQUENCE DESCRIPTION: SEQ ID NO:99:

| Val | Pro | Tyr | Arg | Asn<br>5 | Ala | Ser | Gly | Val | Tyr<br>10 | His | Val | Thr | Asn | Asp<br>15 |
|---|---|---|---|---|---|---|---|---|---|---|---|---|---|---|
| Cys | Pro | Asn | Ser | Ser<br>20 | Ile | Val | Tyr | Glu | Ala<br>25 | Asp | Asp | Leu | Ile | Leu<br>30 |
| His | Ala | Pro | Gly | Cys<br>35 | Val | Pro | Cys | Val | Arg<br>40 | Lys | Asp | Asn | Val | Ser<br>45 |
| Arg | Cys | Trp | Val | His<br>50 | Ile | Thr | Pro | Thr | Leu<br>55 | Ser | Ala | Pro | Ser | Leu<br>60 |
| Gly | Ala | Val | Thr | Ala<br>65 | Pro | Leu | Arg | Arg | Ala<br>70 | Val | Asp | Tyr | Leu | Ala<br>75 |
| Gly | Gly | Ala | Ala | Leu<br>80 | Cys | Ser | Ala | Leu | Tyr<br>85 | Val | Gly | Asp | Val | Cys<br>90 |
| Gly | Ala | Leu | Phe | Leu<br>95 | Val | Gly | Gln | Met | Phe<br>100 | Thr | Tyr | Arg | Pro | Arg<br>105 |
| Gln | His | Ala | Thr | Val<br>110 | Gln | Asp | Cys | Asn | Cys<br>115 | Ser | Ile | Tyr | Ser | Gly<br>120 |
| His | Ile | Thr | Gly | His<br>125 | Arg | Met | Ala | Trp | Asp<br>130 | Met | Met | Met | Asn | Trp<br>135 |

| Ser | Pro | Ala | Thr | Ala | Leu | Val | Met | Ala | Gln | Met | Leu | Arg | Ile | Pro |
|---|---|---|---|---|---|---|---|---|---|---|---|---|---|---|
| | | | | 140 | | | | | 145 | | | | | 150 |

| Gln | Val | Val | Ile | Asp | Ile | Ile | Ala | Gly | Gly | His | Trp | Gly | Val | Leu |
|---|---|---|---|---|---|---|---|---|---|---|---|---|---|---|
| | | | | 155 | | | | | 160 | | | | | 165 |

| Phe | Ala | Ala | Ala | Tyr | Phe | Ala | Ser | Ala | Ala | Asn | Trp | Ala | Lys | Val |
|---|---|---|---|---|---|---|---|---|---|---|---|---|---|---|
| | | | | 170 | | | | | 175 | | | | | 180 |

| Val | Leu | Val | Leu | Phe | Leu | Phe | Ala | Gly | Val | Asp | Ala |
|---|---|---|---|---|---|---|---|---|---|---|---|
| | | | | 185 | | | | | 190 | | |

( 2 ) INFORMATION FOR SEQ ID NO:100:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA7

( x i ) SEQUENCE DESCRIPTION: SEQ ID NO:100:

| Val | Pro | Tyr | Arg | Asn | Ala | Ser | Gly | Val | Tyr | His | Val | Thr | Asn | Asp |
|---|---|---|---|---|---|---|---|---|---|---|---|---|---|---|
| | | | | 5 | | | | | 10 | | | | | 15 |

| Cys | Pro | Asn | Ser | Ser | Ile | Val | Tyr | Glu | Ala | Asp | Asn | Leu | Ile | Leu |
|---|---|---|---|---|---|---|---|---|---|---|---|---|---|---|
| | | | | 20 | | | | | 25 | | | | | 30 |

| His | Ala | Pro | Gly | Cys | Val | Pro | Cys | Val | Arg | Gln | Asn | Asn | Val | Ser |
|---|---|---|---|---|---|---|---|---|---|---|---|---|---|---|
| | | | | 35 | | | | | 40 | | | | | 45 |

| Arg | Cys | Trp | Val | Gln | Ile | Thr | Pro | Thr | Leu | Ser | Ala | Pro | Asn | Leu |
|---|---|---|---|---|---|---|---|---|---|---|---|---|---|---|
| | | | | 50 | | | | | 55 | | | | | 60 |

| Gly | Ala | Val | Thr | Ala | Pro | Leu | Arg | Arg | Ala | Val | Asp | Tyr | Leu | Ala |
|---|---|---|---|---|---|---|---|---|---|---|---|---|---|---|
| | | | | 65 | | | | | 70 | | | | | 75 |

| Gly | Gly | Ala | Ala | Leu | Cys | Ser | Ala | Leu | Tyr | Val | Gly | Asp | Ala | Cys |
|---|---|---|---|---|---|---|---|---|---|---|---|---|---|---|
| | | | | 80 | | | | | 85 | | | | | 90 |

| Gly | Ala | Val | Phe | Leu | Val | Gly | Gln | Met | Phe | Ser | Tyr | Arg | Pro | Arg |
|---|---|---|---|---|---|---|---|---|---|---|---|---|---|---|
| | | | | 95 | | | | | 100 | | | | | 105 |

| Gln | His | Thr | Thr | Val | Gln | Asp | Cys | Asn | Cys | Ser | Ile | Tyr | Ser | Gly |
|---|---|---|---|---|---|---|---|---|---|---|---|---|---|---|
| | | | | 110 | | | | | 115 | | | | | 120 |

| His | Ile | Thr | Gly | His | Arg | Met | Ala | Trp | Asp | Met | Met | Met | Asn | Trp |
|---|---|---|---|---|---|---|---|---|---|---|---|---|---|---|
| | | | | 125 | | | | | 130 | | | | | 135 |

| Ser | Pro | Thr | Thr | Ala | Leu | Val | Met | Ala | Gln | Leu | Leu | Arg | Ile | Pro |
|---|---|---|---|---|---|---|---|---|---|---|---|---|---|---|
| | | | | 140 | | | | | 145 | | | | | 150 |

| Gln | Val | Val | Ile | Asp | Ile | Ile | Ala | Gly | Gly | His | Trp | Gly | Val | Leu |
|---|---|---|---|---|---|---|---|---|---|---|---|---|---|---|
| | | | | 155 | | | | | 160 | | | | | 165 |

| Phe | Ala | Ala | Ala | Tyr | Phe | Ala | Ser | Ala | Ala | Asn | Trp | Ala | Lys | Val |
|---|---|---|---|---|---|---|---|---|---|---|---|---|---|---|
| | | | | 170 | | | | | 175 | | | | | 180 |

| Val | Leu | Val | Leu | Phe | Leu | Phe | Ala | Gly | Val | Asp | Ala |
|---|---|---|---|---|---|---|---|---|---|---|---|
| | | | | 185 | | | | | 190 | | |

( 2 ) INFORMATION FOR SEQ ID NO:101:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA13

( x i ) SEQUENCE DESCRIPTION: SEQ ID NO:101:

| | | | | | | | | | | | | | | |
|---|---|---|---|---|---|---|---|---|---|---|---|---|---|---|
| Val | Pro | Tyr | Arg | Asn | Ala | Ser | Gly | Val | Tyr | His | Val | Thr | Asn | Asp |
| | | | | 5 | | | | | 10 | | | | | 15 |
| Cys | Pro | Asn | Ser | Ser | Ile | Val | Tyr | Glu | Ala | Asp | Asp | Leu | Ile | Leu |
| | | | | 20 | | | | | 25 | | | | | 30 |
| His | Ala | Pro | Gly | Cys | Val | Pro | Cys | Val | Arg | Gln | Gly | Asn | Val | Ser |
| | | | | 35 | | | | | 40 | | | | | 45 |
| Arg | Cys | Trp | Val | Gln | Ile | Thr | Pro | Thr | Leu | Ser | Ala | Pro | Ser | Leu |
| | | | | 50 | | | | | 55 | | | | | 60 |
| Gly | Ala | Val | Thr | Ala | Pro | Leu | Arg | Arg | Ala | Val | Asp | Tyr | Leu | Ala |
| | | | | 65 | | | | | 70 | | | | | 75 |
| Gly | Gly | Ala | Ala | Leu | Cys | Ser | Ala | Leu | Tyr | Val | Gly | Asp | Ala | Cys |
| | | | | 80 | | | | | 85 | | | | | 90 |
| Gly | Ala | Val | Phe | Leu | Val | Gly | Gln | Met | Phe | Thr | Tyr | Ser | Pro | Arg |
| | | | | 95 | | | | | 100 | | | | | 105 |
| Arg | His | Asn | Val | Val | Gln | Asp | Cys | Asn | Cys | Ser | Ile | Tyr | Ser | Gly |
| | | | | 110 | | | | | 115 | | | | | 120 |
| His | Ile | Thr | Gly | His | Arg | Met | Ala | Trp | Asp | Met | Met | Asn | Trp |
| | | | | 125 | | | | | 130 | | | | 135 |
| Ser | Pro | Thr | Thr | Ala | Leu | Val | Met | Ala | Gln | Leu | Leu | Arg | Ile | Pro |
| | | | | 140 | | | | | 145 | | | | | 150 |
| Gln | Val | Val | Ile | Asp | Ile | Ile | Ala | Gly | Ala | His | Trp | Gly | Val | Leu |
| | | | | 155 | | | | | 160 | | | | | 165 |
| Phe | Ala | Ala | Ala | Tyr | Tyr | Ala | Ser | Ala | Ala | Asn | Trp | Ala | Lys | Val |
| | | | | 170 | | | | | 175 | | | | | 180 |
| Val | Leu | Val | Leu | Phe | Leu | Phe | Ala | Gly | Val | Asp | Ala | | | |
| | | | | 185 | | | | | 190 | | | | | |

( 2 ) INFORMATION FOR SEQ ID NO:102:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: HK2

( x i ) SEQUENCE DESCRIPTION: SEQ ID NO:102:

| | | | | | | | | | | | | | | |
|---|---|---|---|---|---|---|---|---|---|---|---|---|---|---|
| Leu | Thr | Tyr | Gln | Asn | Ser | Ser | Gln | Leu | Tyr | His | Leu | Thr | Asn | Asp |
| | | | | 1 | | | | | 10 | | | | | 15 |
| Cys | Pro | Asn | Ser | Ser | Ile | Val | Leu | Glu | Ala | Asp | Ala | Met | Ile | Leu |
| | | | | 20 | | | | | 25 | | | | | 30 |
| His | Leu | Pro | Gln | Cys | Leu | Pro | Cys | Val | Arg | Val | Asp | Asp | Arg | Ser |
| | | | | 35 | | | | | 40 | | | | | 45 |
| Thr | Cys | Trp | His | Ala | Val | Thr | Pro | Thr | Leu | Ala | Ile | Pro | Asn | Ala |
| | | | | 50 | | | | | 55 | | | | | 60 |
| Ser | Thr | Pro | Ala | Thr | Gln | Phe | Arg | Arg | His | Val | Asp | Leu | Leu | Ala |
| | | | | 65 | | | | | 70 | | | | | 75 |
| Gln | Ala | Ala | Val | Val | Cys | Ser | Ser | Leu | Tyr | Ile | Gln | Asp | Leu | Cys |
| | | | | 80 | | | | | 85 | | | | | 90 |
| Gln | Ser | Leu | Phe | Leu | Ala | Gln | Gln | Leu | Phe | Thr | Phe | Gln | Pro | Arg |
| | | | | 95 | | | | | 100 | | | | | 105 |
| Arg | His | Trp | Thr | Val | Gln | Asp | Cys | Asn | Cys | Ser | Ile | Tyr | Thr | Gln |
| | | | | 110 | | | | | 115 | | | | | 120 |

| | | | | | | | | | | | | |
|---|---|---|---|---|---|---|---|---|---|---|---|---|
| His | Val | Thr | Gln | His 125 | Arg | Met | Ala | Trp | Asp 130 | Met | Met | Met | Asn | Trp 135 |
| Ser | Pro | Thr | Thr | Thr 140 | Leu | Val | Leu | Ser | Ser 145 | Ile | Leu | Arg | Val | Pro 150 |
| Glu | Ile | Cys | Ala | Ser 155 | Val | Ile | Phe | Gln | Gln 160 | His | Trp | Gln | Ile | Leu 165 |
| Leu | Ala | Val | Ala | Tyr 170 | Phe | Gln | Met | Ala | Gln 175 | Asn | Trp | Leu | Lys | Val 180 |
| Leu | Ala | Val | Leu | Phe 185 | Leu | Phe | Ala | Gln | Val 190 | Glu | Ala | | | |

( 2 ) INFORMATION FOR SEQ ID NO: 103:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK7

( x i ) SEQUENCE DESCRIPTION: SEQ ID NO: 103:

| | | | | | | | | | | | | |
|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGT | CGC | CCA | CAG | GAC | GTC | AAG | TTC | CCG | GGT | 78 |
| GGC | GGT | CAG | ATC | GTT | GGT | GGA | GTT | TAC | TTG | TTG | CCG | CGC | 117 |
| AGG | GGC | CCT | AGA | TTG | GGT | GTG | CGC | GCG | CCG | AGG | AAG | ACT | 156 |
| TCC | GAG | CGG | TCG | CAA | CCT | CGA | GGT | AGA | CGT | CAG | CCT | ATC | 195 |
| CCC | AAG | GCA | CGT | CGG | CCC | GAG | GGC | AGG | ACC | TGG | GCT | CAG | 234 |
| CCC | GGG | TAC | CCT | TGG | CCC | CTC | TAT | GGC | AAT | GAG | GGC | TGC | 273 |
| GGG | TGG | GCG | GGA | TGG | CTC | CTG | TCT | CCC | CGT | GGC | TCT | CGG | 312 |
| CCT | AGC | TGG | GGC | CCC | ACA | GAC | CCC | CGG | CGC | AGG | TCG | CGC | 351 |
| AAT | TTG | GGT | AAA | GTC | ATC | GAT | ACC | CTT | ACG | TGC | GGC | TTC | 390 |
| GCC | GAC | CTC | ATG | GGG | TAC | ATA | CCG | CTC | GTC | GGC | GCC | CCT | 429 |
| CTT | GGA | GGC | GCT | GCC | AGG | GCC | CTG | GCG | CAT | GGC | GTC | CGG | 468 |
| GTT | CTG | GAA | GAC | GGC | GTG | AAC | TAT | GCA | ACA | GGG | AAC | CTT | 507 |
| CCT | GGT | TGC | TCT | TTC | TCT | ATC | TTC | CTT | TGC | CCT | GCT | CTC | 546 |
| TCT | TGC | CTG | ACC | GTG | CCC | GCT | TCG | GCC | | | | | 573 |

( 2 ) INFORMATION FOR SEQ ID NO: 104:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US11

( x i ) SEQUENCE DESCRIPTION: SEQ ID NO: 104:

| | | | | | | | | | | | | |
|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGT | CGC | CCA | CAG | GAC | GTC | AAG | TTC | CCG | GGT | 78 |
| GGC | GGT | CAG | ATC | GTT | GGT | GGA | GTT | TAC | TTG | TTG | CCG | CGC | 117 |

| | | | | | | | | | | | | | |
|---|---|---|---|---|---|---|---|---|---|---|---|---|---|
| AGG | GGC | CCT | AGA | TTG | GGT | GTG | CGC | GCG | ACG | AGG | AAG | ACT | 156 |
| TCC | GAG | CGG | TCG | CAA | CCT | CGA | GGT | AGA | CGT | CAG | CCT | ATC | 195 |
| CCC | AAG | GCA | CGT | CGG | CCC | GAG | GGC | AGG | ACC | TGG | GCT | CAG | 234 |
| CCC | GGG | TAC | CCT | TGG | CCC | CTC | TAT | GGC | AAT | GAG | GGC | TGC | 273 |
| GGG | TGG | GCG | GGA | TGG | CTC | CTG | TCT | CCC | CGT | GGC | TCT | CGG | 312 |
| CCT | AGC | TGG | GGC | CCC | ACG | GAC | CCC | CGG | CGT | AGG | TCG | CGC | 351 |
| AAT | TTG | GGT | AAG | GTC | ATC | GAT | ACC | CTT | ACG | TGC | GGC | TTC | 390 |
| GCC | GAC | CTC | ATG | GGG | TAC | ATA | CCG | CTC | GTC | GGC | GCC | CCT | 429 |
| CTC | GGA | GGC | GCT | GCC | AGG | GCC | CTG | GCG | CAT | GGC | GTC | CGG | 468 |
| GTT | CTG | GAA | GAC | GGC | GTG | AAC | TAT | GCA | ACA | GGG | AAC | CTT | 507 |
| CCT | GGT | TGC | TCT | TTC | TCT | ATC | TTC | CTT | CTG | GCC | CTG | CTC | 546 |
| TCT | TGC | CTG | ACT | GTG | CCC | GCT | TCA | GCC | | | | | 573 |

(2) INFORMATION FOR SEQ ID NO: 105:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S14

(xi) SEQUENCE DESCRIPTION: SEQ ID NO: 105:

| | | | | | | | | | | | | | |
|---|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGT | CGC | CCA | CAG | GAC | GTC | AAG | TTC | CCG | GGT | 78 |
| GGC | GGT | CAG | ATC | GTT | GGT | GGA | GTT | TAC | TTG | TTG | CCG | CGC | 117 |
| AGG | GGC | CCT | AGA | TTG | GGT | GTG | CGC | GCG | ACG | AGG | AAG | ACT | 156 |
| TCC | GAG | CGG | TCG | CAA | CCT | CGA | GGT | AGA | CGT | CAG | CCT | ATC | 195 |
| CCC | AAG | GCA | CGT | CGG | CCC | GAG | GGC | AGG | ACC | TGG | GCT | CAG | 234 |
| CCC | GGG | TAT | CCT | TGG | CCC | CTC | TAT | GGC | AAT | GAG | GGC | TGC | 273 |
| GGG | TGG | GCG | GGA | TGG | CTC | CTG | TCT | CCC | CGT | GGC | TCT | CGG | 312 |
| CCT | AGC | TGG | GGC | CCC | ACA | GAC | CCC | CGG | CGT | AGG | TCG | CGC | 351 |
| AAT | TTG | GGT | AAG | GTC | ATC | GAT | ACC | CTC | ACG | TGC | GGC | TTC | 390 |
| GCC | GAC | CTC | ATG | GGG | TAC | ATA | CCG | CTC | GTC | GGC | GCC | CCC | 429 |
| CTC | GGG | GGC | GCT | GCC | AGG | GCC | CTG | GCG | CAT | GGC | GTC | CGG | 468 |
| GTT | CTG | GAA | GAC | GGC | GTG | AAC | TAT | GCA | ACA | GGG | AAC | CTT | 507 |
| CCT | GGT | TGC | TCT | TTC | TCT | ATC | TTC | CTC | CTA | GCC | CTG | CTT | 546 |
| TCT | TGC | CTG | ACT | GTG | CCC | GCT | TCA | GCC | | | | | 573 |

(2) INFORMATION FOR SEQ ID NO: 106:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (vi) ORIGINAL SOURCE:

(A) ORGANISM: homosapiens
(C) INDIVIDUAL ISOLATE: SW1

(xi) SEQUENCE DESCRIPTION: SEQ ID NO: 106:

| | | | | | | | | | | | | | |
|---|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGT | CGC | CCA | CAG | GAC | GTC | AAG | TTC | CCG | GGT | 78 |
| GGC | GGT | CAG | ATC | GTT | GGT | GGA | GTT | TAC | TTG | TTG | CCG | CGC | 117 |
| AGG | GGC | CCT | AGA | TTG | GGT | GTG | CGC | GCG | ACG | AGG | AAG | ACT | 156 |
| TCC | GAG | CGG | TCG | CAA | CCT | CGA | GGT | AGA | CGT | CAG | CCT | ATC | 195 |
| CCC | AAG | GCG | CGT | CGG | CCC | GAG | GGC | AGG | ACC | TGG | GCT | CAG | 234 |
| CCC | GGG | TAT | CCT | TGG | CCC | CTC | TAT | GGC | AAT | GAG | GGC | TGC | 273 |
| GGA | TGG | GCG | GGA | TGG | CTC | CTG | TCC | CCC | CGT | GGC | TCT | CGG | 312 |
| CCT | AGC | TGG | GGC | CCT | ACA | GAC | CCC | CGG | CGT | AGG | TCG | CGC | 351 |
| AAT | TTG | GGT | AAG | GTC | ATC | GAT | ACC | CTC | ACG | TGC | GGC | TTC | 390 |
| GCC | GAC | CTC | ATG | GGG | TAC | ATT | CCG | CTC | GTC | GGC | GCC | CCT | 429 |
| CTT | GGA | GGC | GCT | GCC | AGG | GCC | CTG | GCG | CAT | GGC | GTC | CGG | 468 |
| GTT | CTG | GAA | GAC | GGC | GTG | AAC | TAT | GCA | ACA | GGG | AAC | CTT | 507 |
| CCT | GGT | TGC | TCT | TTC | TCT | ATC | TTC | CTT | CTG | GCC | CTG | CTT | 546 |
| TCT | TGC | CTG | ACA | GTG | CCC | GCG | TCA | GCC | | | | | 573 |

(2) INFORMATION FOR SEQ ID NO: 107:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S18

(xi) SEQUENCE DESCRIPTION: SEQ ID NO: 107:

| | | | | | | | | | | | | | |
|---|---|---|---|---|---|---|---|---|---|---|---|---|---|
| ATG | AGC | ACA | AAT | CCT | AAA | CCT | CAA | AGA | AAA | ACC | AAA | CGT | 39 |
| AAC | ACC | AAC | CGT | CGC | CCA | CAG | GAC | GTT | AAG | TTC | CCG | GGT | 78 |
| GGC | GGT | CAG | ATC | GTT | GGT | GGA | GTT | TAC | TTG | TTG | CCG | CGC | 117 |
| AGG | GGC | CCT | AGA | TTG | GGT | GTG | CGC | GCG | ACG | AGG | AAG | ACT | 156 |
| TCC | GAG | CGG | TCG | CAA | CCT | CGC | GGT | AGA | CGT | CAG | CCT | ATC | 195 |
| CCC | AAG | GCG | CGT | CGG | CCC | GAG | GGC | AGG | ACC | TGG | GCT | CAG | 234 |
| CCC | GGG | TAC | CCT | TGG | CCC | CTC | TAT | GGC | AAT | GAG | GGC | TGC | 273 |
| GGG | TGG | GCG | GGA | TGG | CTC | CTG | TCC | CCC | CGT | GGC | TCC | CGG | 312 |
| CCT | AGC | TGG | GGC | CCT | ACA | GAC | CCC | CGG | CGT | AGG | TCG | CGC | 351 |
| AAT | TTG | GGC | AAA | GTC | ATC | GAT | ACC | CTC | ACG | TGC | GGC | TTC | 390 |
| GCC | GAC | CTC | ATG | GGG | TAC | ATT | CCG | CTC | GTC | GGC | GCC | CCT | 429 |
| CTC | GGA | GGC | GCT | GCC | AGG | GCC | CTG | GCG | CAT | GGC | GTC | CGG | 468 |
| GTT | CTG | GAA | GAC | GGC | GTG | AAC | TAT | GCA | ACA | GGG | AAC | CTT | 507 |
| CCT | GGT | TGC | TCT | TTC | TCT | ATC | TTC | CTT | CTG | GCC | CTG | CTC | 546 |
| TCT | TGT | CTG | ACT | GTG | CCC | GCG | TCA | GCT | | | | | 573 |

( 2 ) INFORMATION FOR SEQ ID NO: 108:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DR4

( x i ) SEQUENCE DESCRIPTION: SEQ ID NO: 108:

```
ATG AGC ACG AAT CCT AAA CCT CAA AGA AAA ACC AAA CGT      39
AAC ACC AAC CGT CGC CCA CAG GAC GTC AAG TTC CCG GGT      78
GGC GGT CAG ATC GTT GGT GGA GTT TAC TTG TTG CCG CGC     117
AGG GGC CCT AGA TTG GGT GTG CGC GCG ACG AGG AAG ACT     156
TCC GAG CGG TCG CAA CCT CGA GGT AGA CGT CAG CCT ATC     195
CCC AAG GCG CGT CGG CCC GAG GGC AGG ACC TGG GCT CAG     234
CCC GGG TAC CCT TGG CCC CTC TAT GGC AAT GAG GGC TGC     273
GGG TGG GCG GGA TGG CTC CTG TCC CCC CGT GGC TCT CGG     312
CCT AGC TGG GGC CCC ACA GAC CCC CGG CGT AGG TCG CGC     351
AAT TTG GGT AAG GTC ATC GAC ACC CTC ACG TGC GGC TTC     390
GCC GAC CTC ATG GGG TAC ATC CCG CTC GTC GGC GCC CCC     429
CTT GGG GGC GCT GCC AGG GCC CTG GCG CAT GGC GTC CGA     468
GTT CTG GAA GAC GGC GTG AAC TAT GCA ACA GGG AAT CTT     507
CCT GGT TGC TCT TTC TCT ATC TTC CTT TTG GCT TTG CTC     546
TCT TGC TTG ACC GTG CCC GCA TCG GCC                     573
```

( 2 ) INFORMATION FOR SEQ ID NO: 109:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA10

( x i ) SEQUENCE DESCRIPTION: SEQ ID NO: 109:

```
ATG AGC ACG AAT CCT AAA CCT CAA AGA AAA ACC AAA CGT      39
AAC ACC AAC CGC CGC CCA CAG GAC GTC AAG TTC CCG GGC      78
GGT GGT CAG ATC GTT GGT GGA GTC TAT CTG TTG CCG CGC     117
AGG GGC CCC AGG TTG GGT GTG CGC GCG ACG AGG AAG ACT     156
TCC GAG CGG TCG CAA CCT CGT GGA AGG CGA CAA CCT ATC     195
CCC AAG GCT CGC CAG CCC GAG GGC AGG ACC TGG GCC CAG     234
CCC GGG TAC CCT TGG CCC CTC TAT GGC AAT GAG GGC TTG     273
GGG TGG GCA GGA TGG CTC CTG TCA CCC CGT GGC TCT CGG     312
CCT AGT TGG GGC CCC ACG GAC CCC CGG CGT AGG TCG CGT     351
AAT TTG GGT AAG GTC ATC GAT ACC CTC ACA TGC GGC TTC     390
```

| | | | | | | | | | | | | |
|---|---|---|---|---|---|---|---|---|---|---|---|---|
| GCC | GAC | CTC | ATG | GGG | TAC | ATT | CCG | CTC | GTC | GGC | GCC | CCT | 429 |
| TTA | GGG | GGC | GCT | GCC | AGG | GCC | TTG | GCG | CAT | GGC | GTC | CGG | 468 |
| GTT | CTG | GAA | GAC | GGC | GTG | AAC | TAT | GCA | ACA | GGG | AAT | TTG | 507 |
| CCC | GGT | TGC | CCT | TTC | TCT | ATC | TTC | CTC | TTG | GCT | TTG | CTG | 546 |
| TCC | TGT | TTA | ACC | ATC | CCA | GCT | TCC | GCT | | | | | 573 |

( 2 ) INFORMATION FOR SEQ ID NO: 110:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S45

( x i ) SEQUENCE DESCRIPTION: SEQ ID NO: 110:

| | | | | | | | | | | | | |
|---|---|---|---|---|---|---|---|---|---|---|---|---|
| ATG | AGC | ACG | AAT | CCT | AAA | CCT | CAA | AGA | CAA | ACC | AAA | CGT | 39 |
| AAC | ACC | AAC | CGC | CGC | CCA | CAG | GAC | GTC | AAG | TTC | CCG | GGT | 78 |
| GGC | GGT | CAG | ATC | GTT | GGT | GGA | GTT | TAC | CTG | TTG | CCG | CGC | 117 |
| AGG | GGC | CCC | AGG | TTG | GGT | GTG | CGC | GCG | ACT | AGG | AAG | ACT | 156 |
| TCC | GAG | CGG | TCA | CAA | CCT | CGT | GGA | CGG | CGA | CAA | CCT | ATC | 195 |
| CCC | AAG | GCT | CGC | CGG | CCC | GAG | GGC | AGG | GCC | TGG | GCC | CAG | 234 |
| CCC | GGG | CAT | CCT | TGG | CCC | CTC | TAT | GGC | AAT | GAG | GGC | TTG | 273 |
| GGG | TGG | GCA | GGA | TGG | CTC | CTG | TCA | CCC | CGT | GGC | TCC | CGG | 312 |
| CCT | AGT | TGG | GGC | CCC | ACG | GAC | CCC | CGG | CGT | AGG | TCG | CGC | 351 |
| AAT | TTG | GGT | AAG | GTC | ATC | GAT | ACC | CTC | ACG | TGC | GGC | TTC | 390 |
| GCC | GAC | CTC | ATG | GGG | TAC | ATT | CCG | CTC | GTC | GGC | GCC | CCC | 429 |
| CTA | GGG | GGC | GCT | GCC | AGA | GCC | TTG | GCG | CAT | GGC | GTC | CGG | 468 |
| GTT | CTG | GAG | GAC | GGC | GTG | AAC | TAT | GCA | ACA | GGG | AAT | CTG | 507 |
| CCC | GGT | TGC | TCT | TTC | TCT | ATC | TTC | CTC | TTG | GCT | CTG | CTG | 546 |
| TCC | TGC | TTG | ACC | ATC | CCA | GCT | TCC | GCT | | | | | 573 |

( 2 ) INFORMATION FOR SEQ ID NO: 111:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: D1

( x i ) SEQUENCE DESCRIPTION: SEQ ID NO: 111:

| | | | | | | | | | | | | |
|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | CTG | TTG | CCG | CGC | 117 |
| AGG | GGC | CCC | AGG | TTG | GGT | GTG | CGC | GCG | ACT | AGG | AAG | ACT | 156 |
| TCC | GAG | CGG | TCG | CAA | CCT | CGT | GGA | AGG | CGA | CAA | CCT | ATC | 195 |

| | | | | | | | | | | | | |
|---|---|---|---|---|---|---|---|---|---|---|---|---|
| CCC | AAG | GCT | CGC | CGG | CCC | GAG | GGT | AGG | GCC | TGG | GCT | CAG | 234 |
| CCC | GGG | TAC | CCT | TGG | CCC | CTC | TAT | GGC | AAC | GAG | GGC | TTG | 273 |
| GGG | TGG | GCA | GGA | TGG | CTC | CTG | TCA | CCC | CGC | GGC | TCC | CGG | 312 |
| CCT | AGT | TGG | GGC | CCC | ACC | GAC | CCC | CGG | CGT | AGG | TCG | CGT | 351 |
| AAT | TTG | GGT | AAG | GTC | ATC | GAT | ACC | CTC | ACA | TGC | GGC | TTC | 390 |
| GCC | GAC | CTC | ATG | GGG | TAC | ATC | CCG | CTC | GTC | GGC | GCC | CCC | 429 |
| CTA | GGG | GGT | GCT | GCC | AGG | GCC | CTG | GCG | CAT | GGC | GTC | CGG | 468 |
| GTT | CTG | GAG | GAC | GGC | GTG | AAT | TAT | GCA | ACA | GGG | AAT | TTG | 507 |
| CCC | GGT | TGC | TCT | TTC | TCT | ATC | TTC | CTC | TTG | GCT | TTG | CTG | 546 |
| TCC | TGT | TTG | ACC | ATC | CCA | GCT | TCC | GCT | | | | | 573 |

(2) INFORMATION FOR SEQ ID NO: 112:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (v i) ORIGINAL SOURCE:
        (A) ORGANISM: homosapiens
        (C) INDIVIDUAL ISOLATE: US6

(x i) SEQUENCE DESCRIPTION: SEQ ID NO: 112:

| | | | | | | | | | | | | |
|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | CTG | TTG | CCG | CGC | 117 |
| AGG | GGC | CCC | AGG | TTG | GGT | GTG | CGC | GCG | ACT | AGG | AAG | ACT | 156 |
| TCC | GAG | CGG | TCG | CAA | CCT | CGT | GGA | AGG | CGA | CAA | CCT | ATC | 195 |
| CCC | AAG | GCT | CGC | CGG | CCC | GAG | GGC | AGG | GCC | TGG | GCT | CAG | 234 |
| CCC | GGG | TAC | CCT | TGG | CCC | CTC | TAT | GGC | AAC | GAG | GGC | ATG | 273 |
| GGG | TGG | GCA | GGA | TGG | CTC | CTG | TCA | CCC | CGT | GGC | TCC | CGG | 312 |
| CCT | AGT | TGG | GGC | CCC | ACG | GAC | CCC | CGG | CGT | AGG | TCG | CGT | 351 |
| AAT | TTG | GGT | AAG | GTC | ATC | GAT | ACC | CTC | ACA | TGC | GGC | TTC | 390 |
| GCC | GAC | CTC | ATG | GGG | TAC | ATT | CCG | CTC | GTC | GGC | GCC | CCC | 429 |
| CTA | GGG | GGC | GCT | GCC | AGG | GCC | TTG | GCG | CAT | GGC | GTC | CGG | 468 |
| GTT | CTG | GAG | GAC | GGC | GTG | AAC | TAT | GCA | ACA | GGG | AAC | TTG | 507 |
| CCC | GGT | TGC | TCT | TTC | TCT | ATC | TTC | CTC | TTG | GCT | TTG | CTG | 546 |
| TCC | TGT | TTG | ACC | ATT | CCA | GCT | TCC | GCT | | | | | 573 |

(2) INFORMATION FOR SEQ ID NO: 113:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (v i) ORIGINAL SOURCE:
        (A) ORGANISM: homosapiens
        (C) INDIVIDUAL ISOLATE: P10

(x i) SEQUENCE DESCRIPTION: SEQ ID NO: 113:

```
ATG  AGC  ACG  AAT  CCT  AAA  CCT  CAA  AGA  AAA  ACC  AAA  CGT                    39
AAC  ACC  AAC  CGC  CGC  CCA  CAG  GAC  GTC  AAG  TTC  CCG  GGC                    78
GGT  GGT  CAG  ATC  GTT  GGT  GGA  GTT  TAC  CTG  TTG  CCG  CGC                   117
AGG  GGC  CCC  AGG  TTG  GGT  GTG  CGC  GCG  ACT  AGG  AAG  ACT                   156
TCC  GAG  CGG  TCG  CAA  CCT  CGT  GGA  AGG  CGA  CAA  CCT  ATC                   195
CCC  AAG  GCT  CGC  CGG  CCC  GAG  GGC  AGG  GCC  TGG  GCT  CAG                   234
CCC  GGG  TAC  CCT  TGG  CCC  CTC  TAT  GGC  AAT  GAG  GGC  TTG                   273
GGG  TGG  GCA  GGA  TGG  CTC  CTG  TCA  CCC  CGT  GGC  TCT  CGG                   312
CCT  AGT  TGG  GGC  CCC  ACG  GAC  CCC  CGG  CGT  AGG  TCG  CGT                   351
AAT  TTG  GGT  AAG  GTC  ATC  GAT  ACC  CTC  ACA  TGC  GGC  TTC                   390
GCC  GAC  CTC  ATG  GGG  TAC  ATT  CCG  CTC  GTC  GGC  GCC  CCC                   429
CTA  GGG  GGC  GCT  GCC  AGG  GCC  CTG  GCG  CAT  GGC  GTC  CGG                   468
GTT  CTG  GAG  GAC  GGC  GTG  AAC  TAT  GCA  ACA  GGG  AAT  CTG                   507
CCC  GGT  TGC  TCT  TTC  TCT  ATC  TTC  CTC  TTG  GCT  TTG  CTG                   546
TCC  TGC  CTG  ACC  ATC  CCA  GCG  TCC  GCT                                        573
```

( 2 ) INFORMATION FOR SEQ ID NO: 114:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK1

( x i ) SEQUENCE DESCRIPTION: SEQ ID NO: 114:

```
ATG  AGC  ACG  AAT  CCT  AAA  CCT  CAA  AGA  AAA  ACC  AAA  CGT                    39
AAC  ACC  AAC  CGC  CGC  CCA  CAG  GAC  GTC  AAG  TTC  CCG  GGC                    78
GGT  GGT  CAG  ATC  GTT  GGT  GGA  GTT  TAC  CTG  TTG  CCG  CGC                   117
AGG  GGC  CCC  AGG  TTG  GGT  GTG  CGC  GCG  ACT  AGG  AAG  ACT                   156
TCC  GAG  CGG  TCG  CAA  CCT  CGT  GGA  AGG  CGA  CAA  CCT  ATC                   195
CCC  AAG  GCT  CGC  CGG  CCC  GAG  GGC  AGG  GCC  TGG  GCT  CAG                   234
CCC  GGG  TAC  CCT  TGG  CCC  CTC  TAT  GGC  AAT  GAG  GGC  ATG                   273
GGG  TGG  GCA  GGA  TGG  CTC  CTG  TCA  CCC  CGC  GGC  TCT  CGG                   312
CCT  AGT  TGG  GGC  CCC  AAC  GAC  CCC  CGG  CGT  AGG  TCG  CGT                   351
AAT  TTG  GGT  AAG  GTC  ATC  GAT  ACC  CTC  ACA  TGC  GGC  TTC                   390
GCC  GAC  CTC  ATG  GGG  TAC  ATT  CCG  CTC  GTC  GGC  GCC  CCC                   429
CTA  GGG  GGC  GCT  GCC  AGG  GCC  CTG  GCG  CAT  GGC  GTC  CGG                   468
GTT  CTG  GAG  GAC  GGC  GTG  AAC  TAC  GCA  ACA  GGG  AAT  TTG                   507
CCC  GGT  TGC  TCT  TTC  TCT  ATC  TTC  CTC  TTG  GCT  CTG  TTG                   546
TCC  TGT  TTG  ACC  ATC  CCA  GCT  TCC  GCC                                        573
```

( 2 ) INFORMATION FOR SEQ ID NO: 115:

( i ) SEQUENCE CHARACTERISTICS:
        ( A ) LENGTH: 573 base pairs ( B ) TYPE: nucleic acid
( C ) STRANDEDNESS: single
( D ) TOPOLOGY: linear ( v i ) ORIGINAL SOURCE:
( A ) ORGANISM: homosapiens
( C ) INDIVIDUAL ISOLATE: T10

( x i ) SEQUENCE DESCRIPTION: SEQ ID NO: 115:

| | | | | | | | | | | | | |   |
|---|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | CTG | TTG | CCG | CGC | 117 |
| AGG | GGC | CCC | AGG | TTG | GGT | GTG | CGC | GCG | ACT | AGG | AAG | ACT | 156 |
| TCC | GAG | CGG | TCG | CAA | CCT | CGT | GGA | AGG | CGA | CAG | CCT | ATC | 195 |
| CCC | AAG | GCT | CGC | CAG | CCC | GAG | GGC | AGG | GCC | TGG | GCT | CAG | 234 |
| CCC | GGG | TAC | CCT | TGG | CCC | CTC | TAT | GGC | AAT | GAG | GGC | ATG | 273 |
| GGG | TGG | GCA | GGA | TGG | CTC | CTG | TCA | CCC | CGT | GGC | TCC | CGG | 312 |
| CCT | AGT | TGG | GGC | CCC | ACA | GAC | CCC | CGG | CGT | AGG | TCG | CGT | 351 |
| AAT | TTG | GGT | AAG | GTC | ATC | GAT | ACC | CTC | ACA | TGC | GGC | TTC | 390 |
| GCC | GAC | CTC | ATG | GGG | TAC | ATT | CCG | CTC | GTC | GGC | GCC | CCC | 429 |
| CTA | GGG | GGC | GCT | GCC | AGG | GCT | CTG | GCA | CAT | GGT | GTC | CGG | 468 |
| GTT | CTG | GAG | GAC | GGC | GTG | AAC | TAT | GCA | ACA | GGG | AAT | TTG | 507 |
| CCC | GGT | TGC | TCT | TTT | TCT | ATC | TTC | CTC | TTG | GCT | CTG | CTG | 546 |
| TCT | TGT | CTG | ACC | ATC | CCA | GCT | TCC | GCT | | | | | 573 |

( 2 ) INFORMATION FOR SEQ ID NO: 116:

( i ) SEQUENCE CHARACTERISTICS:
( A ) LENGTH: 573 base pairs
( B ) TYPE: nucleic acid
( C ) STRANDEDNESS: single
( D ) TOPOLOGY: linear ( v i ) ORIGINAL SOURCE:
( A ) ORGANISM: homosapiens
( C ) INDIVIDUAL ISOLATE: SW2

( x i ) SEQUENCE DESCRIPTION: SEQ ID NO: 116:

| | | | | | | | | | | | | |   |
|---|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCA | CAG | GAC | GTC | AAG | TTC | CCG | GGC | 78 |
| GGT | GGC | CAG | ATC | GTT | GGT | GGA | GTT | TAC | CTG | TTG | CCG | CGC | 117 |
| AGG | GGC | CCC | CGG | TTG | GGT | GTG | CGC | GCG | ACT | AGG | AAG | ACT | 156 |
| TCC | GAG | CGG | TCG | CAA | CCT | CGT | GGA | AGG | CGA | CAA | CCT | ATC | 195 |
| CCC | AAG | GCT | CGC | CAG | CCC | GAG | GGC | AGG | GCC | TGG | GCT | CAG | 234 |
| CCT | GGG | TAC | CCC | TGG | CCC | CTC | TAT | GGC | AAT | GAG | GGC | ATG | 273 |
| GGA | TGG | GCA | GGA | TGG | CTC | CTG | TCC | CCC | CGC | GGC | TCT | CGG | 312 |
| CCT | AGT | TGG | GGC | CCC | ACT | GAC | CCC | CGG | CGT | AGG | TCG | CGT | 351 |
| AAT | TTG | GGT | AAG | GTC | ATC | GAT | ACC | CTC | ACA | TGC | GGC | TTC | 390 |
| GCC | GAC | CTC | ATG | GGG | TAC | ATT | CCG | CTC | GTC | GGC | GCC | CCC | 429 |
| CTA | GGG | GGC | GCT | GCC | AGG | GCC | CTG | GCG | CAT | GGT | GTC | CGG | 468 |
| GTC | CTG | GAG | GAC | GGC | GTG | AAC | TAT | GCA | ACA | GGG | AAT | CTG | 507 |

| | |
|---|---|
| CCC GGT TGC TCC TTT TCT ATC TTC CTC TTG GCT TTG CTG | 546 |
| TCC TGT CTG ACC ATC CCA GCT TCC GCT | 573 |

( 2 ) INFORMATION FOR SEQ ID NO: 117:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: IND3

( x i ) SEQUENCE DESCRIPTION: SEQ ID NO: 117:

| | |
|---|---|
| ATG AGC ACG AAT CCT AAA CCT CAA AGA AAA ACC AAA CGT | 39 |
| AAC ACC AAC CGC CGC CCA CAG GAC GTC AAG TTC CCG GGC | 78 |
| GGT GGC CAG ATC GTT GGT GGA GTT TAC CTG TTG CCG CGC | 117 |
| AGG GGC CCC AGG TTG GGT GTG CGC GCG ACT AGG AAG ACT | 156 |
| TCC GAG CGG TCG CAA CCT CGT GGA AGG CGA CAA CCT ATC | 195 |
| CCC AAG GCT CGC CGG CCC GAG GGT AGG GCC TGG GCT CAG | 234 |
| CCC GGG TAC CCT TGG CCC CTC TAT GGC AAT GAG GGC TTG | 273 |
| GGG TGG GCA GGA TGG CTC CTG TCA CCC CGC GGT TCT CGG | 312 |
| CCT AGT TGG GGC CCC ACA GAC CCC CGG CGT AGG TCG CGT | 351 |
| AAT TTG GGT AAA GTC ATC GAT ACC CTC ACA TGC GGC TTC | 390 |
| GCC GAC CTC ATG GGG TAC ATC CCG CTC GTC GGC GCC CCC | 429 |
| CTA GGG GGC GCT GCC AGG GCC CTG GCG CAT GGC GTC CGG | 468 |
| GTC CTG GAG GAC GGC GTG AAC TAT GCA ACA GGG AAC TTG | 507 |
| CCC GGT TGC TCT TTC TCT ATC TTC CTT TTA GCT TTG CTA | 546 |
| TCC TGT TTG ACC ATC CCA GCT TCC GCT | 573 |

( 2 ) INFORMATION FOR SEQ ID NO: 118:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: IND8

( x i ) SEQUENCE DESCRIPTION: SEQ ID NO: 118:

| | |
|---|---|
| ATG AGC ACG AAT CCT AAA CCT CAA AGA AAA ACC AAA CGT | 39 |
| AAC ACC AAC CGC CGC CCA CAG GAC GTC AAG TTC CCG GGC | 78 |
| GGT GGC CAG ATC GTT GGT GGA GTT TAC CTG TTG CCG CGC | 117 |
| AGG GGC CCC AGG TTG GGT GTG CGC GCG ACT AGG AAG ACT | 156 |
| TCC GAG CGG TCG CAA CCT CGT GGA AGG CGA CAA CCT ATC | 195 |
| CCC AAG GCT CGC CGG CCC GAG GGT AGG GCC TGG GCT CAG | 234 |
| CCC GGG CAC CCT TGG CCC CTC TAT GGC AAT GAG GGC TTG | 273 |
| GGG TGG GCA GGA TGG CTC CTG TCA CCC CGC GGC TCT CGG | 312 |

| | | | | | | | | | | | | |
|---|---|---|---|---|---|---|---|---|---|---|---|---|
|CCT|AGT|TGG|GGC|CCC|ACA|GAC|CCC|CGG|CGT|AGG|TCG|CGT|351|
|AAT|TTG|GGT|AAG|GTC|ATC|GAT|ACC|CTC|ACA|TGC|GGC|TTC|390|
|GCC|GAC|CTC|ATG|GGG|TAC|ATC|CCG|CTC|GTC|GGC|GCC|CCC|429|
|CTA|GGG|GGT|GCT|GCC|AGG|GCC|CTG|GCG|CAT|GGC|GTC|CGG|468|
|GTC|CTG|GAG|GAC|GGC|GTG|AAC|TAT|GCA|ACA|GGG|AAC|TTG|507|
|CCC|GGT|TGC|TCT|TTC|TCT|ATC|TTC|CTT|TTG|GCT|TTG|CTA|546|
|TCC|TGT|TTG|ACC|GTC|CCA|GCT|TCC|GCT| | | | |573|

( 2 ) INFORMATION FOR SEQ ID NO: 119:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S9

( x i ) SEQUENCE DESCRIPTION: SEQ ID NO: 119:

| | | | | | | | | | | | | |
|---|---|---|---|---|---|---|---|---|---|---|---|---|
|ATG|AGC|ACG|AAT|CCT|AAA|CCT|CAA|AGA|AAA|ACC|AAA|CGT|39|
|AAC|ACC|AAC|CGC|CGC|CCA|CAG|GAC|GTT|AAG|TTC|CCG|GGC|78|
|GGT|GGT|CAG|ATC|GTC|GGT|GGA|GTT|TAC|CTG|TTG|CCG|CGC|117|
|AGG|GGC|CCC|AGG|TTG|GGT|GTG|CGC|GCA|ACT|AGG|AAG|ACT|156|
|TCC|GAG|CGG|TCG|CAA|CCT|CGT|GGA|AGG|CGA|CAA|CCT|ATC|195|
|CCC|AAG|GCT|CGC|CAT|CCC|GAG|GGC|AGG|GCC|TGG|GCT|CAG|234|
|CCC|GGG|TAC|CCT|TGG|CCC|CTC|TAC|GGC|AAT|GAG|GGC|TTG|273|
|GGG|TGG|GCA|GGA|TGG|CTC|CTG|TCA|CCC|CGT|GGC|TCT|CGG|312|
|CCT|AGT|TGG|GGC|CCC|AAT|GAC|CCC|CGG|CGT|AGG|TCG|CGT|351|
|AAT|TTG|GGT|AAG|GTC|ATC|GAT|ACC|CTC|ACA|TGC|GGC|TTT|390|
|GCC|GAC|CTC|ATG|GGG|TAC|ATT|CCG|CTC|GTC|GGC|GCC|CCC|429|
|CTA|GGG|GGC|GCT|GCC|AGG|GCT|CTG|GCG|CAT|GGC|GTC|CGG|468|
|GTT|CTG|GAG|GAC|GGC|GTG|AAC|TAT|GCA|ACA|GGG|AAC|CTC|507|
|CCC|GGT|TGC|TCT|TTC|TCT|ATC|TTC|CTT|CTG|GCT|TTG|CTG|546|
|TCC|TGT|TTG|ACC|ATC|CCA|GCT|TCC|GCT| | | | |573|

( 2 ) INFORMATION FOR SEQ ID NO: 120:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK3

( x i ) SEQUENCE DESCRIPTION: SEQ ID NO: 120:

| | | | | | | | | | | | | |
|---|---|---|---|---|---|---|---|---|---|---|---|---|
|ATG|AGC|ACG|AAT|CCT|AAA|CCT|CAA|AGA|AAA|ACC|AAA|CGT|39|
|AAC|ACC|AAC|CGC|CGC|CCA|CAG|GAC|GTC|AAG|TTC|CCG|GGC|78|
|GGT|GGT|CAG|ATC|GTT|GGT|GGA|GTT|TAC|CTG|TTG|CCG|CGC|117|

| | | | | | | | | | | | | | |
|---|---|---|---|---|---|---|---|---|---|---|---|---|---|
| AGG | GGC | CCC | AGG | TTG | GGT | GTG | CGC | GCG | ACC | AGG | AAG | ACT | 156 |
| TCA | GAG | CGG | TCG | CAA | CCT | CGT | GGA | AGG | CGA | CAA | CCT | ATC | 195 |
| CCC | AAG | GCT | CGC | CAA | CCC | GAG | GGC | AGG | ACC | TGG | GCT | CAG | 234 |
| CCC | GGG | TAT | CCT | TGG | CCC | CTC | TAT | GGC | AAC | GAG | GGC | ATG | 273 |
| GGG | TGG | GCA | GGA | TGG | CTC | CTG | TCA | CCC | CGC | GGC | TCT | CGG | 312 |
| CCT | AAT | TGG | GGC | CCC | ACG | GAC | CCC | CGG | CGT | AGG | TCG | CGC | 351 |
| AAT | TTG | GGT | AAG | GTC | ATC | GAT | ACC | CTC | ACG | TGC | GGC | TTC | 390 |
| GCC | GAC | CTC | ATG | GGG | TAC | ATC | CCG | CTC | GTC | GGT | GCC | CCC | 429 |
| CTA | GGG | GGC | GTT | GCC | AGA | GCC | TTG | GCA | CAT | GGT | GTC | CGG | 468 |
| GTT | CTG | GAG | GAC | GGC | GTG | AAC | TAT | GCA | ACA | GGG | AAT | TTA | 507 |
| CCC | GGT | TGC | TCT | TTC | TCT | ATC | TTC | CTC | TTG | GCT | TTG | CTG | 546 |
| TCC | TGC | TTG | ACC | ACC | CCA | GCT | TCC | GCT | | | | | 573 |

( 2 ) INFORMATION FOR SEQ ID NO: 121:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK5

( x i ) SEQUENCE DESCRIPTION: SEQ ID NO: 121:

| | | | | | | | | | | | | | |
|---|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | CTG | TTG | CCG | CGC | 117 |
| AGG | GGC | CCC | AGG | TTG | GGT | GTG | CGC | GCG | ACC | AGG | AAG | ACT | 156 |
| TCC | GAG | CGG | TCG | CAA | CCT | CGT | GGA | AGG | CGA | CAA | CCT | ATC | 195 |
| CCC | AAG | GCT | CGC | CGA | CCC | GAG | GGC | AGG | ACC | TGG | GCT | CAG | 234 |
| CCC | GGG | TAT | CCT | TGG | CCC | CTC | TAT | GGC | AAT | GAG | GGC | ATG | 273 |
| GGG | TGG | GCA | GGA | TGG | CTC | CTG | TCA | CCC | CAT | GGC | TCT | CGG | 312 |
| CCT | AGT | TGG | GGC | CCC | ACG | GAC | CCC | CGG | CGT | AGG | TCG | CGT | 351 |
| AAT | TTG | GGT | AAG | GTC | ATC | GAT | ACC | CTC | ACG | TGC | GGC | TTC | 390 |
| GCC | GAC | CTC | ATG | GGG | TAC | ATC | CCG | CTC | GTC | GGC | GCC | CCC | 429 |
| CTA | GGG | GGC | GTT | GCC | AGA | GCC | CTG | GCA | CAC | GGT | GTC | CGG | 468 |
| GTT | CTG | GAG | GAC | GGC | GTG | AAC | TAC | GCA | ACA | GGG | AAT | ATA | 507 |
| CCC | GGT | TGC | TCT | TTC | TCT | ATC | TTC | CTT | TTG | GCT | TTG | CTG | 546 |
| TCC | TGT | CTG | ACC | ACC | CCA | GTT | TCC | GCT | | | | | 573 |

( 2 ) INFORMATION FOR SEQ ID NO: 122:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:

(A) ORGANISM: homosapiens
(C) INDIVIDUAL ISOLATE: HK4

(xi) SEQUENCE DESCRIPTION: SEQ ID NO: 122:

| | | | | | | | | | | | | |
|---|---|---|---|---|---|---|---|---|---|---|---|---|
| ATG | AGC | ACG | AAT | CCT | AAA | CCT | CAA | AGA | AAG | ACC | AAA | CGT | 39 |
| AAC | ACC | AAC | CGC | CGC | CCA | CAG | GAC | GTT | AAG | TTC | CCG | GGC | 78 |
| GGT | GGC | CAG | ATC | GTC | GGT | GGA | GTT | TAC | CTG | TTG | CCG | CGC | 117 |
| AGG | GGC | CCC | AGG | TTG | GGT | GTG | CGC | GCG | ACT | AGG | AAG | ACT | 156 |
| TCC | GAG | CGG | TCG | CAA | CCT | CGT | GGA | AGG | CGA | CAA | CCT | ATC | 195 |
| CCC | AAG | GCT | CGC | CAA | CCC | GAG | GGC | AGG | ACC | TGG | GCT | CAG | 234 |
| CCC | GGG | TAC | CCT | TGG | CCC | CTC | TAT | GGC | AAT | GAG | GGC | ATG | 273 |
| GGG | TGG | GCA | GGA | TGG | CTC | CTG | TCA | CCC | CGC | GGC | TCT | CGG | 312 |
| CCT | AGT | TGG | GGC | CCC | ACG | GAC | CCC | CGG | CGT | AGG | TCG | CGC | 351 |
| AAT | TTG | GGT | AAG | GTC | ATC | GAT | ACC | CTC | ACA | TGC | GGC | TTC | 390 |
| GCC | GAC | CTC | ATG | GGG | TAC | ATT | CCG | CTC | GTC | GGC | GCC | CCC | 429 |
| TTA | GGG | GGC | GTT | GCC | AGA | GCC | CTG | GCA | CAT | GGT | GTC | CGG | 468 |
| GTT | GTG | GAG | GAC | GGC | GTG | AAC | TAT | GCA | ACA | GGG | AAT | TTG | 507 |
| CCC | GGT | TGC | TCT | TTC | TCT | ATC | TTC | CTC | TTG | GCT | CTG | CTG | 546 |
| TCC | TGT | TTG | ACC | ATC | CCA | GCT | TCC | GCT | | | | 573 |

(2) INFORMATION FOR SEQ ID NO: 123:

(i) SEQUENCE CHARACTERISTICS:
(A) LENGTH: 573 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: P8

(xi) SEQUENCE DESCRIPTION: SEQ ID NO: 123:

| | | | | | | | | | | | | |
|---|---|---|---|---|---|---|---|---|---|---|---|---|
| ATG | AGC | ACG | ACT | CCT | AAA | CCT | CAA | AGA | AAA | ACC | AAA | CGT | 39 |
| AAC | ACC | AGC | CGC | CGC | CCA | CAG | GAC | GTT | AAG | TTC | CCG | GGC | 78 |
| GGT | GGT | CAG | ATC | GTT | GGT | GGA | GTT | TAC | CTG | TTG | CCG | CGC | 117 |
| AGG | GGC | CCC | AGG | TTG | GGT | GTG | CGC | GCG | ACT | AGG | AAG | ACT | 156 |
| TCC | GAG | CGA | TCG | CAA | CCT | CGT | GGC | AGG | CGA | CAA | CCT | ATC | 195 |
| CCC | AAG | GCT | CGC | CGG | CCC | GAG | GGT | AGG | GCC | TGG | GCT | CAG | 234 |
| CCC | GGG | CAC | CCT | TGG | CCC | CTC | TAT | GCC | AAT | GAG | GGC | TTG | 273 |
| GGG | TGG | GCG | GGA | TGG | CTC | CTG | TCA | CCC | CGC | GGC | TCC | CGG | 312 |
| CCT | AGT | TGG | GGC | CCC | ACG | GAC | CCC | CGG | CGT | AGG | TCG | CGC | 351 |
| AAT | TTG | GGT | AAG | GTC | ATC | GAT | ACC | CTC | ACA | TGC | GGC | TTC | 390 |
| GCC | GAC | CTC | ATG | GGG | TAC | ATT | CCG | CTC | GTC | GGC | GGC | CCC | 429 |
| CTA | GGG | GGC | GTT | GCC | AGG | GCC | CTG | GCG | CAT | GGC | GTC | CGG | 468 |
| GTT | GTG | GAG | GAC | GGC | GTG | AAC | TAT | GCA | ACA | GGG | AAT | CTG | 507 |
| CCT | GGT | TGC | TCT | TTC | TCT | ATC | TTC | CTT | TTG | GCT | TTG | CTG | 546 |
| TCT | TGT | CTG | ACC | ATC | CCA | GCT | TCC | GCT | | | | 573 |

( 2 ) INFORMATION FOR SEQ ID NO: 124:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T3

( x i ) SEQUENCE DESCRIPTION: SEQ ID NO: 124:

```
ATG AGC ACG AAT CCT AAA CCT CAA AGA AAA ACC AAA CGT           39
AAC ACC AAC CGC CGC CCA CAG GAC GTT AAG TTC CCG GGC           78
GGT GGT CAG ATC GTT GGT GGA GTT TAC CTG TTG CCG CGC          117
AGG GGC CCC AGG TTG GGT GTG CGC GCG ACT AGG AAG ACT          156
TCC GAG CGG TCG CAA CCT CGT GGA AGG CGA CAA CCT ATC          195
CCC AAG GCT CGC CGG CCC GAG GGT AGG GCC TGG GCT CAG          234
CCC GGG TAC CCT TGG CCC CTC TAT GGC GAC GAG GGC ATG          273
GGG TGG GCA GGA TGG CTC CTG TCA CCC CGC GGC TCC CGG          312
CCT AAT TGG GGC CCC ACA GAC CCC CGG CGT AGG TCG CGT          351
AAT CTG GGT AAG GTC ATC GAT ACC CTC ACA TGC GGC TTC          390
GCC GAC CTC ATG GGG TAC ATT CCG CTC GTC GGC GCT CCC          429
TTA GGG GGC GTT GCC AGG GCC CTG GCG CAT GGC GTC CGG          468
GTT CTG GAG GAC GGC GTG AAT TAC GCA ACA GGG AAT TTG          507
CCT GGT TGC TCT TTC TCT ATC TTC CTC TTG GCT TTG CTG          546
TCC TGC TTG ACC ATC CCA GCT TCC GCT                          573
```

( 2 ) INFORMATION FOR SEQ ID NO: 125:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T4

( x i ) SEQUENCE DESCRIPTION: SEQ ID NO: 125:

```
ATG AGC ACA AAT CCT AAA CCT CAA AGA AAA ACC AAA AGA           39
AAC ACC AAC CGT CGC CCA CAG GAC GTT AAG TTC CCG GGC           78
GGC GGC CAG ATC GTT GGC GGA GTA TAC TTG TTG CCG CGC          117
AGG GGC CCC AGG TTG GGT GTG CGC GCG ACA AGG AAG ACT          156
TCG GAG CGA TCC CAG CCA CGT GGG AGG CGC CAG CCC ATC          195
CCC AAA GAT CGG CGC TCC ACT GGC AAG TCC TGG GGA AAA          234
CCA GGA TAT CCC TGG CCC CTG TAT GGG AAT GAG GGA CTC          273
GGC TGG GCA GGA TGG CTC CTG TCC CCC CGA GGT TCC CGT          312
CCC TCC TGG GGC CCC AAT GAC CCC CGG CAT AGG TCG CGC          351
AAC GTG GGT AAG GTC ATC GAT ACC CTA ACG TGC AGC CTT          390
```

```
GCC  GAC  CTC  ATG  GGG  TAC  GTC  CCC  GTC  GTA  GGC  GGC  CCG              429

TTG  GGT  GGC  GTC  GCC  AGA  GCT  CTC  GCG  CAT  GGC  GTG  AGA              468

GTC  CTG  GAG  GAC  GGG  GTT  AAT  TAT  GCA  ACA  GGG  AAC  TTA              507

CCT  GGT  TGC  TCC  TTT  TCT  ATT  TTC  TTG  CTG  GCC  CTA  CTG              546

TCC  TGC  ATC  ACC  ATT  CCA  GTC  TCC  GCT                                  573
```

( 2 ) INFORMATION FOR SEQ ID NO: 126:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US10

( x i ) SEQUENCE DESCRIPTION: SEQ ID NO: 126:

```
ATG  AGC  ACA  AAT  CCT  AAA  CCT  CAA  AGA  AAA  ACC  AAA  AGA              39

AAC  ACT  AAC  CGT  CGC  CCA  CAA  GAC  GTT  AAG  TTT  CCG  GGC              78

GGC  GGC  CAG  ATC  GTT  GGC  GGA  GTA  TAC  TTG  TTG  CCG  CGC              117

AGG  GGC  CCC  AGG  TTG  GGT  GTG  CGC  GCG  ACA  AGG  AAG  ACT              156

TCG  GAG  CGG  TCC  CAG  CCA  CGT  GGG  AGG  CGC  CAG  CCC  ATC              195

CCC  AAA  GAT  CGG  CGC  CCC  ACT  GGC  AAG  TCC  TGG  GGA  AAA              234

CCA  GGA  TAC  CCT  TGG  CCC  CTA  TAT  GGG  AAT  GAG  GGA  CTC              273

GGC  TGG  GCA  GGA  TGG  CTC  CTG  TCC  CCC  CGA  GGT  TCC  CGT              312

CCC  TCT  TGG  GGC  CCC  ACT  GAT  CCC  CGG  CAT  AGG  TCG  CGC              351

AAC  GTG  GGT  AAG  GTC  ATC  GAT  ACC  CTA  ACG  TGC  GGC  TTT              390

GCC  GAC  CTC  ATG  GGA  TAC  ATC  CCC  GTC  GTG  GGC  GCT  CCG              429

CTT  GGT  GGC  GTC  GCC  AGA  GCT  CTC  GCG  CAT  GGC  GTG  AGG              468

GTC  CTG  GAG  GAC  GGG  GTT  AAT  TAT  GCA  ACA  GGG  AAC  TTA              507

CCC  GGT  TGC  TCC  TTT  TCT  ATC  TTC  TTG  CTG  GCC  TTA  CTG              546

TCC  TGC  ATC  ACC  ATT  CCA  GTC  TCT  GCT                                  573
```

( 2 ) INFORMATION FOR SEQ ID NO: 127:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T9

( x i ) SEQUENCE DESCRIPTION: SEQ ID NO: 127:

```
ATG  AGC  ACA  AAT  CCA  AAA  CCC  CAA  AGA  AAA  ACC  ATA  AGA              39

AAC  ACC  AAC  CGT  CGC  CCA  CAG  GAC  GTT  AAG  TTC  CCG  GGC              78

GGC  GGC  CAG  ATC  GTT  GGC  GGA  GTA  TAC  TTG  TTG  CCG  CGC              117

AGG  GGC  CCT  AGG  TTG  GGT  GTG  CGC  ACG  ACA  AGG  AAG  ACT              156

TCG  GAG  CGG  TCC  CAG  CCA  CGT  GGG  AGG  CGC  CAG  CCC  ATC              195
```

| | | | | | | | | | | | | | |
|---|---|---|---|---|---|---|---|---|---|---|---|---|---|
| CCC | AAA | GAT | CGG | CGC | TCC | ACT | GGC | AAG | TCC | TGG | GGA | AAA | 234 |
| CCA | GGA | TAC | CCC | TGG | CCT | CTA | TAT | GGG | AAT | GAG | GGA | CTC | 273 |
| GGC | TGG | GCG | GGA | TGG | CTC | CTG | TCC | CCC | CGA | GGT | TCC | CGT | 312 |
| CCC | TCT | TGG | GGC | CCC | AGT | GAC | CCC | CGG | CAT | AGG | TCG | CGC | 351 |
| AAC | GTG | GGT | AAG | GTC | ATC | GAT | ACC | CTA | ACG | TGC | GGC | TTT | 390 |
| GCC | GAC | CTC | ATG | GGG | TAC | ATC | CCC | GTC | GTA | GGC | GCC | CCG | 429 |
| CTT | GGT | GGC | GTT | GCC | AGA | GCT | CTC | GCG | CAC | GGC | GTG | AGA | 468 |
| GTC | CTG | GAG | GAC | GGG | GTT | AAT | TAT | GCA | ACA | GGG | AAC | CTA | 507 |
| CCT | GGT | TGC | TCT | TTT | TCT | ATC | TTC | TTG | CTG | GCC | CTA | CTG | 546 |
| TCC | TGC | ATC | ACC | ACT | CCG | GCC | TCT | GCT | | | | | 573 |

(2) INFORMATION FOR SEQ ID NO: 128:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T2

(xi) SEQUENCE DESCRIPTION: SEQ ID NO: 128:

| | | | | | | | | | | | | | |
|---|---|---|---|---|---|---|---|---|---|---|---|---|---|
| ATG | AGC | ACA | ATT | CCT | AAA | CCT | CAA | AGA | AAA | ACC | AAA | AGA | 39 |
| AAC | ACT | AAC | CGT | CGC | CCA | CAA | GAC | GTT | AAG | TTT | CCG | GGC | 78 |
| GGC | GGC | CAG | ATC | GTT | GGC | GGA | GTA | TAC | TTG | CTG | CCG | CGC | 117 |
| AGG | GGC | CCC | AGG | TTG | GGT | GTG | CGC | GCG | ACA | AGG | AAG | ACT | 156 |
| TCG | GAG | CGG | TCC | CAG | CCT | CGT | GGA | AGG | CGC | CAG | CCC | ATC | 195 |
| CCT | AAA | GAT | CGG | CGC | TCC | ACT | GGC | AAG | TCC | TGG | GGA | AAA | 234 |
| CCA | GGA | TAC | CCC | TGG | CCC | CTG | TAT | GGG | AAT | GAG | GGG | CTC | 273 |
| GGC | TGG | GCA | GGA | TGG | CTC | CTG | TCC | CCC | CGA | GGT | TCT | CGT | 312 |
| CCC | TCT | TGG | GGC | CCC | AAT | GAC | CCC | CGG | CAT | AGG | TCG | CGC | 351 |
| AAT | GTG | GGT | AAA | GTC | ATC | GAT | ACC | CTA | ACG | TGC | GGC | TTT | 390 |
| GCC | GAC | CTC | ATG | GGG | TAC | ATC | CCC | GTC | GTA | GGC | GCC | CCG | 429 |
| CTT | GGT | GGT | GTC | GCC | AGA | GCT | CTT | GCG | CAT | GGC | GTG | AGA | 468 |
| GTC | CTG | GAG | GAC | GGA | GTT | AAT | TAT | GCA | ACA | GGT | AAC | TTA | 507 |
| CCC | GGT | TGC | TCC | TTT | TCT | ATC | TTC | TTG | CTA | GCC | CTG | CTG | 546 |
| TCC | TGC | ATC | ACT | ATT | CCG | GTT | TCA | GCT | | | | | 573 |

(2) INFORMATION FOR SEQ ID NO: 129:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T8

(xi) SEQUENCE DESCRIPTION: SEQ ID NO: 129:

| | | | | | | | | | | | | |
|---|---|---|---|---|---|---|---|---|---|---|---|---|
| ATG | AGC | ACA | AAT | CCT | AAA | CCT | CAA | AGA | AAA | ACC | AAA | AGA | 39 |
| AAC | ACA | AAC | CGC | CGC | CCA | CAG | GAC | GTC | AAG | TTC | CCG | GGT | 78 |
| GGC | GGC | CAG | ATC | GTT | GGC | GGA | GTT | TAC | TTG | CTG | CCG | CGC | 117 |
| AGG | GGC | CCT | AGG | TTG | GGT | GTG | CGC | GCG | ACA | AGG | AAG | ACT | 156 |
| TCC | GAG | CGA | TCC | CAG | CCG | CGT | GGG | AGA | CGC | CAG | CCC | ATC | 195 |
| CCG | AAA | GAT | CGG | CGC | TCC | ACC | GGC | AAG | TCC | TGG | GGA | AAA | 234 |
| CCA | GGA | TAT | CCT | TGG | CCT | CTT | TAC | GGA | AAC | GAG | GGC | TGC | 273 |
| GGT | TGG | GCA | GGT | TGG | CTC | CTG | TCC | CCC | CGC | GGG | TCT | CGT | 312 |
| CCT | ACT | TGG | GGC | CCC | ACT | GAC | CCC | CGG | CAT | AGA | TCA | CGT | 351 |
| AAT | TTG | GGC | AGA | GTC | ATC | GAT | ACC | ATT | ACA | TGT | GGT | TTT | 390 |
| GCC | GAC | CTC | ATG | GGG | TAC | ATC | CCT | GTC | GTT | GGC | GCC | CCG | 429 |
| GTC | GGA | GGC | GTC | GCC | AGA | GCT | CTG | GCA | CAT | GGT | GTT | AGG | 468 |
| GTC | CTG | GAA | GAC | GGG | ATA | AAC | TAT | GCA | ACA | GGG | AAT | TTG | 507 |
| CCT | GGT | TGC | TCT | TTT | TCT | ATC | TTC | TTG | CTT | GCT | CTT | CTG | 546 |
| TCA | TGC | TTC | ACA | GTG | CCA | GTG | TCT | GCA | | | | | 573 |

( 2 ) INFORMATION FOR SEQ ID NO: 130:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US1

( x i ) SEQUENCE DESCRIPTION: SEQ ID NO: 130:

| | | | | | | | | | | | | |
|---|---|---|---|---|---|---|---|---|---|---|---|---|
| ATG | AGC | ACA | AAT | CCT | AAA | CCT | CAA | AGA | AAA | ACC | AAA | AGA | 39 |
| AAC | ACA | AAC | CGC | CGC | CCA | CAG | GAC | GTC | AAG | TTC | CCG | GGT | 78 |
| GGC | GGT | CAG | ATC | GTT | GGC | GGA | GTT | TAC | TTG | CTG | CCG | CGC | 117 |
| AGG | GGC | CCC | AGG | TTG | GGT | GTG | CGC | GCG | ACA | AGG | AAG | ACT | 156 |
| TCC | GAG | CGA | TCC | CAG | CCG | CGT | GGG | AGA | CGC | CAG | CCC | ATC | 195 |
| CCG | AAA | GAT | CGG | CGC | TCC | ACC | GGC | AAG | TCC | TGG | GGA | AAG | 234 |
| CCA | GGA | TAT | CCT | TGG | CCT | CTG | TAC | GGA | AAC | GAG | GGC | TGC | 273 |
| GGC | TGG | GCA | GGT | TGG | CTC | CTG | TCC | CCC | CGC | GGG | TCT | CGT | 312 |
| CCT | ACT | TGG | GGC | CCC | ACT | GAC | CCC | CGG | CAC | AGA | TCA | CGT | 351 |
| AAC | TTG | GGC | AAG | GTC | ATC | GAT | ACC | ATT | ACG | TGT | GGT | TTT | 390 |
| GCC | GAC | CTC | ATG | GGG | TAC | ATC | CCT | GTC | GTT | GGC | GCC | CCG | 429 |
| GTC | GGA | GGC | GTC | GCC | AGA | GCT | CTG | GCA | CAC | GGT | GTT | AGG | 468 |
| GTC | CTG | GAA | GAC | GGG | ATA | AAT | TAC | GCA | ACA | GGG | AAT | CTG | 507 |
| CCT | GGT | TGC | TCC | TTT | TCT | ATC | TTC | TTA | CTT | GCT | CTT | CTG | 546 |
| TCG | TGC | GCC | ACG | GTG | CCG | GTG | TCT | GCA | | | | | 573 |

( 2 ) INFORMATION FOR SEQ ID NO: 131:

( i ) SEQUENCE CHARACTERISTICS:
        ( A ) LENGTH: 573 base pairs (B) TYPE: nucleic acid
    (C) STRANDEDNESS: single
    (D) TOPOLOGY: linear (vi) ORIGINAL SOURCE:
    (A) ORGANISM: homosapiens
    (C) INDIVIDUAL ISOLATE: DK11

(xi) SEQUENCE DESCRIPTION: SEQ ID NO: 131:

```
ATG AGC ACA AAT CCT AAA CCT CAA AGA AAA ACC AAA AGA              39
AAT ACA AAC CGC CGC CCA CAG GAC GTT AAG TTC CCG GGT              78
GGC GGC CAG ATC GTT GGC GGA GTT TAC TTG CTG CCG CGC             117
AGG GGC CCC AGG TTG GGT GTG CGC ACG ACA AGG AAG ACT             156
TCC GAG CGA TCC CAG CCG CGT GGG AGA CGC CAG CCC ATC             195
CCG AAA GAT CGG CGC TCC ACC GGC AAG CCC TGG GGA AAG             234
CCA GGA TAT CCT TGG CCC CTG TAT GGA AAC GAG GGC TGC             273
GGC TGG GCA GGT TGG CTC CTG TCC CCC CGC GGG TCT CAT             312
CCT AAT TGG GGC CCC ACT GAC CCC CGG CAT AAA TCA CGC             351
AAT TTG GGT AAA GTC ATC GAC ACC ATT ACG TGT GGT TTT             390
GCC GAC CTC ATG GGG TAC ATC CCT GTC GTC GGC GCC CCG             429
GTC GGA GGC GTC GCC AGA GCT CTG GCA CAC GGT GTT AGA             468
GTC CTG GAA GAC GGG ATA AAT TAC GCA ACA GGG AAT CTG             507
CCT GGT TGC TCT TTT TCT ATC TTC TTA CTT GCT CTT CTG             546
TCA TGC TGC ACA GTG CCA GTG TCT GCG                             573
```

(2) INFORMATION FOR SEQ ID NO: 132:

(i) SEQUENCE CHARACTERISTICS:
    (A) LENGTH: 573 base pairs
    (B) TYPE: nucleic acid
    (C) STRANDEDNESS: single
    (D) TOPOLOGY: linear (vi) ORIGINAL SOURCE:
    (A) ORGANISM: homosapiens
    (C) INDIVIDUAL ISOLATE: SW3

(xi) SEQUENCE DESCRIPTION: SEQ ID NO: 132:

```
ATG AGC ACA AAT CCT AAA CCT CAA AGA AAA ACC AAA AGA              39
AAT ACA AAC CGC CGC CCA CAG GAC GTT AAG TTC CCG GGT              78
GGC GGC CAG ATC GTT GGC GGA GTT TAC TTG CTG CCG CGC             117
AGG GGC CCC AGG TTG GGT GTG CGC GCG ACA AGG AAG ACT             156
TCC GAG CGA TCC CAG CCG CGT GGG AGA CGC CAG CCC ATC             195
CCG AAA GAT CGG CGC TCC ACC GGC AAG TCC TGG GGA AAG             234
CCA GGA TAT CCT TGG CCC CTG TAT GGA AAC GAG GGC TGC             273
GGC TGG GCA GGT TGG CTC CTG TCC CCC CGC GGG TCT CAT             312
CCT AAT TGG GGC CCC ACT GAC CCC CGG CAT AGA TCA CGC             351
AAT TTG GGC AAA GTC ATC GAC ACC ATT ACG TGT GGT TTT             390
GCC GAC CTC ATG GGG TAC ATC CCT GTC GTT GGC GCC CCG             429
GTC GGA GGC GTC GCC AGA GCT CTG GCA CAC GGT GTT AGA             468
GTC CTG GAA GAC GGG ATA AAT TAC GCA ACA GGG AAT CTG             507
```

| | | | | | | | | | | |
|---|---|---|---|---|---|---|---|---|---|---|
| CCT | GGT | TGC | TCT | TTT | TCT | ATC | TTC | TTA | CTT | GCT | CTT | CTG | 546 |
| TCG | TGC | TTC | ACA | GTG | CCA | GTG | TCT | GCG | | | | | 573 |

( 2 ) INFORMATION FOR SEQ ID NO: 133:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK8

( x i ) SEQUENCE DESCRIPTION: SEQ ID NO: 133:

| | | | | | | | | | | | | | |
|---|---|---|---|---|---|---|---|---|---|---|---|---|---|
| ATG | AGC | ACA | AAT | CCT | AAA | CCT | CAA | AGA | AAA | ACC | AAA | AGA | 39 |
| AAC | ACA | AAC | CGC | CGC | CCA | CAG | GAC | GTT | AAG | TTC | CCG | GGT | 78 |
| GGC | GGC | CAG | ATC | GTT | GGC | GGA | GTT | TAC | TTG | CTG | CCG | CGC | 117 |
| AGG | GGC | CCC | AGG | TTG | GGT | GTG | CGC | GCG | ACA | AGG | AAG | TCT | 156 |
| TCC | GAG | CGA | TCC | CAG | CCG | CGT | GGG | AGG | CGC | CAG | CCC | ATC | 195 |
| CCG | AAA | GAT | CGG | CGC | TCC | ACC | GGC | AAG | TCC | TGG | GGA | AAA | 234 |
| CCG | GGA | TAT | CCT | TGG | CCC | CTG | TAT | GGA | AAC | GAG | GGC | TGC | 273 |
| GGC | TGG | GCA | GGT | TGG | CTC | CTG | TCC | CCC | CGC | GGG | TCT | CGT | 312 |
| CCT | ACT | TGG | GGC | CCC | ACT | GAC | CCC | CGG | CAT | AGA | TCA | CGC | 351 |
| AAT | TTG | GGC | AAA | GTC | ATC | GAC | ACC | ATT | ACG | TGT | GGT | TTT | 390 |
| GCC | GAC | CTC | ATG | GGG | TAC | ATC | CCT | GTC | GTT | GGC | GCC | CCG | 429 |
| GTT | GGA | GGC | GTC | GCC | AGA | GCT | CTG | GCA | CAC | GGT | GTT | AGG | 468 |
| GTC | CTG | GAA | GAC | GGG | ATA | AAT | TAC | GCA | ACA | GGG | AAT | TTG | 507 |
| CCT | GGT | TGC | TCT | TTT | TCT | ATC | TTC | TTG | CTT | GCT | CTT | CTG | 546 |
| TCG | TGC | TGC | ACA | GTG | CCA | GTG | TCT | GCG | | | | | 573 |

( 2 ) INFORMATION FOR SEQ ID NO: 134:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S83

( x i ) SEQUENCE DESCRIPTION: SEQ ID NO: 134:

| | | | | | | | | | | | | | |
|---|---|---|---|---|---|---|---|---|---|---|---|---|---|
| ATG | AGC | ACA | AAT | CCT | AAA | CCT | CAA | AGA | AAA | ACC | AAA | AGA | 39 |
| AAC | ACT | AAC | CGC | CGC | CCA | CAG | GAC | GTC | AAG | TTC | CCG | GGC | 78 |
| GGT | GGC | CAG | ATC | GTT | GGC | GGA | GTA | TAC | TTG | CTG | CCG | CGC | 117 |
| AGG | GGC | CCG | AGA | TTG | GGT | GTG | CGC | GCG | ACG | AGG | AAA | ACT | 156 |
| TCC | GAA | CGG | TCC | CAG | CCA | CGT | GGG | AGG | CGC | CAG | CCC | ATC | 195 |
| CCT | AAA | GAT | CGG | CGC | ACC | ACT | GGC | AAG | TCC | TGG | GGA | AGG | 234 |
| CCA | GGA | TAC | CCT | TGG | CCC | CTG | TAT | GGG | AAT | GAG | GGC | CTC | 273 |
| GGC | TGG | GCA | GGG | TGG | CTC | CTG | TCC | CCC | CGC | GGT | TCT | CGC | 312 |

| | | | | | | | | | | | | |
|---|---|---|---|---|---|---|---|---|---|---|---|---|
| CCT | TCA | TGG | GGC | CCC | ACC | GAC | CCC | CGG | CAT | AAA | TCG | CGC | 351 |
| AAC | TTG | GGT | AAG | GTC | ATC | GAT | ACC | CTA | ACG | TGC | GGT | TTT | 390 |
| GCC | GAC | CTC | ATG | GGG | TAC | ATA | CCC | GTC | GTT | GGC | GCT | CCC | 429 |
| GTT | GGC | GGC | GTT | GCC | AGA | GCC | CTC | GCC | CAT | GGG | GTG | AGG | 468 |
| GTT | CTG | GAG | GAC | GGG | ATA | AAT | TAT | GCA | ACG | GGG | AAT | TTG | 507 |
| CCC | GGT | TGC | TCT | TTC | TCT | ATC | TTT | CTC | TTG | GCC | CTC | TTG | 546 |
| TCT | TGC | ATC | TCT | GTG | CCA | GTT | TCC | GCC | | | | | 573 |

( 2 ) INFORMATION FOR SEQ ID NO: 135:

( i ) SEQUENCE CHARACTERISTICS:
    ( A ) LENGTH: 573 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: HK10

( x i ) SEQUENCE DESCRIPTION: SEQ ID NO: 135:

| | | | | | | | | | | | | |
|---|---|---|---|---|---|---|---|---|---|---|---|---|
| ATG | AGC | ACA | CTT | CCT | AAA | CCT | CAA | AGA | AAA | ACC | AAA | AGA | 39 |
| AAC | ACC | ATC | CGT | CGC | CCA | CAG | GAC | GTT | AAG | TTC | CCG | GGT | 78 |
| GGC | GGA | CAG | ATC | GTT | GGT | GGA | GTA | TAC | GTG | TTG | CCG | CGC | 117 |
| AGG | GGC | CCA | CGA | TTG | GGT | GTG | CGC | GCG | ACG | CGT | AAA | ACT | 156 |
| TCT | GAA | CGG | TCG | CAG | CCT | CGC | GGA | CGA | CGA | CAG | CCT | ATC | 195 |
| CCC | AAG | GCG | CGT | CGG | AGC | GAA | GGC | CGG | TCC | TGG | GCT | CAG | 234 |
| CCC | GGG | TAC | CCT | TGG | CCC | CTC | TAT | GGT | AAC | GAG | GGC | TGC | 273 |
| GGG | TGG | GCA | GGA | TGG | CTC | CTG | TCC | CCA | CGC | GGC | TCC | CGT | 312 |
| CCA | TCT | TGG | GGC | CCA | AAC | GAC | CCC | CGG | CGA | CGG | TCC | CGC | 351 |
| AAT | TTG | GGT | AAA | GTC | ATC | GAT | ACC | CTT | ACG | TGC | GGA | TTC | 390 |
| GCC | GAC | CTC | ATG | GGG | TAC | ATC | CCG | CTC | GTC | GGC | GCT | CCC | 429 |
| GTA | GGA | GGC | GTC | GCA | AGA | GCC | CTC | GCG | CAT | GGC | GTG | AGG | 468 |
| GCC | CTT | GAA | GAC | GGG | ATA | AAT | TTC | GCA | ACA | GGG | AAC | TTG | 507 |
| CCC | GGT | TGC | TCC | TTT | TCT | ATC | TTC | CTT | CTT | GCT | CTG | TTC | 546 |
| TCT | TGC | TTA | ATT | CAT | CCA | GCA | GCT | AGT | | | | | 573 |

( 2 ) INFORMATION FOR SEQ ID NO: 136:

( i ) SEQUENCE CHARACTERISTICS:
    ( A ) LENGTH: 573 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: S52

( x i ) SEQUENCE DESCRIPTION: SEQ ID NO: 136:

| | | | | | | | | | | | | |
|---|---|---|---|---|---|---|---|---|---|---|---|---|
| ATG | AGC | ACA | CTT | CCT | AAA | CCT | CAA | AGA | AAA | ACC | AAA | AGA | 39 |
| AAC | ACC | ATC | CGT | CGC | CCA | CAG | GAC | GTT | AAG | TTC | CCG | GGT | 78 |
| GGC | GGA | CAG | ATC | GTT | GGT | GGA | GTA | TAC | GTG | TTG | CCG | CGC | 117 |

| | | | | | | | | | | | | |
|---|---|---|---|---|---|---|---|---|---|---|---|---|
| AGG | GGC | CCA | CGA | TTG | GGT | GTG | CGC | GCG | ACG | CGT | AAA | ACT | 156 |
| TCT | GAA | CGG | TCA | CAG | CCT | CGC | GGA | CGA | CGA | CAG | CCT | ATC | 195 |
| CCC | AAG | GCG | CGT | CGG | AGC | GAA | GGC | CGG | TCC | TGG | GCT | CAG | 234 |
| CCC | GGG | TAC | CCT | TGG | CCC | CTC | TAT | GGT | AAT | GAG | GGC | TGC | 273 |
| GGG | TGG | GCA | GGG | TGG | CTC | CTG | TCC | CCA | CGC | GGC | TCC | CGT | 312 |
| CCA | TCT | TGG | GGC | CCA | AAC | GAC | CCC | CGG | CGG | AGG | TCC | CGC | 351 |
| AAT | TTG | GGT | AAA | GTC | ATC | GAT | ACC | CTT | ACG | TGC | GGA | TTC | 390 |
| GCC | GAC | CTC | ATG | GGG | TAC | ATC | CCG | CTC | GTC | GGC | GCT | CCC | 429 |
| GTA | GGA | GGC | GTC | GCA | AGA | GCC | CTC | GCG | CAT | GGC | GTG | AGG | 468 |
| GCC | CTT | GAA | GAC | GGG | ATA | AAT | TTT | GCA | ACA | GGG | AAC | TTG | 507 |
| CCC | GGT | TGC | TCC | TTT | TCT | ATC | TTC | CTT | CTT | GCT | CTG | TTC | 546 |
| TCC | TGC | TTA | GTT | CAT | CCT | GCA | GCT | AGT | | | | | 573 |

( 2 ) INFORMATION FOR SEQ ID NO: 137:

( i ) SEQUENCE CHARACTERISTICS:
( A ) LENGTH: 573 base pairs
( B ) TYPE: nucleic acid
( C ) STRANDEDNESS: single
( D ) TOPOLOGY: linear ( v i ) ORIGINAL SOURCE:
( A ) ORGANISM: homosapiens
( C ) INDIVIDUAL ISOLATE: S2

( x i ) SEQUENCE DESCRIPTION: SEQ ID NO: 137:

| | | | | | | | | | | | | |
|---|---|---|---|---|---|---|---|---|---|---|---|---|
| ATG | AGC | ACA | CTT | CCT | AAA | CCT | CAA | AGA | AAA | ACC | AAA | AGA | 39 |
| AAC | ACC | ATC | CGT | CGC | CCA | CAG | GAC | ATC | AAG | TTC | CCG | GGT | 78 |
| GGC | GGA | CAG | ATC | GTT | GGT | GGA | GTA | TAC | GTG | TTG | CCG | CGC | 117 |
| AGG | GGC | CCA | CGA | TTG | GGT | GTG | CGC | GCG | ACG | CGT | AAA | ACT | 156 |
| TCT | GAA | CGG | TCA | CAG | CCT | CGC | GGA | CGG | CGA | CAG | CCT | ATC | 195 |
| CCC | AAG | GCG | CGT | CGG | AGC | GAA | GGC | CGA | TCC | TGG | GCT | CAG | 234 |
| CCC | GGG | TAC | CCT | TGG | CCC | CTC | TAT | GGT | AAC | GAG | GGC | TGC | 273 |
| GGG | TGG | GCA | GGG | TGG | CTC | CTG | TCC | CCA | CGC | GGC | TCC | CGT | 312 |
| CCA | TCT | TGG | GGC | CCA | AAT | GAC | CCC | CGG | CGG | AGG | TCC | CGC | 351 |
| AAT | TTG | GGT | AAA | GTC | ATC | GAT | ACC | CTT | ACG | TGC | GGC | TTC | 390 |
| GCC | GAC | CTC | ATG | GGG | TAC | ATC | CCG | CTC | GTC | GGC | GCT | CCC | 429 |
| GTA | GGA | GGC | GTC | GCA | AGA | GCC | CTC | GCG | CAT | GGC | GTG | AGG | 468 |
| GCC | CTT | GAA | GAC | GGG | ATA | AAT | TTT | GCA | ACA | GGG | AAC | TTG | 507 |
| CCC | GGT | TGC | TCT | TTT | TCT | ATC | TTC | CTT | CTT | GCC | CTG | TTC | 546 |
| TCT | TGC | TTA | ATT | CAT | CCA | GCA | GCT | AGT | | | | | 573 |

( 2 ) INFORMATION FOR SEQ ID NO: 138:

( i ) SEQUENCE CHARACTERISTICS:
( A ) LENGTH: 573 base pairs
( B ) TYPE: nucleic acid
( C ) STRANDEDNESS: single
( D ) TOPOLOGY: linear ( v i ) ORIGINAL SOURCE:

(A) ORGANISM: homosapiens
(C) INDIVIDUAL ISOLATE: DK12

(xi) SEQUENCE DESCRIPTION: SEQ ID NO: 138:

| | | | | | | | | | | | | |
|---|---|---|---|---|---|---|---|---|---|---|---|---|
| ATG | AGC | ACA | CTT | CCT | AAA | CCT | CAA | AGA | AAA | ACC | AAA | AGA | 39 |
| AAC | ACC | ATC | CGT | CGC | CCA | CAG | GAC | GTC | AAG | TTC | CCG | GGT | 78 |
| GGC | GGA | CAG | ATC | GTT | GGT | GGA | GTA | TAC | GTG | TTG | CCG | CGC | 117 |
| AGG | GGC | CCA | CGA | TTG | GGT | GTG | CGC | GCG | ACG | CGT | AAA | ACT | 156 |
| TCT | GAA | CGG | TCA | CAG | CCT | CGC | GGA | CGG | CGA | CAG | CCT | ATC | 195 |
| CCC | AAG | GCG | CGT | CGG | AGC | GAA | GGC | CGG | TCC | TGG | GCT | CAG | 234 |
| CCT | GGG | TAC | CCT | TGG | CCC | CTC | TAT | GGT | AAC | GAG | GGC | TGC | 273 |
| GGG | TGG | GCA | GGG | TGG | CTC | CTG | TCC | CCA | CGC | GGC | TCC | CGT | 312 |
| CCA | TCT | TGG | GGC | CCA | AAC | GAC | CCC | CGG | CGG | AGG | TCC | CGC | 351 |
| AAT | TTG | GGT | AAG | GTC | ATC | GAT | ACC | CTC | ACG | TGC | GGA | TTC | 390 |
| GCC | GAC | CTC | ATG | GGG | TAC | ATC | CCG | CTC | GTC | GGC | GCT | CCT | 429 |
| GTA | GGG | GGC | GTC | GCA | AGA | GCC | CTC | GCG | CAT | GGC | GTG | AGG | 468 |
| GCC | CTT | GAA | GAC | GGG | ATA | AAT | TTC | GCA | ACA | GGG | AAC | TTG | 507 |
| CCC | GGT | TGC | TCC | TTT | TCT | ATC | TTC | CTT | CTT | GCT | CTG | TTC | 546 |
| TCT | TGC | CTA | ATT | CAT | CCA | GCA | GCT | AGT | | | | | 573 |

(2) INFORMATION FOR SEQ ID NO: 139:

(i) SEQUENCE CHARACTERISTICS:
 (A) LENGTH: 573 base pairs
 (B) TYPE: nucleic acid
 (C) STRANDEDNESS: single
 (D) TOPOLOGY: linear (vi) ORIGINAL SOURCE:
 (A) ORGANISM: homosapiens
 (C) INDIVIDUAL ISOLATE: Z4

(xi) SEQUENCE DESCRIPTION: SEQ ID NO: 139:

| | | | | | | | | | | | | |
|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCC | ATG | GAC | GTA | AAG | TTC | CCG | GGT | 78 |
| GGT | GGC | CAG | ATC | GTT | GGC | GGA | GTT | TAC | TTG | TTG | CCG | CGC | 117 |
| AGG | GGC | CCC | AGG | TTG | GGT | GTG | CGC | GCG | ACT | CGA | AAG | ACT | 156 |
| TCG | GAG | CGG | TCG | CAA | CCT | CGT | GGC | AGG | CGT | CAA | CCT | ATC | 195 |
| CCC | AAG | GCG | CGC | CAG | CCA | GAG | GGC | AGA | TCC | TGG | GCG | CAG | 234 |
| CCC | GGG | TAC | CCT | TGG | CCC | CTC | TAT | GGC | AAT | GAG | GGC | TGC | 273 |
| GGG | TGG | GCA | GGG | TGG | CTC | CTG | TCT | CCT | CGC | GGC | TCT | CGG | 312 |
| CCA | TCT | TGG | GGC | CCA | AAT | GAT | CCC | CGG | CGG | AGA | TCG | CGC | 351 |
| AAT | CTG | GGT | AAG | GTC | ATC | GAT | ACC | CTG | ACG | TGC | GGC | TTC | 390 |
| GCC | GAC | CTC | ATG | GGA | TAC | ATC | CCG | ATC | GTG | GGC | GCC | CCC | 429 |
| GTG | GGG | GGC | GTC | GCC | AGG | GCT | CTG | GCG | CAT | GGC | GTC | AGG | 468 |
| GCT | GTG | GAG | GAC | GGG | ATT | AAC | TAT | GCA | ACA | GGG | AAT | CTT | 507 |
| CCC | GGT | TGC | TCT | TTC | TCT | ATC | TTC | CTT | TTG | GCA | CTT | CTT | 546 |
| TCG | TGC | CTC | ACT | GTT | CCA | GCG | TCG | GCT | | | | | 573 |

( 2 ) INFORMATION FOR SEQ ID NO: 140:

( i ) SEQUENCE CHARACTERISTICS:
    ( A ) LENGTH: 573 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: Z8

( x i ) SEQUENCE DESCRIPTION: SEQ ID NO: 140:

```
ATG AGC ACG AAT CCT AAA CCT CAA AGA AAA ACC AAA CGT            39
AAC ACC AAC CGC CGC CCT ATG GAT GTA AAA TTC CCA GGC            78
GGC GGC CAG ATC GTT GGC GGA GTT TAC TTG TTG CCG CGC           117
AGG GGC CCC AGG TTG GGT GTG CGC GCG ACT CGG AAG ACT           156
TCG GAG CGG TCG CAA CCT CGT GGC AGG CGT CAG CCT ATC           195
CCC AAG GCA CGT CGG TCC GAG GGT AGG TCC TGG GCT CAG           234
CCC GGG TAC CCA TGG CCT CTT TAC GGT AAT GAA GGC TGT           273
GGG TGG GCA GGT TGG CTC CTG TCC CCC CGC GGC TCT CGA           312
CCG TCT TGG GGC CCA AAT GAT CCC CGG CGG AGG TCG CGC           351
AAT TTG GGT AAG GTC ATC GAT ACC CTC ACG TGC GGC TTC           390
GCC GAC CTC ATG GGA TAC ATC CCG CTC GTG GGC GCC CCA           429
GTA GGA GGC GTC GCC AGA GCC CTG GCG CAT GGC GTC AGG           468
GCT GTG GAG GAC GGG ATC AAC TAT GCA ACA GGG AAC CTT           507
CCT GGT TGC TCT TTC TCT ATC TTC CTC TTG GCA CTT CTC           546
TCG TGC CTA ACC GTC CCA GCG TCT GCT                           573
```

( 2 ) INFORMATION FOR SEQ ID NO: 141:

( i ) SEQUENCE CHARACTERISTICS:
    ( A ) LENGTH: 573 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: Z1

( x i ) SEQUENCE DESCRIPTION: SEQ ID NO: 141:

```
ATG AGC ACA AAT CCT AAA CCT CAA AGA AAA ACC AAA CGT            39
AAC ACC AAC CGT CGC CCC ATG GAT GTG AAA TTC CCG GGC            78
GGC GGC CAG ATC GTT GGC GGA GTT TAC TTG CTG CCG CGC           117
AGG GGC CCC CGG TTG GGT GTG CGC GCA GCT CGG AAG ACT           156
TCG GAG CGG TCA CAA CCT CGT GGC AGG CGT CAG CCT ATC           195
CCC AAG GCG CGC CGG TCC GAG GGC AGG TCC TGG GCT CAG           234
CCC GGG TAC CCT TGG CCC CTT TAC GGC AAT GAG GGC TGT           273
GGG TGG GCA GGG TGG CTC CTG TCC CCC CGC GGT TCC AGG           312
CCG TCT TGG GGC CCC AAT GAT CCC CGG CGT AGG TCC CGT           351
AAT CTG GGT AAA GTC ATC GAT ACC CTG ACG TGT GGC TTC           390
```

```
GCC GAC CTC ATG GGA TAC ATT CCG CTC GTA GGC GCC CCT                    429

GTG GGT GGC GTC GCC AGG GCC CTG GCG CAT GGC GTC AGG                    468

GCC GTG GAG GAC GGA ATT AAC TAC GCA ACA GGG AAC CTT                    507

CCT GGT TGC TCT TTC TCT ATC TTT CTT CTT GCA CTT CTC                    546

TCG TGC CTG ACA ACA CCA GCA TCT GCC                                    573
```

( 2 ) INFORMATION FOR SEQ ID NO: 142:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z5

( x i ) SEQUENCE DESCRIPTION: SEQ ID NO: 142:

```
ATG AGC ACG AAT CCT AAA CCT CAA AGA AAA ACC AAA CGT                     39

AAC ACC AAC CGC CGC CCC ATG GAT GTA AAA TTC CCG GGT                     78

GGT GGT CAG ATC GTT GGC GGA GTT TAC TTG TTG CCG CGC                    117

AGG GGC CCC AGG TTG GGT GTG CGC GCG ACT CGG AAG ACT                    156

TCG GAG CGG TCG CAA CCT CGC GGC AGG CGT CAG CCT ATC                    195

CCC CAG GCA CGT CGG TCC GAG GGC AGG TCC TGG GCT CAG                    234

CCC GGG TAC CCT TGG CCT CTT TAT GGC AAT GAG GGC TGT                    273

GGG TGG GCA GGG TGG CTC CTG TCC CCC CGC GGA TCT CGG                    312

CCA TCT TGG GGC CAA AAT GAT CCC CGG CGT AGG TCC CGC                    351

AAT CTG GGT AAG GTC ATC GAT ACC CTG ACG TGT GGC TTC                    390

GCC GAC CTC ATG GGA TAC ATT CCG CTC GTC GGC GCC CCA                    429

GTA GGT GGC GTC GCC AGG GCC TTG GCG CAT GGC GTC AGG                    468

GCC CTG GAG GAC GGA ATC AAC TAT GCA ACA GGG AAT CTT                    507

CCT GGT TGC TCC TTT TCT ATC TTC CTA CTT GCA CTT TTC                    546

TCG TGC TTG ACA ACA CCG GCA TCC GCT                                    573
```

( 2 ) INFORMATION FOR SEQ ID NO: 143:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z6

( x i ) SEQUENCE DESCRIPTION: SEQ ID NO: 143:

```
ATG AGC ACG AAT CCT AAA CCT CAA AGA AAA ACC AAA CGT                     39

AAC ACC AAC CGC CGC CCC ATG GAC GTT AAG TTC CCG GGT                     78

GGT GGC CAG ATC GTT GGC GGA GTT TAC TTG TTG CCG CGC                    117

AGG GGC CCC AGG TTG GGT GTG CGC GCG ACT AGG AAG ACT                    156

TCG GAG CGG TCG CAA CCT CGT GGG AGA CGC CAG CCT ATC                    195
```

| | | | | | | | | | | | | |
|---|---|---|---|---|---|---|---|---|---|---|---|---|
| CCC | AAG | GCA | CGT | CGA | TCT | GAG | GGA | AGG | TCC | TGG | GCT | CAG | 234 |
| CCC | GGG | TAT | CCA | TGG | CCT | CTT | TAC | GGT | AAT | GAG | GGT | TGC | 273 |
| GGG | TGG | GCG | GGA | TGG | CTC | CTG | TCA | CCC | CGT | GGC | TCT | CGA | 312 |
| CCG | TCT | TGG | GGT | CCA | AAT | GAT | CCC | CGG | CGA | AGG | TCC | CGC | 351 |
| AAC | TTG | GGT | AAG | GTC | ATC | GAT | ACT | CTA | ACT | TGC | GGT | TTC | 390 |
| GCC | GAT | CTC | ATG | GGA | TAC | ATC | CCG | CTC | GTA | GGC | GCC | CCC | 429 |
| GTG | GGC | GGC | GTC | GCC | AGG | GCC | CTG | GCA | CAT | GGT | GTT | AGG | 468 |
| GCT | GTG | GAG | GAC | GGG | ATC | AAT | TAT | GCA | ACA | GGG | AAT | CTT | 507 |
| CCC | GGT | TGC | TCT | TTC | TCT | ATC | TTC | CTC | TTG | GCA | CTT | CTT | 546 |
| TCG | TGC | CTA | ACT | GTT | CCC | ACC | TCG | GCC | | | | | 573 |

( 2 ) INFORMATION FOR SEQ ID NO: 144:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z7

( x i ) SEQUENCE DESCRIPTION: SEQ ID NO: 144:

| | | | | | | | | | | | | |
|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCC | ATG | GAC | GTT | AAG | TTC | CCG | GGC | 78 |
| GGT | GGC | CAG | ATC | GTT | GGC | GGA | GTT | TAC | TTG | TTG | CCG | CGC | 117 |
| AGG | GGC | CCC | AGA | TTG | GGT | GTG | CGC | ACA | ACT | AGG | AAG | ACT | 156 |
| TCG | GAG | CGG | TCG | CAA | CCT | CGT | GGG | AGA | CGT | CAG | CCT | ATC | 195 |
| CCC | AAG | GCA | CGT | CGA | TCT | GAG | GGA | AGG | TCC | TGG | GCT | CAA | 234 |
| CCC | GGG | TAC | CCA | TGG | CCT | CTT | TAC | GGT | AAC | GAG | GGT | TGC | 273 |
| GGG | TGG | GCA | GGA | TGG | CTC | TTG | TCA | CCC | CGT | GGC | TCT | CGA | 312 |
| CCG | TCT | TGG | GGC | CCA | AAT | GAT | CCC | CGG | CGA | AGG | TCC | CGC | 351 |
| AAC | TTG | GGT | AAG | GTC | ATC | GAT | ACC | CTA | ACC | TGC | GGC | TTT | 390 |
| GCC | GAC | CTC | ATG | GGA | TAC | ATC | CCG | CTC | GTA | GGC | GCC | CCC | 429 |
| GTG | GGC | GGC | GTC | GCC | AGG | GCC | CTA | GCG | CAT | GGC | GTT | AGG | 468 |
| GCT | CTG | GAG | GAC | GGG | ATT | AAT | TAT | GCA | ACA | GGG | AAC | CTT | 507 |
| CCC | GGT | TGC | TCT | TTT | TCT | ATC | TTC | CTC | TTG | GCA | CTT | CTT | 546 |
| TCG | TGC | CTG | ACT | GTT | CCC | GCC | TCG | GCC | | | | | 573 |

( 2 ) INFORMATION FOR SEQ ID NO: 145:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK13

( x i ) SEQUENCE DESCRIPTION: SEQ ID NO: 145:

-continued

| | | | | | | | | | | | | | |
|---|---|---|---|---|---|---|---|---|---|---|---|---|---|
| ATG | AGC | ACG | AAT | CCT | AAA | CCT | CAA | AGA | AAA | ACC | AAA | CGT | 39 |
| AAC | ACC | AAC | CGC | CGC | CCA | ATG | GAC | GTT | AAG | TTC | CCG | GGT | 78 |
| GGC | GGC | CAG | ATC | GTT | GGC | GGA | GTT | TAC | TTG | TTG | CCG | CGC | 117 |
| AGG | GGC | CCT | AGA | TTG | GGT | GTG | CGC | GCG | ACT | AGG | AAG | ACT | 156 |
| TCG | GAG | CGG | TCG | CAA | CCT | CGT | GGG | AGG | CGC | CAG | CCT | ATC | 195 |
| CCC | AAG | GCG | CGC | CAA | CTC | GAG | GGT | AGG | TCC | TGG | GCT | CAG | 234 |
| CCT | GGG | TAT | CCT | TGG | CCC | CTT | TAC | GGC | AAT | GAG | GGC | TGC | 273 |
| GGG | TGG | GCG | GGA | TGG | CTC | CTG | TCA | CCC | CGT | GGC | TCT | CGG | 312 |
| CCG | TCT | TGG | GGC | CCG | AAT | GAT | CCC | CGG | CGG | AGG | TCC | CGC | 351 |
| AAC | TTG | GGT | AAG | GTC | ATC | GAT | ACC | CTA | ACT | TGC | GGC | TTC | 390 |
| GCC | GAC | CTC | ATG | GGA | TAC | ATC | CCG | GTC | GTA | GGC | GCC | CCC | 429 |
| GTG | GGT | GGC | GTC | GCC | AGA | GCC | CTG | GCG | CAT | GGC | GTC | AGG | 468 |
| CTT | CTG | GAG | GAC | GGG | GTC | AAT | TAT | GCA | ACA | GGG | AAT | CTT | 507 |
| CCC | GGT | TGC | TCT | TTC | TCT | ATC | TTC | CTC | TTG | GCA | CTG | CTC | 546 |
| TCG | TGC | CTG | ACT | GTT | CCC | GCT | TCG | GCC | | | | | 573 |

( 2 ) INFORMATION FOR SEQ ID NO: 146:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA4

( x i ) SEQUENCE DESCRIPTION: SEQ ID NO: 146:

| | | | | | | | | | | | | | |
|---|---|---|---|---|---|---|---|---|---|---|---|---|---|
| ATG | AGC | ACG | AAT | CCT | AAA | CCT | CAA | AGA | AAA | ACC | AAA | AGA | 39 |
| AAC | ACC | AAC | CGC | CGC | CCA | CAG | GAC | GTT | AAG | TTC | CCG | GGC | 78 |
| GGT | GGT | CAG | ATC | GTT | GGT | GGA | GTC | TAC | TTG | TTG | CCG | CGC | 117 |
| AGG | GGC | CCT | AGG | TTG | GGT | GTG | CGC | GCG | ACT | CGG | AAG | ACT | 156 |
| TCA | GAA | CGG | TCG | CAA | CCC | CGT | GGG | CGG | CGC | CAG | CCT | ATT | 195 |
| CCC | AAG | GCG | CGC | CAA | CCC | ACG | GGC | CGG | TCC | TGG | GGT | CAA | 234 |
| CCC | GGG | TAC | CCT | TGG | CCC | CTT | TAC | GCC | AAT | GAG | GGC | CTC | 273 |
| GGG | TGG | GCA | GGG | TGG | TTG | CTC | TCC | CCC | CGA | GGC | TCT | CGG | 312 |
| CCT | AAT | TGG | GGC | CCC | AAT | GAC | CCC | CGG | CGA | AAG | TCG | CGC | 351 |
| AAT | TTG | GGT | AAG | GTC | ATC | GAT | ACC | CTA | ACG | TGC | GGA | TTC | 390 |
| CCC | GAC | CTC | ATG | GGG | TAC | ATC | CCG | CTC | GTA | GGC | GGC | CCC | 429 |
| GTT | GGG | GGC | GTC | GCA | AGG | GCC | CTT | GCA | CAT | GGT | GTG | AGG | 468 |
| GTT | CTT | GAG | GAC | GGG | GTA | AAC | TAT | GCA | ACG | GGG | AAT | TTG | 507 |
| CCC | GGT | TGC | TCT | TTC | TCT | ATC | TTT | ATC | CTT | GCA | CTT | CTC | 546 |
| TCG | TGC | CTG | ACC | GTC | CCG | GCC | TCT | GCA | | | | | 573 |

( 2 ) INFORMATION FOR SEQ ID NO: 147:

( i ) SEQUENCE CHARACTERISTICS:
        ( A ) LENGTH: 573 base pairs

-continued (B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA5

(xi) SEQUENCE DESCRIPTION: SEQ ID NO: 147:

| ATG | AGC | ACG | AAT | CCT | AAA | CCT | CAA | AGA | AAA | ACC | AAA | AGA | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | TTG | TTG | CCG | CGC | 117 |
| AGG | GGC | CCT | AGA | TTG | GGT | GTG | CGC | GCG | ACT | CGG | AAG | ACT | 156 |
| TCA | GAA | CGG | TCG | CAA | CCC | CGT | GGG | CGG | CGC | CAG | CCT | ATT | 195 |
| CCC | AAG | GCG | CGC | CAA | CCC | ACG | GGC | CGG | TCC | TGG | GGT | CAA | 234 |
| CCC | GGG | TAC | CCT | TGG | CCC | CTT | TAC | GCC | AAT | GAG | GGC | CTC | 273 |
| GGG | TGG | GCA | GGG | TGG | TTG | CTC | TCC | CCC | CGA | GGC | TCT | CGG | 312 |
| CCT | AAT | TGG | GGC | CCC | AAT | GAC | CCC | CGG | CGA | AAA | TCG | CGC | 351 |
| AAT | TTG | GGT | AAG | GTC | ATC | GAT | ACC | CTA | ACG | TGC | GGA | TTC | 390 |
| GCC | GAC | CTC | ATG | GGG | TAC | ATC | CCG | CTC | GTA | GGC | GGC | CCC | 429 |
| GTT | GGG | GGC | GTC | GCA | AGG | GCC | CTC | GCA | CAT | GGT | GTG | AGG | 468 |
| GTT | CTT | GAG | GAC | GGG | GTA | AAC | TAT | GCA | ACA | GGG | AAT | TTG | 507 |
| CCC | GGT | TGC | TCT | TTC | TCT | ATC | TTT | ATC | CTT | GCA | CTT | CTC | 546 |
| TCG | TGC | TTG | ACC | GTC | CCA | GCC | TCT | GCA | | | | | 573 |

(2) INFORMATION FOR SEQ ID NO: 148:

(i) SEQUENCE CHARACTERISTICS:
(A) LENGTH: 573 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA7

(xi) SEQUENCE DESCRIPTION: SEQ ID NO: 148:

| ATG | AGC | ACG | AAT | CCT | AAA | CCT | CAA | AGA | AAA | ACC | AAA | AGA | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | TTG | TTG | CCG | CGC | 117 |
| AGG | GGC | CCT | AGG | TTG | GGT | GTG | CGC | GCG | ACT | CGG | AAG | ACT | 156 |
| TCA | GAA | CGG | TCG | CAA | CCC | CGT | GGG | CGG | CGC | CAG | CCT | ATT | 195 |
| CCC | AAG | GCG | CGC | CAA | CCC | ACG | GGC | CGG | TCC | TGG | GGT | CAA | 234 |
| CCC | GGG | TAC | CCT | TGG | CCC | CTT | TAC | GCC | AAT | GAG | GGC | CTC | 273 |
| GGG | TGG | GCA | GGG | TGG | TTG | CTC | TCC | CCC | CGA | GGC | TCT | CGG | 312 |
| CCT | AAT | TGG | GGC | CCC | AAT | GAC | CCC | CGG | CGA | AAG | TCG | CGC | 351 |
| AAT | TTG | GGT | AAG | GTC | ATC | GAC | ACC | CTA | ACA | TGC | GGA | TTC | 390 |
| GCC | GAC | CTC | ATG | GGG | TAC | ATC | CCG | CTC | GTA | GGC | GGC | CCC | 429 |
| GTT | GGG | GGC | GTC | GCA | AGG | GCT | CTC | GCA | CAC | GGT | GTG | AGG | 468 |
| GTT | CTT | GAG | GAC | GGG | GTA | AAT | TAC | GCA | ACA | GGG | AAT | CTG | 507 |

```
CCC  GGT  TGC  TCT  TTC  TCT  ATC  TTT  ATC  CTT  GCA  CTT  CTC                      546
TCG  TGC  CTG  ACC  GTC  CCA  GCC  TCC  GCA                                          573
```

( 2 ) INFORMATION FOR SEQ ID NO: 149:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA1

( x i ) SEQUENCE DESCRIPTION: SEQ ID NO: 149:

```
ATG  AGC  ACG  AAT  CCT  AAA  CCT  CAA  AGA  AAA  ACC  AAA  AGA                      39
AAC  ACC  AAC  CTC  CGC  CCA  CAG  GAC  GTC  AAG  TTC  CCG  GGC                      78
GGT  GGT  CAG  ATC  GTT  GGT  GGA  GTT  TAC  TTG  TTG  CCG  CGC                      117
AGG  GGC  CCC  AGG  TTG  GGT  GTG  CGC  GCG  ACT  CGG  AAG  ACT                      156
TCG  GAA  CGG  TCG  CAA  CCC  CGT  GGG  CGG  CGC  CAG  CCT  ATT                      195
CCC  AAG  GCG  CGC  CAA  CCC  ACG  GGC  CGG  TCC  TGG  GGT  CAA                      234
CCC  GGG  TAC  CCT  TGG  CCC  CTT  TAC  GCC  AAT  GAG  GGC  CTC                      273
GGG  TGG  GCA  GGG  TGG  TTG  CTC  TCC  CCC  CGA  GGC  TCT  CGG                      312
CCT  AAT  TGG  GGC  CCC  AAT  GAC  CCC  CGG  CGG  AAG  TCG  CGC                      351
AAT  TTG  GGT  AAG  GTC  ATC  GAT  ACC  CTA  ACG  TGC  GGA  TTC                      390
GCC  GAC  CTC  ATG  GGG  TAC  ATC  CCG  CTC  GTA  GGC  GGC  CCC                      429
GTT  GGG  GGC  GTC  GCA  AGG  GCT  CTC  GCA  CAC  GGT  GTG  AGG                      468
GTT  CTT  GAG  GAC  GGG  GTA  AAC  TAC  GCA  ACA  GGG  AAT  TTG                      507
CCC  GGT  TGC  TCT  TTC  TCT  ATC  TTT  ATC  CTT  GCA  CTT  CTT                      546
TCC  TGT  CTG  ATC  ATC  CCG  GCC  TCT  GCA                                          573
```

( 2 ) INFORMATION FOR SEQ ID NO: 150:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA3

( x i ) SEQUENCE DESCRIPTION: SEQ ID NO: 150:

```
ATG  AGC  ACG  AAT  CCT  AAA  CCT  CAA  AGA  AAA  ACC  AAA  AGA                      39
AAC  ACC  AAC  CGC  CGC  CCA  CAG  GAC  GTC  AAG  TTC  CCG  GGC                      78
GGT  GGT  CAG  ATC  GTT  GGT  GGA  GTT  TAC  TTG  TTG  CCG  CGC                      117
AGG  GGC  CCC  AGG  TTG  GGT  GTG  CGC  GCG  ACT  CGG  AAG  ACT                      156
TCA  GAA  CGG  TCG  CAA  CCC  CGT  GGA  CGG  CGC  CAG  CCT  ATT                      195
CCC  AAG  GCT  CGC  CAG  CCC  ACG  GGC  CGG  TCC  TGG  GGT  CAA                      234
CCC  GGG  TAC  CCT  TGG  CCC  CTT  TAC  GCC  AAT  GAG  GGC  CTC                      273
GAG  TGG  GCA  GGG  TGG  TTG  CTC  TCC  CCC  CGA  GGC  TCT  CGG                      312
```

| | | | | | | | | | | | | |
|---|---|---|---|---|---|---|---|---|---|---|---|---|
|CCT|AGT|TGG|GGC|CCC|AAC|GAC|CCC|CGG|CGG|AAA|TCG|CGC| 351
|AAT|TTG|GGT|AAG|GTC|ATC|GAT|ACC|CTA|ACG|TGC|GGA|TTC| 390
|GCC|GAT|CTC|ATG|GGG|TAC|ATC|CCG|CTC|GTA|GGC|GGC|CCC| 429
|GTT|GGG|GGC|GTC|GCA|AGG|GCT|CTC|GCA|CAT|GGT|GTG|AGG| 468
|GTT|CTT|GAG|GAC|GGG|GTA|AAC|TAC|GCA|ACA|GGG|AAT|TTA| 507
|CCC|GGT|TGC|TCT|TTC|TCT|ATC|TTT|ATC|CTT|GCA|CTT|CTT| 546
|TCA|TGC|CTG|ACC|GTC|CCG|GCC|TCT|GCA| | | | | 573

( 2 ) INFORMATION FOR SEQ ID NO: 151:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA13

( x i ) SEQUENCE DESCRIPTION: SEQ ID NO: 151:

| | | | | | | | | | | | | |
|---|---|---|---|---|---|---|---|---|---|---|---|---|
|ATG|AGC|ACG|AAT|CCT|AAA|CCT|CAA|AGA|AAA|ACC|AAA|AGA| 39
|AAC|ACC|AAC|CGC|CGC|CCA|CAG|GAC|GTC|AAG|TTC|CCG|GGC| 78
|GGT|GGT|CAG|ATC|GTT|GGT|GGA|GTT|TAC|TTG|TTG|CCG|CGC| 117
|AGG|GGC|CCT|AGG|TTG|GGT|GTG|CGC|GCA|ACT|CGG|AAG|ACT| 156
|TCA|GAA|CGG|TCG|CAA|CCC|CGT|GGA|CGG|CGT|CAG|CCT|ATC| 195
|CCC|AAG|GCG|CGC|CAG|CCC|ACG|GGC|CGG|TCC|TGG|GGT|CAA| 234
|CCC|GGG|TAC|CCT|TGG|CCC|CTT|TAT|GCC|AAT|GAG|GGC|CTC| 273
|GGG|TGG|GCA|GGG|TGG|TTG|CTC|TCC|CCC|CGA|GGC|TCT|CGG| 312
|CCT|AAT|TGG|GGC|CCC|AAT|GAC|CCC|CGG|CGG|AAA|TCG|CGC| 351
|AAC|TTG|GGT|AAG|GTC|ATC|GAT|ACC|CTG|ACG|TGC|GGA|TTC| 390
|GCC|GAC|CTC|ATG|GGG|TAC|ATC|CCG|CTC|GTA|GGC|GGC|CCC| 429
|GTT|GGG|GGC|GTC|GCA|AGG|GCT|CTC|GCA|CAC|GGT|GTG|AGG| 468
|GTC|CTT|GAG|GAC|GGG|GTA|AAC|TAT|GCA|ACA|GGG|AAT|TTA| 507
|CCC|GGT|TGC|TCT|TTC|TCT|ATC|TTT|ATC|CTT|GCA|CTT|CTT| 546
|TCA|TGC|CTG|ACT|GTC|CCG|ACC|TCT|GCC| | | | | 573

( 2 ) INFORMATION FOR SEQ ID NO: 152:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA6

( x i ) SEQUENCE DESCRIPTION: SEQ ID NO: 152:

| | | | | | | | | | | | | |
|---|---|---|---|---|---|---|---|---|---|---|---|---|
|ATG|AGC|ACG|AAT|CCT|AAA|CCT|CAA|AGA|AAA|ACC|CAA|AGA| 39
|AAC|ACC|AAC|CGC|CGC|CCA|CAG|GAC|GTC|AAG|TTC|CCG|GGC| 78
|GGT|GGT|CAG|ATC|GTT|GGT|GGA|GTT|TAC|TTG|TTG|CCG|CGC| 117

| | | | | | | | | | | | | | |
|---|---|---|---|---|---|---|---|---|---|---|---|---|---|
| AGG | GGC | CCT | CGT | ATG | GGT | GTG | CGC | GCG | ACT | CGG | AAG | ACT | 156 |
| TCG | GAA | CGG | TCG | CAA | CCC | CGT | GGA | CGG | CGT | CAG | CCT | ATT | 195 |
| CCC | AAG | GCG | CGC | CAA | TCC | GCG | GGT | CGG | TCC | TGG | GGT | CAA | 234 |
| CCC | GGG | TAC | CCT | TGG | CCC | CTT | TAC | GCC | AAT | GAG | GGC | CTC | 273 |
| GGG | TGG | GCA | GGG | TGG | TTG | CTC | TCC | CCC | CGA | GGC | TCT | CGG | 312 |
| CCT | AAT | TGG | GGC | CCC | AAT | GAC | CCC | CGG | CGA | AAA | TCG | CGC | 351 |
| AAT | TTG | GGT | AAG | GTC | ATC | GAT | ACC | CTA | ACG | TGC | GGA | TTC | 390 |
| GCC | GAC | CTC | ATG | GGG | TAC | ATC | CCG | CTC | GTA | GGC | GGC | CCC | 429 |
| GTT | GGG | GGC | GTC | GCA | AGG | GCT | CTC | GCA | CAC | GGT | GTG | AGG | 468 |
| GTT | CTT | GAG | GAC | GGG | GTA | AAC | TAT | GCA | ACA | GGG | AAT | TTG | 507 |
| CCC | GGT | TGC | TCT | TTC | TCT | ATC | TTT | GTC | CTT | GCA | CTT | CTC | 546 |
| TCG | TGC | CTA | ACC | GTC | CCT | GCC | TCT | GCA | | | | | 573 |

( 2 ) INFORMATION FOR SEQ ID NO: 153:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA11

( x i ) SEQUENCE DESCRIPTION: SEQ ID NO: 153:

| | | | | | | | | | | | | | |
|---|---|---|---|---|---|---|---|---|---|---|---|---|---|
| ATG | AGC | ACG | AAT | CCT | AAA | CCT | CAA | AGA | AAA | ACC | AAA | AGA | 39 |
| AAC | ACC | AAC | CGC | CGC | CCA | CAG | GAC | GTC | AAG | TTC | CCG | GGC | 78 |
| GGT | GGT | CAG | ATC | GTT | GGT | GGA | GTT | TAC | TTG | TTG | CCG | CGC | 117 |
| AGG | GGC | CCT | AGG | TTG | GGT | GTG | CGC | GCG | ACT | CGG | AAG | ACT | 156 |
| TCA | GAA | CGG | TCG | CAA | CCC | CGT | GGG | CGG | CGT | CAG | CCT | ATT | 195 |
| CCC | AAG | GCG | CGC | CAA | CCC | ACG | GGC | CGG | TCC | TGG | GGT | CAA | 234 |
| CCC | GGG | TAC | CCT | TGG | CCC | TTT | TAC | GCC | AAT | GAG | GGC | CTC | 273 |
| GGG | TGG | GCA | GGG | TGG | CTG | CTC | TCC | CCT | CGA | GGC | TCT | CGG | 312 |
| CCT | AAC | TGG | GGC | CCC | AAT | GAC | CCC | CGG | CGA | AGA | TCG | CGC | 351 |
| AAT | TTG | GGC | AAG | GTC | ATC | GAT | ACC | CTA | ACG | TGC | GGA | TTC | 390 |
| GCC | GAC | CTC | ATG | GGG | TAC | ATC | CCG | CTC | GTA | GGC | GGC | CCC | 429 |
| GTT | GGG | GGC | GTC | GCA | AGG | GCC | CTC | GCA | CAC | GGT | GTG | AGA | 468 |
| GCT | CTT | GAG | GAC | GGG | GTA | AAT | TAT | GCA | ACA | GGG | AAT | CTT | 507 |
| CCC | GGT | TGC | TCT | TTC | TCC | ATC | TTT | ATC | CTT | GCA | CTT | CTC | 546 |
| TCG | TGC | TTG | ACC | GTC | CCG | GCC | ACT | GCA | | | | | 573 |

( 2 ) INFORMATION FOR SEQ ID NO: 154:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( v i ) ORIGINAL SOURCE:

(A) ORGANISM: homosapiens
(C) INDIVIDUAL ISOLATE: HK2

(xi) SEQUENCE DESCRIPTION: SEQ ID NO: 154:

| | | | | | | | | | | | | |
|---|---|---|---|---|---|---|---|---|---|---|---|---|
| ATG | AGC | ACA | CTT | CCA | AAA | CCC | CAA | AGA | AAA | ACC | AAA | AGA | 39 |
| AAC | ACC | AAC | CGT | CGC | CCA | ACG | GAC | GTC | AAG | TTC | CCG | GGT | 78 |
| GGC | GGT | CAG | ATC | GTT | GGC | GGA | GTT | TAC | TTG | TTG | CCG | CGC | 117 |
| AGG | GGC | CCC | CGG | TTG | GGT | GTG | CGC | GCG | ACG | AGA | AAG | ACT | 156 |
| TCC | GAG | CGA | TCC | CAG | CCC | AGA | GGC | AGG | CGC | CAA | CCT | ATA | 195 |
| CCA | AAG | GCG | CGC | CAG | CCC | CAG | GGC | AGG | CAC | TGG | GCT | CAG | 234 |
| CCC | GGA | TAC | CCT | TGG | CCT | CTT | TAT | GGA | AAC | GAG | GGC | TGT | 273 |
| GGG | TGG | GCA | GGT | TGG | CTC | CTG | TCC | CCC | CGC | GGC | TCC | CGG | 312 |
| CCA | CAT | TGG | GGC | CCC | AAT | GAC | CCC | CGG | CGT | CGA | TCC | CGG | 351 |
| AAT | TTG | GGT | AAG | GTC | ATC | GAT | ACC | CTA | ACG | TGT | GGG | TTC | 390 |
| GCC | GAT | CTC | ATG | GGG | TAC | ATT | CCC | GTC | GTG | GGC | GCG | CCT | 429 |
| TTG | GGC | GGC | GTC | GCG | GCT | GCG | CTC | GCA | CAT | GGC | GTG | AGG | 468 |
| GCA | ATC | GAG | GAC | GGG | ATC | AAT | TAT | GCA | ACA | GGG | AAT | CTC | 507 |
| CCC | GGT | TGC | TCT | TTC | TCT | ATC | TTC | CTT | TTG | GCA | CTA | CTC | 546 |
| TCG | TGC | CTC | ACA | ACG | CCA | GCT | TCG | GCT | | | | | 573 |

(2) INFORMATION FOR SEQ ID NO: 155:

(i) SEQUENCE CHARACTERISTICS:
(A) LENGTH: 191 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK7

(xi) SEQUENCE DESCRIPTION: SEQ ID NO: 155:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |

| Thr | Asn | Arg | Arg | Pro | Gln | Asp | Val | Lys | Phe | Pro | Gly | Gly | Gly |
|---|---|---|---|---|---|---|---|---|---|---|---|---|---|
| 15 | | | | | 20 | | | | | 25 | | | |

| Gln | Ile | Val | Gly | Gly | Val | Tyr | Leu | Leu | Pro | Arg | Arg | Gly | Pro |
|---|---|---|---|---|---|---|---|---|---|---|---|---|---|
| | | 30 | | | | | 35 | | | | | 40 | |

| Arg | Leu | Gly | Val | Arg | Ala | Pro | Arg | Lys | Thr | Ser | Glu | Arg | Ser |
|---|---|---|---|---|---|---|---|---|---|---|---|---|---|
| | | | 45 | | | | | 50 | | | | | 55 |

| Gln | Pro | Arg | Gly | Arg | Arg | Gln | Pro | Ile | Pro | Lys | Ala | Arg | Arg |
|---|---|---|---|---|---|---|---|---|---|---|---|---|---|
| | | | | 60 | | | | | 65 | | | | 70 |

| Pro | Glu | Gly | Arg | Thr | Trp | Ala | Gln | Pro | Gly | Tyr | Pro | Trp | Pro |
|---|---|---|---|---|---|---|---|---|---|---|---|---|---|
| | | | | | 75 | | | | | 80 | | | |

| Leu | Tyr | Gly | Asn | Glu | Gly | Cys | Gly | Trp | Ala | Gly | Trp | Leu | Leu |
|---|---|---|---|---|---|---|---|---|---|---|---|---|---|
| 85 | | | | | 90 | | | | | 95 | | | |

| Ser | Pro | Arg | Gly | Ser | Arg | Pro | Ser | Trp | Gly | Pro | Thr | Asp | Pro |
|---|---|---|---|---|---|---|---|---|---|---|---|---|---|
| | | 100 | | | | | 105 | | | | | 110 | |

| Arg | Arg | Arg | Ser | Arg | Asn | Leu | Gly | Lys | Val | Ile | Asp | Thr | Leu |
|---|---|---|---|---|---|---|---|---|---|---|---|---|---|
| | | | | 115 | | | | 120 | | | | | 125 |

| Thr | Cys | Gly | Phe | Ala | Asp | Leu | Met | Gly | Tyr | Ile | Pro | Leu | Val |
|---|---|---|---|---|---|---|---|---|---|---|---|---|---|
| | | | | 130 | | | | | 135 | | | | 140 |

Gly Ala Pro Leu Gly Gly Ala Ala Arg Ala Leu Ala His Gly
                145                 150

Val Arg Val Leu Glu Asp Gly Val Asn Tyr Ala Thr Gly Asn
155                 160                 165

Leu Pro Gly Cys Ser Phe Ser Ile Phe Leu Leu Ala Leu Leu
    170                 175                 180

Ser Cys Leu Thr Val Pro Ala Ser Ala
        185                 190

( 2 ) INFORMATION FOR SEQ ID NO: 156:

( i ) SEQUENCE CHARACTERISTICS:
        ( A ) LENGTH: 191 amino acids
        ( B ) TYPE: amino acid
        ( C ) STRANDEDNESS: single
        ( D ) TOPOLOGY: unknown ( v i ) ORIGINAL SOURCE:
        ( A ) ORGANISM: homosapiens
        ( C ) INDIVIDUAL ISOLATE: US11

( x i ) SEQUENCE DESCRIPTION: SEQ ID NO: 156:

Met Ser Thr Asn Pro Lys Pro Gln Arg Lys Thr Lys Arg Asn
1               5                   10

Thr Asn Arg Arg Pro Gln Asp Val Lys Phe Pro Gly Gly Gly
15                  20                  25

Gln Ile Val Gly Gly Val Tyr Leu Leu Pro Arg Arg Gly Pro
    30                  35                  40

Arg Leu Gly Val Arg Ala Thr Arg Lys Thr Ser Glu Arg Ser
        45                  50                  55

Gln Pro Arg Gly Arg Arg Gln Pro Ile Pro Lys Ala Arg Arg
            60                  65                  70

Pro Glu Gly Arg Thr Trp Ala Gln Pro Gly Tyr Pro Trp Pro
                75                  80

Leu Tyr Gly Asn Glu Gly Cys Gly Trp Ala Gly Trp Leu Leu
85                  90                  95

Ser Pro Arg Gly Ser Arg Pro Ser Trp Gly Pro Thr Asp Pro
    100                 105                 110

Arg Arg Arg Ser Arg Asn Leu Gly Lys Val Ile Asp Thr Leu
        115                 120                 125

Thr Cys Gly Phe Ala Asp Leu Met Gly Tyr Ile Pro Leu Val
            130                 135                 140

Gly Ala Pro Leu Gly Gly Ala Ala Arg Ala Leu Ala His Gly
                145                 150

Val Arg Val Leu Glu Asp Gly Val Asn Tyr Ala Thr Gly Asn
155                 160                 165

Leu Pro Gly Cys Ser Phe Ser Ile Phe Leu Leu Ala Leu Leu
    170                 175                 180

Ser Cys Leu Thr Val Pro Ala Ser Ala
        185                 190

( 2 ) INFORMATION FOR SEQ ID NO: 157:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:

(A) ORGANISM: homosapiens
(C) INDIVIDUAL ISOLATE: S14

(xi) SEQUENCE DESCRIPTION: SEQ ID NO: 157:

| Met | Ser | Thr | Asn | Pro | Lys | Pro | Gln | Arg | Lys | Thr | Lys | Arg | Asn |
|-----|-----|-----|-----|-----|-----|-----|-----|-----|-----|-----|-----|-----|-----|
| 1   |     |     |     | 5   |     |     |     |     | 10  |     |     |     |     |
| Thr | Asn | Arg | Arg | Pro | Gln | Asp | Val | Lys | Phe | Pro | Gly | Gly | Gly |
| 15  |     |     |     | 20  |     |     |     |     | 25  |     |     |     |     |
| Gln | Ile | Val | Gly | Gly | Val | Tyr | Leu | Leu | Pro | Arg | Arg | Gly | Pro |
|     | 30  |     |     |     | 35  |     |     |     |     | 40  |     |     |     |
| Arg | Leu | Gly | Val | Arg | Ala | Thr | Arg | Lys | Thr | Ser | Glu | Arg | Ser |
|     |     | 45  |     |     |     | 50  |     |     |     |     |     | 55  |     |
| Gln | Pro | Arg | Gly | Arg | Arg | Gln | Pro | Ile | Pro | Lys | Ala | Arg | Arg |
|     |     |     | 60  |     |     |     |     | 65  |     |     |     |     | 70  |
| Pro | Glu | Gly | Arg | Thr | Trp | Ala | Gln | Pro | Gly | Tyr | Pro | Trp | Pro |
|     |     |     |     | 75  |     |     |     |     | 80  |     |     |     |     |
| Leu | Tyr | Gly | Asn | Glu | Gly | Cys | Gly | Trp | Ala | Gly | Trp | Leu | Leu |
| 85  |     |     |     |     | 90  |     |     |     |     | 95  |     |     |     |
| Ser | Pro | Arg | Gly | Ser | Arg | Pro | Ser | Trp | Gly | Pro | Thr | Asp | Pro |
|     | 100 |     |     |     |     | 105 |     |     |     |     | 110 |     |     |
| Arg | Arg | Arg | Ser | Arg | Asn | Leu | Gly | Lys | Val | Ile | Asp | Thr | Leu |
|     |     | 115 |     |     |     |     | 120 |     |     |     |     | 125 |     |
| Thr | Cys | Gly | Phe | Ala | Asp | Leu | Met | Gly | Tyr | Ile | Pro | Leu | Val |
|     |     |     | 130 |     |     |     |     | 135 |     |     |     |     | 140 |
| Gly | Ala | Pro | Leu | Gly | Gly | Ala | Ala | Arg | Ala | Leu | Ala | His | Gly |
|     |     |     |     | 145 |     |     |     |     | 150 |     |     |     |     |
| Val | Arg | Val | Leu | Glu | Asp | Gly | Val | Asn | Tyr | Ala | Thr | Gly | Asn |
| 155 |     |     |     |     | 160 |     |     |     |     | 165 |     |     |     |
| Leu | Pro | Gly | Cys | Ser | Phe | Ser | Ile | Phe | Leu | Leu | Ala | Leu | Leu |
|     | 170 |     |     |     |     | 175 |     |     |     |     | 180 |     |     |
| Ser | Cys | Leu | Thr | Val | Pro | Ala | Ser | Ala |     |     |     |     |     |
|     |     | 185 |     |     |     |     | 190 |     |     |     |     |     |     |

(2) INFORMATION FOR SEQ ID NO: 158:

(i) SEQUENCE CHARACTERISTICS:
(A) LENGTH: 191 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SW1

(xi) SEQUENCE DESCRIPTION: SEQ ID NO: 158:

| Met | Ser | Thr | Asn | Pro | Lys | Pro | Gln | Arg | Lys | Thr | Lys | Arg | Asn |
|-----|-----|-----|-----|-----|-----|-----|-----|-----|-----|-----|-----|-----|-----|
| 1   |     |     |     | 5   |     |     |     |     | 10  |     |     |     |     |
| Thr | Asn | Arg | Arg | Pro | Gln | Asp | Val | Lys | Phe | Pro | Gly | Gly | Gly |
| 15  |     |     |     | 20  |     |     |     |     | 25  |     |     |     |     |
| Gln | Ile | Val | Gly | Gly | Val | Tyr | Leu | Leu | Pro | Arg | Arg | Gly | Pro |
|     | 30  |     |     |     | 35  |     |     |     |     | 40  |     |     |     |
| Arg | Leu | Gly | Val | Arg | Ala | Thr | Arg | Lys | Thr | Ser | Glu | Arg | Ser |
|     |     | 45  |     |     |     | 50  |     |     |     |     |     | 55  |     |
| Gln | Pro | Arg | Gly | Arg | Arg | Gln | Pro | Ile | Pro | Lys | Ala | Arg | Arg |
|     |     |     | 60  |     |     |     |     | 65  |     |     |     |     | 70  |
| Pro | Glu | Gly | Arg | Thr | Trp | Ala | Gln | Pro | Gly | Tyr | Pro | Trp | Pro |
|     |     |     |     | 75  |     |     |     |     | 80  |     |     |     |     |

| Leu | Tyr | Gly | Asn | Glu | Gly | Cys | Gly | Trp | Ala | Gly | Trp | Leu | Leu |
| 85 | | | | 90 | | | | | 95 | | | | |

| Ser | Pro | Arg | Gly | Ser | Arg | Pro | Ser | Trp | Gly | Pro | Thr | Asp | Pro |
| | 100 | | | | | 105 | | | | | 110 | | |

| Arg | Arg | Arg | Ser | Arg | Asn | Leu | Gly | Lys | Val | Ile | Asp | Thr | Leu |
| | | | 115 | | | | 120 | | | | | 125 | |

| Thr | Cys | Gly | Phe | Ala | Asp | Leu | Met | Gly | Tyr | Ile | Pro | Leu | Val |
| | | | 130 | | | | | 135 | | | | | 140 |

| Gly | Ala | Pro | Leu | Gly | Gly | Ala | Ala | Arg | Ala | Leu | Ala | His | Gly |
| | | | | 145 | | | | | 150 | | | | |

| Val | Arg | Val | Leu | Glu | Asp | Gly | Val | Asn | Tyr | Ala | Thr | Gly | Asn |
| 155 | | | | | 160 | | | | | 165 | | | |

| Leu | Pro | Gly | Cys | Ser | Phe | Ser | Ile | Phe | Leu | Leu | Ala | Leu | Leu |
| | 170 | | | | | 175 | | | | | | 180 | |

| Ser | Cys | Leu | Thr | Val | Pro | Ala | Ser | Ala | | | | | |
| | | | 185 | | | | | 190 | | | | | |

( 2 ) INFORMATION FOR SEQ ID NO: 159:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S18

( x i ) SEQUENCE DESCRIPTION: SEQ ID NO: 159:

| Met | Ser | Thr | Asn | Pro | Lys | Pro | Gln | Arg | Lys | Thr | Lys | Arg | Asn |
| 1 | | | | 5 | | | | | 10 | | | | |

| Thr | Asn | Arg | Arg | Pro | Gln | Asp | Val | Lys | Phe | Pro | Gly | Gly | Gly |
| 15 | | | | | 20 | | | | | 25 | | | |

| Gln | Ile | Val | Gly | Gly | Val | Tyr | Leu | Leu | Pro | Arg | Arg | Gly | Pro |
| | | 30 | | | | | 35 | | | | | 40 | |

| Arg | Leu | Gly | Val | Arg | Ala | Thr | Arg | Lys | Thr | Ser | Glu | Arg | Ser |
| | | | 45 | | | | | 50 | | | | | 55 |

| Gln | Pro | Arg | Gly | Arg | Arg | Gln | Pro | Ile | Pro | Lys | Ala | Arg | Arg |
| | | | | 60 | | | | | 65 | | | | 70 |

| Pro | Glu | Gly | Arg | Thr | Trp | Ala | Gln | Pro | Gly | Tyr | Pro | Trp | Pro |
| | | | | | 75 | | | | | 80 | | | |

| Leu | Tyr | Gly | Asn | Glu | Gly | Cys | Gly | Trp | Ala | Gly | Trp | Leu | Leu |
| 85 | | | | 90 | | | | | 95 | | | | |

| Ser | Pro | Arg | Gly | Ser | Arg | Pro | Ser | Trp | Gly | Pro | Thr | Asp | Pro |
| | 100 | | | | | 105 | | | | | 110 | | |

| Arg | Arg | Arg | Ser | Arg | Asn | Leu | Gly | Lys | Val | Ile | Asp | Thr | Leu |
| | | | 115 | | | | 120 | | | | | 125 | |

| Thr | Cys | Gly | Phe | Ala | Asp | Leu | Met | Gly | Tyr | Ile | Pro | Leu | Val |
| | | | 130 | | | | | 135 | | | | | 140 |

| Gly | Ala | Pro | Leu | Gly | Gly | Ala | Ala | Arg | Ala | Leu | Ala | His | Gly |
| | | | | 145 | | | | | 150 | | | | |

| Val | Arg | Val | Leu | Glu | Asp | Gly | Val | Asn | Tyr | Ala | Thr | Gly | Asn |
| 155 | | | | | 160 | | | | | 165 | | | |

| Leu | Pro | Gly | Cys | Ser | Phe | Ser | Ile | Phe | Leu | Leu | Ala | Leu | Leu |
| | 170 | | | | | 175 | | | | | | 180 | |

| Ser | Cys | Leu | Thr | Val | Pro | Ala | Ser | Ala | | | | | |
| | | | 185 | | | | | 190 | | | | | |

(2) INFORMATION FOR SEQ ID NO: 160:

(i) SEQUENCE CHARACTERISTICS:
    (A) LENGTH: 191 amino acids
    (B) TYPE: amino acid
    (C) STRANDEDNESS: unknown
    (D) TOPOLOGY: unknown (vi) ORIGINAL SOURCE:
    (A) ORGANISM: homosapiens
    (C) INDIVIDUAL ISOLATE: DR4

(xi) SEQUENCE DESCRIPTION: SEQ ID NO: 160:

```
Met Ser Thr Asn Pro Lys Pro Gln Arg Lys Thr Lys Arg Asn
 1           5                  10
Thr Asn Arg Arg Pro Gln Asp Val Lys Phe Pro Gly Gly Gly
15               20              25
Gln Ile Val Gly Gly Val Tyr Leu Leu Pro Arg Arg Gly Pro
        30              35              40
Arg Leu Gly Val Arg Ala Thr Arg Lys Thr Ser Glu Arg Ser
            45              50              55
Gln Pro Arg Gly Arg Arg Gln Pro Ile Pro Lys Ala Arg Arg
                60              65              70
Pro Glu Gly Arg Thr Trp Ala Gln Pro Gly Tyr Pro Trp Pro
                    75              80
Leu Tyr Gly Asn Glu Gly Cys Gly Trp Ala Gly Trp Leu Leu
85                  90              95
Ser Pro Arg Gly Ser Arg Pro Ser Trp Gly Pro Thr Asp Pro
    100             105             110
Arg Arg Arg Ser Arg Asn Leu Gly Lys Val Ile Asp Thr Leu
            115             120             125
Thr Cys Gly Phe Ala Asp Leu Met Gly Tyr Ile Pro Leu Val
                130             135             140
Gly Ala Pro Leu Gly Gly Ala Ala Arg Ala Leu Ala His Gly
                    145             150
Val Arg Val Leu Glu Asp Gly Val Asn Tyr Ala Thr Gly Asn
155             160             165
Leu Pro Gly Cys Ser Phe Ser Ile Phe Leu Leu Ala Leu Leu
    170             175             180
Ser Cys Leu Thr Val Pro Ala Ser Ala
        185             190
```

(2) INFORMATION FOR SEQ ID NO: 161:

(i) SEQUENCE CHARACTERISTICS:
    (A) LENGTH: 191 amino acids
    (B) TYPE: amino acid
    (C) STRANDEDNESS: unknown
    (D) TOPOLOGY: unknown (vi) ORIGINAL SOURCE:
    (A) ORGANISM: homosapiens
    (C) INDIVIDUAL ISOLATE: SA10

(xi) SEQUENCE DESCRIPTION: SEQ ID NO: 161:

```
Met Ser Thr Asn Pro Lys Pro Gln Arg Lys Thr Lys Arg Asn
 1           5                  10
Thr Asn Arg Arg Pro Gln Asp Val Lys Phe Pro Gly Gly Gly
15               20              25
Gln Ile Val Gly Gly Val Tyr Leu Leu Pro Arg Arg Gly Pro
```

|   | 30 |   |   |   | 35 |   |   |   | 40 |   |   |
|---|---|---|---|---|---|---|---|---|---|---|---|

Arg Leu Gly Val Arg Ala Thr Arg Lys Thr Ser Glu Arg Ser
         45                      50                    55

Gln Pro Arg Gly Arg Arg Gln Pro Ile Pro Lys Ala Arg Gln
             60                  65                    70

Pro Glu Gly Arg Thr Trp Ala Gln Pro Gly Tyr Pro Trp Pro
                 75                      80

Leu Tyr Gly Asn Glu Gly Leu Gly Trp Ala Gly Trp Leu Leu
 85                      90                   95

Ser Pro Arg Gly Ser Arg Pro Ser Trp Gly Pro Thr Asp Pro
     100                 105                 110

Arg Arg Arg Ser Arg Asn Leu Gly Lys Val Ile Asp Thr Leu
         115                 120                 125

Thr Cys Gly Phe Ala Asp Leu Met Gly Tyr Ile Pro Leu Val
             130                 135                     140

Gly Ala Pro Leu Gly Gly Ala Ala Arg Ala Leu Ala His Gly
                 145                 150

Val Arg Val Leu Glu Asp Gly Val Asn Tyr Ala Thr Gly Asn
155                  160                 165

Leu Pro Gly Cys Pro Phe Ser Ile Phe Leu Leu Ala Leu Leu
     170                 175                 180

Ser Cys Leu Thr Ile Pro Ala Ser Ala
             185             190

( 2 ) INFORMATION FOR SEQ ID NO: 162:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S45

( x i ) SEQUENCE DESCRIPTION: SEQ ID NO: 162:

Met Ser Thr Asn Pro Lys Pro Gln Arg Ala Thr Lys Arg Asn
 1               5                   10

Thr Asn Arg Arg Pro Gln Asp Val Lys Phe Pro Gly Gly Gly
 15                  20                  25

Gln Ile Val Gly Gly Val Tyr Leu Leu Pro Arg Arg Gly Pro
     30                  35                  40

Arg Leu Gly Val Arg Ala Thr Arg Lys Thr Ser Glu Arg Ser
         45                  50                      55

Gln Pro Arg Gly Arg Arg Gln Pro Ile Pro Lys Ala Arg Arg
             60                  65                    70

Pro Glu Gly Arg Ala Trp Ala Gln Pro Gly His Pro Trp Pro
                 75                      80

Leu Tyr Gly Asn Glu Gly Leu Gly Trp Ala Gly Trp Leu Leu
 85                      90                   95

Ser Pro Arg Gly Ser Arg Pro Ser Trp Gly Pro Thr Asp Pro
     100                 105                 110

Arg Arg Arg Ser Arg Asn Leu Gly Lys Val Ile Asp Thr Leu
         115                 120                 125

Thr Cys Gly Phe Ala Asp Leu Met Gly Tyr Ile Pro Leu Val
             130                 135                     140

Gly Ala Pro Leu Gly Gly Ala Ala Arg Ala Leu Ala His Gly
                145                 150

Val Arg Val Leu Glu Asp Gly Val Asn Tyr Ala Thr Gly Asn
155                 160                 165

Leu Pro Gly Cys Ser Phe Ser Ile Phe Leu Leu Ala Leu Leu
    170                 175                 180

Ser Cys Leu Thr Ile Pro Ala Ser Ala
        185                 190

( 2 ) INFORMATION FOR SEQ ID NO: 163:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: D1

( x i ) SEQUENCE DESCRIPTION: SEQ ID NO: 163:

Met Ser Thr Asn Pro Lys Pro Gln Arg Lys Thr Lys Arg Asn
1                   5                   10

Thr Asn Arg Arg Pro Gln Asp Val Lys Phe Pro Gly Gly Gly
15                  20                  25

Gln Ile Val Gly Gly Val Tyr Leu Leu Pro Arg Arg Gly Pro
    30                  35                  40

Arg Leu Gly Val Arg Ala Thr Arg Lys Thr Ser Glu Arg Ser
        45                  50                  55

Gln Pro Arg Gly Arg Arg Gln Pro Ile Pro Lys Ala Arg Arg
            60                  65                  70

Pro Glu Gly Arg Ala Trp Ala Gln Pro Gly Tyr Pro Trp Pro
                75                  80

Leu Tyr Gly Asn Glu Gly Leu Gly Trp Ala Gly Trp Leu Leu
85                  90                  95

Ser Pro Arg Gly Ser Arg Pro Ser Trp Gly Pro Thr Asp Pro
    100                 105                 110

Arg Arg Arg Ser Arg Asn Leu Gly Lys Val Ile Asp Thr Leu
        115                 120                 125

Thr Cys Gly Phe Ala Asp Leu Met Gly Tyr Ile Pro Leu Val
            130                 135                 140

Gly Ala Pro Leu Gly Gly Ala Ala Arg Ala Leu Ala His Gly
                145                 150

Val Arg Val Leu Glu Asp Gly Val Asn Tyr Ala Thr Gly Asn
155                 160                 165

Leu Pro Gly Cys Ser Phe Ser Ile Phe Leu Leu Ala Leu Leu
    170                 175                 180

Ser Cys Leu Thr Ile Pro Ala Ser Ala
        185                 190

( 2 ) INFORMATION FOR SEQ ID NO: 164:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens ( C ) INDIVIDUAL ISOLATE: US6

( x i ) SEQUENCE DESCRIPTION: SEQ ID NO: 164:

```
Met  Ser  Thr  Asn  Pro  Lys  Pro  Gln  Arg  Lys  Thr  Lys  Arg  Asn
 1              5                   10
Thr  Asn  Arg  Arg  Pro  Gln  Asp  Val  Lys  Phe  Pro  Gly  Gly  Gly
15                  20                       25
Gln  Ile  Val  Gly  Gly  Val  Tyr  Leu  Leu  Pro  Arg  Arg  Gly  Pro
     30                       35                     40
Arg  Leu  Gly  Val  Arg  Ala  Thr  Arg  Lys  Thr  Ser  Glu  Arg  Ser
          45                       50                      55
Gln  Pro  Arg  Gly  Arg  Arg  Gln  Pro  Ile  Pro  Lys  Ala  Arg  Arg
               60                       65                          70
Pro  Glu  Gly  Arg  Ala  Trp  Ala  Gln  Pro  Gly  Tyr  Pro  Trp  Pro
                    75                       80
Leu  Tyr  Gly  Asn  Glu  Gly  Met  Gly  Trp  Ala  Gly  Trp  Leu  Leu
 85                      90                            95
Ser  Pro  Arg  Gly  Ser  Arg  Pro  Ser  Trp  Gly  Pro  Thr  Asp  Pro
     100                      105                     110
Arg  Arg  Arg  Ser  Arg  Asn  Leu  Gly  Lys  Val  Ile  Asp  Thr  Leu
               115                      120                      125
Thr  Cys  Gly  Phe  Ala  Asp  Leu  Met  Gly  Tyr  Ile  Pro  Leu  Val
                    130                      135                     140
Gly  Ala  Pro  Leu  Gly  Gly  Ala  Ala  Arg  Ala  Leu  Ala  His  Gly
                         145                      150
Val  Arg  Val  Leu  Glu  Asp  Gly  Val  Asn  Tyr  Ala  Thr  Gly  Asn
155                           160                      165
Leu  Pro  Gly  Cys  Ser  Phe  Ser  Ile  Phe  Leu  Leu  Ala  Leu  Leu
     170                      175                           180
Ser  Cys  Leu  Thr  Ile  Pro  Ala  Ser  Ala
          185                      190
```

( 2 ) INFORMATION FOR SEQ ID NO: 165:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: P10

( x i ) SEQUENCE DESCRIPTION: SEQ ID NO: 165:

```
Met  Ser  Thr  Asn  Pro  Lys  Pro  Gln  Arg  Lys  Thr  Lys  Arg  Asn
 1              5                   10
Thr  Asn  Arg  Arg  Pro  Gln  Asp  Val  Lys  Phe  Pro  Gly  Gly  Gly
15                  20                       25
Gln  Ile  Val  Gly  Gly  Val  Tyr  Leu  Leu  Pro  Arg  Arg  Gly  Pro
     30                       35                     40
Arg  Leu  Gly  Val  Arg  Ala  Thr  Arg  Lys  Thr  Ser  Glu  Arg  Ser
          45                       50                      55
Gln  Pro  Arg  Gly  Arg  Arg  Gln  Pro  Ile  Pro  Lys  Ala  Arg  Arg
               60                       65                          70
Pro  Glu  Gly  Arg  Ala  Trp  Ala  Gln  Pro  Gly  Tyr  Pro  Trp  Pro
                    75                       80
Leu  Tyr  Gly  Asn  Glu  Gly  Leu  Gly  Trp  Ala  Gly  Trp  Leu  Leu
```

| | | | | 85 | | | | | 90 | | | | | 95 | | |
|---|---|---|---|---|---|---|---|---|---|---|---|---|---|---|---|---|

Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu
115 120 125

Thr Cys Gly Phe Ala Asp Leu Met Gly Tyr Ile Pro Leu Val
130 135 140

Gly Ala Pro Leu Gly Gly Ala Ala Arg Ala Leu Ala His Gly
145 150

Val Arg Val Leu Glu Asp Gly Val Asn Tyr Ala Thr Gly Asn
155 160 165

Leu Pro Gly Cys Ser Phe Ser Ile Phe Leu Leu Ala Leu Leu
170 175 180

Ser Cys Leu Thr Ile Pro Ala Ser Ala
185 190

(2) INFORMATION FOR SEQ ID NO: 166:

(i) SEQUENCE CHARACTERISTICS:
        (A) LENGTH: 191 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK1

(xi) SEQUENCE DESCRIPTION: SEQ ID NO: 166:

Met Ser Thr Asn Pro Lys Pro Gln Arg Lys Thr Lys Arg Asn
1 5 10

Thr Asn Arg Arg Pro Gln Asp Val Lys Phe Pro Gly Gly Gly
15 20 25

Gln Ile Val Gly Gly Val Tyr Leu Leu Pro Arg Arg Gly Pro
30 35 40

Arg Leu Gly Val Arg Ala Thr Arg Lys Thr Ser Glu Arg Ser
45 50 55

Gln Pro Arg Gly Arg Arg Gln Pro Ile Pro Lys Ala Arg Arg
60 65 70

Pro Glu Gly Arg Ala Trp Ala Gln Pro Gly Tyr Pro Trp Pro
75 80

Leu Tyr Gly Asn Glu Gly Met Gly Trp Ala Gly Trp Leu Leu
85 90 95

Ser Pro Arg Gly Ser Arg Pro Ser Trp Gly Pro Asn Asp Pro
100 105 110

Arg Arg Arg Ser Arg Asn Leu Gly Lys Val Ile Asp Thr Leu
115 120 125

Thr Cys Gly Phe Ala Asp Leu Met Gly Tyr Ile Pro Leu Val
130 135 140

Gly Ala Pro Leu Gly Gly Ala Ala Arg Ala Leu Ala His Gly
145 150

Val Arg Val Leu Glu Asp Gly Val Asn Tyr Ala Thr Gly Asn
155 160 165

Leu Pro Gly Cys Ser Phe Ser Ile Phe Leu Leu Ala Leu Leu
170 175 180

Ser Cys Leu Thr Ile Pro Ala Ser Ala
185 190

( 2 ) INFORMATION FOR SEQ ID NO: 167:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T10

( x i ) SEQUENCE DESCRIPTION: SEQ ID NO: 167:

```
Met  Ser  Thr  Asn  Pro  Lys  Pro  Gln  Arg  Lys  Thr  Lys  Arg  Asn
 1              5                        10

Thr  Asn  Arg  Arg  Pro  Gln  Asp  Val  Lys  Phe  Pro  Gly  Gly  Gly
15                   20                        25

Gln  Ile  Val  Gly  Gly  Val  Tyr  Leu  Leu  Pro  Arg  Arg  Gly  Pro
     30                        35                        40

Arg  Leu  Gly  Val  Arg  Ala  Thr  Arg  Lys  Thr  Ser  Glu  Arg  Ser
          45                        50                        55

Gln  Pro  Arg  Gly  Arg  Arg  Gln  Pro  Ile  Pro  Lys  Ala  Arg  Gln
               60                        65                        70

Pro  Glu  Gly  Arg  Ala  Trp  Ala  Gln  Pro  Gly  Tyr  Pro  Trp  Pro
                    75                        80

Leu  Tyr  Gly  Asn  Glu  Gly  Met  Gly  Trp  Ala  Gly  Trp  Leu  Leu
85                        90                        95

Ser  Pro  Arg  Gly  Ser  Arg  Pro  Ser  Trp  Gly  Pro  Thr  Asp  Pro
     100                       105                       110

Arg  Arg  Arg  Ser  Arg  Asn  Leu  Gly  Lys  Val  Ile  Asp  Thr  Leu
          115                       120                       125

Thr  Cys  Gly  Phe  Ala  Asp  Leu  Met  Gly  Tyr  Ile  Pro  Leu  Val
               130                       135                       140

Gly  Ala  Pro  Leu  Gly  Gly  Ala  Ala  Arg  Ala  Leu  Ala  His  Gly
                    145                       150

Val  Arg  Val  Leu  Glu  Asp  Gly  Val  Asn  Tyr  Ala  Thr  Gly  Asn
155                       160                       165

Leu  Pro  Gly  Cys  Ser  Phe  Ser  Ile  Phe  Leu  Leu  Ala  Leu  Leu
     170                       175                       180

Ser  Cys  Leu  Thr  Ile  Pro  Ala  Ser  Ala
          185                       190
```

( 2 ) INFORMATION FOR SEQ ID NO: 168:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SW2

( x i ) SEQUENCE DESCRIPTION: SEQ ID NO: 168:

```
Met  Ser  Thr  Asn  Pro  Lys  Pro  Gln  Arg  Lys  Thr  Lys  Arg  Asn
 1              5                        10

Thr  Asn  Arg  Arg  Pro  Gln  Asp  Val  Lys  Phe  Pro  Gly  Gly  Gly
15                   20                        25

Gln  Ile  Val  Gly  Gly  Val  Tyr  Leu  Leu  Pro  Arg  Arg  Gly  Pro
     30                        35                        40
```

| Arg | Leu | Gly | Val | Arg | Ala | Thr | Arg | Lys | Thr | Ser | Glu | Arg | Ser |
|-----|-----|-----|-----|-----|-----|-----|-----|-----|-----|-----|-----|-----|-----|
|     |     |     | 45  |     |     |     | 50  |     |     |     |     | 55  |     |

| Gln | Pro | Arg | Gly | Arg | Arg | Gln | Pro | Ile | Pro | Lys | Ala | Arg | Gln |
|-----|-----|-----|-----|-----|-----|-----|-----|-----|-----|-----|-----|-----|-----|
|     |     |     | 60  |     |     |     | 65  |     |     |     |     | 70  |     |

| Pro | Glu | Gly | Arg | Ala | Trp | Ala | Gln | Pro | Gly | Tyr | Pro | Trp | Pro |
|-----|-----|-----|-----|-----|-----|-----|-----|-----|-----|-----|-----|-----|-----|
|     |     |     |     | 75  |     |     |     | 80  |     |     |     |     |     |

| Leu | Tyr | Gly | Asn | Glu | Gly | Met | Gly | Trp | Ala | Gly | Trp | Leu | Leu |
|-----|-----|-----|-----|-----|-----|-----|-----|-----|-----|-----|-----|-----|-----|
| 85  |     |     |     |     | 90  |     |     |     |     | 95  |     |     |     |

| Ser | Pro | Arg | Gly | Ser | Arg | Pro | Ser | Trp | Gly | Pro | Thr | Asp | Pro |
|-----|-----|-----|-----|-----|-----|-----|-----|-----|-----|-----|-----|-----|-----|
|     | 100 |     |     |     |     | 105 |     |     |     |     | 110 |     |     |

| Arg | Arg | Arg | Ser | Arg | Asn | Leu | Gly | Lys | Val | Ile | Asp | Thr | Leu |
|-----|-----|-----|-----|-----|-----|-----|-----|-----|-----|-----|-----|-----|-----|
|     |     |     | 115 |     |     |     | 120 |     |     |     |     | 125 |     |

| Thr | Cys | Gly | Phe | Ala | Asp | Leu | Met | Gly | Tyr | Ile | Pro | Leu | Val |
|-----|-----|-----|-----|-----|-----|-----|-----|-----|-----|-----|-----|-----|-----|
|     |     |     | 130 |     |     |     |     | 135 |     |     |     |     | 140 |

| Gly | Ala | Pro | Leu | Gly | Gly | Ala | Ala | Arg | Ala | Leu | Ala | His | Gly |
|-----|-----|-----|-----|-----|-----|-----|-----|-----|-----|-----|-----|-----|-----|
|     |     |     |     | 145 |     |     |     |     | 150 |     |     |     |     |

| Val | Arg | Val | Leu | Glu | Asp | Gly | Val | Asn | Tyr | Ala | Thr | Gly | Asn |
|-----|-----|-----|-----|-----|-----|-----|-----|-----|-----|-----|-----|-----|-----|
| 155 |     |     |     |     | 160 |     |     |     |     | 165 |     |     |     |

| Leu | Pro | Gly | Cys | Ser | Phe | Ser | Ile | Phe | Leu | Leu | Ala | Leu | Leu |
|-----|-----|-----|-----|-----|-----|-----|-----|-----|-----|-----|-----|-----|-----|
|     | 170 |     |     |     |     | 175 |     |     |     |     | 180 |     |     |

| Ser | Cys | Leu | Thr | Ile | Pro | Ala | Ser | Ala |
|-----|-----|-----|-----|-----|-----|-----|-----|-----|
|     |     | 185 |     |     |     |     | 190 |     |

( 2 ) INFORMATION FOR SEQ ID NO: 169:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: IND3

( x i ) SEQUENCE DESCRIPTION: SEQ ID NO: 169:

| Met | Ser | Thr | Asn | Pro | Lys | Pro | Gln | Arg | Lys | Thr | Lys | Arg | Asn |
|-----|-----|-----|-----|-----|-----|-----|-----|-----|-----|-----|-----|-----|-----|
| 1   |     |     |     | 5   |     |     |     |     | 10  |     |     |     |     |

| Thr | Asn | Arg | Arg | Pro | Gln | Asp | Val | Lys | Phe | Pro | Gly | Gly | Gly |
|-----|-----|-----|-----|-----|-----|-----|-----|-----|-----|-----|-----|-----|-----|
| 15  |     |     |     |     | 20  |     |     |     |     | 25  |     |     |     |

| Gln | Ile | Val | Gly | Gly | Val | Tyr | Leu | Leu | Pro | Arg | Arg | Gly | Pro |
|-----|-----|-----|-----|-----|-----|-----|-----|-----|-----|-----|-----|-----|-----|
|     |     | 30  |     |     |     |     | 35  |     |     |     |     | 40  |     |

| Arg | Leu | Gly | Val | Arg | Ala | Thr | Arg | Lys | Thr | Ser | Glu | Arg | Ser |
|-----|-----|-----|-----|-----|-----|-----|-----|-----|-----|-----|-----|-----|-----|
|     |     |     | 45  |     |     |     | 50  |     |     |     |     | 55  |     |

| Gln | Pro | Arg | Gly | Arg | Arg | Gln | Pro | Ile | Pro | Lys | Ala | Arg | Arg |
|-----|-----|-----|-----|-----|-----|-----|-----|-----|-----|-----|-----|-----|-----|
|     |     |     | 60  |     |     |     | 65  |     |     |     |     | 70  |     |

| Pro | Glu | Gly | Arg | Ala | Trp | Ala | Gln | Pro | Gly | Tyr | Pro | Trp | Pro |
|-----|-----|-----|-----|-----|-----|-----|-----|-----|-----|-----|-----|-----|-----|
|     |     |     |     | 75  |     |     |     | 80  |     |     |     |     |     |

| Leu | Tyr | Gly | Asn | Glu | Gly | Leu | Gly | Trp | Ala | Gly | Trp | Leu | Leu |
|-----|-----|-----|-----|-----|-----|-----|-----|-----|-----|-----|-----|-----|-----|
| 85  |     |     |     |     | 90  |     |     |     |     | 95  |     |     |     |

| Ser | Pro | Arg | Gly | Ser | Arg | Pro | Ser | Trp | Gly | Pro | Thr | Asp | Pro |
|-----|-----|-----|-----|-----|-----|-----|-----|-----|-----|-----|-----|-----|-----|
|     | 100 |     |     |     |     | 105 |     |     |     |     | 110 |     |     |

| Arg | Arg | Arg | Ser | Arg | Asn | Leu | Gly | Lys | Val | Ile | Asp | Thr | Leu |
|-----|-----|-----|-----|-----|-----|-----|-----|-----|-----|-----|-----|-----|-----|
|     |     |     | 115 |     |     |     | 120 |     |     |     |     | 125 |     |

| Thr | Cys | Gly | Phe | Ala | Asp | Leu | Met | Gly | Tyr | Ile | Pro | Leu | Val |
|-----|-----|-----|-----|-----|-----|-----|-----|-----|-----|-----|-----|-----|-----|
|     |     |     | 130 |     |     |     |     | 135 |     |     |     |     | 140 |

| Gly | Ala | Pro | Leu | Gly | Gly | Ala | Ala | Arg | Ala | Leu | Ala | His | Gly |
|-----|-----|-----|-----|-----|-----|-----|-----|-----|-----|-----|-----|-----|-----|

|     |     |     |     |     | 145 |     |     |     |     | 150 |     |     |     |     |

Val Arg Val Leu Glu Asp Gly Val Asn Tyr Ala Thr Gly Asn
155                     160                 165

Leu Pro Gly Cys Ser Phe Ser Ile Phe Leu Leu Ala Leu Leu
    170                 175                 180

Ser Cys Leu Thr Ile Pro Ala Ser Ala
        185             190

( 2 ) INFORMATION FOR SEQ ID NO: 170:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: IND8

( x i ) SEQUENCE DESCRIPTION: SEQ ID NO: 170:

Met Ser Thr Asn Pro Lys Pro Gln Arg Lys Thr Lys Arg Asn
1               5                   10

Thr Asn Arg Arg Pro Gln Asp Val Lys Phe Pro Gly Gly Gly
15                  20                  25

Gln Ile Val Gly Gly Val Tyr Leu Leu Pro Arg Arg Gly Pro
    30                  35                  40

Arg Leu Gly Val Arg Ala Thr Arg Lys Thr Ser Glu Arg Ser
        45                  50                  55

Gln Pro Arg Gly Arg Arg Gln Pro Ile Pro Lys Ala Arg Arg
            60                  65                  70

Pro Glu Gly Arg Ala Trp Ala Gln Pro Gly His Pro Trp Pro
                75                  80

Leu Tyr Gly Asn Glu Gly Leu Gly Trp Ala Gly Trp Leu Leu
85                  90                  95

Ser Pro Arg Gly Ser Arg Pro Ser Trp Gly Pro Thr Asp Pro
    100                 105                 110

Arg Arg Arg Ser Arg Asn Leu Gly Lys Val Ile Asp Thr Leu
        115                 120                 125

Thr Cys Gly Phe Ala Asp Leu Met Gly Tyr Ile Pro Leu Val
            130                 135                 140

Gly Ala Pro Leu Gly Gly Ala Ala Arg Ala Leu Ala His Gly
                145                 150

Val Arg Val Leu Glu Asp Gly Val Asn Tyr Ala Thr Gly Asn
155                     160                 165

Leu Pro Gly Cys Ser Phe Ser Ile Phe Leu Leu Ala Leu Leu
    170                 175                 180

Ser Cys Leu Thr Val Pro Ala Ser Ala
        185             190

( 2 ) INFORMATION FOR SEQ ID NO: 171:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S9

( x i ) SEQUENCE DESCRIPTION: SEQ ID NO: 171:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |
| Thr | Asn | Arg | Arg | Pro | Gln | Asp | Val | Lys | Phe | Pro | Gly | Gly | Gly |
| 15 | | | | 20 | | | | | 25 | | | | |
| Gln | Ile | Val | Gly | Gly | Val | Tyr | Leu | Leu | Pro | Arg | Arg | Gly | Pro |
| | 30 | | | | 35 | | | | | 40 | | | |
| Arg | Leu | Gly | Val | Arg | Ala | Thr | Arg | Lys | Thr | Ser | Glu | Arg | Ser |
| | | 45 | | | | 50 | | | | | 55 | | |
| Gln | Pro | Arg | Gly | Arg | Arg | Gln | Pro | Ile | Pro | Lys | Ala | Arg | His |
| | | | 60 | | | | 65 | | | | | | 70 |
| Pro | Glu | Gly | Arg | Ala | Trp | Ala | Gln | Pro | Gly | Tyr | Pro | Trp | Pro |
| | | | | 75 | | | | | 80 | | | | |
| Leu | Tyr | Gly | Asn | Glu | Gly | Leu | Gly | Trp | Ala | Gly | Trp | Leu | Leu |
| 85 | | | | | 90 | | | | | 95 | | | |
| Ser | Pro | Arg | Gly | Ser | Arg | Pro | Ser | Trp | Gly | Pro | Asn | Asp | Pro |
| | 100 | | | | | 105 | | | | | 110 | | |
| Arg | Arg | Arg | Ser | Arg | Asn | Leu | Gly | Lys | Val | Ile | Asp | Thr | Leu |
| | | | 115 | | | | 120 | | | | | 125 | |
| Thr | Cys | Gly | Phe | Ala | Asp | Leu | Met | Gly | Tyr | Ile | Pro | Leu | Val |
| | | | 130 | | | | | 135 | | | | | 140 |
| Gly | Ala | Pro | Leu | Gly | Gly | Ala | Ala | Arg | Ala | Leu | Ala | His | Gly |
| | | | | 145 | | | | | 150 | | | | |
| Val | Arg | Val | Leu | Glu | Asp | Gly | Val | Asn | Tyr | Ala | Thr | Gly | Asn |
| 155 | | | | | 160 | | | | | 165 | | | |
| Leu | Pro | Gly | Cys | Ser | Phe | Ser | Ile | Phe | Leu | Leu | Ala | Leu | Leu |
| | 170 | | | | | 175 | | | | | 180 | | |
| Ser | Cys | Leu | Thr | Ile | Pro | Ala | Ser | Ala | | | | | |
| | | 185 | | | | | 190 | | | | | | |

( 2 ) INFORMATION FOR SEQ ID NO: 172:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: HK3

( x i ) SEQUENCE DESCRIPTION: SEQ ID NO: 172:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |
| Thr | Asn | Arg | Arg | Pro | Gln | Asp | Val | Lys | Phe | Pro | Gly | Gly | Gly |
| 15 | | | | 20 | | | | | 25 | | | | |
| Gln | Ile | Val | Gly | Gly | Val | Tyr | Leu | Leu | Pro | Arg | Arg | Gly | Pro |
| | 30 | | | | 35 | | | | | 40 | | | |
| Arg | Leu | Gly | Val | Arg | Ala | Thr | Arg | Lys | Thr | Ser | Glu | Arg | Ser |
| | | 45 | | | | 50 | | | | | 55 | | |
| Gln | Pro | Arg | Gly | Arg | Arg | Gln | Pro | Ile | Pro | Lys | Ala | Arg | Gln |
| | | | 60 | | | | 65 | | | | | | 70 |
| Pro | Glu | Gly | Arg | Thr | Trp | Ala | Gln | Pro | Gly | Tyr | Pro | Trp | Pro |
| | | | | 75 | | | | | 80 | | | | |
| Leu | Tyr | Gly | Asn | Glu | Gly | Met | Gly | Trp | Ala | Gly | Trp | Leu | Leu |
| 85 | | | | | 90 | | | | | 95 | | | |

| Ser | Pro | Arg | Gly | Ser | Arg | Pro | Asn | Trp | Gly | Pro | Thr | Asp | Pro |
|---|---|---|---|---|---|---|---|---|---|---|---|---|---|
| | 100 | | | | 105 | | | | | 110 | | | |

| Arg | Arg | Arg | Ser | Arg | Asn | Leu | Gly | Lys | Val | Ile | Asp | Thr | Leu |
|---|---|---|---|---|---|---|---|---|---|---|---|---|---|
| | | 115 | | | | 120 | | | | | | 125 | |

| Thr | Cys | Gly | Phe | Ala | Asp | Leu | Met | Gly | Tyr | Ile | Pro | Leu | Val |
|---|---|---|---|---|---|---|---|---|---|---|---|---|---|
| | | | 130 | | | | 135 | | | | | | 140 |

| Gly | Ala | Pro | Leu | Gly | Gly | Val | Ala | Arg | Ala | Leu | Ala | His | Gly |
|---|---|---|---|---|---|---|---|---|---|---|---|---|---|
| | | | | 145 | | | | | 150 | | | | |

| Val | Arg | Val | Leu | Glu | Asp | Gly | Val | Asn | Tyr | Ala | Thr | Gly | Asn |
|---|---|---|---|---|---|---|---|---|---|---|---|---|---|
| 155 | | | | | 160 | | | | | 165 | | | |

| Leu | Pro | Gly | Cys | Ser | Phe | Ser | Ile | Phe | Leu | Leu | Ala | Leu | Leu |
|---|---|---|---|---|---|---|---|---|---|---|---|---|---|
| | 170 | | | | | 175 | | | | | 180 | | |

| Ser | Cys | Leu | Thr | Thr | Pro | Ala | Ser | Ala |
|---|---|---|---|---|---|---|---|---|
| | | 185 | | | | | 190 | |

(2) INFORMATION FOR SEQ ID NO: 173:

(i) SEQUENCE CHARACTERISTICS:
  (A) LENGTH: 191 amino acids
  (B) TYPE: amino acid
  (C) STRANDEDNESS: unknown
  (D) TOPOLOGY: unknown (vi) ORIGINAL SOURCE:
  (A) ORGANISM: homosapiens
  (C) INDIVIDUAL ISOLATE: HK5

(xi) SEQUENCE DESCRIPTION: SEQ ID NO: 173:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |

| Thr | Asn | Arg | Arg | Pro | Gln | Asp | Val | Lys | Phe | Pro | Gly | Gly | Gly |
|---|---|---|---|---|---|---|---|---|---|---|---|---|---|
| 15 | | | | | 20 | | | | | 25 | | | |

| Gln | Ile | Val | Gly | Gly | Val | Tyr | Leu | Leu | Pro | Arg | Arg | Gly | Pro |
|---|---|---|---|---|---|---|---|---|---|---|---|---|---|
| | 30 | | | | | 35 | | | | | 40 | | |

| Arg | Leu | Gly | Val | Arg | Ala | Thr | Arg | Lys | Thr | Ser | Glu | Arg | Ser |
|---|---|---|---|---|---|---|---|---|---|---|---|---|---|
| | | 45 | | | | | 50 | | | | | 55 | |

| Gln | Pro | Arg | Gly | Arg | Arg | Gln | Pro | Ile | Pro | Lys | Ala | Arg | Arg |
|---|---|---|---|---|---|---|---|---|---|---|---|---|---|
| | | | 60 | | | | | 65 | | | | | 70 |

| Pro | Glu | Gly | Arg | Thr | Trp | Ala | Gln | Pro | Gly | Tyr | Pro | Trp | Pro |
|---|---|---|---|---|---|---|---|---|---|---|---|---|---|
| | | | | 75 | | | | | 80 | | | | |

| Leu | Tyr | Gly | Asn | Glu | Gly | Met | Gly | Trp | Ala | Gly | Trp | Leu | Leu |
|---|---|---|---|---|---|---|---|---|---|---|---|---|---|
| 85 | | | | | 90 | | | | | 95 | | | |

| Ser | Pro | His | Gly | Ser | Arg | Pro | Ser | Trp | Gly | Pro | Thr | Asp | Pro |
|---|---|---|---|---|---|---|---|---|---|---|---|---|---|
| | 100 | | | | | 105 | | | | | 110 | | |

| Arg | Arg | Arg | Ser | Arg | Asn | Leu | Gly | Lys | Val | Ile | Asp | Thr | Leu |
|---|---|---|---|---|---|---|---|---|---|---|---|---|---|
| | | 115 | | | | 120 | | | | | | 125 | |

| Thr | Cys | Gly | Phe | Ala | Asp | Leu | Met | Gly | Tyr | Ile | Pro | Leu | Val |
|---|---|---|---|---|---|---|---|---|---|---|---|---|---|
| | | | 130 | | | | 135 | | | | | | 140 |

| Gly | Ala | Pro | Leu | Gly | Gly | Val | Ala | Arg | Ala | Leu | Ala | His | Gly |
|---|---|---|---|---|---|---|---|---|---|---|---|---|---|
| | | | | 145 | | | | | 150 | | | | |

| Val | Arg | Val | Leu | Glu | Asp | Gly | Val | Asn | Tyr | Ala | Thr | Gly | Asn |
|---|---|---|---|---|---|---|---|---|---|---|---|---|---|
| 155 | | | | | 160 | | | | | 165 | | | |

| Ile | Pro | Gly | Cys | Ser | Phe | Ser | Ile | Phe | Leu | Leu | Ala | Leu | Leu |
|---|---|---|---|---|---|---|---|---|---|---|---|---|---|
| | 170 | | | | | 175 | | | | | 180 | | |

| Ser | Cys | Leu | Thr | Thr | Pro | Val | Ser | Ala |
|---|---|---|---|---|---|---|---|---|
| | | 185 | | | | | 190 | |

(2) INFORMATION FOR SEQ ID NO: 174:

(i) SEQUENCE CHARACTERISTICS:
   (A) LENGTH: 191 amino acids
   (B) TYPE: amino acid
   (C) STRANDEDNESS: unknown
   (D) TOPOLOGY: unknown (vi) ORIGINAL SOURCE:
   (A) ORGANISM: homosapiens
   (C) INDIVIDUAL ISOLATE: HK4

(xi) SEQUENCE DESCRIPTION: SEQ ID NO: 174:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |
| Thr | Asn | Arg | Arg | Pro | Gln | Asp | Val | Lys | Phe | Pro | Gly | Gly | Gly |
| 15 | | | | 20 | | | | | 25 | | | | |
| Gln | Ile | Val | Gly | Gly | Val | Tyr | Leu | Leu | Pro | Arg | Arg | Gly | Pro |
| | 30 | | | | 35 | | | | | 40 | | | |
| Arg | Leu | Gly | Val | Arg | Ala | Thr | Arg | Lys | Thr | Ser | Glu | Arg | Ser |
| | | 45 | | | | 50 | | | | | 55 | | |
| Gln | Pro | Arg | Gly | Arg | Arg | Gln | Pro | Ile | Pro | Lys | Ala | Arg | Gln |
| | | | 60 | | | | 65 | | | | | | 70 |
| Pro | Glu | Gly | Arg | Thr | Trp | Ala | Gln | Pro | Gly | Tyr | Pro | Trp | Pro |
| | | | | 75 | | | | | 80 | | | | |
| Leu | Tyr | Gly | Asn | Glu | Gly | Met | Gly | Trp | Ala | Gly | Trp | Leu | Leu |
| 85 | | | | | 90 | | | | | 95 | | | |
| Ser | Pro | Arg | Gly | Ser | Arg | Pro | Ser | Trp | Gly | Pro | Thr | Asp | Pro |
| | 100 | | | | | 105 | | | | | 110 | | |
| Arg | Arg | Arg | Ser | Arg | Asn | Leu | Gly | Lys | Val | Ile | Asp | Thr | Leu |
| | | | 115 | | | | 120 | | | | | 125 | |
| Thr | Cys | Gly | Phe | Ala | Asp | Leu | Met | Gly | Tyr | Ile | Pro | Leu | Val |
| | | | 130 | | | | | 135 | | | | | 140 |
| Gly | Ala | Pro | Leu | Gly | Gly | Val | Ala | Arg | Ala | Leu | Ala | His | Gly |
| | | | | 145 | | | | | 150 | | | | |
| Val | Arg | Val | Val | Glu | Asp | Gly | Val | Asn | Tyr | Ala | Thr | Gly | Asn |
| 155 | | | | | 160 | | | | | 165 | | | |
| Leu | Pro | Gly | Cys | Ser | Phe | Ser | Ile | Phe | Leu | Leu | Ala | Leu | Leu |
| | 170 | | | | | 175 | | | | | 180 | | |
| Ser | Cys | Leu | Thr | Ile | Pro | Ala | Ser | Ala | | | | | |
| | | 185 | | | | | 190 | | | | | | |

(2) INFORMATION FOR SEQ ID NO: 175:

(i) SEQUENCE CHARACTERISTICS:
   (A) LENGTH: 191 amino acids
   (B) TYPE: amino acid
   (C) STRANDEDNESS: unknown
   (D) TOPOLOGY: unknown (vi) ORIGINAL SOURCE:
   (A) ORGANISM: homosapiens
   (C) INDIVIDUAL ISOLATE: P8

(xi) SEQUENCE DESCRIPTION: SEQ ID NO: 175:

| Met | Ser | Thr | Thr | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |
| Thr | Ser | Arg | Arg | Pro | Gln | Asp | Val | Lys | Phe | Pro | Gly | Gly | Gly |
| 15 | | | | 20 | | | | | 25 | | | | |
| Gln | Ile | Val | Gly | Gly | Val | Tyr | Leu | Leu | Pro | Arg | Arg | Gly | Pro |
| | 30 | | | | 35 | | | | | 40 | | | |
| Arg | Leu | Gly | Val | Arg | Ala | Thr | Arg | Lys | Thr | Ser | Glu | Arg | Ser |

|     |     |     | 45  |     |     |     | 50  |     |     |     | 55  |     |
| --- | --- | --- | --- | --- | --- | --- | --- | --- | --- | --- | --- | --- |
| Gln | Pro | Arg | Gly | Arg | Arg | Gln | Pro | Ile | Pro | Lys | Ala | Arg | Arg |
|     |     |     | 60  |     |     |     | 65  |     |     |     |     | 70  |
| Pro | Glu | Gly | Arg | Ala | Trp | Ala | Gln | Pro | Gly | His | Pro | Trp | Pro |
|     |     |     |     | 75  |     |     |     | 80  |     |     |     |     |
| Leu | Tyr | Ala | Asn | Glu | Gly | Leu | Gly | Trp | Ala | Gly | Trp | Leu | Leu |
| 85  |     |     |     |     | 90  |     |     |     |     | 95  |     |     |
| Ser | Pro | Arg | Gly | Ser | Arg | Pro | Ser | Trp | Gly | Pro | Thr | Asp | Pro |
|     |     | 100 |     |     |     | 105 |     |     |     |     | 110 |     |     |
| Arg | Arg | Arg | Ser | Arg | Asn | Leu | Gly | Lys | Val | Ile | Asp | Thr | Leu |
|     |     | 115 |     |     |     | 120 |     |     |     |     | 125 |     |     |
| Thr | Cys | Gly | Phe | Ala | Asp | Leu | Met | Gly | Tyr | Ile | Pro | Leu | Val |
|     |     |     | 130 |     |     |     | 135 |     |     |     |     | 140 |
| Gly | Gly | Pro | Leu | Gly | Gly | Val | Ala | Arg | Ala | Leu | Ala | His | Gly |
|     |     |     |     | 145 |     |     |     |     | 150 |     |     |     |
| Val | Arg | Val | Val | Glu | Asp | Gly | Val | Asn | Tyr | Ala | Thr | Gly | Asn |
| 155 |     |     |     |     | 160 |     |     |     |     | 165 |     |     |
| Leu | Pro | Gly | Cys | Ser | Phe | Ser | Ile | Phe | Leu | Leu | Ala | Leu | Leu |
|     | 170 |     |     |     |     | 175 |     |     |     |     | 180 |     |     |
| Ser | Cys | Leu | Thr | Ile | Pro | Ala | Ser | Ala |
|     |     | 185 |     |     |     |     | 190 |     |

( 2 ) INFORMATION FOR SEQ ID NO: 176:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T3

( x i ) SEQUENCE DESCRIPTION: SEQ ID NO: 176:

| Met | Ser | Thr | Asn | Pro | Lys | Pro | Gln | Arg | Lys | Thr | Lys | Arg | Asn |
| --- | --- | --- | --- | --- | --- | --- | --- | --- | --- | --- | --- | --- | --- |
| 1   |     |     |     | 5   |     |     |     |     | 10  |     |     |     |     |
| Thr | Asn | Arg | Arg | Pro | Gln | Asp | Val | Lys | Phe | Pro | Gly | Gly | Gly |
| 15  |     |     |     |     | 20  |     |     |     |     | 25  |     |     |     |
| Gln | Ile | Val | Gly | Gly | Val | Tyr | Leu | Leu | Pro | Arg | Arg | Gly | Pro |
|     |     | 30  |     |     |     |     | 35  |     |     |     |     | 40  |     |
| Arg | Leu | Gly | Val | Arg | Ala | Thr | Arg | Lys | Thr | Ser | Glu | Arg | Ser |
|     |     |     | 45  |     |     |     |     | 50  |     |     |     |     | 55  |
| Gln | Pro | Arg | Gly | Arg | Arg | Gln | Pro | Ile | Pro | Lys | Ala | Arg | Arg |
|     |     |     | 60  |     |     |     |     | 65  |     |     |     |     | 70  |
| Pro | Glu | Gly | Arg | Ala | Trp | Ala | Gln | Pro | Gly | Tyr | Pro | Trp | Pro |
|     |     |     |     | 75  |     |     |     |     | 80  |     |     |     |     |
| Leu | Tyr | Gly | Asp | Glu | Gly | Met | Gly | Trp | Ala | Gly | Trp | Leu | Leu |
| 85  |     |     |     |     | 90  |     |     |     |     | 95  |     |     |     |
| Ser | Pro | Arg | Gly | Ser | Arg | Pro | Asn | Trp | Gly | Pro | Thr | Asp | Pro |
|     |     | 100 |     |     |     | 105 |     |     |     |     | 110 |     |     |
| Arg | Arg | Arg | Ser | Arg | Asn | Leu | Gly | Lys | Val | Ile | Asp | Thr | Leu |
|     |     | 115 |     |     |     | 120 |     |     |     |     | 125 |     |     |
| Thr | Cys | Gly | Phe | Ala | Asp | Leu | Met | Gly | Tyr | Ile | Pro | Leu | Val |
|     |     |     | 130 |     |     |     |     | 135 |     |     |     |     | 140 |
| Gly | Ala | Pro | Leu | Gly | Gly | Val | Ala | Arg | Ala | Leu | Ala | His | Gly |
|     |     |     |     | 145 |     |     |     |     | 150 |     |     |     |     |

| Val | Arg | Val | Leu | Glu | Asp | Gly | Val | Asn | Tyr | Ala | Thr | Gly | Asn |
| 155 | | | | | 160 | | | | 165 | | | | |

| Leu | Pro | Gly | Cys | Ser | Phe | Ser | Ile | Phe | Leu | Leu | Ala | Leu | Leu |
| | 170 | | | | | 175 | | | | 180 | | | |

| Ser | Cys | Leu | Thr | Ile | Pro | Ala | Ser | Ala |
| | | 185 | | | | | 190 | |

( 2 ) INFORMATION FOR SEQ ID NO: 177:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T4

( x i ) SEQUENCE DESCRIPTION: SEQ ID NO: 177:

| Met | Ser | Thr | Asn | Pro | Lys | Pro | Gln | Arg | Lys | Thr | Lys | Arg | Asn |
| 1 | | | | 5 | | | | | 10 | | | | |

| Thr | Asn | Arg | Arg | Pro | Gln | Asp | Val | Lys | Phe | Pro | Gly | Gly | Gly |
| 15 | | | | | 20 | | | | | 25 | | | |

| Gln | Ile | Val | Gly | Gly | Val | Tyr | Leu | Leu | Pro | Arg | Arg | Gly | Pro |
| | | 30 | | | | | 35 | | | | | 40 | |

| Arg | Leu | Gly | Val | Arg | Ala | Thr | Arg | Lys | Thr | Ser | Glu | Arg | Ser |
| | | | 45 | | | | | 50 | | | | | 55 |

| Gln | Pro | Arg | Gly | Arg | Arg | Gln | Pro | Ile | Pro | Lys | Asp | Arg | Arg |
| | | | | 60 | | | | | 65 | | | | 70 |

| Ser | Thr | Gly | Lys | Ser | Trp | Gly | Lys | Pro | Gly | Tyr | Pro | Trp | Pro |
| | | | | | 75 | | | | | 80 | | | |

| Leu | Tyr | Gly | Asn | Glu | Gly | Leu | Gly | Trp | Ala | Gly | Trp | Leu | Leu |
| 85 | | | | | 90 | | | | | 95 | | | |

| Ser | Pro | Arg | Gly | Ser | Arg | Pro | Ser | Trp | Gly | Pro | Asn | Asp | Pro |
| | 100 | | | | | 105 | | | | | 110 | | |

| Arg | His | Arg | Ser | Arg | Asn | Val | Gly | Lys | Val | Ile | Asp | Thr | Leu |
| | | 115 | | | | | 120 | | | | | 125 | |

| Thr | Cys | Ser | Leu | Ala | Asp | Leu | Met | Gly | Tyr | Val | Pro | Val | Val |
| | | | 130 | | | | | 135 | | | | | 140 |

| Gly | Gly | Pro | Leu | Gly | Gly | Val | Ala | Arg | Ala | Leu | Ala | His | Gly |
| | | | | 145 | | | | | 150 | | | | |

| Val | Arg | Val | Leu | Glu | Asp | Gly | Val | Asn | Tyr | Ala | Thr | Gly | Asn |
| 155 | | | | | 160 | | | | 165 | | | | |

| Leu | Pro | Gly | Cys | Ser | Phe | Ser | Ile | Phe | Leu | Leu | Ala | Leu | Leu |
| | 170 | | | | | 175 | | | | 180 | | | |

| Ser | Cys | Ile | Thr | Ile | Pro | Val | Ser | Ala |
| | | 185 | | | | | 190 | |

( 2 ) INFORMATION FOR SEQ ID NO: 178:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: US10

( x i ) SEQUENCE DESCRIPTION: SEQ ID NO: 178:

Met Ser Thr Asn Pro Lys Pro Gln Arg Lys Thr Lys Arg Asn
1               5                   10
Thr Asn Arg Arg Pro Gln Asp Val Lys Phe Pro Gly Gly Gly
15              20                  25
Gln Ile Val Gly Gly Val Tyr Leu Leu Pro Arg Arg Gly Pro
    30              35                  40
Arg Leu Gly Val Arg Ala Thr Arg Lys Thr Ser Glu Arg Ser
        45              50                  55
Gln Pro Arg Gly Arg Arg Gln Pro Ile Pro Lys Asp Arg Arg
            60              65                  70
Pro Thr Gly Lys Ser Trp Gly Lys Pro Gly Tyr Pro Trp Pro
                75              80
Leu Tyr Gly Asn Glu Gly Leu Gly Trp Ala Gly Trp Leu Leu
85                  90                  95
Ser Pro Arg Gly Ser Arg Pro Ser Trp Gly Pro Thr Asp Pro
    100             105                 110
Arg His Arg Ser Arg Asn Val Gly Lys Val Ile Asp Thr Leu
        115             120                 125
Thr Cys Gly Phe Ala Asp Leu Met Gly Tyr Ile Pro Val Val
            130             135                 140
Gly Ala Pro Leu Gly Val Ala Arg Ala Leu Ala His Gly
                145             150
Val Arg Val Leu Glu Asp Gly Val Asn Tyr Ala Thr Gly Asn
155                 160                 165
Leu Pro Gly Cys Ser Phe Ser Ile Phe Leu Leu Ala Leu Leu
    170             175                 180
Ser Cys Ile Thr Ile Pro Val Ser Ala
        185             190

( 2 ) INFORMATION FOR SEQ ID NO: 179:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T9

( x i ) SEQUENCE DESCRIPTION: SEQ ID NO: 179:

Met Ser Thr Asn Pro Lys Pro Gln Arg Lys Thr Ile Arg Asn
1               5                   10
Thr Asn Arg Arg Pro Gln Asp Val Lys Phe Pro Gly Gly Gly
15              20                  25
Gln Ile Val Gly Gly Val Tyr Leu Leu Pro Arg Arg Gly Pro
    30              35                  40
Arg Leu Gly Val Arg Thr Thr Arg Lys Thr Ser Glu Arg Ser
        45              50                  55
Gln Pro Arg Gly Arg Arg Gln Pro Ile Pro Lys Asp Arg Arg
            60              65                  70
Ser Thr Gly Lys Ser Trp Gly Lys Pro Gly Tyr Pro Trp Pro
                75              80
Leu Tyr Gly Asn Glu Gly Leu Gly Trp Ala Gly Trp Leu Leu
85                  90                  95
Ser Pro Arg Gly Ser Arg Pro Ser Trp Gly Pro Ser Asp Pro

|   |   |   | 100 |   |   |   |   | 105 |   |   |   |   | 110 |   |   |
|---|---|---|---|---|---|---|---|---|---|---|---|---|---|---|---|
| Arg | His | Arg | Ser | Arg | Asn | Val | Gly | Lys | Val | Ile | Asp | Thr | Leu |   |   |
|   |   |   | 115 |   |   |   |   | 120 |   |   |   |   | 125 |   |   |
| Thr | Cys | Gly | Phe | Ala | Asp | Leu | Met | Gly | Tyr | Ile | Pro | Val | Val |   |   |
|   |   |   | 130 |   |   |   |   | 135 |   |   |   |   | 140 |   |   |
| Gly | Ala | Pro | Leu | Gly | Gly | Val | Ala | Arg | Ala | Leu | Ala | His | Gly |   |   |
|   |   |   | 145 |   |   |   |   | 150 |   |   |   |   |   |   |   |
| Val | Arg | Val | Leu | Glu | Asp | Gly | Val | Asn | Tyr | Ala | Thr | Gly | Asn |   |   |
| 155 |   |   |   | 160 |   |   |   |   | 165 |   |   |   |   |   |   |
| Leu | Pro | Gly | Cys | Ser | Phe | Ser | Ile | Phe | Leu | Leu | Ala | Leu | Leu |   |   |
|   |   | 170 |   |   |   | 175 |   |   |   |   | 180 |   |   |   |   |
| Ser | Cys | Ile | Thr | Thr | Pro | Ala | Ser | Ala |   |   |   |   |   |   |   |
|   |   | 185 |   |   |   |   | 190 |   |   |   |   |   |   |   |   |

( 2 ) INFORMATION FOR SEQ ID NO: 180:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T2

( x i ) SEQUENCE DESCRIPTION: SEQ ID NO: 180:

|   |   |   |   |   |   |   |   |   |   |   |   |
|---|---|---|---|---|---|---|---|---|---|---|---|
| Met | Ser | Thr | Ile | Pro | Lys | Pro | Gln | Arg | Lys | Thr | Lys | Arg | Asn |
| 1 |   |   |   | 5 |   |   |   |   | 10 |   |   |   |   |
| Thr | Asn | Arg | Arg | Pro | Gln | Asp | Val | Lys | Phe | Pro | Gly | Gly | Gly |
| 15 |   |   |   |   | 20 |   |   |   |   | 25 |   |   |   |
| Gln | Ile | Val | Gly | Gly | Val | Tyr | Leu | Leu | Pro | Arg | Arg | Gly | Pro |
|   |   | 30 |   |   |   |   | 35 |   |   |   |   | 40 |   |
| Arg | Leu | Gly | Val | Arg | Ala | Thr | Arg | Lys | Thr | Ser | Glu | Arg | Ser |
|   |   |   | 45 |   |   |   |   | 50 |   |   |   |   | 55 |
| Gln | Pro | Arg | Gly | Arg | Arg | Gln | Pro | Ile | Pro | Lys | Asp | Arg | Arg |
|   |   |   | 60 |   |   |   |   | 65 |   |   |   |   | 70 |
| Ser | Thr | Gly | Lys | Ser | Trp | Gly | Lys | Pro | Gly | Tyr | Pro | Trp | Pro |
|   |   |   |   | 75 |   |   |   |   | 80 |   |   |   |   |
| Leu | Tyr | Gly | Asn | Glu | Gly | Leu | Gly | Trp | Ala | Gly | Trp | Leu | Leu |
| 85 |   |   |   |   | 90 |   |   |   |   | 95 |   |   |   |
| Ser | Pro | Arg | Gly | Ser | Arg | Pro | Ser | Trp | Gly | Pro | Asn | Asp | Pro |
|   |   | 100 |   |   |   |   | 105 |   |   |   |   | 110 |   |
| Arg | His | Arg | Ser | Arg | Asn | Val | Gly | Lys | Val | Ile | Asp | Thr | Leu |
|   |   |   | 115 |   |   |   |   | 120 |   |   |   |   | 125 |
| Thr | Cys | Gly | Phe | Ala | Asp | Leu | Met | Gly | Tyr | Ile | Pro | Val | Val |
|   |   |   | 130 |   |   |   |   | 135 |   |   |   |   | 140 |
| Gly | Ala | Pro | Leu | Gly | Gly | Val | Ala | Arg | Ala | Leu | Ala | His | Gly |
|   |   |   |   | 145 |   |   |   |   | 150 |   |   |   |   |
| Val | Arg | Val | Leu | Glu | Asp | Gly | Val | Asn | Tyr | Ala | Thr | Gly | Asn |
| 155 |   |   |   |   | 160 |   |   |   |   | 165 |   |   |   |
| Leu | Pro | Gly | Cys | Ser | Phe | Ser | Ile | Phe | Leu | Leu | Ala | Leu | Leu |
|   |   | 170 |   |   |   |   | 175 |   |   |   |   | 180 |   |
| Ser | Cys | Ile | Thr | Ile | Pro | Val | Ser | Ala |   |   |   |   |   |
|   |   | 185 |   |   |   |   | 190 |   |   |   |   |   |   |

( 2 ) INFORMATION FOR SEQ ID NO: 181:

( i ) SEQUENCE CHARACTERISTICS:
    ( A ) LENGTH: 191 amino acids
    ( B ) TYPE: amino acid
    ( C ) STRANDEDNESS: unknown
    ( D ) TOPOLOGY: unknown ( v i ) ORIGINAL SOURCE:
    ( A ) ORGANISM: homosapiens
    ( C ) INDIVIDUAL ISOLATE: T8

( x i ) SEQUENCE DESCRIPTION: SEQ ID NO: 181:

```
Met  Ser  Thr  Asn  Pro  Lys  Pro  Gln  Arg  Lys  Thr  Lys  Arg  Asn
 1               5                        10

Thr  Asn  Arg  Arg  Pro  Gln  Asp  Val  Lys  Phe  Pro  Gly  Gly  Gly
15                    20                        25

Gln  Ile  Val  Gly  Gly  Val  Tyr  Leu  Leu  Pro  Arg  Arg  Gly  Pro
     30                    35                        40

Arg  Leu  Gly  Val  Arg  Ala  Thr  Arg  Lys  Thr  Ser  Glu  Arg  Ser
          45                    50                        55

Gln  Pro  Arg  Gly  Arg  Arg  Gln  Pro  Ile  Pro  Lys  Asp  Arg  Arg
               60                    65                        70

Ser  Thr  Gly  Lys  Ser  Trp  Gly  Lys  Pro  Gly  Tyr  Pro  Trp  Pro
                    75                        80

Leu  Tyr  Gly  Asn  Glu  Gly  Cys  Gly  Trp  Ala  Gly  Trp  Leu  Leu
85                        90                        95

Ser  Pro  Arg  Gly  Ser  Arg  Pro  Thr  Trp  Gly  Pro  Thr  Asp  Pro
     100                      105                       110

Arg  His  Arg  Ser  Arg  Asn  Leu  Gly  Arg  Val  Ile  Asp  Thr  Ile
          115                      120                       125

Thr  Cys  Gly  Phe  Ala  Asp  Leu  Met  Gly  Tyr  Ile  Pro  Val  Val
               130                      135                       140

Gly  Ala  Pro  Val  Gly  Gly  Val  Ala  Arg  Ala  Leu  Ala  His  Gly
                    145                      150

Val  Arg  Val  Leu  Glu  Asp  Gly  Ile  Asn  Tyr  Ala  Thr  Gly  Asn
155                      160                      165

Leu  Pro  Gly  Cys  Ser  Phe  Ser  Ile  Phe  Leu  Leu  Ala  Leu  Leu
     170                      175                      180

Ser  Cys  Phe  Thr  Val  Pro  Val  Ser  Ala
     185                      190
```

( 2 ) INFORMATION FOR SEQ ID NO: 182:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: US1

( x i ) SEQUENCE DESCRIPTION: SEQ ID NO: 182:

```
Met  Ser  Thr  Asn  Pro  Lys  Pro  Gln  Arg  Lys  Thr  Lys  Arg  Asn
 1               5                        10

Thr  Asn  Arg  Arg  Pro  Gln  Asp  Val  Lys  Phe  Pro  Gly  Gly  Gly
15                    20                        25

Gln  Ile  Val  Gly  Gly  Val  Tyr  Leu  Leu  Pro  Arg  Arg  Gly  Pro
     30                    35                        40

Arg  Leu  Gly  Val  Arg  Ala  Thr  Arg  Lys  Thr  Ser  Glu  Arg  Ser
          45                    50                        55
```

| | | | | | | | | | | | |
|---|---|---|---|---|---|---|---|---|---|---|---|
|Gln|Pro|Arg|Gly|Arg|Arg|Gln|Pro|Ile|Pro|Lys|Asp|Arg|Arg|
| | | |60| | | |65| | | |70|
|Ser|Thr|Gly|Lys|Ser|Trp|Gly|Lys|Pro|Gly|Tyr|Pro|Trp|Pro|
| | | |75| | | |80| | | | |
|Leu|Tyr|Gly|Asn|Glu|Gly|Cys|Gly|Trp|Ala|Gly|Trp|Leu|Leu|
|85| | | |90| | | |95| | | | |
|Ser|Pro|Arg|Gly|Ser|Arg|Pro|Thr|Trp|Gly|Pro|Thr|Asp|Pro|
| |100| | | |105| | | | |110| | |
|Arg|His|Arg|Ser|Arg|Asn|Leu|Gly|Lys|Val|Ile|Asp|Thr|Ile|
| | |115| | | |120| | | | |125| |
|Thr|Cys|Gly|Phe|Ala|Asp|Leu|Met|Gly|Tyr|Ile|Pro|Val|Val|
| | | |130| | | |135| | | | |140|
|Gly|Ala|Pro|Val|Gly|Gly|Val|Ala|Arg|Ala|Leu|Ala|His|Gly|
| | | | |145| | | |150| | | | |
|Val|Arg|Val|Leu|Glu|Asp|Gly|Ile|Asn|Tyr|Ala|Thr|Gly|Asn|
|155| | | | |160| | | |165| | | |
|Leu|Pro|Gly|Cys|Ser|Phe|Ser|Ile|Phe|Leu|Leu|Ala|Leu|Leu|
| |170| | | |175| | | | |180| | |
|Ser|Cys|Ala|Thr|Val|Pro|Val|Ser|Ala| | | | | |
| | |185| | | |190| | | | | | | |

( 2 ) INFORMATION FOR SEQ ID NO: 183:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK11

( x i ) SEQUENCE DESCRIPTION: SEQ ID NO: 183:

| | | | | | | | | | | | | | |
|---|---|---|---|---|---|---|---|---|---|---|---|---|---|
|Met|Ser|Thr|Asn|Pro|Lys|Pro|Gln|Arg|Lys|Thr|Lys|Arg|Asn|
|1| | | |5| | | |10| | | | | |
|Thr|Asn|Arg|Arg|Pro|Gln|Asp|Val|Lys|Phe|Pro|Gly|Gly|Gly|
|15| | | |20| | | |25| | | | | |
|Gln|Ile|Val|Gly|Gly|Val|Tyr|Leu|Leu|Pro|Arg|Arg|Gly|Pro|
| |30| | | |35| | | | |40| | | |
|Arg|Leu|Gly|Val|Arg|Thr|Thr|Arg|Lys|Thr|Ser|Glu|Arg|Ser|
| | |45| | | |50| | | | |55| | |
|Gln|Pro|Arg|Gly|Arg|Arg|Gln|Pro|Ile|Pro|Lys|Asp|Arg|Arg|
| | | |60| | | |65| | | |70| | |
|Ser|Thr|Gly|Lys|Pro|Trp|Gly|Lys|Pro|Gly|Tyr|Pro|Trp|Pro|
| | | |75| | | |80| | | | | | |
|Leu|Tyr|Gly|Asn|Glu|Gly|Cys|Gly|Trp|Ala|Gly|Trp|Leu|Leu|
|85| | | |90| | | |95| | | | | |
|Ser|Pro|Arg|Gly|Ser|His|Pro|Asn|Trp|Gly|Pro|Thr|Asp|Pro|
| |100| | | |105| | | | |110| | | |
|Arg|His|Lys|Ser|Arg|Asn|Leu|Gly|Lys|Val|Ile|Asp|Thr|Ile|
| | |115| | | |120| | | | |125| | |
|Thr|Cys|Gly|Phe|Ala|Asp|Leu|Met|Gly|Tyr|Ile|Pro|Val|Val|
| | | |130| | | |135| | | | |140| |
|Gly|Ala|Pro|Val|Gly|Gly|Val|Ala|Arg|Ala|Leu|Ala|His|Gly|
| | | | |145| | | |150| | | | | |
|Val|Arg|Val|Leu|Glu|Asp|Gly|Ile|Asn|Tyr|Ala|Thr|Gly|Asn|

|     |     |     |
| --- | --- | --- |
| 155 | 160 | 165 |

Leu Pro Gly Cys Ser Phe Ser Ile Phe Leu Leu Ala Leu Leu
170                               175                       180

Ser Cys Cys Thr Val Pro Val Ser Ala
185                           190

( 2 ) INFORMATION FOR SEQ ID NO: 184:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SW3

( x i ) SEQUENCE DESCRIPTION: SEQ ID NO: 184:

Met Ser Thr Asn Pro Lys Pro Gln Arg Lys Thr Lys Arg Asn
1                       5                           10

Thr Asn Arg Arg Pro Gln Asp Val Lys Phe Pro Gly Gly Gly
15                      20                      25

Gln Ile Val Gly Gly Val Tyr Leu Leu Pro Arg Arg Gly Pro
30                          35                      40

Arg Leu Gly Val Arg Ala Thr Arg Lys Thr Ser Glu Arg Ser
45                          50                      55

Gln Pro Arg Gly Arg Arg Gln Pro Ile Pro Lys Asp Arg Arg
60                          65                          70

Ser Thr Gly Lys Ser Trp Gly Lys Pro Gly Tyr Pro Trp Pro
75                                  80

Leu Tyr Gly Asn Glu Gly Cys Gly Trp Ala Gly Trp Leu Leu
85                      90                      95

Ser Pro Arg Gly Ser His Pro Asn Trp Gly Pro Thr Asp Pro
100                     105                     110

Arg His Arg Ser Arg Asn Leu Gly Lys Val Ile Asp Thr Ile
115                     120                     125

Thr Cys Gly Phe Ala Asp Leu Met Gly Tyr Ile Pro Val Val
130                         135                         140

Gly Ala Pro Val Gly Gly Val Ala Arg Ala Leu Ala His Gly
145                         150

Val Arg Val Leu Glu Asp Gly Ile Asn Tyr Ala Thr Gly Asn
155                     160                     165

Leu Pro Gly Cys Ser Phe Ser Ile Phe Leu Leu Ala Leu Leu
170                               175                       180

Ser Cys Phe Thr Val Pro Val Ser Ala
185                           190

( 2 ) INFORMATION FOR SEQ ID NO: 185:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK8

( x i ) SEQUENCE DESCRIPTION: SEQ ID NO: 185:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |

| Thr | Asn | Arg | Arg | Pro | Gln | Asp | Val | Lys | Phe | Pro | Gly | Gly | Gly |
|---|---|---|---|---|---|---|---|---|---|---|---|---|---|
| 15 | | | | | 20 | | | | | 25 | | | |

| Gln | Ile | Val | Gly | Gly | Val | Tyr | Leu | Leu | Pro | Arg | Arg | Gly | Pro |
|---|---|---|---|---|---|---|---|---|---|---|---|---|---|
| | | 30 | | | | 35 | | | | | 40 | | |

| Arg | Leu | Gly | Val | Arg | Ala | Thr | Arg | Lys | Ser | Ser | Glu | Arg | Ser |
|---|---|---|---|---|---|---|---|---|---|---|---|---|---|
| | | | 45 | | | | 50 | | | | | 55 | |

| Gln | Pro | Arg | Gly | Arg | Arg | Gln | Pro | Ile | Pro | Lys | Asp | Arg | Arg |
|---|---|---|---|---|---|---|---|---|---|---|---|---|---|
| | | | | 60 | | | | 65 | | | | | 70 |

| Ser | Thr | Gly | Lys | Ser | Trp | Gly | Lys | Pro | Gly | Tyr | Pro | Trp | Pro |
|---|---|---|---|---|---|---|---|---|---|---|---|---|---|
| | | | | | 75 | | | | 80 | | | | |

| Leu | Tyr | Gly | Asn | Glu | Gly | Cys | Gly | Trp | Ala | Gly | Trp | Leu | Leu |
|---|---|---|---|---|---|---|---|---|---|---|---|---|---|
| 85 | | | | | 90 | | | | | 95 | | | |

| Ser | Pro | Arg | Gly | Ser | Arg | Pro | Thr | Trp | Gly | Pro | Thr | Asp | Pro |
|---|---|---|---|---|---|---|---|---|---|---|---|---|---|
| | 100 | | | | | 105 | | | | | 110 | | |

| Arg | His | Arg | Ser | Arg | Asn | Leu | Gly | Lys | Val | Ile | Asp | Thr | Ile |
|---|---|---|---|---|---|---|---|---|---|---|---|---|---|
| | | 115 | | | | | 120 | | | | | 125 | |

| Thr | Cys | Gly | Phe | Ala | Asp | Leu | Met | Gly | Tyr | Ile | Pro | Val | Val |
|---|---|---|---|---|---|---|---|---|---|---|---|---|---|
| | | | 130 | | | | | 135 | | | | | 140 |

| Gly | Ala | Pro | Val | Gly | Gly | Val | Ala | Arg | Ala | Leu | Ala | His | Gly |
|---|---|---|---|---|---|---|---|---|---|---|---|---|---|
| | | | | 145 | | | | | 150 | | | | |

| Val | Arg | Val | Leu | Glu | Asp | Gly | Ile | Asn | Tyr | Ala | Thr | Gly | Asn |
|---|---|---|---|---|---|---|---|---|---|---|---|---|---|
| 155 | | | | | 160 | | | | | 165 | | | |

| Leu | Pro | Gly | Cys | Ser | Phe | Ser | Ile | Phe | Leu | Leu | Ala | Leu | Leu |
|---|---|---|---|---|---|---|---|---|---|---|---|---|---|
| | 170 | | | | | 175 | | | | | 180 | | |

| Ser | Cys | Cys | Thr | Val | Pro | Val | Ser | Ala |
|---|---|---|---|---|---|---|---|---|
| | | 185 | | | | | 190 | |

( 2 ) INFORMATION FOR SEQ ID NO: 186:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S83

( x i ) SEQUENCE DESCRIPTION: SEQ ID NO: 186:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |

| Thr | Asn | Arg | Arg | Pro | Gln | Asp | Val | Lys | Phe | Pro | Gly | Gly | Gly |
|---|---|---|---|---|---|---|---|---|---|---|---|---|---|
| 15 | | | | | 20 | | | | | 25 | | | |

| Gln | Ile | Val | Gly | Gly | Val | Tyr | Leu | Leu | Pro | Arg | Arg | Gly | Pro |
|---|---|---|---|---|---|---|---|---|---|---|---|---|---|
| | | 30 | | | | 35 | | | | | 40 | | |

| Arg | Leu | Gly | Val | Arg | Ala | Thr | Arg | Lys | Thr | Ser | Glu | Arg | Ser |
|---|---|---|---|---|---|---|---|---|---|---|---|---|---|
| | | | 45 | | | | 50 | | | | | 55 | |

| Gln | Pro | Arg | Gly | Arg | Arg | Gln | Pro | Ile | Pro | Lys | Asp | Arg | Arg |
|---|---|---|---|---|---|---|---|---|---|---|---|---|---|
| | | | | 60 | | | | 65 | | | | | 70 |

| Thr | Thr | Gly | Lys | Ser | Trp | Gly | Arg | Pro | Gly | Tyr | Pro | Trp | Pro |
|---|---|---|---|---|---|---|---|---|---|---|---|---|---|
| | | | | | 75 | | | | 80 | | | | |

| Leu | Tyr | Gly | Asn | Glu | Gly | Leu | Gly | Trp | Ala | Gly | Trp | Leu | Leu |
|---|---|---|---|---|---|---|---|---|---|---|---|---|---|
| 85 | | | | | 90 | | | | | 95 | | | |

| Ser | Pro | Arg | Gly | Ser | Arg | Pro | Ser | Trp | Gly | Pro | Thr | Asp | Pro |
|---|---|---|---|---|---|---|---|---|---|---|---|---|---|
| | 100 | | | | | 105 | | | | | 110 | | |

Arg His Lys Ser Arg Asn Leu Gly Lys Val Ile Asp Thr Leu
        115                 120                 125

Thr Cys Gly Phe Ala Asp Leu Met Gly Tyr Ile Pro Val Val
            130                 135                     140

Gly Ala Pro Val Gly Gly Val Ala Arg Ala Leu Ala His Gly
                145                 150

Val Arg Val Leu Glu Asp Gly Ile Asn Tyr Ala Thr Gly Asn
155                 160                 165

Leu Pro Gly Cys Ser Phe Ser Ile Phe Leu Leu Ala Leu Leu
        170             175                 180

Ser Cys Ile Ser Val Pro Val Ser Ala
            185             190

( 2 ) INFORMATION FOR SEQ ID NO: 187:

( i ) SEQUENCE CHARACTERISTICS:
           ( A ) LENGTH: 191 amino acids
           ( B ) TYPE: amino acid
           ( C ) STRANDEDNESS: unknown
           ( D ) TOPOLOGY: unknown ( v i ) ORIGINAL SOURCE:
           ( A ) ORGANISM: homosapiens
           ( C ) INDIVIDUAL ISOLATE: HK10

( x i ) SEQUENCE DESCRIPTION: SEQ ID NO: 187:

Met Ser Thr Leu Pro Lys Pro Gln Arg Lys Thr Lys Arg Asn
1               5                   10

Thr Ile Arg Arg Pro Gln Asp Val Lys Phe Pro Gly Gly Gly
15                  20                  25

Gln Ile Val Gly Gly Val Tyr Val Leu Pro Arg Arg Gly Pro
    30                  35                  40

Arg Leu Gly Val Arg Ala Thr Arg Lys Thr Ser Glu Arg Ser
        45                  50                  55

Gln Pro Arg Gly Arg Arg Gln Pro Ile Pro Lys Ala Arg Arg
            60                  65                  70

Ser Glu Gly Arg Ser Trp Ala Gln Pro Gly Tyr Pro Trp Pro
                75                  80

Leu Tyr Gly Asn Glu Gly Cys Gly Trp Ala Gly Trp Leu Leu
85                  90                  95

Ser Pro Arg Gly Ser Arg Pro Ser Trp Gly Pro Asn Asp Pro
    100                 105                 110

Arg Arg Arg Ser Arg Asn Leu Gly Lys Val Ile Asp Thr Leu
        115                 120                 125

Thr Cys Gly Phe Ala Asp Leu Met Gly Tyr Ile Pro Leu Val
            130                 135                     140

Gly Ala Pro Val Gly Gly Val Ala Arg Ala Leu Ala His Gly
                145                 150

Val Arg Ala Leu Glu Asp Gly Ile Asn Phe Ala Thr Gly Asn
155                 160                 165

Leu Pro Gly Cys Ser Phe Ser Ile Phe Leu Leu Ala Leu Phe
        170             175                 180

Ser Cys Leu Ile His Pro Ala Ala Ser
            185             190

( 2 ) INFORMATION FOR SEQ ID NO: 188:

( i ) SEQUENCE CHARACTERISTICS:

(A) LENGTH: 191 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S52

(xi) SEQUENCE DESCRIPTION: SEQ ID NO: 188:

```
Met Ser Thr Leu Pro Lys Pro Gln Arg Lys Thr Lys Arg Asn
 1               5                  10
Thr Ile Arg Arg Pro Gln Asp Val Lys Phe Pro Gly Gly Gly
 15              20                  25
Gln Ile Val Gly Gly Val Tyr Val Leu Pro Arg Arg Gly Pro
 30                      35                  40
Arg Leu Gly Val Arg Ala Thr Arg Lys Thr Ser Glu Arg Ser
         45                  50                  55
Gln Pro Arg Gly Arg Arg Gln Pro Ile Pro Lys Ala Arg Arg
             60                  65                  70
Ser Glu Gly Arg Ser Trp Ala Gln Pro Gly Tyr Pro Trp Pro
                 75                  80
Leu Tyr Gly Asn Glu Gly Cys Gly Trp Ala Gly Trp Leu Leu
 85                  90                  95
Ser Pro Arg Gly Ser Arg Pro Ser Trp Gly Pro Asn Asp Pro
     100                 105                 110
Arg Arg Arg Ser Arg Asn Leu Gly Lys Val Ile Asp Thr Leu
         115                 120                 125
Thr Cys Gly Phe Ala Asp Leu Met Gly Tyr Ile Pro Leu Val
             130                 135                 140
Gly Ala Pro Val Gly Gly Val Ala Arg Ala Leu Ala His Gly
                 145                 150
Val Arg Ala Leu Glu Asp Gly Ile Asn Phe Ala Thr Gly Asn
 155                 160                 165
Leu Pro Gly Cys Ser Phe Ser Ile Phe Leu Leu Ala Leu Phe
     170                 175                 180
Ser Cys Leu Val His Pro Ala Ala Ser
         185                 190
```

(2) INFORMATION FOR SEQ ID NO: 189:

(i) SEQUENCE CHARACTERISTICS:
(A) LENGTH: 191 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S2

(xi) SEQUENCE DESCRIPTION: SEQ ID NO: 189:

```
Met Ser Thr Leu Pro Lys Pro Gln Arg Lys Thr Lys Arg Asn
 1               5                  10
Thr Ile Arg Arg Pro Gln Asp Ile Lys Phe Pro Gly Gly Gly
 15              20                  25
Gln Ile Val Gly Gly Val Tyr Val Leu Pro Arg Arg Gly Pro
 30                      35                  40
Arg Leu Gly Val Arg Ala Thr Arg Lys Thr Ser Glu Arg Ser
         45                  50                  55
```

```
Gln  Pro  Arg  Gly  Arg  Arg  Gln  Pro  Ile  Pro  Lys  Ala  Arg  Arg
               60                  65                           70

Ser  Glu  Gly  Arg  Ser  Trp  Ala  Gln  Pro  Gly  Tyr  Pro  Trp  Pro
               75                       80

Leu  Tyr  Gly  Asn  Glu  Gly  Cys  Gly  Trp  Ala  Gly  Trp  Leu  Leu
85                       90                            95

Ser  Pro  Arg  Gly  Ser  Arg  Pro  Ser  Trp  Gly  Pro  Asn  Asp  Pro
          100                     105                      110

Arg  Arg  Arg  Ser  Arg  Asn  Leu  Gly  Lys  Val  Ile  Asp  Thr  Leu
               115                120                           125

Thr  Cys  Gly  Phe  Ala  Asp  Leu  Met  Gly  Tyr  Ile  Pro  Leu  Val
               130                     135                           140

Gly  Ala  Pro  Val  Gly  Gly  Val  Ala  Arg  Ala  Leu  Ala  His  Gly
                    145                      150

Val  Arg  Ala  Leu  Glu  Asp  Gly  Ile  Asn  Phe  Ala  Thr  Gly  Asn
155                      160                      165

Leu  Pro  Gly  Cys  Ser  Phe  Ser  Ile  Phe  Leu  Leu  Ala  Leu  Phe
     170                     175                           180

Ser  Cys  Leu  Ile  His  Pro  Ala  Ala  Ser
               185                190
```

( 2 ) INFORMATION FOR SEQ ID NO: 190:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK12

( x i ) SEQUENCE DESCRIPTION: SEQ ID NO: 190:

```
Met  Ser  Thr  Leu  Pro  Lys  Pro  Gln  Arg  Lys  Thr  Lys  Arg  Asn
1                   5                       10

Thr  Ile  Arg  Arg  Pro  Gln  Asp  Val  Lys  Phe  Pro  Gly  Gly  Gly
15                       20                      25

Gln  Ile  Val  Gly  Gly  Val  Tyr  Val  Leu  Pro  Arg  Arg  Gly  Pro
     30                       35                           40

Arg  Leu  Gly  Val  Arg  Ala  Thr  Arg  Lys  Thr  Ser  Glu  Arg  Ser
               45                  50                           55

Gln  Pro  Arg  Gly  Arg  Arg  Gln  Pro  Ile  Pro  Lys  Ala  Arg  Arg
               60                  65                           70

Ser  Glu  Gly  Arg  Ser  Trp  Ala  Gln  Pro  Gly  Tyr  Pro  Trp  Pro
               75                       80

Leu  Tyr  Gly  Asn  Glu  Gly  Cys  Gly  Trp  Ala  Gly  Trp  Leu  Leu
85                       90                            95

Ser  Pro  Arg  Gly  Ser  Arg  Pro  Ser  Trp  Gly  Pro  Asn  Asp  Pro
          100                     105                      110

Arg  Arg  Arg  Ser  Arg  Asn  Leu  Gly  Lys  Val  Ile  Asp  Thr  Leu
               115                120                           125

Thr  Cys  Gly  Phe  Ala  Asp  Leu  Met  Gly  Tyr  Ile  Pro  Leu  Val
               130                     135                           140

Gly  Ala  Pro  Val  Gly  Gly  Val  Ala  Arg  Ala  Leu  Ala  His  Gly
                    145                      150

Val  Arg  Ala  Leu  Glu  Asp  Gly  Ile  Asn  Phe  Ala  Thr  Gly  Asn
155                      160                      165
```

Leu Pro Gly Cys Ser Phe Ser Ile Phe Leu Leu Ala Leu Phe
    170             175             180

Ser Cys Leu Ile His Pro Ala Ala Ser
        185             190

( 2 ) INFORMATION FOR SEQ ID NO: 191:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z4

( x i ) SEQUENCE DESCRIPTION: SEQ ID NO: 191:

Met Ser Thr Asn Pro Lys Pro Gln Arg Lys Thr Lys Arg Asn
 1           5                   10

Thr Asn Arg Arg Pro Met Asp Val Lys Phe Pro Gly Gly Gly
 15              20                  25

Gln Ile Val Gly Gly Val Tyr Leu Leu Pro Arg Arg Gly Pro
    30              35                  40

Arg Leu Gly Val Arg Ala Thr Arg Lys Thr Ser Glu Arg Ser
        45                  50                  55

Gln Pro Arg Gly Arg Arg Gln Pro Ile Pro Lys Ala Arg Gln
            60              65                      70

Pro Glu Gly Arg Ser Trp Ala Gln Pro Gly Tyr Pro Trp Pro
                75              80

Leu Tyr Gly Asn Glu Gly Cys Gly Trp Ala Gly Trp Leu Leu
 85              90                  95

Ser Pro Arg Gly Ser Arg Pro Ser Trp Gly Pro Asn Asp Pro
    100             105                 110

Arg Arg Arg Ser Arg Asn Leu Gly Lys Val Ile Asp Thr Leu
        115             120                 125

Thr Cys Gly Phe Ala Asp Leu Met Gly Tyr Ile Pro Ile Val
            130             135                 140

Gly Ala Pro Val Gly Gly Val Ala Arg Ala Leu Ala His Gly
                145                 150

Val Arg Ala Val Glu Asp Gly Ile Asn Tyr Ala Thr Gly Asn
 155                 160                 165

Leu Pro Gly Cys Ser Phe Ser Ile Phe Leu Leu Ala Leu Leu
    170             175             180

Ser Cys Leu Thr Val Pro Ala Ser Ala
        185             190

( 2 ) INFORMATION FOR SEQ ID NO: 192:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z8

( x i ) SEQUENCE DESCRIPTION: SEQ ID NO: 192:

Met Ser Thr Asn Pro Lys Pro Gln Arg Lys Thr Lys Arg Asn

|  | 1 |  |  |  | 5 |  |  |  |  | 10 |  |  |  |
|---|---|---|---|---|---|---|---|---|---|---|---|---|---|
| Thr | Asn | Arg | Arg | Pro | Met | Asp | Val | Lys | Phe | Pro | Gly | Gly | Gly |
| 15 |  |  |  |  | 20 |  |  |  |  | 25 |  |  |  |
| Gln | Ile | Val | Gly | Gly | Val | Tyr | Leu | Leu | Pro | Arg | Arg | Gly | Pro |
|  | 30 |  |  |  | 35 |  |  |  |  | 40 |  |  |  |
| Arg | Leu | Gly | Val | Arg | Ala | Thr | Arg | Lys | Thr | Ser | Glu | Arg | Ser |
|  |  | 45 |  |  |  | 50 |  |  |  |  |  | 55 |  |
| Gln | Pro | Arg | Gly | Arg | Arg | Gln | Pro | Ile | Pro | Lys | Ala | Arg | Arg |
|  |  |  | 60 |  |  |  |  | 65 |  |  |  |  | 70 |
| Ser | Glu | Gly | Arg | Ser | Trp | Ala | Gln | Pro | Gly | Tyr | Pro | Trp | Pro |
|  |  |  |  | 75 |  |  |  |  | 80 |  |  |  |  |
| Leu | Tyr | Gly | Asn | Glu | Gly | Cys | Gly | Trp | Ala | Gly | Trp | Leu | Leu |
| 85 |  |  |  |  | 90 |  |  |  |  | 95 |  |  |  |
| Ser | Pro | Arg | Gly | Ser | Arg | Pro | Ser | Trp | Gly | Pro | Asn | Asp | Pro |
|  | 100 |  |  |  | 105 |  |  |  |  | 110 |  |  |  |
| Arg | Arg | Arg | Ser | Arg | Asn | Leu | Gly | Lys | Val | Ile | Asp | Thr | Leu |
|  |  | 115 |  |  |  | 120 |  |  |  |  | 125 |  |  |
| Thr | Cys | Gly | Phe | Ala | Asp | Leu | Met | Gly | Tyr | Ile | Pro | Leu | Val |
|  |  |  | 130 |  |  |  |  | 135 |  |  |  |  | 140 |
| Gly | Ala | Pro | Val | Gly | Gly | Val | Ala | Arg | Ala | Leu | Ala | His | Gly |
|  |  |  |  | 145 |  |  |  |  | 150 |  |  |  |  |
| Val | Arg | Ala | Val | Glu | Asp | Gly | Ile | Asn | Tyr | Ala | Thr | Gly | Asn |
| 155 |  |  |  |  | 160 |  |  |  |  | 165 |  |  |  |
| Leu | Pro | Gly | Cys | Ser | Phe | Ser | Ile | Phe | Leu | Leu | Ala | Leu | Leu |
|  | 170 |  |  |  |  | 175 |  |  |  |  | 180 |  |  |
| Ser | Cys | Leu | Thr | Val | Pro | Ala | Ser | Ala |  |  |  |  |  |
|  |  | 185 |  |  |  |  | 190 |  |  |  |  |  |  |

(2) INFORMATION FOR SEQ ID NO: 193:

(i) SEQUENCE CHARACTERISTICS:
        (A) LENGTH: 191 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z1

(xi) SEQUENCE DESCRIPTION: SEQ ID NO: 193:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 |  |  |  | 5 |  |  |  |  | 10 |  |  |  |  |
| Thr | Asn | Arg | Arg | Pro | Met | Asp | Val | Lys | Phe | Pro | Gly | Gly | Gly |
| 15 |  |  |  |  | 20 |  |  |  |  | 25 |  |  |  |
| Gln | Ile | Val | Gly | Gly | Val | Tyr | Leu | Leu | Pro | Arg | Arg | Gly | Pro |
|  | 30 |  |  |  | 35 |  |  |  |  | 40 |  |  |  |
| Arg | Leu | Gly | Val | Arg | Ala | Ala | Arg | Lys | Thr | Ser | Glu | Arg | Ser |
|  |  | 45 |  |  |  | 50 |  |  |  |  |  | 55 |  |
| Gln | Pro | Arg | Gly | Arg | Arg | Gln | Pro | Ile | Pro | Lys | Ala | Arg | Arg |
|  |  |  | 60 |  |  |  |  | 65 |  |  |  |  | 70 |
| Ser | Glu | Gly | Arg | Ser | Trp | Ala | Gln | Pro | Gly | Tyr | Pro | Trp | Pro |
|  |  |  |  | 75 |  |  |  |  | 80 |  |  |  |  |
| Leu | Tyr | Gly | Asn | Glu | Gly | Cys | Gly | Trp | Ala | Gly | Trp | Leu | Leu |
| 85 |  |  |  |  | 90 |  |  |  |  | 95 |  |  |  |
| Ser | Pro | Arg | Gly | Ser | Arg | Pro | Ser | Trp | Gly | Pro | Asn | Asp | Pro |
|  | 100 |  |  |  | 105 |  |  |  |  | 110 |  |  |  |

| Arg | Arg | Arg<br>115 | Ser | Arg | Asn | Leu | Gly<br>120 | Lys | Val | Ile | Asp | Thr<br>125 | Leu |
| Thr | Cys | Gly | Phe<br>130 | Ala | Asp | Leu | Met | Gly<br>135 | Tyr | Ile | Pro | Leu | Val<br>140 |
| Gly | Ala | Pro | Val | Gly<br>145 | Gly | Val | Ala | Arg | Ala<br>150 | Leu | Ala | His | Gly |
| Val<br>155 | Arg | Ala | Val | Glu | Asp<br>160 | Gly | Ile | Asn | Tyr | Ala<br>165 | Thr | Gly | Asn |
| Leu | Pro<br>170 | Gly | Cys | Ser | Phe | Ser<br>175 | Ile | Phe | Leu | Leu | Ala<br>180 | Leu | Leu |
| Ser | Cys | Leu<br>185 | Thr | Thr | Pro | Ala | Ser<br>190 | Ala | | | | | |

( 2 ) INFORMATION FOR SEQ ID NO: 194:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z5

( x i ) SEQUENCE DESCRIPTION: SEQ ID NO: 194:

| Met<br>1 | Ser | Thr | Asn | Pro<br>5 | Lys | Pro | Gln | Arg | Lys<br>10 | Thr | Lys | Arg | Asn |
| Thr<br>15 | Asn | Arg | Arg | Pro | Met<br>20 | Asp | Val | Lys | Phe | Pro<br>25 | Gly | Gly | Gly |
| Gln | Ile<br>30 | Val | Gly | Gly | Val | Tyr<br>35 | Leu | Leu | Pro | Arg | Arg<br>40 | Gly | Pro |
| Arg | Leu | Gly<br>45 | Val | Arg | Ala | Thr | Arg<br>50 | Lys | Thr | Ser | Glu | Arg<br>55 | Ser |
| Gln | Pro | Arg | Gly<br>60 | Arg | Arg | Gln | Pro | Ile<br>65 | Pro | Gln | Ala | Arg | Arg<br>70 |
| Ser | Glu | Gly | Arg | Ser<br>75 | Trp | Ala | Gln | Pro | Gly<br>80 | Tyr | Pro | Trp | Pro |
| Leu<br>85 | Tyr | Gly | Asn | Glu | Gly<br>90 | Cys | Gly | Trp | Ala | Gly<br>95 | Trp | Leu | Leu |
| Ser | Pro<br>100 | Arg | Gly | Ser | Arg | Pro<br>105 | Ser | Trp | Gly | Gln | Asn<br>110 | Asp | Pro |
| Arg | Arg | Arg<br>115 | Ser | Arg | Asn | Leu | Gly<br>120 | Lys | Val | Ile | Asp | Thr<br>125 | Leu |
| Thr | Cys | Gly | Phe<br>130 | Ala | Asp | Leu | Met | Gly<br>135 | Tyr | Ile | Pro | Leu | Val<br>140 |
| Gly | Ala | Pro | Val | Gly<br>145 | Gly | Val | Ala | Arg | Ala<br>150 | Leu | Ala | His | Gly |
| Val<br>155 | Arg | Ala | Leu | Glu | Asp<br>160 | Gly | Ile | Asn | Tyr | Ala<br>165 | Thr | Gly | Asn |
| Leu | Pro<br>170 | Gly | Cys | Ser | Phe | Ser<br>175 | Ile | Phe | Leu | Leu | Ala<br>180 | Leu | Phe |
| Ser | Cys | Leu<br>185 | Thr | Thr | Pro | Ala | Ser<br>190 | Ala | | | | | |

( 2 ) INFORMATION FOR SEQ ID NO: 195:

( i ) SEQUENCE CHARACTERISTICS:
        ( A ) LENGTH: 191 amino acids ( B ) TYPE: amino acid
( C ) STRANDEDNESS: unknown
( D ) TOPOLOGY: unknown ( v i ) ORIGINAL SOURCE:
( A ) ORGANISM: homosapiens
( C ) INDIVIDUAL ISOLATE: Z6

( x i ) SEQUENCE DESCRIPTION: SEQ ID NO: 195:

```
Met Ser Thr Asn Pro Lys Pro Gln Arg Lys Thr Lys Arg Asn
1               5                   10

Thr Asn Arg Arg Pro Met Asp Val Lys Phe Pro Gly Gly Gly
15                  20                  25

Gln Ile Val Gly Gly Val Tyr Leu Leu Pro Arg Arg Gly Pro
        30              35              40

Arg Leu Gly Val Arg Ala Thr Arg Lys Thr Ser Glu Arg Ser
            45              50                  55

Gln Pro Arg Gly Arg Arg Gln Pro Ile Pro Lys Ala Arg Arg
                60              65                  70

Ser Glu Gly Arg Ser Trp Ala Gln Pro Gly Tyr Pro Trp Pro
                75              80

Leu Tyr Gly Asn Glu Gly Cys Gly Trp Ala Gly Trp Leu Leu
85              90              95

Ser Pro Arg Gly Ser Arg Pro Ser Trp Gly Pro Asn Asp Pro
    100             105                 110

Arg Arg Arg Ser Arg Asn Leu Gly Lys Val Ile Asp Thr Leu
        115             120                 125

Thr Cys Gly Phe Ala Asp Leu Met Gly Tyr Ile Pro Leu Val
            130             135                 140

Gly Ala Pro Val Gly Gly Val Ala Arg Ala Leu Ala His Gly
                145             150

Val Arg Ala Val Glu Asp Gly Ile Asn Tyr Ala Thr Gly Asn
155                 160             165

Leu Pro Gly Cys Ser Phe Ser Ile Phe Leu Leu Ala Leu Leu
    170             175                 180

Ser Cys Leu Thr Val Pro Thr Ser Ala
        185             190
```

( 2 ) INFORMATION FOR SEQ ID NO: 196:

( i ) SEQUENCE CHARACTERISTICS:
( A ) LENGTH: 191 amino acids
( B ) TYPE: amino acid
( C ) STRANDEDNESS: unknown
( D ) TOPOLOGY: unknown ( v i ) ORIGINAL SOURCE:
( A ) ORGANISM: homosapiens
( C ) INDIVIDUAL ISOLATE: Z7

( x i ) SEQUENCE DESCRIPTION: SEQ ID NO: 196:

```
Met Ser Thr Asn Pro Lys Pro Gln Arg Lys Thr Lys Arg Asn
1               5                   10

Thr Asn Arg Arg Pro Met Asp Val Lys Phe Pro Gly Gly Gly
15                  20                  25

Gln Ile Val Gly Gly Val Tyr Leu Leu Pro Arg Arg Gly Pro
        30              35              40

Arg Leu Gly Val Arg Thr Thr Arg Lys Thr Ser Glu Arg Ser
            45              50                  55

Gln Pro Arg Gly Arg Arg Gln Pro Ile Pro Lys Ala Arg Arg
```

|     |     | 60  |     |     |     | 65  |     |     |     | 70  |     |
| --- | --- | --- | --- | --- | --- | --- | --- | --- | --- | --- | --- |

Ser Glu Gly Arg Ser Trp Ala Gln Pro Gly Tyr Pro Trp Pro
                75                      80

Leu Tyr Gly Asn Glu Gly Cys Gly Trp Ala Gly Trp Leu Leu
85                      90                      95

Ser Pro Arg Gly Ser Arg Pro Ser Trp Gly Pro Asn Asp Pro
        100                 105                 110

Arg Arg Arg Ser Arg Asn Leu Gly Lys Val Ile Asp Thr Leu
            115                 120                 125

Thr Cys Gly Phe Ala Asp Leu Met Gly Tyr Ile Pro Leu Val
                130                 135                 140

Gly Ala Pro Val Gly Gly Val Ala Arg Ala Leu Ala His Gly
                145                 150

Val Arg Ala Leu Glu Asp Gly Ile Asn Tyr Ala Thr Gly Asn
155                     160                 165

Leu Pro Gly Cys Ser Phe Ser Ile Phe Leu Leu Ala Leu Leu
        170                 175                 180

Ser Cys Leu Thr Val Pro Ala Ser Ala
        185                 190

(2) INFORMATION FOR SEQ ID NO: 197:

(i) SEQUENCE CHARACTERISTICS:
        (A) LENGTH: 191 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK13

(xi) SEQUENCE DESCRIPTION: SEQ ID NO: 197:

Met Ser Thr Asn Pro Lys Pro Gln Arg Lys Thr Lys Arg Asn
1               5                       10

Thr Asn Arg Arg Pro Met Asp Val Lys Phe Pro Gly Gly Gly
15                      20                      25

Gln Ile Val Gly Gly Val Tyr Leu Leu Pro Arg Arg Gly Pro
        30                      35                      40

Arg Leu Gly Val Arg Ala Thr Arg Lys Thr Ser Glu Arg Ser
        45                      50                      55

Gln Pro Arg Gly Arg Arg Gln Pro Ile Pro Lys Ala Arg Gln
                60                      65                      70

Leu Glu Gly Arg Ser Trp Ala Gln Pro Gly Tyr Pro Trp Pro
                75                      80

Leu Tyr Gly Asn Glu Gly Cys Gly Trp Ala Gly Trp Leu Leu
85                      90                      95

Ser Pro Arg Gly Ser Arg Pro Ser Trp Gly Pro Asn Asp Pro
        100                 105                 110

Arg Arg Arg Ser Arg Asn Leu Gly Lys Val Ile Asp Thr Leu
            115                 120                 125

Thr Cys Gly Phe Ala Asp Leu Met Gly Tyr Ile Pro Val Val
                130                 135                 140

Gly Ala Pro Val Gly Gly Val Ala Arg Ala Leu Ala His Gly
                145                 150

Val Arg Leu Leu Glu Asp Gly Val Asn Tyr Ala Thr Gly Asn
155                     160                 165

| Leu | Pro | Gly | Cys | Ser | Phe | Ser | Ile | Phe | Leu | Leu | Ala | Leu | Leu |
|-----|-----|-----|-----|-----|-----|-----|-----|-----|-----|-----|-----|-----|-----|
|     | 170 |     |     |     |     | 175 |     |     |     |     | 180 |     |     |

| Ser | Cys | Leu | Thr | Val | Pro | Ala | Ser | Ala |
|-----|-----|-----|-----|-----|-----|-----|-----|-----|
|     |     | 185 |     |     |     |     | 190 |     |

( 2 ) INFORMATION FOR SEQ ID NO: 198:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA4

( x i ) SEQUENCE DESCRIPTION: SEQ ID NO: 198:

| Met | Ser | Thr | Asn | Pro | Lys | Pro | Gln | Arg | Lys | Thr | Lys | Arg | Asn |
|-----|-----|-----|-----|-----|-----|-----|-----|-----|-----|-----|-----|-----|-----|
| 1   |     |     |     | 5   |     |     |     |     | 10  |     |     |     |     |

| Thr | Asn | Arg | Arg | Pro | Gln | Asp | Val | Lys | Phe | Pro | Gly | Gly | Gly |
|-----|-----|-----|-----|-----|-----|-----|-----|-----|-----|-----|-----|-----|-----|
| 15  |     |     |     |     | 20  |     |     |     |     | 25  |     |     |     |

| Gln | Ile | Val | Gly | Gly | Val | Tyr | Leu | Leu | Pro | Arg | Arg | Gly | Pro |
|-----|-----|-----|-----|-----|-----|-----|-----|-----|-----|-----|-----|-----|-----|
|     | 30  |     |     |     |     | 35  |     |     |     |     | 40  |     |     |

| Arg | Leu | Gly | Val | Arg | Ala | Thr | Arg | Lys | Thr | Ser | Glu | Arg | Ser |
|-----|-----|-----|-----|-----|-----|-----|-----|-----|-----|-----|-----|-----|-----|
|     |     | 45  |     |     |     |     | 50  |     |     |     |     | 55  |     |

| Gln | Pro | Arg | Gly | Arg | Arg | Gln | Pro | Ile | Pro | Lys | Ala | Arg | Gln |
|-----|-----|-----|-----|-----|-----|-----|-----|-----|-----|-----|-----|-----|-----|
|     |     |     |     | 60  |     |     |     |     | 65  |     |     |     | 70  |

| Pro | Thr | Gly | Arg | Ser | Trp | Gly | Gln | Pro | Gly | Tyr | Pro | Trp | Pro |
|-----|-----|-----|-----|-----|-----|-----|-----|-----|-----|-----|-----|-----|-----|
|     |     |     |     | 75  |     |     |     |     | 80  |     |     |     |     |

| Leu | Tyr | Ala | Asn | Glu | Gly | Leu | Gly | Trp | Ala | Gly | Trp | Leu | Leu |
|-----|-----|-----|-----|-----|-----|-----|-----|-----|-----|-----|-----|-----|-----|
| 85  |     |     |     |     | 90  |     |     |     |     | 95  |     |     |     |

| Ser | Pro | Arg | Gly | Ser | Arg | Pro | Asn | Trp | Gly | Pro | Asn | Asp | Pro |
|-----|-----|-----|-----|-----|-----|-----|-----|-----|-----|-----|-----|-----|-----|
|     | 100 |     |     |     |     | 105 |     |     |     |     | 110 |     |     |

| Arg | Arg | Lys | Ser | Arg | Asn | Leu | Gly | Lys | Val | Ile | Asp | Thr | Leu |
|-----|-----|-----|-----|-----|-----|-----|-----|-----|-----|-----|-----|-----|-----|
|     |     |     | 115 |     |     |     |     | 120 |     |     |     |     | 125 |

| Thr | Cys | Gly | Phe | Ala | Asp | Leu | Met | Gly | Tyr | Ile | Pro | Leu | Val |
|-----|-----|-----|-----|-----|-----|-----|-----|-----|-----|-----|-----|-----|-----|
|     |     |     |     | 130 |     |     |     |     | 135 |     |     |     | 140 |

| Gly | Gly | Pro | Val | Gly | Gly | Val | Ala | Arg | Ala | Leu | Ala | His | Gly |
|-----|-----|-----|-----|-----|-----|-----|-----|-----|-----|-----|-----|-----|-----|
|     |     |     |     |     | 145 |     |     |     |     | 150 |     |     |     |

| Val | Arg | Val | Leu | Glu | Asp | Gly | Val | Asn | Tyr | Ala | Thr | Gly | Asn |
|-----|-----|-----|-----|-----|-----|-----|-----|-----|-----|-----|-----|-----|-----|
| 155 |     |     |     |     | 160 |     |     |     |     | 165 |     |     |     |

| Leu | Pro | Gly | Cys | Ser | Phe | Ser | Ile | Phe | Ile | Leu | Ala | Leu | Leu |
|-----|-----|-----|-----|-----|-----|-----|-----|-----|-----|-----|-----|-----|-----|
|     | 170 |     |     |     |     | 175 |     |     |     |     | 180 |     |     |

| Ser | Cys | Leu | Thr | Val | Pro | Ala | Ser | Ala |
|-----|-----|-----|-----|-----|-----|-----|-----|-----|
|     |     | 185 |     |     |     |     | 190 |     |

( 2 ) INFORMATION FOR SEQ ID NO: 199:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA5

( x i ) SEQUENCE DESCRIPTION: SEQ ID NO: 199:

| Met | Ser | Thr | Asn | Pro | Lys | Pro | Gln | Arg | Lys | Thr | Lys | Arg | Asn |
|-----|-----|-----|-----|-----|-----|-----|-----|-----|-----|-----|-----|-----|-----|
| 1   |     |     |     | 5   |     |     |     |     | 10  |     |     |     |     |

| Thr | Asn | Arg | Arg | Pro | Gln | Asp | Val | Lys | Phe | Pro | Gly | Gly | Gly |
| 15 | | | | | 20 | | | | | 25 | | | |

| Gln | Ile | Val | Gly | Gly | Val | Tyr | Leu | Leu | Pro | Arg | Arg | Gly | Pro |
| | 30 | | | | | 35 | | | | | 40 | | |

| Arg | Leu | Gly | Val | Arg | Ala | Thr | Arg | Lys | Thr | Ser | Glu | Arg | Ser |
| | | 45 | | | | | 50 | | | | | 55 | |

| Gln | Pro | Arg | Gly | Arg | Arg | Gln | Pro | Ile | Pro | Lys | Ala | Arg | Gln |
| | | | 60 | | | | | 65 | | | | | 70 |

| Pro | Thr | Gly | Arg | Ser | Trp | Gly | Gln | Pro | Gly | Tyr | Pro | Trp | Pro |
| | | | | 75 | | | | | 80 | | | | |

| Leu | Tyr | Ala | Asn | Glu | Gly | Leu | Gly | Trp | Ala | Gly | Trp | Leu | Leu |
| 85 | | | | | 90 | | | | | 95 | | | |

| Ser | Pro | Arg | Gly | Ser | Arg | Pro | Asn | Trp | Gly | Pro | Asn | Asp | Pro |
| | 100 | | | | | 105 | | | | | 110 | | |

| Arg | Arg | Lys | Ser | Arg | Asn | Leu | Gly | Lys | Val | Ile | Asp | Thr | Leu |
| | | 115 | | | | | 120 | | | | | 125 | |

| Thr | Cys | Gly | Phe | Ala | Asp | Leu | Met | Gly | Tyr | Ile | Pro | Leu | Val |
| | | | 130 | | | | | 135 | | | | | 140 |

| Gly | Gly | Pro | Val | Gly | Gly | Val | Ala | Arg | Ala | Leu | Ala | His | Gly |
| | | | | 145 | | | | | 150 | | | | |

| Val | Arg | Val | Leu | Glu | Asp | Gly | Val | Asn | Tyr | Ala | Thr | Gly | Asn |
| 155 | | | | | 160 | | | | | 165 | | | |

| Leu | Pro | Gly | Cys | Ser | Phe | Ser | Ile | Phe | Ile | Leu | Ala | Leu | Leu |
| | 170 | | | | | 175 | | | | | 180 | | |

| Ser | Cys | Leu | Thr | Val | Pro | Ala | Ser | Ala |
| | | 185 | | | | | 190 | |

( 2 ) INFORMATION FOR SEQ ID NO: 200:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA7

( x i ) SEQUENCE DESCRIPTION: SEQ ID NO: 200:

| Met | Ser | Thr | Asn | Pro | Lys | Pro | Gln | Arg | Lys | Thr | Lys | Arg | Asn |
| 1 | | | | 5 | | | | | 10 | | | | |

| Thr | Asn | Arg | Arg | Pro | Gln | Asp | Val | Lys | Phe | Pro | Gly | Gly | Gly |
| 15 | | | | | 20 | | | | | 25 | | | |

| Gln | Ile | Val | Gly | Gly | Val | Tyr | Leu | Leu | Pro | Arg | Arg | Gly | Pro |
| | 30 | | | | | 35 | | | | | 40 | | |

| Arg | Leu | Gly | Val | Arg | Ala | Thr | Arg | Lys | Thr | Ser | Glu | Arg | Ser |
| | | 45 | | | | | 50 | | | | | 55 | |

| Gln | Pro | Arg | Gly | Arg | Arg | Gln | Pro | Ile | Pro | Lys | Ala | Arg | Gln |
| | | | 60 | | | | | 65 | | | | | 70 |

| Pro | Thr | Gly | Arg | Ser | Trp | Gly | Gln | Pro | Gly | Tyr | Pro | Trp | Pro |
| | | | | 75 | | | | | 80 | | | | |

| Leu | Tyr | Ala | Asn | Glu | Gly | Leu | Gly | Trp | Ala | Gly | Trp | Leu | Leu |
| 85 | | | | | 90 | | | | | 95 | | | |

| Ser | Pro | Arg | Gly | Ser | Arg | Pro | Asn | Trp | Gly | Pro | Asn | Asp | Pro |
| | 100 | | | | | 105 | | | | | 110 | | |

| Arg | Arg | Lys | Ser | Arg | Asn | Leu | Gly | Lys | Val | Ile | Asp | Thr | Leu |

|  |  |  | | 115 |  |  |  | 120 |  |  |  | 125 |  |
|---|---|---|---|---|---|---|---|---|---|---|---|---|---|

Thr Cys Gly Phe Ala Asp Leu Met Gly Tyr Ile Pro Leu Val
            130                    135                   140

Gly Gly Pro Val Gly Gly Val Ala Arg Ala Leu Ala His Gly
                  145                          150

Val Arg Val Leu Glu Asp Gly Val Asn Tyr Ala Thr Gly Asn
   155                       160                  165

Leu Pro Gly Cys Ser Phe Ser Ile Phe Ile Leu Ala Leu Leu
        170                  175                180

Ser Cys Leu Thr Val Pro Ala Ser Ala
           185                   190

( 2 ) INFORMATION FOR SEQ ID NO: 201:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA1

( x i ) SEQUENCE DESCRIPTION: SEQ ID NO: 201:

Met Ser Thr Asn Pro Lys Pro Gln Arg Lys Thr Lys Arg Asn
 1                 5                    10

Thr Asn Leu Arg Pro Gln Asp Val Lys Phe Pro Gly Gly Gly
15                   20                    25

Gln Ile Val Gly Gly Val Tyr Leu Leu Pro Arg Arg Gly Pro
   30                      35                40

Arg Leu Gly Val Arg Ala Thr Arg Lys Thr Ser Glu Arg Ser
      45                    50                55

Gln Pro Arg Gly Arg Arg Gln Pro Ile Pro Lys Ala Arg Gln
         60                  65               70

Pro Thr Gly Arg Ser Trp Gly Gln Pro Gly Tyr Pro Trp Pro
            75                  80

Leu Tyr Ala Asn Glu Gly Leu Gly Trp Ala Gly Trp Leu Leu
85                   90                    95

Ser Pro Arg Gly Ser Arg Pro Asn Trp Gly Pro Asn Asp Pro
   100                  105               110

Arg Arg Lys Ser Arg Asn Leu Gly Lys Val Ile Asp Thr Leu
      115                  120             125

Thr Cys Gly Phe Ala Asp Leu Met Gly Tyr Ile Pro Leu Val
            130                    135                   140

Gly Gly Pro Val Gly Gly Val Ala Arg Ala Leu Ala His Gly
                  145                          150

Val Arg Val Leu Glu Asp Gly Val Asn Tyr Ala Thr Gly Asn
155                   160                  165

Leu Pro Gly Cys Ser Phe Ser Ile Phe Ile Leu Ala Leu Leu
        170                  175                180

Ser Cys Leu Ile Ile Pro Ala Ser Ala
           185                   190

( 2 ) INFORMATION FOR SEQ ID NO: 202:

( i ) SEQUENCE CHARACTERISTICS:
        ( A ) LENGTH: 191 amino acids
        ( B ) TYPE: amino acid (C) STRANDEDNESS: unknown
(D) TOPOLOGY: unknown (vi) ORIGINAL SOURCE:
  (A) ORGANISM: homosapiens
  (C) INDIVIDUAL ISOLATE: SA3

(xi) SEQUENCE DESCRIPTION: SEQ ID NO: 202:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |

| Thr | Asn | Arg | Arg | Pro | Gln | Asp | Val | Lys | Phe | Pro | Gly | Gly | Gly |
|---|---|---|---|---|---|---|---|---|---|---|---|---|---|
| 15 | | | | | 20 | | | | | 25 | | | |

| Gln | Ile | Val | Gly | Gly | Val | Tyr | Leu | Leu | Pro | Arg | Arg | Gly | Pro |
|---|---|---|---|---|---|---|---|---|---|---|---|---|---|
| | | 30 | | | | 35 | | | | | 40 | | |

| Arg | Leu | Gly | Val | Arg | Ala | Thr | Arg | Lys | Thr | Ser | Glu | Arg | Ser |
|---|---|---|---|---|---|---|---|---|---|---|---|---|---|
| | | 45 | | | | | 50 | | | | | 55 | |

| Gln | Pro | Arg | Gly | Arg | Arg | Gln | Pro | Ile | Pro | Lys | Ala | Arg | Gln |
|---|---|---|---|---|---|---|---|---|---|---|---|---|---|
| | | | 60 | | | | | 65 | | | | | 70 |

| Pro | Thr | Gly | Arg | Ser | Trp | Gly | Gln | Pro | Gly | Tyr | Pro | Trp | Pro |
|---|---|---|---|---|---|---|---|---|---|---|---|---|---|
| | | | | 75 | | | | | 80 | | | | |

| Leu | Tyr | Ala | Asn | Glu | Gly | Leu | Glu | Trp | Ala | Gly | Trp | Leu | Leu |
|---|---|---|---|---|---|---|---|---|---|---|---|---|---|
| 85 | | | | | 90 | | | | | 95 | | | |

| Ser | Pro | Arg | Gly | Ser | Arg | Pro | Ser | Trp | Gly | Pro | Asn | Asp | Pro |
|---|---|---|---|---|---|---|---|---|---|---|---|---|---|
| | 100 | | | | | 105 | | | | | 110 | | |

| Arg | Arg | Lys | Ser | Arg | Asn | Leu | Gly | Lys | Val | Ile | Asp | Thr | Leu |
|---|---|---|---|---|---|---|---|---|---|---|---|---|---|
| | | 115 | | | | | 120 | | | | | 125 | |

| Thr | Cys | Gly | Phe | Ala | Asp | Leu | Met | Gly | Tyr | Ile | Pro | Leu | Val |
|---|---|---|---|---|---|---|---|---|---|---|---|---|---|
| | | | 130 | | | | | 135 | | | | | 140 |

| Gly | Gly | Pro | Val | Gly | Gly | Val | Ala | Arg | Ala | Leu | Ala | His | Gly |
|---|---|---|---|---|---|---|---|---|---|---|---|---|---|
| | | | | 145 | | | | | 150 | | | | |

| Val | Arg | Val | Leu | Glu | Asp | Gly | Val | Asn | Tyr | Ala | Thr | Gly | Asn |
|---|---|---|---|---|---|---|---|---|---|---|---|---|---|
| 155 | | | | | 160 | | | | | 165 | | | |

| Leu | Pro | Gly | Cys | Ser | Phe | Ser | Ile | Phe | Ile | Leu | Ala | Leu | Leu |
|---|---|---|---|---|---|---|---|---|---|---|---|---|---|
| | 170 | | | | | 175 | | | | | 180 | | |

| Ser | Cys | Leu | Thr | Val | Pro | Ala | Ser | Ala |
|---|---|---|---|---|---|---|---|---|
| | | 185 | | | | | 190 | |

(2) INFORMATION FOR SEQ ID NO: 203:

(i) SEQUENCE CHARACTERISTICS:
    (A) LENGTH: 191 amino acids
    (B) TYPE: amino acid
    (C) STRANDEDNESS: unknown
    (D) TOPOLOGY: unknown (vi) ORIGINAL SOURCE:
    (A) ORGANISM: homosapiens
    (C) INDIVIDUAL ISOLATE: SA13

(xi) SEQUENCE DESCRIPTION: SEQ ID NO: 203:

| Met | Ser | Thr | Asn | Pro | Lys | Pro | Gln | Arg | Lys | Thr | Lys | Arg | Asn |
|---|---|---|---|---|---|---|---|---|---|---|---|---|---|
| 1 | | | | 5 | | | | | 10 | | | | |

| Thr | Asn | Arg | Arg | Pro | Gln | Asp | Val | Lys | Phe | Pro | Gly | Gly | Gly |
|---|---|---|---|---|---|---|---|---|---|---|---|---|---|
| 15 | | | | | 20 | | | | | 25 | | | |

| Gln | Ile | Val | Gly | Gly | Val | Tyr | Leu | Leu | Pro | Arg | Arg | Gly | Pro |
|---|---|---|---|---|---|---|---|---|---|---|---|---|---|
| | | 30 | | | | 35 | | | | | 40 | | |

| Arg | Leu | Gly | Val | Arg | Ala | Thr | Arg | Lys | Thr | Ser | Glu | Arg | Ser |
|---|---|---|---|---|---|---|---|---|---|---|---|---|---|
| | | 45 | | | | | 50 | | | | | 55 | |

| Gln | Pro | Arg | Gly | Arg | Arg | Gln | Pro | Ile | Pro | Lys | Ala | Arg | Gln |
|---|---|---|---|---|---|---|---|---|---|---|---|---|---|
| | | | 60 | | | | | 65 | | | | | 70 |

-continued

| | | | | | | | | | | | | |
|---|---|---|---|---|---|---|---|---|---|---|---|---|
| Pro | Thr | Gly | Arg | Ser<br>75 | Trp | Gly | Gln | Pro<br>80 | Gly | Tyr | Pro | Trp | Pro |
| Leu<br>85 | Tyr | Ala | Asn | Glu | Gly<br>90 | Leu | Gly | Trp | Ala | Gly<br>95 | Trp | Leu | Leu |
| Ser | Pro<br>100 | Arg | Gly | Ser | Arg | Pro<br>105 | Asn | Trp | Gly | Pro | Asn<br>110 | Asp | Pro |
| Arg | Arg | Lys<br>115 | Ser | Arg | Asn | Leu | Gly<br>120 | Lys | Val | Ile | Asp | Thr<br>125 | Leu |
| Thr | Cys | Gly | Phe<br>130 | Ala | Asp | Leu | Met | Gly<br>135 | Tyr | Ile | Pro | Leu | Val<br>140 |
| Gly | Gly | Pro | Val | Gly<br>145 | Gly | Val | Ala | Arg | Ala<br>150 | Leu | Ala | His | Gly |
| Val<br>155 | Arg | Val | Leu | Glu | Asp<br>160 | Gly | Val | Asn | Tyr | Ala<br>165 | Thr | Gly | Asn |
| Leu | Pro<br>170 | Gly | Cys | Ser | Phe | Ser<br>175 | Ile | Phe | Ile | Leu | Ala<br>180 | Leu | Leu |
| Ser | Cys | Leu<br>185 | Thr | Val | Pro | Thr | Ser<br>190 | Ala | | | | | |

( 2 ) INFORMATION FOR SEQ ID NO: 204:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA6

( x i ) SEQUENCE DESCRIPTION: SEQ ID NO: 204:

| | | | | | | | | | | | | |
|---|---|---|---|---|---|---|---|---|---|---|---|---|
| Met<br>1 | Ser | Thr | Asn | Pro<br>5 | Lys | Pro | Gln | Arg | Lys<br>10 | Thr | Gln | Arg | Asn |
| Thr<br>15 | Asn | Arg | Arg | Pro | Gln<br>20 | Asp | Val | Lys | Phe | Pro<br>25 | Gly | Gly | Gly |
| Gln | Ile<br>30 | Val | Gly | Gly | Val | Tyr<br>35 | Leu | Leu | Pro | Arg | Arg<br>40 | Gly | Pro |
| Arg | Met | Gly<br>45 | Val | Arg | Ala | Thr | Arg<br>50 | Lys | Thr | Ser | Glu | Arg<br>55 | Ser |
| Gln | Pro | Arg | Gly<br>60 | Arg | Arg | Gln | Pro | Ile<br>65 | Pro | Lys | Ala | Arg | Gln<br>70 |
| Ser | Ala | Gly | Arg | Ser<br>75 | Trp | Gly | Gln | Pro | Gly<br>80 | Tyr | Pro | Trp | Pro |
| Leu<br>85 | Tyr | Ala | Asn | Glu | Gly<br>90 | Leu | Gly | Trp | Ala | Gly<br>95 | Trp | Leu | Leu |
| Ser | Pro<br>100 | Arg | Gly | Ser | Arg | Pro<br>105 | Asn | Trp | Gly | Pro | Asn<br>110 | Asp | Pro |
| Arg | Arg | Lys<br>115 | Ser | Arg | Asn | Leu | Gly<br>120 | Lys | Val | Ile | Asp | Thr<br>125 | Leu |
| Thr | Cys | Gly | Phe<br>130 | Ala | Asp | Leu | Met | Gly<br>135 | Tyr | Ile | Pro | Leu | Val<br>140 |
| Gly | Gly | Pro | Val | Gly<br>145 | Gly | Val | Ala | Arg | Ala<br>150 | Leu | Ala | His | Gly |
| Val<br>155 | Arg | Val | Leu | Glu | Asp<br>160 | Gly | Val | Asn | Tyr | Ala<br>165 | Thr | Gly | Asn |
| Leu | Pro<br>170 | Gly | Cys | Ser | Phe | Ser<br>175 | Ile | Phe | Val | Leu | Ala<br>180 | Leu | Leu |

Ser Cys Leu Thr Val Pro Ala Ser Ala
         185                 190

(2) INFORMATION FOR SEQ ID NO: 205:

(i) SEQUENCE CHARACTERISTICS:
        (A) LENGTH: 191 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA11

(xi) SEQUENCE DESCRIPTION: SEQ ID NO: 205:

Met Ser Thr Asn Pro Lys Pro Gln Arg Lys Thr Lys Arg Asn
 1               5                   10

Thr Asn Arg Arg Pro Gln Asp Val Lys Phe Pro Gly Gly Gly
 15              20                  25

Gln Ile Val Gly Gly Val Tyr Leu Leu Pro Arg Arg Gly Pro
     30              35                  40

Arg Leu Gly Val Arg Ala Thr Arg Lys Thr Ser Glu Arg Ser
         45              50                  55

Gln Pro Arg Gly Arg Arg Gln Pro Ile Pro Lys Ala Arg Gln
             60              65                  70

Pro Thr Gly Arg Ser Trp Gly Gln Pro Gly Tyr Pro Trp Pro
                 75              80

Phe Tyr Ala Asn Glu Gly Leu Gly Trp Ala Gly Trp Leu Leu
 85              90                  95

Ser Pro Arg Gly Ser Arg Pro Asn Trp Gly Pro Asn Asp Pro
     100             105                 110

Arg Arg Arg Ser Arg Asn Leu Gly Lys Val Ile Asp Thr Leu
         115             120                 125

Thr Cys Gly Phe Ala Asp Leu Met Gly Tyr Ile Pro Leu Val
             130             135                 140

Gly Gly Pro Val Gly Gly Val Ala Arg Ala Leu Ala His Gly
                 145             150

Val Arg Ala Leu Glu Asp Gly Val Asn Tyr Ala Thr Gly Asn
 155             160                 165

Leu Pro Gly Cys Ser Phe Ser Ile Phe Ile Leu Ala Leu Leu
     170             175                 180

Ser Cys Leu Thr Val Pro Ala Thr Ala
         185                 190

(2) INFORMATION FOR SEQ ID NO: 206:

(i) SEQUENCE CHARACTERISTICS:
        (A) LENGTH: 191 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK2

(xi) SEQUENCE DESCRIPTION: SEQ ID NO: 206:

Met Ser Thr Leu Pro Lys Pro Gln Arg Lys Thr Lys Arg Asn
 1               5                   10

Thr Asn Arg Arg Pro Thr Asp Val Lys Phe Pro Gly Gly Gly

```
                    15                          20                          25
        Gln  Ile  Val  Gly  Gly  Val  Tyr  Leu  Leu  Pro  Arg  Arg  Gly  Pro
                  30                      35                      40

Arg  Leu  Gly  Val  Arg  Ala  Thr  Arg  Lys  Thr  Ser  Glu  Arg  Ser
                      45                      50                      55

Gln  Pro  Arg  Gly  Arg  Arg  Gln  Pro  Ile  Pro  Lys  Ala  Arg  Gln
                          60                      65                      70

Pro  Gln  Gly  Arg  His  Trp  Ala  Gln  Pro  Gly  Tyr  Pro  Trp  Pro
                              75                      80

Leu  Tyr  Gly  Asn  Glu  Gly  Cys  Gly  Trp  Ala  Gly  Trp  Leu  Leu
        85                       90                      95

Ser  Pro  Arg  Gly  Ser  Arg  Pro  His  Trp  Gly  Pro  Asn  Asp  Pro
             100                      105                     110

Arg  Arg  Arg  Ser  Arg  Asn  Leu  Gly  Lys  Val  Ile  Asp  Thr  Leu
                  115                      120                     125

Thr  Cys  Gly  Phe  Ala  Asp  Leu  Met  Gly  Tyr  Ile  Pro  Val  Val
                      130                      135                          140

Gly  Ala  Pro  Leu  Gly  Gly  Val  Ala  Ala  Ala  Leu  Ala  His  Gly
                          145                      150

Val  Arg  Ala  Ile  Glu  Asp  Gly  Ile  Asn  Tyr  Ala  Thr  Gly  Asn
        155                      160                      165

Leu  Pro  Gly  Cys  Ser  Phe  Ser  Ile  Phe  Leu  Leu  Ala  Leu  Leu
             170                      175                     180

Ser  Cys  Leu  Thr  Thr  Pro  Ala  Ser  Ala
                  185                      190
```

( 2 ) INFORMATION FOR SEQ ID NO:207:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

GCGTCCGGGT TCTGGAAGAC GGCGTGAACT ATGCAACAGG    40

( 2 ) INFORMATION FOR SEQ ID NO:208:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:208:

AGGCTTTCAT TGCAGTTCAA GGCCGTGCTA TTGATGTGCC    40

( 2 ) INFORMATION FOR SEQ ID NO:209:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:209:

AAGACGGCGT GAACTATGCA ACAGGGAACC TTCCTGGTTG    40

( 2 ) INFORMATION FOR SEQ ID NO:210:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:210:

AGTTCAAGGC CGTGCTATTG ATGTGCCAAC TGCCGTTGGT    40

( 2 ) INFORMATION FOR SEQ ID NO:211:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:211:

AAGACGGCGT GAATTCTGCA ACAGGGAACC TTCCTGGTTG    40

( 2 ) INFORMATION FOR SEQ ID NO:212:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:212:

AGTTCAAGGC CGTGGAATTC ATGTGCCAAC TGCCGTTGGT    40

( 2 ) INFORMATION FOR SEQ ID NO:213:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( x i ) SEQUENCE DESCRIPTION: SEQ ID NO:213:

ARCTYCGACG TYACATCGAY CTGCTYGTYG GRAGYGCCAC CC    42

( 2 ) INFORMATION FOR SEQ ID NO:214:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:214:

RCARGCCRTC TTGGAYATGA TCGCTGGWGC Y    31

( 2 ) INFORMATION FOR SEQ ID NO:215:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( x i ) SEQUENCE DESCRIPTION: SEQ ID NO:215:

CRATACGACR YCAYGTCGAY TTGCTCGTTG GGGCGGCTRY YT    42

( 2 ) INFORMATION FOR SEQ ID NO:216:

( i ) SEQUENCE CHARACTERISTICS:
( A ) LENGTH: 31 base pairs ( B ) TYPE: nucleic acid
        ( C ) STRANDEDNESS: single
        ( D ) TOPOLOGY: linear ( x i ) SEQUENCE DESCRIPTION: SEQ ID NO:216:

RCAAGCTRTC RTGGAYRTGG TRRCRGGRGC C 31

( 2 ) INFORMATION FOR SEQ ID NO:217:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

TTGCGGACKC ACATYGACAT GGTYGTGATG TCCGCCACGC 40

( 2 ) INFORMATION FOR SEQ ID NO:218:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

GATGCGCGTT CCCGAGGTCA TCWTAGACAT CRTYRGCGGR GCD 43

( 2 ) INFORMATION FOR SEQ ID NO:219:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

AATGGCACCY TGCRCTGCTG GATACAAGTR ACACCTAATG TGGCTGTGAA 50

ACAC 54

( 2 ) INFORMATION FOR SEQ ID NO:220:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

TGARCTAGYC CTYSARGTYG TCTTCGGYGG Y 31

( 2 ) INFORMATION FOR SEQ ID NO:221:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

GCCAACGTCT CTCGATGTTG GGTGCCGGTT GCCCCAATC TCGCCATAAG 50

TCAA 54

( 2 ) INFORMATION FOR SEQ ID NO:222:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:222:

AAGGGCCTGC GAGCACACAT CGATATCATC GTGATGTCTG CTACGG 46

( 2 ) INFORMATION FOR SEQ ID NO:223:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:223:

TTGGTGCGCA TCCCGGAAGT CATCTTGGAT ATTGTTACAG GAGGT 45

( 2 ) INFORMATION FOR SEQ ID NO:224:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:224:

AGTCAGGTAY GTCGGAGCAA CCACCGCYTC GATACGCAGT 40

( 2 ) INFORMATION FOR SEQ ID NO:225:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:225:

AGCCTTCACG TTCAGACCKC GTCGCCATCA AACRGTCCAG ACCTGT 46

( 2 ) INFORMATION FOR SEQ ID NO:226:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:226:

TCCCCCGCYG TGGGTATGGT GGTRGCGCAC RTYCTGCGDY TGCCCCAGAC 50

CKTGTTYGAC ATAMTRGCYG GGGCC 75

( 2 ) INFORMATION FOR SEQ ID NO:227:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:227:

ACGCCGGTGA CGCCTACAGT GGCTGTCGCA CACCCGGGC 39

( 2 ) INFORMATION FOR SEQ ID NO:228:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:228:

ATGAGGGTCC CCACAGCCTT TCTCGACATG GTTGCCGGAG GC 42

( 2 ) INFORMATION FOR SEQ ID NO:229:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:229:

CGCGCCCTAT CCCAACGCAC CGTTAGAGTC CATGCGCAGG 40

( 2 ) INFORMATION FOR SEQ ID NO:230:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:230:

TCAGATCTTA CGGATCCCCT CTATCCTAGG TGACTTGCTC ACCGGGGGT 49

( 2 ) INFORMATION FOR SEQ ID NO:231:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:231:

CAGTCACGCT GCTGGGTGGC CCTTACTCCC ACCGTGGCGG YGYCTTATAT 50

CGGT 54

( 2 ) INFORMATION FOR SEQ ID NO:232:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:232:

TAGCACTCTG GTRGAYCTAC TCRCTGGAGG G 31

( 2 ) INFORMATION FOR SEQ ID NO:233:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:233:

AAGTCTACAT GCTGGGTGTC TCTCACCCCC ACCGTGGCTG CGCAACATCT 50

GAAT 54

( 2 ) INFORMATION FOR SEQ ID NO:234:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:234:

AGGCGCCATG GTCGACCTGC TTGCAGGCGG C        31

( 2 ) INFORMATION FOR SEQ ID NO:235:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:235:

TCAGCCCCGA VYYTCGGAGC GGTCACGGCT CCTCTTCGGA GGG        43

( 2 ) INFORMATION FOR SEQ ID NO:236:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:236:

TGYTACGGAT YCCCCARGTG GTCATHGACA TCATWGCCGG GGSC        44

( 2 ) INFORMATION FOR SEQ ID NO:237:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:237:

CATACCAAAT GCTTCCACGC CCGCAACGGG ATTCCGCAGG        40

( 2 ) INFORMATION FOR SEQ ID NO:238:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:238:

TCTTCTTGCG GGCGCCGCAG TGGTTTGCTC ATCCCTG        37

( 2 ) INFORMATION FOR SEQ ID NO:239:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:239:

ATCTAGCATC TTGAGGGTAC CTGAGATTTG TGCGAGTGTG ATATTTGGTG        50
GC        52

( 2 ) INFORMATION FOR SEQ ID NO:240:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:240:

```
Trp Ile Gln Val Thr Pro Asn Val Ala Val Lys His Arg Gly Ala
                 5                  10                 15
Leu Thr His Asn Leu Arg Xaa His Xaa Asp Xaa Ile Val Met Ala
                20                  25                 30
Ala Thr Val
```

( 2 ) INFORMATION FOR SEQ ID NO:241:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:241:

```
Trp Val Pro Val Ala Pro Asn Leu Ala Ile Ser Gln Pro Gly Ala
                 5                  10                 15
Leu Thr Lys Gly Leu Arg Ala His Ile Asp Ile Ile Val Met Ser
                20                  25                 30
Ala Thr Val
```

( 2 ) INFORMATION FOR SEQ ID NO:242:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:242:

```
Trp Ile Pro Val Xaa Pro Asn Val Ala Val Xaa Xaa Pro Gly Ala
                 5                  10                 15
Leu Thr Gln Gly Leu Arg Thr His Ile Asp Met Val Val Met Ser
                20                  25                 30
Ala Thr Leu
```

( 2 ) INFORMATION FOR SEQ ID NO:243:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:243:

```
Trp Thr Xaa Val Thr Pro Thr Val Ala Val Arg Tyr Val Gly Ala
                 5                  10                 15
Thr Thr Ala Ser Ile Arg Ser His Val Asp Leu Leu Val Gly Ala
                20                  25                 30
Ala Thr Xaa
```

( 2 ) INFORMATION FOR SEQ ID NO:244:

( i ) SEQUENCE CHARACTERISTICS:
        ( A ) LENGTH: 33 amino acids (B) TYPE: amino acid
(C) STRANDEDNESS: unknown
(D) TOPOLOGY: unknown (xi) SEQUENCE DESCRIPTION: SEQ ID NO:244:

Trp Val Ala Leu Xaa Pro Thr Leu Ala Ala Arg Asn Xaa Xaa Xaa
              5                   10                      15

Xaa Thr Xaa Xaa Ile Arg Xaa His Val Asp Leu Leu Val Gly Ala
              20                  25                      30

Ala Xaa Phe (2) INFORMATION FOR SEQ ID NO:245:

(i) SEQUENCE CHARACTERISTICS:
(A) LENGTH: 33 amino acids
(B) TYPE: amino acid
(C) STRANDEDNESS: unknown
(D) TOPOLOGY: unknown (xi) SEQUENCE DESCRIPTION: SEQ ID NO:245:

Trp Val Xaa Xaa Xaa Pro Thr Val Ala Thr Arg Asp Gly Lys Leu
              5                   10                      15

Pro Xaa Xaa Gln Leu Arg Arg Xaa Ile Asp Leu Leu Val Gly Ser
              20                  25                      30

Ala Thr Leu (2) INFORMATION FOR SEQ ID NO:246:

(i) SEQUENCE CHARACTERISTICS:
(A) LENGTH: 33 amino acids
(B) TYPE: amino acid
(C) STRANDEDNESS: unknown
(D) TOPOLOGY: unknown (xi) SEQUENCE DESCRIPTION: SEQ ID NO:246:

Trp Thr Pro Val Thr Pro Thr Val Ala Val Ala His Pro Gly Ala
              5                   10                      15

Pro Leu Glu Ser Phe Arg Arg His Val Asp Leu Met Val Gly Ala
              20                  25                      30

Ala Thr Leu (2) INFORMATION FOR SEQ ID NO:247:

(i) SEQUENCE CHARACTERISTICS:
(A) LENGTH: 33 amino acids
(B) TYPE: amino acid
(C) STRANDEDNESS: unknown
(D) TOPOLOGY: unknown (xi) SEQUENCE DESCRIPTION: SEQ ID NO:247:

Trp Val Ala Leu Thr Pro Thr Val Ala Xaa Xaa Tyr Ile Gly Ala
              5                   10                      15

Pro Leu Xaa Ser Xaa Arg Arg His Val Asp Leu Met Val Gly Ala
              20                  25                      30

Ala Thr Val (2) INFORMATION FOR SEQ ID NO:248:

(i) SEQUENCE CHARACTERISTICS:
(A) LENGTH: 33 amino acids
(B) TYPE: amino acid
(C) STRANDEDNESS: unknown
(D) TOPOLOGY: unknown ( x i ) SEQUENCE DESCRIPTION: SEQ ID NO:248:

Trp Val Ser Leu Thr Pro Thr Val Ala Ala Gln His Leu Asn Ala
                5                   1 0                  1 5

Pro Leu Glu Ser Leu Arg Arg His Val Asp Leu Met Val Gly Gly
                2 0                  2 5                  3 0

Ala Thr Leu ( 2 ) INFORMATION FOR SEQ ID NO:249:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:249:

Trp Val Pro Leu Thr Pro Thr Val Ala Ala Pro Tyr Pro Asn Ala
                5                   1 0                  1 5

Pro Leu Glu Ser Met Arg Arg His Val Asp Leu Met Val Gly Ala
                2 0                  2 5                  3 0

Ala Thr Met ( 2 ) INFORMATION FOR SEQ ID NO:250:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:250:

Trp Val Xaa Ile Thr Pro Thr Leu Ser Ala Pro Xaa Xaa Gly Ala
                5                   1 0                  1 5

Val Thr Ala Pro Leu Arg Arg Xaa Val Asp Tyr Leu Ala Gly Gly
                2 0                  2 5                  3 0

Ala Ala Leu ( 2 ) INFORMATION FOR SEQ ID NO:251:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:251:

Trp His Ala Val Thr Pro Thr Leu Ala Ile Pro Asn Ala Ser Thr
                5                   1 0                  1 5

Pro Ala Thr Gly Phe Arg Arg His Val Asp Leu Leu Ala Gly Ala
                2 0                  2 5                  3 0

Ala Val Val ( 2 ) INFORMATION FOR SEQ ID NO:252:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:252:

Thr Leu Thr Met Ile Leu Ala Tyr Ala Ala Arg Val Pro Glu Leu
                5                   1 0                  1 5

Xaa Leu Xaa Val Val Phe Gly Gly
                    20

( 2 ) INFORMATION FOR SEQ ID NO:253:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:253:

Thr Thr Thr Met Leu Leu Ala Tyr Leu Val Arg Ile Pro Glu Val
                  5                  10                  15
Ile Leu Asp Ile Val Thr Gly Gly
                    20

( 2 ) INFORMATION FOR SEQ ID NO:254:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:254:

Thr Xaa Thr Xaa Ile Leu Ala Tyr Xaa Met Arg Val Pro Glu Val
                  5                  10                  15
Ile Xaa Asp Ile Xaa Xaa Gly Ala
                    20

( 2 ) INFORMATION FOR SEQ ID NO:255:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:255:

Ala Val Gly Met Val Val Ala His Xaa Leu Arg Leu Pro Gln Thr
                  5                  10                  15
Xaa Phe Asp Ile Xaa Ala Gly Ala
                    20

( 2 ) INFORMATION FOR SEQ ID NO:256:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:256:

Thr Xaa Ala Leu Val Xaa Ser Gln Leu Leu Arg Xaa Pro Gln Ala
                  5                  10                  15
Xaa Xaa Asp Xaa Val Xaa Gly Ala
                    20

( 2 ) INFORMATION FOR SEQ ID NO:257:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:257:

Thr Xaa Ala Leu Val Xaa Ala Gln Leu Leu Arg Xaa Pro Gln Ala
                 5                   10                  15
Xaa Leu Asp Met Ile Ala Gly Ala
                 20

( 2 ) INFORMATION FOR SEQ ID NO:258:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:258:

Thr Thr Thr Leu Leu Leu Ala Gln Ile Met Arg Val Pro Thr Ala
                 5                   10                  15
Phe Leu Asp Met Val Ala Gly Gly
                 20

( 2 ) INFORMATION FOR SEQ ID NO:259:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:259:

Thr Thr Thr Leu Xaa Leu Ala Gln Val Met Arg Ile Pro Ser Thr
                 5                   10                  15
Leu Val Asp Leu Leu Xaa Gly Gly
                 20

( 2 ) INFORMATION FOR SEQ ID NO:260:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:260:

Thr Ala Thr Leu Val Leu Ala Gln Leu Met Arg Ile Pro Gly Ala
                 5                   10                  15
Met Val Asp Leu Leu Ala Gly Gly
                 20

( 2 ) INFORMATION FOR SEQ ID NO:261:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:261:

Thr Ser Ala Leu Ile Met Ala Gln Ile Leu Arg Ile Pro Ser Ile
                 5                   10                  15
Leu Gly Asp Leu Leu Thr Gly Gly
                 20

( 2 ) INFORMATION FOR SEQ ID NO:262:

-continued (i) SEQUENCE CHARACTERISTICS:
(A) LENGTH: 23 amino acids
(B) TYPE: amino acid
(C) STRANDEDNESS: unknown
(D) TOPOLOGY: unknown (xi) SEQUENCE DESCRIPTION: SEQ ID NO:262:

Xaa Thr Ala Leu Xaa Met Ala Gln Xaa Leu Arg Ile Pro Gln Val
                  5                   10                  15

Val Ile Asp Ile Ile Ala Gly Xaa
              20

(2) INFORMATION FOR SEQ ID NO:263:

(i) SEQUENCE CHARACTERISTICS:
(A) LENGTH: 23 amino acids
(B) TYPE: amino acid
(C) STRANDEDNESS: unknown
(D) TOPOLOGY: unknown (xi) SEQUENCE DESCRIPTION: SEQ ID NO:263:

Thr Thr Thr Leu Val Leu Ser Ser Ile Leu Arg Val Pro Glu Ile
                  5                   10                  15

Cys Ala Ser Val Ile Phe Gly Gly
              20